US012781249B2

(12) United States Patent
Zanghellini et al.

(10) Patent No.: US 12,781,249 B2
(45) **Date of Patent: *Nov. 3, 2026**

(54) METHODS AND COMPOSITIONS FOR PREPARING TAGATOSE FROM FRUCTOSE

(71) Applicant: Arzeda Corp., Seattle, WA (US)

(72) Inventors: Alexandre Zanghellini, Memphis, TN (US); Kyle Roberts, San Marcos, CA (US); Michael Charles Milner Cockrem, Madison, WI (US); Christopher Dunckley, Seattle, WA (US)

(73) Assignee: Arzeda Corp., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/515,958

(22) Filed: Nov. 21, 2023

(65) Prior Publication Data

US 2024/0368641 A1 Nov. 7, 2024

Related U.S. Application Data

(63) Continuation of application No. 17/341,813, filed on Jun. 8, 2021, now Pat. No. 11,866,758, which is a continuation of application No. 16/503,092, filed on Jul. 3, 2019, now Pat. No. 11,060,119.

(60) Provisional application No. 62/693,681, filed on Jul. 3, 2018, provisional application No. 62/693,660, filed on Jul. 3, 2018.

(51) Int. Cl.
*C12P 7/26* (2006.01)
*C12N 15/113* (2010.01)
*C12N 15/63* (2006.01)

(52) U.S. Cl.
CPC .............. *C12P 7/26* (2013.01); *C12N 15/113* (2013.01); *C12N 15/63* (2013.01)

(58) Field of Classification Search
CPC .. C12P 7/26; C12P 19/02; C12P 19/24; C12N 15/113; C12N 15/63; C12N 9/90
See application file for complete search history.

(56) References Cited

U.S. PATENT DOCUMENTS

| | | | | |
|---|---|---|---|---|
| 6,991,923 | B2 | 1/2006 | Bertelsen et al. | |
| 10,138,506 | B2 | 11/2018 | Wichelecki | |
| 11,060,119 | B2 * | 7/2021 | Zanghellini | C12N 9/90 |
| 11,866,758 | B2 * | 1/2024 | Zanghellini | C12P 19/02 |

FOREIGN PATENT DOCUMENTS

| | | | |
|---|---|---|---|
| CA | 3058589 | A1 | 10/2018 |
| EP | 3006568 | A1 | 4/2016 |
| EP | 3211078 | A1 | 8/2017 |
| WO | WO-2017059278 | A1 | 4/2017 |
| WO | WO-2018182344 | A1 | 10/2018 |
| WO | WO-2018182345 | A1 | 10/2018 |

OTHER PUBLICATIONS

Broun et al., "Catalytic Plasticity of Fatty Acid Modification Enzymes Underlying Chemical Diversity of Plant Lipids," Science, Nov. 1998, vol. 282, pp. 1315-1317.
Database accession No. BDU39962, Dictyoglomus thermophilum F6PE protein, SEQ ID 11, May 18, 2017, 1 page.
Database accession No. B8DZ63, SubName: Full= Tagatose-6-phosphate kinase {EC0:00003131EMBL:ACK41689.1}; EC=2.7.1.144 {EC0:00003131EMBL:ACK41689.1};, Mar. 3, 2009, 1 page.
Datta et al., "Enzyme immobilization: an overview on techniques and support materials," 3 Biotech, 2013, vol. 3: 1-9.
Devos et al., "Practical Limits of Function Prediction," Proteins: Structure, Function, and Genetics, 2000, vol. 41, pp. 98-107.
Extended European Search Report For Application No. 19831065.8 dated Apr. 8, 2022, 11 pages.
International Search Report and Written Opinion of the International Searching Authority for International Application No. PCT/US2019/040613, dated Nov. 22, 2019, 11 pages.
Lee et al., Structure-based prediction and identification of 4-epimerization activity of phosphate sugars in class II aldolases. Nature, Scientific Reports, 2017, 7:1934, 9 pages.
NCBI Reference Sequence: WP_012582774.1, class II D-tagatose-bisphosphate aldolase, non-catalytic subunit [Dictyoglomus turgidum], Apr. 27, 2020, 1 page.
Seffernick et al., "Melamine Deaminase and Atrazine Chlorohydrolase: 98 Percent Identical but Functionally Different," J. Bacterial., Apr. 2001, vol. 183, No. 8, pp. 2405-2410.
UniProtKB Accession No. B5YBD7, UniProtKB/TrEMBL database, Nov. 25, 2008, 6 pages.
Whisstock et al., "Prediction of protein function from protein sequence and structure," Quarterly Reviews of Biophysics, Aug. 2003, 36(3), pp. 307-340.
Witkowski, A. et al., "Conversion of a β-Ketoacyl Synthase to a Malonyl Decarboxylase by Replacement of the Active-Site Cysteine with Glutamine," Biochemistry, 1999, vol. 38, pp. 11643-11650.
GenBank Accession No. ACK41689.1, "Tagatose-6-phosphate kinase [Dictyoglomus turgidum DSM 6724]", Dec. 11, 2013, 2 pages.

* cited by examiner

*Primary Examiner* — Ganapathirama Raghu
(74) *Attorney, Agent, or Firm* — COOLEY LLP

(57) ABSTRACT

Disclosed herein are compositions and methods for preparing tagatose from fructose, more particularly, compositions comprising thermophilic fructose C4-epimerases derived from thermophilic microorganisms and methods for preparing tagatose from fructose using the compositions.

17 Claims, 82 Drawing Sheets

Specification includes a Sequence Listing.

FIG. 17

| | |
|---|---|
| ACTIVE SITE MUTANT | |
| STABILITY/EXPR MUTANT | |
| LYS/CYS ONLY MUTANT | |
| LYS/CYS MUTANT | |
| pA06238 RESIDUE NUMBER | |
| SEQ_ID_NO_6_pA06238 | - - - - - - - - - - - - - - - - - - - - - - - - - - - - - |
| SEQ_ID_NO_1_pA06233 | - - - - - - - - - - - - - - - - - - - - - - - - - - - - - |
| SEQ_ID_NO_2_pA06234 | - - - - - - - - - - - - - - - - - - - - - - - - - - - - - |
| SEQ_ID_NO_3_pA06235 | - - - - - - - - - - - - - - - - - - - - - - - - - - - - - |
| SEQ_ID_NO_4_pA06236 | - - - - - - - - - - - - - - - - - - - - - - - - - - - - - |
| SEQ_ID_NO_5_pA06237 | - - - - - - - - - - - - - - - - - - - - - - - - - - - - - |
| SEQ_ID_NO_7_pA06239 | - - - - - - - - - - - - - - - - - - - - - - - - - - - - - |
| SEQ_ID_NO_8_pA06240 | - - - - - - - - - - - - - - - - - - - - - - - - - - - - - |
| SEQ_ID_NO_9_pA06241 | - - - - - - - - - - - - - - - - - - - - - - - - - - - - - |
| SEQ_ID_NO_10_pA07068 | - - - - - - - - - - - - - - - - - - - - - - - - - - - - - |
| SEQ_ID_NO_11_pA07069 | - - - - - - - - - - - - - - - - - - - - - - - - - - - - - |
| SEQ_ID_NO_12_pA07070 | - - - - - - - - - - - - - - - - - - - - - - - - - - - - - |
| SEQ_ID_NO_13_pA07071 | - - - - - - - - - - - - - - - - - - - - - - - - - - - - - |
| SEQ_ID_NO_14_pA07072 | - - - - - - - - - - - - - - - - - - - - - - - - - - - - - |
| SEQ_ID_NO_15_pA07073 | - - - - - - - - - - - - - - - - - - - - - - - - - - - - - |
| SEQ_ID_NO_16_pA07074 | - - - - - - - - - - - - - - - - - - - - - - - - - - - - - |
| SEQ_ID_NO_17_pA07075 | - - - - - - - - - - - - - - - - - - - - - - - - - - - - - |
| SEQ_ID_NO_18_pA07076 | - - - - - - - - - - - - - - - - - - - - - - - - - - - - - |
| SEQ_ID_NO_19_pA07077 | - - - - - - - - - - - - - - - - - - - - - - - - - - - - - |
| SEQ_ID_NO_20_pA07078 | - - - - - - - - - - - - - - - - - - - - - - - - - - - - - |
| SEQ_ID_NO_21_pA07079 | - - - - - - - - - - - - - - - - - - - - - - - - - - - - - |
| SEQ_ID_NO_22_pA07080 | - - - - - - - - - - - - - - - - - - - - - - - - - - - - - |
| SEQ_ID_NO_23_pA07081 | - - - - - - - - - - - - - - - - - - - - - - - - - - - - - |
| SEQ_ID_NO_321_pA06242 | - - - - - - - - - - - - - - - - - - - M - K L L E E F L K |
| SEQ_ID_NO_322_pA06243 | - - - - - - - - - - - - - - - - - - - - - - M F A E F Q H |
| SEQ_ID_NO_323_pA06244 | - - - - - - - - - - - - - - - - - M A E - N I V E K F E K |
| SEQ_ID_NO_324_pA06245 | M V T V L Q T L L Q R P R P L A E I D R - T S L A R F L - |
| SEQ_ID_NO_325_pA06246 | - - - - - - - - M D I Y E K - - - I - A A A L K D N R H N |
| SEQ_ID_NO_326_pA06247 | - - M E M Q K L Y E E V E N K N I V K N - D L V D L T I - |
| SEQ_ID_NO_327_pA06248 | - - - - - - - - M K Q F L P - - - A - I E L L A K G E L P |
| SEQ_ID_NO_328_pA06249 | - M G N W K D F V K D F C T K E K N - I E V L - R A E A E |
| SEQ_ID_NO_329_pA06250 | - - - - M P S Q L P E P L P V P P E A R - A H - - - - - - |
| SEQ_ID_NO_330_pA06251 | - - - - - - - - - - - - - - - - - - - - - M L K L L N E S |
| SEQ_ID_NO_331_pA06252 | - - - - - - - - - - - - - - - - - - - - - - - - - - - - - |
| SEQ_ID_NO_332_pA06253 | - - - - - - - - - - - - - - M M - L - - - S P E A L A E G |
| SEQ_ID_NO_333_pA06254 | - - - - - - - - - - - - - - - - - - - - - M I G N V L S T |
| SEQ_ID_NO_334_pA06255 | - - - - - - - - - - - - - - - - - - - - - - - - - - - - - |
| SEQ_ID_NO_335_pA06256 | - - - - - - - - - - - - - - - - - - - - - - - - - - - - - |
| SEQ_ID_NO_336_pA06257 | - - - - - - - - - - - - - - - - - - - - - - - - - - - - - |

FIG. 17 CONTINUED

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| ACTIVE SITE MUTANT | | | | | | | | | | | | | | | | | | | | | | | | | | | | | |
| STABILITY/EXPR MUTANT | | | | | | | | | | | | | | | | | | | | | | | | | | | | | |
| LYS/CYS ONLY MUTANT | | | | | | | | | | | | | | | | | | | | | | | | | | | | | |
| LYS/CYS MUTANT | | | | | | | | | | | | | | | | | | | | | | | | | | | | | |

pA06238 RESIDUE NUMBER

```
SEQ_ID_NO_337_pA06258  M V T V L Q T L L Q R P R P L A E I D R - A A L A R F L -
SEQ_ID_NO_338_pA06261  - - - - - - - - - - - - - - - - - - - - - M L N L L E E L
SEQ_ID_NO_339_pA06262  - - - - - - - - - - - - - - - - - - - - - M K E E L S D Y
SEQ_ID_NO_340_pA06263  - - - - - - - - - - - - - - - - M V E K S I L E K L T D F
SEQ_ID_NO_341_pA06264  - - - - - - - - - - - - - - - - M V E K G I L E K L T D F
SEQ_ID_NO_342_pA06265  - - - - - - - - - - - - - - - - - - - - - M I G N V L S T
SEQ_ID_NO_343_pA06266  - - - - - - - - - - - - - - - - - - - - - M I G N V L S T
SEQ_ID_NO_344_pA06267  - - - - - - - - - - - - - - - - - - - - - M I G N V L S T
SEQ_ID_NO_345_pA06268  - - - - - - - - - - - - - - - - - - - - - M I G N V L S T
SEQ_ID_NO_346_pA06269  - - - - - - - - - - - - - - - - - - - - - M V G N V S S V
SEQ_ID_NO_347_pA06270  - - - - - - - - - - - - - - - - - - - - - - - - - - - - -
SEQ_ID_NO_348_pA06271  - - - - - - - - - - - - - - - - - - - - - M V G N V S A V
SEQ_ID_NO_349_pA06272  - - - - - - - - - - - - - - - - - - - - - - - - - - - - -
SEQ_ID_NO_350_pA06273  - - - - - - - - - - - - - - - - - - - - - - - - - - - - -
SEQ_ID_NO_351_pA06274  - - - - - - - - - - - - - - - - - - - - - - - - - - - - -
SEQ_ID_NO_352_pA04536  - - - - - - - - - - - - - - - - - - - - - M V L K V F K D
SEQ_ID_NO_353_pA04539  - - - - - - - - - - - - - - - - - - - - - M I N K V A E Y
SEQ_ID_NO_354_pA07082  - - - - - - - - - - - - - - - - M K E N - K V M N S F S A
SEQ_ID_NO_355_pA07083  - - - - - - - - - - - - - - - M Q S - R E E L - K R A I L
SEQ_ID_NO_356_pA07084  - - M S W K D F A E E L V G T S K E - - - - - A V M K V A
SEQ_ID_NO_357_pA07085  - - M S W K D F A E E L V G T S K E - - - - - A V M K V A
SEQ_ID_NO_358_pA07086  - - M S W K D F A E E L V G T S K D - - - - - A V K K V A
SEQ_ID_NO_359_pA07087  - - - - - - - M V K H F E S - - - V - L E E L S Q R K V P
SEQ_ID_NO_360_pA07088  - - - - - - - - - - - - - - - - - - - - - M I N K V A E Y
SEQ_ID_NO_361_pA07089  - - - - - - - - - - - - - - - - - - - - - - - - - - - - -
SEQ_ID_NO_362_pA07090  - - - - - - - - - - - - - - - - - - - - - M I N K V A E Y
SEQ_ID_NO_363_pA07091  - - - - - - - - - - - - - - M F E R K I E M I N K V A E Y
SEQ_ID_NO_364_pA07092  - - - - - - - - - - - - - - M G M M D K D V L N Q L S S L
SEQ_ID_NO_365_pA07093  - - - - - - - - - - - - - - - - - - - - - M K E E L S N Y
SEQ_ID_NO_366_pA07094  - - M D L N G L L K D V E E - - - I - L A K V D A G E K V
SEQ_ID_NO_367_pA07095  - - - - - - - - - - - - - - - - - - - - - - - - - - - - -
SEQ_ID_NO_368_pA07096  - - - - - - - - - - - - - - - - - - - - - - - - - - - - -
SEQ_ID_NO_369_pA07097  - - - - - - - - - - - - - - - - - - - - - - - - - - - - -
SEQ_ID_NO_370_pA07098  - - - - - - - - - - - - - - - - - - - - - - - - - - - - -
SEQ_ID_NO_371_pA07099  - - - - - - - - - - - - - - - - - - - - - - - - - - - - -
SEQ_ID_NO_372_pA07100  - - - - - - - - - - - - - - - - - - - - - - - - - - - - -
SEQ_ID_NO_373_pA07101  - - - - - - - - - - - - - - - - - - - - - - - - - - - - -
```

FIG. 17 CONTINUED

```
AS MUT
S/E MUT
L/C ONLY
L/C MUT

RESNUM

SEQ_6    - - - - - - - - - - - - - - - - - - - - - - - - - - - - - - - - - - - - -
SEQ_1    - - - - - - - - - - - - - - - - - - - - - - - - - - - - - - - - - - - - -
SEQ_2    - - - - - - - - - - - - - - - - - - - - - - - - - - - - - - - - - - - - -
SEQ_3    - - - - - - - - - - - - - - - - - - - - - - - - - - - - - - - - - - - - -
SEQ_4    - - - - - - - - - - - - - - - - - - - - - - - - - - - - - - - - - - - - -
SEQ_5    - - - - - - - - - - - - - - - - - - - - - - - - - - - - - - - - - - - - -
SEQ_7    - - - - - - - - - - - - - - - - - - - - - - - - - - - - - - - - - - - - -
SEQ_8    - - - - - - - - - - - - - - - - - - - - - - - - - - - - - - - - - - M Q A
SEQ_9    - - - - - - - - - - - - - - - - - - - - - - - - - - - - - - - - - - - - -
SEQ_10   - - - - - - - - - - - - - - - - - - - - - - - - - - - - - - - - - - - - -
SEQ_11   - - - - - - - - - - - - - - - - - - - - - - - - - - - - - - - - - - - - -
SEQ_12   - - - - - - - - - - - - - - - - - - - - - - - - - - - - - - - - - - - - -
SEQ_13   - - - - - - - - - - - - - - - - - - - - - - - - - - - - - - - - - - - - -
SEQ_14   - - - - - - - - - - - - - - - - - - - - - - - - - - - - - - - - - - - - -
SEQ_15   - - - - - - - - - - - - - - - - - - - - - - - - - - - - - - - - - - - - -
SEQ_16   - - - - - - - - - - - - - - - - - - - - - - - - - - - - - - - - - - - - -
SEQ_17   - - - - - - - - - - - - - - - - - - - - - - - - - - - - - - - - - - - - -
SEQ_18   - - - - - - - - - - - - - - - - - - - - - - - - - - - - - - - - - - - - -
SEQ_19   - - - - - - - - - - - - - - - - - - - - - - - - - - - - - - - - - - M Q A
SEQ_20   - - - - - - - - - - - - - - - - - - - - - - - - - - - - - - - - - - M Q A
SEQ_21   - - - - - - - - - - - - - - - - - - - - - - - - - - - - - - - - - - - - -
SEQ_22   - - - - - - - - - - - - - - - - - - - - - - - - - - - - - - - - - - - - -
SEQ_23   - - - - - - - - - - - - - - - - - - - - - - - - - - - - - - - - - - - - -
SEQ_321  A F P G R F K V Y G S S L R I I T D S - Y F F L G N D G K E - - - - - K L
SEQ_322  L T R G K F V P Y A T S L R K S T D A - T F F L V R D E L D - - - - - K Y
SEQ_323  L F K G K Y K I Y Y S S I R K L E K S - F F F M I R D Q K Q - - - - - K Y
SEQ_324  T D V I R Q Q V Y P T S L E P T S E G - V F F L A R D G R E - - - - - K R
SEQ_325  I Q L D G V K I Y P Q S Y V E V D M V - K M I M V K A A E K - - - - - K V
SEQ_326  G E S L K I K A Y P L S V L K K D D A - F F F I G K E N Y D - - - - - K F
SEQ_327  S N S N Q I K V Y E K S Y T V E G N V - H L L M V K N S G E - - - - - K F
SEQ_328  K A F G N Y G V Y P R S I N E V G N A - I V M M A R G E N E - - - - - K C
SEQ_329  - - - - - - - - - P - S F R - L H E G - A A L W L A G A R L - - - - - A V
SEQ_330  L K P L S I F I Y S E S L R K I N D D L Y I F V A K I K D L - - - - - K K
SEQ_331  - - - - - - - - - - - - - - - M N D A - V Y A L G R S S R N - - - - - G T
SEQ_332  L R L Y G L H L I V G S I R E L P D G G A I F A A R Q G S E - - - - - R R
SEQ_333  L E E N G F K V Y P D S L R K L G E N I Y I F V V K R Q N E - - - - - K M
SEQ_334  - - - - - - - - - - - - - - - - - - - - - - - - - - - - - - - - - - - - -
SEQ_335  - - - - - - - - - - - - - - - - - - - - - - - - - - - - - - - - - - - - -
SEQ_336  - - - - M L H V Y L G K I P R P G F G - - - - - - - - - - - - - - - - - -
```

FIG. 17 CONTINUED

```
AS MUT
S/E MUT
L/C ONLY
L/C MUT

RESNUM

SEQ_337 T D L I R Q Q V Y P A S L E P T S E G - V F F L A R D G R E - - - - - K R
SEQ_338 L K P F S I F V Y P Q S L R K I N E E L Y I F V A K I N N T - - - - - K N
SEQ_339 L L K N S F L L Y P D S F R R L R E D V Y I F V A K K D S D - - - - - K K
SEQ_340 L L N H S F V L Y P N S L R K L K E D T Y I F V A K K D A D - - - - - K K
SEQ_341 L L N H S F V L Y P N S L R K L K E D T Y I F V A K K D A D - - - - - K K
SEQ_342 L E E N G F K V Y P D S L R K L G E N I Y I F V V K R Q N E - - - - - K M
SEQ_343 L E E N G F K V Y P D S L R K L G E N I Y I F V V K R Q N E - - - - - K M
SEQ_344 L E E N G F K V Y P D S L M K L G E N I Y I F V V K R Q N E - - - - - K M
SEQ_345 L E E N G F K V Y P D S L R K L G E N I Y I F V V K R Q N E - - - - - K M
SEQ_346 L K E S G F Q I Y P D S L R K L G E N T Y I F V V K K Q K E - - - - - K M
SEQ_347 - - - - - - - - - - - - - - - - - - - - - - - - - - - - - - - - - - - - -
SEQ_348 L K E N G F K I Y P D S L R K L G E S T Y I F V V K K Q K E - - - - - K M
SEQ_349 - - - - - - - - - - - - - - - - - - - - - - - - - - - - - - - - - - - - -
SEQ_350 - - - - - - - - - - - - - - - - - - - - - - - - - - - - - - - - - - - - -
SEQ_351 - - - - - - - - - - - - - - - - - - - - - - - - - - - - - - - - - - - - -
SEQ_352 H F G R G Y E V Y E K S Y R E K D S L - S F F L T K E E E G - - - - - K I
SEQ_353 L S G E G F Y F Y E K S F R K L S E D I Y I F V V K K A N E - - - - - K S
SEQ_354 I Y G N R Y K V Y E K S L K R K E K E - F F F V I K D F Q R - - - - - K Y
SEQ_355 S E F G D Y N I Y S E S I Y R A G G C - V L F L A K D M G Q - - - - - K L
SEQ_356 E Y A E D Y R I Y P R S I I K K D K S - F Y F L A K I D Q K - - - - - K K
SEQ_357 E Y A E D Y R I Y P R S I I K K D K S - F Y F L A K I D Q K - - - - - K K
SEQ_358 E Y A E D Y R I Y P R S I I K K E K S - F Y F L A K I D Q K - - - - - K K
SEQ_359 T S T E E V T V Y T P S F E E H A G S - Q V V M V K S G T E - - - - - K M
SEQ_360 L S R E G F H F Y E K S F R K F S E D I Y I F V V K K A N E - - - - - K S
SEQ_361 - - - - - - - - - - - - - - - - - - - - - - - - - - - - - - - - - - - - -
SEQ_362 L S R E G F Y F Y E K S F R K F S E D I Y I F V V K K A N E - - - - - K S
SEQ_363 L S R E G F Y F Y E K S F R K F S E D I Y I F V V K K A N E - - - - - K S
SEQ_364 L S R H S F V L Y P N S V R N L A E D I Y V F V A K G N A D - - - - - K K
SEQ_365 L L K N S F L L Y P D S F R R L K E D V Y I F V A K K D S D - - - - - K K
SEQ_366 E S L S D A G V Y V P S V Q V D R R N - V Y F I Y H T K D E K D H T V K T
SEQ_367 - - - - - - - - - - - - - - - - - - - - - - - - - - - - - - - - - - - - -
SEQ_368 - - - - - - - - - - - - - - - - - - - - - - - - - - - - - - - - - - - - -
SEQ_369 - - - - - - - - - - - - - - - - - - - - - - - - - - - - - - - - - - - - -
SEQ_370 - - - - - - - - - - - - - - - - - - - - - - - - - - - - - - - - - - - - -
SEQ_371 - - - - - - - - - - - - - - - - - - - - - - - - - - - - - - - - - - - - -
SEQ_372 - - - - - - - - - - - - - - - - - - - - - - - - - - - - - - - - - - - - -
SEQ_373 - - M L D T P R Y L G K L P H L S V G - - - - - - - - - - - - - - - - - -
```

FIG. 17 CONTINUED

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| AS MUT | | | | | | | | | | | | | | | | | | | | | | | | | | | | | | | | | | | | | |
| S/E MUT | | | | | | | | | | | | | | | | | | | | | | | | | | | | | | | | | | | | | |
| L/C ONLY | | | | | | | | | | | | | | | | | | | | | | | | | | | | | | | | | | | | | |
| L/C MUT | | | | | | | | | | | | | | | | | | | | | | | | | | | | | | | | | | | | | |

RESNUM

```
SEQ_6   - - - - - - - - - - - - - - - - - - - - - - - - - - - - - - - - - - - - -
SEQ_1   - - - - - - - - - - - - - - - - - - - - - - - - - - - - - - - - - - - - -
SEQ_2   - - - - - - - - - - - - - - - - - - - - - - - - - - - - - - - - - - - - -
SEQ_3   - - - - - - - - - - - - - - - - - - - - - - - - - - - - - - - - - - - - -
SEQ_4   - - - - - - - - - - - - - - - - - - - - - - - - - - - - - - - - - - - - -
SEQ_5   - - - - - - - - - - - - - - - - - - - - - - - - - - - - - - - - - - - - -
SEQ_7   - - - - - - - - - - M S T L R H I I L - - - - - - - - - - - - - - - - - -
SEQ_8   Q A L L T V P F D R V A T H A R G F V G - - - - - - - - - - - - - - - - -
SEQ_9   - - M T D E D F E P I C E I S E Q F R N - - - - - - - - - - - - - - - Y C
SEQ_10  - - - - - - - - - - - - - - - - - - - - - - - - - - - - - - - - - - - - -
SEQ_11  - - - - - - - - - - - - - - - - - - - - - - - - - - - - - - - - - - - - -
SEQ_12  - - - - - - - - - - - - - - - - - - - - - - - - - - - - - - - - - - - - -
SEQ_13  - - - - - - - - - - - - - - - - - - - - - - - - - - - - - - - - - - - - -
SEQ_14  - - - - - - - - - - - - - - - - - - - - - - - - - - - - - - - - - - - - -
SEQ_15  - - - - - - - - - - - - - - - - - - - - - - - - - - - - - - - - - - - - -
SEQ_16  - - - - - - - - - - - - - - - - - - - - - - - - - - - - - - - - - - - - -
SEQ_17  - - - - - - - - - - - - - - - - - - - - - - - - - - - - - - - - - - - - -
SEQ_18  - - - - - - - - - - - - - - - - - - - - - - - - - - - - - - - - - - - - -
SEQ_19  Q A L L T V P F D R V A T H A R G F V G - - - - - - - - - - - - - - - - -
SEQ_20  H V L L A P S F E Q L A D H R H G F V G - - - - - - - - - - - - - - - - -
SEQ_21  - - - - - - - - - - M A K I P - I Q S A - - - - - - - - - - - - - - - - -
SEQ_22  - - - - - - - - - - M K K I S - I F E I - - - - - - - - - - - - - - - - -
SEQ_23  - - - - - - - - - - - - - - - - - - - - - - - - - - - - - - - - - - - - -
SEQ_321 L F V V G - - K K G I C Q L F D G Q K - - - - - - I G Q I G S N D V L M C
SEQ_322 L I V I G - - K K G I C E L F E G Q K - - - - - - I G E I D R Q D V V L C
SEQ_323 L I S I A - - K K R I C E K F E G K K - - - - - - I G R I N D L D I L M C
SEQ_324 L G I L S - - E A - - - - G L H D F E G V R H Q L S L D G R T L I F Q S C
SEQ_325 I L A Q G - - S G P - - - L F Q E L E G E A Y - - - - - D - - - D Y K V C
SEQ_326 L F V I S - - A G K E N G L L N E F E G E L I - - - D A G K D V T V K K C
SEQ_327 I L A T G - - E G A - - - I F D E L T G T D V - - - - D G - - - K G K A C
SEQ_328 L V V V G - - E D S - - - R L Q E L K G N Q T - - - - E E N G L K V K V C
SEQ_329 L A P P E - - H P - - - - A L T R F R G E V Q - - - H V G D H R - L L R A
SEQ_330 I G I V K - - Q N Q I L Y F S S P Y F S E D K K - - I E G T N F L V N L Y
SEQ_331 L Q L I V - - R G - - - - N S T G F H G E Q Q - - - - - G - - - D A L I C
SEQ_332 I G W I G - - E T S P F P A P D P R M S M R - - - - - - V Q E H L V W I H
SEQ_333 V G I L S - - S S D - V K L N G A Y F S E D K N - - V S D - K L R L N I Y
SEQ_334 - - - - - - - - - - - - - - - - - - - - - - - - - - - - - - - - - - - - -
SEQ_335 - - - - - - - - - - - - - - - - - - - - - - - - - - - - - - - - - - - - -
SEQ_336 - I R I P - - E V V A P P L L S A F K S L G M - - - - - T - G S L M - - -
```

FIG. 17 CONTINUED

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| AS MUT | | | | | | | | | | | | | | | | | | | | | | | | | | | | | | | | | | | | | |
| S/E MUT | | | | | | | | | | | | | | | | | | | | | | | | | | | | | | | | | | | | | |
| L/C ONLY | | | | | | | | | | | | | | | | | | | | | | | | | | | | | | | | | | | | | |
| L/C MUT | | | | | | | | | | | | | | | | | | | | | | | | | | | | | | | | | | | | | |

RESNUM

SEQ_337 L G I L S - - E A - - - - G L H D F E G A R H Q L S L D G R T L I F Q S C
SEQ_338 I G I I K - - Q N Q S I Y F S N P Y F S E D K K - - I E K T G F S V N I Y
SEQ_339 I G L L T - - N G N - F K L S S P H F A E D K Y - - V E E L G F Y I N L Y
SEQ_340 I G I L T - - K E N - F K L T S P Y F V E D K N - - V K E I D F Y L N L Y
SEQ_341 I G I L T - - K E N - F K L S S P Y F V E D K N - - V K E I D F Y L N L Y
SEQ_342 V G I L S - - S S D - V K L N G A Y F S E D K N - - V S D - K L R L N I Y
SEQ_343 V G I L S - - S S D - V K L N G A Y F S E D K N - - V S D - K L R L N I Y
SEQ_344 V G I L S - - S S D - V K L N G A Y F S E D K N - - V S D - K L R L N I Y
SEQ_345 V G I L S - - S S D - V K L N G A Y F S E D K N - - V S D - K L R L N I Y
SEQ_346 I G I L S - - N D E - L K L K E P Y F S E N K K - - I S D - N L Q F N V Y
SEQ_347 - - - - - - - - - - - - - - - - - - - - - - - - - - - - - - - - - - - - -
SEQ_348 I G I L S - - N D E - L N L K E P Y F S E N K K - - I S D - N L Q F N V Y
SEQ_349 - - - - - - - - - - - - - - - - - - - - - - - - - - - - - - - - - - - - -
SEQ_350 - - - - - - - - - - - - - - - - - - - - - - - - - - - - - - - - - - - - -
SEQ_351 - - - - - - - - - - - - - - - - - - - - - - - - - - - - - - - - - - - - -
SEQ_352 L V V A G - - E K A P E G L - S F F K - - - - - - K Q R A E G V S F F F C
SEQ_353 I G L L T - - Q G D - F T L S S P H F T E R K Y - - L K E T G Y Y L N L Y
SEQ_354 L V A A G - - P S Y R I R K R D F Q P D E E G - V A D N E G E F L F Q I C
SEQ_355 L V V V E E E T G S - - - A F D R F V G P Q V - - - Y H P S G K R V K E A
SEQ_356 L V I L N - - K S K - - - N F E L F Q G R I E - - - - E L A G F K A K I G
SEQ_357 L V I L N - - K S K - - - N F E L F Q G R I E - - - - E L A G F K A K I G
SEQ_358 L V I L N - - K S K - - - N F D I F Q G K T E - - - - K L A G F K A K I A
SEQ_359 I V A A G - - A G E - - - L F E A L S G E D I - - - - - G - - - K G K V C
SEQ_360 I G L L T - - Q R D - F T L S S P Y F T E R K Y - - L K E I G Y Y L N L Y
SEQ_361 - - - - - - - - - - - - - - - - - - - - - - - - - - - - - - - - - - - - -
SEQ_362 I G L L T - - Q G D - F T L S S P Y F T E R K Y - - L K E I G Y Y L N L Y
SEQ_363 I G L L T - - Q G D - F T L S S P Y F T E R K Y - - L K E I G Y Y L N L Y
SEQ_364 V G I L S - - K G K A L G F K A P F F A E D I K - - V E A T G F S F N L Y
SEQ_365 I G F L T - - N G N - F K L S S P H F L E D K Y - - V E E L G F Y L N L Y
SEQ_366 L V V Y E - - E N P - - - T I G D F D A L E T - - - L K G E N S T L I T A
SEQ_367 - - - - - - - - - - - - - - - - - - - - - - - - - - - - - - - - - - - - -
SEQ_368 - - - - - - - - - - - - - - - - - - - - - - - - - - - - - - - - - - - - -
SEQ_369 - - - - - - - - - - - - - - - - - - - - - - - - - - - - - - - - - - - - -
SEQ_370 - - - - - - - - - - - - - - - - - - - - - - - - - - - - - - - - - - - - -
SEQ_371 - - - - - - - - - - - - - - - - - - - - - - - - - - - - - - - - - - - - -
SEQ_372 - - - - - - - - - - - - - - - - - - - - - - - - - - - - - - - - - - - - -
SEQ_373 - V R L P - - E V F L E G I M S G F K T G N S - - - - - A - G G V M - - -

FIG. 17 CONTINUED

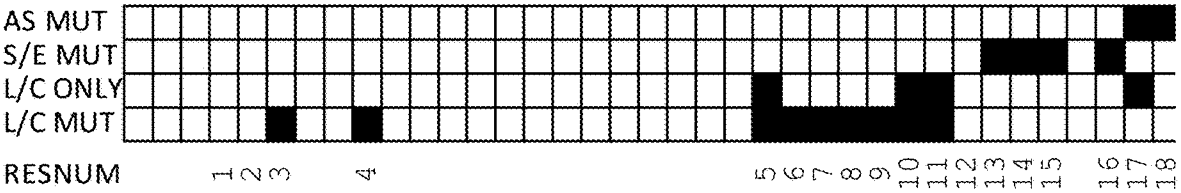

```
SEQ_6   ---MWL--S-------------KDYLRKKGVYS-ICS
SEQ_1   -----M--SLHPLNKLIE-R--HKKGTPVGIYS-VCS
SEQ_2   --MMFG--SPAPLLDMVT-A--QKQGMARGIPS-ICS
SEQ_3   ----MA--KEHPLKELVN-K--QKSGISEGIVS-ICS
SEQ_4   ----MN--TEHPLKNVVK-L--QKKGIPIGIYS-VCS
SEQ_5   ----MS--PQNPLIGLFK-N---REKEFKGIIS-VCS
SEQ_7   ------------RL-IEL-R--EREQIHLTLLA-VCP
SEQ_8   ------------WVAELL-Q--GPLAYQHTLLA-VCP
SEQ_9   NQMLESEYDPKPSKYIFN-I---LQNQKTIVMA-ANP
SEQ_10  ----MN--TEHPLKNVVK-L--QKKGIPIGIYS-VCS
SEQ_11  -----M--QRNYLLDIVE-A--QNNGIHKGIYS-ACS
SEQ_12  -----M--KKHPLQDIVS-L--QKQGIPKGVFS-VCS
SEQ_13  -----M--NHNPLKKIVE-L--QKQGKNVGIYS-VCS
SEQ_14  -MLLKV--KEHPIRELVN-R--YKNGENVGIFS-VCT
SEQ_15  --------MYPVLENILR-A--QQQGEALGIPS-ICS
SEQ_16  ---MER--KVKHLTHMVE-Q--HKRGNANGIYA-VCS
SEQ_17  ---MWL--D-------------SNFLKNRGIFS-ICS
SEQ_18  ---MWL--S-------------KDYLRKKGVYS-ICS
SEQ_19  ------------WVAELL-L--GPLAHQHTLLA-VCP
SEQ_20  ------------WLVDLL-R--GPLAYRHTLLA-VCP
SEQ_21  ------------VKALLE-L--QDEGKGGTLLG-IGP
SEQ_22  ------------VKASLN-M--KGK-DKATLLG-IGP
SEQ_23  --MTDTNYKAKPGSLLFE-S---LMDKETIILA-INP
SEQ_321 KKT-HE--NLLALRK-IINLNPTTINK-KASFG-FGD
SEQ_322 AKN-DR--NCQSLMSLFPSLKPQICNA-KLSFG-FGD
SEQ_323 PTN-DY--NCKVIRT-LFNINPSVCKK-NTSFG-FGD
SEQ_324 PLT-AA--NARALRRHIPWTAPRPLGL-RASVG-CGD
SEQ_325 NCS-HL--NRVVLNKYLPYTKPSAFGKEIATIG-LGD
SEQ_326 NLS-TK--NRKAVQKIFPHTAPIVLGL-CNSFG-CGD
SEQ_327 PLT-YE--NRLVLNKYFDYTVPQAFGTEIATIG-LGD
SEQ_328 PLS-NE--NCYVIRKIFPYTNPQPHKGKNITIG-LGD
SEQ_329 ERR-AE--NAAALRALLPDLQPRPLGL-VTSAG-FGD
SEQ_330 PLN-FE--NYQKLKEIIP-ISPKVCDK-KISFG-TGD
SEQ_331 PLD-AE--NARTLQERLPWLRPQPLGN-RLSFG-FGD
SEQ_332 PWT-WA--HYRILRERLPALSPTRCDR-PASFG-AGD
SEQ_333 PFT-FE--NYVTLNGKFH-IGPTVCRG-NSSFG-TGD
SEQ_334 --------------------MFTILPKKGISLG-LGD
SEQ_335 ------------------MATPGSLSFPRYSIG-TGD
SEQ_336 -LS-FN---RETAPAEYIESSDP-RL---FYFGHTGT
```

FIG. 17 CONTINUED

AS MUT
S/E MUT
L/C ONLY
L/C MUT

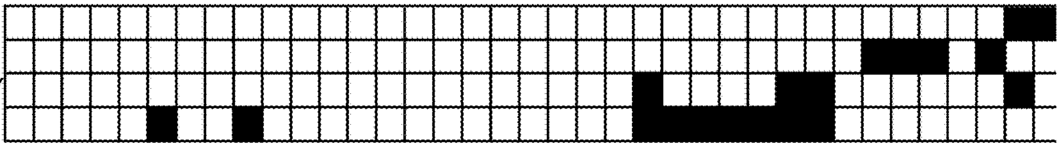

```
RESNUM      1 2 3     4                             5 6 7 8 9 10 11 12 13 14 15   16 17 18
SEQ_337 P L T - A A - - N A R A L R Q H L A W T A P R P L G L - R A S V G - C G D
SEQ_338 P L N - F E - - N Y Q K L K E I I P - I N P K T C N K - K I S F G - T G D
SEQ_339 P L T - Y E - - N Y L I L K D N F G - I S P V T C K E - K A S F G - T G D
SEQ_340 P L S - F E - - N Y L I L K - N F G - I S P T P C R Q - K S S F G - T G D
SEQ_341 P L S - F E - - N Y L I L K - N F G - I S P T P C R Q - K S S F G - T G D
SEQ_342 P F T - F E - - N Y V T L N G K F H - I G P T V C R G - N S S F G - T G D
SEQ_343 P F T - F E - - N Y V T L N G K F H - I G P T V C R G - N S S F G - T G D
SEQ_344 P F T - F E - - N Y V T L N G K F H - I G P T V C R G - N S S F G - T G D
SEQ_345 P F T - F E - - N Y V T L N G K F H - I G P T V C R G - N S S F G - T G D
SEQ_346 S F T - F D - - N Y V T L N G R F H - I G P T I C R E - N A S F G - T G D
SEQ_347 - - - - - - - - - - - - - - - - - - - - M L T I L P N K G I S L G - L G D
SEQ_348 P F T - F D - - N Y V T L N G R F H - I G P T V C R E - N A S F G - T G D
SEQ_349 - - - - - - - - - - - - - - - - - - - - M F T I L P K R G I S L G - L G D
SEQ_350 - - - - - - - - - - - - - - - - - - M T T P G S L S L P R Y S I G - T G D
SEQ_351 - - - - - - - - - - - - - - - - - - - - - - - - - - - - - - - - - - - - -
SEQ_352 E R N - H E - - N L E V L R K Y F P D L K P V R A G L - R A S F G - T G D
SEQ_353 P L T - Y E - - N F V I L K D K F N - I A P A P C D K - K A S F G - M G D
SEQ_354 R L T - H H - - N L T Q L Q S I F N Y L Q P S T T K M - K P S F G - T G D
SEQ_355 P L Q - P V - - N A G I V R E L L P F T A P V A L G A T G L S L G - L G D
SEQ_356 P L S - H Y - - N A E I L R E V F P F T A P S A L G N K K P S I G - L G D
SEQ_357 P L S - H Y - - N A E I L R K V F P F T A P S A L G N K K P S I G - L G D
SEQ_358 P L S - H Y - - N A E I I R E V F P F T A P S K I G N Q T A S I G - L G D
SEQ_359 P L T - H E - - N R L V L N Q F F S Y T A P Q A F G T D I A T M G - L G D
SEQ_360 P L T - Y E - - N F V I L K D K F S - I A P S P C N K - K V S F G - M G D
SEQ_361 - - - - - - - - - - - - - - - M L P Y L V A R P L G L - R K S A G - C G D
SEQ_362 P L T - Y E - - N F V I L K D K F S - I A P S P C N K - K V S F G - M G D
SEQ_363 P L T - Y E - - N F V I L K D K F S - I A P S P C N K - K V S F G - M G D
SEQ_364 P L S - F E - - N Y L I L R D E F G - I A L V P C K N - K A S F G - T G D
SEQ_365 P L T - Y E - - N Y L I L K D N F G - I S P V T C K E - K T S F G - T G D
SEQ_366 A L T - D H - - N N Q A L A K R F P W I K P T S R R N Y K Y T F G - L G D
SEQ_367 - - - - - - - - - - - - - - - - - - - - M F T I L P K K G I S L G - L G D
SEQ_368 - - - - - - - - - - - - - - - - - - - - M F S K L P K Q G I S L G - L G D
SEQ_369 - - - - - - - - - - - - - - - - - - - - M F T I L P K K G I S L G - L G D
SEQ_370 - - - - - - - - - - - - - - - - - - - - M F T I L P K K G I S I G - L G D
SEQ_371 - - - - - - - - - - - - - - - - - - - - - - - M K K L A K Y S F G - M G D
SEQ_372 - - - - - - - - - - - - - - - - - - - - - - - M K Q L E R F S M G - I G D
SEQ_373 - L S - Y H - - - R E T A P E Y V I N A P P G D F E - - - L T R G H T G T
```

FIG. 17 CONTINUED

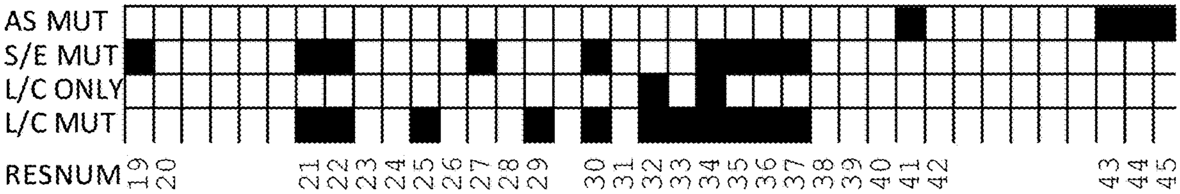

```
SEQ_6   S N - - - - S Y V I E A S I E - F A K E K G D Y I L I E A - - - - - T P H
SEQ_1   A N - - - - P F V L K A A M L - Q A Q K D Q S L L L I E A - - - - - T S N
SEQ_2   A H - - - - P V V L S A A C H - L A R R S G A P L L I E T - - - - - T C N
SEQ_3   S N - - - - E F V I E A S M E - R A L T N G D Y V L I E S - - - - - T A N
SEQ_4   A N - - - - E I V I Q V A M E - K A L S M D S Y V L I E A - - - - - T A N
SEQ_5   S N - - - - E I V L E A V L K - R M K D T N L P I I I E A - - - - - T A N
SEQ_7   N S - - - - A A V L E A A V K - V A A R C H T P M L F A A - - - - - T L N
SEQ_8   N S - - - - E A V T R A A L E - A A A E A N A P L L F A A - - - - - T L N
SEQ_9   R I - - - - G L V T R G I L R - A A K D A D A P I I L E L - - - - - A R S
SEQ_10  A N - - - - E I V I Q V A M E - K A L S M D S Y V L I E A - - - - - T A N
SEQ_11  A N - - - - E Y V I E A A M E - R A K N T N E Y V L I E A - - - - - T A N
SEQ_12  A N - - - - R F V I E T T L E - Y A K M K G T T V L I E A - - - - - T C N
SEQ_13  A N - - - - G Y V I E A A L K - R G K S D G S C V L I E S - - - - - T A N
SEQ_14  S N - - - - E Y V I E A A M E - R V I D K D L D L L I E S - - - - - T A N
SEQ_15  A H - - - - P F V L E A T F R - H A L T T G R T V L I E S - - - - - T C N
SEQ_16  A H - - - - P L V L E A A I R - Y A Q S H Q T P L L I E A - - - - - T S N
SEQ_17  S N - - - - E N V L D A S I E - F A K E K E D F L L I E A - - - - - T C H
SEQ_18  S N - - - - P Y V I E A S V E - F A K E K N D Y I L I E A - - - - - T P H
SEQ_19  N S - - - - E A V T R A A L E - A A A E V N A P L L F A A - - - - - T L N
SEQ_20  N S - - - - E A V T R A A L E - A A R E A N A P L F F A A - - - - - T L N
SEQ_21  M S - - - - T N V L Q A S F E - L A R D Y D F P L M F I A - - - - - S R N
SEQ_22  M S - - - - K T L I K A S M I - L A K E K D F P L M F I A - - - - - S R N
SEQ_23  R I - - - - S L L N K G I L K - A A K D M D A P I I L E L - - - - - A K S
SEQ_321 R I G L A T P A H A K V A K D - - - - - - - - F E V - - - - - - - F P I F A Q
SEQ_322 R L G V A T A A H A Q C V Q K - - - - - - - - E K L - - - - - - - F P I F A Q
SEQ_323 R L G L A T P A H T T L I N K - - - - - - - - Y D V - - - - - - - F P V L A Q
SEQ_324 R L G L A T P G H V R A V R K - - - - - - - - H K L - - - - - - - A P V F A Q
SEQ_325 R L G I A S P G H I Q A V K G - - - - - - - - R E I - - - - - - - R P I L A Q
SEQ_326 R L G V A N A G H I R A I K Q - - - - - - - - S N F - - - - - - - R P I L A Q
SEQ_327 R L G L A S P G H I E T V R E - - - - - - - - K N I - - - - - - - K P V L A Q
SEQ_328 R L G L A S P G H I R L I R D - - - - - - - - L D V - - - - - - - F P V L A Q
SEQ_329 R L G V A T P G H V R A A Q R - - - - - Y G A G V - - - - - - - A P V F A Q
SEQ_330 R L G L I T S A Q L S A L K E - - - - - - - - Y D L - - - - - - - F P I L A Q
SEQ_331 R I G L A T P G H V D A L R S - - - A D P T G R I - - - - - - - A P I F A Q
SEQ_332 R L G M A T A A Q I A A L E R - - - - - - - - Y P V - - - - - - - F P V L A Q
SEQ_333 R L G L V T A A Q L T A L K K - - - - - - - - Y D V - - - - - - - F P I L A Q
SEQ_334 R I G I A T P G H I K V A K K - - - - - - - - Y N F - - - - - - - F P V F A Q
SEQ_335 R F G H E A E A Q L R A V I E - - A G R L G R A L - - - - - - - G I V W - N
SEQ_336 S I - - - - G G F I R S V K E - Y S K A L S V P V E V E A D H V S I L - G
```

FIG. 17 CONTINUED

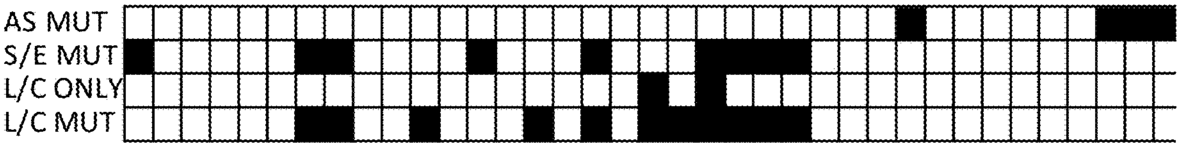

```
RESNUM   19 20 21 22 23 24 25 26 27 28 29 30 31 32 33 34 35 36 37 38 39 40 41 42 43 44 45

SEQ_337 R L G L A T P G H V R A V R K - - - - - - - H K L - - - - - - A P V F A Q
SEQ_338 R L G L V T S A Q L S V L K D - - - - - - - Y N L - - - - - - F P I L A Q
SEQ_339 R L G L A T P A H I K A L K N - - - - - - - Y N V - - - - - - F P V L A Q
SEQ_340 R L G L V T P A H I V A L K E - - - - - - - Y P V - - - - - - F P V L A Q
SEQ_341 R L G L V T P A H I V A L K E - - - - - - - Y P V - - - - - - F P V L V Q
SEQ_342 R L G L V T A A Q L T A L K K - - - - - - - Y D V - - - - - - F P I L A Q
SEQ_343 R L G L V T A A Q L T A L K K - - - - - - - Y D V - - - - - - F P I L A Q
SEQ_344 R L G L V T A A Q L T A L K K - - - - - - - Y D V - - - - - - F P I L A Q
SEQ_345 R L G L V T A A Q L T A L K K - - - - - - - Y D V - - - - - - F P I L A Q
SEQ_346 R L G L A T A A Q L D A L K K - - - - - - - F N V - - - - - - F P I L A Q
SEQ_347 R I G I A T H G H I K V A K K - - - - - - - Y N F - - - - - - F P V F A Q
SEQ_348 R L G M A T A A Q L G A L K K - - - - - - - F D V - - - - - - F P V L A Q
SEQ_349 R I G I A T T G H I K V A K K - - - - - - - Y N F - - - - - - F P V F A Q
SEQ_350 R F G H E A E A Q L R A V I E - - A E R L G M A L - - - - - - G I V W - N
SEQ_351 - - - - - - - - - - - - - - - - - - - - - - - - - - - - - - - - - - - - -
SEQ_352 R L G I T T P A H V R A L K D - - - - - - - S G L - - - - - - F P I F A Q
SEQ_353 R L G L V T A A H I R A V E N - - - - - - - Y D V - - - - - - F P V L A Q
SEQ_354 R L G I A T P A H I Q A F E D - - - - - - - K N I - - - - - - F P I L A Q
SEQ_355 R L G V A S P G H L R L I K K - - - - - - - T G V - - - - - - R P V L A Q
SEQ_356 R L G I A T P G H I E A V K E - - - - - - - S A A - - - - - - M P V F A Q
SEQ_357 R L G I A T P G H I E A V K E - - - - - - - S A A - - - - - - M P V F A Q
SEQ_358 R L G I A T P G H I E A V K K - - - - - - - S N A - - - - - - M P V F A Q
SEQ_359 R L G I A S P G H I D T V K E - - - - - - - R N V - - - - - - K P I L A Q
SEQ_360 R L G L V T A A H I R A V Q N - - - - - - - Y D V - - - - - - F P V L A Q
SEQ_361 R L G L A T P G H I R A L R A T F G R D E D A A M - - - - - - A P I F A Q
SEQ_362 R L G L V T A A H I R A V E N - - - - - - - Y D V - - - - - - F P V L A Q
SEQ_363 R L G L V T A A H I R A V E N - - - - - - - Y D V - - - - - - F P V L A Q
SEQ_364 R L G L A T P A H L D A F K S - - - - - - - Y N M - - - - - - F P V L A Q
SEQ_365 R L G L V T P A H I K V L K N - - - - - - - Y D I - - - - - - F P V L A Q
SEQ_366 R L G N A S N A H L R L F K G - - - - - - - T G I - - - - - - M P V L A Q
SEQ_367 R I G I A T T G H I K V A K K - - - - - - - Y N F - - - - - - F P V F A Q
SEQ_368 R V G L A T P G H I K V A K R - - - - - - - H E F - - - - - - F P V F A Q
SEQ_369 R I G I A T P G H I K V A K K - - - - - - - Y N F - - - - - - F P V F A Q
SEQ_370 R I G I A T P G H I K V A K K - - - - - - - Y N F - - - - - - F P V F A Q
SEQ_371 R F A H Q A S W Q L K A I T E - - I E K Q G I E V - - - - - - T P V W - N
SEQ_372 R F G H Q G K A Q L E A L A E - - A K H L G C T I - - - - - - I P V W - N
SEQ_373 S I - - - - R H Y I E A S V A - K A K E K G V V V E V E A D H V S V S - V
```

FIG. 17 CONTINUED

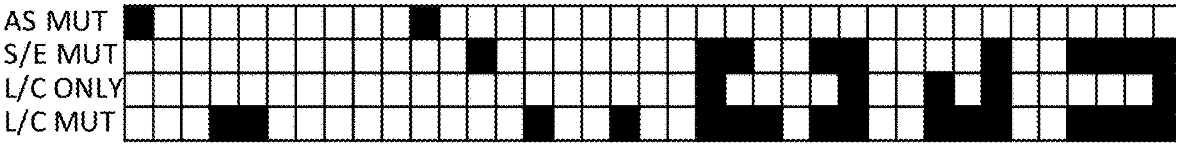

```
RESNUM   46 47 48 49 50  51 52 53  54 55 56 57 58 59 60 61 62 63 64 65 66 67 68 69 70 71 72 73 74 75 76 77 78

SEQ_6    Q V N Q F - - - G G Y - S G M T P E D F K N F V M K I A K E K G L E E D K
SEQ_1    Q V D Q F - - - G G Y - T G M R P E D F K T M T L E L A A E N N Y D P Q G
SEQ_2    Q V N H Q - - - G G Y - S G M T P A D F V R F L R E I L E R E G I P P Q Q
SEQ_3    Q V N Q Y - - - G G Y - I G M T P I E F K K F V F S I A K K V D F P L D K
SEQ_4    Q V N Q Y - - - G G Y - T N M K P I D F R D F V Y S I A K R I N F P E N R
SEQ_5    Q V N Q F - - - G G Y - S G L T P S Q F K E R V I K I A Q K V D F P L E R
SEQ_7    Q V D R D - - - G G Y - T G W T P A Q F V A E M R R Y A V R Y G C T T - P
SEQ_8    Q V D L D - - - G G Y - T G W T P A T L A R F V A D E L A R L D L H I - P
SEQ_9    E C N L E - - - N G Y - T G L Y P S D F S E Q C Y Q A A K D V G Y D I - -
SEQ_10   Q V N Q Y - - - G G Y - T N M K P I D F R D F V Y S I A K R I N F P E N R
SEQ_11   Q V N Q Y - - - G G Y - T G M K P I D F K N F V Y D I A D K I N F D K D K
SEQ_12   Q V N Q F - - - G G Y - T G M T P A D F R E M V F S I A E D I G L P K N K
SEQ_13   Q C D Q N - - - G G Y - T G M T P L D F K N F V L G I A D K V G F D P K R
SEQ_14   Q V N Q D - - - G G Y - T G M Q P K D F V N Y V Y K I A D K V N F P K D R
SEQ_15   Q V N Q H - - - G G Y - T G M T P G D F V A Y V A A L A D R L H F P R E R
SEQ_16   Q V D Q F - - - G G Y - T G M T P E D F Y G F V C C L A E S L D F P T S Q
SEQ_17   Q V N Q F - - - G G Y - T K M T P E S F S K K I F K K A E E M N F N P E R
SEQ_18   Q I N Q F - - - G G Y - S G M T P E D F K N F V M G I I K E K G I E E D R
SEQ_19   Q V D L D - - - G G Y - T G W T P A T L A R F V A D E L A R L D L H I - P
SEQ_20   Q V D L D - - - G G Y - T G W T P A T L A R F V A D E R I R L G L R A - P
SEQ_21   Q V D L D E L G G G Y V N G W N Q Y T F V Q A I R E M A E L T G F D G - L
SEQ_22   Q V D L K E L G G G Y V C N W D Q K S F A S D I K K I A E E V G F N G - L
SEQ_23   E C N L E - - - G G Y - T G F T P S E F S K R A Y E S A E E I G I D I - -
SEQ_321  Q S V R E - - - L S R - T G R T Y K D V L D D A V W G V F E S G Y N F - E
SEQ_322  Q S V R E - - - I S R - T E R N W L D V L H S A V W G V F E S G Y D G - P
SEQ_323  Q S V R E - - - L S R - T H R N F K D V L D S A I W G I F E S G Y E G - E
SEQ_324  Q S I R E - - - M T R - T G R T P Q Q V L D E A M W G V F Q E G W R Q - G
SEQ_325  Q S I R E - - - L N L - T N R T Y R N V L D A A C F A V F Q E G Y K D - G
SEQ_326  Q S I R E - - - L T R - T N R T P D D V M D A A V W A V L Q E G Y K D - G
SEQ_327  Q S I R E - - - L T L - T N R S M N D M L D A A A F A V F Q E G Y K G - G
SEQ_328  Q S I R E - - - L N L - T G R T Y E D V I S A A A W A V F Q E G Y T K - G
SEQ_329  Q S I R E - - - M T R - T G R T P Q E V L D D A T W G A F A A G W R G - A
SEQ_330  Q S P R E - - - L I K - T K R D F K D V L L K S A M G V L E T G Y T G - K
SEQ_331  Q S V R E - - - N Q R - L N R T P Q E V M T A A V W S L F A E N W R L - P
SEQ_332  Q S P R E - - - L A R - T G R D F R S V L L D A A W G V F A S G F A G - P
SEQ_333  Q S P R E - - - L I K - T N R D F K D V L L K V V L G V L E T G Y I G - H
SEQ_334  Q S I R E - - - L N F - T G R T F T D V R K D V L N A L V E E N Y V G - N
SEQ_335  K S Y R E - - - H T I - I G S R P E D V R R M A D R A V S S L G W E G - P
SEQ_336  S V E R A - - - L K K - I A G V P V E E - - - - P L S E E E V S W S I - G
```

FIG. 17 CONTINUED

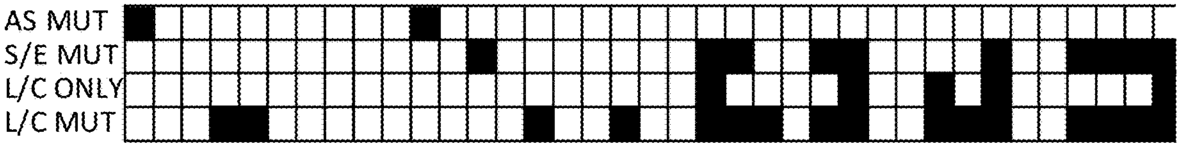

```
RESNUM   46 47 48 49 50  51 52 53  54 55 56 57 58 59 60 61 62 63 64 65 66 67 68 69 70 71 72 73 74 75 76 77 78
SEQ_337 Q S I R E - - - M T R - T G R T P Q Q V L D E A M W G V F Q E G W R Q - G
SEQ_338 Q S P R E - - - L I K - T K R D F K D V L L K S V I G V L E I G Y T D - S
SEQ_339 Q S P R E - - - L V K - T H R D F K D V F L K V I L G V L E A G Y A G - G
SEQ_340 Q S P R E - - - L E K - T H R D F K D A L L K V I L G V L E A G Y T G - E
SEQ_341 Q S P R E - - - L E K - T R R D F K D A L L K V I L G V L E A G Y T G - E
SEQ_342 Q S P R E - - - L I K - T N R D F K D V L L K V V L G V L E T G Y I G - H
SEQ_343 Q S P R E - - - L I K - T N R D F K D V L L K V V L G V L E T G Y I G - H
SEQ_344 Q S P R E - - - L I K - T N R D F K D V L L K V V L G V L E T G Y I G - H
SEQ_345 Q S P R E - - - L I K - T N R D F K D V L L K V V L G V L E T G Y I G - H
SEQ_346 Q S P R E - - - L V K - T N R D F K D V L L K V V L G V L E T G Y I G - H
SEQ_347 Q S I R E - - - L N F - T G R T F S D V R K D V L N A L I E E N Y V G - N
SEQ_348 Q S P R E - - - L V K - T N R D F K D V L L K V V L G V L E T G Y I G - H
SEQ_349 Q S I R E - - - L N F - T G R T F I D V R K D A L N A L V E E N Y V G - N
SEQ_350 K S Y R E - - - H T I - I G S R P E D V R R M A D K A V S A L E W E G - P
SEQ_351 - - - - - - - - - - - - - - - - - - - - - - - - - - - - - - - - - - - - -
SEQ_352 Q S V R E - - - N E R - T G R T W R D V L D D A T W G V F Q E G Y S E - G
SEQ_353 Q S P R E - - - L M K - T H R S F K E A I L K A I L G V L E E G Y T G - K
SEQ_354 Q S V R E - - - M E R - T E S N W Q K V L D N A I W G C F E A G Y E G - K
SEQ_355 Q S V R E - - - L T L - T N R T Y S D V L D A A T W A V L Q E G Y E G - G
SEQ_356 Q S V R E - - - L N L - T G R T F K S V L D D V S W A V F Q E G Y Q A - G
SEQ_357 Q S V R E - - - L N L - T G R T F K S V L D D V S W A V F Q E G Y Q A - G
SEQ_358 Q S V K E - - - L K L - T G R S F K S V L D D V S W A V F Q E G Y Q N - G
SEQ_359 Q S I R E - - - L T L - L N R T M T D I L D A A A F A V F Q E G Y K D - G
SEQ_360 Q S P R E - - - L M K - T H R S F R E A I L K A I L G V L E E G Y T G - K
SEQ_361 Q S I R E - - - N A R - T G R T P Q E V M D D A M W G V F Q E G W R A - G
SEQ_362 Q S P R E - - - L M K - T H R S F K E A I L K A I L G V L E E G Y T G - K
SEQ_363 Q S P R E - - - L M K - T H R S F K E A I L K A I L G V L E E G Y T G - K
SEQ_364 Q S P R E - - - L E K - T H R D F R D V L L K A V L G V L E A G Y T G - E
SEQ_365 Q S P R E - - - L V K - T N R D F K D V L L K A I L G V L E A G Y A G - G
SEQ_366 Q S I R E - - - L T L - M H R T N T D V L L S A S W A V F E E G F T F - G
SEQ_367 Q S I R E - - - L N F - T G R T F T D V R K D V L N A L I E E N Y V G - N
SEQ_368 Q S I R E - - - L N F - T G R T F H D V K K D V E N A V I K E N Y E G - K
SEQ_369 Q S I R E - - - L N F - T G R T F T D V R K D V L N A L V E E N Y V G - N
SEQ_370 Q S I R E - - - L N F - T G R T F R D V R K D V L N A L V E E N Y V G - N
SEQ_371 K S N R E - - - H T T - I G S K P E D N R D A A Q K A I Q K A G W S K - P
SEQ_372 K S Y R E - - - H S I - I H T E P G Q V R K E A D W A V A A L G W Q D - P
SEQ_373 S S - E A - - - V K R - I S G G G T H R - - - - V L S E E E V R S A L - K
```

FIG. 17 CONTINUED

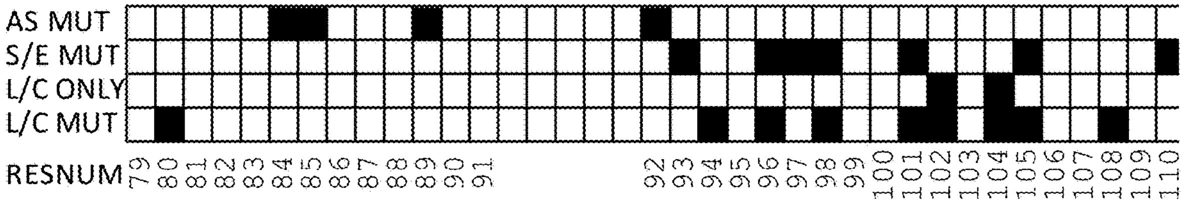

```
RESNUM   79 80 81 82 83 84 85 86 87 88 89 90 91                   92 93 94 95 96 97 98 99 100 101 102 103 104 105 106 107 108 109 110
SEQ_6    I I L G G D H L G P L P W - - - - - - Q D E P S P T A M N K A K D L I R A F
SEQ_1    L I L G G D H L G P N R W - - - - - - T K L S A S R A M D Y A R E Q I A A Y
SEQ_2    V I L G G D H L G P Y P W - - - - - - R K E P A E T A I A Q A L E M V R A Y
SEQ_3    L I L G G D H L G P L I W - - - - - - K N E S S N L A L A K A S E L I K E Y
SEQ_4    I I L G G D H L G P L P W - - - - - - K N Q Q A K K A M E E A K E L V K Q F
SEQ_5    I I L G G D H L G P F V W - - - - - - R D Q E P E I A M E Y A K Q M I K E Y
SEQ_7    L Y P C L D H G G P W L K D R H A Q E K L P L D Q A M H E V K L S L T A C
SEQ_8    V V L G L D H G G P W K K D L H A R N R L S F E E T F Q A V L R A I E A C
SEQ_9    W A L H A D H I G I K K - - - - - - - - - - - G D R E D I E K T K E L V K A Q
SEQ_10   I I L G G D H L G P L P W - - - - - - K N Q Q A K K A M E E A K E L V K Q F
SEQ_11   I I L G G D H L G P L T W - - - - - - S K E T E K E A M A K S H E L V K E Y
SEQ_12   I I L G G D H L G P N P W - - - - - - K G Q P S D Q A M R N A I E M I R E Y
SEQ_13   L F L G G D H L G P L T F - - - - - - A G M D E A Q A M E N A E E L I R H Y
SEQ_14   I I L G G D H L G P L T W - - - - - - T K L V Q E E A M E K A K V L I R D Y
SEQ_15   I L L G G D H L G P N P W - - - - - - R D R P A D Q A L N Q A R I L V Q E Y
SEQ_16   L I L G G D H L G P N R W - - - - - - Q N L P A Q Q A M A N A D D L I K S Y
SEQ_17   L L L G G D H L G P E P W - - - - - - K N E N A D T A M D K A K Q L V I E F
SEQ_18   V I L G G D H L G P L P W - - - - - - Q D E P S S S A M K K A K D L I R A F
SEQ_19   V V L G L D H G G P W K K D L H A R N R L S F A E T V Q A V L R A I E A C
SEQ_20   V V L G L D H G G P W K K D W H V R N R L P Y E A T L Q A V L R A I E A C
SEQ_21   Y Y V C R D H G G P W Q R D K E R N D H L P V E E A M A L G K K S Y L A D
SEQ_22   Y F L C R D H G G P W Q R D N E R N A H L P E N E A M E L G K K S Y L E D
SEQ_23   W S L H A D H I G I K K - - - - - - - - - - - G T D E E I E S I K K L V K A Q
SEQ_321  F G A D A D H V K - - - - - - - - - - - - - - - - - - - - - E I E D L E K A
SEQ_322  F G A D A D H V K - - - - - - - - - - - - - - - - - - - - - K I E D L E S A
SEQ_323  F G A D A D H V K - - - - - - - - - - - - - - - - - - - - - D I N D L M Q A
SEQ_324  Y G A D A D H L K - - - - - - - - - - - - - - - - - - - - - T E E D A D R C
SEQ_325  F G A D G D H L K - - - - - - - - - - - - - - - - - - - - - T E E D I Q S A
SEQ_326  F G S D A D H L K - - - - - - - - - - - - - - - - - - - - - T F E D I D L M
SEQ_327  Y G A D G D H I K - - - - - - - - - - - - - - - - - - - - - E E S D I Q Y A
SEQ_328  Y G A D G D H L K - - - - - - - - - - - - - - - - - - - - - T A E E V K M S
SEQ_329  L G A D A D H Q K - - - - - - - - - - - - - - - - - - - - - T V A D L E R C
SEQ_330  Y G A D A D H I K - - - - - - - - - - - - - - - - - - - - - D E K Y L M E A
SEQ_331  W G A D A D H V K - - - - - - - - - - - - - - - - - - - - - E P E H L A P Y
SEQ_332  F G A D A D H L Q - - - - - - - - - - - - - - - - - - - - - D D E Q L R A A
SEQ_333  F G A D A D H I K - - - - - - - - - - - - - - - - - - - - - D E Y Y L L E G
SEQ_334  S G F D G D H L K - - - - - - - - - - - - - - - - - - - - - S D E E I Q Y A
SEQ_335  Y F V D A D H I T - - - - - - - - - - - - - - - - - - - - - T K T V - D L F
SEQ_336  Y V E - - R - - - - - - - - - - - - - - - - - - - - - - - - - - - E L R E A A
```

FIG. 17 CONTINUED

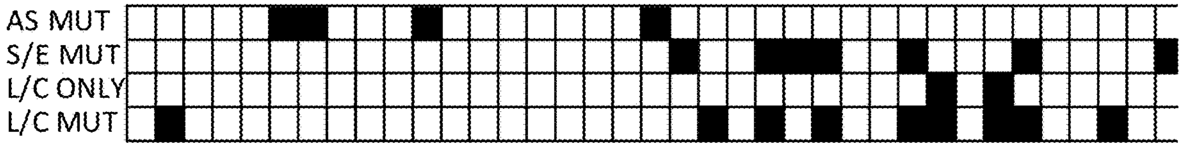

```
RESNUM   79 80 81 82 83 84 85 86 87 88 89 90 91 92 93 94 95 96 97 98 99 100 101 102 103 104 105 106 107 108 109 110
SEQ_337  YGADADHLK--------------------TEEDADRC
SEQ_338  YGADADHIK--------------------DEKYLMEA
SEQ_339  YGADADHIK--------------------DEKYLIEA
SEQ_340  FGADADHIK--------------------DEKYLLRA
SEQ_341  FGADADHIK--------------------DEKYLLRA
SEQ_342  FGADADHIK--------------------DEYYLLEG
SEQ_343  FGADADHIK--------------------DEYYLLEG
SEQ_344  FGADADHIK--------------------DEYYLLEG
SEQ_345  FGADADHIK--------------------DEYNLLEG
SEQ_346  YGADADHIK--------------------DEKYLLEG
SEQ_347  SGFDGDHLK--------------------SDEEIQYA
SEQ_348  YGADADHIK--------------------DEKYLLEG
SEQ_349  SGFDGDHLK--------------------SDEEIQYA
SEQ_350  YFVDADHIT--------------------TKTV-ELF
SEQ_351  -------------------------------------
SEQ_352  FGADADHVK--------------------RPEDLVSA
SEQ_353  FGADADHIK--------------------DENYLMEA
SEQ_354  FGADADHVK--------------------DLKNLKEA
SEQ_355  FGADGDHLK--------------------TAEEIKGA
SEQ_356  FAADADHLK--------------------EKPDIKEA
SEQ_357  FAADADHLK--------------------EKPDIKEA
SEQ_358  FGADADRLK--------------------EKPEIKEA
SEQ_359  YGADADHIK--------------------LESDIEHA
SEQ_360  FGADADHIK--------------------DENYLMEA
SEQ_361  FGADADHLK--------------------TLADVDIC
SEQ_362  FGADADHIK--------------------DENYLMEA
SEQ_363  FGADADHIK--------------------DENYLMEA
SEQ_364  FGADADHIK--------------------DERYLLEA
SEQ_365  FGADADHIK--------------------DEKYLMEA
SEQ_366  WGADGDHVK--------------------TEYEVDYA
SEQ_367  SGFDGDHLK--------------------SDEEIQYA
SEQ_368  SGFDGDHLK--------------------TDEEIKMA
SEQ_369  SGFDGDHLK--------------------SDEEIQYA
SEQ_370  SGFDGDHLK--------------------SDEEIQYA
SEQ_371  WYIDADHIN--------------------LDTV-DNF
SEQ_372  YHVDADHIS--------------------MKTV-DLF
SEQ_373  YIE--D-------------------------EIREAV
```

FIG. 17 CONTINUED

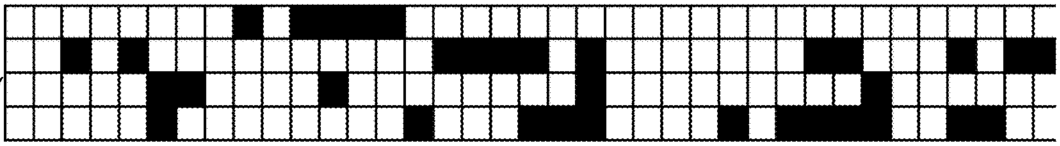

```
RESNUM   111 112 113 114 115 116 117 118 119 120 121 122 123 124 125 126 127 128 129 130 131 132 133 134 135 136 137 138 139 140 141 142 143
SEQ_6    V E S G Y K K I H I D C S M P L S D D P K - - - - V L P Y E K I A E R T R
SEQ_1    V K A G F S K I H L D A T M P L Q N D A T D S A G R L P V E T I A Q R T A
SEQ_2    V Q A G Y T K I H L D A S M P C A D D D P - - E R P L P L E R I A R R A A
SEQ_3    V L A G Y T K I H I D T S M R L K D D T - - - - - D F N T E I I A Q R S A
SEQ_4    V M A G F T K I H V D T S M L L G D D N I - - N I K L D T E T I A E R G A
SEQ_5    I K A G F T K I H I D T S M P L K G E N - - - - - S I D D E I I A K R T A
SEQ_7    L E A G Y A L L H I D P T V D R T L P P G - - - E A P L V P I V V E R T V
SEQ_8    L D A G Y G L L H L D P T V D L E L S P G - - - T P V P I P R I V E R S V
SEQ_9    I D A G Y T S F A I D A S H L F N F Q G G D L R E E L K D N I D A T - - T
SEQ_10   V M A G F T K I H V D T S M F L G D D N I - - N I K L D T E T I A E R G A
SEQ_11   V M A G F T K I H L D T S M Y L A D D D R - - S K K L A T E V I A R R G A
SEQ_12   A K A G F T K L H L D A S M R L A D D P G N E N E P L N P E V I A E R T A
SEQ_13   V G A G F T K I H I D T S M K V A S D D P - - N T R L S D E T I A K R G A
SEQ_14   V L A G F T K I H I D T S M P I Y D D L E - - K G V F G D D L I A E R A A
SEQ_15   V R A G Y G K I H L D A S M A C G G D P A - - D A P L D K A V A A E R A A
SEQ_16   V A A G F K K I H L D C S M S C E D D P V - - - - P L T D A I V A E R A A
SEQ_17   V K N G F N K I H L D C S M P L K G D S D - - - - F - S T T L V A D R E A
SEQ_18   V E S G Y K K I H L D C S M S L S D D P V - - - - V L S P E K I A E R E R
SEQ_19   L D A G Y G L L H L D P T V D L E L P P G - - - T P V P I P R I V E R T V
SEQ_20   L D A G Y G L L H L D P T V D L E L P P G - - - T P V P I P R I V E R T V
SEQ_21   I E A G F D L L M I D P T K D P - F E I G - - - K V I P L E K V I E R T V
SEQ_22   L I N G F D L L H I D P T K D P - Y I V G - - - K T V P M E I V L K R T I
SEQ_23   I D A G Y T S F A I D A S H L F N F R G G N L R E E L K D N I E A T - - T
SEQ_321  S N E G F T M Y T V D P S D H I K - D V S - - - - K L S Q K E F Q S L Y Q
SEQ_322  A R A G Y T M F T I D P S D H V K - D P A - - - - K F D K R E L V R F Y E
SEQ_323  A Y E G Y S M Y T V D P S D H V K - N I D - - - - K I N Q G E L V E F Y K
SEQ_324  I E A G F T F F T I D P S A Y V D N E V D - - - - T A D A A T L E A K V A
SEQ_325  L D L G F T M I T L D C S E M I D N T I D - - - - K L T D T E V E E K Y Y
SEQ_326  L N A G F T M F T F D P S E H V D N E A D - - - - N Y S E D Q L K Q K L G
SEQ_327  L S L G A S M I T L D C S D H I D N T I E - - - - K A S P E V L D E K F N
SEQ_328  L N V G M T M I T L D C S E H I D N S A A - - - - H A G L S E L R E K Y S
SEQ_329  A A A G F T L F T V D P S D H V D D S A H - - - - G A P A S D L E A K V A
SEQ_330  I D A G Y T M Y T L D I S D F I E - K I K - - - - D L S E K A L K E K - -
SEQ_331  V A A G Y T F Y T I D P S D H V D N A A H - - - - T D D L A V L R S K C E
SEQ_332  A E A G Y S L Y T F D L R R A L A - R G P - - - - - - - - - - - - - R P - -
SEQ_333  I N A G Y T M Y T L D L S E Q L I - D I S - - - - S L N P S E M R N K - -
SEQ_334  L D S G I T M L T L D C S E H M N - K D S - - - - S I - - - - - - - - - -
SEQ_335  L - D S A D F F T I D V A E A I G K G E V - - - - S P Q E E E - - D L - -
SEQ_336  E A G G V D F V T I D T C E L I D Y S Y D - - - - K V G A E E V A A A Y E
```

FIG. 17 CONTINUED

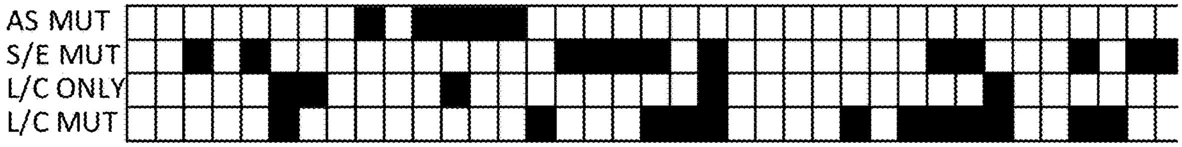

```
RESNUM   111 112 113 114 115 116 117 118 119 120 121 122 123 124 125 126 127 128 129 130 131 132 133 134 135 136 137 138 139 140 141 142 143
SEQ_337 I E A G F T F F T I D P S A Y V D N E V D - - - - T A D A A T L E A K V A
SEQ_338 I D A G Y T M Y T L D I S D F I E - R I E - - - - N L T S K E I R E K - -
SEQ_339 I D A G Y T M Y T L D L S D L L V - K I S - - - - D M P K S Q L K E K - -
SEQ_340 I E A G Y T M Y T L D V S E L L T - K I L - - - - D I S S N Q V M - - - -
SEQ_341 I E A G Y T M Y T L D V S E L L T - K I S - - - - D I S S N Q V M - - - -
SEQ_342 I N A G Y T M Y T L D L S E Q L I - D I S - - - - S L N P S E M R N K - -
SEQ_343 I N A G Y T M Y T L D L S E Q L I - D I S - - - - S L N A S E M R N K - -
SEQ_344 I N A G Y T M Y T L D L S E Q L I - D I S - - - - S L N P S E M R N K - -
SEQ_345 I N A G Y T M Y T L D L S E Q L I - D I S - - - - S L N A S E M R N K - -
SEQ_346 I D A G Y T M Y T L D L S E Q L F - D V S - - - - G A T S L E I K E K - -
SEQ_347 L D S G I T M L T L D C S E H M N N K D S - - - - S I - - - - - - - - - -
SEQ_348 I D A G Y T M Y T L D L S E Q L F - D I S - - - - G A T P S A I K E K - -
SEQ_349 L D S G I T M L T L D C S E H M N - K D S - - - - S I - - - - - - - - - -
SEQ_350 L - D S S D F F T I D V A E A I G Q E E I - - - - S P Q E E E - - D L - -
SEQ_351 - - - - - - - - - - - - - - - - - - - - - - - - - - - - - - - - - - - - -
SEQ_352 A R E G F T M F T I D P S D H V R - N L S - - - - K L T E K E R N E K F E
SEQ_353 I D A G Y T M Y T L D L S D M L V - K L S - - - - D Y T E S Q L K E K - -
SEQ_354 I D C G F T F Y T I D P S D H I D A N I L - - - - K L D K D E L R N K Y Q
SEQ_355 L D L G F T M I T L D A S A H I D N T V G - - - - Q K A A K Q V A E L Y H
SEQ_356 L D L G Y T M L T L D C T D Y I N D D L D - - - - Q M S E S E I E N A Y A
SEQ_357 L D L G Y T M L T L D C T D Y I N D D L D - - - - Q M S E S E V E N A Y A
SEQ_358 L D L G Y T M L T L D C T D Y I N D N F D - - - - Q T A E S D I E S A Y A
SEQ_359 L Q L G F S F L T L D C S E Q I R N D V E - - - - S Q T S D E I Q N E F A
SEQ_360 I D A G Y T M Y T L D L S D M L V - K L S - - - - D Y T E S Q L K E K - -
SEQ_361 A A A G Y T F Y T V D P G D H V D D E A N - - - - T A A F P A L E A R V D
SEQ_362 I D A G Y T M Y T L D L S D M L V - K L S - - - - D Y T E S Q L K E K - -
SEQ_363 I D A G Y T M Y T L D L S D M L V - K L S - - - - D Y T E S Q L K E K - -
SEQ_364 A D A G Y T M Y T L D V S E M L V - K G D - - - - V S - - - - - - P D K - -
SEQ_365 I D A G Y T M Y T L D L S D L L V - K I S - - - - D M P E S Q L K E K - -
SEQ_366 V K V G C S M I T L D C T D V I N N D A V - - - - T M S D E E L D K T F N
SEQ_367 L D S G I T M L T L D C S E H M N - K D S - - - - S I - - - - - - - - - -
SEQ_368 I D S G I T M L T L D C S E Y M G - V V S - - - - K I - - - - - - - - - -
SEQ_369 L D S G I T M L T L D C S E H M N - K D S - - - - S I - - - - - - - - - -
SEQ_370 L D S G I T M L T L D C S E H M N - K D S - - - - S V - - - - - - - - - -
SEQ_371 L - E S S D F F T I D V A S Y I G K K G D - - - - S K E E E - - - - T - -
SEQ_372 L - D S S D F F T L D V A D Y T G K A A D - - - - E A S I A - - - - R - -
SEQ_373 S T R N I Y F Y T I D T C D L I D Y S S E - - - - K I A V D E L R T V F K
```

FIG. 17 CONTINUED

AS MUT
S/E MUT
L/C ONLY
L/C MUT

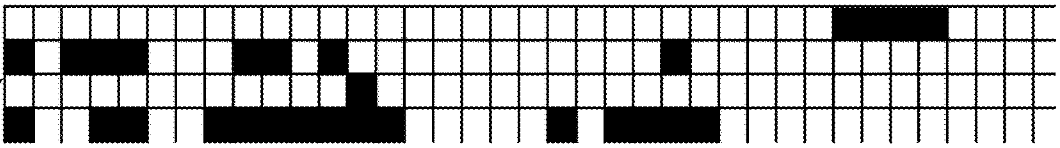

```
RESNUM   144 145 146 147 148 149 150 151 152 153 154 155 156 157 158 159 160 161 162 163 164 165 166 167 168 169
SEQ_6    E L F E I - A E E T A R K Y - - - - - N - F Q P V Y V V G T D V P - - - -
SEQ_1    E L C A V - A E Q T Y R Q S D - - - Q L F P P P V Y I V G S D V P - - - -
SEQ_2    Q L C A A - A E A A - - - - - - - - A G A V Q P V Y V I G S E V P - - - -
SEQ_3    V L L K A - A E N A Y M E L N K N N K N V L H P V Y V I G S E V P - - - -
SEQ_4    I L V S V - A E R A F E E L K K F N P Y A L H P V Y V I G S E V P - - - -
SEQ_5    V L C R I - A E E C F E K I S I N N P Y I T R P V Y V I G A D V P - - - -
SEQ_7    E L I E H - A E Q E R Q R L - - - - - N L P A V A Y E V G T E E - - - - -
SEQ_8    A L L R H - A E T Y R L R R - - - - - N L P P V A Y E V G T E E - - - - -
SEQ_9    E I A K F - I E E Q - - - M - - - - - - - D D R E Y G L E V E V G - - - -
SEQ_10   I L V S V - A E R A F E E L K K S N P Y A L H P V Y V I G S E V P - - - -
SEQ_11   E L C K T - A E E S F K A L K E R N S M A V A P V Y I V G S E V P - - - -
SEQ_12   L L C L E - A E R A F K E S - - - - A G S L R P V Y V I G T D V P - - - -
SEQ_13   R L A R V - A Q D T Y H K L L E S D P D A I A P V Y I V G S E V P - - - -
SEQ_14   I L C N V - A E I A Y R E L L K T N E D A I H P I Y V V G S E V P - - - -
SEQ_15   A L A E A - A E A A F Q R M - - - - G S G T P P C Y V I G T E V P - - - -
SEQ_16   R L A K I - A E A T C R E Q - - - - F G V T D L V Y V I G T E V P - - - -
SEQ_17   E L C A V - A E E T Y E K Y - - - - - G G N R P V Y V V G T E V P - - - -
SEQ_18   E L L E V - A E E T A R K Y - - - - - N - F Q P V Y V V G T D V P - - - -
SEQ_19   A L L R H - A E T Y R L R R - - - - - N L P P V A Y E V G T E E - - - - -
SEQ_20   A L L Q H - A E T Y R Q Q R - - - - - R L P P V A Y E V G T E E - - - - -
SEQ_21   E L I E F - C E K E R Q A R - - - - - D L P E I G Y E V G T E E - - - - -
SEQ_22   E L I E Y - V E R E R K E R - - - - - N L P P I S Y E V G T E E - - - - -
SEQ_23   K V A R F - I D E Q - - - M - - - - - - - E D R D Y G L E V E V G - - - -
SEQ_321  D N K I R - - - - - - R E L - - - E M R Y V G K L Y K F K - D F E - - - F
SEQ_322  E H P M R - - - - - - R T L - - - E M K Y I G K S F T V L - G E K - - - L
SEQ_323  S H P L R - - - - - - K E I - - - E M I Y S G K V F S F E - K S K - - - F
SEQ_324  A L P W E A L E T T L A D L - - - R R A Y L G Q H F Q V G - P Y E - - - L
SEQ_325  Q L P Q S - - - - V R E R Y - - - E T R Y L D K C F E L R - N S K - - - I
SEQ_326  E I D W S G L Q D T S A D A - - - A K R Y V D M T F N I S E R L S - - - L
SEQ_327  A L S E V - - - - V K Q R Y - - - M E Q Y L G K T F E V N - G L T - - - L
SEQ_328  R F T E E - - - - E R E R W - - - E R K Y L N R D V K I G - N Y S - - - F
SEQ_329  A L P W R E L E T T R A D F - - - E - R Y A G R R L E L G - D R E - - - L
SEQ_330  - - - Y E K V S S F S K K I - - - I D K Y A G K R V K I S D E E Y - - - F
SEQ_331  A L P W D I L E T T Y L S L - - - C E N Y C G R T I V A E - K T T - - - L
SEQ_332  - - - W E A L S P L A R S V - - - V A E L A D R R V E A P - Q G P - - - R
SEQ_333  - - - A Q E L S Q V S K D I - - - I K D F S G K K L D I I S D S G - - - Y
SEQ_334  - - - - - - - - - - K D Q I - - - F E Q F Y N K S F F V N - D M P - - - I
SEQ_335  - - - - - - - - - - L A S L - - - G D L L N R E L A I P G L S S P - - - L
SEQ_336  E V F D G - - - D E R R A L - - - E E R Y E G V H Y F L G - G D R V V A V
```

FIG. 17 CONTINUED

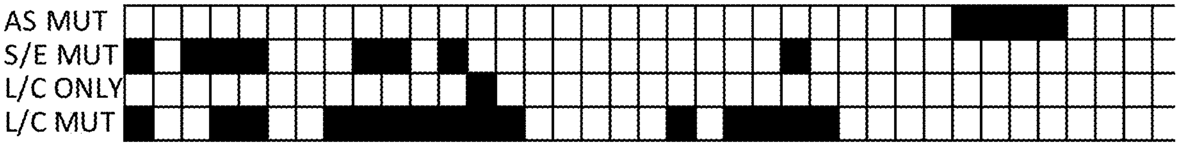

```
RESNUM  144 145 146 147 148 149 150 151 152 153 154 155 156 157 158 159 160 161 162 163 164 165 166 167 168 169
SEQ_337 A L P W D A L E T T L A D L - - - R R A Y L G Q H F Q V G - P Y E - - - L
SEQ_338 - - - Y E K I S S F S K K I - - - I E K Y A G K K I K I S N E E Y - - - F
SEQ_339 - - - A Q S L S S Q S R E I - - - I D R F K G K K F S I S T D E D - - - F
SEQ_340 - - - - - Q I S P Q S K E I - - - I E A F K G K K I S I S - E E E - - - Y
SEQ_341 - - - - - Q I S P Q S K E I - - - I E A F K G K K I S I S - E E E - - - Y
SEQ_342 - - - A Q E L S Q V S K D I - - - I K D F S G K K L D I I S D S G - - - Y
SEQ_343 - - - A Q E L S Q V S K D I - - - I K D F S G K K L D I I S D S G - - - Y
SEQ_344 - - - A Q E L S Q V S K D I - - - I K D F S G K K L D I I S D S G - - - Y
SEQ_345 - - - A Q E L S Q V S K D I - - - I K D F S G K K L D I I S D S G - - - Y
SEQ_346 - - - A K T L S D V S R K I - - - V E D F S G K S L N V G - F G G - - - H
SEQ_347 - - - - - - - - - - K E R I - - - F D Q F Y N K S F F V N - D M P - - - I
SEQ_348 - - - A E A L S D V S K K I - - - V E D F S G Q S L N V G - L E G - - - H
SEQ_349 - - - - - - - - - - K D Q I - - - F E Q F Y N K S F F V N - D M P - - - I
SEQ_350 - - - - - - - - - - L S S L - - - D D L L N R E L A I P G L S N P - - - L
SEQ_351 - - - - - - - - - - - - - - - - - - - - - - - - - - - - - - - - - - - - -
SEQ_352 E I L R K - - - - - - E R I - - - D R I Y L G K K Y S V L - G E K - - - I
SEQ_353 - - - A E K L N I T S K R I - - - I E R F K G K K F V M P T K E A - - - F
SEQ_354 Q L P E K - - - - - - D A L - - - E N S Y L N K E Y Q I G - S Q K - - - L
SEQ_355 T L P A D - - - - Y T A D M - - - E E H Y L G K A F I V G - G M A - - - I
SEQ_356 E V P D Y - - - - L R E G L - - - E N Q Y L N K T F V L N S G Y Q - - - L
SEQ_357 E V P D Y - - - - L R E G L - - - E N Q Y L N K T F V L N S G Y Q - - - L
SEQ_358 E V P D Y - - - - L R D G L - - - E S K Y L N K T F V L N S G Y Q - - - L
SEQ_359 S L S D E - - - - K R A Y F - - - S N Y Y L D Q T F N V H - E R Q - - - I
SEQ_360 - - - A E K L N I T S K R I - - - I E K F K G K K F V M P T E E A - - - F
SEQ_361 A L P W D V L D S S P A D L - - - A A R L A D R P I D L G - T L K - - - V
SEQ_362 - - - A E K L N I T S K R I - - - I E R F K G K K F V M P T K E A - - - F
SEQ_363 - - - A E K L N I T S K R I - - - I E K F K G K K F V M P T E E A - - - F
SEQ_364 - - - A D H L S Q H S R D I - - - I K D F S G K R I S F E - G G E - - - Y
SEQ_365 - - - A Q S L S S Q S R E I - - - I D R Y K G K K F S I S T D E D - - - F
SEQ_366 A L D D D - - - - Q K K Y F - - - N D T Y L D K T F D L G N G N S - - - V
SEQ_367 - - - - - - - - - - K D Q I - - - F E Q F Y N K S F F V N - D M P - - - I
SEQ_368 - - - - - - - - - - K E K I - - - Y K G F Y G K T F K V K - D L D - - - L
SEQ_369 - - - - - - - - - - K D Q I - - - F E Q F Y N K S F F V N - D M P - - - I
SEQ_370 - - - - - - - - - - K E S I - - - F D Q F Y N K S F F V N - D M P - - - I
SEQ_371 - - - - - - - - - - F I S K - - - M K P L I G N L N I P G V N S P - - - F
SEQ_372 - - - - - - - - - - F V A K - - - H Q H C I G K L Q I P G I E Q P - - - I
SEQ_373 D L Y P A - - - - - - - S L - - - I E R Y K D I N V V V N - G T R - - - I
```

FIG. 17 CONTINUED

```
AS MUT
S/E MUT
L/C ONLY
L/C MUT
RESNUM                                                            170 171 172     173 174 175 176
SEQ_6    - - - - - - - - - - - - - - - - - - - - - - - - - - - - I A G - - G G E E
SEQ_1    - - - - - - - - - - - - - - - - - - - - - - - - - - - - I P G - - G A Q E
SEQ_2    - - - - - - - - - - - - - - - - - - - - - - - - - - - - P P G - - G A Q G
SEQ_3    - - - - - - - - - - - - - - - - - - - - - - - - - - - - I P G - - G S Q G
SEQ_4    - - - - - - - - - - - - - - - - - - - - - - - - - - - - V P G - - G S Q K
SEQ_5    - - - - - - - - - - - - - - - - - - - - - - - - - - - - P P G - - G E S S
SEQ_7    - - - - - - - - - - - - - - - - - - - - - - - - - - - - - - - - - - - - -
SEQ_8    - - - - - - - - - - - - - - - - - - - - - - - - - - - - - - - - - - - - -
SEQ_9    - - - - - - - - - - - - - - - - - - - - - - - - - - - - E I G - - R E - -
SEQ_10   - - - - - - - - - - - - - - - - - - - - - - - - - - - - V P G - - G S Q K
SEQ_11   - - - - - - - - - - - - - - - - - - - - - - - - - - - - I P G - - G I Q D
SEQ_12   - - - - - - - - - - - - - - - - - - - - - - - - - - - - P P G - - G A Q N
SEQ_13   - - - - - - - - - - - - - - - - - - - - - - - - - - - - I P G - - G A V G
SEQ_14   - - - - - - - - - - - - - - - - - - - - - - - - - - - - V P G - - G V Q A
SEQ_15   - - - - - - - - - - - - - - - - - - - - - - - - - - - - P P G - - G A Q G
SEQ_16   - - - - - - - - - - - - - - - - - - - - - - - - - - - - V P G - - G A H E
SEQ_17   - - - - - - - - - - - - - - - - - - - - - - - - - - - - A P G - - G S T N
SEQ_18   - - - - - - - - - - - - - - - - - - - - - - - - - - - - V A G - - G G E E
SEQ_19   - - - - - - - - - - - - - - - - - - - - - - - - - - - - - - - - - - - - -
SEQ_20   - - - - - - - - - - - - - - - - - - - - - - - - - - - - - - - - - - - - -
SEQ_21   - - - - - - - - - - - - - - - - - - - - - - - - - - - - - - - - - - - - -
SEQ_22   - - - - - - - - - - - - - - - - - - - - - - - - - - - - - - - - - - - - -
SEQ_23   - - - - - - - - - - - - - - - - - - - - - - - - - - - - E I G - - R E - -
SEQ_321  R M T D - E E F A E I F V T Y I D A I E H V C K C Y D V L K A K - G - K P
SEQ_322  T F D E - E N F A E V F V T Y I D A I E H V E K C Y R A L R A V - C K T S
SEQ_323  T M E D - K E L F R I F V T Y V D A I E H V V K C Y E A I K N T - K - K N
SEQ_324  S F E E - R T L M Q A L A K Y G G A I A H T A R M Y R H I A G R M G N R P
SEQ_325  C F S K - E N L M K N V L I Y G A A A D F I V A I Y E K Q I K H - R D Q K
SEQ_326  T I Q E - S D F L R A Y A K Y G N A I A H I K K M Y D Y L A S K A D K D T
SEQ_327  T L D E - T E L K K N V L L Y D K A I D Y T T H V Y N E Y I S K - E N R A
SEQ_328  H I S E - E D L I R M A C V Y G G A I R H T L D I Y H N I I A K - C G R P
SEQ_329  V L A R - E A V L R A G A K Y A R A V L H V A T L Y R H L E G K - - G A P
SEQ_330  E L S Y - N E L C K S A I V Y E K A L S F V E M V Y E I L K S K - - L S E
SEQ_331  H F D K - E T L L R A L A K Y G R A L A H T V R I A A A L R T A L G G T S
SEQ_332  T L E E - S A L R A A A C R Y E P A L E E V V R G A E I L R D Q - - G I D
SEQ_333  V V S E - E E L Y K S A V A Y E N A M K F V D K V N N I L K E K - - L S D
SEQ_334  E Y S D K N E L N K I V S I Y A S V I E R V I D V W N K F P K V - N K K E
SEQ_335  A I S E - E T A R G T I R A Y W P A V R E A A R I Y R R I E Q G - A S R P
SEQ_336  R L S R - E D V A R L A V K Y R R S L D Y A E R I Y R A A R E A - M G V E
```

FIG. 17 CONTINUED

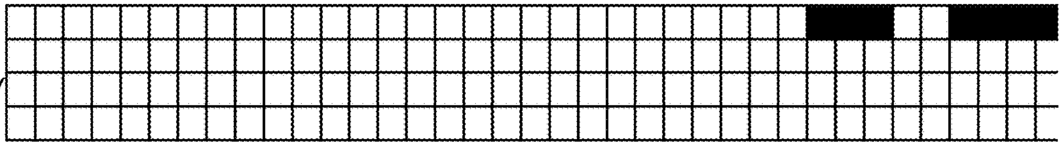

```
RESNUM                                                         170 171 172         173 174 175 176
SEQ_337 S F E E - R T L L Q A L A K Y G G A I A H T A R V Y R H I A G R M G N R P
SEQ_338 E L S Y - D E L C K S A I V Y E K A L S F V E M V Y E I L R S K - - L L E
SEQ_339 A V S E - D E L Y K S A L T Y E K A M K F V E K V Y G I L K D R - - L Q H
SEQ_340 T I R E - D E L Y K S A L I Y E K A M N F V E K V Y S I L K E K - - V K D
SEQ_341 T I R E - D E L Y K S A L I Y E K A M N F V E K V Y S I L K E K - - V K D
SEQ_342 V V S E - E E L Y K S A V A Y E N S M K F V D K V N N I L K E K - - L S D
SEQ_343 V V S E - E E L Y K S A V A Y E N A M K F V D K V N N I L K E K - - L S D
SEQ_344 V V S E - E E L Y K S A V A Y E N A M K F V D K V N N I L K E K - - L S D
SEQ_345 V V S E - E E L Y K S A V A Y E N A M K F V D K V N N I L K E K - - L S D
SEQ_346 L V S E - D E L L K S A V A Y E A A M K F V E K V N D I L K E K - - L N D
SEQ_347 E Y S N K N E L N K I V S I Y A G V I E R V I D V W N K F P K V - N K K E
SEQ_348 L V S E - D E L L K S A I A Y E G A M K F V E K V N D I L K E K - - L N D
SEQ_349 E Y S D K N E L N K I V S I Y A S V I E R V I D V W N K F P K V - N K K E
SEQ_350 T I S E - E T A R E T I R A Y W P A V R E A A R I H Q R I E K G - T S R P
SEQ_351 - - - - - - - - - - - - - - - - - - - - - - - - - - M R A K E L - F G E D
SEQ_352 E F D E - K N L R D A A L V Y Y D A I A H V D M M Y Q I L K D E - T - P D
SEQ_353 T V S E - E E L Y K S A L T Y E K A M D F V E K V Y G I L K D K - - V K N
SEQ_354 T F T Q - D I L I E I V L T Y L E A I K H V E K C Y K F L K D S - H K G D
SEQ_355 T F D T - E T L Q R L V L T Y G K A L A F M G Y I Y H T L I V N - A G R E
SEQ_356 E Y N Q - D N F K E I V L I Y Y K M L D F A K E I Q H - L I K T - S A R N
SEQ_357 E Y N Q - D N F K E I V L I Y Y K M L D F A K E I Q H - L I K T - S A R N
SEQ_358 E Y N K - V N F K K I V L S Y Y Q I L D F V K E I Q H - L I K R - S A R D
SEQ_359 S F D Q - A N L A K N V L V Y G E A I D F M E H V Y H T Y L Q S - L D R D
SEQ_360 T V S E - E E L Y K S A L T Y E K A M D F V E K V Y G I L K D K - - V K N
SEQ_361 T L D R - E T L W R A A A K Y G R A V A H T V T M Y R H L A G A M G E R P
SEQ_362 T V S E - E E L Y K S A L T Y E K A M D F V E K V Y G I L K D K - - V K N
SEQ_363 T V S E - E E L Y K S A L T Y E K A M D F V E K V Y G I L K D K - - V K N
SEQ_364 T V K E - E E L Y R S A V I Y E K A M N F V E R V H G L L K E R - - L K D
SEQ_365 V V S E - D E L Y K S A L T Y E K A M K F V E K V Y G I L K D R - - L Q H
SEQ_366 H F T K - H D V E E S V L T F Y G A I L F A A D I Y K K F V V P - - - Y N
SEQ_367 E Y S D K N E L N E I V S I Y A S V I E R V I D V W N K F P K V - N K K E
SEQ_368 E Y S Q - E E L E K I L S I Y S G V I E R I I Y I W N N F P K V - K N K D
SEQ_369 E Y S D K N E L N K I V S I Y A S V I E R V I D V W N K F P K V - N K K E
SEQ_370 E Y S D K N E L N K I V S I Y G G V I E R V I D V W N K F P K V - N K K E
SEQ_371 K I T E - Q Q L R N I A G Q Y L H A A F M A G E T Y K Y I E S V K G K G N
SEQ_372 T I T E - T T L T S V A R K Y L L A I Q E A G K L Y R H I A N K K G P E N
SEQ_373 R F D E - E K V M R L S L K L M R S I D V S E R I Y R I I K E M - T P W P
```

FIG. 17 CONTINUED

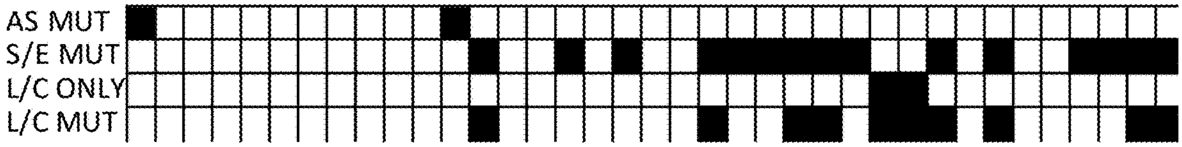

| | |
|---|---|
| RESNUM | 177 178 179 180 181 182 183 184 185 186 187 188 189 190 191 192 193 194 195 196 197 198 199 200 201 |
| SEQ_6 | E----------GVTSVEDFRSAISSLKKYFN--DVPN |
| SEQ_1 | AL------NQIHITEVKEVQQTIDHVRRAFEKNGLEA |
| SEQ_2 | QE------ARLHVTTPQEAQAALDAFREAFLQAGLTP |
| SEQ_3 | SD------ESLQITDAKDFENTVEIFKDVFSKYGLIN |
| SEQ_4 | ENN-----NEIQVTKPTDFEETVEVYKSTFYKYGLGN |
| SEQ_5 | IC--------QTITTKDELERSLEYFKEAFKKEGIEH |
| SEQ_7 | --------VHGGLVNFDNFVAFLDLLKARLEQRALMH |
| SEQ_8 | --------VGGGLQAEARMAEFLDRLWTALDREGLP- |
| SEQ_9 | DE------HGRVLTNPEEAVT----FIKALNENGV-- |
| SEQ_10 | ENN-----NEIQVTKPADFEETVEVYKSTFYKYGLGN |
| SEQ_11 | EE------EGIQVTKPEDFLETVKVYKAEFKDKGIDE |
| SEQ_12 | EG------KSIHVTSVQDFERTVELTKKAFFDHGLYE |
| SEQ_13 | AV-----DQGVQVTKVEDFKNTVATFEKAFREQGLDE |
| SEQ_14 | EEAEEEIENGIKVTRVEDFKNTVEVFKKKFKEHGVEE |
| SEQ_15 | DD------MPLAITAPREVAETIELTQAAFRRRGLEA |
| SEQ_16 | TL------TELEVTTPDAARATLEAHRHALEKEGLND |
| SEQ_17 | EV--------PEVTSIEELDEMIEELQNAFLRLGLKN |
| SEQ_18 | E----------GITSVEDFRVAISSLKKYFE--DVPR |
| SEQ_19 | --------VGGGLQAEARMAEFLDRLWTALDREGLP- |
| SEQ_20 | --------VGGGLQAEARMAEFLDRLWTVLDREGLP- |
| SEQ_21 | --------TNGGLTSTETYETFILRLQEELGRRDLP- |
| SEQ_22 | --------TNGGLTSEEAYETFIKTLIEELDKRNLP- |
| SEQ_23 | DE------YGRVLTQPEEAVT----FIKALNENGV-- |
| SEQ_321 | FDFEVSIDETAVPTTPLAHIF----IVKELRRRGIDF |
| SEQ_322 | FDLEVSIDETSVPTTSLAHIF----FVQELVRRGVEF |
| SEQ_323 | FDFEVSIDETSIPTSPLAHIF----IVHELRRRGVDF |
| SEQ_324 | FELEMSVDETEVPTSPAEHFF----VARELQRLGVRW |
| SEQ_325 | IDFEVSIDETVTPTTPEAHYF----VAREIYDRQVDI |
| SEQ_326 | FEIEVSVDETESVTSPFEHFF----FANELNRLGVKY |
| SEQ_327 | IDFEISIDETETVTSPISHFF----VANELINRGVKV |
| SEQ_328 | IDFEMSIDETLTPTSPASHYF----VAQELIDGGVEI |
| SEQ_329 | FELEVSVDETATPTSHAEHAV----VALELRRLGVRW |
| SEQ_330 | FDIEVSIDEGERDTTPEDHFF----VAQFLHDKGIDF |
| SEQ_331 | FDLEMSVDETDTPTSAHEHFF----IANELLRRNIPL |
| SEQ_332 | ADLEVSVDETEEETTPEAHAF----IAVYLQRRGVAL |
| SEQ_333 | FDMEISIDEGGKVTTLEDHLY----VAEYLHRNGIDF |
| SEQ_334 | VTFEVSVDETDVPTDEKTHFL----ISKYIYDEGVKI |
| SEQ_335 | FVVEVSMDETDEPQRPPELLL----ILAMIRKAGIPA |
| SEQ_336 | LGFEVAFDETPGVSEAREVFF----YLSELLRRGLRV |

FIG. 17 CONTINUED

| RESNUM | 177 | | | | | | | | | | | 178 | 179 | 180 | 181 | 182 | 183 | 184 | 185 | 186 | 187 | 188 | 189 | 190 | 191 | 192 | 193 | 194 | 195 | 196 | 197 | | | 198 | 199 | 200 | 201 |
|---|---|---|---|---|---|---|---|---|---|---|---|---|---|---|---|---|---|---|---|---|---|---|---|---|---|---|---|---|---|---|---|---|---|---|---|---|---|
| AS MUT | ■ | | | | | | | | | | | ■ | | | | | | | | | | | | | | | | | | | | | | | | | |
| S/E MUT | | | | | | | | | | | | | ■ | | | ■ | | ■ | | | ■ | ■ | ■ | ■ | ■ | ■ | | | ■ | | ■ | | | ■ | ■ | ■ | ■ |
| L/C ONLY | | | | | | | | | | | | | | | | | | | | | | | | | | | ■ | ■ | | | | | | | | | |
| L/C MUT | | | | | | | | | | | | | ■ | | | | | | | | ■ | | | ■ | ■ | | ■ | ■ | ■ | | ■ | | | | | ■ | ■ |
| SEQ_337 | F | E | L | E | M | S | V | D | E | T | E | V | P | T | S | P | A | E | H | F | F | - | - | - | - | V | A | R | E | L | Q | R | L | G | V | R | W |
| SEQ_338 | F | D | I | E | V | S | I | D | E | G | E | R | D | T | T | P | E | D | H | F | F | - | - | - | - | V | V | Q | F | L | H | E | K | G | I | D | F |
| SEQ_339 | F | D | L | E | I | S | I | D | E | G | E | K | D | T | T | V | E | D | H | I | F | - | - | - | - | V | A | E | Y | L | H | R | K | G | I | D | F |
| SEQ_340 | F | D | L | E | I | S | I | D | E | G | E | K | D | T | T | V | E | D | H | I | F | - | - | - | - | V | A | E | Y | L | H | K | K | G | I | D | F |
| SEQ_341 | F | D | L | E | I | S | I | D | E | G | E | K | D | T | T | V | E | D | H | I | F | - | - | - | - | V | A | E | Y | L | H | K | K | G | I | D | F |
| SEQ_342 | F | D | M | E | I | S | I | D | E | G | G | K | V | T | T | L | E | D | H | L | Y | - | - | - | - | V | A | E | Y | L | H | R | S | G | I | D | F |
| SEQ_343 | F | D | M | E | I | S | I | D | E | G | G | K | V | T | T | L | E | D | H | L | Y | - | - | - | - | V | A | E | Y | L | H | R | N | G | I | D | F |
| SEQ_344 | F | D | M | E | I | S | I | D | E | G | G | K | V | T | T | L | E | D | H | L | Y | - | - | - | - | V | A | E | Y | L | H | R | N | G | I | D | F |
| SEQ_345 | F | D | M | E | I | S | I | D | E | G | G | K | V | T | T | L | E | D | H | L | Y | - | - | - | - | V | A | E | Y | L | H | R | N | G | I | D | F |
| SEQ_346 | F | D | L | E | I | S | I | D | E | G | G | K | V | T | T | L | E | D | H | L | F | - | - | - | - | V | A | E | Y | L | H | R | N | G | I | D | F |
| SEQ_347 | V | T | F | E | V | S | V | D | E | T | D | V | P | T | D | E | K | T | H | F | L | - | - | - | - | I | S | K | Y | I | Y | D | E | G | V | K | I |
| SEQ_348 | F | D | L | E | I | S | I | D | E | G | G | K | V | T | T | L | E | D | H | L | F | - | - | - | - | V | A | E | Y | L | H | R | N | G | I | D | F |
| SEQ_349 | V | T | F | E | V | S | V | D | E | T | D | V | P | T | D | E | K | T | H | F | L | - | - | - | - | I | S | K | Y | I | Y | D | E | G | V | K | I |
| SEQ_350 | F | V | V | E | V | S | M | D | E | T | A | D | P | Q | R | P | P | E | L | L | L | - | - | - | - | I | L | A | M | I | R | K | A | G | I | P | A |
| SEQ_351 | V | S | I | E | I | A | L | D | E | S | P | S | E | T | Q | L | K | E | L | F | F | - | - | - | - | Y | I | N | E | L | L | Y | K | G | L | R | F |
| SEQ_352 | F | D | F | E | V | S | V | D | E | T | E | T | P | T | S | P | L | F | H | I | F | - | - | - | - | V | V | E | E | L | R | R | R | G | V | E | F |
| SEQ_353 | F | D | L | E | I | S | I | D | E | G | D | K | D | T | T | V | E | D | H | I | F | - | - | - | - | V | A | E | Y | L | H | E | K | G | I | D | F |
| SEQ_354 | F | E | L | E | V | S | V | D | E | T | P | T | P | T | S | P | L | A | H | L | W | - | - | - | - | I | A | S | E | L | Q | R | R | G | V | D | F |
| SEQ_355 | V | D | F | E | I | S | I | D | E | T | A | T | P | T | T | P | A | A | H | Y | F | - | - | - | - | V | A | S | E | L | G | R | M | G | V | K | F |
| SEQ_356 | V | D | F | E | I | S | I | D | E | T | S | T | P | T | T | P | E | A | H | F | F | - | - | - | - | V | A | N | E | L | K | R | N | N | I | E | V |
| SEQ_357 | V | D | F | E | I | S | I | D | E | T | S | T | P | T | T | P | E | A | H | F | F | - | - | - | - | V | A | N | E | L | K | R | N | N | I | E | V |
| SEQ_358 | V | D | L | E | I | S | I | A | D | S | L | N | S | T | S | P | E | A | H | F | F | - | - | - | - | V | A | N | E | F | K | R | N | N | I | E | V |
| SEQ_359 | V | D | F | E | I | S | I | D | E | T | E | T | V | T | S | P | E | A | H | F | F | - | - | - | - | V | A | E | E | L | R | R | R | G | V | K | V |
| SEQ_360 | F | D | L | E | I | S | I | D | E | G | D | K | D | T | T | V | E | D | H | I | F | - | - | - | - | V | A | E | Y | L | H | E | K | G | I | D | F |
| SEQ_361 | F | E | L | E | M | S | V | D | E | T | A | T | V | T | S | L | A | E | H | V | Y | - | - | - | - | I | A | A | E | L | Q | R | L | G | V | R | C |
| SEQ_362 | F | D | L | E | I | S | I | D | E | G | D | K | D | T | T | V | E | D | H | I | F | - | - | - | - | V | A | E | Y | L | H | E | K | G | I | D | F |
| SEQ_363 | F | D | L | E | I | S | I | D | E | G | D | K | D | T | T | V | E | D | H | I | F | - | - | - | - | V | A | E | Y | L | H | E | K | G | I | D | F |
| SEQ_364 | F | D | L | E | V | S | I | D | E | G | D | R | D | T | T | V | E | D | H | I | F | - | - | - | - | V | A | E | Y | L | H | R | R | G | I | D | F |
| SEQ_365 | F | D | L | E | I | S | I | D | E | G | E | K | D | T | T | V | E | D | H | I | F | - | - | - | - | V | V | E | Y | L | H | R | K | G | I | D | F |
| SEQ_366 | L | D | F | E | I | S | M | D | E | T | P | Y | Q | T | T | N | P | N | H | F | F | - | - | - | - | F | G | N | E | L | H | K | R | G | I | V | P |
| SEQ_367 | V | S | F | E | V | S | V | D | E | T | D | V | P | T | D | E | K | T | H | F | L | - | - | - | - | I | S | K | Y | I | N | D | E | G | V | K | I |
| SEQ_368 | V | S | F | E | V | S | I | D | E | T | N | I | P | T | D | E | K | T | H | F | L | - | - | - | - | L | S | K | Y | L | Y | D | E | G | I | T | I |
| SEQ_369 | V | T | F | E | V | S | V | D | E | T | D | V | P | T | D | E | K | T | H | F | L | - | - | - | - | I | S | K | Y | I | Y | D | E | G | V | K | I |
| SEQ_370 | V | S | F | E | V | S | V | D | E | T | D | V | P | T | D | E | K | T | H | F | L | - | - | - | - | I | S | K | Y | I | Y | D | E | G | V | K | I |
| SEQ_371 | F | I | T | E | V | S | M | D | E | V | P | E | P | Q | T | P | V | E | L | F | F | - | - | - | - | I | L | A | M | L | A | H | Y | G | V | P | A |
| SEQ_372 | F | I | T | E | V | S | I | D | E | T | D | Q | P | Q | G | P | E | D | L | L | F | - | - | - | - | I | L | A | M | I | A | D | E | G | I | P | A |
| SEQ_373 | F | G | I | E | I | A | F | D | E | T | P | V | T | S | D | P | H | E | L | F | F | - | - | - | - | V | L | N | E | L | R | T | R | G | I | P | V |

FIG. 17 CONTINUED

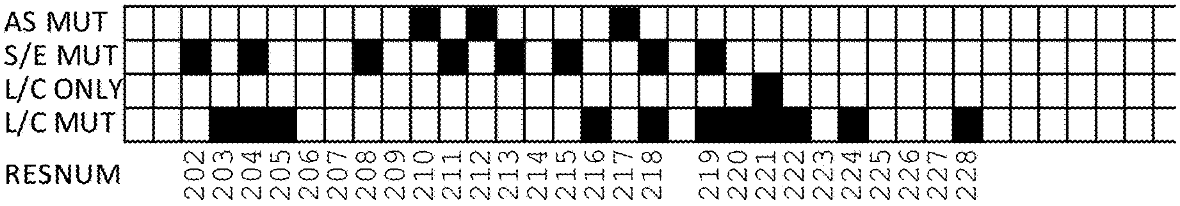

```
SEQ_6    --IWDRVVGFVIMLGIGFS-YDKVFEYDRD--------
SEQ_1    --AYERVCAVVVQPGVEFA-DQIVFEYAPD--------
SEQ_2    --VWERVIALVVQPGVEFG-VDSIHAYQRE--------
SEQ_3    --EWENIVAFVVQPGVEFG-NDFVHEYKRD--------
SEQ_4    --AWEDVVAVVVQAGVEFG-VEDIHEYDHQ--------
SEQ_5    --VFDYVVAVVANFGVEFG-SDEIVDFDME--------
SEQ_7    --AWPAFV--VAQVGTDLH----TTYFDPS--------
SEQ_8    ---HPVFV--VGDIGTRLD----TRTFDFE--------
SEQ_9    ---YPQVLAIAN------G-SAHGNTYDSQGRLIEQV
SEQ_10   --AWEDVVAVVVQPGVEFG-VENIHEYDHQ--------
SEQ_11   --VWNRVIGVVVQPGVEFG-DESVHEYNRE--------
SEQ_12   --AWGRVIAVVVQPGVEFG-NEHIFEYDRN--------
SEQ_13   --AWDNVIGVVVQPGVEEK-DSGCTEYDRE--------
SEQ_14   --AFNYVVGVVVQPGVEFS-SDTVWKYERE--------
SEQ_15   --AWERVIAVVVQPGVEFG-DEQVHPYDRA--------
SEQ_16   --IWPRIIGLVVQPGVEFD-HAHVCDYQPH--------
SEQ_17   --AWDRVIAIVVRLGIGFG-GDSVSEYESE--------
SEQ_18   --IWDRIIGFVIMLGIGFN-YEKVFEYDRI--------
SEQ_19   ---HPIFV--VGDIGTRLD----TRTFDFE--------
SEQ_20   ---RPVFV--VGDIGTRLD----THTFDFE--------
SEQ_21   ---MPTFI--VGQTGTLVRKTEQAGRFSFE--------
SEQ_22   ---KPSFI--VGQTGTLTRLTENVGNFNTK--------
SEQ_23   ---YPQVLAIAN------G-SAHGNTYDEYGHLIEQV
SEQ_321  KTLALRFSG-EWQKGIDYIGD--MEMFRKE--------
SEQ_322  RTLALRFPG-EWQKGIDYVGD--IDLFSEN--------
SEQ_323  QTLALRFVG-QWQKAIDYIGD--LSVLESE--------
SEQ_324  ISLAPRFVG-RLEKGVDYIGD--LEEFEAH--------
SEQ_325  NSMAPRFCG-EFQKGIDYIGD--IHQFEKE--------
SEQ_326  VSLAPRFIG-DFEKGIDYKGD--LNVFKTE--------
SEQ_327  VSLAPRFCG-EFQKGIDYIGD--VEQFEVE--------
SEQ_328  TSLAPRFCG-EFQKGIDYIGD--LKQFTDE--------
SEQ_329  VGLAPRFVG-RFEKGVDYRGD--LGELKAD--------
SEQ_330  KSLAPKFPG-EFQKGIDYIGD--IKEFERA--------
SEQ_331  VSLAPRFVG-KFQKGVDYMGN--LAEFEAE--------
SEQ_332  WSLAPRFPG-VFEKAVDYEGE--VERFAQA--------
SEQ_333  FSIAPKFPG-EFEKAVDYIGD--LDEFLLE--------
SEQ_334  DTLAPRFPG-EFQKAIDYIGN--IQEFKKS--------
SEQ_335  RTIAPKFSG-AFYKGVDYVGD--PHTFARE--------
SEQ_336  DFIAPNV---GFRKREDYSGD--LHALYER--------
```

FIG. 17 CONTINUED

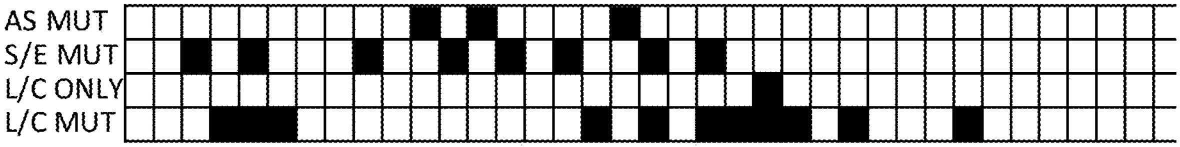

RESNUM 202 203 204 205 206 207 208 209 210 211 212 213 214 215 216 217 218 219 220 221 222 223 224 225 226 227 228

SEQ_337 I S L A P R F V G - R L E K G V D Y I G D - - L E E F E A H - - - - - - - -
SEQ_338 K S L A P K F P G - E F Q K G I D Y I G D - - I K K F E N E - - - - - - - -
SEQ_339 W S L A P K F P G - E F Q K A I D Y K G D - - I K K F T S G - - - - - - - -
SEQ_340 W S L A P K F P G - E F Q K A I D Y K G D - - I N K F A V E - - - - - - - -
SEQ_341 W S L A P K F P G - E F Q K A I D Y K G D - - I N K F A V E - - - - - - - -
SEQ_342 F S I A P K F P G - E F E K A V D Y I G D - - L D E F S L E - - - - - - - -
SEQ_343 F S I A P K F P G - E F E K A V D Y I G D - - L D E F L L E - - - - - - - -
SEQ_344 F S I A P K F P G - E F E K A V D Y I G D - - L D E F L L E - - - - - - - -
SEQ_345 F S I A P K F P G - E F E K A V D Y I G D - - L D E F L L E - - - - - - - -
SEQ_346 F S I A P K F P G - E F E K A I D Y V G D - - V N E F E R E - - - - - - - -
SEQ_347 D T L A P R F P G - E F Q K A I D Y I G N - - L Q E F K K S - - - - - - - -
SEQ_348 F S I A P K F P G - E F E K A I D Y V G D - - V D E F K K A - - - - - - - -
SEQ_349 D T L A P R F P G - E F Q K G I D Y I G N - - I Q E F K K S - - - - - - - -
SEQ_350 R T I A P K F S G - S F Y K G V D Y V G D - - P E V F A R E - - - - - - - -
SEQ_351 E F I A P N I - - - G F R K R E D Y R G D - - L Q E L Y N R - - - - - - - -
SEQ_352 T N L A L R F I G - E W E K G I D Y K G D - - L A Q F E R E - - - - - - - -
SEQ_353 W S L A P K F P G - E F Q K A I D Y I G D - - V D K F A V E - - - - - - - -
SEQ_354 Q N L A P H F I G - D W E K G I D Y I G N - - I D T F K E E - - - - - - - -
SEQ_355 T S L A P R F C G - E F Q K G I D Y I G D - - L Y Q F E D E - - - - - - - -
SEQ_356 N S L A P R F V G - E F Q K G I D Y I G D - - L E Q F E K E - - - - - - - -
SEQ_357 N S L A P R F V G - E F Q K G I D Y I G D - - L E Q F E K E - - - - - - - -
SEQ_358 N S L A L N F V G - E F Q K G I D Y I G D - - L E K F E K D - - - - - - - -
SEQ_359 E S L A P R F C G - E F Q K G I D Y I G D - - M D Q F E K E - - - - - - - -
SEQ_360 W S L A P K F P G - E F Q K A I D Y I G D - - V D K F A V E - - - - - - - -
SEQ_361 V S L A P R Y V G - T F E K G V D Y I G D - - L D A F E Q S - - - - - - - -
SEQ_362 W S L A P K F P G - E F Q K A I D Y I G D - - V D K F A V E - - - - - - - -
SEQ_363 W S L A P K F P G - E F Q K A I D Y I G D - - V D K F A V E - - - - - - - -
SEQ_364 W S L A P K F P G - E F E K A V D Y R G D - - I D K F T V E - - - - - - - -
SEQ_365 W S L A P K F P G - E F Q K A I D Y K G D - - I K K F T S E - - - - - - - -
SEQ_366 T T M A P R F Y G - E F Q K A I D Y I G D - - K D R F E R E - - - - - - - -
SEQ_367 D T L A P R F P G - E F Q K G I D Y I G N - - V Q E F K K S - - - - - - - -
SEQ_368 D T L A P R F P G - E F Q K G I D Y I G N - - I K E F K N S - - - - - - - -
SEQ_369 D T L A P R F P G - E F Q K A I D Y I G N - - I Q E F K K S - - - - - - - -
SEQ_370 D T L A P R F P G - E F Q K G I D Y I G N - - I Q E F K K S - - - - - - - -
SEQ_371 Q T I A P K F T G - R F N K G V D Y V G D - - I E T F R K E - - - - - - - -
SEQ_372 Q T I A P K F T G - R F N K G V D Y V G N - - L T Q F E R E - - - - - - - -
SEQ_373 D F I A P N V - - - G F Q K R E D F T G D - - L E T L H S R - - - - - - - -

FIG. 17 CONTINUED

AS MUT
S/E MUT
L/C ONLY
L/C MUT

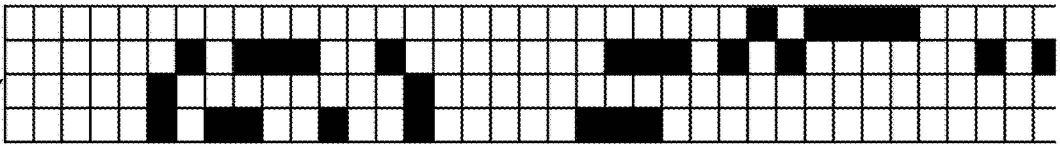

RESNUM 229 230 231 232 233 234 235 236 237 238 239 240 241 242 243 244 245 246 247 248 249 250 251 252 253 254 255

```
SEQ_6   ------KVRGILEEVK------REDLFVEGHSTDYQARY
SEQ_1   ------RAAALKDFIES-----HSQLVYEAHSTDYQTAP
SEQ_2   ------AARPLKTFIEG-----VPGMVYEAHSTDYQTRA
SEQ_3   ------EAKELTDALKN-----YKTFVFEGHSTDYQTRE
SEQ_4   ------QAENLVSALKK-----YPNLVFEAHSTDYQPAK
SEQ_5   ------KVKPLKELLAK-----Y-NIVFEGHSTDYQTKE
SEQ_7   ------AAQRLTEIVRP-----T-GALLKGHYTDWVENP
SEQ_8   ------RARRLDALVRR-----Y-GALIKGHYTDDVDRL
SEQ_9   SIDIPQTIKVAQALKEN---NLKVRIAQHG----ITG
SEQ_10  ------QAENLVSALKK-----YPNLVFEAHSTDYQPAK
SEQ_11  ------KAEKLVNSLRG-----VKGIVFEGHSTDYQTKT
SEQ_12  ------RARELTEAIKK-----HPNIVFEGHSTDYQTAK
SEQ_13  ------KAKDLMASIQE-----FPNLVFEGHSTDYQTKI
SEQ_14  ------KAKDLSKALKE-----YDNLVFEAHSTDYQSPK
SEQ_15  ------AAAGLARAIEP-----YGRLVYEAHSTDYQTRQ
SEQ_16  ------KAVALSKMVEA-----YDTLLFEAHSTDYQTPQ
SEQ_17  ------KTKELCTYLSRY----YPSLYFEAHSTDYQTAG
SEQ_18  ------KVRKILEEVK------KENLFVEGHSTDYQTKR
SEQ_19  ------RACRLDALVRR-----Y-GALIKGHYTDDVDRL
SEQ_20  ------RARRLDALVRR-----Y-GALIKGHYTDGVDRL
SEQ_21  ------NAADLAKMAKK-----Y-GVGLKEHNGDYLDDV
SEQ_22  ------NSKKLADIAKK-----Y-SVGLKEHNGDYLDEA
SEQ_23  SIDIPQTMAVARALRDN---NLNVRIAQHG----ITG
SEQ_321 ---IITHSKISKEL--------GGYKLSLHSGSD----
SEQ_322 ---LDKHVAIVKMF--------TGYRLSLHSGSD----
SEQ_323 ---LSMHCEIVKSL--------SGYRLSLHSGSD----
SEQ_324 ---LKLHVAIARTL--------GPYKLSLHSGSD----
SEQ_325 ---FQVHAEIADHF---------GYKISIHSGSD----
SEQ_326 ---YEKHLDITKYF--------GSYKISLHSGSD----
SEQ_327 ---LREHALIAEHF---------GYKLSIHSGSD----
SEQ_328 ---FAVHAAIADHF---------GYKISVHSGSD----
SEQ_329 ---LAGHAALARSL--------GPYKLSLHSGSD----
SEQ_330 ---LKKHYALTKAL--------EGYRLSLHSGSD----
SEQ_331 ---LIRHVAVMRHF--------HCYKLSVHTGSD----
SEQ_332 ---AALHTAVARTF--------GGHRLSLHSGSE----
SEQ_333 ---LKKHYQLSRMI--------GGYKISLHSGSD----
SEQ_334 ---LIKQDKIAKYF---------GYRLSIHSGSD----
SEQ_335 ---FEDDLCVVRYAREQFALPEGLKLSVHSGSD----
SEQ_336 ---LRNLHAVVSSM---------NAYLSIHSGSGSHPY
```

FIG. 17 CONTINUED

AS MUT
S/E MUT
L/C ONLY
L/C MUT

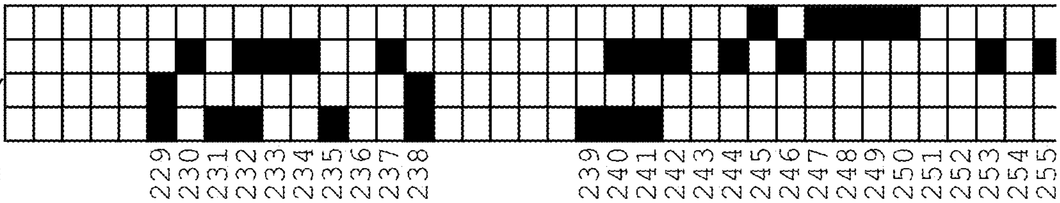

RESNUM 229 230 231 232 233 234 235 236 237 238 239 240 241 242 243 244 245 246 247 248 249 250 251 252 253 254 255

```
SEQ_337 ---LKLHVAIARTL-------GPYKLSLHSGSD----
SEQ_338 ---LKKQYALTKAL-------EGYRLSLHSGSD----
SEQ_339 ---LKKHYFLSKKL-------GGYKLSLHSGSD----
SEQ_340 ---LKKHYAISQQL-------GGYKLSLHSGSD----
SEQ_341 ---LKKHYAISQQF-------GGYKLSLHSGSD----
SEQ_342 ---LKKHYQLSRMI-------GGYKISLHSGSD----
SEQ_343 ---LKKHYQLSRMI-------GGYKISLHSGSD----
SEQ_344 ---LKKHYQLSRMI-------GGYKISLHSGSD----
SEQ_345 ---LKKHYQLSRMI-------GGYKISLHSGSD----
SEQ_346 ---LKKHYDLTKLI-------GGYKLSLHSGSD----
SEQ_347 ---LIKQDKIAKYF--------GYRLSIHSGSD----
SEQ_348 ---LKKHYDLTKLI-------GGYKLSLHSGSD----
SEQ_349 ---LIKQDKIAKYF--------GYRLSIHSGSD----
SEQ_350 ---FEDDLCVVRYAREAFRLPEGLKLSVHSGSD----
SEQ_351 ---VRKLHTIASNN--------GVYLSIHSGSGAHPY
SEQ_352 ---IKMHAEIARMF-------EGYKISLHSGSD----
SEQ_353 ---LKKHQFLSREF-------GGYKLSLHSGSD----
SEQ_354 ---FKLHCQIASQM-------GGYKLSLHSGSD----
SEQ_355 ---FKRHAAIADHF--------GYRLSIHSGSD----
SEQ_356 ---FKVHADIADRF--------GYKLSIHSGSD----
SEQ_357 ---FKVHADIADRF--------GYKLSIHSGSD----
SEQ_358 ---FEIHADIADRF--------GYKLSIHSGSD----
SEQ_359 ---LKEHADIAKHF--------GYKLSIHSGSD----
SEQ_360 ---LKKHQFLSREF-------GGYKLSLHSGSD----
SEQ_361 ---IAQHMAVSRTF-------GPYKLSLHSGSD----
SEQ_362 ---LKKHQFLSREF-------GGYKLSLHSGSD----
SEQ_363 ---LKKHQFLSREF-------GGYKLSLHSGSD----
SEQ_364 ---LNKHCAVARML-------GGYRLSLHSGSD----
SEQ_365 ---LKKHYFLTKEL-------GGYKLSLHSGSD----
SEQ_366 ---FVLHEAIAEYF--------GYKLSIHSGSD----
SEQ_367 ---LIKQEKIAKYF--------GYRLSIHSGSD----
SEQ_368 ---LMKHHKIASYF--------GYRLSIHSGSD----
SEQ_369 ---LIKQNKIAKYF--------GYRLSIHSGSD----
SEQ_370 ---LIKQDKIAKYF--------GYRLSIHSGSD----
SEQ_371 ---YEANLMVIDYAIQKFGFPPELKLSIHSGSD----
SEQ_372 ---FNQDILVIAYASKEFGLPKNLKLSVHSGSD----
SEQ_373 ---VKTLHEVASFF--------GSLLSFHSGSGSSPY
```

FIG. 17 CONTINUED

| RESNUM | 256 | 257 | 258 | 259 | 260 | 261 | 262 | 263 | 264 | 265 | 266 | 267 | 268 | 269 | 270 | 271 | 272 | 273 | 274 | 275 | 276 | 277 |
|---|---|---|---|---|---|---|---|---|---|---|---|---|---|---|---|---|---|---|---|---|---|---|
| AS MUT | | | | | | | | | | | | | | ■ | ■ | ■ | ■ | | | | | |
| S/E MUT | ■ | | | ■ | | | ■ | | | | ■ | | | | | | | ■ | | | | |
| L/C ONLY | | | | | | | | | | | | | | ■ | | | | | | | | |
| L/C MUT | | | ■ | | | | ■ | | | | | | | | | | | | | | | |

```
SEQ_6    ALRNMVEDGVRIL---------------KVGPALTAA
SEQ_1    LLRQMVKDHFAIL---------------KVGPALTFA
SEQ_2    SLRALVEDHFSIL---------------KVGPALTFA
SEQ_3    SLKQMVEDGIAIL---------------KVGPALTFA
SEQ_4    LLKEMVRDGFAIL---------------KVGPELTFA
SEQ_5    NLKRMVECGIAIL---------------KVGPALTFT
SEQ_7    AD--YPRVGMGGA---------------NVGPEFTAA
SEQ_8    DL--YPKAGIGGA---------------NVGPGLAAI
SEQ_9    TPRELIHDHFPHG-------------EIIKGNVGTFY
SEQ_10   LLKEMVRDGFAIL---------------KVGPELTFA
SEQ_11   KLKEMVEDGIAIL---------------KVGPALTYG
SEQ_12   ALKEMVEDGVAIL---------------KVGPALTFA
SEQ_13   KLRELVEDGVGIL---------------KVGPALTFA
SEQ_14   SLREMVLDGFNIL---------------KVGPALTFG
SEQ_15   ALRDLVADHFAIL---------------KVGPALTFA
SEQ_16   ALRQLVKDHFAIL---------------KVGPALTFA
SEQ_17   SLKQMVKDGIRIL---------------KVGPALTDA
SEQ_18   ALRDMVEDGVRIL---------------KVGPALTAS
SEQ_19   DL--YPKAGIGGA---------------NVGPGLAAI
SEQ_20   DL--YPQAGIGGA---------------NVGPGLAAI
SEQ_21   ILLAHIPSQITAT---------------NVAPQYGTE
SEQ_22   ILLEHPALGITAM---------------NVAPEFGSV
SEQ_23   TPIEMIHNHFPHG-------------DIIKGNVGTFY
SEQ_321  --------KFSVYPIFSEAT----EGEFHVKTAGTN-
SEQ_322  --------KFSVYPILAEKT----DRTIHVKTAGTS-
SEQ_323  --------KFSVYRIFTHYC----DGKLHVKTAGTS-
SEQ_324  --------KFALYPLFARHA----GELFHLKTAGTS-
SEQ_325  --------KFSVFQTIGRYT----EGRFHVKTAGTN-
SEQ_326  --------KFSAYRVIGSLK----GAYTHVKTAGTS-
SEQ_327  --------KFMVFPIIAEYT----KGVFHVKTAGTN-
SEQ_328  --------KFKVFPVVGEKT----NGRYHLKTAGTN-
SEQ_329  --------KFSVYPLIAEAT----GGMVHLKTAGTS-
SEQ_330  --------KFSIYKIFYKIT----EGNFHIKTSGTS-
SEQ_331  --------KFSIYPILARCA----GENVHIKTAGTS-
SEQ_332  --------KFRILPVFREAT----GGRFHVKTSGTT-
SEQ_333  --------KFSIYRIFSDIT----EKNFHIKTSGTS-
SEQ_334  --------KFSIYPIIGEVT----QGNYHLKTSGTS-
SEQ_335  --------KFSLYPLVREILSRHPQEGVHLKTAGTT-
SEQ_336  SDK-----GFGVWGVVGRAT----GGAVKYKMSGVL-
```

FIG. 17 CONTINUED

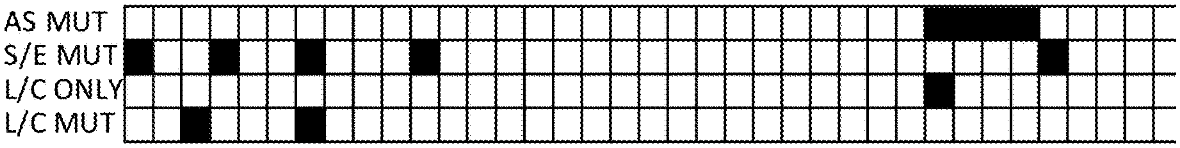

| RESNUM | 256 257 258 259 260 261 262 263 264 265 266 267 268 269 270 271 272 273 274 275 276 277 |
|---|---|
| SEQ_337 | - - - - - - - - - K F A L Y P L F A R H A - - - - G E L F H L K T A G T S - |
| SEQ_338 | - - - - - - - - - K F S I Y K S F Y K I T - - - - E G N F H I K T S G T S - |
| SEQ_339 | - - - - - - - - - K F S I Y K I F N E I T - - - - E G N F H I K T S G T S - |
| SEQ_340 | - - - - - - - - - K F S I Y E I F S E V T - - - - Q H S F H I K T S G T S - |
| SEQ_341 | - - - - - - - - - K F S I Y E I F S E V T - - - - Q H S F H I K T S G T S - |
| SEQ_342 | - - - - - - - - - K F S I Y R I F S D I T - - - - E K N F H I K T S G T S - |
| SEQ_343 | - - - - - - - - - K F S I Y R I F S D I T - - - - E K N F H I K T S G T S - |
| SEQ_344 | - - - - - - - - - K F S I Y R I F S D I T - - - - E K N F H I K T S G T S - |
| SEQ_345 | - - - - - - - - - K F S I Y R I F S D I T - - - - E K N F H I K T S G T S - |
| SEQ_346 | - - - - - - - - - K F S I Y K I F S Q T T - - - - E K N F H I K T S G T S - |
| SEQ_347 | - - - - - - - - - K F S I Y P I I G E V T - - - - Q G N Y H L K T S G T S - |
| SEQ_348 | - - - - - - - - - K F S I Y K I F S Q T T - - - - E R N F H I K T S G T S - |
| SEQ_349 | - - - - - - - - - K F S I Y P I I G E V T - - - - Q G N Y H L K T S G T S - |
| SEQ_350 | - - - - - - - - - K F S L Y P L I K D I L S R H P Q E G V H L K T A G T T - |
| SEQ_351 | S D K - - - - - - G V G V W S T I G R A T - - - - D G L V K Y K M S G V L - |
| SEQ_352 | - - - - - - - - - K F S V Y P A F A S A T - - - - G G L F H V K T A G T S - |
| SEQ_353 | - - - - - - - - - K F S I Y K V F S E I T - - - - E G E F H I K T S G T S - |
| SEQ_354 | - - - - - - - - - K F S V Y P I F A E E T - - - - N G Y F H V K T A G T S - |
| SEQ_355 | - - - - - - - - - K F S V F P I I G Q Y T - - - - R G R V H I K T A G T N - |
| SEQ_356 | - - - - - - - - - K F S V F P I I G R H T - - - - Q G R V H V K T A G T N - |
| SEQ_357 | - - - - - - - - - K F S V F P I I G R H T - - - - Q G R V H V K T A G T N - |
| SEQ_358 | - - - - - - - - - K F S I F P I I G R Q T - - - - E G R A H I K T A G T N - |
| SEQ_359 | - - - - - - - - - K F S V F P I I G K Y T - - - - D G L L H I K T A G T N - |
| SEQ_360 | - - - - - - - - - K F S I Y K V F S E I T - - - - E R E F H I K T S G T S - |
| SEQ_361 | - - - - - - - - - K F S I Y P I A S R V A - - - - G D L V H L K T A G T S - |
| SEQ_362 | - - - - - - - - - K F S I Y K V F S E I T - - - - E G E F H I K T S G T S - |
| SEQ_363 | - - - - - - - - - K F S I Y K V F S E I T - - - - E G E F H I K T S G T S - |
| SEQ_364 | - - - - - - - - - K F S V Y R I F N D A T - - - - Q H N F H I K T S G T S - |
| SEQ_365 | - - - - - - - - - K F S I Y K I F N E I T - - - - E G N F H I K T S G T S - |
| SEQ_366 | - - - - - - - - - K L S V Y E I I G R V A - - - - K N G W H V K T A G T N - |
| SEQ_367 | - - - - - - - - - K F S I Y P I I G E V T - - - - Q G N Y H L K T S G T S - |
| SEQ_368 | - - - - - - - - - K F S I Y P Y V S Q I T - - - - Q G N Y H L K T S G T S - |
| SEQ_369 | - - - - - - - - - K F S I Y P I I G E V T - - - - Q G N Y H L K T S G T S - |
| SEQ_370 | - - - - - - - - - K F S I Y P I I G E V T - - - - Q G N Y H L K T S G T S - |
| SEQ_371 | - - - - - - - - - K F S I Y P V I K E L S Q K H - N K G F H L K T A G T T - |
| SEQ_372 | - - - - - - - - - K F S I Y P I I K K A I Y T H - H A G L H L K T A G T T - |
| SEQ_373 | S M K - - - - - - G K G V H D I I R R A A - - - - G G L F K Y K I S G V Y - |

FIG. 17 CONTINUED

AS MUT
S/E MUT
L/C ONLY
L/C MUT

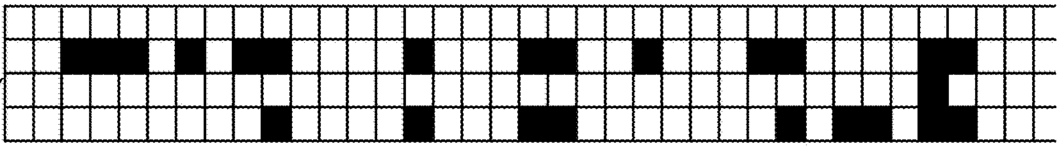

```
RESNUM   278 279 280 281 282 283 284 285 286 287 288 289 290 291 292 293 294 295 296 297 298 299 300 301 302 303 304 305 306
SEQ_6    F R R G V F L L S N I - - E D - - - E I I P E - - - R E R S N I K R V I L
SEQ_1    L R E A I F A L A F M - - E K - - - E L L P L H R A L K P S A I L E T L D
SEQ_2    Y R E A V F A L E H I - - E R - - - E I L - G R Q D M P L S R L S E V L D
SEQ_3    L R E A L I A L N N I - - E N - - - E L L N N V D S I K L S N F T N V L V
SEQ_4    L R E G L F A L N I I - - E K - - - E L F K D N H D I E M S N F I D I L D
SEQ_5    L R E A L V A L S H I - - E E - - - E I Y S N - E K E K L S R F R E V L L
SEQ_7    E F E A L E A L E R R - - E Q - - - R L C A N - R K L Q P A C F L A A L E
SEQ_8    E F E A L E A L V E E - - A R - - - - - - - - - - R R G L S V T F D Q A I R
SEQ_9    M N L V W D A F K L F - - E P - - - E L Y N D I W N W T V E N Y K Q K S P
SEQ_10   L R E G L F A L N I I - - E K - - - E L F K D N H D I E M S N F I D I L D
SEQ_11   L R E A L F A L N H I - - E N - - - E I F K Y R A D I K L S N F I N V L E
SEQ_12   L R E A F F A L S S I - - E K - - - E L F Y D T P G L - C S N F V E V V E
SEQ_13   M R E G M F A L E N I - - E K - - - E L I Y G - T D I T P S G F Q D A L E
SEQ_14   F R E A A F A L N K I - - E E - - - E M F R F R P D I E E S R F I Q T L D
SEQ_15   F R E A V F A L A A V - - E E - - - E W L A G Q A G V V L S R L R E E L E
SEQ_16   L R E A L F S L A A I - - E E - - - E L L P A K A - - - S S G L R H V L E
SEQ_17   Y R R G M F A L N F I - - E K - - - E S I D E - - - E K Q S R L V E N V L
SEQ_18   F R R G V F L L S S I - - E D - - - E L I S E - - - D K R S N I K K V V L
SEQ_19   E F E A L E V L V D E - - A R - - - - - - - - - - R R G L S V T F D Q A I R
SEQ_20   E F E A L E A L V A E - - A H - - - - - - - - - - R R K L P V T F D R T I R
SEQ_21   E T R A L L K L A K L - - E E - - - K L K E Q G L I G Q P S K V K D V L L
SEQ_22   E T Q A Y L K L I E V - - E N - - - N L Y E H G I I S K K S N L E K V I K
SEQ_23   L N L V W D V L K V F - - E P - - - Q L Y G D I W D W T I E N F S E K Y P
SEQ_321  Y L E A I R V V A V K - - D P - - - E L Y R E I H K F A L T K F E Q D R K
SEQ_322  Y L E A I R V V A K F - - A P - - - D L Y R Q I H K Y A L S R F D Q D K A
SEQ_323  Y L E A I R T V A E A - - S P - - - S L Y R N I H K Y A L T C F E K D N T
SEQ_324  Y L E A L R A V A E L - - D P - - - P L F R E I L D F A R D R Y E T D R A
SEQ_325  W L E A V R V V A E K - - N P - - - N L Y R K M H Q Y A L E H F D E A R A
SEQ_326  Y L E A L R V V A A K - - E P - - - A L F R D I L D F C R D L Y E T E K R
SEQ_327  W L E A I R V I A A T - - N P - - - D L Y R R M H V F A L E N F E E A L K
SEQ_328  W L E A V R V I A R H - - K P - - - D L Y R R M H A F A L E H L E D A K K
SEQ_329  Y L E A L R V A A Q V - - A P - - - G L F R E I L T L G R E R F A V D K Q
SEQ_330  W L E A V K V I A K F - - F P - - - D L F V E L Y Q I A L E N L E E S K K
SEQ_331  Y L E A L R V A A L R - - A P - - - D L F R Q M L E T G R T C Y E K D K K
SEQ_332  W L Q A V R V V A R A - - V P - - - A L F A E L Y A I A R A H L E E S R R
SEQ_333  W L Q A I N L I Y N Y - - D K - - - E F Y R E L Y K I A L E N L E E S K K
SEQ_334  Y L E A I K V V A Q K - - D P - - - E F F K K I W Q T C L D K R E E M D K
SEQ_335  W L E E V A G L A E A - - G G E A L A L A K E I A L T C Y S M I E E L C A
SEQ_336  V Q L L L E V M A S Y P P G S E T R R L Y E E I Y S E V V E H L R W V V K
```

FIG. 17 CONTINUED

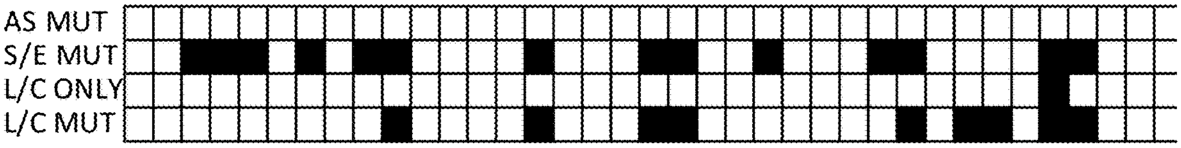

| RESNUM | 278 | 279 | 280 | 281 | 282 | 283 | 284 | 285 | 286 | 287 | 288 | | | 289 | 290 | | | | 291 | 292 | 293 | 294 | 295 | | | | 296 | 297 | 298 | 299 | 300 | 301 | 302 | 303 | 304 | 305 | 306 |
|---|---|---|---|---|---|---|---|---|---|---|---|---|---|---|---|---|---|---|---|---|---|---|---|---|---|---|---|---|---|---|---|---|---|---|---|---|---|
| SEQ_337 | Y | L | E | A | L | R | A | V | A | E | L | - | - | D | P | - | - | - | P | L | F | R | E | I | L | D | F | A | R | D | R | Y | E | T | D | R | A |
| SEQ_338 | W | L | E | A | V | K | T | I | A | R | Y | - | - | S | P | - | - | - | D | L | F | L | E | L | Y | H | I | A | L | E | N | L | E | E | S | K | K |
| SEQ_339 | W | L | Q | A | I | N | I | I | F | E | R | - | - | D | K | - | - | - | D | L | F | N | D | L | Y | K | I | A | L | D | N | L | E | E | S | K | K |
| SEQ_340 | W | L | Q | A | V | N | L | I | F | E | K | - | - | N | K | - | - | - | K | L | F | Y | E | L | Y | K | I | A | L | N | N | L | E | E | S | K | K |
| SEQ_341 | W | L | Q | A | V | N | L | I | F | E | K | - | - | D | K | - | - | - | K | L | F | Y | E | L | Y | K | I | A | L | N | N | L | E | E | S | K | K |
| SEQ_342 | W | L | Q | A | I | N | L | I | Y | N | Y | - | - | D | K | - | - | - | E | F | Y | R | E | L | Y | K | I | A | L | E | N | L | E | E | S | K | K |
| SEQ_343 | W | L | Q | A | I | N | L | I | Y | N | Y | - | - | D | K | - | - | - | E | F | Y | R | E | L | Y | K | I | A | L | E | N | L | E | E | S | K | K |
| SEQ_344 | W | L | Q | A | I | N | L | I | Y | D | Y | - | - | D | K | - | - | - | E | F | Y | R | E | L | Y | K | I | A | L | E | N | L | E | E | S | K | K |
| SEQ_345 | W | L | Q | A | V | N | L | I | Y | K | F | - | - | D | K | - | - | - | E | F | Y | R | K | L | Y | K | I | A | L | S | N | L | E | E | S | K | K |
| SEQ_346 | W | L | Q | A | V | N | L | I | Y | K | S | - | - | D | K | - | - | - | E | F | Y | R | E | L | Y | K | I | A | L | S | N | L | E | E | S | K | K |
| SEQ_347 | Y | L | E | A | I | K | I | V | A | Q | K | - | - | D | P | - | - | - | E | F | F | K | K | I | W | K | T | C | L | D | K | R | E | E | M | D | K |
| SEQ_348 | W | L | Q | A | V | N | L | I | Y | K | S | - | - | D | R | - | - | - | E | F | Y | R | E | L | Y | K | I | A | L | S | N | L | E | E | S | K | K |
| SEQ_349 | Y | L | E | A | I | K | V | V | A | Q | K | - | - | D | P | - | - | - | E | F | F | K | K | I | W | Q | T | C | L | D | K | R | E | E | M | D | K |
| SEQ_350 | W | L | E | E | V | T | G | L | A | E | S | - | - | G | G | E | A | L | A | L | A | K | E | I | A | L | T | C | Y | S | M | I | E | E | L | C | A |
| SEQ_351 | I | Q | L | L | L | E | V | M | S | R | F | P | K | G | S | T | V | R | R | V | Y | E | E | I | Y | D | A | V | L | D | H | L | K | K | D | I | S |
| SEQ_352 | Y | L | E | A | V | K | V | I | S | M | V | - | - | N | P | - | - | - | E | L | F | R | E | I | Y | R | C | T | L | D | H | F | E | E | D | R | K |
| SEQ_353 | W | F | Q | A | V | N | L | I | F | E | K | - | - | D | K | - | - | - | E | L | F | K | E | L | Y | Q | I | A | L | Y | N | L | E | E | S | K | K |
| SEQ_354 | W | L | E | A | V | K | A | I | V | V | C | - | - | D | P | - | - | - | A | L | Y | R | E | M | Y | E | F | A | L | K | C | F | E | K | D | S | F |
| SEQ_355 | W | L | E | A | L | R | V | V | A | R | I | - | - | N | P | - | - | - | A | L | F | R | E | I | Y | A | F | A | G | E | V | F | G | E | A | K | K |
| SEQ_356 | W | L | E | A | I | R | V | V | A | E | N | - | - | N | P | - | - | - | S | L | Y | R | D | I | H | A | Y | A | L | K | K | F | E | A | A | K | E |
| SEQ_357 | W | L | E | A | I | R | V | V | A | E | N | - | - | N | P | - | - | - | S | L | Y | R | D | I | H | A | Y | A | L | K | K | F | E | A | A | K | E |
| SEQ_358 | W | L | E | A | I | R | V | V | A | E | N | - | - | D | P | - | - | - | S | L | Y | R | E | I | H | S | Y | A | L | K | K | F | E | E | A | K | E |
| SEQ_359 | W | L | E | A | V | R | V | V | A | Q | E | - | - | N | P | - | - | - | D | L | Y | R | R | M | H | V | Y | A | E | E | H | F | E | E | T | L | K |
| SEQ_360 | W | L | Q | A | V | N | L | I | F | E | K | - | - | D | K | - | - | - | K | L | F | K | E | L | Y | Q | I | A | L | Y | N | L | E | E | S | K | K |
| SEQ_361 | Y | L | E | A | L | R | A | I | A | A | M | - | - | A | P | - | - | - | D | L | F | R | Q | I | V | A | F | A | R | E | R | Y | P | T | D | R | A |
| SEQ_362 | W | L | Q | A | V | N | L | I | F | E | K | - | - | D | K | - | - | - | E | L | F | K | E | L | Y | Q | I | A | L | Y | N | L | E | E | S | K | K |
| SEQ_363 | W | L | Q | A | V | N | L | I | F | E | K | - | - | D | K | - | - | - | K | L | F | K | E | L | Y | Q | I | A | L | Y | N | L | E | E | S | K | K |
| SEQ_364 | W | L | Q | A | L | N | V | I | H | E | K | - | - | D | R | - | - | - | Q | L | F | K | E | L | Y | N | I | A | L | D | N | L | E | E | S | K | K |
| SEQ_365 | W | L | Q | A | I | S | L | I | F | E | K | - | - | D | K | - | - | - | D | L | F | N | D | L | Y | K | I | A | L | D | N | L | E | E | S | K | K |
| SEQ_366 | W | L | E | A | L | R | V | I | A | H | K | - | - | D | P | - | - | - | E | F | M | V | E | L | Y | K | Y | A | Y | E | H | L | D | D | V | K | D |
| SEQ_367 | F | L | E | A | I | K | V | V | A | Q | K | - | - | D | P | - | - | - | E | F | F | K | K | I | W | Q | T | C | L | D | K | R | E | E | M | D | K |
| SEQ_368 | Y | L | Q | A | L | K | I | I | A | Q | K | - | - | A | P | - | - | - | D | F | F | K | E | I | W | K | T | C | L | D | K | R | T | E | M | D | K |
| SEQ_369 | Y | L | E | A | I | K | V | V | A | Q | K | - | - | D | P | - | - | - | E | F | F | K | K | I | W | Q | T | C | L | D | K | R | E | E | M | D | K |
| SEQ_370 | Y | L | E | A | I | K | V | I | A | Q | K | - | - | D | P | - | - | - | E | F | F | K | K | I | W | Q | T | C | L | D | K | R | E | E | M | D | K |
| SEQ_371 | W | L | E | E | V | I | G | L | A | M | A | - | - | G | G | E | A | L | L | F | V | K | N | I | Y | S | R | A | L | D | N | I | E | K | L | C | A |
| SEQ_372 | W | L | E | E | L | I | G | L | A | S | A | - | - | G | D | E | G | L | R | I | V | Q | Q | I | Y | R | E | T | Y | Y | R | F | D | E | L | C | A |
| SEQ_373 | F | E | L | L | M | Q | L | M | S | R | S | D | I | - | P | S | V | R | R | L | Y | E | E | I | Y | D | A | V | I | E | L | L | E | D | Q | V | K |

FIG. 17 CONTINUED

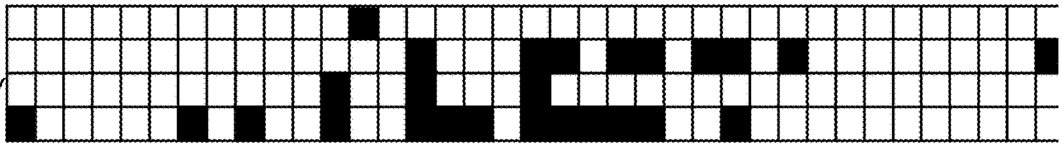

```
RESNUM   307 308 309 310 311 312 313 314 315 316 317 318 319 320 321 322 323 324 325 326 327 328 329 330 331 332 333 334
SEQ_6    E T M L R D D R Y W R K Y Y K D S - K R L E L D I W Y N - - - - - - - - L
SEQ_1    Q T M D K N P A Y W Q K H Y G G T K E E V R F A Q R F S - - - - - - - - L
SEQ_2    E V M L N D P R H W Q G Y F A G A P A E Q A L A R R Y S - - - - - - - - F
SEQ_3    S E M I N N P E H W K N H Y F G D D A R K K F L C K Y S - - - - - - - - Y
SEQ_4    T A M L N N P K Y W E Q Y Y Y G D D N K I R I A R K Y S - - - - - - - - Y
SEQ_5    N T M L T C K D H W S K Y F D E N D K L I K S K L L Y S - - - - - - - - Y
SEQ_7    E A V V A S D - R W R K W L Q P D E I G K P F A E L T P A R - - R R W L V
SEQ_8    R A V V E S G - R W T K W L Q P E E K G Q P F D A L D P E R - - Q R W L V
SEQ_9    D K - - - T D S E I F G K Y S K F A I K Q F F D R I Y S - - - - - - - - V
SEQ_10   T A M L N N P K Y - - - - - - - - - - - - - - - - - - - - - - - - - - - -
SEQ_11   T S M V E E P T H W K Q H Y H G D A E D I K Y A M R Y S - - - - - - - - Y
SEQ_12   R A M L D N P K H W E K Y Y Q G E E R E N R L A R K Y S - - - - - - - - F
SEQ_13   A E M L K E G K H W R K H Y Q G T E L E L R M K R K Y S - - - - - - - - F
SEQ_14   Y N M V K H P E N W I K H Y S G T S E N I R F S R M Y S - - - - - - - - L
SEQ_15   A A M I Q D P T H W R G Y Y R G D E R H Q R L A R R Y S - - - - - - - - Y
SEQ_16   N V M L D R P E Y W Q S H Y H G D G N A R R L A R G Y S - - - - - - - - Y
SEQ_17   K V M D E Y P R Y W E D Y Y N S V G K T L R L D Q M Y S - - - - - - - - Y
SEQ_18   E T M L K D D K Y W R K Y Y K D S - E R L E L D I W Y N - - - - - - - - L
SEQ_19   R A V V E S G - R W T K W L Q P E E K G R P F E A L D P E R - - Q R W L V
SEQ_20   Q A V I E S G - R W Q K W L R P E E K G R P F E A L P P E R - - Q R W L V
SEQ_21   Y H S I K S E - R W R K W M V G S Q R E L S V E E I V K D E E L S T E I L
SEQ_22   E E A V K S L - R W K K W M V G D K V N L S I E E V L S D K D L T D L I T
SEQ_23   D K - - - S E N E I F G K Y S K Y A I K E F F D R I Y S - - - - - - - - V
SEQ_321  S Y H V T T D - - - - - - - - - - - - - L S K - - I P D V D K M K N - - -
SEQ_322  S Y H V T T E - - - - - - - - - - - - - L S K - - I P D V D K L E D - - -
SEQ_323  S Y H V T A D - - - - - - - - - - - - - I N K - - I P D V D N V E D - - -
SEQ_324  T Y H V S A L - - - - - - - - - - - - - L E R - - V P K A S D V P D - - -
SEQ_325  Y Y H V T T D - - - - - - - - - - - - - I E G - - I V P L E K V N D - - -
SEQ_326  S Y H V S A D - - - - - - - - - - - - - I N K - - V K P A N Q Y S D - - -
SEQ_327  Y Y H V T P D - - - - - - - - - - - - - L N S - - F E K L E N V E D - - -
SEQ_328  Y Y H I G A K - - - - - - - - - - - - - V E N - - I P A L E T L A D - - -
SEQ_329  S Y H I S A A - - - - - - - - - - - - - L A R - - V S E A D T L T D - - -
SEQ_330  A Y K V N I T - - - - - - - - - - - - - K E E - - F P K E I K E - - - - -
SEQ_331  T Y F L D C R - - - - - - - - - - - - - P E R - - V P P A A T L D D - - -
SEQ_332  D Y P I A L Q - - - - - - - - - - - - - P E A - - L P P A L P D - - - - -
SEQ_333  S Y K V L I K - - - - - - - - - - - - - R E D - - F C K E P E L - - - - -
SEQ_334  Y Y H L S C D - - - - - - - - - - - - - P F S - - V P K - - - - - D - - -
SEQ_335  P Y A A V I D - - - - - - - - - - - - - I D P E R L P S P G E I E E W S S
SEQ_336  A K A S L Y S - - - - - - - - - - - - - P E L E T L L - - K R Y E A - - -
```

FIG. 17 CONTINUED

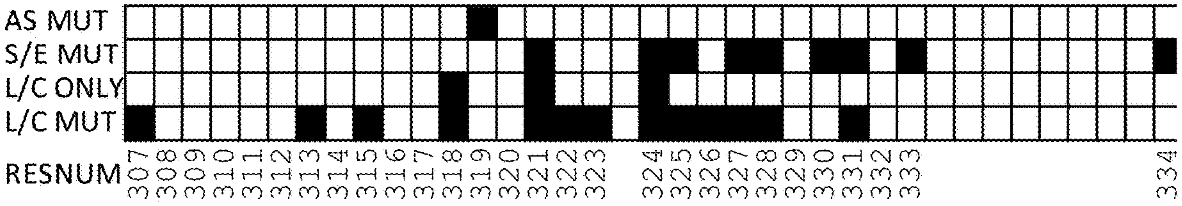

SEQ_337 T Y H V S A L - - - - - - - - - - - - - L E R - - V P K A S D V P D - - -
SEQ_338 A Y K V S I T - - - - - - - - - - - - - K E E - - F P K E I K E - - - - -
SEQ_339 A Y K V L I D - - - - - - - - - - - - - R D D - - F P Q T I Q T - - - - -
SEQ_340 A Y K V L I D - - - - - - - - - - - - - K D D - - F A E E P N L - - - - -
SEQ_341 A Y K V L I D - - - - - - - - - - - - - K D D - - F A E E P N L - - - - -
SEQ_342 S Y K V L I K - - - - - - - - - - - - - R E D - - F C K E P E L - - - - -
SEQ_343 S Y K V L I K - - - - - - - - - - - - - R E D - - F C K E P E L - - - - -
SEQ_344 S Y K V L I K - - - - - - - - - - - - - K E D - - F G K E P E L - - - - -
SEQ_345 S Y K V L I K - - - - - - - - - - - - - K D D - - F K D E P E L - - - - -
SEQ_346 S Y K V L I K - - - - - - - - - - - - - K D D - - F K D E P E L - - - - -
SEQ_347 Y Y H L S C D - - - - - - - - - - - - - P F S - - V P K - - - - - N - - -
SEQ_348 S Y K V L I K - - - - - - - - - - - - - K D D - - F K D E P E L - - - - -
SEQ_349 Y Y H L S C D - - - - - - - - - - - - - P F S - - V P K - - - - - D - - -
SEQ_350 P Y A A V I D - - - - - - - - - - - - - I N P D R L P S P G E I E D W S S
SEQ_351 R G R G L A S - - - - - - - - - - - - - E T L R K M I - - E D Y E E - - -
SEQ_352 S Y H I S A D - - - - - - - - - - - - - L S K - - V P E V E K V K D - - -
SEQ_353 A Y K V L I D - - - - - - - - - - - - - K K D - - F P E N I N L - - - - -
SEQ_354 S Y L L S T D - - - - - - - - - - - - - L Q K - - I P N I K E L Q D - - -
SEQ_355 Y Y H V T T D - - - - - - - - - - - - - L T R - - L P D V A A M A D - - -
SEQ_356 Y Y H V T T D - - - - - - - - - - - - - L D K - - V P E L A R M S D - - -
SEQ_357 Y Y H V T T D - - - - - - - - - - - - - L D K - - V P E L A R M S D - - -
SEQ_358 F Y Q V N T D - - - - - - - - - - - - - L S K - - V P E L A V M S D - - -
SEQ_359 Y Y H V T P D - - - - - - - - - - - - - L D S - - V T P L K E Q P D - - -
SEQ_360 A Y K V L I D - - - - - - - - - - - - - K K D - - F P E N I N L - - - - -
SEQ_361 S Y H V S A E - - - - - - - - - - - - - L E K - - M P D I A G W P D - - -
SEQ_362 A Y K V L I D - - - - - - - - - - - - - K K D - - F P E N I N L - - - - -
SEQ_363 A Y K V L I D - - - - - - - - - - - - - K K D - - F P E N I N L - - - - -
SEQ_364 A Y K I S I Y - - - - - - - - - - - - - R Q D - - F E E G L D L - - - - -
SEQ_365 A Y K V L I D - - - - - - - - - - - - - R D D - - F P Q T I Q T - - - - -
SEQ_366 F Y V F N A Q - - - - - - - - - - - - - T D G K - A P K P E N V T V - - -
SEQ_367 Y Y H L S C N - - - - - - - - - - - - - P F S - - V P K - - - - - D - - -
SEQ_368 Y Y H L S C D - - - - - - - - - - - - - P F S - - V P K - - - - - D - - -
SEQ_369 Y Y H L S C D - - - - - - - - - - - - - P F S - - V P K - - - - - D - - -
SEQ_370 Y Y H L S C D - - - - - - - - - - - - - P F S - - V P K - - - - - D - - -
SEQ_371 P Y A D V I D - - - - - - - - - - - - - I N T D N L P K L S E V N N W T G
SEQ_372 P Y A T V I D - - - - - - - - - - - - - I H K D K L P E P N S V Q A W N G
SEQ_373 R K G E L Y D - - - - - - - - - - - - - E V L V K R L - - E E H R K - - -

FIG. 17 CONTINUED

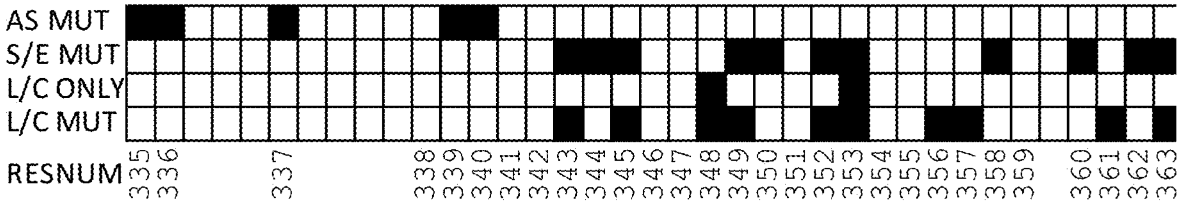

```
SEQ_6   L D - - - R - - - - - I R Y Y W E Y E D V K M V L N K L F E N F S - E G V D
SEQ_1   S D - - - R - - - - - I R Y Y W P F P K V Q K A L R Q L L K N L Q Q I S I P
SEQ_2   S D - - - R - - - - - I R Y Y W H H P A A Q E A V R R L L A N L I E T P P P
SEQ_3   S D - - - R - - - - - C R Y Y L P T R N V K N S L N L L I R N L E N V K I P
SEQ_4   S D - - - R - - - - - C R Y Y L I E N E V R A S M S R L F K N L T N V E I P
SEQ_5   L D - - - R - - - - - W R Y Y F E N E S V K S A V Y S L I G N L E N V K I P
SEQ_7   Q T - - - G - - - - - A R Y V W T A P K V I A A R E Q L Y A H L S L V Q - -
SEQ_8   A T - - - G - - - - - S R Y V W T H P A V L Q A R R E L Y E A L A P W - - -
SEQ_9   N E - - - D - - - - - T K R - - - - - - - - - - - - - A I D A M A Y A E - T
SEQ_10  - - - - - - - - - - - - - - - - - - - - - - - - - - - - - - - - - - - - - -
SEQ_11  S D - - - R - - - - - C R Y Y M P T E A V N K A M N I L I E N L E S V E I P
SEQ_12  L D - - - R - - - - - L R Y Y W N L P E V R T A V N K L I T N L E T K E I P
SEQ_13  S D - - - R - - - - - C R Y Y M P T P A V E A A K E R L I S N L R T L G I P
SEQ_14  S D - - - R - - - - - C R Y Y M P N E E V E Y S F N K M I N N L D K E E I P
SEQ_15  S D - - - R - - - - - A R Y Y W P R P S V Q A A L E R L L H N L E A A P P P
SEQ_16  S D - - - R - - - - - V R Y Y W P D S Q I D D A F E R L V R N L A D E P I P
SEQ_17  F D - - - R - - - - - I R Y Y W G F E E V E K S K N R L I E N L K - - D M Q
SEQ_18  L D - - - R - - - - - I R Y Y W E Y K E I K I A L N R L F E N F S - E G V D
SEQ_19  A T - - - G - - - - - S R Y V W T H P A V L Q A R R E L Y E A L A P W - - -
SEQ_20  A T - - - G - - - - - S R Y V W T H P A V R Q A R H Q L Y Q V L A P W - - -
SEQ_21  D I - - - A - - - - - G H Y T F N I D E V K E E I N K L Y R N L S K A H - -
SEQ_22  E I - - - S - - - - - G H Y T F N N E R V K C E I Q L M F D N L N K A G - -
SEQ_23  G D - - - D - - - - - T I R - - - - - - - - - - - - - A V E S R A Y A D - T
SEQ_321 E E - - - - - - - - - L V K L L D M P D S R Q L I H I T Y G S V L - - - - -
SEQ_322 S E - - - - - - - - - L P S L L D Q P D S R Q L I H I T Y G S V L - - - - -
SEQ_323 S K - - - - - - - - - V V N L L D I P E V R Q L I H I T Y G S V L - - - - -
SEQ_324 D A - - - - - - - - - L P A L L E Q F D T R Q V L H V T F G S V L - - - - -
SEQ_325 H E - - - - - - - - - L S Q Y M N E N N A R Q L L H I T Y G I L L - - - - -
SEQ_326 T E - - - - - - - - - L I E L F N Q N D T R Q V L H V T F G K V L - - - - -
SEQ_327 A K - - - - - - - - - L P E Y M N N D A A R Q L F H V T Y G L L L - - - - -
SEQ_328 S E - - - - - - - - - L P E L M N R D D S R Q V M H I T Y G H I L - - - - -
SEQ_329 D E - - - - - - - - - L P R L L D D D D A R Q V L H V T F G S A L - - - - -
SEQ_330 - D - - - - - - - - - Y M E F L H K D N V R Q L F H I S Y G V L L - - - - -
SEQ_331 A D - - - - - - - - - L P N L L D Q F D A R Q L L H V T F G S I L - - - - -
SEQ_332 - D - - - - - - - - - P E A A L A D R A V R Q L F H I S Y G V L L - - - - -
SEQ_333 - N - - - - - - - - - N P K F I L K P E I K Q L F H I S F G V L L - - - - -
SEQ_334 L S - - - - - - - - - P T E Y L Q N P D A R Q T L H V S Y M F V L - - - - -
SEQ_335 G R F V E A L E H D P S N P S Y N R D F R Q L I H V G Y K V A A - - - - -
SEQ_336 A Q - - - - - - - - - - - - D R F D P R A D V F R H Y - F Y V F Q - - - - -
```

FIG. 17 CONTINUED

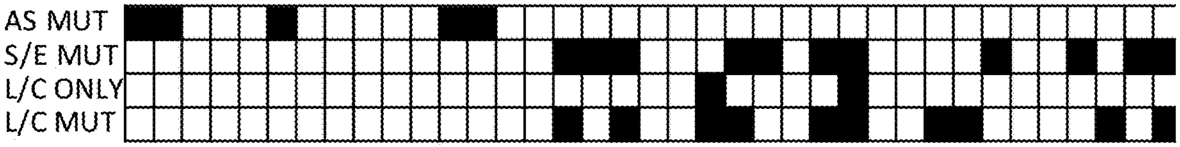

```
RESNUM  335 336 337 338 339 340 341 342 343 344 345 346 347 348 349 350 351 352 353 354 355 356 357 358 359 360 361 362 363
SEQ_337 D A - - - - - - - - L P A L L E Q F D T R Q V L H V T F G S V L - - - - -
SEQ_338 - D - - - - - - - - Y I E F L K K P N V R Q L F H I S Y G V L L - - - - -
SEQ_339 - E - - - - - - - - D S Q I L L K P E I K Q L F H I S Y G V L L - - - - -
SEQ_340 - E - - - - - - - - N V Q I L S Q P E I K Q L F H I S Y G V L L - - - - -
SEQ_341 - E - - - - - - - - N A Q I L S Q P E I K Q L F H I S Y G V L L - - - - -
SEQ_342 - N - - - - - - - - N P N F I L K P E I K Q L F H I S F G V L L - - - - -
SEQ_343 - N - - - - - - - - N P K F I L K P E I K Q L F H I S F G V L L - - - - -
SEQ_344 - N - - - - - - - - N P K F I L K P E I K Q L F H I S F G V L L - - - - -
SEQ_345 - D - - - - - - - - N P E F T L R P E I K Q L F H I S F G V L L - - - - -
SEQ_346 - D - - - - - - - - N S E F I I R P E I K Q L F H I S F G V L L - - - - -
SEQ_347 L S - - - - - - - - P T E Y L Q N P D A R Q T L H V S Y M F V L - - - - -
SEQ_348 - D - - - - - - - - N P E F I V R P E I K Q L F H I S F G V L L - - - - -
SEQ_349 L S - - - - - - - - P T E Y L K N P D A R Q T L H V S Y M F V L - - - - -
SEQ_350 G R F V E A L E H D P S N P S Y N R D F R Q L I H V G Y K V A A - - - - -
SEQ_351 H S - - - - - - - - - - - N K Y D V R A D V F R H Y - F F V F Q - - - - -
SEQ_352 E D - - - - - - - - L P G L F E D I N V R Q L I H V T Y G S V L - - - - -
SEQ_353 - E - - - - - - - - D S Q I V S K P E I K Q L F H I S Y G V L L - - - - -
SEQ_354 K E - - - - - - - - L I Q L F S N N N A R Q L I H I T Y G S I L - - - - -
SEQ_355 D G - - - - - - - - L P T V L D H N D A R Q M L H I T Y G L V L - - - - -
SEQ_356 Q E - - - - - - - - L G E L L E I N E V R Q L L H I T Y G F I L - - - - -
SEQ_357 Q E - - - - - - - - L G E L L E I N E V R Q L L H I T Y G F I L - - - - -
SEQ_358 Q E - - - - - - - - L G E L L E I D A V R Q L L H I T Y G F I L - - - - -
SEQ_359 D Q - - - - - - - - L P E Y M N H D A A R Q L F H V T Y G I L L - - - - -
SEQ_360 - E - - - - - - - - D S Q I V S K P E I K Q L F H I S Y G V L L - - - - -
SEQ_361 D R - - - - - - - - L P E L L N D F H A R E I L H V T F G S V L - - - - -
SEQ_362 - E - - - - - - - - D S Q I V S K P E I K Q L F H I S Y G V L L - - - - -
SEQ_363 - E - - - - - - - - D S Q I V S K P E I K Q L F H I S Y G V L L - - - - -
SEQ_364 - D - - - - - - - - N L H V L Q N P K V K Q L L H I S Y G V L L - - - - -
SEQ_365 - E - - - - - - - - D S Q I L S K P E I K Q L F H I S Y G V L L - - - - -
SEQ_366 D N - - - - - - - - V V D V L S D D D G R Q V L H T M Y G S L M - - - - -
SEQ_367 L S - - - - - - - - P T E Y L K N P D A R Q T L H V S Y M F V L - - - - -
SEQ_368 L K - - - - - - - - P I E Y L N N P D A R Q T L H V S Y M F V L - - - - -
SEQ_369 L S - - - - - - - - P T E Y L K N I D A R Q T L H V S Y M F V L - - - - -
SEQ_370 L S - - - - - - - - P T E Y L Q N P D A R Q T L H V S Y M F V L - - - - -
SEQ_371 E E F A N A L R H V P D H P M Y N P D L R Q L I H V A Y K L A A - - - - -
SEQ_372 E T Y A A A L R H I E N H P Q Y N P H F R Q L L H V G Y K V A A - - - - -
SEQ_373 K S - - - - - - - - L N G Y V R D S E S P V F R Y Y - S F L A L - - - - -
```

FIG. 17 CONTINUED

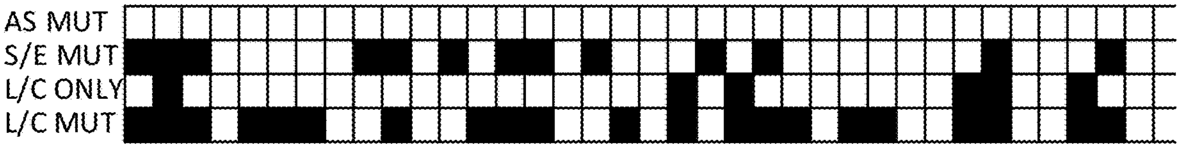

```
RESNUM   364 365 366 367 368 369 370 371 372 373   374 375 376 377 378 379 380 381 382 383 384 385 386 387 388 389 390 391 392 393 394 395 396 397 398 399
SEQ_6    I K F I Y Q Y F Y D - S Y F D V R E G K M K N D P R E L I K K E I K R V L
SEQ_1    L T L V S Q F M P E - E Y Q R I R Q G T L T N D P Q A L I L N K I Q S V L
SEQ_2    L S L L S Q Y L P R - E Y E M V R A G E I S S H P Q D L I R A H I Q H T L
SEQ_3    M T L I S Q F M P L - Q Y D N I R R G L I K N E P I S L I K N A I M N R L
SEQ_4    L T L I S Q Y M P I - Q Y E K I R M G L L K N D P E N L V K D K I G N C I
SEQ_5    P W L V S Q Y F P S - Q Y Q K M R K K D L K N G A A D L I L D K I G E V I
SEQ_7    - - - - - - - - - - - - - - - - - - - - - - A D P H A Y V V E S V A R S I
SEQ_8    - - - - - - - - - - - - - - - - - - - - - - L D A D A F V R T R I K A R L
SEQ_9    L Y F L K S F N A E R T A S I V R D G I K - - - - - - - - - - - - - - - -
SEQ_10   - - - - - - - - - - - - - - - - - - - - - - - - - - - - - - - - - - - - -
SEQ_11   L T I I D Q Y M P M - Q Y K K I R E G L I Q N K P K E L I K D R I G D Y I
SEQ_12   L T L I S Q F M P M - Q Y Q K I R N G L L R K D P I S L I K D R I T L V L
SEQ_13   L N L L S Q F M P I - Q Y T K V R E G L L V N D P V E L V E D R I I N T I
SEQ_14   I A L I S Q Y M H N - Q Y K K V R D G E L K P K G L N L L K D F I G E Y V
SEQ_15   L T L L S Q Y L P V - Q Y W S V R E G L L E P T P R S L I V D K I I Q V L
SEQ_16   L P L I S Q Y L P L - Q Y G K V R E G A L K S T P R E L I I D H I Q D I L
SEQ_17   M N L I R Q Y L P E - Q Y E K I R E N K L N K D P R A L I N Y E I K K V L
SEQ_18   I R Y I Y Q Y F Y D - S Y F K V R E G K I R N D P R E L I K N E I K K V L
SEQ_19   - - - - - - - - - - - - - - - - - - - - - - L D A D A F V R E R I K A R L
SEQ_20   - - - - - - - - - - - - - - - - - - - - - - L D A D A F V R A R I K A R L
SEQ_21   - - - - - - - - - - - - - - - - - - - - - - I D G Q R F V V D H I K R S I
SEQ_22   - - - - - - - - - - - - - - - - - - - - - - V D G E K Y V I N K I K D S I
SEQ_23   L V F L K A F K A A G M A E H V R K N L - - - - - - - - - - - - - - - - -
SEQ_321  - - - - - - - - - - - - - - - - - - T A K D E N G R W L F K E R I L K V L
SEQ_322  - - - - - - - - - - - - - - - - - - T A K K - E G R S L F K D R I M R V L
SEQ_323  - - - - - - - - - - - - - - - - - - T E K I - N G K Y L F R D E I Y R I L
SEQ_324  - - - - - - - - - - - - - - - - - - T A T D A D G R P R F R D R L L A V L
SEQ_325  - - - - - - - - - - - - - - - - - - Q A K D A S G Q Y L F R E D F F Y T L
SEQ_326  - - - - - - - - - - - - - - - - - - T E K D S S G H F L F K D K I M K C L
SEQ_327  - - - - - - - - - - - - - - - - - - T A K G E N D T F L F R D E F F K T L
SEQ_328  - - - - - - - - - - - - - - - - - - Q A K D E N G N P L F K D E L Y K V L
SEQ_329  - - - - - - - - - - - - - - - - - - D - - - - - - - - R Y R A P L L R V L
SEQ_330  - - - - - - - - - - - - - - - - - - D E K R K - - - - - - - - E I Y D L L
SEQ_331  - - - - - - - - - - - - - - - - - - T T H G A - - - - - - - - A L R N L L
SEQ_332  - - - - - - - - - - - - - - - - - - R E R G P - - - - - - - - A I R A L L
SEQ_333  - - - - - - - - - - - - - - - - - - N L K R K - - - - - - - - E I V D F L
SEQ_334  - - - - - - - - - - - - - - - - - - N - - - - - P Q Y D F R E K F F E I L
SEQ_335  - - - - - - - - - - - - - - - - - - Q M G E - - - - - - - - - R F H Q A L
SEQ_336  - - - - - - - - - - - - - - - - - - A L R D E G G A R R L R E R L V E H Y
```

FIG. 17 CONTINUED

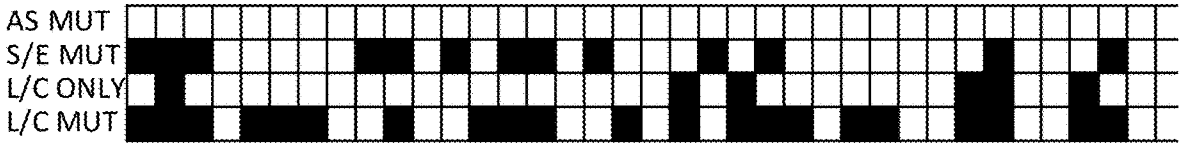

RESNUM 364 365 366 367 368 369 370 371 372 373 374 375 376 377 378 379 380 381 382 383 384 385 386 387 388 389 390 391 392 393 394 395 396 397 398 399

```
SEQ_337 ------------------TATDADGRPRFRDRLLAVL
SEQ_338 ------------------DEKRE--------EIYEIL
SEQ_339 ------------------DERRK--------EIYEVL
SEQ_340 ------------------DEKKE--------EIYDVL
SEQ_341 ------------------DEKKE--------EIYDVL
SEQ_342 ------------------DLKRK--------EMVDFL
SEQ_343 ------------------NLKRK--------EIVDFL
SEQ_344 ------------------DLKRK--------EIVDFL
SEQ_345 ------------------DLKGK--------EIKDML
SEQ_346 ------------------DLKGK--------EIKDML
SEQ_347 ------------------N-----PQYDFREKFFEIL
SEQ_348 ------------------DLKGK--------EIKDML
SEQ_349 ------------------N-----PQYDFREKFIEIL
SEQ_350 ------------------QMGE---------RFHEAL
SEQ_351 ------------------CIRDDSGVRYLRNRVIELF
SEQ_352 ------------------KDAS------LKERLFKTL
SEQ_353 ------------------EERKK--------QIFEVL
SEQ_354 ------------------REKDSQNRYKFRDRIYKVL
SEQ_355 ------------------TAANADGSYRFKDALYELL
SEQ_356 ------------------QDKK-DGRYIFRDKLYKFW
SEQ_357 ------------------QDKK-DGRYIFRDKLYKFW
SEQ_358 ------------------QDKK-DGRYIFRDRLYKLL
SEQ_359 ------------------TAKDDAGNDLFRDEFFDTL
SEQ_360 ------------------EERKK--------QIFEVL
SEQ_361 ------------------N------HPPFREPFFTAL
SEQ_362 ------------------EERKK--------QIFEVL
SEQ_363 ------------------EERKK--------QIFEVL
SEQ_364 ------------------DEKRQ--------EIYEVL
SEQ_365 ------------------DERRK--------EIYEVL
SEQ_366 ------------------NLKH-NYHYVFRDKFWDIL
SEQ_367 ------------------N-----PQYDFREKFFEIL
SEQ_368 ------------------N-----PKYDFRNRFFEIL
SEQ_369 ------------------N-----PQYDFREKFFEIL
SEQ_370 ------------------N-----PQYDFRKKFFEIL
SEQ_371 ------------------ENIN---------QFNSFL
SEQ_372 ------------------ELGE---------TYLKAL
SEQ_373 ------------------NIR-RNGERYLRNAIVELY
```

FIG. 17 CONTINUED

AS MUT
S/E MUT
L/C ONLY
L/C MUT

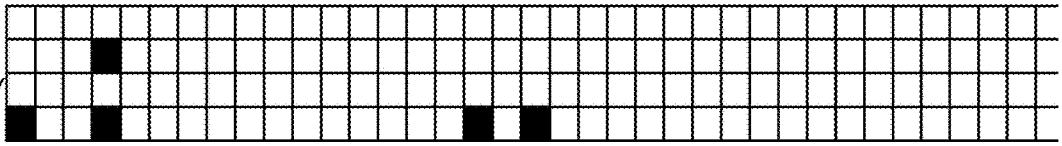

```
RESNUM   400 401 402 403 404 405 ... 406 407 408
SEQ_6    E D Y S Y A - - - - - - - - - I N - L - - - - - - - - - - - - - - - - - -
SEQ_1    K Q Y A E A - - - - - - - - - T Q - I Q N S L T F T Q N Q N S L A M E R L
SEQ_2    E D Y A A A - - - - - - - - - C G - - - - - - - - - - - - - - - - - - - -
SEQ_3    N D Y Y Y A - - - - - - - - - I K - P - - - - - - - - - - - - - - - - - -
SEQ_4    D K Y L Y A - - - - - - - - - T N - P T S G E F K L I - - - - - - - - - -
SEQ_5    D H Y V Y A - - - - - - - - - V K - E - - - - - - - - - - - - - - - - - -
SEQ_7    E R Y I D A - - - - - - - - - F N - L Y D A A T L L G - - - - - - - - - -
SEQ_8    M D Y F R A - - - - - - - - - F N - L I H F N E R L Q A F L P E - - - - -
SEQ_9    - - - - - - - - - - - - - - - - - - - - - - - - - - - - - - - - - - - - -
SEQ_10   - - - - - - - - - - - - - - - - - - - - - - - - - - - - - - - - - - - - -
SEQ_11   D D Y L Y A - - - - - - - - - L R - - - - - - - - - - - - - - - - - - - -
SEQ_12   D D Y Y F A - - - - - - - - - T H - P E C - - - - - - - - - - - - - - - -
SEQ_13   D E Y L Y A - - - - - - - - - T H - Q K E L L - - - - - - - - - - - - - -
SEQ_14   D D Y I F A - - - - - - - - - V E - D K - - - - - - - - - - - - - - - - -
SEQ_15   N D Y T W A - - - - - - - - - C G - G - - - - - - - - - - - - - - - - - -
SEQ_16   Q Q Y H A A - - - - - - - - - C E - G V T T Q N A - - - - - - - - - - - -
SEQ_17   N D Y Q K S - - - - - - - - - V I - L E - - - - - - - - - - - - - - - - -
SEQ_18   E D Y H Y A - - - - - - - - - V N - L - - - - - - - - - - - - - - - - - -
SEQ_19   M D Y F R A - - - - - - - - - F N - L I H F N E R L Q A F L P E - - - - -
SEQ_20   M D Y F R A - - - - - - - - - F N - L I G F N E R L Q A F L P N - - - - -
SEQ_21   R N Y V E C - - - - - - - - - F N - L K G L T S R I K E K L N G S K N A -
SEQ_22   D K Y I K Y - - - - - - - - - F N - L E G F T T K V L S N V - - - - - - -
SEQ_23   - - - - - - - - - - - - - - - - - - - - - - - - - - - - - - - - - - - - -
SEQ_321  Q E N E D L - - - H Y D F V E K H - M R K H L S L L G L E R R I E K - - -
SEQ_322  F E H E A E - - - H Y D F L K K H - L G K H I Q L L G V - - - - - - - - -
SEQ_323  H E N E F L - - - H Y K R I R D H - L G K H L E L L K N - - - - - - - - -
SEQ_324  Q E N E E T - - - Y Y R L L E A H - F D R H L A P F D A E - - - - - - - -
SEQ_325  E Q H E A E - - - Y D E A L R K H - I G R H L E Q L G K - - - - - - - - -
SEQ_326  V E N E E S - - - H Y E F L E K H - F L K H L E C F K - - - - - - - - - -
SEQ_327  D K Y E E E - - - Y R D A L V S H - I G K H I E L L G L - - - - - - - - -
SEQ_328  Y E Y E E E - - - Y A N A L K K H - I G R H L E G L G L L - - - - - - - -
SEQ_329  E A H D E A - - - Y Q A G L A A H - F A K H L T P F A E V A P - - - - - -
SEQ_330  N Q K E K E - - - H Y Q Y V S E N - I K K H L K N L F E E E - - - - - - -
SEQ_331  A T Y P N D - - - Y R S A L R D H - F A R H I Q P F V Q A - - - - - - - -
SEQ_332  E A H E A E - - - H F T A V R E N - L E R H L E A L L K - - - - - - - - -
SEQ_333  N K Y E E E - - - H Y K M V S K N - I D N H L K E I F Y K N - - - - - - -
SEQ_334  T K Y Q N E - - - Y H E N V A N H - I E K H V K E L K I E E K S - - - - -
SEQ_335  E A H R E V - - - I A A R V T R N L L E R H I I P L F P G D I P - - - - -
SEQ_336  R E N P G L R E R Y E K E L - R G L V E R L A S Q L G Y A G N A Y R Y R V
```

FIG. 17 CONTINUED

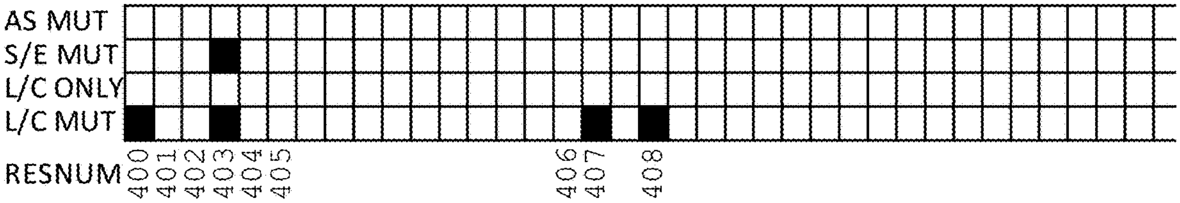

```
SEQ_337 QENEET---YYRLLEAH-FDRHLAPFDAK--------
SEQ_338 NKNEKE---HYQYVSEN-IRKHLKNLFEEE-------
SEQ_339 NKYEEE---HYEFVSKN-IENHLKEIFNI--------
SEQ_340 DKYEEE---HYQFVSAN-IKNHLGKIFNN--------
SEQ_341 DKYEEE---HYQFVSAN-IKNHLEKIFNK--------
SEQ_342 NKYEEE---HYKMVSKN-IDNHLKEIFYKN-------
SEQ_343 NKYEEE---HYKMVSKN-IDNHLKEIFYKN-------
SEQ_344 NKYEEE---HYKMVSKN-IDNHLKEIFYKN-------
SEQ_345 NDYEEE---HYKMVSDN-IENHLKEIYYEK-------
SEQ_346 YDYEEE---HYKMVSDN-IENHLKEIFYEK-------
SEQ_347 TKYQNE---YHQNVANH-IEKHVKELKVEEKS-----
SEQ_348 YEHEEE---HYKMVSNN-IENHLKEIYYEK-------
SEQ_349 TKYQNE---YHQNAANH-IEKHVKELKVEEKIHKQKN
SEQ_350 EAHREV---IAARVTRNLLERHIIPLFPGGAA-----
SEQ_351 NEVKELRDRYREEV-ANLITREAEALGYINSVIRYRK
SEQ_352 EQNEEL---FYETVAKH-IKRHVDLLEG---------
SEQ_353 NKYEEE---HYEFVRKN-IENHFKEIFSK--------
SEQ_354 FENEDI---HYENVSKH-IRHHLGLLSV---------
SEQ_355 FDHEDE---YYAALERH-IGRHLEKLTENLKG-----
SEQ_356 DEYDKE---YRRALERH-IGRHLNKLGFYKN------
SEQ_357 DEYDKE---YRRALERH-IGRHLNKLGFYKN------
SEQ_358 DEYDKD---YRSGLERH-IGRHLNKLGFYKN------
SEQ_359 LNKEDA---YRQALAHH-IGRHLDLLGLSKKVGIE--
SEQ_360 NKYEEE---HYEFVRKN-IENHFKEIFSK--------
SEQ_361 RTHEET---YSEMLERH-FCRHFAPFAG---------
SEQ_362 NKYEEE---HYEFVRKN-IENHFKEIFSK--------
SEQ_363 NKYEEE---HYEFVRKN-VENHFKEIFSK--------
SEQ_364 NQHEAE---HYRYVSDN-IKKHLELLK----------
SEQ_365 NKYEEE---HYEFVSKN-IKNHLKEIFNI--------
SEQ_366 LKNQDL---YDKYLNIH-IAEHIDLLQGKYKTKEEAL
SEQ_367 TKYQNE---YHENVANH-IEKHVKELKIEETIHKQKK
SEQ_368 TKYENE---YHIEVAEH-IKRHVKELKIPEKIQN---
SEQ_369 TKYQNE---YYENVANH-IEKHVKELKIEETK-----
SEQ_370 TKYQNE---YHENVAHH-IEKHVKELKVEETK-----
SEQ_371 EQHSEI---VGKCVFENLYKRHAERLFVFSN------
SEQ_372 EAHEHH---IALQVKENLLDRHIRPIFIQ--------
SEQ_373 LEDKGFREQVDREI-SALTVAFLDSLGFRGNVRLLR-
```

FIG. 17 CONTINUED

| | | | | | | | | | | | | | |
|---|---|---|---|---|---|---|---|---|---|---|---|---|---|
| AS MUT | | | | | | | | | | | | | |
| S/E MUT | | | | | | | | | | | | | |
| L/C ONLY | | | | | | | | | | | | | |
| L/C MUT | | | | | | | | | | | | | |
| RESNUM | | | | | | | | | | | | | |
| SEQ_6 | - | - | - | - | - | - | - | - | - | - | - | - | - |
| SEQ_1 | - | - | - | - | - | - | - | - | - | - | - | - | - |
| SEQ_2 | - | - | - | - | - | - | - | - | - | - | - | - | - |
| SEQ_3 | - | - | - | - | - | - | - | - | - | - | - | - | - |
| SEQ_4 | - | - | - | - | - | - | - | - | - | - | - | - | - |
| SEQ_5 | - | - | - | - | - | - | - | - | - | - | - | - | - |
| SEQ_7 | - | - | - | - | - | - | - | - | - | - | - | - | - |
| SEQ_8 | - | - | - | - | - | - | - | - | - | - | - | - | - |
| SEQ_9 | - | - | - | - | - | - | - | - | - | - | - | - | - |
| SEQ_10 | - | - | - | - | - | - | - | - | - | - | - | - | - |
| SEQ_11 | - | - | - | - | - | - | - | - | - | - | - | - | - |
| SEQ_12 | - | - | - | - | - | - | - | - | - | - | - | - | - |
| SEQ_13 | - | - | - | - | - | - | - | - | - | - | - | - | - |
| SEQ_14 | - | - | - | - | - | - | - | - | - | - | - | - | - |
| SEQ_15 | - | - | - | - | - | - | - | - | - | - | - | - | - |
| SEQ_16 | - | - | - | - | - | - | - | - | - | - | - | - | - |
| SEQ_17 | - | - | - | - | - | - | - | - | - | - | - | - | - |
| SEQ_18 | - | - | - | - | - | - | - | - | - | - | - | - | - |
| SEQ_19 | - | - | - | - | - | - | - | - | - | - | - | - | - |
| SEQ_20 | - | - | - | - | - | - | - | - | - | - | - | - | - |
| SEQ_21 | - | - | - | - | - | - | - | - | - | - | - | - | - |
| SEQ_22 | - | - | - | - | - | - | - | - | - | - | - | - | - |
| SEQ_23 | - | - | - | - | - | - | - | - | - | - | - | - | - |
| SEQ_321 | - | - | - | - | - | - | - | - | - | - | - | - | - |
| SEQ_322 | - | - | - | - | - | - | - | - | - | - | - | - | - |
| SEQ_323 | - | - | - | - | - | - | - | - | - | - | - | - | - |
| SEQ_324 | - | - | - | - | - | - | - | - | - | - | - | - | - |
| SEQ_325 | - | - | - | - | - | - | - | - | - | - | - | - | - |
| SEQ_326 | - | - | - | - | - | - | - | - | - | - | - | - | - |
| SEQ_327 | - | - | - | - | - | - | - | - | - | - | - | - | - |
| SEQ_328 | - | - | - | - | - | - | - | - | - | - | - | - | - |
| SEQ_329 | - | - | - | - | - | - | - | - | - | - | - | - | - |
| SEQ_330 | - | - | - | - | - | - | - | - | - | - | - | - | - |
| SEQ_331 | - | - | - | - | - | - | - | - | - | - | - | - | - |
| SEQ_332 | - | - | - | - | - | - | - | - | - | - | - | - | - |
| SEQ_333 | - | - | - | - | - | - | - | - | - | - | - | - | - |
| SEQ_334 | - | - | - | - | - | - | - | - | - | - | - | - | - |
| SEQ_335 | - | - | - | - | - | - | - | - | - | - | - | - | - |
| SEQ_336 | V | Y | A | - | - | - | - | - | - | - | - | - | - |

FIG. 17 CONTINUED

| | | | | | | | | | | | | | |
|---|---|---|---|---|---|---|---|---|---|---|---|---|---|
| AS MUT | | | | | | | | | | | | | |
| S/E MUT | | | | | | | | | | | | | |
| L/C ONLY | | | | | | | | | | | | | |
| L/C MUT | | | | | | | | | | | | | |
| RESNUM | | | | | | | | | | | | | |
| SEQ_337 | - | - | - | - | - | - | - | - | - | - | - | - | - |
| SEQ_338 | - | - | - | - | - | - | - | - | - | - | - | - | - |
| SEQ_339 | - | - | - | - | - | - | - | - | - | - | - | - | - |
| SEQ_340 | - | - | - | - | - | - | - | - | - | - | - | - | - |
| SEQ_341 | - | - | - | - | - | - | - | - | - | - | - | - | - |
| SEQ_342 | - | - | - | - | - | - | - | - | - | - | - | - | - |
| SEQ_343 | - | - | - | - | - | - | - | - | - | - | - | - | - |
| SEQ_344 | - | - | - | - | - | - | - | - | - | - | - | - | - |
| SEQ_345 | - | - | - | - | - | - | - | - | - | - | - | - | - |
| SEQ_346 | - | - | - | - | - | - | - | - | - | - | - | - | - |
| SEQ_347 | - | - | - | - | - | - | - | - | - | - | - | - | - |
| SEQ_348 | - | - | - | - | - | - | - | - | - | - | - | - | - |
| SEQ_349 | - | - | - | - | - | - | - | - | - | - | - | - | - |
| SEQ_350 | - | - | - | - | - | - | - | - | - | - | - | - | - |
| SEQ_351 | Y | E | Y | S | - | - | - | - | - | - | - | - | - |
| SEQ_352 | - | - | - | - | - | - | - | - | - | - | - | - | - |
| SEQ_353 | - | - | - | - | - | - | - | - | - | - | - | - | - |
| SEQ_354 | - | - | - | - | - | - | - | - | - | - | - | - | - |
| SEQ_355 | - | - | - | - | - | - | - | - | - | - | - | - | - |
| SEQ_356 | - | - | - | - | - | - | - | - | - | - | - | - | - |
| SEQ_357 | - | - | - | - | - | - | - | - | - | - | - | - | - |
| SEQ_358 | - | - | - | - | - | - | - | - | - | - | - | - | - |
| SEQ_359 | - | - | - | - | - | - | - | - | - | - | - | - | - |
| SEQ_360 | - | - | - | - | - | - | - | - | - | - | - | - | - |
| SEQ_361 | - | - | - | - | - | - | - | - | - | - | - | - | - |
| SEQ_362 | - | - | - | - | - | - | - | - | - | - | - | - | - |
| SEQ_363 | - | - | - | - | - | - | - | - | - | - | - | - | - |
| SEQ_364 | - | - | - | - | - | - | - | - | - | - | - | - | - |
| SEQ_365 | - | - | - | - | - | - | - | - | - | - | - | - | - |
| SEQ_366 | A | A | L | E | P | K | T | D | I | S | K | E | Y |
| SEQ_367 | - | - | - | - | - | - | - | - | - | - | - | - | - |
| SEQ_368 | - | - | - | - | - | - | - | - | - | - | - | - | - |
| SEQ_369 | - | - | - | - | - | - | - | - | - | - | - | - | - |
| SEQ_370 | - | - | - | - | - | - | - | - | - | - | - | - | - |
| SEQ_371 | - | - | - | - | - | - | - | - | - | - | - | - | - |
| SEQ_372 | - | - | - | - | - | - | - | - | - | - | - | - | - |
| SEQ_373 | - | - | - | - | - | - | - | - | - | - | - | - | - |

FIG. 20

| | 13 | 14 | 15 | 16 | 19 | 21 | 22 | 27 | 30 | 34 | 35 | 36 | 37 | 54 | 62 | 63 | 66 | 67 | 72 | 75 | 76 | 77 | 78 | 93 | 96 | 97 | 98 | 101 | 105 |
|---|---|---|---|---|---|---|---|---|---|---|---|---|---|---|---|---|---|---|---|---|---|---|---|---|---|---|---|---|---|
| **SEQ_ID_NO_6_pA06238** | V | Y | S | I | S | S | Y | S | F | K | G | D | Y | S | K | N | M | K | K | E | E | D | K | D | S | P | T | N | D |
| SEQ_ID_NO_46_pA12584 | . | . | . | . | . | . | . | . | . | . | . | . | . | . | . | . | . | . | . | P | . | . | . | . | A | E | . | . | . |
| SEQ_ID_NO_47_pA12585 | . | . | . | . | . | . | . | . | . | . | . | . | . | . | . | . | . | . | . | . | . | . | . | . | . | E | . | . | . |
| SEQ_ID_NO_48_pA12586 | . | . | . | . | . | . | . | . | . | . | . | . | . | . | . | . | . | . | L | . | . | . | . | . | A | E | . | . | . |
| SEQ_ID_NO_49_pA12587 | . | . | . | . | . | . | . | . | . | . | . | . | . | . | . | . | . | . | . | . | . | . | . | . | A | E | . | . | . |
| SEQ_ID_NO_50_pA12588 | . | . | . | . | . | P | . | . | . | . | . | . | . | . | . | . | . | . | . | P | . | . | . | . | E | E | . | . | . |
| SEQ_ID_NO_51_pA12589 | . | . | . | . | . | P | . | . | . | . | . | . | . | . | . | . | . | . | . | . | . | . | . | . | A | . | . | . | . |
| SEQ_ID_NO_52_pA12590 | . | . | . | . | . | . | . | . | . | . | . | . | . | . | . | . | . | . | . | . | . | . | . | . | A | E | . | . | . |
| SEQ_ID_NO_53_pA12591 | . | . | . | . | . | . | . | . | . | . | . | . | . | . | . | . | . | . | . | . | . | . | . | . | A | E | . | . | . |
| SEQ_ID_NO_54_pA12592 | . | . | . | . | . | . | . | . | . | . | . | . | . | . | . | . | . | . | . | P | . | . | . | . | . | E | . | . | . |
| SEQ_ID_NO_55_pA12593 | . | . | . | . | . | . | . | . | . | . | . | . | . | . | . | . | . | . | . | P | . | . | . | . | . | . | . | . | . |
| SEQ_ID_NO_56_pA12594 | . | . | . | . | . | . | . | . | . | . | . | . | . | . | . | . | . | . | . | . | . | . | . | . | . | . | . | . | . |
| SEQ_ID_NO_57_pA12595 | . | . | . | . | . | P | . | . | . | . | . | . | . | . | . | . | . | . | . | . | . | . | . | . | . | E | . | . | . |
| SEQ_ID_NO_58_pA12596 | . | . | . | . | . | . | . | . | . | . | . | . | . | . | . | . | . | . | . | . | . | . | . | . | . | . | . | . | . |
| SEQ_ID_NO_59_pA12597 | . | . | . | . | . | . | . | . | . | . | . | . | . | . | . | . | . | . | . | P | . | . | . | . | . | E | . | . | . |
| SEQ_ID_NO_60_pA12598 | . | . | . | . | . | . | . | . | . | . | . | . | . | . | . | . | . | . | . | . | . | . | . | . | . | . | . | . | . |
| SEQ_ID_NO_61_pA12599 | . | . | . | . | . | . | . | . | . | . | . | . | . | . | . | . | . | . | . | . | . | . | . | . | . | . | . | . | . |
| SEQ_ID_NO_62_pA12600 | . | . | . | . | . | . | . | . | . | . | . | . | . | T | . | . | . | . | . | . | . | . | . | . | A | . | . | . | . |
| SEQ_ID_NO_63_pA12601 | . | . | . | . | . | . | . | . | . | . | . | . | . | T | . | . | . | . | . | . | . | . | . | . | A | E | . | E | . |
| SEQ_ID_NO_64_pA12602 | . | . | . | . | . | . | . | . | . | R | . | . | . | T | . | . | . | . | . | . | . | . | . | . | A | . | . | . | . |
| SEQ_ID_NO_65_pA12603 | . | . | . | . | . | P | . | . | . | . | . | . | . | T | . | . | . | . | . | . | . | . | . | . | A | . | . | . | . |
| SEQ_ID_NO_66_pA12604 | . | . | . | . | . | . | . | . | . | R | . | . | . | . | . | . | . | . | . | . | . | . | . | . | . | E | . | . | . |
| SEQ_ID_NO_67_pA12605 | . | . | . | . | . | . | . | . | . | . | . | . | . | T | . | . | . | . | . | P | . | . | . | . | A | E | . | . | . |
| SEQ_ID_NO_68_pA12606 | . | . | . | . | . | . | . | . | . | . | . | . | . | T | . | . | . | . | . | P | . | . | . | . | A | . | . | . | . |
| SEQ_ID_NO_69_pA12607 | . | . | . | . | . | P | . | . | . | . | . | . | . | T | . | . | . | . | . | . | . | . | . | . | A | E | . | . | . |
| SEQ_ID_NO_70_pA12608 | . | . | . | . | . | P | . | A | . | . | . | . | . | T | . | . | . | . | . | . | . | . | R | . | . | D | E | E | . |
| SEQ_ID_NO_71_pA12609 | . | . | . | . | . | . | . | A | . | D | . | . | P | T | . | . | . | . | . | P | . | . | . | . | . | . | . | . | . |
| SEQ_ID_NO_72_pA12610 | . | . | . | . | . | P | . | . | . | . | . | . | . | . | . | . | . | . | . | . | . | . | . | . | . | . | . | . | . |
| SEQ_ID_NO_73_pA12611 | . | . | . | . | . | P | . | . | . | . | . | . | P | . | . | . | . | . | . | . | . | . | . | . | . | . | E | . | . |
| SEQ_ID_NO_74_pA12612 | . | . | . | . | . | . | W | . | . | . | . | . | . | T | . | . | . | . | . | . | . | . | . | . | . | . | . | . | . |
| SEQ_ID_NO_75_pA12613 | . | . | . | . | . | . | . | . | . | . | . | . | . | . | . | . | . | . | . | . | . | . | . | . | . | E | . | E | . |
| SEQ_ID_NO_76_pA12614 | . | . | . | . | . | . | . | A | . | . | . | . | . | T | . | . | . | . | . | P | . | . | . | . | . | . | E | E | . |
| SEQ_ID_NO_77_pA12615 | . | F | . | . | . | . | . | . | . | . | . | . | . | . | . | . | . | . | . | . | . | . | . | . | . | E | . | . | . |
| SEQ_ID_NO_78_pA12616 | . | . | . | . | . | . | . | . | . | . | . | . | . | . | . | . | . | . | . | . | . | . | . | . | . | E | . | . | . |
| SEQ_ID_NO_79_pA12617 | . | . | . | . | . | . | . | . | . | . | . | . | . | . | . | . | . | . | . | . | . | . | . | . | A | E | . | . | . |
| SEQ_ID_NO_80_pA12618 | . | . | . | . | . | P | . | . | . | . | . | . | . | . | . | . | . | . | . | P | . | . | . | . | . | . | . | . | . |
| SEQ_ID_NO_81_pA12619 | . | . | . | . | . | . | . | . | . | . | . | . | . | T | . | . | . | . | L | . | . | . | . | . | . | E | . | . | . |
| SEQ_ID_NO_82_pA12620 | . | . | . | . | N | . | . | . | . | . | . | . | . | . | . | . | . | . | V | . | . | . | . | . | A | E | . | . | . |
| SEQ_ID_NO_83_pA12621 | . | . | . | . | . | K | . | . | . | . | . | . | . | . | . | . | . | . | . | P | . | . | . | . | . | E | . | . | . |
| SEQ_ID_NO_84_pA12622 | . | . | . | . | . | . | . | A | . | . | . | . | . | . | . | . | . | . | . | P | . | . | . | . | . | . | . | . | . |
| SEQ_ID_NO_85_pA12623 | . | . | . | . | . | P | . | A | . | . | . | . | . | . | . | . | . | . | . | . | . | . | . | . | . | E | . | . | . |
| SEQ_ID_NO_86_pA12624 | . | . | . | . | . | . | . | A | . | . | . | . | . | . | . | . | . | . | . | P | . | . | . | . | A | . | . | . | . |
| SEQ_ID_NO_87_pA12625 | . | . | . | . | . | . | . | A | . | . | . | . | . | . | . | . | . | . | . | . | . | . | . | . | . | . | . | E | . |
| SEQ_ID_NO_88_pA12626 | . | . | . | . | . | . | . | . | . | . | . | . | . | . | . | . | . | . | . | . | . | . | . | . | A | . | . | . | . |
| SEQ_ID_NO_89_pA12627 | . | . | . | . | . | . | . | A | . | . | . | . | . | . | . | . | . | . | . | P | . | . | . | . | . | . | . | . | . |
| SEQ_ID_NO_90_pA12628 | . | . | . | . | . | . | . | A | . | . | . | . | . | T | . | . | . | . | . | . | . | . | . | . | A | . | . | . | . |

FIG. 20 CONTINUED

| | 13 | 14 | 15 | 16 | 19 | 21 | 22 | 27 | 30 | 34 | 35 | 36 | 37 | 54 | 62 | 63 | 66 | 67 | 72 | 75 | 76 | 77 | 78 | 93 | 96 | 97 | 98 | 101 | 105 |
|---|---|---|---|---|---|---|---|---|---|---|---|---|---|---|---|---|---|---|---|---|---|---|---|---|---|---|---|---|---|
| **SEQ_ID_NO_6_pA06238** | V | Y | S | I | S | S | Y | S | F | K | G | D | Y | S | K | N | M | K | K | E | E | D | K | D | S | P | T | N | D |
| SEQ_ID_NO_91_pA12629 | . | . | . | . | . | P | W | . | . | . | . | . | . | T | . | . | . | . | . | P | . | . | . | . | . | . | . | . | . |
| SEQ_ID_NO_92_pA12630 | . | . | . | . | . | P | . | . | . | . | . | . | . | . | . | . | . | . | . | P | . | . | . | . | A | . | . | E | . |
| SEQ_ID_NO_93_pA12631 | . | . | . | . | . | . | . | A | . | . | . | . | . | . | . | . | . | . | . | . | . | . | . | . | . | . | . | . | . |
| SEQ_ID_NO_94_pA12632 | . | . | . | . | . | . | . | . | . | . | . | . | . | . | . | . | . | . | . | P | . | . | . | . | A | E | . | . | . |
| SEQ_ID_NO_95_pA12633 | . | . | . | . | . | P | . | A | . | . | . | . | . | . | . | . | . | . | . | . | . | . | . | . | . | E | . | . | . |
| SEQ_ID_NO_96_pA12634 | . | . | . | . | . | . | . | . | . | . | . | . | . | T | . | . | . | . | . | P | . | . | . | . | A | E | . | . | . |
| SEQ_ID_NO_97_pA12635 | . | . | . | . | . | . | . | . | . | . | . | . | . | T | . | . | . | . | . | . | . | . | . | . | . | E | . | . | . |
| SEQ_ID_NO_98_pA12636 | . | . | . | . | . | . | W | . | . | D | . | . | P | T | . | . | . | . | . | P | . | . | . | . | . | . | . | . | . |
| SEQ_ID_NO_99_pA12637 | . | . | . | . | . | P | W | A | . | . | . | T | . | T | . | . | . | . | . | P | . | . | . | . | . | E | E | . | . |
| SEQ_ID_NO_100_pA12638 | . | . | . | . | . | P | . | A | . | . | . | . | . | . | . | . | . | . | . | P | . | . | . | . | . | E | . | E | . |
| SEQ_ID_NO_101_pA12639 | . | . | . | . | . | . | W | . | . | . | . | S | . | . | . | . | . | . | . | P | . | . | . | . | . | D | . | E | . |
| SEQ_ID_NO_102_pA12640 | . | . | . | . | . | . | . | . | . | . | . | . | . | T | R | . | . | . | . | . | . | . | . | . | . | E | . | . | . |
| SEQ_ID_NO_103_pA12641 | I | . | . | . | . | P | . | A | . | . | . | . | . | T | . | . | . | . | . | P | . | . | . | . | . | E | E | . | . |
| SEQ_ID_NO_104_pA12642 | . | . | . | . | . | . | . | A | . | . | . | . | . | . | . | . | . | . | . | . | . | . | . | . | A | . | E | E | . |
| SEQ_ID_NO_105_pA12643 | . | . | . | . | . | . | . | A | . | . | D | . | . | . | . | . | . | . | L | P | . | . | . | . | . | E | . | . | . |
| SEQ_ID_NO_106_pA12644 | . | . | . | . | . | . | . | . | . | . | . | . | . | . | . | . | . | . | . | . | . | . | . | . | . | E | . | . | . |
| SEQ_ID_NO_107_pA12645 | . | . | . | . | . | . | . | A | . | . | . | . | . | . | . | . | . | . | L | P | . | . | . | . | . | . | . | . | . |
| SEQ_ID_NO_108_pA12646 | . | . | . | . | . | P | . | A | . | . | . | . | . | T | . | . | . | . | V | . | . | . | R | . | . | E | . | . | . |
| SEQ_ID_NO_109_pA12647 | . | . | . | . | . | . | . | A | . | . | . | . | . | . | . | . | . | . | . | . | . | . | . | . | . | . | . | . | . |
| SEQ_ID_NO_110_pA12648 | . | . | . | . | . | . | . | A | . | . | . | . | . | . | . | . | . | . | . | . | . | . | . | . | . | . | . | E | . |
| SEQ_ID_NO_111_pA12649 | . | . | . | . | . | P | . | A | . | . | . | . | . | T | . | . | . | . | . | P | . | . | . | . | . | E | . | E | . |
| SEQ_ID_NO_112_pA12650 | . | . | . | . | . | E | . | . | . | . | . | . | . | T | . | . | . | . | . | . | . | . | . | . | A | . | . | . | E |
| SEQ_ID_NO_113_pA12651 | . | . | . | . | . | E | . | . | . | . | . | . | . | T | . | . | . | . | . | P | . | . | . | . | . | . | . | E | . |
| SEQ_ID_NO_114_pA12652 | . | . | . | . | . | . | . | . | . | . | . | . | . | T | . | . | . | . | . | P | . | . | . | . | . | E | . | E | . |
| SEQ_ID_NO_115_pA12653 | . | . | . | . | . | . | . | A | . | . | . | . | . | T | . | . | . | . | . | P | . | . | . | . | . | E | E | A | . |
| SEQ_ID_NO_116_pA12654 | . | . | . | . | . | P | . | C | . | . | . | . | . | T | . | . | . | . | . | P | . | . | . | . | . | . | E | . | . |
| SEQ_ID_NO_117_pA12655 | . | . | . | . | . | P | . | . | . | . | D | . | . | T | . | . | . | . | . | . | . | . | . | . | . | E | . | . | . |
| SEQ_ID_NO_118_pA12656 | . | . | . | . | . | P | . | . | . | . | . | . | . | . | . | . | . | . | . | P | . | . | . | . | . | E | E | A | . |
| SEQ_ID_NO_119_pA12657 | . | . | . | . | . | . | W | A | . | . | . | . | . | T | . | . | . | . | . | P | . | . | . | . | A | E | . | A | . |
| SEQ_ID_NO_120_pA12658 | . | . | . | . | . | P | . | . | . | . | . | S | . | T | . | R | . | . | . | P | . | . | . | H | . | D | . | E | . |
| SEQ_ID_NO_121_pA12659 | . | . | . | . | . | . | W | A | . | . | . | . | . | . | R | R | . | . | . | . | . | . | . | . | A | E | E | . | E |
| SEQ_ID_NO_122_pA12660 | I | . | . | . | . | P | . | . | . | D | . | . | P | . | . | R | Y | . | . | P | . | . | . | . | . | D | E | . | . |
| SEQ_ID_NO_123_pA12661 | . | . | . | . | . | P | W | A | . | . | . | . | . | T | . | . | . | . | . | P | . | . | . | . | . | E | . | . | . |
| SEQ_ID_NO_124_pA12662 | . | . | . | . | . | P | W | . | . | . | . | . | P | T | . | . | Y | . | . | . | . | N | . | . | . | E | . | . | . |
| SEQ_ID_NO_125_pA12663 | . | . | . | . | . | P | . | . | . | . | . | . | . | T | . | . | . | . | . | . | . | . | . | . | A | E | . | K | . |
| SEQ_ID_NO_126_pA12664 | . | F | . | . | . | K | . | A | . | M | H | . | . | . | . | . | . | . | L | P | . | . | . | . | A | . | . | . | . |
| SEQ_ID_NO_127_pA12665 | . | . | . | . | . | . | . | A | . | . | D | . | . | T | . | . | . | . | . | P | . | . | . | . | A | . | . | . | . |
| SEQ_ID_NO_128_pA12666 | . | . | . | . | . | . | . | . | . | M | . | . | P | T | . | . | F | . | . | P | P | . | . | . | A | . | . | . | . |
| SEQ_ID_NO_129_pA12667 | . | . | . | . | . | . | . | A | . | . | . | . | . | T | . | . | F | . | . | P | P | . | . | . | . | E | . | . | E |
| SEQ_ID_NO_130_pA12668 | . | . | . | . | . | . | . | . | . | . | . | . | . | . | . | . | F | . | . | . | . | . | . | . | A | . | Q | E | E |
| SEQ_ID_NO_131_pA12669 | . | . | A | . | . | P | . | . | . | . | D | . | . | T | . | . | . | . | . | P | . | . | . | . | A | . | E | A | . |
| SEQ_ID_NO_132_pA12670 | . | . | . | . | . | P | . | . | . | Y | . | . | . | T | . | R | . | . | . | . | . | . | R | . | A | E | . | A | . |
| SEQ_ID_NO_133_pA12671 | . | . | . | . | . | P | . | A | . | . | . | . | . | . | R | . | . | . | . | P | . | . | . | . | . | E | . | . | . |
| SEQ_ID_NO_134_pA12672 | . | . | . | . | . | . | W | . | . | . | . | . | . | . | R | R | Y | Q | . | P | . | . | . | H | A | . | . | A | . |
| SEQ_ID_NO_135_pA12673 | I | . | . | . | . | P | W | A | H | D | . | . | . | T | . | R | . | . | . | P | . | . | . | H | A | E | E | E | E |
| SEQ_ID_NO_136_pA12674 | I | . | . | V | . | P | W | A | . | . | . | S | . | . | . | . | Y | . | . | . | . | N | . | H | . | . | E | A | . |

FIG. 20 CONTINUED

| | 110 | 113 | 115 | 126 | 127 | 128 | 129 | 131 | 135 | 136 | 140 | 142 | 143 | 144 | 146 | 147 | 148 | 151 | 152 | 154 | 160 | 179 | 182 | 184 | 187 | 188 | 189 | 190 | 191 |
|---|---|---|---|---|---|---|---|---|---|---|---|---|---|---|---|---|---|---|---|---|---|---|---|---|---|---|---|---|---|
| **SEQ_ID_NO_6_pA06238** | F | S | Y | L | S | D | D | K | Y | E | E | T | R | E | F | E | I | E | T | R | P | V | V | D | S | A | I | S | S |
| SEQ_ID_NO_46_pA12584 | . | A | . | . | . | . | . | . | . | . | . | . | . | . | . | . | . | . | . | . | A | . | . | . | . | T | L | . | V |
| SEQ_ID_NO_47_pA12585 | . | A | . | . | . | . | . | . | L | . | . | . | V | . | . | K | . | . | . | . | . | . | P | . | . | . | . | . | Y |
| SEQ_ID_NO_48_pA12586 | . | A | . | . | . | . | . | . | . | . | . | . | A | . | . | . | . | . | A | . | A | . | . | . | . | M | . | . | T |
| SEQ_ID_NO_49_pA12587 | . | A | . | . | . | . | . | . | . | . | . | . | V | . | . | . | . | . | . | . | . | . | . | . | . | . | . | . | T |
| SEQ_ID_NO_50_pA12588 | . | A | . | . | . | . | . | . | . | . | . | . | . | . | . | . | . | . | . | . | . | . | . | . | . | . | L | . | I |
| SEQ_ID_NO_51_pA12589 | . | . | . | . | . | . | . | . | . | . | . | . | . | . | . | . | . | . | . | . | . | . | . | . | . | . | . | . | . |
| SEQ_ID_NO_52_pA12590 | . | . | . | . | . | . | . | . | . | . | . | . | . | . | . | . | . | . | . | . | . | . | P | . | . | . | . | . | T |
| SEQ_ID_NO_53_pA12591 | . | A | . | . | . | . | . | . | . | . | . | . | . | . | . | . | . | . | . | . | E | . | P | . | . | . | . | . | I |
| SEQ_ID_NO_54_pA12592 | . | . | . | . | . | . | . | . | . | . | . | . | . | . | . | . | . | . | . | . | . | . | P | . | . | . | . | . | . |
| SEQ_ID_NO_55_pA12593 | . | A | . | . | . | . | . | . | . | . | . | . | . | . | C | . | . | . | . | . | . | . | . | . | . | . | . | D | . |
| SEQ_ID_NO_56_pA12594 | . | . | . | . | . | . | . | . | . | . | . | . | . | . | . | R | . | . | . | . | . | . | P | . | . | . | . | . | L |
| SEQ_ID_NO_57_pA12595 | . | . | . | . | . | . | . | . | L | . | . | . | . | . | . | . | . | . | . | . | . | . | . | . | . | . | . | . | . |
| SEQ_ID_NO_58_pA12596 | . | . | . | . | . | . | . | . | . | . | . | . | . | . | . | . | . | . | . | . | . | . | . | . | . | . | . | . | . |
| SEQ_ID_NO_59_pA12597 | . | . | . | . | . | . | . | . | P | . | . | . | . | . | . | . | . | . | . | . | . | . | . | . | . | . | . | . | L |
| SEQ_ID_NO_60_pA12598 | . | A | . | . | . | . | . | . | . | . | . | . | . | . | . | . | . | . | . | . | . | . | . | . | . | . | . | . | . |
| SEQ_ID_NO_61_pA12599 | . | . | . | . | . | . | . | . | . | . | . | . | A | . | . | . | . | . | . | . | . | . | P | . | . | . | . | . | . |
| SEQ_ID_NO_62_pA12600 | . | . | . | . | . | . | . | . | . | . | . | . | A | . | . | . | . | . | . | . | . | . | . | . | . | M | . | . | V |
| SEQ_ID_NO_63_pA12601 | . | A | . | . | . | . | . | . | . | . | . | . | A | . | . | . | . | . | . | . | . | . | . | . | . | . | . | . | . |
| SEQ_ID_NO_64_pA12602 | . | A | . | . | . | . | . | . | . | . | . | . | . | . | . | . | . | . | . | . | . | . | . | . | . | T | . | . | . |
| SEQ_ID_NO_65_pA12603 | . | A | . | . | . | . | . | . | . | . | . | . | A | . | . | . | . | . | . | . | . | . | . | . | . | . | . | . | I |
| SEQ_ID_NO_66_pA12604 | . | A | . | . | . | . | . | . | . | . | . | . | . | . | . | . | . | . | . | . | . | . | . | . | . | . | . | . | . |
| SEQ_ID_NO_67_pA12605 | . | A | . | C | A | . | . | . | . | . | . | . | V | . | . | . | . | . | . | . | . | . | P | . | . | T | . | . | T |
| SEQ_ID_NO_68_pA12606 | . | A | . | . | . | . | . | . | . | . | I | . | . | . | . | R | . | . | . | . | . | . | . | . | . | M | . | . | T |
| SEQ_ID_NO_69_pA12607 | . | . | . | . | . | . | . | . | . | . | . | . | . | . | . | . | . | . | . | . | . | . | P | . | . | . | . | . | . |
| SEQ_ID_NO_70_pA12608 | . | A | . | C | A | . | . | . | . | . | . | . | . | . | . | R | . | . | . | . | . | . | P | . | . | T | . | . | T |
| SEQ_ID_NO_71_pA12609 | . | A | . | C | A | . | . | . | . | . | . | . | . | . | C | . | . | . | . | . | . | . | . | . | . | . | . | . | . |
| SEQ_ID_NO_72_pA12610 | . | A | . | . | A | . | . | . | . | . | . | . | . | . | . | . | . | R | . | . | . | . | . | . | . | T | . | . | . |
| SEQ_ID_NO_73_pA12611 | . | . | . | . | . | . | . | . | . | . | . | . | . | . | C | . | . | . | . | . | . | . | . | . | . | T | . | . | . |
| SEQ_ID_NO_74_pA12612 | . | . | . | C | . | . | . | . | . | . | . | . | . | . | . | . | . | R | . | . | . | . | P | . | . | T | . | . | . |
| SEQ_ID_NO_75_pA12613 | . | A | . | . | A | . | . | . | . | . | . | . | . | . | . | . | . | . | . | . | . | . | . | . | . | . | . | . | . |
| SEQ_ID_NO_76_pA12614 | . | A | . | . | . | . | . | . | . | . | . | . | . | . | . | . | . | . | . | . | . | . | . | . | . | T | . | . | . |
| SEQ_ID_NO_77_pA12615 | Y | . | F | . | . | . | . | . | M | . | . | . | A | . | . | K | . | . | . | . | . | . | . | . | . | . | . | . | Y |
| SEQ_ID_NO_78_pA12616 | . | A | . | . | . | . | . | . | . | . | . | . | . | . | . | . | . | . | . | . | . | . | P | . | . | F | . | . | . |
| SEQ_ID_NO_79_pA12617 | . | A | . | . | . | . | . | . | . | . | . | . | . | . | . | K | . | . | . | . | A | . | A | . | . | . | . | . | I |
| SEQ_ID_NO_80_pA12618 | . | . | . | . | . | . | . | . | . | . | . | . | A | . | . | . | V | . | . | . | . | . | . | . | . | . | . | . | I |
| SEQ_ID_NO_81_pA12619 | . | . | . | . | . | . | . | . | . | . | . | . | . | . | . | . | . | . | . | . | . | . | . | . | . | M | . | . | T |
| SEQ_ID_NO_82_pA12620 | . | . | . | . | . | . | . | . | . | . | . | . | . | . | . | . | . | . | . | . | . | . | . | . | . | . | . | D | T |
| SEQ_ID_NO_83_pA12621 | . | A | . | . | . | . | . | . | . | . | . | . | V | . | . | . | . | . | . | . | . | . | . | . | . | . | . | . | T |
| SEQ_ID_NO_84_pA12622 | . | . | . | . | . | . | . | . | L | . | . | . | . | . | . | R | . | . | . | . | . | . | P | . | . | . | . | E | T |
| SEQ_ID_NO_85_pA12623 | . | A | . | . | . | . | . | . | T | . | . | . | . | . | . | . | . | . | . | . | . | . | . | . | . | . | . | . | . |
| SEQ_ID_NO_86_pA12624 | . | . | . | . | . | . | . | . | . | . | . | . | . | . | . | . | . | . | . | . | . | . | . | . | . | . | . | . | . |
| SEQ_ID_NO_87_pA12625 | . | A | . | . | . | . | . | . | P | . | . | . | . | . | . | . | . | . | . | . | . | . | . | . | E | . | . | E | . |
| SEQ_ID_NO_88_pA12626 | . | . | . | . | . | . | . | . | L | . | . | . | . | . | . | . | . | R | . | . | . | . | P | . | . | . | . | D | . |
| SEQ_ID_NO_89_pA12627 | . | . | . | . | . | . | . | . | . | . | . | . | . | . | . | . | . | . | . | . | . | . | . | . | R | . | . | . | . |
| SEQ_ID_NO_90_pA12628 | . | . | . | . | . | . | . | . | . | . | . | . | . | . | C | . | . | . | . | . | . | . | P | . | . | . | . | . | . |

FIG. 20 CONTINUED

| | 110 | 113 | 115 | 126 | 127 | 128 | 129 | 131 | 135 | 136 | 140 | 142 | 143 | 144 | 146 | 147 | 148 | 151 | 152 | 154 | 160 | 179 | 182 | 184 | 187 | 188 | 189 | 190 | 191 |
|---|---|---|---|---|---|---|---|---|---|---|---|---|---|---|---|---|---|---|---|---|---|---|---|---|---|---|---|---|---|
| **SEQ_ID_NO_6_pA06238** | F | S | Y | L | S | D | D | K | Y | E | E | T | R | E | F | E | I | E | T | R | P | V | V | D | S | A | I | S | S |
| SEQ_ID_NO_91_pA12629 | . | A | . | . | . | . | . | . | . | . | . | . | . | . | . | . | . | . | . | . | . | . | P | . | . | . | . | . | . |
| SEQ_ID_NO_92_pA12630 | . | . | . | . | A | . | . | . | . | . | . | . | . | . | . | . | . | . | . | . | . | . | . | . | . | T | . | . | T |
| SEQ_ID_NO_93_pA12631 | . | A | . | . | . | . | . | . | . | . | I | . | A | . | . | . | . | . | . | . | . | . | P | . | . | M | . | . | T |
| SEQ_ID_NO_94_pA12632 | . | . | . | . | A | . | . | . | . | . | . | . | V | . | . | . | . | . | . | . | . | . | P | . | . | . | . | . | T |
| SEQ_ID_NO_95_pA12633 | . | A | . | . | A | . | . | . | . | . | . | . | . | . | . | . | . | . | A | . | . | . | . | . | . | M | . | . | V |
| SEQ_ID_NO_96_pA12634 | . | . | . | . | . | . | . | . | . | . | . | . | . | . | . | . | . | . | . | . | . | . | . | . | . | T | . | . | . |
| SEQ_ID_NO_97_pA12635 | . | . | . | . | A | . | . | . | . | . | . | . | A | . | . | . | . | . | . | . | . | . | . | . | . | . | . | . | . |
| SEQ_ID_NO_98_pA12636 | . | A | . | . | . | . | . | . | . | . | . | . | . | . | C | . | . | . | . | . | . | . | . | . | . | T | . | . | . |
| SEQ_ID_NO_99_pA12637 | . | . | . | . | A | . | . | . | . | . | . | . | . | . | . | R | . | . | . | . | . | . | . | . | . | . | . | . | L |
| SEQ_ID_NO_100_pA12638 | . | A | . | . | . | . | . | . | . | . | . | . | . | . | . | K | . | . | . | . | . | . | P | . | . | T | . | E | . |
| SEQ_ID_NO_101_pA12639 | . | A | . | C | A | . | . | . | . | . | . | . | . | . | . | . | . | . | . | . | . | . | P | . | . | . | . | . | . |
| SEQ_ID_NO_102_pA12640 | . | A | . | . | . | . | . | . | . | . | . | . | . | . | . | . | . | . | . | . | . | . | . | . | . | . | . | . | . |
| SEQ_ID_NO_103_pA12641 | . | . | . | C | . | . | . | . | . | . | . | . | . | . | C | R | . | . | . | . | . | . | . | . | . | T | . | E | . |
| SEQ_ID_NO_104_pA12642 | . | . | . | C | . | . | . | . | . | . | . | . | . | . | . | . | . | . | . | . | . | . | . | . | . | . | . | . | . |
| SEQ_ID_NO_105_pA12643 | Y | A | . | . | . | . | . | . | M | . | . | . | . | . | . | K | . | . | . | . | . | . | . | . | . | . | . | . | L |
| SEQ_ID_NO_106_pA12644 | . | . | . | . | . | . | . | . | K | . | . | . | V | . | . | . | . | . | . | . | . | . | . | . | . | . | . | . | . |
| SEQ_ID_NO_107_pA12645 | . | . | . | . | . | . | . | . | . | . | . | . | . | . | . | . | . | . | . | . | . | . | . | . | . | . | . | . | V |
| SEQ_ID_NO_108_pA12646 | . | . | . | . | . | . | . | . | . | . | . | . | . | . | . | . | . | . | . | . | . | . | . | . | . | . | . | D | I |
| SEQ_ID_NO_109_pA12647 | . | A | . | . | . | . | . | . | L | . | . | . | . | . | . | . | . | . | . | . | . | . | . | . | . | M | . | D | T |
| SEQ_ID_NO_110_pA12648 | . | A | . | . | . | . | . | . | L | . | . | . | . | . | . | K | V | . | . | . | . | . | . | . | . | . | . | . | . |
| SEQ_ID_NO_111_pA12649 | . | . | . | . | . | . | . | . | L | . | . | . | . | . | . | . | . | . | . | . | . | . | . | . | E | . | . | E | Y |
| SEQ_ID_NO_112_pA12650 | . | A | . | . | . | . | . | . | L | . | . | . | . | . | . | . | . | . | . | . | . | . | P | . | . | . | . | E | A |
| SEQ_ID_NO_113_pA12651 | . | A | . | . | . | . | . | . | M | . | . | . | . | . | . | K | . | . | . | . | . | . | . | . | . | . | . | E | . |
| SEQ_ID_NO_114_pA12652 | . | A | . | . | . | . | . | . | T | . | . | . | . | . | . | . | V | . | . | . | . | . | . | . | E | . | . | E | . |
| SEQ_ID_NO_115_pA12653 | . | A | . | . | A | . | . | . | . | . | . | . | . | . | . | . | . | . | . | . | . | . | . | . | . | . | . | . | V |
| SEQ_ID_NO_116_pA12654 | . | A | . | . | A | . | . | . | . | . | . | . | . | . | . | . | . | . | . | . | . | . | P | . | . | F | . | . | V |
| SEQ_ID_NO_117_pA12655 | . | . | . | . | . | . | . | . | Q | . | . | . | A | . | . | . | . | . | . | . | . | . | . | . | . | T | . | . | . |
| SEQ_ID_NO_118_pA12656 | . | . | . | . | . | . | . | . | . | . | . | . | V | . | . | . | . | . | . | . | . | . | P | . | . | . | . | . | . |
| SEQ_ID_NO_119_pA12657 | . | A | . | . | A | . | . | . | . | . | . | . | A | . | . | . | . | . | . | . | . | . | . | . | . | . | . | . | . |
| SEQ_ID_NO_120_pA12658 | . | . | F | C | A | . | . | . | N | . | . | . | . | . | . | R | . | . | . | . | . | . | P | . | R | T | . | . | . |
| SEQ_ID_NO_121_pA12659 | . | A | . | C | A | . | . | . | . | . | . | . | . | . | . | . | . | R | . | . | . | . | P | . | K | . | . | E | A |
| SEQ_ID_NO_122_pA12660 | . | . | . | C | . | . | . | . | . | . | . | . | . | . | . | . | . | . | . | . | . | I | . | . | . | . | . | E | L |
| SEQ_ID_NO_123_pA12661 | . | . | . | . | . | . | . | . | . | . | . | . | A | R | . | . | . | . | . | . | . | . | . | . | . | T | . | . | A |
| SEQ_ID_NO_124_pA12662 | . | . | . | . | A | . | . | . | . | . | . | . | . | . | . | . | . | . | . | . | . | . | . | . | . | T | . | E | A |
| SEQ_ID_NO_125_pA12663 | . | A | . | . | . | . | . | . | K | . | . | . | V | . | . | . | . | . | . | Q | . | . | K | . | . | F | . | . | T |
| SEQ_ID_NO_126_pA12664 | . | . | . | . | . | . | . | . | . | . | . | . | . | . | C | . | . | . | . | . | A | . | . | . | T | . | . | . | . |
| SEQ_ID_NO_127_pA12665 | . | . | F | . | . | . | . | . | . | . | . | . | . | . | . | K | V | . | A | . | A | . | . | . | . | M | . | E | V |
| SEQ_ID_NO_128_pA12666 | . | . | . | . | . | . | . | . | . | . | . | . | . | . | . | . | V | . | A | . | . | . | P | . | . | . | . | D | Y |
| SEQ_ID_NO_129_pA12667 | . | A | . | . | . | . | . | . | D | . | . | E | . | . | . | K | . | . | . | . | . | I | . | . | R | F | . | E | . |
| SEQ_ID_NO_130_pA12668 | . | . | . | . | . | . | . | . | P | . | . | . | . | . | . | . | . | . | . | Q | . | . | P | E | N | M | . | E | . |
| SEQ_ID_NO_131_pA12669 | . | A | . | . | . | . | . | A | . | . | . | . | . | . | . | . | . | . | . | . | . | . | P | . | . | . | . | . | T |
| SEQ_ID_NO_132_pA12670 | . | A | . | . | . | . | . | . | . | . | . | . | . | . | . | K | . | . | . | . | . | . | P | . | . | . | . | E | V |
| SEQ_ID_NO_133_pA12671 | . | A | . | . | A | . | E | . | . | . | . | . | A | . | . | . | . | . | . | . | . | I | . | . | . | . | . | . | T |
| SEQ_ID_NO_134_pA12672 | Y | . | F | C | . | G | . | . | . | . | . | . | A | R | . | . | V | R | . | . | . | . | . | . | K | . | . | E | . |
| SEQ_ID_NO_135_pA12673 | Y | . | F | . | . | . | . | A | . | D | . | . | A | . | C | R | V | . | . | . | . | . | . | . | K | . | . | . | . |
| SEQ_ID_NO_136_pA12674 | . | . | . | C | A | G | . | A | Q | . | . | . | . | . | C | . | . | . | . | . | . | . | P | . | K | . | . | . | . |

FIG. 20 CONTINUED

| | 192 | 195 | 197 | 198 | 199 | 200 | 201 | 202 | 204 | 208 | 211 | 213 | 215 | 218 | 219 | 230 | 232 | 233 | 234 | 237 | 240 | 241 | 242 | 244 | 246 | 253 | 255 | 256 | 259 |
|---|---|---|---|---|---|---|---|---|---|---|---|---|---|---|---|---|---|---|---|---|---|---|---|---|---|---|---|---|---|
| **SEQ_ID_NO_6_pA06238** | L | Y | N | D | V | P | N | I | D | G | I | L | I | S | Y | V | G | I | L | V | E | D | L | V | G | A | Y | A | N |
| SEQ_ID_NO_46_pA12584 | . | A | K | . | L | . | . | . | . | . | . | . | . | . | . | . | E | . | M | . | . | . | . | . | A | D | . | . | A |
| SEQ_ID_NO_47_pA12585 | . | . | . | . | I | . | . | . | . | . | . | . | . | . | . | . | E | . | . | . | . | . | . | . | A | . | . | . | . |
| SEQ_ID_NO_48_pA12586 | . | . | . | . | . | . | . | . | . | . | . | . | . | . | . | . | K | . | . | . | . | . | . | . | . | . | . | . | . |
| SEQ_ID_NO_49_pA12587 | . | . | . | . | . | . | . | . | . | . | . | . | . | . | . | . | D | . | . | . | . | . | . | . | . | S | . | . | . |
| SEQ_ID_NO_50_pA12588 | . | . | . | . | . | . | . | . | . | . | . | . | . | . | . | . | E | L | . | . | . | . | . | . | . | . | . | . | . |
| SEQ_ID_NO_51_pA12589 | . | . | . | . | . | . | . | . | . | . | . | . | . | . | . | . | E | . | . | . | . | . | . | . | . | . | . | . | . |
| SEQ_ID_NO_52_pA12590 | . | . | . | . | . | . | . | . | . | . | . | . | . | . | . | . | E | . | . | . | . | . | . | . | . | . | . | . | . |
| SEQ_ID_NO_53_pA12591 | . | . | . | K | . | . | . | . | . | . | . | . | . | . | . | . | . | . | . | . | . | . | . | . | A | . | . | . | . |
| SEQ_ID_NO_54_pA12592 | . | . | K | . | . | . | . | . | . | . | . | . | . | . | . | . | . | . | . | . | . | . | . | . | A | S | . | . | . |
| SEQ_ID_NO_55_pA12593 | . | . | . | . | . | . | . | . | . | . | . | . | . | . | . | . | . | . | . | . | . | . | . | . | . | . | . | . | . |
| SEQ_ID_NO_56_pA12594 | . | . | . | . | . | . | . | . | . | . | . | . | . | . | . | . | . | . | . | . | . | . | . | . | . | . | . | . | . |
| SEQ_ID_NO_57_pA12595 | . | . | . | . | . | . | . | . | . | . | . | . | . | . | . | . | . | . | . | . | . | . | . | . | . | . | . | . | . |
| SEQ_ID_NO_58_pA12596 | . | . | . | . | . | . | . | A | . | . | . | . | . | . | . | . | . | . | . | . | . | . | . | . | . | . | . | . | . |
| SEQ_ID_NO_59_pA12597 | . | . | E | . | . | . | . | . | . | . | . | . | . | . | . | . | . | . | . | . | . | . | . | . | . | . | . | . | . |
| SEQ_ID_NO_60_pA12598 | . | . | . | . | . | . | . | . | . | . | . | . | . | . | . | . | . | . | . | . | . | . | . | . | . | . | . | . | . |
| SEQ_ID_NO_61_pA12599 | . | . | . | . | . | . | . | . | . | . | . | . | . | . | . | . | . | . | . | . | . | . | . | . | . | . | . | . | . |
| SEQ_ID_NO_62_pA12600 | . | . | . | . | . | . | . | . | . | A | . | . | . | . | . | . | E | . | . | . | T | . | . | . | . | S | . | . | . |
| SEQ_ID_NO_63_pA12601 | . | . | . | . | . | . | . | . | . | . | . | . | . | . | . | . | E | . | . | . | . | . | . | . | A | . | . | . | . |
| SEQ_ID_NO_64_pA12602 | . | . | K | . | . | . | . | . | . | . | . | . | . | . | . | . | . | . | . | . | . | . | . | . | A | . | . | . | . |
| SEQ_ID_NO_65_pA12603 | . | . | . | . | . | . | . | . | . | . | . | . | . | . | . | . | . | . | . | . | . | . | . | . | . | . | . | . | . |
| SEQ_ID_NO_66_pA12604 | . | . | . | . | . | . | . | . | . | . | . | . | . | . | . | . | E | . | . | . | . | . | . | . | . | . | . | . | . |
| SEQ_ID_NO_67_pA12605 | . | . | K | . | H | . | . | . | . | A | . | . | . | . | . | . | E | . | . | . | . | . | . | . | C | S | . | . | . |
| SEQ_ID_NO_68_pA12606 | . | . | . | . | . | . | . | . | . | . | . | . | . | . | . | . | . | . | . | . | . | . | . | . | . | . | . | . | W |
| SEQ_ID_NO_69_pA12607 | . | . | . | . | . | . | . | . | . | A | . | . | . | . | . | . | . | . | . | . | T | . | . | . | . | . | . | . | . |
| SEQ_ID_NO_70_pA12608 | . | . | E | . | H | . | . | M | . | . | . | . | V | . | H | . | D | . | . | . | T | . | . | . | . | . | . | . | . |
| SEQ_ID_NO_71_pA12609 | . | . | . | . | . | . | . | . | . | . | . | . | . | . | H | . | . | . | . | . | . | . | . | . | . | . | . | . | W |
| SEQ_ID_NO_72_pA12610 | . | . | . | . | . | . | . | . | . | . | . | . | . | . | . | . | D | . | . | . | T | . | . | . | . | . | . | . | . |
| SEQ_ID_NO_73_pA12611 | . | . | . | . | . | . | . | . | . | . | . | . | . | . | H | . | . | . | . | . | . | . | . | . | . | . | . | . | W |
| SEQ_ID_NO_74_pA12612 | . | . | . | . | . | . | . | . | . | . | . | . | . | . | H | . | E | . | . | . | . | . | . | . | . | . | . | . | . |
| SEQ_ID_NO_75_pA12613 | . | . | . | . | H | . | . | . | . | . | . | . | . | . | H | . | . | . | . | . | T | . | . | . | . | . | . | . | W |
| SEQ_ID_NO_76_pA12614 | . | . | . | . | . | . | . | . | . | . | . | . | . | . | . | . | . | . | . | . | T | . | . | . | . | . | . | . | . |
| SEQ_ID_NO_77_pA12615 | . | . | . | . | . | . | . | . | . | . | . | . | . | . | . | . | . | . | . | . | . | . | . | . | A | . | . | . | . |
| SEQ_ID_NO_78_pA12616 | . | . | . | . | . | . | . | . | . | . | . | . | . | . | . | . | E | . | . | L | . | . | . | . | . | S | . | . | . |
| SEQ_ID_NO_79_pA12617 | . | . | . | . | . | . | . | . | . | . | . | . | . | . | . | . | D | . | . | . | . | . | . | . | A | . | . | . | . |
| SEQ_ID_NO_80_pA12618 | . | . | . | . | . | . | . | . | . | . | . | . | . | . | . | . | . | . | . | . | . | . | . | L | . | . | . | . | . |
| SEQ_ID_NO_81_pA12619 | . | . | . | K | . | . | . | . | . | . | . | . | . | . | . | . | E | . | . | . | . | . | . | . | . | . | . | . | . |
| SEQ_ID_NO_82_pA12620 | . | . | K | . | . | . | . | . | . | . | . | . | . | . | . | . | E | . | . | . | . | . | . | . | A | . | . | . | . |
| SEQ_ID_NO_83_pA12621 | . | . | . | . | I | . | . | . | . | A | . | . | . | . | . | . | E | . | . | . | . | . | . | L | A | . | . | . | A |
| SEQ_ID_NO_84_pA12622 | . | . | . | . | . | . | . | . | . | . | . | . | . | . | . | . | . | . | . | . | T | . | . | . | . | . | . | . | . |
| SEQ_ID_NO_85_pA12623 | E | . | . | . | . | . | . | . | . | . | . | . | . | . | D | . | . | . | . | . | . | . | . | . | . | . | . | . | . |
| SEQ_ID_NO_86_pA12624 | . | . | . | . | . | . | . | . | . | . | . | . | . | . | . | . | D | . | . | . | . | . | . | . | . | . | . | . | . |
| SEQ_ID_NO_87_pA12625 | . | . | . | . | . | . | . | . | . | . | . | . | . | . | . | . | . | . | . | . | . | . | . | . | . | . | . | . | . |
| SEQ_ID_NO_88_pA12626 | . | . | . | . | . | . | . | . | . | . | . | . | . | . | . | . | D | . | . | . | . | . | . | . | . | . | . | . | . |
| SEQ_ID_NO_89_pA12627 | . | . | . | . | . | . | . | . | . | . | . | . | . | . | . | . | . | . | . | . | . | . | . | . | . | . | . | . | . |
| SEQ_ID_NO_90_pA12628 | . | . | . | . | . | . | . | . | . | . | . | . | . | . | . | . | . | . | . | . | . | . | . | . | . | . | . | . | . |

FIG. 20 CONTINUED

| | 192 | 195 | 197 | 198 | 199 | 200 | 201 | 202 | 204 | 208 | 211 | 213 | 215 | 218 | 219 | 230 | 232 | 233 | 234 | 237 | 240 | 241 | 242 | 244 | 246 | 253 | 255 | 256 | 259 |
|---|---|---|---|---|---|---|---|---|---|---|---|---|---|---|---|---|---|---|---|---|---|---|---|---|---|---|---|---|---|
| **SEQ_ID_NO_6_pA06238** | L | Y | N | D | V | P | N | I | D | G | I | L | I | S | Y | V | G | I | L | V | E | D | L | V | G | A | Y | A | N |
| SEQ_ID_NO_91_pA12629 | . | . | E | . | . | . | . | . | . | . | . | . | . | . | . | . | . | . | . | . | T | . | . | . | V | . | . | . | . |
| SEQ_ID_NO_92_pA12630 | . | . | E | . | H | . | R | . | . | A | . | . | . | . | . | . | E | . | . | . | T | . | . | . | C | . | . | . | . |
| SEQ_ID_NO_93_pA12631 | . | . | . | . | . | . | . | . | . | . | . | . | . | . | . | . | E | . | . | . | . | . | W | . | A | F | . | . | W |
| SEQ_ID_NO_94_pA12632 | . | . | . | . | C | . | . | . | . | . | . | . | . | . | . | . | . | . | . | L | . | . | . | . | . | . | . | . | . |
| SEQ_ID_NO_95_pA12633 | . | . | . | . | . | . | . | . | . | . | . | . | . | . | . | . | E | . | . | . | . | . | . | . | . | . | . | . | . |
| SEQ_ID_NO_96_pA12634 | . | . | . | . | . | . | . | . | . | . | . | M | . | . | . | . | E | . | . | . | . | . | . | . | . | . | . | . | . |
| SEQ_ID_NO_97_pA12635 | . | . | . | . | . | . | . | . | . | . | . | . | . | . | . | . | . | . | . | . | . | . | . | . | . | . | . | . | . |
| SEQ_ID_NO_98_pA12636 | . | . | . | . | . | . | . | . | . | . | . | . | . | . | . | . | D | . | . | . | . | . | . | . | . | . | . | . | . |
| SEQ_ID_NO_99_pA12637 | . | . | E | . | H | . | . | . | . | . | . | . | . | . | . | . | E | . | . | . | . | P | . | . | . | . | E | . | . |
| SEQ_ID_NO_100_pA12638 | . | . | . | . | . | . | . | . | . | . | . | . | . | . | H | . | . | . | . | . | . | . | . | . | . | . | D | . | . |
| SEQ_ID_NO_101_pA12639 | . | . | E | . | . | . | . | . | . | . | . | . | . | . | H | . | . | . | . | . | . | P | . | . | . | S | D | . | . |
| SEQ_ID_NO_102_pA12640 | . | . | . | . | . | . | . | . | . | . | . | . | . | . | . | . | E | . | . | . | T | . | . | . | . | . | . | . | W |
| SEQ_ID_NO_103_pA12641 | . | . | . | . | . | . | . | A | . | . | . | . | . | . | . | . | . | . | . | . | . | P | . | . | . | . | . | . | W |
| SEQ_ID_NO_104_pA12642 | . | . | . | . | . | . | . | . | . | . | . | . | . | . | H | . | . | . | . | . | T | . | . | . | . | T | . | . | . |
| SEQ_ID_NO_105_pA12643 | . | . | K | . | . | . | . | . | . | . | . | . | . | . | . | . | E | . | . | . | . | . | . | . | . | . | . | . | . |
| SEQ_ID_NO_106_pA12644 | . | . | . | . | . | . | . | . | . | . | . | . | . | . | . | . | D | . | . | L | . | . | . | . | . | . | . | . | . |
| SEQ_ID_NO_107_pA12645 | F | . | K | . | L | . | . | . | . | . | V | . | . | . | . | . | E | . | . | . | . | . | . | . | . | . | . | . | . |
| SEQ_ID_NO_108_pA12646 | . | . | . | K | . | . | . | . | . | . | . | . | . | . | . | . | . | . | . | . | . | . | . | . | . | . | . | . | . |
| SEQ_ID_NO_109_pA12647 | . | . | E | . | . | . | . | . | . | . | . | . | . | . | . | . | . | . | . | . | . | . | . | . | . | . | . | . | . |
| SEQ_ID_NO_110_pA12648 | F | . | K | . | . | . | . | . | . | . | . | . | . | . | . | . | . | . | . | . | T | . | . | . | . | D | K | . | D |
| SEQ_ID_NO_111_pA12649 | . | . | E | . | L | . | . | . | . | . | . | . | . | . | . | . | D | . | . | . | . | . | . | . | . | D | . | . | . |
| SEQ_ID_NO_112_pA12650 | . | . | . | . | . | . | . | . | . | . | . | . | . | . | . | . | . | . | . | . | T | . | . | . | . | T | . | . | . |
| SEQ_ID_NO_113_pA12651 | . | . | . | . | . | . | . | . | . | . | . | . | . | . | . | . | P | . | . | . | . | . | . | . | . | . | . | . | . |
| SEQ_ID_NO_114_pA12652 | F | . | . | . | . | . | . | . | . | . | . | . | . | . | D | . | D | . | A | . | . | . | . | . | . | . | . | . | . |
| SEQ_ID_NO_115_pA12653 | . | . | K | . | L | . | . | . | . | . | . | M | . | . | . | . | E | . | . | . | . | . | . | . | A | . | . | . | W |
| SEQ_ID_NO_116_pA12654 | . | . | . | . | . | . | . | . | . | . | . | . | . | . | . | . | E | . | . | . | . | . | . | . | . | S | E | . | . |
| SEQ_ID_NO_117_pA12655 | . | . | K | . | . | . | . | . | . | . | . | . | . | . | . | . | E | . | . | . | . | . | . | . | A | . | . | . | . |
| SEQ_ID_NO_118_pA12656 | . | . | . | . | . | . | . | . | . | A | . | . | . | . | . | . | . | . | . | . | T | . | . | . | V | S | . | . | . |
| SEQ_ID_NO_119_pA12657 | . | . | . | . | . | . | . | . | . | . | . | . | . | . | . | . | E | . | . | . | T | . | . | L | . | . | . | . | . |
| SEQ_ID_NO_120_pA12658 | . | . | . | . | H | . | . | . | . | . | . | . | . | . | H | . | . | . | . | . | . | . | . | . | A | . | E | . | W |
| SEQ_ID_NO_121_pA12659 | . | . | A | . | . | . | . | . | . | . | . | . | . | . | . | . | E | . | . | . | T | . | . | . | . | . | D | . | . |
| SEQ_ID_NO_122_pA12660 | H | . | K | . | . | . | . | . | . | . | . | . | . | . | H | . | D | . | . | . | . | . | . | . | . | . | . | . | W |
| SEQ_ID_NO_123_pA12661 | . | . | . | . | H | . | . | . | . | . | . | . | . | . | H | A | . | . | . | . | . | . | . | . | . | . | . | . | W |
| SEQ_ID_NO_124_pA12662 | . | . | . | . | . | . | . | . | . | . | . | . | . | . | H | . | E | . | . | . | T | . | . | . | . | . | . | . | . |
| SEQ_ID_NO_125_pA12663 | . | . | D | . | . | . | . | . | . | . | . | . | . | . | . | . | E | . | . | L | . | . | . | . | . | D | Q | . | R |
| SEQ_ID_NO_126_pA12664 | . | A | K | . | L | . | K | . | . | . | . | . | . | . | . | . | . | . | . | . | . | . | . | . | . | . | K | L | . |
| SEQ_ID_NO_127_pA12665 | . | . | . | . | I | . | . | . | . | . | . | . | . | . | . | . | . | . | . | . | . | . | . | . | . | . | . | . | . |
| SEQ_ID_NO_128_pA12666 | F | . | K | . | . | . | . | A | . | . | . | . | . | . | . | . | . | . | . | . | . | G | . | . | . | D | . | . | E |
| SEQ_ID_NO_129_pA12667 | . | . | . | . | . | . | . | . | . | . | . | . | . | . | . | . | P | . | . | . | T | . | . | . | . | D | Q | . | . |
| SEQ_ID_NO_130_pA12668 | F | . | D | . | . | . | . | . | . | . | . | . | . | G | . | . | D | . | . | . | T | . | . | . | . | S | K | . | . |
| SEQ_ID_NO_131_pA12669 | . | . | . | . | . | . | . | . | . | . | . | . | . | . | . | . | E | . | . | . | T | . | . | . | A | . | . | . | W |
| SEQ_ID_NO_132_pA12670 | . | . | E | . | H | . | . | A | . | A | . | . | . | . | . | . | E | . | . | . | . | . | . | . | C | . | E | . | . |
| SEQ_ID_NO_133_pA12671 | . | . | . | . | H | . | R | . | . | . | . | . | . | . | H | . | . | . | . | . | T | . | . | . | V | P | E | . | . |
| SEQ_ID_NO_134_pA12672 | . | . | . | . | H | . | . | A | . | . | . | . | V | . | . | . | E | . | . | . | . | P | . | . | . | . | . | . | . |
| SEQ_ID_NO_135_pA12673 | F | . | Q | . | . | . | Q | . | N | . | . | . | . | . | . | . | D | . | . | . | . | P | . | . | . | N | D | . | . |
| SEQ_ID_NO_136_pA12674 | F | . | . | . | H | G | . | . | . | . | . | . | . | . | . | A | E | . | . | . | T | . | . | . | . | . | D | . | . |

FIG. 20 CONTINUED

| | 262 | 266 | 273 | 280 | 281 | 282 | 284 | 286 | 287 | 290 | 291 | 292 | 295 | 296 | 297 | 302 | 303 | 321 | 324 | 325 | 327 | 328 | 330 | 331 | 333 | 334 | 343 | 344 | 345 |
|---|---|---|---|---|---|---|---|---|---|---|---|---|---|---|---|---|---|---|---|---|---|---|---|---|---|---|---|---|---|
| **SEQ_ID_NO_6_pA06238** | E | R | A | R | G | V | L | S | N | D | E | I | E | R | E | K | R | K | K | R | E | L | I | W | N | L | E | Y | E |
| SEQ_ID_NO_46_pA12584 | . | . | . | . | . | . | . | . | . | . | . | . | . | . | . | . | . | . | . | . | . | . | . | . | S | . | . | . | . |
| SEQ_ID_NO_47_pA12585 | . | . | . | . | A | . | . | . | . | . | . | . | . | . | . | . | . | . | . | . | . | F | . | . | . | . | . | . | . |
| SEQ_ID_NO_48_pA12586 | . | . | . | . | . | . | . | . | . | . | . | . | . | . | . | . | . | . | . | . | . | . | . | . | . | . | . | . | . |
| SEQ_ID_NO_49_pA12587 | . | . | . | . | . | . | . | . | . | . | . | . | . | . | . | . | . | . | . | . | . | . | . | . | . | . | . | . | . |
| SEQ_ID_NO_50_pA12588 | . | . | . | . | A | . | . | . | . | . | . | . | . | . | . | . | . | . | . | . | . | . | . | . | . | . | . | . | . |
| SEQ_ID_NO_51_pA12589 | . | . | . | . | . | . | . | . | . | . | . | . | . | . | . | . | . | . | . | . | . | . | . | . | . | . | . | . | . |
| SEQ_ID_NO_52_pA12590 | . | . | . | . | . | . | . | A | . | . | . | . | . | . | . | . | . | . | . | E | . | . | . | . | . | . | . | . | . |
| SEQ_ID_NO_53_pA12591 | . | . | . | . | . | . | . | . | . | . | . | . | . | . | . | . | . | . | . | . | . | . | . | . | . | . | . | . | . |
| SEQ_ID_NO_54_pA12592 | . | . | . | . | A | . | . | V | . | . | . | . | . | . | . | . | . | . | . | . | . | . | . | . | . | . | . | . | . |
| SEQ_ID_NO_55_pA12593 | . | . | . | . | . | . | . | . | . | . | . | . | . | . | . | . | . | . | . | . | . | . | . | . | . | . | . | H | . |
| SEQ_ID_NO_56_pA12594 | . | . | . | . | A | . | . | . | . | . | . | . | . | . | . | . | . | . | . | . | . | . | . | . | . | . | . | . | . |
| SEQ_ID_NO_57_pA12595 | . | . | . | . | . | . | . | . | . | . | . | . | . | . | . | . | . | . | . | . | . | . | . | . | . | . | . | . | P |
| SEQ_ID_NO_58_pA12596 | . | . | . | . | . | . | . | . | . | . | . | . | . | . | . | . | . | . | . | . | . | . | . | . | . | . | . | . | . |
| SEQ_ID_NO_59_pA12597 | . | . | . | . | . | . | . | . | . | . | . | . | . | . | . | . | . | . | . | . | . | . | . | . | . | . | . | . | . |
| SEQ_ID_NO_60_pA12598 | . | . | . | . | . | . | . | . | . | . | . | . | . | . | . | . | . | . | . | . | . | . | . | . | S | . | . | . | . |
| SEQ_ID_NO_61_pA12599 | . | . | . | . | . | . | . | . | . | . | . | . | . | . | . | . | . | . | . | . | . | . | . | . | . | . | . | H | P |
| SEQ_ID_NO_62_pA12600 | . | V | . | . | . | . | . | A | . | . | . | . | . | . | . | . | . | . | . | E | . | . | L | . | . | . | . | . | P |
| SEQ_ID_NO_63_pA12601 | . | . | . | . | A | . | . | . | . | . | . | . | F | E | . | . | . | . | . | . | . | . | . | . | . | . | . | . | . |
| SEQ_ID_NO_64_pA12602 | . | . | . | . | . | . | . | . | D | . | . | . | . | . | . | . | . | . | . | . | . | . | . | . | . | . | . | . | . |
| SEQ_ID_NO_65_pA12603 | . | . | . | . | . | . | . | . | . | . | . | . | . | . | . | . | . | . | . | . | . | . | . | . | . | . | . | . | . |
| SEQ_ID_NO_66_pA12604 | . | . | . | . | . | . | . | . | . | . | . | . | . | . | . | . | . | . | . | . | . | . | . | . | . | . | . | . | . |
| SEQ_ID_NO_67_pA12605 | . | V | . | . | A | . | . | . | D | . | . | . | . | . | . | . | . | . | . | . | . | . | . | . | . | . | . | . | P |
| SEQ_ID_NO_68_pA12606 | . | . | . | . | . | . | . | . | . | . | . | . | . | . | . | . | . | . | . | . | . | . | . | . | . | . | . | . | . |
| SEQ_ID_NO_69_pA12607 | . | . | . | . | . | . | . | . | . | . | . | . | . | . | . | . | . | . | . | . | . | . | . | . | . | . | . | . | . |
| SEQ_ID_NO_70_pA12608 | . | . | W | . | A | . | . | . | . | . | . | . | . | . | . | . | . | . | . | . | . | . | . | . | . | . | . | H | P |
| SEQ_ID_NO_71_pA12609 | . | V | . | . | . | . | . | . | . | . | . | . | . | . | . | . | . | . | . | . | . | . | . | . | S | . | . | . | P |
| SEQ_ID_NO_72_pA12610 | . | . | . | . | . | . | . | . | . | . | . | . | . | . | . | . | . | . | . | . | . | . | . | . | . | . | . | H | . |
| SEQ_ID_NO_73_pA12611 | . | . | . | . | . | . | . | . | . | . | . | . | . | . | . | . | . | . | . | . | . | . | . | . | . | . | . | . | . |
| SEQ_ID_NO_74_pA12612 | . | . | . | . | . | . | . | . | . | . | . | . | . | . | . | . | . | . | . | . | . | . | . | . | . | . | . | . | P |
| SEQ_ID_NO_75_pA12613 | . | . | . | . | . | . | . | . | . | . | . | . | . | . | . | . | . | . | . | . | . | . | . | . | . | . | . | H | . |
| SEQ_ID_NO_76_pA12614 | . | . | . | . | . | . | . | . | . | . | . | . | . | . | G | . | . | . | . | . | . | . | . | . | . | . | . | . | . |
| SEQ_ID_NO_77_pA12615 | . | . | . | . | A | . | . | . | . | . | . | . | . | . | . | . | . | . | . | . | . | F | . | . | . | . | . | . | . |
| SEQ_ID_NO_78_pA12616 | . | . | . | . | . | . | . | . | . | . | . | . | . | . | . | . | . | . | . | . | . | . | . | . | . | . | . | . | . |
| SEQ_ID_NO_79_pA12617 | . | . | . | . | . | . | . | A | . | . | . | . | . | . | . | . | . | . | . | E | . | . | . | . | . | . | . | . | . |
| SEQ_ID_NO_80_pA12618 | . | . | . | . | . | . | . | . | . | . | . | . | . | . | . | . | . | . | . | . | . | . | . | . | . | . | . | . | P |
| SEQ_ID_NO_81_pA12619 | . | . | . | . | . | . | . | . | . | . | . | . | . | . | . | . | . | . | . | E | . | . | . | . | . | . | . | . | . |
| SEQ_ID_NO_82_pA12620 | . | . | . | . | A | . | . | . | . | . | . | . | . | . | . | . | . | . | . | . | . | . | . | . | . | . | . | . | . |
| SEQ_ID_NO_83_pA12621 | . | . | . | . | A | . | . | A | . | . | . | . | . | . | . | . | . | . | . | . | . | . | . | . | . | . | . | . | P |
| SEQ_ID_NO_84_pA12622 | . | . | . | . | . | . | . | . | . | . | . | . | . | . | . | . | . | . | . | . | . | . | . | . | . | . | . | H | . |
| SEQ_ID_NO_85_pA12623 | . | . | . | . | A | . | . | A | . | . | . | . | . | . | . | . | . | . | . | . | . | . | . | . | . | . | . | H | P |
| SEQ_ID_NO_86_pA12624 | . | . | . | . | . | . | . | A | . | . | . | . | . | . | . | . | . | . | . | . | . | . | . | . | . | . | . | . | P |
| SEQ_ID_NO_87_pA12625 | . | . | . | . | . | . | . | . | . | . | . | . | . | . | . | . | . | . | . | . | . | . | . | . | . | . | . | H | . |
| SEQ_ID_NO_88_pA12626 | . | . | . | . | . | . | . | . | . | . | . | . | . | . | . | . | . | . | . | . | . | . | . | . | . | . | . | . | . |
| SEQ_ID_NO_89_pA12627 | . | . | . | . | A | . | . | . | . | . | . | . | . | . | . | . | . | . | . | . | . | . | . | . | . | . | . | . | . |
| SEQ_ID_NO_90_pA12628 | . | . | . | . | . | . | . | . | . | . | . | . | . | . | . | . | . | . | . | . | . | . | . | . | . | . | . | H | . |

FIG. 20 CONTINUED

| | 262 | 266 | 273 | 280 | 281 | 282 | 284 | 286 | 287 | 290 | 291 | 292 | 295 | 296 | 297 | 302 | 303 | 321 | 324 | 325 | 327 | 328 | 330 | 331 | 333 | 334 | 343 | 344 | 345 |
|---|---|---|---|---|---|---|---|---|---|---|---|---|---|---|---|---|---|---|---|---|---|---|---|---|---|---|---|---|---|
| **SEQ_ID_NO_6_pA06238** | E | R | A | R | G | V | L | S | N | D | E | I | E | R | E | K | R | K | K | R | E | L | I | W | N | L | E | Y | E |
| SEQ_ID_NO_91_pA12629 | . | . | . | . | . | . | . | A | . | . | . | . | . | . | . | . | . | . | . | E | . | . | L | . | . | . | . | H | P |
| SEQ_ID_NO_92_pA12630 | . | . | . | . | . | . | . | A | D | . | . | . | . | E | . | . | . | . | . | . | . | . | . | . | A | . | . | . | . |
| SEQ_ID_NO_93_pA12631 | . | . | . | . | A | . | . | . | . | . | . | . | . | . | . | . | . | . | . | E | . | . | . | . | A | . | . | . | . |
| SEQ_ID_NO_94_pA12632 | . | . | . | . | . | . | . | . | . | . | . | . | . | . | . | . | . | . | . | . | . | . | . | . | . | . | . | H | . |
| SEQ_ID_NO_95_pA12633 | . | V | W | . | . | . | . | A | D | . | . | . | . | . | . | . | . | . | . | . | . | . | . | . | A | . | . | . | P |
| SEQ_ID_NO_96_pA12634 | . | . | . | . | . | . | . | . | . | . | . | . | . | . | . | . | . | . | . | . | . | . | . | . | . | . | . | H | . |
| SEQ_ID_NO_97_pA12635 | . | . | . | . | . | . | . | . | . | . | . | . | . | . | . | . | . | . | . | . | . | . | . | . | . | . | . | . | P |
| SEQ_ID_NO_98_pA12636 | . | A | . | . | . | . | . | A | . | . | . | . | . | E | . | . | . | . | . | . | . | . | . | . | . | . | . | H | P |
| SEQ_ID_NO_99_pA12637 | . | . | . | . | . | . | . | . | D | . | . | . | . | . | . | . | . | . | . | . | . | . | . | . | . | . | . | H | . |
| SEQ_ID_NO_100_pA12638 | . | . | . | . | A | . | . | . | . | . | . | . | . | . | . | . | . | . | . | . | . | . | . | . | . | . | N | H | . |
| SEQ_ID_NO_101_pA12639 | . | . | . | . | . | . | . | A | . | . | . | . | . | E | . | . | . | . | . | . | . | . | . | . | . | . | N | . | P |
| SEQ_ID_NO_102_pA12640 | . | . | . | . | . | . | . | A | . | . | . | . | . | . | G | . | . | . | . | . | . | . | . | . | . | . | . | . | . |
| SEQ_ID_NO_103_pA12641 | . | . | . | . | A | . | . | . | . | . | . | . | . | E | . | . | E | . | . | . | . | . | . | H | . | . | . | . | P |
| SEQ_ID_NO_104_pA12642 | . | . | . | . | . | . | . | . | . | . | . | . | . | Y | . | . | . | . | . | . | . | . | . | . | . | . | . | H | P |
| SEQ_ID_NO_105_pA12643 | . | . | . | . | A | . | K | . | . | . | . | L | . | . | . | . | . | . | . | . | . | F | . | . | . | . | . | . | . |
| SEQ_ID_NO_106_pA12644 | . | . | . | . | . | . | . | A | . | K | . | . | . | . | . | . | . | . | . | . | . | . | . | . | . | . | . | H | . |
| SEQ_ID_NO_107_pA12645 | . | . | . | . | . | . | . | A | . | . | . | . | . | . | . | . | . | . | . | . | . | . | . | . | . | . | . | . | . |
| SEQ_ID_NO_108_pA12646 | . | . | . | . | . | . | . | A | . | . | . | . | . | . | . | . | . | . | . | E | . | . | . | . | . | . | . | . | . |
| SEQ_ID_NO_109_pA12647 | . | . | . | . | . | . | . | . | . | . | . | . | . | . | . | . | . | . | . | E | . | . | . | . | . | . | . | . | . |
| SEQ_ID_NO_110_pA12648 | . | . | . | . | A | . | . | A | . | K | . | . | . | . | . | . | . | . | . | . | . | . | . | . | . | . | . | . | P |
| SEQ_ID_NO_111_pA12649 | . | . | . | . | . | . | . | . | . | . | . | . | . | D | . | . | . | . | . | . | . | . | . | . | . | . | . | H | P |
| SEQ_ID_NO_112_pA12650 | . | . | . | . | . | . | . | A | . | . | . | . | . | . | . | . | . | . | . | . | . | . | . | . | . | . | . | . | . |
| SEQ_ID_NO_113_pA12651 | . | . | . | . | . | . | . | . | . | . | . | . | . | . | . | . | . | . | . | . | . | . | . | . | . | . | . | H | . |
| SEQ_ID_NO_114_pA12652 | . | . | . | . | . | . | . | A | . | . | . | . | . | . | K | . | . | . | . | . | R | . | . | . | . | . | . | . | . |
| SEQ_ID_NO_115_pA12653 | . | . | . | . | . | . | . | A | D | . | . | . | . | . | . | . | . | H | . | . | . | . | . | . | S | . | . | H | P |
| SEQ_ID_NO_116_pA12654 | . | . | . | . | . | . | . | D | . | K | D | . | . | . | . | . | . | . | . | . | . | . | . | . | S | . | . | H | . |
| SEQ_ID_NO_117_pA12655 | . | . | . | . | A | . | . | . | D | . | . | . | P | . | . | . | . | . | . | . | . | F | . | . | A | . | . | . | . |
| SEQ_ID_NO_118_pA12656 | . | V | . | . | . | . | . | A | . | . | . | . | . | . | . | . | . | H | . | D | . | . | . | . | . | . | . | H | . |
| SEQ_ID_NO_119_pA12657 | . | . | . | . | . | . | . | D | . | . | . | . | . | . | . | . | . | . | . | . | . | . | . | . | . | . | . | . | . |
| SEQ_ID_NO_120_pA12658 | . | A | . | . | A | . | . | . | D | . | . | . | . | . | . | . | . | . | D | . | . | . | . | H | S | . | . | H | . |
| SEQ_ID_NO_121_pA12659 | . | . | . | . | . | . | . | A | . | . | . | . | . | Y | R | . | E | . | D | . | . | . | . | . | . | . | N | . | P |
| SEQ_ID_NO_122_pA12660 | . | A | . | . | . | . | . | . | . | . | D | . | . | . | . | . | E | . | D | . | . | . | . | . | S | . | . | H | . |
| SEQ_ID_NO_123_pA12661 | . | . | . | . | . | . | . | A | D | . | . | . | . | . | . | . | . | . | E | . | R | . | . | H | . | . | . | H | P |
| SEQ_ID_NO_124_pA12662 | Q | A | . | . | . | . | . | A | . | . | . | . | . | Y | . | . | . | . | . | . | . | . | . | . | S | . | . | H | P |
| SEQ_ID_NO_125_pA12663 | . | . | . | . | . | I | . | A | . | Q | . | L | . | . | . | L | . | . | . | . | . | . | . | . | . | . | . | H | . |
| SEQ_ID_NO_126_pA12664 | . | . | . | . | A | . | . | . | . | . | . | . | . | . | . | L | . | . | . | . | . | . | . | . | . | . | . | H | . |
| SEQ_ID_NO_127_pA12665 | . | . | . | . | . | . | . | . | . | . | . | . | . | . | . | . | . | . | . | . | . | . | . | . | . | . | . | . | . |
| SEQ_ID_NO_128_pA12666 | . | . | . | . | . | . | . | A | . | . | . | . | . | D | K | . | . | . | E | . | R | . | . | . | S | . | . | H | P |
| SEQ_ID_NO_129_pA12667 | . | . | . | . | A | . | . | A | . | N | . | . | . | . | . | . | . | . | E | . | R | . | . | . | . | Y | . | . | P |
| SEQ_ID_NO_130_pA12668 | . | . | . | . | . | . | . | . | . | N | . | . | . | . | K | . | . | . | . | . | R | . | . | . | . | . | . | . | P |
| SEQ_ID_NO_131_pA12669 | . | V | . | . | A | . | . | . | D | A | . | . | . | . | . | . | . | T | D | . | . | . | . | . | . | . | . | . | . |
| SEQ_ID_NO_132_pA12670 | . | . | . | . | A | . | . | . | D | K | . | . | . | . | H | . | . | . | D | . | . | . | . | . | . | . | . | . | . |
| SEQ_ID_NO_133_pA12671 | . | V | . | . | . | . | . | . | D | . | . | . | . | E | . | . | . | . | . | . | . | . | . | . | . | . | . | . | . |
| SEQ_ID_NO_134_pA12672 | . | A | . | . | A | . | . | A | D | K | . | . | . | . | H | . | E | R | E | N | R | . | . | . | S | . | . | H | P |
| SEQ_ID_NO_135_pA12673 | . | . | . | E | . | . | . | A | D | . | . | . | . | E | Q | . | . | . | . | Q | R | W | . | . | S | . | N | . | . |
| SEQ_ID_NO_136_pA12674 | . | . | . | . | A | . | . | . | . | . | . | . | . | . | Q | . | E | . | . | N | . | . | . | H | S | . | N | H | . |

FIG. 20 CONTINUED

| | 349 | 350 | 352 | 353 | 358 | 360 | 362 | 363 | 364 | 365 | 366 | 372 | 373 | 374 | 376 | 377 | 379 | 383 | 385 | 393 | 397 | 403 |
|---|---|---|---|---|---|---|---|---|---|---|---|---|---|---|---|---|---|---|---|---|---|---|
| **SEQ_ID_NO_6_pA06238** | M | V | N | K | F | E | V | D | I | K | F | Y | D | S | F | D | R | M | N | K | R | S |
| SEQ_ID_NO_46_pA12584 | . | . | . | . | . | . | . | . | . | . | . | . | . | Q | . | . | . | . | . | . | . | . |
| SEQ_ID_NO_47_pA12585 | . | . | . | . | . | . | . | . | . | . | . | . | . | . | . | . | . | . | . | . | . | A |
| SEQ_ID_NO_48_pA12586 | K | . | . | . | . | . | . | . | . | . | . | . | . | . | . | . | . | . | . | . | . | . |
| SEQ_ID_NO_49_pA12587 | . | . | . | . | . | . | . | . | . | . | . | . | . | Q | . | . | . | L | . | . | . | . |
| SEQ_ID_NO_50_pA12588 | K | . | . | . | . | . | . | . | . | . | . | . | . | . | . | . | . | . | . | . | . | . |
| SEQ_ID_NO_51_pA12589 | K | A | . | . | . | . | . | . | . | . | . | . | . | . | . | . | . | . | . | . | . | . |
| SEQ_ID_NO_52_pA12590 | . | . | . | . | . | . | . | . | . | . | . | . | . | . | . | . | . | . | . | . | . | . |
| SEQ_ID_NO_53_pA12591 | . | . | . | . | . | . | . | . | . | . | . | . | . | . | . | . | . | . | . | . | . | . |
| SEQ_ID_NO_54_pA12592 | K | . | . | . | . | . | . | . | . | . | . | P | . | . | . | . | . | . | . | . | . | Y |
| SEQ_ID_NO_55_pA12593 | . | . | . | . | . | . | . | . | . | . | . | P | . | . | . | . | . | . | . | . | . | . |
| SEQ_ID_NO_56_pA12594 | . | . | . | . | . | . | . | . | . | . | . | . | . | Q | . | . | . | . | . | . | . | . |
| SEQ_ID_NO_57_pA12595 | . | . | . | . | . | . | . | . | . | . | . | . | . | . | . | . | . | . | . | . | . | . |
| SEQ_ID_NO_58_pA12596 | . | . | . | . | . | . | . | . | . | . | . | P | . | . | . | . | . | . | . | . | . | . |
| SEQ_ID_NO_59_pA12597 | . | . | . | . | . | . | . | . | . | . | . | . | . | . | . | . | . | . | . | . | . | . |
| SEQ_ID_NO_60_pA12598 | . | . | . | . | . | . | . | . | . | . | . | . | . | . | . | . | . | . | . | . | . | . |
| SEQ_ID_NO_61_pA12599 | . | . | . | . | . | . | . | . | . | . | . | . | . | . | . | . | . | . | . | . | . | . |
| SEQ_ID_NO_62_pA12600 | . | . | . | . | . | . | . | . | . | . | . | . | . | . | R | . | . | . | . | . | . | . |
| SEQ_ID_NO_63_pA12601 | . | . | . | . | L | D | . | . | . | . | . | . | . | . | . | . | . | L | . | . | . | . |
| SEQ_ID_NO_64_pA12602 | . | A | . | . | . | . | . | . | . | . | . | . | . | . | . | . | . | . | . | . | . | . |
| SEQ_ID_NO_65_pA12603 | R | . | . | . | . | . | . | . | . | . | . | . | . | . | . | . | . | . | . | . | . | . |
| SEQ_ID_NO_66_pA12604 | . | . | . | . | . | . | . | . | . | . | . | . | . | . | . | . | . | . | . | . | . | . |
| SEQ_ID_NO_67_pA12605 | . | A | . | . | . | D | I | . | . | . | . | . | . | . | R | . | . | . | . | . | . | . |
| SEQ_ID_NO_68_pA12606 | . | . | . | . | . | D | . | . | . | . | . | . | . | A | . | . | . | . | P | . | . | . |
| SEQ_ID_NO_69_pA12607 | . | . | . | . | . | . | . | . | . | . | . | . | . | C | . | . | . | . | . | . | . | . |
| SEQ_ID_NO_70_pA12608 | . | A | . | . | . | . | . | P | . | . | . | . | . | C | . | . | . | . | . | . | . | . |
| SEQ_ID_NO_71_pA12609 | . | A | . | . | . | . | . | P | . | . | . | . | . | . | . | . | . | . | . | . | . | . |
| SEQ_ID_NO_72_pA12610 | . | A | . | . | L | . | . | . | . | . | L | . | . | . | . | . | . | . | . | . | . | . |
| SEQ_ID_NO_73_pA12611 | . | . | . | . | . | . | . | P | . | . | . | . | . | . | . | . | . | . | . | . | . | . |
| SEQ_ID_NO_74_pA12612 | . | A | . | . | L | . | . | . | . | . | . | . | . | . | . | . | . | . | . | . | . | . |
| SEQ_ID_NO_75_pA12613 | . | . | . | . | . | . | . | . | . | . | . | . | . | . | . | . | . | . | . | . | . | . |
| SEQ_ID_NO_76_pA12614 | . | A | . | . | . | . | . | . | . | . | . | . | . | . | . | . | . | . | . | . | . | . |
| SEQ_ID_NO_77_pA12615 | K | . | . | . | . | . | . | . | . | . | . | . | . | . | . | . | . | . | . | . | . | A |
| SEQ_ID_NO_78_pA12616 | T | . | . | . | . | . | . | . | . | . | . | . | . | . | . | . | . | L | . | . | . | . |
| SEQ_ID_NO_79_pA12617 | K | . | . | . | . | . | . | . | . | . | . | . | . | . | . | . | . | . | . | . | . | . |
| SEQ_ID_NO_80_pA12618 | . | . | . | . | . | . | . | . | . | . | . | . | . | . | . | . | . | . | . | . | . | . |
| SEQ_ID_NO_81_pA12619 | . | . | . | . | . | . | . | . | . | . | . | . | . | . | . | . | . | . | . | . | . | A |
| SEQ_ID_NO_82_pA12620 | . | . | . | . | . | . | . | . | . | . | . | P | . | . | . | . | . | . | . | . | . | Y |
| SEQ_ID_NO_83_pA12621 | . | . | . | . | . | . | . | . | . | . | . | P | . | Q | . | . | . | . | . | . | . | . |
| SEQ_ID_NO_84_pA12622 | K | . | . | . | . | . | . | . | . | . | . | . | . | Q | . | . | . | . | . | . | . | . |
| SEQ_ID_NO_85_pA12623 | . | . | . | . | . | . | . | . | . | . | . | . | . | . | E | . | . | . | . | . | . | . |
| SEQ_ID_NO_86_pA12624 | . | . | . | . | . | . | . | . | . | . | . | P | . | . | . | . | . | . | . | . | . | . |
| SEQ_ID_NO_87_pA12625 | . | . | . | . | . | . | . | . | . | . | . | . | . | . | . | . | . | . | . | . | . | . |
| SEQ_ID_NO_88_pA12626 | . | . | . | . | . | . | . | . | . | R | . | . | . | . | . | . | . | . | . | . | . | . |
| SEQ_ID_NO_89_pA12627 | . | . | . | . | . | . | . | . | . | . | . | . | . | . | . | . | . | . | . | . | . | . |
| SEQ_ID_NO_90_pA12628 | . | A | . | . | . | . | . | . | . | . | . | . | . | . | . | . | . | . | . | . | . | A |

FIG. 20 CONTINUED

| | 349 | 350 | 352 | 353 | 358 | 360 | 362 | 363 | 364 | 365 | 366 | 372 | 373 | 374 | 376 | 377 | 379 | 383 | 385 | 393 | 397 | 403 |
|---|---|---|---|---|---|---|---|---|---|---|---|---|---|---|---|---|---|---|---|---|---|---|
| **SEQ_ID_NO_6_pA06238** | M | V | N | K | F | E | V | D | I | K | F | Y | D | S | F | D | R | M | N | K | R | S |
| SEQ_ID_NO_91_pA12629 | . | . | . | . | . | . | . | . | . | . | . | . | . | . | R | . | . | . | . | . | . | . |
| SEQ_ID_NO_92_pA12630 | R | . | . | . | . | . | . | . | . | . | . | . | . | C | . | . | . | . | . | . | . | . |
| SEQ_ID_NO_93_pA12631 | . | A | . | . | . | D | . | . | . | . | . | . | . | . | . | . | C | . | P | . | . | . |
| SEQ_ID_NO_94_pA12632 | A | . | . | . | L | . | . | . | . | . | . | . | . | . | . | . | . | . | . | . | . | . |
| SEQ_ID_NO_95_pA12633 | K | . | . | . | . | . | I | . | . | . | . | . | . | . | . | . | . | . | . | . | . | . |
| SEQ_ID_NO_96_pA12634 | . | . | . | . | . | . | . | . | . | . | . | . | . | C | . | . | . | . | . | . | . | . |
| SEQ_ID_NO_97_pA12635 | K | A | . | . | . | . | . | . | . | . | . | . | . | . | . | . | . | . | . | . | . | . |
| SEQ_ID_NO_98_pA12636 | . | . | . | . | . | . | . | . | . | . | . | . | . | . | . | . | . | . | . | H | . | . |
| SEQ_ID_NO_99_pA12637 | . | A | . | . | . | . | . | . | . | T | . | . | . | C | . | . | . | . | . | . | . | . |
| SEQ_ID_NO_100_pA12638 | . | A | . | . | . | D | . | . | . | . | . | . | . | . | . | . | . | . | . | H | . | . |
| SEQ_ID_NO_101_pA12639 | . | . | . | . | . | . | . | . | . | T | . | . | . | . | R | . | . | . | . | . | . | . |
| SEQ_ID_NO_102_pA12640 | . | . | . | . | . | . | . | . | . | . | . | . | . | . | H | . | . | . | . | . | . | . |
| SEQ_ID_NO_103_pA12641 | A | A | . | . | . | D | . | . | . | . | . | . | . | A | H | . | . | . | . | . | . | . |
| SEQ_ID_NO_104_pA12642 | A | . | . | . | . | . | . | . | . | . | L | . | . | . | . | . | . | . | . | . | . | . |
| SEQ_ID_NO_105_pA12643 | K | . | . | . | . | . | . | . | . | . | . | P | . | . | K | . | . | . | . | . | . | . |
| SEQ_ID_NO_106_pA12644 | T | . | . | . | . | . | . | . | . | . | . | . | . | . | . | . | . | L | . | . | . | . |
| SEQ_ID_NO_107_pA12645 | . | . | . | . | . | . | . | . | . | . | . | . | . | Q | . | . | . | . | . | . | . | . |
| SEQ_ID_NO_108_pA12646 | K | . | . | . | . | . | . | . | . | . | . | . | . | . | . | . | . | . | . | . | . | . |
| SEQ_ID_NO_109_pA12647 | . | . | . | . | . | . | . | . | . | . | . | . | . | . | Q | . | . | . | . | . | . | . |
| SEQ_ID_NO_110_pA12648 | C | . | . | . | . | . | . | . | . | R | . | . | . | Q | . | . | . | . | . | . | . | . |
| SEQ_ID_NO_111_pA12649 | . | . | . | . | . | . | . | . | . | R | . | . | . | . | . | . | . | . | . | . | . | . |
| SEQ_ID_NO_112_pA12650 | . | . | . | . | . | . | . | . | . | R | . | . | . | . | . | . | . | . | . | . | . | . |
| SEQ_ID_NO_113_pA12651 | K | . | . | . | . | . | . | . | . | R | . | . | . | . | . | . | . | . | . | . | . | A |
| SEQ_ID_NO_114_pA12652 | . | A | . | R | . | . | . | . | . | . | . | . | . | . | . | . | . | . | . | . | . | . |
| SEQ_ID_NO_115_pA12653 | A | A | . | . | . | . | . | . | . | . | . | . | . | . | . | . | . | . | . | . | . | . |
| SEQ_ID_NO_116_pA12654 | . | A | . | . | L | . | I | . | . | . | L | . | . | T | . | . | . | . | . | . | . | . |
| SEQ_ID_NO_117_pA12655 | A | . | . | . | . | . | . | . | . | . | . | P | . | . | . | . | . | . | . | . | . | . |
| SEQ_ID_NO_118_pA12656 | . | . | . | . | . | . | . | . | . | . | L | . | . | . | . | . | . | . | . | . | . | . |
| SEQ_ID_NO_119_pA12657 | R | A | . | . | . | . | . | . | . | . | . | . | . | . | . | . | . | . | . | . | . | . |
| SEQ_ID_NO_120_pA12658 | A | . | . | . | . | D | . | . | . | . | . | . | . | . | . | . | . | L | . | H | . | A |
| SEQ_ID_NO_121_pA12659 | A | A | . | . | L | . | . | . | . | . | L | . | . | . | . | . | . | . | . | . | . | . |
| SEQ_ID_NO_122_pA12660 | . | A | . | . | . | . | . | P | . | . | . | . | . | . | . | . | . | L | . | H | . | . |
| SEQ_ID_NO_123_pA12661 | E | . | . | R | . | D | . | . | W | . | . | . | . | . | H | . | . | . | . | . | . | . |
| SEQ_ID_NO_124_pA12662 | A | A | . | . | . | . | . | P | . | T | . | . | . | . | . | . | . | . | . | . | . | A |
| SEQ_ID_NO_125_pA12663 | K | . | . | . | . | . | . | . | . | . | . | . | . | Q | . | . | . | L | . | . | . | . |
| SEQ_ID_NO_126_pA12664 | . | . | . | . | . | . | . | . | . | . | . | . | . | Q | . | . | . | . | . | . | . | . |
| SEQ_ID_NO_127_pA12665 | K | . | . | . | . | . | . | . | . | . | . | . | . | . | . | . | . | . | . | . | . | . |
| SEQ_ID_NO_128_pA12666 | . | A | . | . | . | . | . | . | . | . | . | P | . | . | . | . | . | . | . | . | . | . |
| SEQ_ID_NO_129_pA12667 | K | . | . | . | . | . | . | . | . | . | . | . | . | . | . | . | . | . | . | . | . | . |
| SEQ_ID_NO_130_pA12668 | A | . | . | . | . | . | . | . | . | R | . | . | . | . | . | . | . | . | . | . | . | . |
| SEQ_ID_NO_131_pA12669 | K | . | . | . | . | D | I | . | . | . | . | . | . | A | H | . | C | . | P | . | . | A |
| SEQ_ID_NO_132_pA12670 | A | . | . | . | . | . | . | . | . | . | . | . | . | C | . | . | . | . | . | . | K | . |
| SEQ_ID_NO_133_pA12671 | A | . | E | . | . | . | . | . | . | . | . | P | A | C | . | . | . | . | . | . | . | . |
| SEQ_ID_NO_134_pA12672 | . | . | . | . | . | . | . | . | . | . | . | . | . | C | H | A | . | . | . | . | . | . |
| SEQ_ID_NO_135_pA12673 | . | A | E | . | . | . | . | P | . | . | . | . | . | A | . | . | . | L | . | . | . | . |
| SEQ_ID_NO_136_pA12674 | . | . | E | . | . | . | I | . | W | . | . | . | . | . | R | . | . | . | . | . | . | H |

FIG. 22 Continued

Positions: 5, 10, 11, 17, 32, 34, 62, 67, 70, 72, 78, 102, 104, 116, 117, 122, 131, 137, 155, 193, 194, 221, 226, 238, 268, 302, 318, 321, 324, 348, 353, 365, 382, 384, 392, 393, 396

| | |
|---|---|
| **SEQ_ID_NO_6_pA06238** | KKKCKKKKKKKKKKKCKKKKKKKKKKKKKKKKKKKKK |
| SEQ_ID_NO_187_pA14334 | W.Y.MT..RLMYFY.VQ..AA..WLLDDDL..RDLY. |
| SEQ_ID_NO_188_pA14335 | ANQLQE.TRLQRRRWTE.E.R.RSLR.D...RRD... |
| SEQ_ID_NO_189_pA14336 | LA.GLY..QL...T..R.E.AI.S.IDDELL..Q..M |
| SEQ_ID_NO_190_pA14337 | .NLIMLYT.TL..LWAE.N..VR.IM.DDLW.RRL.R |
| SEQ_ID_NO_191_pA14338 | ..Q..ER..L..R..A.E.E.QR...DDDRRR.D... |
| SEQ_ID_NO_192_pA14339 | ALQ.I.V.RLLYRL..ELE...R...DD.VL.RTR.. |
| SEQ_ID_NO_193_pA14340 | M.QS.LVTRL.YQ...YL.Q.VRW.LDD..LS.RLHI |
| SEQ_ID_NO_194_pA14341 | HN..LT.SQ.LLRT..EL..R.RS..DD...RL.... |
| SEQ_ID_NO_195_pA14342 | FLL.MLVTR.LYQI..ELNQAIRW.LDDDLWSRD... |
| SEQ_ID_NO_196_pA14343 | L.V.LMVSQ.L.......R.A.R..L.DEL.R.Q.Y. |
| SEQ_ID_NO_197_pA14344 | WNQT.TRT.L.R....QQH.ERT..QDD..R.R.... |
| SEQ_ID_NO_198_pA14345 | L.L.ITVSQL...T..ELEE..A.....ELL.LRLY. |
| SEQ_ID_NO_199_pA14346 | ..L....S.L..I..TR..EAIA..LDDELLSL.L.M |
| SEQ_ID_NO_200_pA14347 | H.VGIT..QLL.R.L.E.E.TIR.N..D.LLRL..YI |
| SEQ_ID_NO_201_pA14348 | FMLIMLVTRLLLQIVTEENQAVRSILDDDLLSRRLHM |
| SEQ_ID_NO_202_pA14349 | WNQIQTRTRLRRRHVVQTHEERTRVQDDDRRHRD... |
| SEQ_ID_NO_203_pA14350 | ANQTQERTRLQRRR..EEEETQRS.QDDDRRRRD... |
| SEQ_ID_NO_204_pA14351 | L..GIMV..LLL.T.TELEQR.R.NIDDELLS.RLY. |
| SEQ_ID_NO_205_pA14352 | FNQ.QQRTR.QRQQ..ETNQSTRS.QDDDRRSRE... |
| SEQ_ID_NO_206_pA14353 | LNEVQHRQRLRRRR..REEETRNS.RDDSRQRNQ... |
| SEQ_ID_NO_207_pA14354 | LNVISFVQRIMLFWVAREEAAIQSVLDDSLLRNRLFF |
| SEQ_ID_NO_208_pA14355 | LNL.LMVSQ.LYRT..ELEQRIRS.IDDELLSLE... |
| SEQ_ID_NO_209_pA14356 | LAL.ITVSQ.LYIT..ELEEAIAS.LDDELLSLE... |
| SEQ_ID_NO_210_pA14357 | WRR.QQRTR.QRRR..QEDRTRTS.QEDDRRRRE... |
| SEQ_ID_NO_211_pA14358 | MMQSMLVTRLMLRI..YLNASIRS.LDDDLWSRRLYM |
| SEQ_ID_NO_212_pA14359 | FLLTMLYQRLRYVR..LEEEAVAS.MDDSRLSRRLYI |
| SEQ_ID_NO_213_pA14360 | LNQSQRRTRLRRRQVTEEEESRSSVQDDSRRSRQ... |
| SEQ_ID_NO_214_pA14361 | LAVGLYVRQLRLRT..RIEEAINS.LDDELLRLRLYI |
| SEQ_ID_NO_215_pA14362 | ANVGITVSQLLYRT..ELEERIRS.IDDELLRLTLYI |
| SEQ_ID_NO_216_pA14363 | ANVGIMVSQLRYISLTELEEAIASNLDDERLSLRLYI |
| SEQ_ID_NO_217_pA14364 | LRVGIMVSQLLYRTLTRLRIAIRSNLDDELLRLRLYI |
| SEQ_ID_NO_218_pA14365 | RRR.RRRRR.RRRR..RRRRRRRR.RRRRRRRRR... |
| SEQ_ID_NO_219_pA14366 | RRRRRRRRRRRRRR..RRRRRRRR.RRRRRRRRRRRR |
| SEQ_ID_NO_220_pA14367 | RRRRRRRRRRRRRRRRRRRRRRRRRRRRRRRRRRRRR |
| SEQ_ID_NO_221_pA14368 | ...........Y....Q....R....DD......... |
| SEQ_ID_NO_222_pA14369 | ...........L....E....I....DD......... |
| SEQ_ID_NO_223_pA14370 | ...........R....E....T....DD......... |
| SEQ_ID_NO_224_pA14371 | ...T.......R....Q....R..V.DD......... |
| SEQ_ID_NO_225_pA14372 | ...L.......L....E....R..L.DD......... |
| SEQ_ID_NO_226_pA14373 | ...G.......Y....E....I....DD......... |
| SEQ_ID_NO_227_pA14374 | ...S.......L....E....V....DD......... |
| SEQ_ID_NO_228_pA14375 | ...T.......R....E....Q....DD......... |
| SEQ_ID_NO_229_pA14376 | ...G.......L....E....Q..N.DD......... |
| SEQ_ID_NO_230_pA14377 | ...G....................N............ |

FIG. 23

Positions: 3 4 5 6 7 8 9 10 11 21 22 25 29 30 32 33 34 35 36 37 49 50 56 59 62 63 64 66 67 70 71 72 75

```
SEQ_ID_NO_6_pA06238     LSKDYLRKKSYEEFKEKGDYQFMEKNFMKKEKE
SEQ_ID_NO_232_pA15875   ERRENGQREE.RR.R.RH.RHR..RREERR.ED
SEQ_ID_NO_233_pA15876   ERRRHGEERE.R..RQR.RD.H...R..ER.ED
SEQ_ID_NO_234_pA15877   .R.QNNEPVP....M.LS..FQ..RR..ERS.D
SEQ_ID_NO_235_pA15878   .RQRNGEPVE....Q.SNT.HR.RRR.EERS.D
SEQ_ID_NO_236_pA15879   .RHQNNEPVP....Q.SNS..H...E..RRS.D
SEQ_ID_NO_237_pA15880   .RQRNGQRWE.RR..QRDQ.HR.RRR.EQR.E.
SEQ_ID_NO_238_pA15881   .ERH.NLERP....RNRHLPI..TRD..DRR.D
SEQ_ID_NO_239_pA15882   ERRE.GQRER....RTRH.RHR...RE.RR..D
SEQ_ID_NO_240_pA15883   .RHQ.GQEEE.RR.QR.HERHR.RREE.RR.ED
SEQ_ID_NO_241_pA15884   EEHRHGQEFE......Q.T.HR..RR.EERR.D
SEQ_ID_NO_242_pA15885   .R.QNNE.RP....R.RN.......R..ERS.D
SEQ_ID_NO_243_pA15886   .E.QNNQDRP....R.RDQ......R..ERQ..
SEQ_ID_NO_244_pA15887   .RHE.GQRER....QTRHERHR...RE.RR..D
SEQ_ID_NO_245_pA15888   .EHH.G.PQE.RR.QRQHHPHR..RR.EQR.E.
SEQ_ID_NO_246_pA15889   .RHH.NEPQP....QHRHEP.H..RR..ERR.D
SEQ_ID_NO_247_pA15890   EE.RHG.ERE....I.M.Y.WSW.RR.EERR.D
SEQ_ID_NO_248_pA15891   .RHQNNEPVP..RAQQTNT..H..RE..RRSTD
SEQ_ID_NO_249_pA15892   .R.QNNEPVP....M.LDL.....RE..RRS.D
SEQ_ID_NO_250_pA15893   ER.QNGERHE....ITRHER....RREERR..D
SEQ_ID_NO_251_pA15894   .R.QNNEPVP......LN......RR..ERS.D
SEQ_ID_NO_252_pA15895   .R.Q.NEPVP....M.LNT......E..RRS.D
SEQ_ID_NO_253_pA15896   ERRQNGQ.EE.R....RHSRHR...RE.RR..D
SEQ_ID_NO_254_pA15897   .ERE.G...E.....TR..RHR.RREE.RR...
SEQ_ID_NO_255_pA15898   E..RHG.EHEW...IR..Y...W.RR.EE.R..
SEQ_ID_NO_256_pA15899   .R.RNGEPVR....QQYNRE...RRR.EE.S..
SEQ_ID_NO_257_pA15900   EEH.HNQPIP.R...HRHE..H..RR..ERQQD
SEQ_ID_NO_258_pA15901   E..RHNEPRPW...MRQ.......RQ..ERR.D
SEQ_ID_NO_259_pA15902   .QQRNGQ.WE.R..Q.SNT......R..QR.HD
SEQ_ID_NO_260_pA15903   EEH.H.T.IP....Q.Q....H...R..ERR.D
SEQ_ID_NO_261_pA15904   .ERH.NLP.......NRHEP...TRD.Y....D
SEQ_ID_NO_262_pA15905   EE.E.GQEQE....I.Q.Y.HRW.RR.EERR.D
SEQ_ID_NO_263_pA15906   .PHH.G.PFEW.R.MRLHYPHRWTA..YERRLS
SEQ_ID_NO_264_pA15907   .R.QNNE.VP....MRLN..FQ..RE..RRS.D
SEQ_ID_NO_265_pA15908   .RHQNNEPVP..RHQRHN...H...E..RRSTD
SEQ_ID_NO_266_pA15909   EEH...Q.FE......Q.TEHR..RR.EERR.D
SEQ_ID_NO_267_pA15910   .RHE.GQPEE.R...R.HER.....RE.RR.ED
SEQ_ID_NO_268_pA15911   .MVQNNIPIP....M..NS......R..ERS..
SEQ_ID_NO_269_pA15912   ...Q.N...P......LDQ.............D
SEQ_ID_NO_270_pA15913   .....NEP.P.....HIHEP....RR...R..D
SEQ_ID_NO_271_pA15914   .R..NNEPVP......LS..FQ...E..RRS..
SEQ_ID_NO_272_pA15915   .R.QNNEPVP....MRTN.......E..RRS.D
SEQ_ID_NO_273_pA15916   .E.H.G.EQEW...MQLHNPWSW.RR.EERR.D
SEQ_ID_NO_274_pA15917   .RHQ.NE.VP...HQ.HN...H...R..ERS.D
SEQ_ID_NO_275_pA15918   .R.QNNE.VP........Y......E..RRS..
SEQ_ID_NO_276_pA15919   .DHH.G.PF....AMNQHYPHRW.RR.E....S
SEQ_ID_NO_277_pA15920   ERHE.GQAFE....ITRHERHR.SRDEFRR..D
SEQ_ID_NO_278_pA15921   .RFH.NEPIE....MHIHYP...TRD...R..D
SEQ_ID_NO_279_pA15922   ELH.NGQRFE.....NRHWR.....RE.RR...
SEQ_ID_NO_280_pA15923   EE...GQRRE......R.E..HW.RQ.EERR.D
SEQ_ID_NO_281_pA15924   .EHH.GQ.QQ......QHHPHR..RR.EERR.D
SEQ_ID_NO_282_pA15925   .LHQ.GQRFEWRQ.ITRHHRHR...RE.RR.E.
```

FIG. 23 Continued

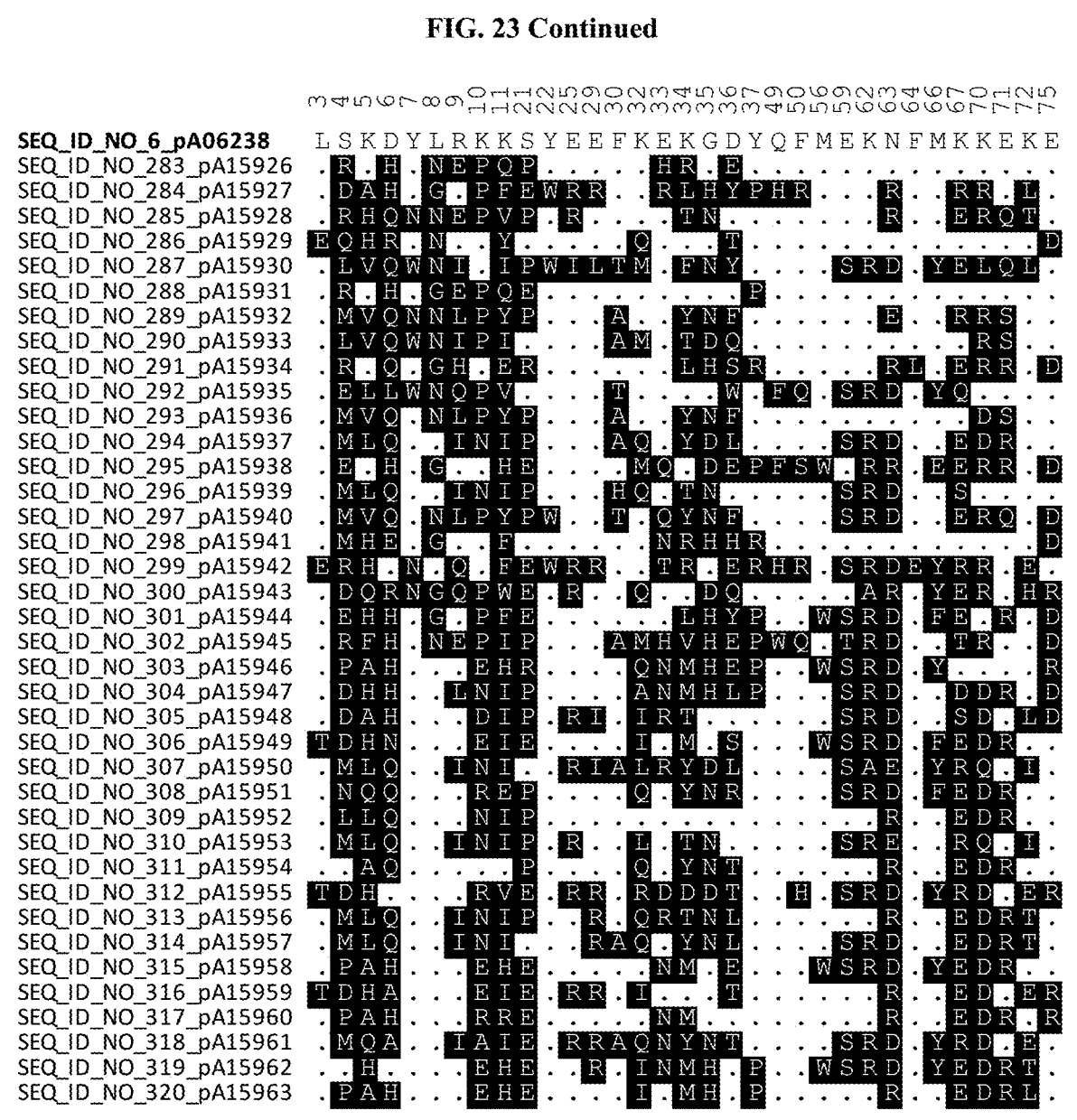

| | 3 4 5 6 7 8 9 10 11 21 22 25 29 30 32 33 34 35 36 37 49 50 56 59 62 63 64 66 67 70 71 72 75 |
|---|---|
| **SEQ_ID_NO_6_pA06238** | L S K D Y L R K K S Y E E F K E K G D Y Q F M E K N F M K K E K E |
| SEQ_ID_NO_283_pA15926 | . R . H . N E P Q P . . . . . H R . E . . . . . . . . . . . . . . |
| SEQ_ID_NO_284_pA15927 | . D A H . G . P F E W R R . . R L H Y P H R . . . R . . R R . L . |
| SEQ_ID_NO_285_pA15928 | . R H Q N N E P V P . R . . . . T N . . . . . . . R . . E R Q T . |
| SEQ_ID_NO_286_pA15929 | E Q H R . N . . Y . . . . . Q . . . T . . . . . . . . . . . . . D |
| SEQ_ID_NO_287_pA15930 | . L V Q W N I . I P W I L T M . F N Y . . . . S R D . Y E L Q L . |
| SEQ_ID_NO_288_pA15931 | . R . H . G E P Q E . . . . . . . . . P . . . . . . . . . . . . . |
| SEQ_ID_NO_289_pA15932 | . M V Q N N L P Y P . . . A . . Y N F . . . . . . E . . R R S . . |
| SEQ_ID_NO_290_pA15933 | . L V Q W N I P I . . . . A M . T D Q . . . . . . . . . . R S . . |
| SEQ_ID_NO_291_pA15934 | . R . Q . G H . E R . . . . . . L H S R . . . . . R L . E R R . D |
| SEQ_ID_NO_292_pA15935 | . E L L W N Q P V . . . . T . . . . W . F Q . S R D . Y Q . . . . |
| SEQ_ID_NO_293_pA15936 | . M V Q . N L P Y P . . . A . . Y N F . . . . . . . . . . D S . . |
| SEQ_ID_NO_294_pA15937 | . M L Q . . I N I P . . . A Q . Y D L . . . . S R D . . E D R . . |
| SEQ_ID_NO_295_pA15938 | . E . H . G . . H E . . . . M Q . D E P F S W . R R . E E R R . D |
| SEQ_ID_NO_296_pA15939 | . M L Q . . I N I P . . . H Q . T N . . . . . S R D . . S . . . . |
| SEQ_ID_NO_297_pA15940 | . M V Q . N L P Y P W . . T . Q Y N F . . . . S R D . . E R Q . D |
| SEQ_ID_NO_298_pA15941 | . M H E . G . . F . . . . . . N R H H R . . . . . . . . . . . . D |
| SEQ_ID_NO_299_pA15942 | E R H . N . Q . F E W R R . . T R . E R H R . S R D E Y R R . E . |
| SEQ_ID_NO_300_pA15943 | . D Q R N G Q P W E . R . . Q . . D Q . . . . . A R . Y E R . H R |
| SEQ_ID_NO_301_pA15944 | . E H H . G . P F E . . . . . . L H Y P . . W S R D . F E . R . D |
| SEQ_ID_NO_302_pA15945 | . R F H . N E P I P . . . A M H V H E P W Q . T R D . . T R . . D |
| SEQ_ID_NO_303_pA15946 | . P A H . . . E H R . . . . Q N M H E P . . W S R D . Y . . . . R |
| SEQ_ID_NO_304_pA15947 | . D H H . . L N I P . . . . A N M H L P . . . S R D . . D D R . D |
| SEQ_ID_NO_305_pA15948 | . D A H . . . D I P . R I . I R T . . . . . . S R D . . S D . L D |
| SEQ_ID_NO_306_pA15949 | T D H N . . . E I E . . . . I . M . S . . . W S R D . F E D R . . |
| SEQ_ID_NO_307_pA15950 | . M L Q . . I N I . . R I A L R Y D L . . . . S A E . Y R Q . I . |
| SEQ_ID_NO_308_pA15951 | . N Q Q . . . R E P . . . . Q . Y N R . . . . S R D . F E D R . . |
| SEQ_ID_NO_309_pA15952 | . L L Q . . . N I P . . . . . . . . . . . . . . . R . . E D R . . |
| SEQ_ID_NO_310_pA15953 | . M L Q . . I N I P . R . . L . T N . . . . . S R E . . R Q . I . |
| SEQ_ID_NO_311_pA15954 | . . A Q . . . . . P . . . . Q . Y N T . . . . . . R . . E D R . . |
| SEQ_ID_NO_312_pA15955 | T D H . . . . R V E . R R . R D D D T . . H . S R D . Y R D . E R |
| SEQ_ID_NO_313_pA15956 | . M L Q . . I N I P . . R . Q R T N L . . . . . . R . . E D R T . |
| SEQ_ID_NO_314_pA15957 | . M L Q . . I N I . . . R A Q . Y N L . . . . S R D . . E D R T . |
| SEQ_ID_NO_315_pA15958 | . P A H . . . E H E . . . . . N M . E . . . W S R D . Y E D R . . |
| SEQ_ID_NO_316_pA15959 | T D H A . . . E I E . R R . I . . . T . . . . . . R . . E D . E R |
| SEQ_ID_NO_317_pA15960 | . P A H . . . R R E . . . . . N M . . . . . . . . R . . E D R . R |
| SEQ_ID_NO_318_pA15961 | . M Q A . . I A I E . R R A Q N Y N T . . . . S R D . Y R D . E . |
| SEQ_ID_NO_319_pA15962 | . . H . . . . E H E . . R . I N M H . P . . W S R D . Y E D R T . |
| SEQ_ID_NO_320_pA15963 | . P A H . . . E H E . . . . I . M H . P . . . . . R . . E D R L . |

FIG. 23 Continued

| | 76 | 77 | 78 | 80 | 94 | 96 | 98 | 101 | 102 | 104 | 105 | 108 | 116 | 125 | 129 | 130 | 131 | 132 | 134 | 135 | 136 | 137 | 140 | 141 | 144 | 147 | 148 | 150 | 151 | 152 | 153 | 154 | 155 | 156 |
|---|---|---|---|---|---|---|---|---|---|---|---|---|---|---|---|---|---|---|---|---|---|---|---|---|---|---|---|---|---|---|---|---|---|---|
| SEQ_ID_NO_6_pA06238 | E | D | K | I | E | S | T | N | K | K | D | R | K | P | D | P | K | V | P | Y | E | K | E | R | E | E | I | E | E | T | A | R | K | Y |
| SEQ_ID_NO_232_pA15875 | . | R | R | . | R | R | E | . | E | R | Q | . | D | . | E | . | E | . | D | . | R | E | . | Q | Q | . | E | . | R | R | R | T | E | R |
| SEQ_ID_NO_233_pA15876 | . | R | R | R | R | E | E | Q | E | R | E | . | R | . | . | . | . | . | . | Q | . | E | R | . | . | . | V | . | R | R | R | Q | E | . |
| SEQ_ID_NO_234_pA15877 | . | R | M | . | L | E | Q | E | Y | R | Q | . | Q | . | . | . | E | T | D | W | R | R | . | . | . | . | . | . | R | . | S | P | P | V |
| SEQ_ID_NO_235_pA15878 | . | R | R | . | R | E | E | Q | E | R | E | . | R | . | Q | S | E | T | D | . | R | E | R | Q | . | R | E | . | . | . | . | T | T | D |
| SEQ_ID_NO_236_pA15879 | . | R | R | . | Q | E | E | Q | E | R | E | . | L | . | Q | . | E | T | D | . | R | E | R | H | . | Q | . | . | . | . | S | P | P | R |
| SEQ_ID_NO_237_pA15880 | P | R | R | . | R | E | E | E | E | R | E | . | E | . | . | S | E | T | D | . | R | E | R | . | . | R | E | . | . | . | . | T | T | D |
| SEQ_ID_NO_238_pA15881 | . | R | D | . | L | A | E | D | R | R | Q | . | R | . | Q | . | E | . | H | W | D | E | . | L | . | R | V | . | . | V | . | Q | D | . |
| SEQ_ID_NO_239_pA15882 | . | R | R | . | R | R | E | . | E | R | Q | . | R | . | E | . | . | . | . | W | . | E | . | Q | Q | . | E | . | R | R | R | T | E | . |
| SEQ_ID_NO_240_pA15883 | . | R | Q | . | R | R | E | . | E | R | Q | . | R | . | E | . | . | . | . | . | . | E | R | Q | . | . | E | . | R | R | . | . | . | . |
| SEQ_ID_NO_241_pA15884 | . | R | M | . | Q | R | . | . | E | R | E | . | T | . | . | . | E | . | . | D | . | E | R | . | . | . | E | . | R | H | R | Q | Q | . |
| SEQ_ID_NO_242_pA15885 | . | R | R | . | L | . | E | R | R | E | E | . | R | . | . | . | E | T | . | W | . | . | . | . | R | . | . | . | R | . | . | P | E | V |
| SEQ_ID_NO_243_pA15886 | . | . | M | . | . | E | . | E | . | R | Q | . | R | . | Q | . | E | T | D | W | R | E | R | L | . | . | . | . | R | . | . | P | E | V |
| SEQ_ID_NO_244_pA15887 | . | . | . | . | R | . | E | E | E | . | E | . | R | . | E | . | E | . | . | . | . | . | . | . | . | . | . | . | . | . | R | T | Q | . |
| SEQ_ID_NO_245_pA15888 | . | R | M | . | R | E | E | . | E | R | E | . | W | . | . | S | E | T | D | . | R | R | . | . | . | R | E | . | . | . | . | . | G | . |
| SEQ_ID_NO_246_pA15889 | . | R | L | . | Q | E | E | . | Q | Q | E | . | L | . | Q | . | E | . | . | . | . | E | . | H | . | R | V | . | . | . | . | Q | D | . |
| SEQ_ID_NO_247_pA15890 | P | . | M | . | L | E | R | E | Y | R | E | . | L | . | R | . | D | E | . | R | . | E | R | W | D | . | . | . | R | Y | R | Q | T | F |
| SEQ_ID_NO_248_pA15891 | . | R | R | . | Q | E | E | E | Q | R | Q | . | L | . | . | . | E | T | D | . | R | R | . | . | . | . | . | . | R | . | S | P | P | R |
| SEQ_ID_NO_249_pA15892 | . | R | M | . | . | . | . | . | . | R | E | . | Q | . | . | . | E | T | . | W | . | . | . | . | . | . | . | . | R | . | . | P | P | V |
| SEQ_ID_NO_250_pA15893 | . | R | L | . | . | . | . | . | . | E | E | . | Y | . | L | . | E | . | D | W | R | E | . | . | R | . | . | . | . | R | R | T | Q | Q |
| SEQ_ID_NO_251_pA15894 | . | R | M | . | L | E | Q | H | Y | E | Q | . | R | . | . | . | E | T | D | W | R | R | . | . | R | . | . | . | R | . | . | P | P | V |
| SEQ_ID_NO_252_pA15895 | . | R | R | . | L | . | Q | E | Y | . | E | . | Q | . | . | . | E | T | . | . | . | . | . | . | . | . | . | . | . | . | . | P | P | V |
| SEQ_ID_NO_253_pA15896 | . | R | R | . | R | . | E | . | E | R | Q | . | R | . | . | . | . | . | . | . | . | . | . | . | . | R | E | . | . | R | . | . | . | . |
| SEQ_ID_NO_254_pA15897 | . | . | R | . | R | R | E | E | E | . | E | . | . | . | E | . | . | . | . | . | . | E | . | Q | . | . | . | . | . | . | . | . | . | . |
| SEQ_ID_NO_255_pA15898 | P | R | M | . | . | E | . | Q | . | R | E | . | . | . | . | . | D | . | . | D | . | E | R | . | . | . | . | . | R | Y | R | Q | Q | F |
| SEQ_ID_NO_256_pA15899 | P | R | R | L | . | E | . | Q | . | R | E | . | R | . | . | . | E | T | D | W | R | E | R | . | . | . | . | . | R | . | . | . | T | . |
| SEQ_ID_NO_257_pA15900 | . | R | Q | . | R | E | E | E | E | R | Q | . | H | . | . | . | . | . | . | . | . | E | R | . | . | . | . | R | . | . | . | . | E | E |
| SEQ_ID_NO_258_pA15901 | . | R | M | . | L | E | R | E | Y | R | Q | . | I | . | Q | . | D | R | . | L | . | E | R | L | . | . | . | . | R | Y | . | Q | E | F |
| SEQ_ID_NO_259_pA15902 | . | R | R | . | R | E | E | . | R | R | E | . | R | . | . | . | . | . | D | . | R | E | R | . | . | R | E | . | . | Q | S | S | T | D |
| SEQ_ID_NO_260_pA15903 | . | R | M | . | . | E | E | E | Q | . | Q | . | Y | . | Q | . | . | . | . | . | . | E | R | Q | . | . | . | . | . | . | Q | Q | E | T |
| SEQ_ID_NO_261_pA15904 | L | R | D | . | L | A | E | S | R | E | E | . | R | . | Q | . | E | . | H | W | W | E | L | L | D | A | V | . | . | V | . | . | . | F |
| SEQ_ID_NO_262_pA15905 | . | R | M | . | R | E | E | R | E | E | E | . | L | . | W | . | D | E | . | R | . | W | R | W | R | . | . | . | R | Y | R | Q | T | F |
| SEQ_ID_NO_263_pA15906 | . | S | M | . | L | E | V | . | E | R | E | . | W | . | W | S | E | T | H | W | Q | V | D | W | . | R | E | . | . | Q | . | . | G | F |
| SEQ_ID_NO_264_pA15907 | . | R | M | . | L | R | Q | E | Y | R | Q | . | R | . | . | . | . | . | D | W | R | I | . | W | . | . | . | . | R | . | S | P | P | V |
| SEQ_ID_NO_265_pA15908 | . | R | R | . | Q | E | E | . | Q | E | E | . | Q | . | . | . | E | T | D | . | R | R | . | . | R | . | V | . | R | . | S | P | P | Q |
| SEQ_ID_NO_266_pA15909 | . | . | . | R | Q | E | . | E | E | R | E | . | T | . | . | . | D | E | . | R | . | E | R | . | . | . | D | . | R | H | . | Q | . | . |
| SEQ_ID_NO_267_pA15910 | . | R | Q | . | . | R | . | . | . | . | . | . | R | . | E | . | . | . | D | . | R | E | . | Q | . | . | . | . | . | . | R | T | E | . |
| SEQ_ID_NO_268_pA15911 | . | . | M | . | . | A | . | S | . | Q | E | . | L | . | Q | . | E | T | D | W | R | E | I | L | I | . | V | . | R | V | . | P | P | V |
| SEQ_ID_NO_269_pA15912 | . | R | R | . | . | E | . | E | . | R | Q | . | R | . | Q | . | . | . | D | W | R | E | R | L | . | . | . | . | R | . | . | P | E | V |
| SEQ_ID_NO_270_pA15913 | . | R | L | . | . | . | . | . | . | Q | E | . | R | . | . | . | . | . | . | . | . | . | . | . | . | R | . | . | . | . | . | Q | D | F |
| SEQ_ID_NO_271_pA15914 | . | . | M | . | L | E | Q | E | Y | . | Q | . | . | . | Q | . | E | T | D | . | R | E | R | L | . | . | . | . | . | . | S | P | P | Q |
| SEQ_ID_NO_272_pA15915 | . | R | M | . | . | E | . | . | . | . | . | . | Q | . | Q | . | . | . | D | . | R | E | R | L | . | . | . | . | . | . | . | P | P | V |
| SEQ_ID_NO_273_pA15916 | . | R | L | . | L | E | Q | Q | Y | Q | E | . | E | . | . | . | E | T | D | W | R | R | . | . | . | R | . | . | . | . | . | S | G | F |
| SEQ_ID_NO_274_pA15917 | . | R | R | . | Q | E | E | E | Q | . | E | . | R | . | . | . | . | . | D | . | R | R | . | . | . | . | . | . | . | . | S | P | P | Q |
| SEQ_ID_NO_275_pA15918 | . | . | . | . | L | . | Q | E | Y | . | E | . | R | . | . | . | E | T | . | . | . | . | . | . | . | . | . | . | . | . | S | P | P | V |
| SEQ_ID_NO_276_pA15919 | L | S | M | . | Y | . | W | . | E | R | E | . | . | . | . | S | E | T | . | W | R | . | . | W | . | R | E | . | . | Q | . | . | G | F |
| SEQ_ID_NO_277_pA15920 | . | R | L | . | Y | R | W | . | E | R | Q | . | Y | . | E | . | E | . | . | W | P | E | . | . | D | . | E | . | R | R | R | T | Q | F |
| SEQ_ID_NO_278_pA15921 | . | R | L | . | L | A | Q | T | Y | . | E | . | L | . | . | . | E | . | H | W | . | E | . | . | . | . | . | . | . | . | . | . | . | . |
| SEQ_ID_NO_279_pA15922 | . | N | M | . | . | . | . | . | . | . | . | . | Y | . | E | . | E | . | . | W | P | . | . | . | . | . | . | . | . | . | R | T | Q | Q |
| SEQ_ID_NO_280_pA15923 | P | . | . | . | L | E | E | R | E | . | E | . | . | . | . | . | S | . | . | . | Q | E | R | . | . | . | . | A | . | . | . | . | D | Q |
| SEQ_ID_NO_281_pA15924 | . | R | L | . | R | . | E | E | E | R | . | . | . | . | . | S | E | T | . | . | R | . | . | . | . | R | E | . | . | . | . | . | . | . |
| SEQ_ID_NO_282_pA15925 | . | N | M | . | Y | R | W | E | E | . | E | . | Y | . | L | . | E | . | H | W | S | E | . | Q | . | . | . | . | . | . | R | T | Q | Q |

FIG. 23 Continued

| | 76 | 77 | 78 | 80 | 94 | 96 | 98 | 101 | 102 | 104 | 105 | 108 | 116 | 125 | 129 | 130 | 131 | 132 | 134 | 135 | 136 | 137 | 140 | 141 | 144 | 147 | 148 | 150 | 151 | 152 | 153 | 154 | 155 | 156 |
|---|---|---|---|---|---|---|---|---|---|---|---|---|---|---|---|---|---|---|---|---|---|---|---|---|---|---|---|---|---|---|---|---|---|---|
| SEQ_ID_NO_6_pA06238 | E | D | K | I | E | S | T | N | K | K | D | R | K | P | D | P | K | V | P | Y | E | K | E | R | E | E | I | E | E | T | A | R | K | Y |
| SEQ_ID_NO_283_pA15926 | . | . | . | . | . | . | . | . | . | . | . | . | . | . | . | . | . | . | . | . | . | . | . | . | . | . | . | . | . | . | . | . | D | . |
| SEQ_ID_NO_284_pA15927 | . | N | M | . | Y | . | W | Q | E | . | E | . | W | . | . | S | E | T | . | . | . | . | . | . | . | . | . | . | . | . | . | . | G | F |
| SEQ_ID_NO_285_pA15928 | . | . | R | . | . | . | . | E | . | R | Q | . | . | . | Q | . | E | T | . | . | . | . | . | Q | . | . | . | . | R | . | S | P | P | Q |
| SEQ_ID_NO_286_pA15929 | . | R | M | . | . | . | . | . | . | . | . | . | Y | . | . | . | D | R | . | . | . | . | . | . | . | . | . | . | . | . | Q | Q | E | T |
| SEQ_ID_NO_287_pA15930 | L | . | M | . | L | A | R | T | Y | R | Q | . | L | . | Q | . | E | T | D | W | R | Q | I | Y | . | . | V | . | R | V | . | P | P | V |
| SEQ_ID_NO_288_pA15931 | . | . | . | . | . | . | . | . | . | . | . | . | E | . | . | . | . | . | . | . | . | . | . | . | . | . | . | . | . | . | . | . | G | F |
| SEQ_ID_NO_289_pA15932 | . | . | M | . | . | A | . | . | . | . | . | . | . | . | Q | . | E | T | D | . | R | I | I | Y | . | . | . | . | . | . | . | P | P | V |
| SEQ_ID_NO_290_pA15933 | . | . | M | . | . | A | . | . | . | . | . | . | . | . | Q | . | E | T | D | . | R | Q | I | Y | . | . | . | . | . | . | . | P | P | V |
| SEQ_ID_NO_291_pA15934 | . | R | L | . | . | . | . | Q | . | R | E | . | Y | . | E | . | E | . | . | . | . | . | . | . | Q | . | . | . | R | Y | R | . | . | . |
| SEQ_ID_NO_292_pA15935 | L | . | . | . | L | A | Q | E | Y | . | I | . | L | A | Q | . | Y | Y | D | . | R | Q | I | Y | . | . | . | . | . | . | . | P | P | V |
| SEQ_ID_NO_293_pA15936 | R | . | M | . | . | . | . | . | . | . | . | . | . | . | . | . | . | . | . | W | . | . | . | . | . | . | . | . | . | . | . | P | P | V |
| SEQ_ID_NO_294_pA15937 | R | N | R | . | . | A | . | A | . | E | E | . | T | . | . | . | E | T | . | L | . | V | . | . | R | . | V | . | R | . | . | . | E | . |
| SEQ_ID_NO_295_pA15938 | P | . | . | Q | Y | E | Q | Q | W | R | E | . | E | . | W | . | . | . | . | . | . | V | . | W | . | R | . | . | . | . | . | . | . | F |
| SEQ_ID_NO_296_pA15939 | . | N | R | . | . | A | . | E | . | R | Q | . | T | . | . | . | E | T | . | L | . | V | . | . | . | . | V | . | R | . | . | . | E | . |
| SEQ_ID_NO_297_pA15940 | . | R | M | . | L | . | Q | E | Y | . | E | . | L | . | . | . | . | . | . | W | . | . | . | . | . | . | . | . | . | . | . | . | . | . |
| SEQ_ID_NO_298_pA15941 | . | R | L | . | . | R | . | . | . | R | E | . | Y | . | E | . | . | . | H | W | S | R | . | D | D | . | E | . | R | R | . | . | . | E |
| SEQ_ID_NO_299_pA15942 | . | . | R | . | Y | . | W | E | E | . | E | . | Y | . | E | . | E | . | . | W | P | . | . | . | . | . | . | . | . | . | R | T | Q | F |
| SEQ_ID_NO_300_pA15943 | . | . | R | . | . | . | . | Q | . | R | E | . | Y | . | . | . | . | . | . | W | P | . | . | . | . | . | V | . | R | V | . | Q | W | . |
| SEQ_ID_NO_301_pA15944 | L | R | L | . | . | . | . | . | . | . | . | . | . | . | . | . | . | . | . | . | . | . | . | . | . | . | . | . | . | . | . | . | . | . |
| SEQ_ID_NO_302_pA15945 | . | R | L | . | L | A | Q | T | Y | Q | I | . | L | . | W | S | E | . | . | W | . | L | . | L | . | R | V | . | . | V | G | Q | D | M |
| SEQ_ID_NO_303_pA15946 | L | . | L | . | L | E | I | Q | Y | R | E | . | . | . | . | . | E | T | D | L | T | R | . | . | . | R | E | . | . | . | . | . | . | . |
| SEQ_ID_NO_304_pA15947 | R | N | L | . | L | A | Q | D | Y | R | Q | . | T | . | . | . | E | . | . | . | . | V | . | . | . | R | V | . | . | . | . | . | E | . |
| SEQ_ID_NO_305_pA15948 | R | N | L | . | L | A | R | E | Y | R | Q | I | T | . | . | . | E | R | . | L | . | V | R | . | . | . | . | . | R | Y | . | Q | E | . |
| SEQ_ID_NO_306_pA15949 | R | N | L | . | L | E | R | R | Y | E | E | . | T | . | . | . | E | . | . | L | . | R | . | . | R | . | V | . | R | Y | R | Q | Q | . |
| SEQ_ID_NO_307_pA15950 | . | N | R | . | . | A | . | . | . | . | . | . | T | . | . | . | E | T | . | L | . | V | . | . | . | . | . | . | . | . | . | . | E | . |
| SEQ_ID_NO_308_pA15951 | R | N | R | . | . | E | . | . | . | R | E | . | . | . | . | S | E | T | . | . | P | R | . | . | I | . | E | . | R | . | . | . | E | . |
| SEQ_ID_NO_309_pA15952 | R | . | . | . | L | A | Q | E | Y | . | E | . | T | . | . | . | . | . | . | L | . | V | . | . | . | . | . | . | . | . | . | . | E | . |
| SEQ_ID_NO_310_pA15953 | . | . | R | . | . | . | . | A | . | E | E | . | . | . | . | . | E | T | . | L | . | . | . | . | R | . | V | . | R | . | . | . | E | . |
| SEQ_ID_NO_311_pA15954 | R | N | R | . | . | . | . | A | . | E | E | . | . | . | . | . | . | . | . | L | . | . | . | . | R | . | V | . | R | . | . | . | E | . |
| SEQ_ID_NO_312_pA15955 | R | . | L | . | R | E | E | . | E | R | E | . | . | . | R | . | S | S | . | . | P | R | . | . | . | . | E | . | R | Y | . | E | Q | . |
| SEQ_ID_NO_313_pA15956 | R | N | R | . | L | A | Q | E | Y | . | E | . | . | . | . | . | E | T | . | . | . | V | . | . | . | . | . | . | . | . | . | . | E | . |
| SEQ_ID_NO_314_pA15957 | R | N | R | . | . | A | . | E | . | R | Q | . | T | . | . | . | . | . | . | L | . | V | . | . | . | . | V | . | R | . | . | . | . | . |
| SEQ_ID_NO_315_pA15958 | R | . | R | . | . | . | . | . | . | . | . | . | . | . | . | . | E | T | . | . | D | . | . | . | . | . | . | . | . | . | . | . | Q | M |
| SEQ_ID_NO_316_pA15959 | R | . | L | . | . | E | . | Q | . | R | E | . | T | . | . | . | E | . | D | D | . | R | R | . | . | . | V | . | R | Y | R | Q | Q | . |
| SEQ_ID_NO_317_pA15960 | R | . | L | . | . | E | . | . | . | R | E | . | D | . | . | . | E | T | A | L | P | R | . | . | . | R | E | . | . | . | . | . | Q | M |
| SEQ_ID_NO_318_pA15961 | R | N | R | . | L | E | Q | Q | Y | R | E | . | T | . | . | S | E | T | . | . | P | R | . | . | . | . | V | . | R | . | . | . | E | . |
| SEQ_ID_NO_319_pA15962 | R | N | L | . | . | E | . | Q | . | R | E | . | D | . | . | . | E | T | A | L | P | R | . | . | . | R | E | . | . | A | . | . | . | M |
| SEQ_ID_NO_320_pA15963 | R | N | L | . | L | . | Q | Q | Y | R | E | . | T | . | . | . | . | . | . | L | P | . | . | . | . | R | E | . | . | . | . | . | Q | M |

FIG. 23 Continued

| | 157 | 158 | 159 | 160 | 161 | 169 | 177 | 180 | 191 | 193 | 194 | 195 | 197 | 200 | 201 | 203 | 204 | 205 | 216 | 218 | 219 | 220 | 221 | 222 | 224 | 228 | 229 | 231 | 232 | 235 | 238 | 239 | 240 | 241 |
|---|---|---|---|---|---|---|---|---|---|---|---|---|---|---|---|---|---|---|---|---|---|---|---|---|---|---|---|---|---|---|---|---|---|---|
| SEQ_ID_NO_6_pA06238 | N | F | Q | P | V | V | S | S | S | K | K | Y | N | P | N | W | D | R | G | S | Y | D | K | V | E | D | K | R | G | E | K | R | E | D |
| SEQ_ID_NO_232_pA15875 | D | R | . | . | . | . | R | E | Y | E | R | . | P | . | . | . | . | . | . | T | R | . | R | . | Q | E | E | . | R | . | R | . | T | . |
| SEQ_ID_NO_233_pA15876 | E | E | E | . | . | . | R | E | H | E | E | . | P | . | . | R | . | . | . | T | R | . | R | . | Q | . | . | . | . | . | . | . | T | . |
| SEQ_ID_NO_234_pA15877 | P | N | T | I | . | . | . | E | T | E | R | . | E | . | . | R | . | . | N | . | . | R | T | . | . | . | Q | E | E | R | E | . | T | . |
| SEQ_ID_NO_235_pA15878 | P | N | E | T | . | R | . | E | E | E | R | . | R | D | . | R | . | . | T | . | R | . | R | . | . | . | Q | . | E | . | R | . | T | . |
| SEQ_ID_NO_236_pA15879 | P | N | . | T | . | . | . | E | A | E | R | . | E | . | . | R | . | . | N | . | . | R | E | . | . | . | Q | E | E | R | E | . | T | . |
| SEQ_ID_NO_237_pA15880 | P | N | R | T | . | R | . | E | Y | R | Q | . | Q | . | . | . | . | . | T | . | R | R | R | . | . | . | Q | . | E | . | R | . | T | . |
| SEQ_ID_NO_238_pA15881 | P | N | L | L | . | I | . | E | A | R | R | . | . | L | . | . | . | . | R | . | . | . | R | . | M | . | R | . | E | . | R | . | V | P |
| SEQ_ID_NO_239_pA15882 | . | . | . | . | E | . | R | E | E | . | R | . | P | . | . | R | . | . | . | . | R | . | . | . | . | . | . | . | . | . | . | . | . | . |
| SEQ_ID_NO_240_pA15883 | . | . | . | . | E | . | R | E | E | . | R | . | P | . | . | R | . | . | . | . | R | . | . | . | . | . | Q | . | E | . | R | . | . | . |
| SEQ_ID_NO_241_pA15884 | P | T | E | . | . | . | R | E | A | Q | R | . | P | E | . | R | . | . | . | T | R | . | R | . | Q | . | R | . | E | . | R | . | T | . |
| SEQ_ID_NO_242_pA15885 | P | N | E | M | . | . | . | . | T | E | R | . | E | . | . | R | . | . | . | . | . | . | . | . | . | . | . | . | . | . | . | . | T | . |
| SEQ_ID_NO_243_pA15886 | P | N | E | M | . | . | . | E | T | . | R | . | S | . | . | A | . | . | N | . | . | R | E | . | . | . | R | . | E | . | . | . | . | . |
| SEQ_ID_NO_244_pA15887 | . | . | . | . | E | . | . | E | Q | Q | R | H | P | E | . | R | . | . | . | . | R | . | . | . | . | . | Q | . | E | . | R | . | T | . |
| SEQ_ID_NO_245_pA15888 | P | . | . | . | . | R | . | E | Y | R | Q | . | . | R | . | . | . | . | R | . | R | . | R | . | . | . | Q | . | E | . | R | . | H | . |
| SEQ_ID_NO_246_pA15889 | P | . | . | L | . | . | . | E | H | R | Q | . | R | . | . | . | . | . | R | . | . | . | R | . | . | . | Q | . | E | . | R | . | . | P |
| SEQ_ID_NO_247_pA15890 | R | T | E | . | . | . | . | E | Y | Q | R | . | P | . | . | R | . | . | . | T | R | R | R | . | Q | . | R | . | E | . | R | . | T | . |
| SEQ_ID_NO_248_pA15891 | P | N | . | T | . | . | . | E | H | R | Q | . | S | . | . | H | . | . | N | . | . | R | T | . | . | . | Q | E | E | R | R | . | T | . |
| SEQ_ID_NO_249_pA15892 | P | N | T | M | . | . | . | . | T | R | R | . | S | . | . | A | R | . | N | . | . | R | T | . | . | . | . | . | . | . | R | . | T | . |
| SEQ_ID_NO_250_pA15893 | . | T | E | F | . | I | . | E | W | R | R | . | P | . | . | R | . | . | . | . | R | . | . | . | . | . | A | . | . | . | R | . | . | . |
| SEQ_ID_NO_251_pA15894 | P | N | E | M | . | . | . | . | T | R | R | . | S | . | . | A | R | . | N | . | . | . | R | . | Q | . | Q | . | E | . | R | . | T | . |
| SEQ_ID_NO_252_pA15895 | P | N | T | M | . | . | . | E | . | R | . | . | S | . | . | . | . | . | . | . | . | . | . | . | . | . | Q | . | E | . | . | . | T | . |
| SEQ_ID_NO_253_pA15896 | . | . | . | . | E | . | . | E | Y | . | R | . | P | . | . | R | . | . | . | . | . | . | . | . | . | . | . | . | . | . | R | . | . | . |
| SEQ_ID_NO_254_pA15897 | . | . | . | . | . | . | . | E | . | E | R | . | P | E | . | R | . | . | . | T | R | . | R | . | Q | . | . | . | . | . | . | . | T | . |
| SEQ_ID_NO_255_pA15898 | . | . | . | . | . | . | R | E | A | . | R | . | P | . | . | L | . | . | . | . | R | . | . | . | . | . | R | . | E | . | . | . | . | . |
| SEQ_ID_NO_256_pA15899 | P | N | E | F | . | R | . | E | W | R | R | . | Q | . | . | . | . | . | T | . | . | Q | R | . | . | . | N | . | E | . | R | . | T | . |
| SEQ_ID_NO_257_pA15900 | E | . | G | S | . | . | . | E | H | R | Q | . | Q | . | E | . | R | L | . | T | R | . | Q | . | Q | . | R | . | E | . | . | . | N | . |
| SEQ_ID_NO_258_pA15901 | D | R | E | M | . | . | . | E | A | E | R | . | D | . | . | R | . | . | . | T | . | . | Q | . | . | . | R | E | E | R | Q | . | T | . |
| SEQ_ID_NO_259_pA15902 | P | N | E | T | . | R | . | E | E | R | R | Q | Q | . | . | H | . | . | T | . | R | R | R | . | . | . | Q | . | E | . | . | . | . | . |
| SEQ_ID_NO_260_pA15903 | D | R | E | . | . | . | . | E | H | E | R | . | D | . | . | R | . | . | . | T | . | R | T | . | . | . | R | . | E | . | . | . | T | . |
| SEQ_ID_NO_261_pA15904 | . | . | . | L | . | I | . | Y | Y | . | E | A | R | . | . | . | . | . | R | . | . | . | R | . | . | S | R | E | E | . | . | . | . | . |
| SEQ_ID_NO_262_pA15905 | . | T | E | M | . | . | . | E | Y | R | R | . | P | . | . | R | . | . | . | T | R | R | R | . | Q | . | R | . | E | . | . | . | T | . |
| SEQ_ID_NO_263_pA15906 | . | . | W | . | I | R | . | E | Y | R | R | . | . | R | . | . | . | . | R | . | R | . | R | . | . | S | Q | E | P | R | S | . | Y | . |
| SEQ_ID_NO_264_pA15907 | P | N | E | M | . | . | . | E | T | R | E | . | S | . | . | Y | . | . | N | . | . | T | E | . | . | . | . | . | . | . | . | . | . | . |
| SEQ_ID_NO_265_pA15908 | P | N | . | T | . | . | . | E | . | E | R | . | E | . | . | R | . | . | N | . | . | . | R | . | Q | . | Q | . | E | . | R | . | T | . |
| SEQ_ID_NO_266_pA15909 | P | E | E | . | . | . | . | E | R | . | E | . | P | . | . | R | . | . | . | . | R | . | . | . | . | . | R | . | E | . | . | . | . | . |
| SEQ_ID_NO_267_pA15910 | . | . | . | . | E | . | . | E | H | E | R | H | P | E | . | R | . | . | . | T | R | . | R | . | Q | . | Q | . | E | . | . | . | T | . |
| SEQ_ID_NO_268_pA15911 | P | N | L | M | . | . | . | E | W | Y | R | . | S | . | . | A | . | . | . | . | . | . | . | . | . | . | . | . | . | . | S | . | . | . |
| SEQ_ID_NO_269_pA15912 | P | N | E | M | . | . | . | E | T | . | R | . | S | . | . | A | . | . | . | . | . | . | . | . | . | . | R | E | E | R | E | . | . | . |
| SEQ_ID_NO_270_pA15913 | P | . | L | . | . | . | . | E | . | R | . | . | R | . | . | . | . | . | R | . | . | R | E | . | . | . | . | . | . | . | . | . | M | . |
| SEQ_ID_NO_271_pA15914 | P | N | . | . | . | . | . | E | . | R | . | . | S | . | . | . | . | . | . | . | . | . | . | . | . | . | Q | . | E | . | . | . | T | . |
| SEQ_ID_NO_272_pA15915 | P | N | T | I | . | . | . | E | . | R | E | . | E | . | . | . | . | . | . | . | . | . | . | . | . | . | Q | . | E | . | . | . | T | . |
| SEQ_ID_NO_273_pA15916 | P | . | R | . | I | R | . | E | Y | R | Q | . | . | R | . | . | . | . | R | . | R | . | R | . | . | . | Q | . | E | . | R | . | Y | . |
| SEQ_ID_NO_274_pA15917 | P | N | E | T | . | . | . | E | . | R | . | . | S | . | . | H | . | . | . | . | . | . | . | . | . | . | Q | . | E | . | . | . | T | . |
| SEQ_ID_NO_275_pA15918 | P | N | E | M | . | . | . | E | T | R | Q | . | E | . | . | Y | . | . | . | . | . | . | . | . | . | . | Q | . | E | . | . | . | T | . |
| SEQ_ID_NO_276_pA15919 | P | . | . | . | . | R | . | E | E | R | E | . | R | L | . | . | . | . | R | . | R | . | R | . | . | S | Q | E | P | R | W | . | Y | . |
| SEQ_ID_NO_277_pA15920 | . | T | E | . | W | I | R | E | W | R | R | . | P | M | . | Y | . | . | . | T | R | . | R | . | Y | . | A | . | P | W | S | . | T | . |
| SEQ_ID_NO_278_pA15921 | . | . | . | L | . | I | . | Y | Y | . | E | . | R | . | . | . | . | . | R | . | . | . | V | . | . | S | Q | E | E | . | . | . | . | . |
| SEQ_ID_NO_279_pA15922 | . | T | E | F | W | I | . | E | W | . | R | . | P | . | . | L | . | . | . | T | R | . | T | . | Y | . | A | . | P | . | . | . | . | . |
| SEQ_ID_NO_280_pA15923 | E | . | G | R | . | . | . | E | Y | R | R | . | S | . | R | . | . | Q | . | . | R | . | . | . | . | . | Q | . | E | . | . | . | . | . |
| SEQ_ID_NO_281_pA15924 | . | . | . | . | . | R | . | E | Y | . | E | . | R | . | . | R | . | . | . | . | R | . | . | . | . | . | Q | . | E | . | R | . | . | . |
| SEQ_ID_NO_282_pA15925 | . | T | E | F | Y | I | . | E | Q | R | R | H | P | M | . | Y | . | . | . | . | R | . | . | . | . | . | A | . | P | . | . | . | T | . |

FIG. 23 Continued

| | 157 | 158 | 159 | 160 | 161 | 179 | 187 | 190 | 191 | 193 | 194 | 195 | 197 | 200 | 201 | 203 | 204 | 205 | 216 | 218 | 219 | 220 | 221 | 222 | 224 | 228 | 229 | 231 | 232 | 235 | 238 | 239 | 240 | 241 |
|---|---|---|---|---|---|---|---|---|---|---|---|---|---|---|---|---|---|---|---|---|---|---|---|---|---|---|---|---|---|---|---|---|---|---|
| SEQ_ID_NO_6_pA06238 | N | F | Q | P | V | V | S | S | S | K | K | Y | N | P | N | W | D | R | G | S | Y | D | K | V | E | D | K | R | G | E | K | R | E | D |
| SEQ_ID_NO_283_pA15926 | P | . | . | . | . | . | . | . | . | . | . | . | . | . | . | . | . | . | R | . | . | . | R | . | . | . | Q | . | E | . | R | . | . | P |
| SEQ_ID_NO_284_pA15927 | . | . | W | . | I | . | . | . | . | . | . | . | . | . | . | . | . | . | R | . | R | . | R | . | . | . | . | . | . | . | S | . | . | . |
| SEQ_ID_NO_285_pA15928 | P | N | . | . | . | . | . | . | . | . | . | . | . | . | . | . | . | . | . | . | . | . | . | . | . | . | Q | . | E | . | . | . | . | . |
| SEQ_ID_NO_286_pA15929 | D | R | . | . | . | . | . | . | . | E | . | . | D | . | . | R | . | . | . | . | . | . | . | . | . | . | R | . | E | . | . | . | T | . |
| SEQ_ID_NO_287_pA15930 | P | N | L | M | . | . | . | E | T | L | R | . | S | . | . | A | S | . | . | . | . | . | . | . | . | S | Q | L | P | . | . | . | T | . |
| SEQ_ID_NO_288_pA15931 | P | . | R | . | I | R | . | . | . | . | . | . | . | . | . | . | . | . | R | . | R | . | R | I | . | . | Q | . | E | . | . | . | . | . |
| SEQ_ID_NO_289_pA15932 | P | N | . | M | . | . | . | . | . | . | . | . | . | . | . | . | . | . | . | . | . | . | . | . | . | . | . | . | . | . | S | . | . | . |
| SEQ_ID_NO_290_pA15933 | P | N | . | M | . | . | . | . | . | L | . | . | S | . | . | A | N | . | . | . | . | . | . | . | . | S | Q | E | E | R | S | . | T | . |
| SEQ_ID_NO_291_pA15934 | . | T | . | . | . | . | . | E | . | R | R | . | P | . | . | R | . | . | . | . | R | . | . | . | . | . | . | . | . | . | . | . | T | . |
| SEQ_ID_NO_292_pA15935 | P | N | L | M | . | . | . | E | T | . | R | . | S | . | . | F | . | . | . | . | . | . | . | . | . | . | . | . | . | . | . | . | . | . |
| SEQ_ID_NO_293_pA15936 | P | N | . | M | . | . | . | E | T | Y | R | . | S | . | . | A | . | . | . | . | . | . | . | . | . | . | . | . | . | . | . | . | . | . |
| SEQ_ID_NO_294_pA15937 | . | N | . | E | . | . | . | D | T | R | R | . | E | . | . | Y | N | . | . | . | . | . | . | . | . | . | . | . | . | . | . | . | T | . |
| SEQ_ID_NO_295_pA15938 | . | . | R | . | I | R | . | . | L | . | . | . | . | . | . | . | . | . | R | . | R | . | R | . | . | . | Q | . | E | . | R | . | . | . |
| SEQ_ID_NO_296_pA15939 | . | N | . | E | . | . | . | . | T | R | D | . | S | . | . | Y | N | . | R | . | . | . | Q | . | . | S | Q | E | E | R | S | . | T | . |
| SEQ_ID_NO_297_pA15940 | . | . | E | M | . | . | . | . | T | L | A | . | S | . | . | A | R | . | . | . | . | . | . | . | . | . | . | . | . | . | . | . | T | . |
| SEQ_ID_NO_298_pA15941 | . | T | . | F | E | I | Q | E | Q | I | R | H | P | L | . | L | . | . | . | T | R | . | T | . | Y | . | A | . | P | . | . | . | T | . |
| SEQ_ID_NO_299_pA15942 | . | T | E | F | W | I | . | E | W | . | R | . | P | . | . | L | . | . | . | T | R | . | T | . | Y | . | A | . | P | . | . | . | . | . |
| SEQ_ID_NO_300_pA15943 | P | N | L | F | . | R | . | E | W | R | R | . | E | L | . | . | . | . | . | . | . | . | . | . | . | S | Q | F | P | . | . | . | T | R |
| SEQ_ID_NO_301_pA15944 | . | . | . | . | . | R | . | . | . | . | . | . | . | . | . | . | . | . | R | . | R | . | R | . | . | S | Q | . | P | . | . | . | . | . |
| SEQ_ID_NO_302_pA15945 | P | . | L | M | . | I | . | Y | Y | F | L | . | . | L | . | R | . | . | R | . | . | . | V | . | M | S | Q | E | E | R | S | . | Y | P |
| SEQ_ID_NO_303_pA15946 | . | . | . | . | . | I | . | D | R | R | E | . | . | . | . | . | . | . | R | . | . | . | Q | . | . | . | Q | . | P | . | . | . | . | . |
| SEQ_ID_NO_304_pA15947 | . | . | . | A | . | I | . | E | L | R | R | . | . | . | . | . | . | . | R | . | . | . | I | . | . | S | Q | E | E | R | S | . | . | N |
| SEQ_ID_NO_305_pA15948 | . | V | . | . | . | . | A | E | A | R | R | . | D | . | . | F | . | . | . | . | . | E | T | . | . | S | R | E | E | R | S | . | D | Q |
| SEQ_ID_NO_306_pA15949 | . | V | . | . | . | . | A | E | A | R | R | . | S | M | . | Y | . | . | . | . | . | Q | T | . | Y | S | R | E | P | R | S | . | T | . |
| SEQ_ID_NO_307_pA15950 | . | N | . | E | . | . | . | . | T | R | D | . | S | . | . | Y | N | . | R | . | . | . | Q | . | . | S | Q | E | E | R | S | . | T | . |
| SEQ_ID_NO_308_pA15951 | . | N | . | . | . | . | . | E | Y | R | R | . | L | . | . | . | . | . | R | . | . | . | Q | . | . | . | N | . | P | . | . | . | . | R |
| SEQ_ID_NO_309_pA15952 | . | N | . | E | . | . | . | D | T | R | R | . | S | . | . | Y | . | . | . | . | . | . | . | . | . | . | . | . | . | . | S | . | . | . |
| SEQ_ID_NO_310_pA15953 | . | N | . | E | . | . | . | D | T | R | R | . | S | . | . | Y | N | . | . | . | . | . | . | . | . | S | Q | E | E | R | S | . | T | . |
| SEQ_ID_NO_311_pA15954 | . | N | . | E | . | . | . | E | T | E | R | . | S | . | . | F | . | . | R | . | . | . | Q | . | . | . | . | . | . | . | S | . | . | . |
| SEQ_ID_NO_312_pA15955 | . | L | . | . | . | . | . | E | Y | R | E | . | R | E | . | . | . | . | . | . | . | . | . | . | . | S | Q | E | P | R | S | . | T | . |
| SEQ_ID_NO_313_pA15956 | . | N | . | E | . | . | . | . | . | R | D | . | S | . | . | Y | . | . | . | . | . | . | . | . | . | S | Q | A | P | . | . | . | T | . |
| SEQ_ID_NO_314_pA15957 | . | . | . | E | . | . | . | E | T | R | A | . | S | . | . | Y | . | . | R | . | . | . | Q | . | . | . | . | . | . | . | . | . | . | . |
| SEQ_ID_NO_315_pA15958 | . | . | . | . | . | . | . | E | R | R | E | . | R | . | . | . | . | . | . | . | G | . | . | . | . | . | . | . | . | . | S | . | . | . |
| SEQ_ID_NO_316_pA15959 | R | V | . | . | . | . | R | D | A | R | R | . | S | . | . | F | . | . | . | . | G | . | Q | . | . | S | R | E | P | R | S | . | . | . |
| SEQ_ID_NO_317_pA15960 | . | . | R | . | . | I | . | E | Y | R | R | . | . | . | . | . | . | . | . | . | G | . | . | . | . | S | Q | . | P | . | . | . | . | . |
| SEQ_ID_NO_318_pA15961 | D | N | . | . | . | . | . | E | Y | R | R | . | E | M | . | . | . | . | R | . | . | Q | T | . | . | S | Q | E | P | R | S | S | T | . |
| SEQ_ID_NO_319_pA15962 | . | . | R | . | . | I | . | E | Y | R | R | . | . | . | . | . | . | . | R | . | . | . | Q | . | . | S | Q | . | P | . | . | . | . | . |
| SEQ_ID_NO_320_pA15963 | . | . | . | . | . | I | . | D | E | R | R | . | . | . | . | . | . | . | . | . | . | . | . | . | . | . | Q | . | P | . | . | . | . | . |

FIG. 23 Continued

| | 258 | 262 | 287 | 290 | 291 | 292 | 297 | 299 | 300 | 302 | 303 | 307 | 313 | 315 | 318 | 321 | 322 | 323 | 324 | 325 | 326 | 327 | 328 | 331 | 343 | 345 | 348 | 349 | 352 | 353 | 356 | 357 | 361 | 363 |
|---|---|---|---|---|---|---|---|---|---|---|---|---|---|---|---|---|---|---|---|---|---|---|---|---|---|---|---|---|---|---|---|---|---|---|
| SEQ_ID_NO_6_pA06238 | R | E | N | D | E | I | E | S | N | K | R | E | D | Y | K | K | D | S | K | R | L | E | L | W | E | E | K | M | N | K | E | N | G | D |
| SEQ_ID_NO_232_pA15875 | . | . | E | R | . | . | R | Q | D | R | . | . | . | . | D | D | T | . | D | E | H | R | R | E | D | P | R | E | R | R | . | . | . | . |
| SEQ_ID_NO_233_pA15876 | . | R | E | R | . | . | R | Q | D | R | . | . | . | . | D | E | T | . | D | Q | . | R | . | E | D | P | R | E | R | R | . | . | . | . |
| SEQ_ID_NO_234_pA15877 | E | R | Q | R | . | . | H | . | D | R | . | . | P | . | D | D | . | . | P | Q | . | . | E | . | . | P | E | E | R | Q | . | . | . | . |
| SEQ_ID_NO_235_pA15878 | . | . | R | R | . | . | H | . | . | E | E | R | . | . | N | E | . | . | D | Q | . | R | E | . | D | P | R | E | R | Q | . | . | . | . |
| SEQ_ID_NO_236_pA15879 | . | . | Q | R | . | . | H | . | . | Q | E | Q | P | . | D | D | . | . | P | Q | . | . | E | . | D | P | E | E | R | Q | . | . | . | . |
| SEQ_ID_NO_237_pA15880 | . | . | E | R | . | . | R | . | . | R | E | R | . | . | . | E | . | . | D | E | . | . | E | E | D | P | R | R | E | E | R | . | . | . |
| SEQ_ID_NO_238_pA15881 | . | Q | L | . | . | . | R | . | E | R | . | . | P | . | D | D | . | . | D | . | . | Y | W | L | D | P | R | T | E | R | R | . | P | P |
| SEQ_ID_NO_239_pA15882 | . | . | . | . | . | Q | . | Q | . | . | . | . | . | . | D | D | T | . | D | . | H | R | E | . | . | . | . | R | E | E | R | . | . | . |
| SEQ_ID_NO_240_pA15883 | . | Q | E | R | . | Q | . | . | . | R | E | R | . | . | . | D | T | . | D | . | H | R | E | E | D | P | R | E | R | . | . | . | . | . |
| SEQ_ID_NO_241_pA15884 | . | R | E | R | . | . | R | Q | D | R | . | . | . | . | D | E | T | . | . | Q | . | . | E | E | D | P | R | R | . | E | R | . | . | . |
| SEQ_ID_NO_242_pA15885 | . | . | Q | R | . | . | H | . | D | R | . | . | . | . | . | D | . | . | D | Q | . | . | . | . | . | . | . | R | E | E | R | . | . | . |
| SEQ_ID_NO_243_pA15886 | E | R | Q | R | . | . | H | . | . | E | . | . | . | . | . | D | . | . | D | Q | . | . | E | . | D | . | R | R | E | E | R | . | . | . |
| SEQ_ID_NO_244_pA15887 | . | . | E | R | . | . | R | Q | D | R | . | . | . | . | N | D | T | . | D | E | H | R | R | E | N | P | E | E | R | R | . | . | . | . |
| SEQ_ID_NO_245_pA15888 | . | . | E | R | . | . | R | . | D | R | . | . | . | . | D | E | T | . | E | Q | . | . | R | . | D | P | R | E | R | R | . | . | P | . |
| SEQ_ID_NO_246_pA15889 | . | . | Q | . | . | . | . | . | . | R | Q | . | P | . | D | D | . | . | D | . | . | . | E | . | D | . | R | R | E | R | R | . | P | . |
| SEQ_ID_NO_247_pA15890 | . | R | E | R | . | . | R | Q | . | R | E | R | . | . | D | E | T | . | D | . | . | . | E | E | D | P | R | E | R | R | . | . | . | . |
| SEQ_ID_NO_248_pA15891 | E | R | Q | R | . | . | H | . | D | R | . | . | P | . | D | D | . | . | P | Q | . | . | E | . | D | . | R | R | E | Q | R | . | . | . |
| SEQ_ID_NO_249_pA15892 | . | . | . | . | . | . | H | . | . | . | . | . | . | . | D | D | . | . | P | Q | . | . | E | . | . | P | R | E | R | L | . | . | . | . |
| SEQ_ID_NO_250_pA15893 | . | . | E | R | . | E | R | Q | D | R | . | . | . | W | N | D | T | . | D | . | H | R | E | E | D | P | R | E | E | R | R | . | . | . |
| SEQ_ID_NO_251_pA15894 | E | R | . | . | . | . | H | . | . | . | . | . | . | . | D | . | . | . | . | . | . | . | . | . | . | . | . | R | E | L | R | . | . | . |
| SEQ_ID_NO_252_pA15895 | E | R | Q | R | . | . | H | . | D | R | . | . | P | . | D | D | . | . | P | Q | . | . | . | . | D | P | R | R | E | A | R | . | . | . |
| SEQ_ID_NO_253_pA15896 | . | . | . | . | . | Q | . | . | . | . | . | . | . | . | D | . | . | . | . | . | . | . | . | . | N | P | R | E | R | . | . | . | . | . |
| SEQ_ID_NO_254_pA15897 | . | . | E | R | . | Q | . | . | D | R | . | . | . | . | D | D | T | . | . | E | H | . | R | E | D | P | R | E | R | . | . | . | . | . |
| SEQ_ID_NO_255_pA15898 | . | R | E | R | . | . | R | Q | D | R | . | . | . | . | D | E | T | . | D | Q | . | R | E | E | D | P | R | E | E | R | R | . | . | . |
| SEQ_ID_NO_256_pA15899 | . | . | E | R | . | . | H | . | . | R | E | R | P | . | D | R | . | . | E | E | . | R | R | E | N | P | E | R | Q | Q | R | . | . | . |
| SEQ_ID_NO_257_pA15900 | . | . | R | . | . | . | . | . | . | R | E | R | . | . | D | D | . | . | D | . | . | . | . | . | D | . | E | R | R | . | . | . | D | . |
| SEQ_ID_NO_258_pA15901 | . | . | L | E | . | . | . | Q | D | R | . | . | P | . | D | D | . | . | D | . | . | . | . | . | D | . | R | R | E | L | R | . | . | . |
| SEQ_ID_NO_259_pA15902 | . | . | E | R | . | . | . | . | . | R | E | R | . | . | . | E | . | . | E | Q | . | R | E | E | . | . | . | . | . | . | . | . | . | . |
| SEQ_ID_NO_260_pA15903 | . | . | H | Q | . | . | . | Q | D | Q | . | . | P | . | D | D | . | . | D | Q | . | . | E | . | D | . | R | R | E | H | R | . | . | . |
| SEQ_ID_NO_261_pA15904 | . | L | . | . | . | . | R | . | E | . | . | . | . | . | . | D | . | . | . | . | . | . | W | . | . | . | . | R | E | R | R | . | P | . |
| SEQ_ID_NO_262_pA15905 | . | R | . | . | . | . | R | Q | . | . | . | . | . | . | . | E | T | . | . | . | . | . | E | . | Q | . | R | R | E | E | R | . | . | . |
| SEQ_ID_NO_263_pA15906 | . | L | E | . | R | . | R | . | E | M | . | . | . | . | D | E | T | G | P | Q | . | . | W | F | D | P | R | E | R | R | . | . | P | P |
| SEQ_ID_NO_264_pA15907 | . | . | Q | R | . | . | H | . | . | Q | . | . | . | . | . | R | . | D | H | Q | . | . | . | . | D | . | R | R | E | L | R | . | . | . |
| SEQ_ID_NO_265_pA15908 | E | R | . | . | . | . | H | . | . | . | . | . | . | . | D | . | . | . | . | . | . | . | . | . | D | . | E | R | R | Q | . | . | . | . |
| SEQ_ID_NO_266_pA15909 | . | . | . | . | . | . | R | Q | . | . | . | . | . | . | D | E | T | . | D | Q | . | R | E | . | Q | D | R | E | R | R | . | . | . | . |
| SEQ_ID_NO_267_pA15910 | . | . | . | . | . | Q | . | . | . | . | . | . | . | . | N | D | T | . | . | . | H | . | E | . | . | . | . | . | . | . | . | . | . | . |
| SEQ_ID_NO_268_pA15911 | . | L | L | R | . | . | H | . | D | L | . | . | P | . | D | R | . | . | P | A | . | . | D | L | . | . | . | R | E | L | R | . | . | . |
| SEQ_ID_NO_269_pA15912 | . | . | . | . | . | . | . | . | . | . | . | . | P | . | D | D | . | . | P | Q | . | . | . | . | D | P | E | R | R | . | . | . | . | . |
| SEQ_ID_NO_270_pA15913 | . | . | L | E | . | . | . | . | . | R | E | R | . | . | . | . | . | . | D | E | . | . | E | . | D | . | E | R | R | . | . | . | P | . |
| SEQ_ID_NO_271_pA15914 | . | . | Q | R | . | . | . | . | . | Q | . | . | . | . | . | D | . | . | P | Q | . | . | . | . | D | P | E | R | R | . | . | . | . | . |
| SEQ_ID_NO_272_pA15915 | . | . | Q | R | . | . | . | . | D | R | . | . | P | . | D | D | . | . | P | Q | . | . | . | . | . | . | . | . | . | . | . | . | . | . |
| SEQ_ID_NO_273_pA15916 | . | Q | L | E | . | . | R | . | D | R | . | . | . | . | D | E | T | . | D | Q | . | R | . | . | D | P | R | E | R | R | . | . | P | . |
| SEQ_ID_NO_274_pA15917 | . | . | Q | Q | . | . | . | . | . | R | E | R | . | . | . | D | . | . | P | Q | . | . | . | . | D | . | E | R | R | . | . | . | . | . |
| SEQ_ID_NO_275_pA15918 | . | . | Q | R | . | . | . | . | . | Q | . | . | . | . | D | D | . | . | P | Q | . | . | . | . | . | . | . | . | . | . | . | . | . | . |
| SEQ_ID_NO_276_pA15919 | . | L | L | . | . | . | R | . | E | P | . | . | P | . | D | E | T | . | D | Q | . | R | W | L | . | . | . | R | E | Q | R | . | P | P |
| SEQ_ID_NO_277_pA15920 | . | . | L | . | . | . | R | Q | E | L | . | . | P | W | D | D | T | . | W | W | H | . | W | F | D | P | R | E | E | R | R | . | . | H |
| SEQ_ID_NO_278_pA15921 | . | L | . | . | . | . | R | . | Q | . | . | . | P | . | D | D | . | . | D | . | . | I | W | . | D | P | Y | Y | L | L | W | . | P | P |
| SEQ_ID_NO_279_pA15922 | . | . | L | . | . | . | R | Q | E | L | . | . | . | . | . | S | T | . | . | S | H | . | W | F | D | P | R | E | R | R | . | . | . | H |
| SEQ_ID_NO_280_pA15923 | . | . | R | . | . | . | . | . | D | R | . | . | . | . | . | E | . | . | . | . | H | . | . | . | Y | P | R | E | R | . | . | . | . | . |
| SEQ_ID_NO_281_pA15924 | . | . | . | . | . | . | . | . | . | . | . | . | . | . | . | E | T | . | D | Q | . | R | E | . | Q | P | Q | E | R | . | . | . | P | . |
| SEQ_ID_NO_282_pA15925 | . | . | . | . | . | Q | . | . | . | . | . | . | . | . | . | D | T | . | . | D | H | . | W | . | D | P | R | E | R | . | . | . | . | H |

FIG. 23 Continued

```
Positions: 258 262 287 290 291 292 297 299 300 302 303 307 313 315 318 321 322 323 324 325 326 327 328 331 343 345 348 349 352 353 356 357 361 363

SEQ_ID_NO_6_pA06238      RENDEIESNKREDYKKDSKRLELWEEKMNKENGD
SEQ_ID_NO_283_pA15926    ..Q......R.....D..D.....D.ERR...P.
SEQ_ID_NO_284_pA15927    .LER..R.RRD...DET.DQ.RYENPEERR..PP
SEQ_ID_NO_285_pA15928    ERQR..H..QEQP.DD..PQ....D.RREQR...
SEQ_ID_NO_286_pA15929    .......Q....P.D............RERR...
SEQ_ID_NO_287_pA15930    ......H.....P.DR..PA..D....RELR...
SEQ_ID_NO_288_pA15931    ..ER....DR.....E...Q...EDPRER...P.
SEQ_ID_NO_289_pA15932    .LLR..H.DL.....R..PA...FMPWTML....
SEQ_ID_NO_290_pA15933    .LLR....DL..P.DR..PA...L..........
SEQ_ID_NO_291_pA15934    ..ER....DR.....DT..EH.REYPERR.....
SEQ_ID_NO_292_pA15935    .LLR....DL..P.D........L..........
SEQ_ID_NO_293_pA15936    .LLR....DL.............LD.AR......
SEQ_ID_NO_294_pA15937    .LFQ.....L..P.DD..E....LNPETR.....
SEQ_ID_NO_295_pA15938    ...............ET.DQ.R..DPRER...P.
SEQ_ID_NO_296_pA15939    .L.R..L..L..P.DD..E....L.PEERQ....
SEQ_ID_NO_297_pA15940    .LLR....DL..P.DR..PA...L..........
SEQ_ID_NO_298_pA15941    .....Q.........ST..SH.W.YPEWR....H
SEQ_ID_NO_299_pA15942    ..LF.Q...LER...ST..SH.WF.........H
SEQ_ID_NO_300_pA15943    .L......................DPRR.....H
SEQ_ID_NO_301_pA15944    .LL.....DP.....ET.DQ.RWLDPRER...PP
SEQ_ID_NO_302_pA15945    .LL...R.QI..P.DD..D..YWLLPWYLLW.P.
SEQ_ID_NO_303_pA15946    .QR......RER...RT.ED.RY..PQERR..PP
SEQ_ID_NO_304_pA15947    .LHE.....IERP.DD..E...YL.PRTELR.PP
SEQ_ID_NO_305_pA15948    LRHE...A.IERP.DD..E...YL.PLTERR...
SEQ_ID_NO_306_pA15949    .QER.....IERP.DRT.ED..YLNPRERR....
SEQ_ID_NO_307_pA15950    .LFQ.....L..P.DR..ED...L.PETR.....
SEQ_ID_NO_308_pA15951    ...............R..ED.R..NPENR.....
SEQ_ID_NO_309_pA15952    .LFQ.....L..P.D........L..........
SEQ_ID_NO_310_pA15953    .L....L.....P.DD..E........IELR...
SEQ_ID_NO_311_pA15954    ......L........D..E........IELR...
SEQ_ID_NO_312_pA15955    ..RE.....IER..NR..EG..YL.........P
SEQ_ID_NO_313_pA15956    .LFQ.....LER...........L.PETR.....
SEQ_ID_NO_314_pA15957    .L.E.....LERP.D........L.PETR.....
SEQ_ID_NO_315_pA15958    .QR......IER...RT..G..YLNPRER...P.
SEQ_ID_NO_316_pA15959    .R.....A......D.........NPRERR....
SEQ_ID_NO_317_pA15960    ..R......IER...STG.D..YLNPRERR....
SEQ_ID_NO_318_pA15961    .LRQ..L..LER..NR..ED.RYLNPEQRERH..
SEQ_ID_NO_319_pA15962    .Q............DRT.EG.RY.NPRER.....
SEQ_ID_NO_320_pA15963    .Q............DST..D..Y.NPRER...PP
```

FIG. 23 Continued

| | 364 | 365 | 366 | 368 | 369 | 370 | 373 | 375 | 376 | 377 | 380 | 382 | 384 | 385 | 386 | 388 | 389 | 392 | 393 | 396 | 397 | 400 | 403 | 407 | 408 |
|---|---|---|---|---|---|---|---|---|---|---|---|---|---|---|---|---|---|---|---|---|---|---|---|---|---|
| SEQ_ID_NO_6_pA06238 | I | K | F | Y | Q | Y | D | Y | F | D | E | K | K | N | D | R | E | K | K | K | R | E | S | N | L |
| SEQ_ID_NO_232_pA15875 | P | E | . | R | E | . | R | . | E | R | D | E | R | . | . | . | . | E | E | R | Q | . | R | D | R |
| SEQ_ID_NO_233_pA15876 | E | R | R | . | E | . | E | . | Q | . | D | R | R | . | . | . | . | R | E | R | . | . | E | D | G |
| SEQ_ID_NO_234_pA15877 | E | R | . | . | . | . | . | . | . | . | N | N | D | T | . | . | . | . | . | . | . | . | A | Q | . |
| SEQ_ID_NO_235_pA15878 | E | R | . | . | R | . | . | . | . | . | D | R | Q | . | . | . | . | . | . | . | . | . | R | E | . |
| SEQ_ID_NO_236_pA15879 | E | R | . | . | R | . | . | . | . | . | . | . | . | . | . | . | . | . | . | . | . | . | R | E | . |
| SEQ_ID_NO_237_pA15880 | E | R | . | . | R | . | . | . | . | H | D | R | R | . | . | . | . | E | Q | R | E | . | R | E | . |
| SEQ_ID_NO_238_pA15881 | L | E | H | R | D | . | . | . | E | . | D | R | E | . | . | . | . | . | . | . | . | . | A | D | T |
| SEQ_ID_NO_239_pA15882 | P | E | . | R | R | . | . | . | E | . | N | R | R | . | . | . | . | . | . | . | . | . | R | E | R |
| SEQ_ID_NO_240_pA15883 | . | R | . | . | R | . | R | . | E | . | . | R | Q | . | . | . | . | H | R | E | E | Q | R | E | R |
| SEQ_ID_NO_241_pA15884 | E | R | . | . | . | . | . | . | Q | . | D | R | T | . | . | . | . | . | . | . | . | . | . | H | R |
| SEQ_ID_NO_242_pA15885 | E | R | . | . | . | . | . | . | . | . | N | R | . | . | . | . | . | . | . | . | . | . | A | Q | . |
| SEQ_ID_NO_243_pA15886 | E | R | . | . | . | . | . | . | . | . | N | R | E | . | . | . | . | . | . | . | . | . | A | E | . |
| SEQ_ID_NO_244_pA15887 | P | E | . | R | R | . | . | . | E | . | . | R | Q | . | . | . | . | . | . | . | . | . | R | E | R |
| SEQ_ID_NO_245_pA15888 | . | R | . | . | R | . | . | . | E | . | D | R | Q | P | . | . | . | L | H | E | E | R | . | . | D |
| SEQ_ID_NO_246_pA15889 | . | R | . | . | R | . | . | . | E | . | D | R | E | P | . | . | . | . | . | . | . | . | R | D | T |
| SEQ_ID_NO_247_pA15890 | P | R | . | . | R | . | . | . | E | . | R | Q | T | . | . | . | . | . | . | . | . | . | A | W | D |
| SEQ_ID_NO_248_pA15891 | E | R | . | . | . | . | . | . | . | . | N | R | S | . | . | . | . | L | A | E | H | R | W | E | . |
| SEQ_ID_NO_249_pA15892 | E | R | . | . | . | . | . | . | . | . | . | . | Q | . | . | . | . | . | . | . | . | . | . | R | . |
| SEQ_ID_NO_250_pA15893 | . | R | R | . | E | . | . | . | E | . | . | R | R | . | . | . | . | . | . | . | . | . | R | E | N |
| SEQ_ID_NO_251_pA15894 | E | R | . | . | . | . | . | . | . | . | N | N | S | . | . | . | D | R | . | A | L | . | A | Q | . |
| SEQ_ID_NO_252_pA15895 | . | . | . | . | . | . | . | . | . | . | . | . | D | T | . | . | . | . | . | . | L | . | . | . | . |
| SEQ_ID_NO_253_pA15896 | P | E | . | R | R | . | . | . | E | . | D | R | D | . | . | . | R | E | . | . | . | . | . | H | R |
| SEQ_ID_NO_254_pA15897 | . | R | . | . | . | . | . | . | E | . | . | R | . | . | . | . | . | . | . | . | . | . | R | E | . |
| SEQ_ID_NO_255_pA15898 | E | R | Y | . | . | . | . | . | Q | . | D | R | T | . | . | . | R | L | . | Q | L | . | A | Y | D |
| SEQ_ID_NO_256_pA15899 | E | R | . | . | R | . | . | . | . | . | . | . | Q | . | . | . | . | R | . | R | I | . | A | E | . |
| SEQ_ID_NO_257_pA15900 | E | R | . | . | R | . | E | . | E | . | R | R | D | T | . | . | . | . | H | . | . | R | R | Q | R |
| SEQ_ID_NO_258_pA15901 | E | R | Y | . | . | . | . | . | E | . | R | R | E | P | . | . | R | H | . | I | L | . | A | L | T |
| SEQ_ID_NO_259_pA15902 | E | R | . | . | R | . | . | . | . | . | . | . | Q | . | . | . | . | R | R | . | E | . | R | E | . |
| SEQ_ID_NO_260_pA15903 | E | R | . | . | R | . | . | . | E | . | R | R | E | P | . | . | . | . | . | . | . | . | . | . | R |
| SEQ_ID_NO_261_pA15904 | . | . | . | . | . | . | . | . | E | . | D | R | E | P | . | . | . | . | . | . | . | . | A | D | . |
| SEQ_ID_NO_262_pA15905 | E | R | Y | . | . | . | . | . | Q | . | D | R | . | . | . | . | . | . | . | . | . | . | A | W | R |
| SEQ_ID_NO_263_pA15906 | P | D | . | R | D | H | E | W | R | . | D | R | R | P | . | . | . | Y | H | E | L | R | A | L | D |
| SEQ_ID_NO_264_pA15907 | . | . | . | . | . | . | . | . | . | . | N | N | Q | . | . | . | . | . | . | M | L | . | A | Q | . |
| SEQ_ID_NO_265_pA15908 | . | . | . | . | . | . | . | . | . | R | N | E | D | T | . | . | . | L | A | E | . | . | . | Q | . |
| SEQ_ID_NO_266_pA15909 | . | . | . | . | . | . | . | . | . | . | . | . | . | . | . | . | . | . | . | . | . | . | . | H | R |
| SEQ_ID_NO_267_pA15910 | . | R | . | . | R | . | . | . | E | . | . | R | Q | . | . | . | R | H | H | E | . | R | R | E | R |
| SEQ_ID_NO_268_pA15911 | . | . | . | . | . | . | . | . | . | . | . | . | . | . | . | . | . | . | . | . | . | . | . | L | . |
| SEQ_ID_NO_269_pA15912 | E | R | . | . | . | . | . | . | . | . | . | . | E | . | . | . | . | R | . | . | . | . | . | . | . |
| SEQ_ID_NO_270_pA15913 | . | R | . | . | R | . | . | . | E | . | D | R | E | P | . | . | . | . | . | . | . | . | A | F | T |
| SEQ_ID_NO_271_pA15914 | P | R | Y | . | R | . | . | A | . | . | N | N | . | . | . | . | . | . | . | . | . | . | A | Q | . |
| SEQ_ID_NO_272_pA15915 | . | . | . | . | . | . | . | . | . | . | . | . | . | . | . | . | . | . | . | M | L | . | L | Q | . |
| SEQ_ID_NO_273_pA15916 | P | R | . | . | R | . | R | . | E | . | D | R | Q | P | . | . | . | R | . | R | L | . | . | . | D |
| SEQ_ID_NO_274_pA15917 | . | . | . | . | . | . | . | . | . | . | . | . | Q | . | . | . | . | . | . | . | . | . | . | Q | . |
| SEQ_ID_NO_275_pA15918 | E | R | . | . | . | . | . | . | . | . | . | . | Q | . | . | . | . | . | . | . | . | . | . | E | . |
| SEQ_ID_NO_276_pA15919 | P | E | . | R | R | . | . | W | E | . | D | R | R | P | . | . | . | . | . | . | . | . | W | L | D |
| SEQ_ID_NO_277_pA15920 | P | E | . | R | R | . | . | . | E | . | N | R | R | . | . | . | . | . | . | . | . | . | Y | F | W |
| SEQ_ID_NO_278_pA15921 | L | E | H | R | D | . | . | . | E | . | D | R | S | . | . | . | . | . | . | . | . | . | A | W | T |
| SEQ_ID_NO_279_pA15922 | P | S | . | R | D | . | . | . | E | . | . | R | . | . | . | . | . | . | . | . | . | . | W | Y | W |
| SEQ_ID_NO_280_pA15923 | E | R | . | R | R | . | . | . | E | . | N | R | . | . | . | . | . | . | . | . | . | . | W | . | R |
| SEQ_ID_NO_281_pA15924 | E | E | . | R | R | . | . | . | . | . | . | . | R | P | . | . | . | . | . | . | . | . | . | . | . |
| SEQ_ID_NO_282_pA15925 | P | S | . | R | D | . | R | . | E | . | . | R | R | . | . | . | . | F | R | R | E | Q | Y | F | W |

FIG. 23 Continued

| | 364 365 366 368 369 370 373 375 376 377 380 382 384 385 386 388 389 392 393 396 397 400 403 407 408 |
|---|---|
| SEQ_ID_NO_6_pA06238 | I K F Y Q Y D Y F D E K K N D R E K K K R E S N L |
| SEQ_ID_NO_283_pA15926 | . R . . R . . . . . . . E P . . . . . . . . R D T |
| SEQ_ID_NO_284_pA15927 | P E . R R . . . E . D R Q P . . . F H E L R A L D |
| SEQ_ID_NO_285_pA15928 | E R . . . . . . . . N N . . . . . . . . . . R Q . |
| SEQ_ID_NO_286_pA15929 | E R . . R . . . E . R R E P . . . . . . . . . . . |
| SEQ_ID_NO_287_pA15930 | . . . . . . . . . A . . S . . . D L W . L L W I . |
| SEQ_ID_NO_288_pA15931 | . . . . . . . . E . D R R P . . . . . . . . . . N |
| SEQ_ID_NO_289_pA15932 | E R . . L . . . . . . . . . . . . . . . . . W I . |
| SEQ_ID_NO_290_pA15933 | . . . . . . . . . . . . L . . . . . . . . . W L . |
| SEQ_ID_NO_291_pA15934 | . . . . . . N . E . . R Q . . . . . . . S . . H R |
| SEQ_ID_NO_292_pA15935 | E R Y . L . . . . A R E . . . . . . W I L Y W I . |
| SEQ_ID_NO_293_pA15936 | . . . . . . . . . . L R . . . . . . . . . . W I . |
| SEQ_ID_NO_294_pA15937 | P R . . . . . . . . R L . . . . . . . . . . F I . |
| SEQ_ID_NO_295_pA15938 | . R . . R . . . E . R Q R P . . . . . . . . . H D |
| SEQ_ID_NO_296_pA15939 | P R Y . . . . . . . . . Q . . . . . . . . . T Q . |
| SEQ_ID_NO_297_pA15940 | E R Y . L . . . . A . . S . . . D L W I L Y W I . |
| SEQ_ID_NO_298_pA15941 | P S . R D . . . E . . R . . . . . . . . . . Y F . |
| SEQ_ID_NO_299_pA15942 | P S . L . . . . . . . . R . . . . H . M . . Y F W |
| SEQ_ID_NO_300_pA15943 | E S . . R . . . . . N N . . . . . . . . . . . E . |
| SEQ_ID_NO_301_pA15944 | . D . R R . . . . . . . R P . . . . . . . . . . D |
| SEQ_ID_NO_302_pA15945 | L R . L R . . . E . D R S . . . . . . . . . W . . |
| SEQ_ID_NO_303_pA15946 | P N . . . . . . E . R L R P . . . . . . . . A H D |
| SEQ_ID_NO_304_pA15947 | L S . . . . . . E . R L E . . . . . . . . . A . . |
| SEQ_ID_NO_305_pA15948 | M R Y . . . . . E R R E T P . . . L T M L . A . D |
| SEQ_ID_NO_306_pA15949 | P R L . . . . . E . R L T . . . . . . . . . A H D |
| SEQ_ID_NO_307_pA15950 | . . . . . . . . . S R L S . . . D L Y M L . F I . |
| SEQ_ID_NO_308_pA15951 | P R . . . . . . . . . . . . . . . . . . . . A E . |
| SEQ_ID_NO_309_pA15952 | P R . . . . . . . . . . . . . . . . . . . . . . . |
| SEQ_ID_NO_310_pA15953 | P R . . . . . . . R N D . . . . . . Y . . . L Q . |
| SEQ_ID_NO_311_pA15954 | P R . . . . . . . . . . Q . . . . . . . . . . . . |
| SEQ_ID_NO_312_pA15955 | . N . . . . E . E N R L Q . . . R L E M . R A R . |
| SEQ_ID_NO_313_pA15956 | . . . . . . . . . S . L S . . . D L Y M L . L Q . |
| SEQ_ID_NO_314_pA15957 | . . . . . . . . . . R L S . . . D L A I L R F H . |
| SEQ_ID_NO_315_pA15958 | . . . . . . . . . . . . R P . . . . . . . . A H D |
| SEQ_ID_NO_316_pA15959 | P R Y . . . E . E . R L R . . . D L A M L R . . D |
| SEQ_ID_NO_317_pA15960 | L S L . . . . . E . R L . . . . . . . . . . . H D |
| SEQ_ID_NO_318_pA15961 | P R . . . . . . . R N E R . . . D E A Q E . F I . |
| SEQ_ID_NO_319_pA15962 | . . . . . . R . . . . L R . . . . L A M E R A H D |
| SEQ_ID_NO_320_pA15963 | L S . . . . L . . . . L E P H E R R A M E R . H D |

METHODS AND COMPOSITIONS FOR PREPARING TAGATOSE FROM FRUCTOSE

CROSS-REFERENCE TO RELATED APPLICATION

The present application is a continuation of U.S. application Ser. No. 17/341,813, filed Jun. 8, 2021, which is a continuation of U.S. application Ser. No. 16/503,092, filed Jul. 3, 2019, now U.S. Pat. No. 11,060,119, which claims priority to and the benefit of U.S. Provisional Patent Application No. 62/693,681, filed Jul. 3, 2018, and U.S. Provisional Patent Application No. 62/693,660, filed Jul. 3, 2018, each of which is herein incorporated by reference in its entirety.

REFERENCE TO AN ELECTRONIC SEQUENCE LISTING

The contents of the electronic sequence listing (ARZE_028_03US_SeqList_ST26.xml; Size: 712,274 bytes; and Date of Creation: Nov. 20, 2023) are herein incorporated by reference in its entirety.

FIELD OF THE INVENTION

The invention described herein generally relates to the fields of microbiology, biochemistry, and organic chemistry.

BACKGROUND

As problems with obesity and diabetes continue to rise globally, it is of growing importance to have access to alternative low-calorie sweeteners that provide health benefits over traditional sweeteners. D-tagatose is a naturally occurring sweetener that is GRAS (generally recognized as safe) for use in food and beverages. It is 92% as sweet as sucrose and has less than half the caloric value. Importantly, D-tagatose has a taste profile very similar to sucrose and does not have a lingering bitterness characteristic of related alternative sugars such as psicose (allulose). D-tagatose has been suggested to have several positive health benefits including non-tooth decaying, anti-hyperglycemic, and a positive prebiotic effect.

The ketohexose monosaccharide D-tagatose is a C4-epimer of D-fructose. Therefore, D-tagatose is a reducing sugar that undergoes browning reactions and can be used as a "drop-in" replacement for typical bulk sweeteners. There exist established methods to produce D-tagatose from galactose (commonly produced from lactose) using both chemical and biocatalytic means. However, the high cost of generating the galactose feedstock makes the galactose route less attractive than a process that can utilize lower-cost feedstocks such as fructose, glucose, or sucrose.

SUMMARY OF THE INVENTION

The present disclosure provides compositions and methods for producing tagatose by epimerizing fructose at carbon number 4. The present disclosure allows the use of fructose as the source material for tagatose production, which is more economical than using galactose as the source material.

In one aspect, the disclosure provides a polypeptide comprising an amino acid sequence having at least 60% sequence identity to any one of SEQ ID NOs:1-444, wherein the polypeptide has D-fructose C4-epimerase activity. In further embodiments, the polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or at least 99.9% identical to any one of SEQ ID NOs: 1-444, wherein the polypeptide has D-fructose C4-epimerase activity.

In other embodiments, the polypeptide comprises one or more modifications at the amino acid residue corresponding to position L3, S4, K5, D6, Y7, L8, R9, K10, K11, V13, Y14, S15, I16, C17, S18, S19, S21, Y22, E25, S27, E29, F30, K32, E33, K34, G35, D36, Y37, E41, T43, P44, H45, Q46, Q49, F50, Y53, S54, M56, E59, K62, N63, F64, M66, K67, K70, E71, K72, E75, E76, D77, K78, I80, D84, H85, L89, Q92, D93, E94, S96, P97, T98, N101, K102, K104, D105, R108, F110, S113, Y115, K116, K117, H119, D121, C122, S123, M124, P125, L126, S127, D128, D129, P130, K131, V132, P134, Y135, E136, K137, E140, R141, T142, R143, E144, F146, E147, I148, E150, E151, T152, A153, R154, K155, Y156, N157, F158, Q159, P160, V161, T166, D167, V168, P169, I170, A171, G172, G173, G174, E175, E176, E177, G178, V179, V182, D184, S187, A188, I189, S190, S191, L192, K193, K194, Y195, N197, D198, V199, P200, N201, I202, W203, D204, R205, G208, V210, I211, M212, L213, I215, G216, F217, S218, Y219, D220, K221, V222, E224, D228, K229, V230, R231, G232, I233, L234, E235, V237, K238, R239, E240, D241, L242, V244, E245, G246, H247, S248, T249, D250, A253, Y255, A256, R258, N259, E262, R266, K269, V270, G271, P272, A273, R280, G281, V282, L284, S286, N287, D290, E291, I292, E295, R296, E297, S299, N300, K302, R303, E307, D313, Y315, K318, Y319, K321, D322, S323, K324, R325, L326, E327, L328, I330, W331, N333, L334, L335, D336, R337, R339, Y340, E343, Y344, E345, K348, M349, V350, N352, K353, E356, N357, F358, E360, G361, V362, D363, I364, K365, F366, Y368, Q369, Y370, Y372, D373, S374, Y375, F376, D377, R379, E380, K382, M383, K384, N385, D386, R388, E389, K392, K393, K396, R397, E400, S403, N407, or L408 of SEQ ID NO:6; or combinations thereof.

In some embodiments, the polypeptide comprises one or more of modifications: L3E, L3T, S4M, S4D, S4R, S4L, S4Q, S4N, S4E, S4P, K5F, K5M, K5L, K5R, K5W, K5H, K5Q, K5V, K5A, D6R, D6L, D6H, D6Q, D6N, D6A, D6E, Y7W, Y7H, Y7N, L8N, L8G, R9L, R9T, R9H, R9Q, R9E, R9I, K10M, K10D, K10R, K10L, K10V, K10N, K10A, K10E, K10P, K111F, K11L, K11R, K11Y, K11W, K11V, K11Q, K11H, K11E, K11I, V13L, Y14F, S15A, I16V, C17S, C17L, C17R, C17T, C17G, C17V, C17A, C17L, S18N, S18A, S19N, S21K, S21R, S21Q, S21E, S21P, Y22W, E25R, E25L, S27C, S27A, E29Q, E29R, E29L, E29L, F30H, F30T, F30A, K32S, K32M, K32L, K32R, K32Q, K32A, K32L, E33R, E33T, E33H, E33Q, E33N, E33D, K34F, K34S, K34M, K34R, K34L, K34Y, K34T, K34H, K34Q, K34V, K34E, K34D, K34L, G35D, G35N, G35H, G35S, D36F, D36S, D36R, D36L, D36Y, D36T, D36W, D36H, D36Q, D36N, D36E, Y37D, Y37P, Y37R, Y37E, E41Q, E41A, H45F, H45K, H45Q, H45A, Q46S, Q46R, Q46T, Q46W, Q46A, Q49F, Q49H, Q49I, Q49W, F50Q, F50H, F50R, F50S, Y53F, Y53V, Y53S, Y53A, S54T, M56W, E59R, E59S, E59T, K62V, K62R, K62Y, K62A, N63E, N63D, N63R, N63Q, F64E, F64L, M66F, M66E, M66Y, K67S, K67R, K67T, K67Q, K67E, K67D, K70D, K70Q, K70R, K70L, E71Q, E71R, E71S, K72L, K72R, K72T, K72V, K72Q, K72H, K72E, K72L, E75D, E75P, E75R, E75S, E76P, E76L, E76R, D77N, D77R, D77S, K78M, K78R, K78L, K78Q, K78D, I80Q, I80R, I80L, D84P, D84N, D84G, D84A, H85A, L89S, L89G, Q92M, Q92D, Q92G, Q92A, Q92P, D93H, E94Q, E94R, E94Y, E94L, S96E, S96R, S96A, P97E, P97D, T98R, T98W, T98V, T98Q, T98E, T98L, N101S, N101D, N101R, N101T, N101H, N101Q, N101A, N101E, N101K, K102L, K102R, K102Y, K102W, K102Q, K102E, K104F, K104R, K104V, K104Q, K104N, K104E, K104L, D105E, D105Q, D105I, R108I, F110Y, Si 13A, Y115F, K116S, K116R, K116L, K116Y, K116T, K116W, K116H, K116Q, K116E, K116D, K116L, K117M, K117L, K117R, K117W, K117V, H119S, H119G, H119N, H119A, H119P, D121N, D121A, C122R, C122G, C122T, C122V, C122A, C122E, C122K, S123M, S123R, S123T, S123A, M124K, M124R, P125A, L126C, S127A, D128G, D129R, D129L, D129W, D129Q, D129E, P130S, K131S, K131R, K131L, K131Y, K131Q, K131A, K131E, K131D, V132S, V132R, V132Y, V132T, V132E, P134D, P134H, P134A, Y135K, Y135M, Y135D, Y135L, Y135R, Y135T, Y135W, Y135Q, Y135N, Y135P, E136S, E136R, E136P, E136W, E136T, E136Q, E136D, K137L, K137R, K137T, K137W, K137V, K137Q, K137E, K137L, E140D, E140R, E140L, E140L, R141L, R141Y, R141W, R141H, R141Q, R141D, T142E, R143V, R143A, E144Q, E144D, E144R, E144L, F146C, E147Q, E147K, E147R, E147A, I148E, I148V, I148D, E150R, E150A, E151R, T152R, T152Y, T152V, T152H, T152Q, T152A, A153Q, A153R, A153G, A153S, R154S, R154T, R154Q, R154E, R154P, K155R, K155Y, K155P, K155T, K155H, K155N, K155Q, K155G, K155W, K155E, K155D, Y156F, Y156M, Y156R, Y156T, Y156V, Y156Q, Y156E, Y156D, N157E, N157D, N157R, N157P, F158R, F158L, F158T, F158V, F158N, F158E, Q159R, Q159L, Q159G, Q159T, Q159W, Q159E, P160F, P160S, P160M, P160L, P160R, P160T, P160A, P160E, P160I, V161E, V161I, V161Y, V161W, T166M, T166L, T166L, D167T, D167V, D167Q, D167N, D167A, V168M, V168R, I170M, I170K, I170T, A171P, G173S, E175K, E175V, E175R, E176F, E176Y, G178P, V179R, V179L, V182P, V182K, V182A, D184E, S187R, S187T, S187N, S187Q, S187A, S187E, S187K, A188M, A188F, A188T, I189L, S190E, S190D, S190Y, S191L, S191R, S191Y, S191T, S191W, S191V, S191H, S191Q, S191A, S191E, S191L, L192F, L192H, K193F, K193R, K193L, K193Y, K193Q, K193A, K193E, K193L, K194S, K194R, K194L, K194T, K194Q, K194A, K194E, K194D, Y195H, Y195Q, Y195A, N197S, N197D, N197R, N197L, N197P, N197Q, N197A, N197E, N197K, D198K, V199H, V199L, V199I, V199C, P200M, P200L, P200R, P200G, P200E, P200D, N201Q, N201K, N201R, N201E, I202M, 1202A, W203F, W203R, W203L, W203Y, W203H, W203A, D204N, D204R, D204S, R205Q, R205L, G208A, V210P, V210T, I211V, M212K, M212L, M212R, L213M, I215V, G216N, G216R, G216T, S218T, S218G, Y219D, Y219H, Y219R, Y219G, D220Q, D220R, D220E, D220T, K221R, K221T, K221V, K221Q, K221E, K221I, V222L, E224M, E224Q, E224Y, D228E, D228S, K229S, K229R, K229T, K229N, K229Q, K229A, K229E, V230A, R231E, R231L, R231F, R231A, G232D, G232R, G232P, G232E, G232K, I233L, L234M, L234A, E235W, E235R, V237L, K238S, K238R, K238W, K238Q, K238E, R239S, E240M, E240Y, E240T, E240V, E240N, E240H, E240D, D241R, D241G, D241Q, D241N, D241P, L242W, V244L, E245Q, E245A, G246C, G246V, G246A, H247A, T249S, D250N, D250A, A253S, A253P, A253T, A253N, A253D, Y255E, Y255D, Y255Q, Y255K, A256L, R258E, R258L, N259R, N259W, N259A, N259E, N259D, E262Q, E262R, E262L, R266V, R266A, K269L, K269R, K269V, K269N, K269L, G271D, G271A, A273W, R280E, G281A, V282L, L284K, S286D, S286V, S286A, N287F, N287R, N287L, N287H, N287Q, N287E, N287D, D290F, D290R, D290Q, D290N, D290A, D290E, D290K, E291D, E291R, I292Q, I292L, I292E, E295P, R296E, R296D, R296Y, E297R, E297L, E297G, E297H, E297Q, E297K, S299Q, S299A, N300E, N300D, N300Q, N300R, K302M, K302L, K302R, K302Q, K302E, K302P, K302L, R303E, R303D, R303Q, E307Q, E307R, D313P, Y315W, K318E, K318D, K318R, K318N, K321S, K321R, K321T, K321H, K321E, K321D, D322T, S323D, S323G, K324S, K324R, K324P, K324W, K324H, K324E, K324D, R325S, R325G, R325W, R325N, R325Q, R325A, R325E, R325D, L326H, E327R, E327L, E327Y, L328F, L328R, L328Y, L328W, L328E, L328D, I330L, W331E, W3311H, W331L, W331F, N333A, N333S, L334Y, R339E, R339T, R339A, R339G, Y340F, Y340R, Y340H, Y340A, Y340P, E343M, E343L, E343Y, E343Q, E343N, E343D, Y344H, E345D, E345P, K348R, K348L, K348Y, K348W, K348V, K348Q, K348A, K348E, M349R, M349Y, M349C, M349T, M349W, M349N, M349Q, M349A, M349E, M349K, M349L, V350A, N352M, N352R, N352L, N352Q, N352E, K353R, K353L, K353W, K353H, K353Q, K353A, K353E, E356W, E356R, N357H, F358L, E360D, G361D, G361P, V362L, D363P, D363H, I364M, I364L, I364W, I364E, I364P, K365S, K365R, K365T, K365H, K365N, K365E, K365D, F366H, F366L, F366R, F366Y, Y368R, Y368L, Q369E, Q369D, Q369R, Q369L, Y370H, Y372P, D373R, D373L, D373N, D373A, D373E, S374C, S374Q, S374T, S374A, Y375W, Y375A, F376R, F376H, F376Q, F376E, F376K, D377S, D377R, D377H, D377N, D377A, R379C, E380D, E380N, E380R, E380L, K382R, K382L, K382N, K382Q, K382E, K382D, M383L, K384S, K384L, K384R, K384T, K384Q, K384E, K384D, N385P, N385T, D386H, R388E, E389D, E389R, K392F, K392M, K392R, K392L, K392Y, K392H, K392E, K393F, K393L, K393R, K393Y, K393T, K393W, K393H, K393Q, K393A, K393E, K396F, K396M, K396L, K396R, K396Q, K396A, K396E, K396L, R397S, R397L, R397H, R397Q, R397E, R397K, R397L, E400Q, E400R, E400Y, E400L, S403F, S403R, S403L, S403Y, S403T, S403W, S403H, S403A, S403E, N407F, N407R, N407L, N407Y, N407W, N407H, N407Q, N407E, N407D, N407L, L408R, L408T, L408G, L408W, L408N, or L408D; or combinations thereof.

In other embodiments, the polypeptide comprises one or more of modifications at the amino acid residue corresponding to position C17, S18, E41, T43, P44, H45, Q46, Y53, D84, H85, L89, Q92, H119, D121, C122, S123, M124, T166, D167, V168, P169, I170, A171, G172, G173, G174, E175, E176, E177, G178, V210, M212, F217, E245, H247, S248, T249, D250, K269, V270, G271, P272, Y319, L335, D336, R337, R339, or Y340 of SEQ ID NO: 6; or combinations thereof.

In some embodiments, the polypeptide comprises one or more of modifications: C17A, C17T, S18A, S18N, E41A, E41Q, H45F, H45A, H45K, H45Q, Q46R, Q46S, Q46A, Q46W, Q46T, Y53F, Y53A, Y53S, Y53V, D84G, D84A, D84N, D84P, H85A, L89G, L89S, Q92M, Q92D, Q92P, Q92G, Q92A, H119N, H119S, H119P, H119G, H119A, D121A, D121N, C122G, C122K, C122E, S123A, S123M, S123R, S123T, M124K, M124R, T166L, T166M, T166L, D167N, D167V, D167A, D167Q, D167T, V168M, V168R, I170M, I170K, I170T, A171P, G173S, E175K, E175V, E175R, E176F, E176Y, G178P, V210P, V210T, M212L, M212K, M212R, E245A, E245Q, H247A, T249S, D250A, D250N, G271D, G271A, R339G, R339A, R339E, R339T, Y340F, Y340H, Y340R, Y340P, or Y340A; or combinations thereof.

In other embodiments, the polypeptide comprises one or more of modifications at the amino acid residue corresponding to position V13, Y14, S15, I16, S19, S21, Y22, S27, F30, K34, G35, D36, Y37, S54, K62, N63, M66, K67, K72, E75, E76, D77, K78, D93, S96, P97, T98, N101, D105, F110, S113, Y115, L126, S127, D128, D129, K131, Y135, E136, E140, T142, R143, E144, F146, E147, I148, E151, T152, R154, P160, V179, V182, D184, S187, A188, I189, S190, S191, L192, Y195, N197, D198, V199, P200, N201, I202, D204, G208, I211, L213, I215, S218, Y219, V230, G232, I233, L234, V237, E240, D241, L242, V244, G246, A253, Y255, A256, N259, E262, R266, A273, R280, G281, V282, L284, S286, N287, D290, E291, I292, E295, R296, E297, K302, R303, K321, K324, R325, E327, L328, I330, W331, N333, L334, E343, Y344, E345, M349, V350, N352, K353, F358, E360, V362, D363, I364, K365, F366, Y372, D373, S374, F376, D377, R379, M383, N385, K393, R397, or S403 of SEQ ID NO:6; or combinations thereof.

In some embodiments, the polypeptide comprises one or more of modifications: V13L, Y14F, S15A, I16V, S19N, S21P, S21E, S21K, Y22W, S27A, S27C, F30H, K34D, K34M, K34R, K34Y, G35D, G35H, D36T, D36S, Y37P, S54T, K62R, N63R, M66F, M66Y, K67Q, K72V, K72L, E75P, E76P, D77N, K78R, D93H, S96E, S96A, P97D, P97E, T98E, T98Q, N101E, N101A, N101K, D105E, F110Y, S113A, Y115F, L126C, S127A, D128G, D129E, K131A, Y135P, Y135Q, Y135K, Y135N, Y135T, Y135M, Y135D, Y135L, E136D, E140I, T142E, R143V, R143A, E144R, F146C, E147R, E147K, I148V, E151R, T152A, R154Q, P160E, P160A, V179L, V182P, V182A, V182K, D184E, S187K, S187N, S187T, S187E, S187R, A188F, A188M, A188T, I189L, S190D, S190E, S191I, S191T, S191V, S191Y, S191A, S191L, L192F, L192H, Y195A, N197Q, N197K, N197E, N197D, N197A, D198K, V199L, V199H, V199L, V199C, P200G, N201R, N201Q, N201K, I202M, 1202A, D204N, G208A, 1211V, L213M, I215V, S218G, Y219D, Y219H, V230A, G232D, G232E, G232K, G232P, I233L, L234M, L234A, V237L, E240T, D241P, D241G, L242W, V244L, G246V, G246A, G246C, A253P, A253N, A253T, A253D, A253S, Y255D, Y255E, Y255Q, Y255K, A256L, N259R, N259E, N259W, N259D, N259A, E262Q, R266V, R266A, A273W, R280E, G281A, V282L, L284K, S286V, S286D, S286A, N287D, D290N, D290A, D290Q, D290K, E291D, I292L, E295P, R296D, R296E, R296Y, E297Q, E297K, E297G, E297H, E297R, K302L, R303E, K321T, K321H, K321R, K324D, K324E, R325D, R325N, R325E, R325Q, E327R, L328F, L328W, 1330L, W331H, N333A, N333S, L334Y, E343N, Y344H, E345P, M349K, M349C, M349T, M349E, M349R, M349A, V350A, N352E, K353R, F358L, E360D, V362L, D363P, 1364W, K365T, K365R, F366L, Y372P, D373A, S374T, S374Q, S374A, S374C, F376Q, F376K, F376E, F376H, F376R, D377A, R379C, M383L, N385P, K393H, R397K, S403H, S403Y, or S403A; or combinations thereof.

In other embodiments, the polypeptide comprises one or more of modifications at the amino acid residue corresponding to position K5, K10, K11, C17, K32, K34, K62, K67, K70, K72, K78, K102, K104, K116, K117, C122, K131, K137, K155, K193, K194, K221, K229, K238, K269, K302, K318, K321, K324, K348, K353, K365, K382, K384, K392, K393, or K396 of SEQ ID NO:6; or combinations thereof.

In some embodiments, the polypeptide comprises one or more of modifications: K5H, K5M, K5L, K5A, K5R, K5W, K5F, K10M, K10L, K10R, K10A, K10V, K10N, K11Q, K11Y, K11E, K11L, K11R, K11V, C17T, C17L, C17L, C17A, C17R, C17V, C17G, C17S, K32Q, K32L, K32M, K32L, K32R, K32S, K34T, K34Q, K34Y, K34E, K34H, K34M, K34L, K34R, K34F, K62R, K62Y, K62V, K67R, K67T, K67Q, K67S, K70R, K70Q, K72T, K72L, K72L, K72R, K72V, K78R, K78Q, K78M, K78L, K102R, K102Y, K102L, K104Q, K104L, K104R, K104V, K104N, K104F, K116T, K116Q, K116Y, K116H, K116L, K116L, K116R, K116W, K116S, K117M, K117L, K117R, K117V, K117W, C122R, C122T, C122A, C122V, K131Q, K131Y, K131E, K131L, K131R, K137T, K137Q, K137E, K137L, K137L, K137R, K155Y, K155E, K155H, K155R, K155D, K155N, K193Q, K193E, K193L, K193R, K193A, K194T, K194E, K194R, K194A, K194S, K221Q, K221T, K221I, K221R, K221V, K229T, K229Q, K229R, K229A, K229N, K229S, K238R, K238W, K238S, K269L, K269L, K269R, K269V, K269N, K302Q, K302L, K302M, K302L, K302R, K318R, K318D, K318E, K321R, K321D, K324R, K324D, K324E, K324S, K348V, K348R, K348L, K353W, K353R, K353Q, K353L, K365R, K365H, K365S, K382R, K382N, K382L, K384T, K384Q, K384E, K384L, K384D, K384R, K384S, K392R, K392M, K392L, K393Y, K393H, K393L, K393R, K393F, K396L, K396M, K396L, K396R, or K396F; or combinations thereof.

In other embodiments, the polypeptide comprises one or more of modifications at the amino acid residue corresponding to position L3, S4, K5, D6, Y7, L8, R9, K10, K11, S21, Y22, E25, E29, F30, K32, E33, K34, G35, D36, Y37, Q49, F50, M56, E59, K62, N63, F64, M66, K67, K70, E71, K72, E75, E76, D77, K78, I80, E94, S96, T98, N101, K102, K104, D105, R108, K116, P125, D129, P130, K131, V132, P134, Y135, E136, K137, E140, R141, E144, E147, I148, E150, E151, T152, A153, R154, K155, Y156, N157, F158, Q159, P160, V161, V179, S187, S190, S191, K193, K194, Y195, N197, P200, N201, W203, D204, R205, G216, S218, Y219, D220, K221, V222, E224, D228, K229, R231, G232, E235, K238, R239, E240, D241, R258, E262, N287, D290, E291, I292, E297, S299, N300, K302, R303, E307, D313, Y315, K318, K321, D322, S323, K324, R325, L326, E327, L328, W331, E343, E345, K348, M349, N352, K353, E356, N357, G361, D363, I364, K365, F366, Y368, Q369, Y370, D373, Y375, F376, D377, E380, K382, K384, N385, D386, R388, E389, K392, K393, K396, R397, E400, S403, N407, or L408 of SEQ ID NO:6; or combinations thereof.

In some embodiments, the polypeptide comprises one or more of modifications: L3E, L3T, S4L, S4D, S4R, S4N, S4P, S4E, S4Q, S4M, K5L, K5V, K5A, K5H, K5R, K5F, K5Q, D6L, D6A, D6H, D6R, D6N, D6E, D6Q, Y7W, Y7N, Y7H, L8N, L8G, R9L, R9I, R9H, R9E, R9Q, R9T, K10D, K10A, K10R, K10N, K10P, K10E, K11I, K11V, K11H, K11Y, K11R, K11F, K11W, K11E, K11Q, S21R, S21E, S21Q, S21P, Y22W, E25R, E25L, E29L, E29R, E29Q, E29L, F30A, F30H, F30T, K32L, K32L, K32A, K32R, K32Q, K32M, E33D, E33H, E33R, E33N, E33Q, E33T, K34L, K34D, K34L, K34S, K34V, K34H, K34Y, K34R, K34F, K34Q, K34T, K34M, G35D, G35N, G35H, G35S, D36L, D36S, D36H, D36Y, D36R, D36E, D36N, D36F, D36W, D36Q, D36T, Y37E, Y37R, Y37D, Y37P, Q49W, Q49L, Q49H, Q49F, F50R, F50Q, F50H, F50S, M56W, E59R, E59S, E59T, K62R, K62A, N63R, N63E, N63D, N63Q, F64L, F64E, M66E, M66F, M66Y, K67D, K67S, K67R, K67E, K67Q, K67T, K70L, K70R, K70D, K70Q, E71R, E71Q, E71S, K72L, K72L, K72H, K72E, K72Q, K72T, E75R, E75D, E75S, E76L, E76R, E76P, D77R, D77N, D77S, K78L, K78R, K78D, K78Q, K78M, I80L, I80R, 180Q, E94L, E94R, E94Q, E94Y, S96R, S96E, S96A, T98L, T98V, T98R, T98W, T98E, T98Q, N101D, N101S, N101A, N101H, N101R, N101E, N101Q, N101T, K102Y, K102R, K102W, K102E, K102Q, K104R, K104E, K104Q, D105E, D105Q, D105L, R108I, K116L, K1161, K116H, K116Y, K116R, K116E, K116W, K116D, K116Q, K116T, P125A, D129L, D129R, D129W, D129E, D129Q, P130S, K131D, K131E, K131S, K131Y, V132S, V132Y, V132R, V132E, V132T, P134A, P134D, P134H, Y135L, Y135D, Y135R, Y135W, Y135Q, E136S, E136R, E136P, E136W, E136D, E136Q, E136T, K137L, K137L, K137V, K137R, K137W, K137E, K137Q, E140L, E140R, E140D, E140L, R141L, R141D, R141H, R141Y, R141W, R141Q, E144R, E144Q, E144D, E144L, E147R, E147Q, E147A, I148D, I148E, I148V, E150R, E150A, E151R, T152V, T152A, T152H, T152Y, T152R, T152Q, A153R, A153Q, A153G, A153S, R154S, R154P, R154E, R154Q, R154T, K155G, K155E, K155P, K155W, K155D, K155Q, K155T, Y156V, Y156R, Y156E, Y156F, Y156D, Y156Q, Y156T, Y156M, N157E, N157D, N157R, N157P, F158L, F158V, F158R, F158N, F158E, F158T, Q159L, Q159G, Q159R, Q159W, Q159E, Q159T, P160L, P160I, P160S, P160A, P160R, P160F, P160E, P160T, P160M, V161W, V161E, V161I, V161Y, V179R, V179L, S187R, S187Q, S187A, S190D, S190E, S190Y, S191L, S191A, S191H, S191Y, S191R, S191W, S191E, S191Q, S191T, K193L, K193L, K193Y, K193R, K193F, K193E, K193Q, K194L, K194D, K194A, K194R, K194E, K194Q, Y195A, Y195Q, Y195H, N197L, N197D, N197S, N197R, N197P, N197E, N197Q, P200L, P200D, P200R, P200E, P200M, N201R, N201E, W203L, W203A, W203H, W203Y, W203R, W203F, D204R, D204N, D204S, R205L, R205Q, G216R, G216N, G216T, S218T, Y219R, Y219G, D220E, D220R, D220Q, D220T, K221I, K221V, K221R, K221E, K221Q, K221T, V222L, E224Q, E224Y, E224M, D228E, D228S, K229A, K229R, K229N, K229E, K229Q, R231L, R231A, R231E, R231F, G232R, G232E, G232P, E235R, E235W, K238S, K238R, K238W, K238E, K238Q, R239S, E240V, E240H, E240Y, E240N, E240D, E240T, E240M, D241R, D241N, D241Q, D241P, R258L, R258E, E262L, E262R, E262Q, N287L, N287H, N287R, N287F, N287E, N287Q, D290R, D290E, D290Q, D290F, E291R, 1292E, 1292Q, E297L, E297R, E297H, S299A, S299Q, N300E, N300D, N300R, N300Q, K302L, K302L, K302R, K302P, K302E, K302Q, K302M, R303D, R303E, R303Q, E307R, E307Q, D313P, Y315W, K318D, K318N, K321E, K321D, K321R, K321S, D322T, S323D, S323G, K324D, K324H, K324P, K324W, K324E, R325D, R325S, R325A, R325G, R325W, R325E, R325Q, L326H, E327R, E327L, E327Y, L328D, L328Y, L328R, L328W, L328E, W331L, W331E, W331F, E343L, E343Y, E343N, E343D, E343Q, E343M, E345D, E345P, K348L, K348A, K348Y, K348R, K348W, K348E, K348Q, M349L, M349Y, M349R, M349N, M349W, M349E, M349Q, M349T, N352L, N352R, N352E, N352Q, N352M, K353L, K353A, K353H, K353R, K353E, K353Q, E356R, E356W, N357H, G361D, G361P, D363H, D363P, I364L, I364E, I364P, I364M, K365D, K365S, K365R, K365N, K365E, F366L, F366R, F366H, F366Y, Y368L, Y368R, Q369L, Q369R, Q369E, Q369D, Y370H, D373L, D373R, D373E, D373N, Y375W, Y375A, F376R, F376E, F376Q, D377S, D377A, D377H, D377R, D377N, E380L, E380R, E380D, E380N, K382L, K382D, K382R, K382N, K382E, K382Q, K384L, K384S, K384R, K384E, K384D, K384Q, K384T, N385P, N385T, D386H, R388E, E389R, E389D, K392L, K392H, K392Y, K392R, K392F, K392E, K393A, K393H, K393Y, K393R, K393W, K393E, K393Q, K393T, K396L, K396A, K396R, K396E, K396Q, K396M, R397L, R397L, R397S, R397H, R397E, R397Q, E400L, E400R, E400Q, E400Y, S403L, S403A, S403Y, S403R, S403F, S403W, S403E, S403T, N407L, N407D, N407L, N407H, N407Y, N407R, N407F, N407W, N407E, N407Q, L408G, L408R, L408N, L408W, L408D, or L408T; or combinations thereof.

In one aspect, the disclosure provides polynucleotides encoding any of the polypeptides disclosed herein. The present disclosure also provides constructs, vectors, plasmids that comprises the polynucleotides.

In another aspect, the disclosure provides a microorganism expressing any of the polypeptides disclosed herein. In some embodiments, the disclosure provides a microorganism expressing a polypeptide comprising an amino acid sequence that is at least 60%, at least 65%, at least 70%, at least 75%, at least 80%, at least 85%, at least 90%, at least 95%, at least 98%, or at least 99% identical to an amino acid sequence selected from the group consisting of SEQ ID NOs: 1-444. In some embodiments, the microorganism is modified. In some embodiments, wherein the modified microorganism is genetically modified. In some embodiments, the modified microorganism is non-naturally occurring.

In some embodiments, the modified microorganism is derived from *Escherichia coli*, (hereinafter referred to as *E. coli*), *Corynebacterum glutamicum*, *Aspergillus oryzae*, *Pichia pastoris*, *Bacillus subtilis*, *Caldithrix abyssi*, *Anaerolinea thermophila*, *Thermoanaerobacterium thermosaccharolyticum*, *Thermoanaerobacter thermohydrosulfuricus*, *Caldicellulosiruptor kronotskyensis*, *Dictyoglomus turgidum*, *Caldilinea aerophila*, *Rhodothermus marinus*, *Methanohalobium evestigatum*, *Clostridium cavendishii*, *Kosmologa olearia*, *Butyricicoccus pullicaecorum*, *Clostridium thermobutyricum*, *Litorilinea aerophila*, *Enterobacter mori.*, *Caldisericum exile*, *Dictyoglomus thermophilum*, *Rhodothermus profundi*, *Caldibacillus debilis.*, *Caloramator quimbayensis*, *Methanosalsum zhilinae*, *Pseudothermotoga thermarum*, *Pseudothermotoga hypogea*, *Pseudothermotoga lettingae*, *Geosporobacter subterraneus*, *Melioribacter roseus*, *Lysinibacillus sphaericus*, *Clostridium stercorarium*, *Truepera radiovictrix*, *Thermoflexus hugenholtzii*, *Petrotoga mobilis*, *Spirochaeta thermophila*, *Thermofilum pendens*, *Thermoanaerobacter siderophilus*, *Thermoanaerobacter mathranii*, *Thermoanaerobacter italicus*, *Thermoanaerobacterium xylanolyticum*, *Thermoanaerobacterium saccharolyticum*, *Ignisphaera aggregans*, *Thermotoga maritima*, *Caldanaerobacter subterraneus*, *Mesotoga infera*, *Thermosinus carboxydivorans*, *Halanaerobium congolense*, *Halanaerobium saccharolyticum*, *Gracilibacillus halophilus*, *Caldicoprobacter faecalis*, *Thermoanaerobacter uzonensis*, *Lactobacillus ingluviei*, *Petrotoga mexicana*, *Defluviitoga tunisiensis*, *Petrotoga miotherma*, *Petrotoga olearia*, *Thermophagus xiamenensis*, *Treponema caldarium*, *Thermofilum uzonense*.

In some embodiments, the polypeptides disclosed herein or microorganism expressing the polypeptide is immobilized. In some embodiments, the polypeptide or the microorganism expressing the polypeptide is immobilized to a carrier or support. In some embodiments, the carrier or support is an organic composition. In some embodiments, the carrier or support is an inorganic composition.

In another aspect, the disclosure provides a method of producing tagatose, the method comprising: (a) contacting fructose with any of the polypeptide disclosed herein or a microorganism expressing the polypeptide; and (b) converting fructose to tagatose. In some embodiments, the method comprises: (a) contacting fructose with a polypeptide or a microorganism expressing the polypeptide, wherein the polypeptide comprises an amino acid sequence that is at least 60%, 65%, 70%, 75%, 80%, 85%, 90%, 95%, or 98% identical to an amino acid sequence selected from the group consisting of SEQ ID NOs: 1-444; and (b) converting fructose to tagatose. In some embodiments, step (b) converts fructose to tagatose through C4-epimerization of fructose. In some embodiments, the polypeptide comprises an amino acid sequence selected from the group consisting of SEQ ID NOs: 1-444. In some embodiments, the polypeptide consists essentially of an amino acid sequence selected from the group consisting of SEQ ID NOs: 1-444. In some embodiments, the polypeptide consists of an amino acid sequence selected from the group consisting of SEQ ID NOs: 1-444. In some embodiments, the polypeptide is capable of converting fructose to tagatose through C4-epimerization of fructose. In some embodiments, the polypeptide has D-fructose C4-epimerase activity.

A method for producing a tagatose composition, comprising the steps of: (a) providing a starting composition comprising greater than about 0.3%, about 0.5%, about 1%, about 2%, about 3%, about 4%, about 5%, about 10%, about 20%, about 30%, about 40%, about 50%, about 60%, about 70%, about 80%, about 90% of fructose by weight; (b) contacting the starting composition with any of the polypeptide disclosed herein or a microorganism expressing the polypeptide; and (c) producing a tagatose composition comprising tagatose. In some embodiments, the polypeptide is capable of converting fructose to tagatose through epimerization at the carbon-4 position of fructose.

In one aspect, the disclosure provides a method for producing a tagatose composition, comprising the steps of: (a) providing a starting composition comprising greater than about 0.3%, about 0.5%, about 1%, about 2%, about 3%, about 4%, about 5%, about 10%, about 20%, about 30%, about 40%, about 50%, about 60%, about 70%, about 80%, about 90% of fructose by weight; (b) contacting the starting composition with any of the polypeptide disclosed herein or a microorganism expressing the polypeptide; and (c) producing a tagatose composition comprising tagatose. In some embodiments, the polypeptide is capable of converting fructose to tagatose through epimerization at the carbon-4 position of fructose.

In some embodiments, the tagatose composition comprises tagatose in an amount greater than about 0.1%, about 0.2%, about 0.3%, about 0.5%, about 1%, about 5%, about 10%, about 15%, about 20%, about 25%, about 30%, about 35%, or about 40% by weight. In some embodiments, contacting fructose with the polypeptide or the microorganism expressing the polypeptide is performed at a temperature between about 40° C. and about 100° C. In some embodiments, the contacting of fructose with the polypeptide or the microorganism expressing the polypeptide is performed at between about pH 4.5 and about pH 8. In some embodiments, the contacting of fructose with the polypeptide or the microorganism expressing the polypeptide is performed in the presence of a metal ion.

In some embodiments, the tagatose product is separated from the feed stock (fructose, glucose, and/or sucrose, etc.) through chromatographic means. In some embodiments, the isolated tagatose is further purified with crystallization.

DESCRIPTION OF THE DRAWINGS

The invention can be more completely understood with reference to the following drawings.

FIG. 17 depicts a sequence alignment of the native thermophilic FC4Es (SEQ ID NOs: 1-23 and SEQ ID NOs: 321-373). The residues are numbered based on the pA06238 sequence (SEQ ID NO: 6). Black squares at the top of the alignment show residue positions that were mutated in Example 12 (Active Site Mutant), Example 13 (Stability Expression Mutant), and Example 14 (Lys/Cys Only Mutant and Lys/Cys Mutant).

FIG. 20 depicts the sequence alignment of all computationally designed stability/expression mutants from Example 13 (SEQ ID NOs 46-136). Only residue positions that were mutated in at least one mutant FC4E are shown. Amino acids that were not mutated are shown as a ".".

FIG. 23 depicts the sequence alignment of all lysine/cysteine mutants from Example 14 that allowed surrounding residues to mutate (SEQ ID NOs 232-320). Only residue positions that were mutated in at least one mutant FC4E are shown. Amino acids that were not mutated are shown as a ".".

DETAILED DESCRIPTION

I. Definitions

Figure 1:
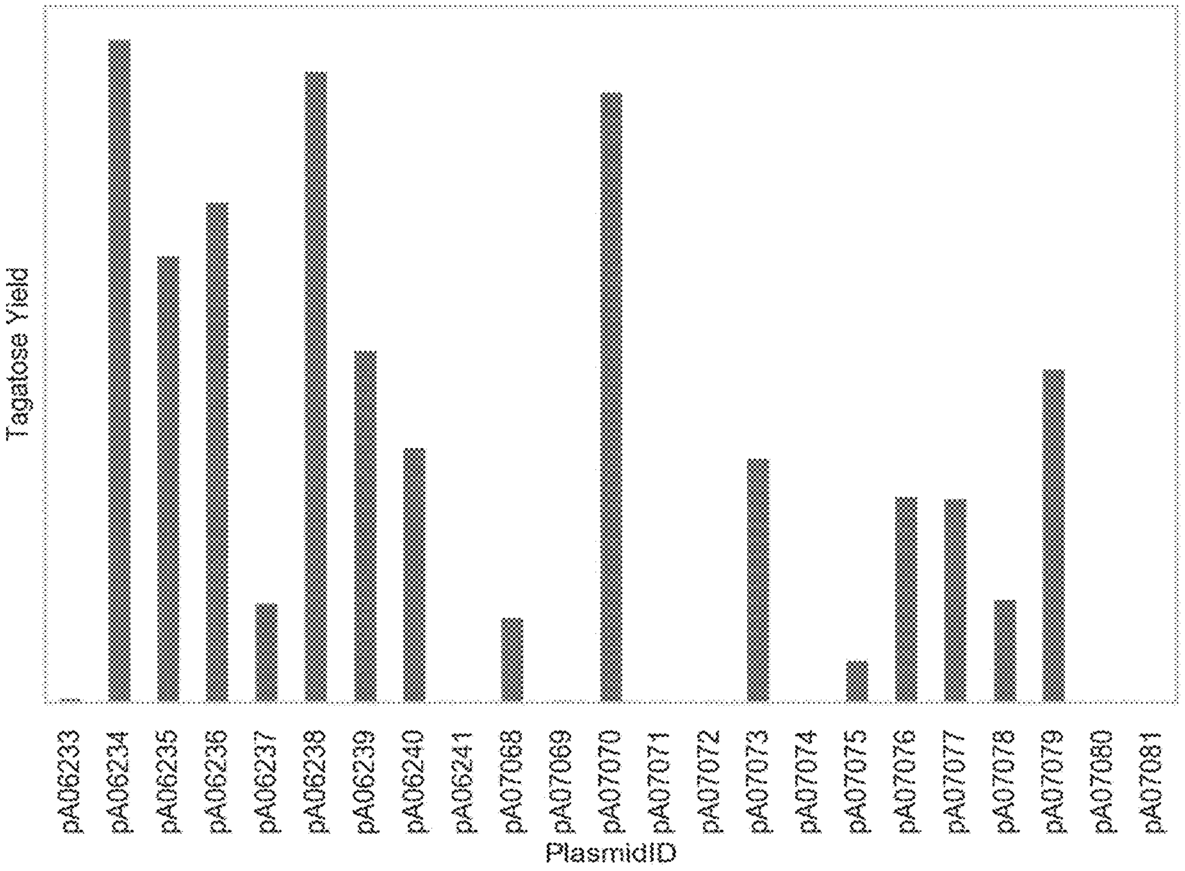
FIG. 1 depicts the measured fructose to tagatose yield for twenty-three thermophilic D-fructose C4-epimerases (Scaffold1). The FC4Es were reacted with 20 mM fructose at 60° C. overnight.

Hereinafter, the present invention will be described in more detail based on specific embodiments and examples. However, the scope the of the disclosure is not limited to these embodiments and examples. Descriptions of details apparent to those skilled in the art having ordinary knowledge in this technical field or relevant field will be omitted herein.

As used herein, the term CN refers to a carbon position defined in accordance with IUPAC nomenclature, wherein N is an integer of 1 or more. Specifically, "epimerization at the carbon 4 position" is expressed as "C4-epimerization."

As used herein, fructose refers to the monosaccharide D-fructose and tagatose refers to the monosaccharide D-tagatose.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., CABIOS. 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "modification" of an amino acid residue refers to substitution of a different amino acid residue for an original amino acid residue, deletion of an original amino acid residue, or addition of an extra amino acid residue. The "modification" preferably refers to substitution of a different amino acid residue for an original amino acid residue. Specifically, in the present invention, "modification of the charge of an amino acid residue" preferably refers to amino acid substitutions.

II. Polypeptides

In one aspect, the disclosure provides a polypeptide comprising an amino acid sequence having at least 60% sequence identity to any one of SEQ ID NOs:1-444, wherein the polypeptide has D-fructose C4-epimerase activity. In further embodiments, the polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or at least 99.9% identical to any one of SEQ ID NOs: 1-444, wherein the polypeptide has D-fructose C4-epimerase activity. In some embodiments, the polypeptide comprises an amino acid sequence selected from the group consisting of SEQ ID NOs: 1-444. In some embodiments, the polypeptide is capable of converting fructose to tagatose through epimerization at carbon-4 position of fructose.

In some embodiments, the polypeptide consists essentially of an amino acid sequence that is at least 65% identical to any one of SEQ ID NOs: 1-444, wherein the polypeptide has D-fructose C4-epimerase activity. In some embodiments, the polypeptide consists essentially of an amino acid sequence that is at least 70% identical to any one of SEQ ID NOs: 1-444, wherein the polypeptide has D-fructose C4-epimerase activity. In some embodiments, the polypeptide consists essentially of an amino acid sequence that is at least 75% identical to any one of SEQ ID NOs: 1-444, wherein the polypeptide has D-fructose C4-epimerase activity. In some embodiments, the polypeptide consists essentially of an amino acid sequence that is at least 80% identical to any one of SEQ ID NOs: 1-444, wherein the polypeptide has D-fructose C4-epimerase activity. In some embodiments, the polypeptide consists essentially of an amino acid sequence that is at least 85% identical to any one of SEQ ID NOs: 1-444, wherein the polypeptide has D-fructose C4-epimerase activity. In some embodiments, the polypeptide consists essentially of an amino acid sequence that is at least 90% identical to any one of SEQ ID NOs: 1-444, wherein the polypeptide has D-fructose C4-epimerase activity. In some embodiments, the polypeptide consists essentially of an amino acid sequence that is at least 95% identical to any one of SEQ ID NOs: 1-444, wherein the polypeptide has D-fructose C4-epimerase activity. In some embodiments, the polypeptide consists essentially of an amino acid sequence that is at least 98% identical to any one of SEQ ID NOs: 1-444, wherein the polypeptide has D-fructose C4-epimerase activity. In some embodiments, the polypeptide consists essentially of an amino acid sequence that is at least 99% identical to any one of SEQ ID NOs: 1-444, wherein the polypeptide has D-fructose C4-epimerase activity.

In other embodiments, the polypeptide comprises one or more modifications at the amino acid residue corresponding to position L3, S4, K5, D6, Y7, L8, R9, K10, K11, V13, Y14, S15, I16, C17, S18, S19, S21, Y22, E25, S27, E29, F30, K32, E33, K34, G35, D36, Y37, E41, T43, P44, H45, Q46, Q49, F50, Y53, S54, M56, E59, K62, N63, F64, M66, K67, K70, E71, K72, E75, E76, D77, K78, I80, D84, H85, L89, Q92, D93, E94, S96, P97, T98, N101, K102, K104, D105, R108, F110, S113, Y115, K116, K117, H119, D121, C122, S123, M124, P125, L126, S127, D128, D129, P130, K131, V132, P134, Y135, E136, K137, E140, R141, T142, R143, E144, F146, E147, I148, E150, E151, T152, A153, R154, K155, Y156, N157, F158, Q159, P160, V161, T166, D167, V168, P169, I170, A171, G172, G173, G174, E175, E176, E177, G178, V179, V182, D184, S187, A188, I189, S190, S191, L192, K193, K194, Y195, N197, D198, V199, P200, N201, I202, W203, D204, R205, G208, V210, I211, M212, L213, I215, G216, F217, S218, Y219, D220, K221, V222, E224, D228, K229, V230, R231, G232, I233, L234, E235, V237, K238, R239, E240, D241, L242, V244, E245, G246, H247, S248, T249, D250, A253, Y255, A256, R258, N259, E262, R266, K269, V270, G271, P272, A273, R280, G281, V282, L284, S286, N287, D290, E291, I292, E295, R296, E297, S299, N300, K302, R303, E307, D313, Y315, K318, Y319, K321, D322, S323, K324, R325, L326, E327, L328, I330, W331, N333, L334, L335, D336, R337, R339, Y340, E343, Y344, E345, K348, M349, V350, N352, K353, E356, N357, F358, E360, G361, V362, D363, I364, K365, F366, Y368, Q369, Y370, Y372, D373, S374, Y375, F376, D377, R379, E380, K382, M383, K384, N385, D386, R388, E389, K392, K393, K396, R397, E400, S403, N407, or L408 of SEQ ID NO:6; or combinations thereof.

In further embodiments, the polypeptide comprises one or more of modifications: (1) the amino acid residue corresponding to position L3 of SEQ ID NO:6 is GLU, or THR; (2) the amino acid residue corresponding to position S4 of SEQ ID NO:6 is ARG, ASN, ASP, GLN, GLU, LEU, MET, or PRO; (3) the amino acid residue corresponding to position K5 of SEQ ID NO:6 is ALA, ARG, GLN, HIS, LEU, MET, PHE, TRP, or VAL; (4) the amino acid residue corresponding to position D6 of SEQ ID NO:6 is ALA, ARG, ASN, GLN, GLU, HIS, or LEU; (5) the amino acid residue corresponding to position Y7 of SEQ ID NO:6 is ASN, HIS, or TRP; (6) the amino acid residue corresponding to position L8 of SEQ ID NO:6 is ASN, or GLY; (7) the amino acid residue corresponding to position R9 of SEQ ID NO:6 is GLN, GLU, HIS, ILE, LEU, or THR; (8) the amino acid residue corresponding to position K10 of SEQ ID NO:6 is ALA, ARG, ASN, ASP, GLU, LEU, MET, PRO, or VAL; (9) the amino acid residue corresponding to position K11 of SEQ ID NO:6 is ARG, GLN, GLU, HIS, ILE, LEU, PHE, TRP, TYR, or VAL; (10) the amino acid residue corresponding to position V13 of SEQ ID NO:6 is ILE; (11) the amino acid residue corresponding to position Y14 of SEQ ID NO:6 is PHE; (12) the amino acid residue corresponding to position S15 of SEQ ID NO:6 is ALA; (13) the amino acid residue corresponding to position 116 of SEQ ID NO:6 is VAL; (14) the amino acid residue corresponding to position C17 of SEQ ID NO:6 is ALA, ARG, GLY, ILE, LEU, SER, THR, or VAL; (15) the amino acid residue corresponding to position S18 of SEQ ID NO:6 is ALA, or ASN; (16) the amino acid residue corresponding to position S19 of SEQ ID NO:6 is ASN; (17) the amino acid residue corresponding to position S21 of SEQ ID NO:6 is ARG, GLN, GLU, LYS, or PRO; (18) the amino acid residue corresponding to position Y22 of SEQ ID NO:6 is TRP; (19) the amino acid residue corresponding to position E25 of SEQ ID NO:6 is ARG, or ILE; (20) the amino acid residue corresponding to position S27 of SEQ ID NO:6 is ALA, or CYS; (21) the amino acid residue corresponding to position E29 of SEQ ID NO:6 is ARG, GLN, ILE, or LEU; (22) the amino acid residue corresponding to position F30 of SEQ ID NO:6 is ALA, HIS, or THR; (23) the amino acid residue corresponding to position K32 of SEQ ID NO:6 is ALA, ARG, GLN, ILE, LEU, MET, or SER; (24) the amino acid residue corresponding to position E33 of SEQ ID NO:6 is ARG, ASN, ASP, GLN, HIS, or THR; (25) the amino acid residue corresponding to position K34 of SEQ ID NO:6 is ARG, ASP, GLN, GLU, HIS, ILE, LEU, MET, PHE, SER, THR, TYR, or VAL; (26) the amino acid residue corresponding to position G35 of SEQ ID NO:6 is ASN, ASP, HIS, or SER; (27) the amino acid residue corresponding to position D36 of SEQ ID NO:6 is ARG, ASN, GLN, GLU, HIS, LEU, PHE, SER, THR, TRP, or TYR; (28) the amino acid residue corresponding to position Y37 of SEQ ID NO:6 is ARG, ASP, GLU, or PRO; (29) the amino acid residue corresponding to position E41 of SEQ ID NO:6 is ALA, or GLN; (30) the amino acid residue corresponding to position H45 of SEQ ID NO:6 is ALA, GLN, LYS, or PHE; (31) the amino acid residue corresponding to position Q46 of SEQ ID NO:6 is ALA, ARG, SER, THR, or TRP; (32) the amino acid residue corresponding to position Q49 of SEQ ID NO:6 is HIS, ILE, PHE, or TRP; (33) the amino acid residue corresponding to position F50 of SEQ ID NO:6 is ARG, GLN, HIS, or SER; (34) the amino acid residue corresponding to position Y53 of SEQ ID NO:6 is ALA, PHE, SER, or VAL; (35) the amino acid residue corresponding to position S54 of SEQ ID NO:6 is THR; (36) the amino acid residue corresponding to position M56 of SEQ ID NO:6 is TRP; (37) the amino acid residue corresponding to position E59 of SEQ ID NO:6 is ARG, SER, or THR; (38) the amino acid residue corresponding to position K62 of SEQ ID NO:6 is ALA, ARG, TYR, or VAL; (39) the amino acid residue corresponding to position N63 of SEQ ID NO:6 is ARG, ASP, GLN, or GLU; (40) the amino acid residue corresponding to position F64 of SEQ ID NO:6 is GLU, or LEU; (41) the amino acid residue corresponding to position M66 of SEQ ID NO:6 is GLU, PHE, or TYR; (42) the amino acid residue corresponding to position K67 of SEQ ID NO:6 is ARG, ASP, GLN, GLU, SER, or THR; (43) the amino acid residue corresponding to position K70 of SEQ ID NO:6 is ARG, ASP, GLN, or LEU; (44) the amino acid residue corresponding to position E71 of SEQ ID NO:6 is ARG, GLN, or SER; (45) the amino acid residue corresponding to position K72 of SEQ ID NO:6 is ARG, GLN, GLU, HIS, ILE, LEU, THR, or VAL; (46) the amino acid residue corresponding to position E75 of SEQ ID NO:6 is ARG, ASP, PRO, or SER; (47) the amino acid residue corresponding to position E76 of SEQ ID NO:6 is ARG, LEU, or PRO; (48) the amino acid residue corresponding to position D77 of SEQ ID NO:6 is ARG, ASN, or SER; (49) the amino acid residue corresponding to position K78 of SEQ ID NO:6 is ARG, ASP, GLN, LEU, or MET; (50) the amino acid residue corresponding to position 180 of SEQ ID NO:6 is ARG, GLN, or LEU; (51) the amino acid residue corresponding to position D84 of SEQ ID NO:6 is ALA, ASN, GLY, or PRO; (52) the amino acid residue corresponding to position H85 of SEQ ID NO:6 is ALA; (53) the amino acid residue corresponding to position L89 of SEQ ID NO:6 is GLY, or SER; (54) the amino acid residue corresponding to position Q92 of SEQ ID NO:6 is ALA, ASP, GLY, MET, or PRO; (55) the amino acid residue corresponding to position D93 of SEQ ID NO:6 is HIS; (56) the amino acid residue corresponding to position E94 of SEQ ID NO:6 is ARG, GLN, LEU, or TYR; (57) the amino acid residue corresponding to position S96 of SEQ ID NO:6 is ALA, ARG, or GLU; (58) the amino acid residue corresponding to position P97 of SEQ ID NO:6 is ASP, or GLU; (59) the amino acid residue corresponding to position T98 of SEQ ID NO:6 is ARG, GLN, GLU, ILE, TRP, or VAL; (60) the amino acid residue corresponding to position N101 of SEQ ID NO:6 is ALA, ARG, ASP, GLN, GLU, HIS, LYS, SER, or THR; (61) the amino acid residue corresponding to position K102 of SEQ ID NO:6 is ARG, GLN, GLU, LEU, TRP, or TYR; (62) the amino acid residue corresponding to position K104 of SEQ ID NO:6 is ARG, ASN, GLN, GLU, ILE, PHE, or VAL; (63) the amino acid residue corresponding to position D105 of SEQ ID NO:6 is GLN, GLU, or ILE; (64) the amino acid residue corresponding to position R108 of SEQ ID NO:6 is ILE; (65) the amino acid residue corresponding to position F110 of SEQ ID NO:6 is TYR; (66) the amino acid residue corresponding to position S113 of SEQ ID NO:6 is ALA; (67) the amino acid residue corresponding to position Y115 of SEQ ID NO:6 is PHE; (68) the amino acid residue corresponding to position K116 of SEQ ID NO:6 is ARG, ASP, GLN, GLU, HIS, ILE, LEU, SER, THR, TRP, or TYR; (69) the amino acid residue corresponding to position K117 of SEQ ID NO:6 is ARG, LEU, MET, TRP, or VAL; (70) the amino acid residue corresponding to position H119 of SEQ ID NO:6 is ALA, ASN, GLY, PRO, or SER; (71) the amino acid residue corresponding to position D121 of SEQ ID NO:6 is ALA, or ASN; (72) the amino acid residue corresponding to position C122 of SEQ ID NO:6 is ALA, ARG, GLU, GLY, LYS, THR, or VAL; (73) the amino acid residue corresponding to position S123 of SEQ ID NO:6 is ALA, ARG, MET, or THR; (74) the amino acid residue corresponding to position M124 of SEQ ID NO:6 is ARG, or LYS; (75) the amino acid residue corresponding to position P125 of SEQ ID NO:6 is ALA; (76) the amino acid residue corresponding to position L126 of SEQ ID NO:6 is CYS; (77) the amino acid residue corresponding to position S127 of SEQ ID NO:6 is ALA; (78) the amino acid residue corresponding to position D128 of SEQ ID NO:6 is GLY; (79) the amino acid residue corresponding to position D129 of SEQ ID NO:6 is ARG, GLN, GLU, LEU, or TRP; (80) the amino acid residue corresponding to position P130 of SEQ ID NO:6 is SER; (81) the amino acid residue corresponding to position K131 of SEQ ID NO:6 is ALA, ARG, ASP, GLN, GLU, LEU, SER, or TYR; (82) the amino acid residue corresponding to position V132 of SEQ ID NO:6 is ARG, GLU, SER, THR, or TYR; (83) the amino acid residue corresponding to position P134 of SEQ ID NO:6 is ALA, ASP, or HIS; (84) the amino acid residue corresponding to position Y135 of SEQ ID NO:6 is ARG, ASN, ASP, GLN, LEU, LYS, MET, PRO, THR, or TRP; (85) the amino acid residue corresponding to position E136 of SEQ ID NO:6 is ARG, ASP, GLN, PRO, SER, THR, or TRP; (86) the amino acid residue corresponding to position K137 of SEQ ID NO:6 is ARG, GLN, GLU, ILE, LEU, THR, TRP, or VAL; (87) the amino acid residue corresponding to position E140 of SEQ ID NO:6 is ARG, ASP, ILE, or LEU; (88) the amino acid residue corresponding to position R141 of SEQ ID NO:6 is ASP, GLN, HIS, LEU, TRP, or TYR; (89) the amino acid residue corresponding to position T142 of SEQ ID NO:6 is GLU; (90) the amino acid residue corresponding to position R143 of SEQ ID NO:6 is ALA, or VAL; (91) the amino acid residue corresponding to position E144 of SEQ ID NO:6 is ARG, ASP, GLN, or ILE; (92) the amino acid residue corresponding to position F146 of SEQ ID NO:6 is CYS; (93) the amino acid residue corresponding to position E147 of SEQ ID NO:6 is ALA, ARG, GLN, or LYS; (94) the amino acid residue corresponding to position 1148 of SEQ ID NO:6 is ASP, GLU, or VAL; (95) the amino acid residue corresponding to position E150 of SEQ ID NO:6 is ALA, or ARG; (96) the amino acid residue corresponding to position E151 of SEQ ID NO:6 is ARG; (97) the amino acid residue corresponding to position T152 of SEQ ID NO:6 is ALA, ARG, GLN, HIS, TYR, or VAL; (98) the amino acid residue corresponding to position A153 of SEQ ID NO:6 is ARG, GLN, GLY, or SER; (99) the amino acid residue corresponding to position R154 of SEQ ID NO:6 is GLN, GLU, PRO, SER, or THR; (100) the amino acid residue corresponding to position K155 of SEQ ID NO:6 is ARG, ASN, ASP, GLN, GLU, GLY, HIS, PRO, THR, TRP, or TYR; (101) the amino acid residue corresponding to position Y156 of SEQ ID NO:6 is ARG, ASP, GLN, GLU, MET, PHE, THR, or VAL; (102) the amino acid residue corresponding to position N157 of SEQ ID NO:6 is ARG, ASP, GLU, or PRO; (103) the amino acid residue corresponding to position F158 of SEQ ID NO:6 is ARG, ASN, GLU, LEU, THR, or VAL; (104) the amino acid residue corresponding to position Q159 of SEQ ID NO:6 is ARG, GLU, GLY, LEU, THR, or TRP; (105) the amino acid residue corresponding to position P160 of SEQ ID NO:6 is ALA, ARG, GLU, ILE, LEU, MET, PHE, SER, or THR; (106) the amino acid residue corresponding to position V161 of SEQ ID NO:6 is GLU, ILE, TRP, or TYR; (107) the amino acid residue corresponding to position T166 of SEQ ID NO:6 is ILE, LEU, or MET; (108) the amino acid residue corresponding to position D167 of SEQ ID NO:6 is ALA, ASN, GLN, THR, or VAL; (109) the amino acid residue corresponding to position V168 of SEQ ID NO:6 is ARG, or MET; (110) the amino acid residue corresponding to position I170 of SEQ ID NO:6 is LYS, MET, or THR; (111) the amino acid residue corresponding to position A171 of SEQ ID NO:6 is PRO; (112) the amino acid residue corresponding to position G173 of SEQ ID NO:6 is SER; (113) the amino acid residue corresponding to position E175 of SEQ ID NO:6 is ARG, LYS, or VAL; (114) the amino acid residue corresponding to position E176 of SEQ ID NO:6 is PHE, or TYR; (115) the amino acid residue corresponding to position G178 of SEQ ID NO:6 is PRO; (116) the amino acid residue corresponding to position V179 of SEQ ID NO:6 is ARG, or ILE; (117) the amino acid residue corresponding to position V182 of SEQ ID NO:6 is ALA, LYS, or PRO; (118) the amino acid residue corresponding to position D184 of SEQ ID NO:6 is GLU; (119) the amino acid residue corresponding to position S187 of SEQ ID NO:6 is ALA, ARG, ASN, GLN, GLU, LYS, or THR; (120) the amino acid residue corresponding to position A188 of SEQ ID NO:6 is MET, PHE, or THR; (121) the amino acid residue corresponding to position 1189 of SEQ ID NO:6 is LEU; (122) the amino acid residue corresponding to position S190 of SEQ ID NO:6 is ASP, GLU, or TYR; (123) the amino acid residue corresponding to position S191 of SEQ ID NO:6 is ALA, ARG, GLN, GLU, HIS, ILE, LEU, THR, TRP, TYR, or VAL; (124) the amino acid residue corresponding to position L192 of SEQ ID NO:6 is HIS, or PHE; (125) the amino acid residue corresponding to position K193 of SEQ ID NO:6 is ALA, ARG, GLN, GLU, ILE, LEU, PHE, or TYR; (126) the amino acid residue corresponding to position K194 of SEQ ID NO:6 is ALA, ARG, ASP, GLN, GLU, LEU, SER, or THR; (127) the amino acid residue corresponding to position Y195 of SEQ ID NO:6 is ALA, GLN, or HIS; (128) the amino acid residue corresponding to position N197 of SEQ ID NO:6 is ALA, ARG, ASP, GLN, GLU, LEU, LYS, PRO, or SER; (129) the amino acid residue corresponding to position D198 of SEQ ID NO:6 is LYS; (130) the amino acid residue corresponding to position V199 of SEQ ID NO:6 is CYS, HIS, ILE, or LEU; (131) the amino acid residue corresponding to position P200 of SEQ ID NO:6 is ARG, ASP, GLU, GLY, LEU, or MET; (132) the amino acid residue corresponding to position N201 of SEQ ID NO:6 is ARG, GLN, GLU, or LYS; (133) the amino acid residue corresponding to position 1202 of SEQ ID NO:6 is ALA, or MET; (134) the amino acid residue corresponding to position W203 of SEQ ID NO:6 is ALA, ARG, HIS, LEU, PHE, or TYR; (135) the amino acid residue corresponding to position D204 of SEQ ID NO:6 is ARG, ASN, or SER; (136) the amino acid residue corresponding to position R205 of SEQ ID NO:6 is GLN, or LEU; (137) the amino acid residue corresponding to position G208 of SEQ ID NO:6 is ALA; (138) the amino acid residue corresponding to position V210 of SEQ ID NO:6 is PRO, or THR; (139) the amino acid residue corresponding to position I211 of SEQ ID NO:6 is VAL; (140) the amino acid residue corresponding to position M212 of SEQ ID NO:6 is ARG, LEU, or LYS; (141) the amino acid residue corresponding to position L213 of SEQ ID NO:6 is MET; (142) the amino acid residue corresponding to position I215 of SEQ ID NO:6 is VAL; (143) the amino acid residue corresponding to position G216 of SEQ ID NO:6 is ARG, ASN, or THR; (144) the amino acid residue corresponding to position S218 of SEQ ID NO:6 is GLY, or THR; (145) the amino acid residue corresponding to position Y219 of SEQ ID NO:6 is ARG, ASP, GLY, or HIS; (146) the amino acid residue corresponding to position D220 of SEQ ID NO:6 is ARG, GLN, GLU, or THR; (147) the amino acid residue corresponding to position K221 of SEQ ID NO:6 is ARG, GLN, GLU, ILE, THR, or VAL; (148) the amino acid residue corresponding to position V222 of SEQ ID NO:6 is ILE; (149) the amino acid residue corresponding to position E224 of SEQ ID NO:6 is GLN, MET, or TYR; (150) the amino acid residue corresponding to position D228 of SEQ ID NO:6 is GLU, or SER; (151) the amino acid residue corresponding to position K229 of SEQ ID NO:6 is ALA, ARG, ASN, GLN, GLU, SER, or THR; (152) the amino acid residue corresponding to position V230 of SEQ ID NO:6 is ALA; (153) the amino acid residue corresponding to position R231 of SEQ ID NO:6 is ALA, GLU, LEU, or PHE; (154) the amino acid residue corresponding to position G232 of SEQ ID NO:6 is ARG, ASP, GLU, LYS, or PRO; (155) the amino acid residue corresponding to position I233 of SEQ ID NO:6 is LEU; (156) the amino acid residue corresponding to position L234 of SEQ ID NO:6 is ALA, or MET; (157) the amino acid residue corresponding to position E235 of SEQ ID NO:6 is ARG, or TRP; (158) the amino acid residue corresponding to position V237 of SEQ ID NO:6 is LEU; (159) the amino acid residue corresponding to position K238 of SEQ ID NO:6 is ARG, GLN, GLU, SER, or TRP; (160) the amino acid residue corresponding to position R239 of SEQ ID NO:6 is SER; (161) the amino acid residue corresponding to position E240 of SEQ ID NO:6 is ASN, ASP, HIS, MET, THR, TYR, or VAL; (162) the amino acid residue corresponding to position D241 of SEQ ID NO:6 is ARG, ASN, GLN, GLY, or PRO; (163) the amino acid residue corresponding to position L242 of SEQ ID NO:6 is TRP; (164) the amino acid residue corresponding to position V244 of SEQ ID NO:6 is LEU; (165) the amino acid residue corresponding to position E245 of SEQ ID NO:6 is ALA, or GLN; (166) the amino acid residue corresponding to position G246 of SEQ ID NO:6 is ALA, CYS, or VAL; (167) the amino acid residue corresponding to position H247 of SEQ ID NO:6 is ALA; (168) the amino acid residue corresponding to position T249 of SEQ ID NO:6 is SER; (169) the amino acid residue corresponding to position D250 of SEQ ID NO:6 is ALA, or ASN; (170) the amino acid residue corresponding to position A253 of SEQ ID NO:6 is ASN, ASP, PRO, SER, or THR; (171) the amino acid residue corresponding to position Y255 of SEQ ID NO:6 is ASP, GLN, GLU, or LYS; (172) the amino acid residue corresponding to position A256 of SEQ ID NO:6 is LEU; (173) the amino acid residue corresponding to position R258 of SEQ ID NO:6 is GLU, or LEU; (174) the amino acid residue corresponding to position N259 of SEQ ID NO:6 is ALA, ARG, ASP, GLU, or TRP; (175) the amino acid residue corresponding to position E262 of SEQ ID NO:6 is ARG, GLN, or LEU; (176) the amino acid residue corresponding to position R266 of SEQ ID NO:6 is ALA, or VAL; (177) the amino acid residue corresponding to position K269 of SEQ ID NO:6 is ARG, ASN, ILE, LEU, or VAL; (178) the amino acid residue corresponding to position G271 of SEQ ID NO:6 is ALA, or ASP; (179) the amino acid residue corresponding to position A273 of SEQ ID NO:6 is TRP; (180) the amino acid residue corresponding to position R280 of SEQ ID NO:6 is GLU; (181) the amino acid residue corresponding to position G281 of SEQ ID NO:6 is ALA; (182) the amino acid residue corresponding to position V282 of SEQ ID NO:6 is ILE; (183) the amino acid residue corresponding to position L284 of SEQ ID NO:6 is LYS; (184) the amino acid residue corresponding to position S286 of SEQ ID NO:6 is ALA, ASP, or VAL; (185) the amino acid residue corresponding to position N287 of SEQ ID NO:6 is ARG, ASP, GLN, GLU, HIS, LEU, or PHE; (186) the amino acid residue corresponding to position D290 of SEQ ID NO:6 is ALA, ARG, ASN, GLN, GLU, LYS, or PHE; (187) the amino acid residue corresponding to position E291 of SEQ ID NO:6 is ARG, or ASP; (188) the amino acid residue corresponding to position I292 of SEQ ID NO:6 is GLN, GLU, or LEU; (189) the amino acid residue corresponding to position E295 of SEQ ID NO:6 is PRO; (190) the amino acid residue corresponding to position R296 of SEQ ID NO:6 is ASP, GLU, or TYR; (191) the amino acid residue corresponding to position E297 of SEQ ID NO:6 is ARG, GLN, GLY, HIS, LEU, or LYS; (192) the amino acid residue corresponding to position S299 of SEQ ID NO:6 is ALA, or GLN; (193) the amino acid residue corresponding to position N300 of SEQ ID NO:6 is ARG, ASP, GLN, or GLU; (194) the amino acid residue corresponding to position K302 of SEQ ID NO:6 is ARG, GLN, GLU, ILE, LEU, MET, or PRO; (195) the amino acid residue corresponding to position R303 of SEQ ID NO:6 is ASP, GLN, or GLU; (196) the amino acid residue corresponding to position E307 of SEQ ID NO:6 is ARG, or GLN; (197) the amino acid residue corresponding to position D313 of SEQ ID NO:6 is PRO; (198) the amino acid residue corresponding to position Y315 of SEQ ID NO:6 is TRP; (199) the amino acid residue corresponding to position K318 of SEQ ID NO:6 is ARG, ASN, ASP, or GLU; (200) the amino acid residue corresponding to position K321 of SEQ ID NO:6 is ARG, ASP, GLU, HIS, SER, or THR; (201) the amino acid residue corresponding to position D322 of SEQ ID NO:6 is THR; (202) the amino acid residue corresponding to position S323 of SEQ ID NO:6 is ASP, or GLY; (203) the amino acid residue corresponding to position K324 of SEQ ID NO:6 is ARG, ASP, GLU, HIS, PRO, SER, or TRP; (204) the amino acid residue corresponding to position R325 of SEQ ID NO:6 is ALA, ASN, ASP, GLN, GLU, GLY, SER, or TRP; (205) the amino acid residue corresponding to position L326 of SEQ ID NO:6 is HIS; (206) the amino acid residue corresponding to position E327 of SEQ ID NO:6 is ARG, ILE, or TYR; (207) the amino acid residue corresponding to position L328 of SEQ ID NO:6 is ARG, ASP, GLU, PHE, TRP, or TYR; (208) the amino acid residue corresponding to position I330 of SEQ ID NO:6 is LEU; (209) the amino acid residue corresponding to position W331 of SEQ ID NO:6 is GLU, HIS, LEU, or PHE; (210) the amino acid residue corresponding to position N333 of SEQ ID NO:6 is ALA, or SER; (211) the amino acid residue corresponding to position L334 of SEQ ID NO:6 is TYR; (212) the amino acid residue corresponding to position R339 of SEQ ID NO:6 is ALA, GLU, GLY, or THR; (213) the amino acid residue corresponding to position Y340 of SEQ ID NO:6 is ALA, ARG, HIS, PHE, or PRO; (214) the amino acid residue corresponding to position E343 of SEQ ID NO:6 is ASN, ASP, GLN, LEU, MET, or TYR; (215) the amino acid residue corresponding to position Y344 of SEQ ID NO:6 is HIS;

(216) the amino acid residue corresponding to position E345 of SEQ ID NO:6 is ASP, or PRO; (217) the amino acid residue corresponding to position K348 of SEQ ID NO:6 is ALA, ARG, GLN, GLU, LEU, TRP, TYR, or VAL; (218) the amino acid residue corresponding to position M349 of SEQ ID NO:6 is ALA, ARG, ASN, CYS, GLN, GLU, ILE, LYS, THR, TRP, or TYR; (219) the amino acid residue corresponding to position V350 of SEQ ID NO:6 is ALA; (220) the amino acid residue corresponding to position N352 of SEQ ID NO:6 is ARG, GLN, GLU, LEU, or MET; (221) the amino acid residue corresponding to position K353 of SEQ ID NO:6 is ALA, ARG, GLN, GLU, HIS, LEU, or TRP; (222) the amino acid residue corresponding to position E356 of SEQ ID NO:6 is ARG, or TRP; (223) the amino acid residue corresponding to position N357 of SEQ ID NO:6 is HIS; (224) the amino acid residue corresponding to position F358 of SEQ ID NO:6 is LEU; (225) the amino acid residue corresponding to position E360 of SEQ ID NO:6 is ASP; (226) the amino acid residue corresponding to position G361 of SEQ ID NO:6 is ASP, or PRO; (227) the amino acid residue corresponding to position V362 of SEQ ID NO:6 is ILE; (228) the amino acid residue corresponding to position D363 of SEQ ID NO:6 is HIS, or PRO; (229) the amino acid residue corresponding to position 1364 of SEQ ID NO:6 is GLU, LEU, MET, PRO, or TRP; (230) the amino acid residue corresponding to position K365 of SEQ ID NO:6 is ARG, ASN, ASP, GLU, HIS, SER, or THR; (231) the amino acid residue corresponding to position F366 of SEQ ID NO:6 is ARG, HIS, LEU, or TYR; (232) the amino acid residue corresponding to position Y368 of SEQ ID NO:6 is ARG, or LEU; (233) the amino acid residue corresponding to position Q369 of SEQ ID NO:6 is ARG, ASP, GLU, or LEU; (234) the amino acid residue corresponding to position Y370 of SEQ ID NO:6 is HIS; (235) the amino acid residue corresponding to position Y372 of SEQ ID NO:6 is PRO; (236) the amino acid residue corresponding to position D373 of SEQ ID NO:6 is ALA, ARG, ASN, GLU, or LEU; (237) the amino acid residue corresponding to position S374 of SEQ ID NO:6 is ALA, CYS, GLN, or THR; (238) the amino acid residue corresponding to position Y375 of SEQ ID NO:6 is ALA, or TRP; (239) the amino acid residue corresponding to position F376 of SEQ ID NO:6 is ARG, GLN, GLU, HIS, or LYS; (240) the amino acid residue corresponding to position D377 of SEQ ID NO:6 is ALA, ARG, ASN, HIS, or SER; (241) the amino acid residue corresponding to position R379 of SEQ ID NO:6 is CYS; (242) the amino acid residue corresponding to position E380 of SEQ ID NO:6 is ARG, ASN, ASP, or LEU; (243) the amino acid residue corresponding to position K382 of SEQ ID NO:6 is ARG, ASN, ASP, GLN, GLU, or LEU; (244) the amino acid residue corresponding to position M383 of SEQ ID NO:6 is LEU; (245) the amino acid residue corresponding to position K384 of SEQ ID NO:6 is ARG, ASP, GLN, GLU, LEU, SER, or THR; (246) the amino acid residue corresponding to position N385 of SEQ ID NO:6 is PRO, or THR; (247) the amino acid residue corresponding to position D386 of SEQ ID NO:6 is HIS; (248) the amino acid residue corresponding to position R388 of SEQ ID NO:6 is GLU; (249) the amino acid residue corresponding to position E389 of SEQ ID NO:6 is ARG, or ASP; (250) the amino acid residue corresponding to position K392 of SEQ ID NO:6 is ARG, GLU, HIS, LEU, MET, PHE, or TYR; (251) the amino acid residue corresponding to position K393 of SEQ ID NO:6 is ALA, ARG, GLN, GLU, HIS, LEU, PHE, THR, TRP, or TYR; (252) the amino acid residue corresponding to position K396 of SEQ ID NO:6 is ALA, ARG, GLN, GLU, ILE, LEU, MET, or PHE; (253) the amino acid residue corresponding to position R397 of SEQ ID NO:6 is GLN, GLU, HIS, ILE, LEU, LYS, or SER; (254) the amino acid residue corresponding to position E400 of SEQ ID NO:6 is ARG, GLN, LEU, or TYR; (255) the amino acid residue corresponding to position S403 of SEQ ID NO:6 is ALA, ARG, GLU, HIS, LEU, PHE, THR, TRP, or TYR; (256) the amino acid residue corresponding to position N407 of SEQ ID NO:6 is ARG, ASP, GLN, GLU, HIS, ILE, LEU, PHE, TRP, or TYR; or (257) the amino acid residue corresponding to position L408 of SEQ ID NO:6 is ARG, ASN, ASP, GLY, THR, or TRP; or combinations thereof.

In some embodiments, the polypeptide comprises one or more of modifications: L3E, L3T, S4M, S4D, S4R, S4L, S4Q, S4N, S4E, S4P, K5F, K5M, K5L, K5R, K5W, K5H, K5Q, K5V, K5A, D6R, D6L, D6H, D6Q, D6N, D6A, D6E, Y7W, Y7H, Y7N, L8N, L8G, R9L, R9T, R9H, R9Q, R9E, R9I, K10M, K10D, K10R, K10L, K10V, K10N, K10A, K10E, K10P, K11F, K11L, K11R, K11Y, K11W, K11V, K11Q, K11H, K11E, K11I, V13L, Y14F, S15A, I16V, C17S, C17L, C17R, C17T, C17G, C17V, C17A, C17L, S18N, S18A, S19N, S21K, S21R, S21Q, S21E, S21P, Y22W, E25R, E25L, S27C, S27A, E29Q, E29R, E29L, E29L, F30H, F30T, F30A, K32S, K32M, K32L, K32R, K32Q, K32A, K32L, E33R, E33T, E33H, E33Q, E33N, E33D, K34F, K34S, K34M, K34R, K34L, K34Y, K34T, K34H, K34Q, K34V, K34E, K34D, K34L, G35D, G35N, G35H, G35S, D36F, D36S, D36R, D36L, D36Y, D36T, D36W, D36H, D36Q, D36N, D36E, Y37D, Y37P, Y37R, Y37E, E41Q, E41A, H45F, H45K, H45Q, H45A, Q46S, Q46R, Q46T, Q46W, Q46A, Q49F, Q49H, Q49I, Q49W, F50Q, F50H, F50R, F50S, Y53F, Y53V, Y53S, Y53A, S54T, M56W, E59R, E59S, E59T, K62V, K62R, K62Y, K62A, N63E, N63D, N63R, N63Q, F64E, F64L, M66F, M66E, M66Y, K67S, K67R, K67T, K67Q, K67E, K67D, K70D, K70Q, K70R, K70L, E71Q, E71R, E71S, K72L, K72R, K72T, K72V, K72Q, K72H, K72E, K72L, E75D, E75P, E75R, E75S, E76P, E76L, E76R, D77N, D77R, D77S, K78M, K78R, K78L, K78Q, K78D, I80Q, I80R, I80L, D84P, D84N, D84G, D84A, H85A, L89S, L89G, Q92M, Q92D, Q92G, Q92A, Q92P, D93H, E94Q, E94R, E94Y, E94L, S96E, S96R, S96A, P97E, P97D, T98R, T98W, T98V, T98Q, T98E, T98L, N101S, N101D, N101R, N101T, N101H, N101Q, N101A, N101E, N101K, K102L, K102R, K102Y, K102W, K102Q, K102E, K104F, K104R, K104V, K104Q, K104N, K104E, K104L, D105E, D105Q, D105I, R108I, F110Y, S113A, Y115F, K116S, K116R, K116L, K116Y, K116T, K116W, K116H, K116Q, K116E, K116D, K116L, K117M, K117L, K117R, K117W, K117V, H119S, H119G, H119N, H119A, H119P, D121N, D121A, C122R, C122G, C122T, C122V, C122A, C122E, C122K, S123M, S123R, S123T, S123A, M124K, M124R, P125A, L126C, S127A, D128G, D129R, D129L, D129W, D129Q, D129E, P130S, K131S, K131R, K131L, K131Y, K131Q, K131A, K131E, K131D, V132S, V132R, V132Y, V132T, V132E, P134D, P134H, P134A, Y135K, Y135M, Y135D, Y135L, Y135R, Y135T, Y135W, Y135Q, Y135N, Y135P, E136S, E136R, E136P, E136W, E136T, E136Q, E136D, K137L, K137R, K137T, K137W, K137V, K137Q, K137E, K137L, E40D, E40R, E140L, E40L, R141L, R141Y, R141W, R141H, R141Q, R141D, T142E, R143V, R143A, E144Q, E144D, E144R, E144L, F146C, E147Q, E147K, E147R, E147A, I148E, I148V, I148D, E150R, E150A, E151R, T152R, T152Y, T152V, T152H, T152Q, T152A, A153Q, A153R, A153G, A153S, R154S, R154T, R154Q, R154E, R154P, K155R, K155Y, K155P, K155T, K155H, K155N, K155Q, K155G, K155W, K155E, K155D, Y156F, Y156M, Y156R, Y156T, Y156V, Y156Q, Y156E, Y156D, N157E, N157D, N157R, N157P, F158R, F158L, F158T, F158V, F158N, F158E, Q159R, Q159L, Q159G, Q159T, Q159W, Q159E, P160F, P160S, P160M, P160L, P160R, P160T, P160A, P160E, P160I, V161E, V161I, V161Y, V161W, T166M, T166L, T166L, D167T, D167V, D167Q, D167N, D167A, V168M, V168R, I170M, I170K, I170T, A171P, G173S, E175K, E175V, E175R, E176F, E176Y, G178P, V179R, V179L, V182P, V182K, V182A, D184E, S187R, S187T, S187N, S187Q, S187A, S187E, S187K, A188M, A188F, A188T, I189L, S190E, S190D, S190Y, S191L, S191R, S191Y, S191T, S191W, S191V, S191H, S191Q, S191A, S191E, S191L, L192F, L192H, K193F, K193R, K193L, K193Y, K193Q, K193A, K193E, K193L, K194S, K194R, K194L, K194T, K194Q, K194A, K194E, K194D, Y195H, Y195Q, Y195A, N197S, N197D, N197R, N197L, N197P, N197Q, N197A, N197E, N197K, D198K, V199H, V199L, V199L, V199C, P200M, P200L, P200R, P200G, P200E, P200D, N201Q, N201K, N201R, N201E, I202M, I202A, W203F, W203R, W203L, W203Y, W203H, W203A, D204N, D204R, D204S, R205Q, R205L, G208A, V210P, V210T, I211V, M212K, M212L, M212R, L213M, I215V, G216N, G216R, G216T, S218T, S218G, Y219D, Y219H, Y219R, Y219G, D220Q, D220R, D220E, D220T, K221R, K221T, K221V, K221Q, K221E, K221I, V222L, E224M, E224Q, E224Y, D228E, D228S, K229S, K229R, K229T, K229N, K229Q, K229A, K229E, V230A, R231E, R231L, R231F, R231A, G232D, G232R, G232P, G232E, G232K, I233L, L234M, L234A, E235W, E235R, V237L, K238S, K238R, K238W, K238Q, K238E, R239S, E240M, E240Y, E240T, E240V, E240N, E240H, E240D, D241R, D241G, D241Q, D241N, D241P, L242W, V244L, E245Q, E245A, G246C, G246V, G246A, H247A, T249S, D250N, D250A, A253S, A253P, A253T, A253N, A253D, Y255E, Y255D, Y255Q, Y255K, A256L, R258E, R258L, N259R, N259W, N259A, N259E, N259D, E262Q, E262R, E262L, R266V, R266A, K269L, K269R, K269V, K269N, K269L, G271D, G271A, A273W, R280E, G281A, V282L, L284K, S286D, S286V, S286A, N287F, N287R, N287L, N287H, N287Q, N287E, N287D, D290F, D290R, D290Q, D290N, D290A, D290E, D290K, E291D, E291R, I292Q, I292L, I292E, E295P, R296E, R296D, R296Y, E297R, E297L, E297G, E297H, E297Q, E297K, S299Q, S299A, N300E, N300D, N300Q, N300R, K302M, K302L, K302R, K302Q, K302E, K302P, K302L, R303E, R303D, R303Q, E307Q, E307R, D313P, Y315W, K318E, K318D, K318R, K318N, K321S, K321R, K321T, K321H, K321E, K321D, D322T, S323D, S323G, K324S, K324R, K324P, K324W, K324H, K324E, K324D, R325S, R325G, R325W, R325N, R325Q, R325A, R325E, R325D, L326H, E327R, E327L, E327Y, L328F, L328R, L328Y, L328W, L328E, L328D, I330L, W331E, W3311H, W33IL, W331F, N333A, N333S, L334Y, R339E, R339T, R339A, R339G, Y340F, Y340R, Y340H, Y340A, Y340P, E343M, E343L, E343Y, E343Q, E343N, E343D, Y344H, E345D, E345P, K348R, K348L, K348Y, K348W, K348V, K348Q, K348A, K348E, M349R, M349Y, M349C, M349T, M349W, M349N, M349Q, M349A, M349E, M349K, M349L, V350A, N352M, N352R, N352L, N352Q, N352E, K353R, K353L, K353W, K353H, K353Q, K353A, K353E, E356W, E356R, N357H, F358L, E360D, G361D, G361P, V362L, D363P, D363H, I364M, I364L, I364W, I364E, I364P, K365S, K365R, K365T, K365H, K365N, K365E, K365D, F366H, F366L, F366R, F366Y, Y368R, Y368L, Q369E, Q369D, Q369R, Q369L, Y370H, Y372P, D373R, D373L, D373N, D373A, D373E, S374C, S374Q, S374T, S374A, Y375W, Y375A, F376R, F376H, F376Q, F376E, F376K, D377S, D377R, D377H, D377N, D377A, R379C, E380D, E380N, E380R, E380L, K382R, K382L, K382N, K382Q, K382E, K382D, M383L, K384S, K384L, K384R, K384T, K384Q, K384E, K384D, N385P, N385T, D386H, R388E, E389D, E389R, K392F, K392M, K392R, K392L, K392Y, K392H, K392E, K393F, K393L, K393R, K393Y, K393T, K393W, K393H, K393Q, K393A, K393E, K396F, K396M, K396L, K396R, K396Q, K396A, K396E, K396L, R397S, R397L, R397H, R397Q, R397E, R397K, R397L, E400Q, E400R, E400Y, E400L, S403F, S403R, S403L, S403Y, S403T, S403W, S403H, S403A, S403E, N407F, N407R, N407L, N407Y, N407W, N407H, N407Q, N407E, N407D, N407L, L408R, L408T, L408G, L408W, L408N, or L408D; or combinations thereof.

In other embodiments, the polypeptide comprises one or more of modifications at the amino acid residue corresponding to position C17, S18, E41, T43, P44, H45, Q46, Y53, D84, H85, L89, Q92, H119, D121, C122, S123, M124, T166, D167, V168, P169, I170, A171, G172, G173, G174, E175, E176, E177, G178, V210, M212, F217, E245, H247, S248, T249, D250, K269, V270, G271, P272, Y319, L335, D336, R337, R339, or Y340 of SEQ ID NO: 6; or combinations thereof.

In further embodiments, the polypeptide comprises one or more of modifications: (1) the amino acid residue corresponding to position C17 of SEQ ID NO:6 is ALA, or THR; (2) the amino acid residue corresponding to position S18 of SEQ ID NO:6 is ALA, or ASN; (3) the amino acid residue corresponding to position E41 of SEQ ID NO:6 is ALA, or GLN; (4) the amino acid residue corresponding to position H45 of SEQ ID NO:6 is ALA, GLN, LYS, or PHE; (5) the amino acid residue corresponding to position Q46 of SEQ ID NO:6 is ALA, ARG, SER, THR, or TRP; (6) the amino acid residue corresponding to position Y53 of SEQ ID NO:6 is ALA, PHE, SER, or VAL; (7) the amino acid residue corresponding to position D84 of SEQ ID NO:6 is ALA, ASN, GLY, or PRO; (8) the amino acid residue corresponding to position H85 of SEQ ID NO:6 is ALA; (9) the amino acid residue corresponding to position L89 of SEQ ID NO:6 is GLY, or SER; (10) the amino acid residue corresponding to position Q92 of SEQ ID NO:6 is ALA, ASP, GLY, MET, or PRO; (11) the amino acid residue corresponding to position H119 of SEQ ID NO:6 is ALA, ASN, GLY, PRO, or SER; (12) the amino acid residue corresponding to position D121 of SEQ ID NO:6 is ALA, or ASN; (13) the amino acid residue corresponding to position C122 of SEQ ID NO:6 is GLU, GLY, or LYS; (14) the amino acid residue corresponding to position S123 of SEQ ID NO:6 is ALA, ARG, MET, or THR; (15) the amino acid residue corresponding to position M124 of SEQ ID NO:6 is ARG, or LYS; (16) the amino acid residue corresponding to position T166 of SEQ ID NO:6 is ILE, LEU, or MET; (17) the amino acid residue corresponding to position D167 of SEQ ID NO:6 is ALA, ASN, GLN, THR, or VAL; (18) the amino acid residue corresponding to position V168 of SEQ ID NO:6 is ARG, or MET; (19) the amino acid residue corresponding to position 1170 of SEQ ID NO:6 is LYS, MET, or THR; (20) the amino acid residue corresponding to position A171 of SEQ ID NO:6 is PRO; (21) the amino acid residue corresponding to position G173 of SEQ ID NO:6 is SER; (22) the amino acid residue corresponding to position E175 of SEQ ID NO:6 is ARG, LYS, or VAL; (23) the amino acid residue corresponding to position E176 of SEQ ID NO:6 is PHE, or TYR; (24) the amino acid residue corresponding to position G178 of SEQ ID NO:6 is PRO; (25) the amino acid residue corresponding to position V210 of SEQ ID NO:6 is PRO, or THR; (26) the amino acid residue corresponding to position M212 of SEQ ID NO:6 is ARG, LEU, or LYS; (27) the amino acid residue corresponding to position E245 of SEQ ID NO:6 is ALA, or GLN; (28) the amino acid residue corresponding to position H247 of SEQ ID NO:6 is ALA; (29) the amino acid residue corresponding to position T249 of SEQ ID NO:6 is SER; (30) the amino acid residue corresponding to position D250 of SEQ ID NO:6 is ALA, or ASN; (31) the amino acid residue corresponding to position G271 of SEQ ID NO:6 is ALA, or ASP; (32) the amino acid residue corresponding to position R339 of SEQ ID NO:6 is ALA, GLU, GLY, or THR; or (33) the amino acid residue corresponding to position Y340 of SEQ ID NO:6 is ALA, ARG, HIS, PHE, or PRO; or combinations thereof.

In some embodiments, the polypeptide comprises one or more of modifications: C17A, C17T, S18A, S18N, E41A, E41Q, H45F, H45A, H45K, H45Q, Q46R, Q46S, Q46A, Q46W, Q46T, Y53F, Y53A, Y53S, Y53V, D84G, D84A, D84N, D84P, H85A, L89G, L89S, Q92M, Q92D, Q92P, Q92G, Q92A, H119N, H119S, H119P, H119G, H119A, D121A, D121N, C122G, C122K, C122E, S123A, S123M, S123R, S123T, M124K, M124R, T166L, T166M, T166L, D167N, D167V, D167A, D167Q, D167T, V168M, V168R, I170M, I170K, I170T, A171P, G173S, E175K, E175V, E175R, E176F, E176Y, G178P, V210P, V210T, M212L, M212K, M212R, E245A, E245Q, H247A, T249S, D250A, D250N, G271D, G271A, R339G, R339A, R339E, R339T, Y340F, Y340H, Y340R, Y340P, or Y340A; or combinations thereof.

In other embodiments, the polypeptide comprises one or more of modifications at the amino acid residue corresponding to position V13, Y14, S15, I16, S19, S21, Y22, S27, F30, K34, G35, D36, Y37, S54, K62, N63, M66, K67, K72, E75, E76, D77, K78, D93, S96, P97, T98, N101, D105, F110, S113, Y115, L126, S127, D128, D129, K131, Y135, E136, E140, T142, R143, E144, F146, E147, I148, E151, T152, R154, P160, V179, V182, D184, S187, A188, I189, S190, S191, L192, Y195, N197, D198, V199, P200, N201, I202, D204, G208, I211, L213, I215, S218, Y219, V230, G232, I233, L234, V237, E240, D241, L242, V244, G246, A253, Y255, A256, N259, E262, R266, A273, R280, G281, V282, L284, S286, N287, D290, E291, I292, E295, R296, E297, K302, R303, K321, K324, R325, E327, L328, I330, W331, N333, L334, E343, Y344, E345, M349, V350, N352, K353, F358, E360, V362, D363, I364, K365, F366, Y372, D373, S374, F376, D377, R379, M383, N385, K393, R397, or S403 of SEQ ID NO:6; or combinations thereof.

In further embodiments, the polypeptide comprises one or more of modifications: (1) the amino acid residue corresponding to position V13 of SEQ ID NO:6 is ILE; (2) the amino acid residue corresponding to position Y14 of SEQ ID NO:6 is PHE; (3) the amino acid residue corresponding to position S15 of SEQ ID NO:6 is ALA; (4) the amino acid residue corresponding to position 116 of SEQ ID NO:6 is VAL; (5) the amino acid residue corresponding to position S19 of SEQ ID NO:6 is ASN; (6) the amino acid residue corresponding to position S21 of SEQ ID NO:6 is GLU, LYS, or PRO; (7) the amino acid residue corresponding to position Y22 of SEQ ID NO:6 is TRP; (8) the amino acid residue corresponding to position S27 of SEQ ID NO:6 is ALA, or CYS; (9) the amino acid residue corresponding to position F30 of SEQ ID NO:6 is HIS; (10) the amino acid residue corresponding to position K34 of SEQ ID NO:6 is ARG, ASP, MET, or TYR; (11) the amino acid residue corresponding to position G35 of SEQ ID NO:6 is ASP, or HIS; (12) the amino acid residue corresponding to position D36 of SEQ ID NO:6 is SER, or THR; (13) the amino acid residue corresponding to position Y37 of SEQ ID NO:6 is PRO; (14) the amino acid residue corresponding to position S54 of SEQ ID NO:6 is THR; (15) the amino acid residue corresponding to position K62 of SEQ ID NO:6 is ARG; (16) the amino acid residue corresponding to position N63 of SEQ ID NO:6 is ARG; (17) the amino acid residue corresponding to position M66 of SEQ ID NO:6 is PHE, or TYR; (18) the amino acid residue corresponding to position K67 of SEQ ID NO:6 is GLN; (19) the amino acid residue corresponding to position K72 of SEQ ID NO:6 is LEU, or VAL; (20) the amino acid residue corresponding to position E75 of SEQ ID NO:6 is PRO; (21) the amino acid residue corresponding to position E76 of SEQ ID NO:6 is PRO; (22) the amino acid residue corresponding to position D77 of SEQ ID NO:6 is ASN; (23) the amino acid residue corresponding to position K78 of SEQ ID NO:6 is ARG; (24) the amino acid residue corresponding to position D93 of SEQ ID NO:6 is HIS; (25) the amino acid residue corresponding to position S96 of SEQ ID NO:6 is ALA, or GLU; (26) the amino acid residue corresponding to position P97 of SEQ ID NO:6 is ASP, or GLU; (27) the amino acid residue corresponding to position T98 of SEQ ID NO:6 is GLN, or GLU; (28) the amino acid residue corresponding to position N101 of SEQ ID NO:6 is ALA, GLU, or LYS; (29) the amino acid residue corresponding to position D105 of SEQ ID NO:6 is GLU; (30) the amino acid residue corresponding to position F110 of SEQ ID NO:6 is TYR; (31) the amino acid residue corresponding to position S113 of SEQ ID NO:6 is ALA; (32) the amino acid residue corresponding to position Y115 of SEQ ID NO:6 is PHE; (33) the amino acid residue corresponding to position L126 of SEQ ID NO:6 is CYS; (34) the amino acid residue corresponding to position S127 of SEQ ID NO:6 is ALA; (35) the amino acid residue corresponding to position D128 of SEQ ID NO:6 is GLY; (36) the amino acid residue corresponding to position D129 of SEQ ID NO:6 is GLU; (37) the amino acid residue corresponding to position K131 of SEQ ID NO:6 is ALA; (38) the amino acid residue corresponding to position Y135 of SEQ ID NO:6 is ASN, ASP, GLN, LEU, LYS, MET, PRO, or THR; (39) the amino acid residue corresponding to position E136 of SEQ ID NO:6 is ASP; (40) the amino acid residue corresponding to position E140 of SEQ ID NO:6 is ILE; (41) the amino acid residue corresponding to position T142 of SEQ ID NO:6 is GLU; (42) the amino acid residue corresponding to position R143 of SEQ ID NO:6 is ALA, or VAL; (43) the amino acid residue corresponding to position E144 of SEQ ID NO:6 is ARG; (44) the amino acid residue corresponding to position F146 of SEQ ID NO:6 is CYS; (45) the amino acid residue corresponding to position E147 of SEQ ID NO:6 is ARG, or LYS; (46) the amino acid residue corresponding to position 1148 of SEQ ID NO:6 is VAL; (47) the amino acid residue corresponding to position E151 of SEQ ID NO:6 is ARG; (48) the amino acid residue corresponding to position T152 of SEQ ID NO:6 is ALA; (49) the amino acid residue corresponding to position R154 of SEQ ID NO:6 is GLN; (50) the amino acid residue corresponding to position P160 of SEQ ID NO:6 is ALA, or GLU; (51) the amino acid residue corresponding to position V179 of SEQ ID NO:6 is ILE; (52) the amino acid residue corresponding to position V182 of SEQ ID NO:6 is ALA, LYS, or PRO; (53) the amino acid residue corresponding to position D184 of SEQ ID NO:6 is GLU; (54) the amino acid residue corresponding to position S187 of SEQ ID NO:6 is ARG, ASN, GLU, LYS, or THR; (55) the amino acid residue corresponding to position A188 of SEQ ID NO:6 is MET, PHE, or THR; (56) the amino acid residue corresponding to position 1189 of SEQ ID NO:6 is LEU; (57) the amino acid residue corresponding to position S190 of SEQ ID NO:6 is ASP, or GLU; (58) the amino acid residue corresponding to position S191 of SEQ ID NO:6 is ALA, ILE, LEU, THR, TYR, or VAL; (59) the amino acid residue corresponding to position L192 of SEQ ID NO:6 is HIS, or PHE; (60) the amino acid residue corresponding to position Y195 of SEQ ID NO:6 is ALA; (61) the amino acid residue corresponding to position N197 of SEQ ID NO:6 is ALA, ASP, GLN, GLU, or LYS; (62) the amino acid residue corresponding to position D198 of SEQ ID NO:6 is LYS; (63) the amino acid residue corresponding to position V199 of SEQ ID NO:6 is CYS, HIS, ILE, or LEU; (64) the amino acid residue corresponding to position P200 of SEQ ID NO:6 is GLY; (65) the amino acid residue corresponding to position N201 of SEQ ID NO:6 is ARG, GLN, or LYS; (66) the amino acid residue corresponding to position 1202 of SEQ ID NO:6 is ALA, or MET; (67) the amino acid residue corresponding to position D204 of SEQ ID NO:6 is ASN; (68) the amino acid residue corresponding to position G208 of SEQ ID NO:6 is ALA; (69) the amino acid residue corresponding to position 1211 of SEQ ID NO:6 is VAL; (70) the amino acid residue corresponding to position L213 of SEQ ID NO:6 is MET; (71) the amino acid residue corresponding to position 1215 of SEQ ID NO:6 is VAL; (72) the amino acid residue corresponding to position S218 of SEQ ID NO:6 is GLY; (73) the amino acid residue corresponding to position Y219 of SEQ ID NO:6 is ASP, or HIS; (74) the amino acid residue corresponding to position V230 of SEQ ID NO:6 is ALA; (75) the amino acid residue corresponding to position G232 of SEQ ID NO:6 is ASP, GLU, LYS, or PRO; (76) the amino acid residue corresponding to position 1233 of SEQ ID NO:6 is LEU; (77) the amino acid residue corresponding to position L234 of SEQ ID NO:6 is ALA, or MET; (78) the amino acid residue corresponding to position V237 of SEQ ID NO:6 is LEU; (79) the amino acid residue corresponding to position E240 of SEQ ID NO:6 is THR; (80) the amino acid residue corresponding to position D241 of SEQ ID NO:6 is GLY, or PRO; (81) the amino acid residue corresponding to position L242 of SEQ ID NO:6 is TRP; (82) the amino acid residue corresponding to position V244 of SEQ ID NO:6 is LEU; (83) the amino acid residue corresponding to position G246 of SEQ ID NO:6 is ALA, CYS, or VAL; (84) the amino acid residue corresponding to position A253 of SEQ ID NO:6 is ASN, ASP, PRO, SER, or THR; (85) the amino acid residue corresponding to position Y255 of SEQ ID NO:6 is ASP, GLN, GLU, or LYS; (86) the amino acid residue corresponding to position A256 of SEQ ID NO:6 is LEU; (87) the amino acid residue corresponding to position N259 of SEQ ID NO:6 is ALA, ARG, ASP, GLU, or TRP; (88) the amino acid residue corresponding to position E262 of SEQ ID NO:6 is GLN; (89) the amino acid residue corresponding to position R266 of SEQ ID NO:6 is ALA, or VAL; (90) the amino acid residue corresponding to position A273 of SEQ ID NO:6 is TRP; (91) the amino acid residue corresponding to position R280 of SEQ ID NO:6 is GLU; (92) the amino acid residue corresponding to position G281 of SEQ ID NO:6 is ALA; (93) the amino acid residue corresponding to position V282 of SEQ ID NO:6 is ILE; (94) the amino acid residue corresponding to position L284 of SEQ ID NO:6 is LYS; (95) the amino acid residue corresponding to position S286 of SEQ ID NO:6 is ALA, ASP, or VAL; (96) the amino acid residue corresponding to position N287 of SEQ ID NO:6 is ASP; (97) the amino acid residue corresponding to position D290 of SEQ ID NO:6 is ALA, ASN, GLN, or LYS; (98) the amino acid residue corresponding to position E291 of SEQ ID NO:6 is ASP; (99) the amino acid residue corresponding to position 1292 of SEQ ID NO:6 is LEU; (100) the amino acid residue corresponding to position E295 of SEQ ID NO:6 is PRO; (101) the amino acid residue corresponding to position R296 of SEQ ID NO:6 is ASP, GLU, or TYR; (102) the amino acid residue corresponding to position E297 of SEQ ID NO:6 is ARG, GLN, GLY, HIS, or LYS; (103) the amino acid residue corresponding to position K302 of SEQ ID NO:6 is LEU; (104) the amino acid residue corresponding to position R303 of SEQ ID NO:6 is GLU; (105) the amino acid residue corresponding to position K321 of SEQ ID NO:6 is ARG, HIS, or THR; (106) the amino acid residue corresponding to position K324 of SEQ ID NO:6 is ASP, or GLU; (107) the amino acid residue corresponding to position R325 of SEQ ID NO:6 is ASN, ASP, GLN, or GLU; (108) the amino acid residue corresponding to position E327 of SEQ ID NO:6 is ARG; (109) the amino acid residue corresponding to position L328 of SEQ ID NO:6 is PHE, or TRP; (110) the amino acid residue corresponding to position 1330 of SEQ ID NO:6 is LEU; (111) the amino acid residue corresponding to position W331 of SEQ ID NO:6 is HIS; (112) the amino acid residue corresponding to position N333 of SEQ ID NO:6 is ALA, or SER; (113) the amino acid residue corresponding to position L334 of SEQ ID NO:6 is TYR; (114) the amino acid residue corresponding to position E343 of SEQ ID NO:6 is ASN; (115) the amino acid residue corresponding to position Y344 of SEQ ID NO:6 is HIS; (116) the amino acid residue corresponding to position E345 of SEQ ID NO:6 is PRO; (117) the amino acid residue corresponding to position M349 of SEQ ID NO:6 is ALA, ARG, CYS, GLU, LYS, or THR; (118) the amino acid residue corresponding to position V350 of SEQ ID NO:6 is ALA; (119) the amino acid residue corresponding to position N352 of SEQ ID NO:6 is GLU; (120) the amino acid residue corresponding to position K353 of SEQ ID NO:6 is ARG; (121) the amino acid residue corresponding to position F358 of SEQ ID NO:6 is LEU; (122) the amino acid residue corresponding to position E360 of SEQ ID NO:6 is ASP; (123) the amino acid residue corresponding to position V362 of SEQ ID NO:6 is ILE; (124) the amino acid residue corresponding to position D363 of SEQ ID NO:6 is PRO; (125) the amino acid residue corresponding to position 1364 of SEQ ID NO:6 is TRP; (126) the amino acid residue corresponding to position K365 of SEQ ID NO:6 is ARG, or THR; (127) the amino acid residue corresponding to position F366 of SEQ ID NO:6 is LEU; (128) the amino acid residue corresponding to position Y372 of SEQ ID NO:6 is PRO; (129) the amino acid residue corresponding to position D373 of SEQ ID NO:6 is ALA; (130) the amino acid residue corresponding to position S374 of SEQ ID NO:6 is ALA, CYS, GLN, or THR; (131) the amino acid residue corresponding to position F376 of SEQ ID NO:6 is ARG, GLN, GLU, HIS, or LYS; (132) the amino acid residue corresponding to position D377 of SEQ ID NO:6 is ALA; (133) the amino acid residue corresponding to position R379 of SEQ ID NO:6 is CYS; (134) the amino acid residue corresponding to position M383 of SEQ ID NO:6 is LEU; (135) the amino acid residue corresponding to position N385 of SEQ ID NO:6 is PRO; (136) the amino acid residue corresponding to position K393 of SEQ ID NO:6 is HIS; (137) the amino acid residue corresponding to position R397 of SEQ ID NO:6 is LYS; or (138) the amino acid residue corresponding to position S403 of SEQ ID NO:6 is ALA, HIS, or TYR; or combinations thereof.

In some embodiments, the polypeptide comprises one or more of modifications: V13L, Y14F, S15A, I16V, S19N, S21P, S21E, S21K, Y22W, S27A, S27C, F30H, K34D, K34M, K34R, K34Y, G35D, G35H, D36T, D36S, Y37P, S54T, K62R, N63R, M66F, M66Y, K67Q, K72V, K72L, E75P, E76P, D77N, K78R, D93H, S96E, S96A, P97D, P97E, T98E, T98Q, N101E, N101A, N101K, D105E, F110Y, S113A, Y115F, L126C, S127A, D128G, D129E, K131A, Y135P, Y135Q, Y135K, Y135N, Y135T, Y135M, Y135D, Y135L, E136D, E140I, T142E, R143V, R143A, E144R, F146C, E147R, E147K, I148V, E151R, T152A, R154Q, P160E, P160A, V179L, V182P, V182A, V182K, D184E, S187K, S187N, S187T, S187E, S187R, A188F, A188M, A188T, I189L, S190D, S190E, S191I, S191T, S191V, S191Y, S191A, S191L, L192F, L192H, Y195A, N197Q, N197K, N197E, N197D, N197A, D198K, V199L, V199H, V199L, V199C, P200G, N201R, N201Q, N201K, I202M, 1202A, D204N, G208A, 1211V, L213M, I215V, S218G, Y219D, Y219H, V230A, G232D, G232E, G232K, G232P, I233L, L234M, L234A, V237L, E240T, D241P, D241G, L242W, V244L, G246V, G246A, G246C, A253P, A253N, A253T, A253D, A253S, Y255D, Y255E, Y255Q, Y255K, A256L, N259R, N259E, N259W, N259D, N259A, E262Q, R266V, R266A, A273W, R280E, G281A, V282L, L284K, S286V, S286D, S286A, N287D, D290N, D290A, D290Q, D290K, E291D, 1292L, E295P, R296D, R296E, R296Y, E297Q, E297K, E297G, E297H, E297R, K302L, R303E, K321T, K321H, K321R, K324D, K324E, R325D, R325N, R325E, R325Q, E327R, L328F, L328W, 1330L, W331H, N333A, N333S, L334Y, E343N, Y344H, E345P, M349K, M349C, M349T, M349E, M349R, M349A, V350A, N352E, K353R, F358L, E360D, V362L, D363P, 1364W, K365T, K365R, F366L, Y372P, D373A, S374T, S374Q, S374A, S374C, F376Q, F376K, F376E, F376H, F376R, D377A, R379C, M383L, N385P, K393H, R397K, S403H, S403Y, or S403A; or combinations thereof.

In other embodiments, the polypeptide comprises one or more of modifications at the amino acid residue corresponding to position K5, K10, K11, C17, K32, K34, K62, K67, K70, K72, K78, K102, K104, K116, K117, C122, K131, K137, K155, K193, K194, K221, K229, K238, K269, K302, K318, K321, K324, K348, K353, K365, K382, K384, K392, K393, or K396 of SEQ ID NO:6; or combinations thereof.

In further embodiments, the polypeptide comprises one or more of modifications: (1) the amino acid residue corresponding to position K5 of SEQ ID NO:6 is ALA, ARG, HIS, LEU, MET, PHE, or TRP; (2) the amino acid residue corresponding to position K10 of SEQ ID NO:6 is ALA, ARG, ASN, LEU, MET, or VAL; (3) the amino acid residue corresponding to position K11 of SEQ ID NO:6 is ARG, GLN, GLU, LEU, TYR, or VAL; (4) the amino acid residue corresponding to position C17 of SEQ ID NO:6 is ALA, ARG, GLY, ILE, LEU, SER, THR, or VAL; (5) the amino acid residue corresponding to position K32 of SEQ ID NO:6 is ARG, GLN, ILE, LEU, MET, or SER; (6) the amino acid residue corresponding to position K34 of SEQ ID NO:6 is ARG, GLN, GLU, HIS, LEU, MET, PHE, THR, or TYR; (7) the amino acid residue corresponding to position K62 of SEQ ID NO:6 is ARG, TYR, or VAL; (8) the amino acid residue corresponding to position K67 of SEQ ID NO:6 is ARG, GLN, SER, or THR; (9) the amino acid residue corresponding to position K70 of SEQ ID NO:6 is ARG, or GLN; (10) the amino acid residue corresponding to position K72 of SEQ ID NO:6 is ARG, ILE, LEU, THR, or VAL; (11) the amino acid residue corresponding to position K78 of SEQ ID NO:6 is ARG, GLN, LEU, or MET; (12) the amino acid residue corresponding to position K102 of SEQ ID NO:6 is ARG, LEU, or TYR; (13) the amino acid residue corresponding to position K104 of SEQ ID NO:6 is ARG, ASN, GLN, ILE, PHE, or VAL; (14) the amino acid residue corresponding to position K116 of SEQ ID NO:6 is ARG, GLN, HIS, ILE, LEU, SER, THR, TRP, or TYR; (15) the amino acid residue corresponding to position K117 of SEQ ID NO:6 is ARG, LEU, MET, TRP, or VAL; (16) the amino acid residue corresponding to position C122 of SEQ ID NO:6 is ALA, ARG, THR, or VAL; (17) the amino acid residue corresponding to position K131 of SEQ ID NO:6 is ARG, GLN, GLU, LEU, or TYR; (18) the amino acid residue corresponding to position K137 of SEQ ID NO:6 is ARG, GLN, GLU, ILE, LEU, or THR; (19) the amino acid residue corresponding to position K155 of SEQ ID NO:6 is ARG, ASN, ASP, GLU, HIS, or TYR; (20) the amino acid residue corresponding to position K193 of SEQ ID NO:6 is ALA, ARG, GLN, GLU, or ILE; (21) the amino acid residue corresponding to position K194 of SEQ ID NO:6 is ALA, ARG, GLU, SER, or THR; (22) the amino acid residue corresponding to position K221 of SEQ ID NO:6 is ARG, GLN, ILE, THR, or VAL; (23) the amino acid residue corresponding to position K229 of SEQ ID NO:6 is ALA, ARG, ASN, GLN, SER, or THR; (24) the amino acid residue corresponding to position K238 of SEQ ID NO:6 is ARG, SER, or TRP; (25) the amino acid residue corresponding to position K269 of SEQ ID NO:6 is ARG, ASN, ILE, LEU, or VAL; (26) the amino acid residue corresponding to position K302 of SEQ ID NO:6 is ARG, GLN, ILE, LEU, or MET; (27) the amino acid residue corresponding to position K318 of SEQ ID NO:6 is ARG, ASP, or GLU; (28) the amino acid residue corresponding to position K321 of SEQ ID NO:6 is ARG, or ASP; (29) the amino acid residue corresponding to position K324 of SEQ ID NO:6 is ARG, ASP, GLU, or SER; (30) the amino acid residue corresponding to position K348 of SEQ ID NO:6 is ARG, LEU, or VAL; (31) the amino acid residue corresponding to position K353 of SEQ ID NO:6 is ARG, GLN, LEU, or TRP; (32) the amino acid residue corresponding to position K365 of SEQ ID NO:6 is ARG, HIS, or SER; (33) the amino acid residue corresponding to position K382 of SEQ ID NO:6 is ARG, ASN, or LEU; (34) the amino acid residue corresponding to position K384 of SEQ ID NO:6 is ARG, ASP, GLN, GLU, LEU, SER, or THR; (35) the amino acid residue corresponding to position K392 of SEQ ID NO:6 is ARG, LEU, or MET; (36) the amino acid residue corresponding to position K393 of SEQ ID NO:6 is ARG, HIS, LEU, PHE, or TYR; or (37) the amino acid residue corresponding to position K396 of SEQ ID NO:6 is ARG, ILE, LEU, MET, or PHE; or combinations thereof.

In some embodiments, the polypeptide comprises one or more of modifications: K5H, K5M, K5L, K5A, K5R, K5W, K5F, K10M, K10L, K10R, K10A, K10V, K10N, K11Q, K11Y, K11E, K11L, K11R, K11V, C17T, C17L, C17L, C17A, C17R, C17V, C17G, C17S, K32Q, K32L, K32M, K32L, K32R, K32S, K34T, K34Q, K34Y, K34E, K34H, K34M, K34L, K34R, K34F, K62R, K62Y, K62V, K67R, K67T, K67Q, K67S, K70R, K70Q, K72T, K72L, K72L, K72R, K72V, K78R, K78Q, K78M, K78L, K102R, K102Y, K102L, K104Q, K104L, K104R, K104V, K104N, K104F, K116T, K116Q, K116Y, K116H, K116L, K116L, K116R, K116W, K1165, K117M, K117L, K117R, K117V, K117W, C122R, C122T, C122A, C122V, K131Q, K131Y, K131E, K131L, K131R, K137T, K137Q, K137E, K137L, K137L, K137R, K155Y, K155E, K155H, K155R, K155D, K155N, K193Q, K193E, K193L, K193R, K193A, K194T, K194E, K194R, K194A, K194S, K221Q, K221T, K221I, K221R, K221V, K229T, K229Q, K229R, K229A, K229N, K229S, K238R, K238W, K238S, K269L, K269L, K269R, K269V, K269N, K302Q, K302L, K302M, K302L, K302R, K318R, K318D, K318E, K321R, K321D, K324R, K324D, K324E, K324S, K348V, K348R, K348L, K353W, K353R, K353Q, K353L, K365R, K365H, K365S, K382R, K382N, K382L, K384T, K384Q, K384E, K384L, K384D, K384R, K384S, K392R, K392M, K392L, K393Y, K393H, K393L, K393R, K393F, K396L, K396M, K396L, K396R, or K396F; or combinations thereof.

In other embodiments, the polypeptide comprises one or more of modifications at the amino acid residue corresponding to position L3, S4, K5, D6, Y7, L8, R9, K10, K11, S21, Y22, E25, E29, F30, K32, E33, K34, G35, D36, Y37, Q49, F50, M56, E59, K62, N63, F64, M66, K67, K70, E71, K72, E75, E76, D77, K78, I80, E94, S96, T98, N101, K102, K104, D105, R108, K116, P125, D129, P130, K131, V132, P134, Y135, E136, K137, E140, R141, E144, E147, I148, E150, E151, T152, A153, R154, K155, Y156, N157, F158, Q159, P160, V161, V179, S187, S190, S191, K193, K194, Y195, N197, P200, N201, W203, D204, R205, G216, S218, Y219, D220, K221, V222, E224, D228, K229, R231, G232, E235, K238, R239, E240, D241, R258, E262, N287, D290, E291, I292, E297, S299, N300, K302, R303, E307, D313, Y315, K318, K321, D322, S323, K324, R325, L326, E327, L328, W331, E343, E345, K348, M349, N352, K353, E356, N357, G361, D363, I364, K365, F366, Y368, Q369, Y370, D373, Y375, F376, D377, E380, K382, K384, N385, D386, R388, E389, K392, K393, K396, R397, E400, S403, N407, or L408 of SEQ ID NO:6; or combinations thereof.

In further embodiments, the polypeptide comprises one or more of modifications: (1) the amino acid residue corresponding to position L3 of SEQ ID NO:6 is GLU, or THR; (2) the amino acid residue corresponding to position S4 of SEQ ID NO:6 is ARG, ASN, ASP, GLN, GLU, LEU, MET, or PRO; (3) the amino acid residue corresponding to position K5 of SEQ ID NO:6 is ALA, ARG, GLN, HIS, LEU, PHE, or VAL; (4) the amino acid residue corresponding to position D6 of SEQ ID NO:6 is ALA, ARG, ASN, GLN, GLU, HIS, or LEU; (5) the amino acid residue corresponding to position Y7 of SEQ ID NO:6 is ASN, HIS, or TRP; (6) the amino acid residue corresponding to position L8 of SEQ ID NO:6 is ASN, or GLY; (7) the amino acid residue corresponding to position R9 of SEQ ID NO:6 is GLN, GLU, HIS, ILE, LEU, or THR; (8) the amino acid residue corresponding to position K10 of SEQ ID NO:6 is ALA, ARG, ASN, ASP, GLU, or PRO; (9) the amino acid residue corresponding to position K11 of SEQ ID NO:6 is ARG, GLN, GLU, HIS, ILE, PHE, TRP, TYR, or VAL; (10) the amino acid residue corresponding to position S21 of SEQ ID NO:6 is ARG, GLN, GLU, or PRO; (11) the amino acid residue corresponding to position Y22 of SEQ ID NO:6 is TRP; (12) the amino acid residue corresponding to position E25 of SEQ ID NO:6 is ARG, or ILE; (13) the amino acid residue corresponding to position E29 of SEQ ID NO:6 is ARG, GLN, ILE, or LEU; (14) the amino acid residue corresponding to position F30 of SEQ ID NO:6 is ALA, HIS, or THR; (15) the amino acid residue corresponding to position K32 of SEQ ID NO:6 is ALA, ARG, GLN, ILE, LEU, or MET; (16) the amino acid residue corresponding to position E33 of SEQ ID NO:6 is ARG, ASN, ASP, GLN, HIS, or THR; (17) the amino acid residue corresponding to position K34 of SEQ ID NO:6 is ARG, ASP, GLN, HIS, ILE, LEU, MET, PHE, SER, THR, TYR, or VAL; (18) the amino acid residue corresponding to position G35 of SEQ ID NO:6 is ASN, ASP, HIS, or SER; (19) the amino acid residue corresponding to position D36 of SEQ ID NO:6 is ARG, ASN, GLN, GLU, HIS, LEU, PHE, SER, THR, TRP, or TYR; (20) the amino acid residue corresponding to position Y37 of SEQ ID NO:6 is ARG, ASP, GLU, or PRO; (21) the amino acid residue corresponding to position Q49 of SEQ ID NO:6 is HIS, ILE, PHE, or TRP; (22) the amino acid residue corresponding to position F50 of SEQ ID NO:6 is ARG, GLN, HIS, or SER; (23) the amino acid residue corresponding to position M56 of SEQ ID NO:6 is TRP; (24) the amino acid residue corresponding to position E59 of SEQ ID NO:6 is ARG, SER, or THR; (25) the amino acid residue corresponding to position K62 of SEQ ID NO:6 is ALA, or ARG; (26) the amino acid residue corresponding to position N63 of SEQ ID NO:6 is ARG, ASP, GLN, or GLU; (27) the amino acid residue corresponding to position F64 of SEQ ID NO:6 is GLU, or LEU; (28) the amino acid residue corresponding to position M66 of SEQ ID NO:6 is GLU, PHE, or TYR; (29) the amino acid residue corresponding to position K67 of SEQ ID NO:6 is ARG, ASP, GLN, GLU, SER, or THR; (30) the amino acid residue corresponding to position K70 of SEQ ID NO:6 is ARG, ASP, GLN, or LEU; (31) the amino acid residue corresponding to position E71 of SEQ ID NO:6 is ARG, GLN, or SER; (32) the amino acid residue corresponding to position K72 of SEQ ID NO:6 is GLN, GLU, HIS, ILE, LEU, or THR; (33) the amino acid residue corresponding to position E75 of SEQ ID NO:6 is ARG, ASP, or SER; (34) the amino acid residue corresponding to position E76 of SEQ ID NO:6 is ARG, LEU, or PRO; (35) the amino acid residue corresponding to position D77 of SEQ ID NO:6 is ARG, ASN, or SER; (36) the amino acid residue corresponding to position K78 of SEQ ID NO:6 is ARG, ASP, GLN, LEU, or MET; (37) the amino acid residue corresponding to position I80 of SEQ ID NO:6 is ARG, GLN, or LEU; (38) the amino acid residue corresponding to position E94 of SEQ ID NO:6 is ARG, GLN, LEU, or TYR; (39) the amino acid residue corresponding to position S96 of SEQ ID NO:6 is ALA, ARG, or GLU; (40) the amino acid residue corresponding to position T98 of SEQ ID NO:6 is ARG, GLN, GLU, ILE, TRP, or VAL; (41) the amino acid residue corresponding to position N101 of SEQ ID NO:6 is ALA, ARG, ASP, GLN, GLU, HIS, SER, or THR; (42) the amino acid residue corresponding to position K102 of SEQ ID NO:6 is ARG, GLN, GLU, TRP, or TYR; (43) the amino acid residue corresponding to position K104 of SEQ ID NO:6 is ARG, GLN, or GLU; (44) the amino acid residue corresponding to position D105 of SEQ ID NO:6 is GLN, GLU, or ILE; (45) the amino acid residue corresponding to position R108 of SEQ ID NO:6 is ILE; (46) the amino acid residue corresponding to position K116 of SEQ ID NO:6 is ARG, ASP, GLN, GLU, HIS, ILE, LEU, THR, TRP, or TYR; (47) the amino acid residue corresponding to position P125 of SEQ ID NO:6 is ALA; (48) the amino acid residue corresponding to position D129 of SEQ ID NO:6 is ARG, GLN, GLU, LEU, or TRP; (49) the amino acid residue corresponding to position P130 of SEQ ID NO:6 is SER; (50) the amino acid residue corresponding to position K131 of SEQ ID NO:6 is ASP, GLU, SER, or TYR; (51) the amino acid residue corresponding to position V132 of SEQ ID NO:6 is ARG, GLU, SER, THR, or TYR; (52) the amino acid residue corresponding to position P134 of SEQ ID NO:6 is ALA, ASP, or HIS; (53) the amino acid residue corresponding to position Y135 of SEQ ID NO:6 is ARG, ASP, GLN, LEU, or TRP; (54) the amino acid residue corresponding to position E136 of SEQ ID NO:6 is ARG, ASP, GLN, PRO, SER, THR, or TRP; (55) the amino acid residue corresponding to position K137 of SEQ ID NO:6 is ARG, GLN, GLU, ILE, LEU, TRP, or VAL; (56) the amino acid residue corresponding to position E140 of SEQ ID NO:6 is ARG, ASP, ILE, or LEU; (57) the amino acid residue corresponding to position R141 of SEQ ID NO:6 is ASP, GLN, HIS, LEU, TRP, or TYR; (58) the amino acid residue corresponding to position E144 of SEQ ID NO:6 is ARG, ASP, GLN, or ILE; (59) the amino acid residue corresponding to position E147 of SEQ ID NO:6 is ALA, ARG, or GLN; (60) the amino acid residue corresponding to position 1148 of SEQ ID NO:6 is ASP, GLU, or VAL; (61) the amino acid residue corresponding to position E150 of SEQ ID NO:6 is ALA, or ARG; (62) the amino acid residue corresponding to position E151 of SEQ ID NO:6 is ARG; (63) the amino acid residue corresponding to position T152 of SEQ ID NO:6 is ALA, ARG, GLN, HIS, TYR, or VAL; (64) the amino acid residue corresponding to position A153 of SEQ ID NO:6 is ARG, GLN, GLY, or SER; (65) the amino acid residue corresponding to position R154 of SEQ ID NO:6 is GLN, GLU, PRO, SER, or THR; (66) the amino acid residue corresponding to position K155 of SEQ ID NO:6 is ASP, GLN, GLU, GLY, PRO, THR, or TRP; (67) the amino acid residue corresponding to position Y156 of SEQ ID NO:6 is ARG, ASP, GLN, GLU, MET, PHE, THR, or VAL; (68) the amino acid residue corresponding to position N157 of SEQ ID NO:6 is ARG, ASP, GLU, or PRO; (69) the amino acid residue corresponding to position F158 of SEQ ID NO:6 is ARG, ASN, GLU, LEU, THR, or VAL; (70) the amino acid residue corresponding to position Q159 of SEQ ID NO:6 is ARG, GLU, GLY, LEU, THR, or TRP; (71) the amino acid residue corresponding to position P160 of SEQ ID NO:6 is ALA, ARG, GLU, ILE, LEU, MET, PHE, SER, or THR; (72) the amino acid residue corresponding to position V161 of SEQ ID NO:6 is GLU, ILE, TRP, or TYR; (73) the amino acid residue corresponding to position V179 of SEQ ID NO:6 is ARG, or ILE; (74) the amino acid residue corresponding to position S187 of SEQ ID NO:6 is ALA, ARG, or GLN; (75) the amino acid residue corresponding to position S190 of SEQ ID NO:6 is ASP, GLU, or TYR; (76) the amino acid residue corresponding to position S191 of SEQ ID NO:6 is ALA, ARG, GLN, GLU, HIS, LEU, THR, TRP, or TYR; (77) the amino acid residue corresponding to position K193 of SEQ ID NO:6 is ARG, GLN, GLU, ILE, LEU, PHE, or TYR; (78) the amino acid residue corresponding to position K194 of SEQ ID NO:6 is ALA, ARG, ASP, GLN, GLU, or LEU; (79) the amino acid residue corresponding to position Y195 of SEQ ID NO:6 is ALA, GLN, or HIS; (80) the amino acid residue corresponding to position N197 of SEQ ID NO:6 is ARG, ASP, GLN, GLU, LEU, PRO, or SER; (81) the amino acid residue corresponding to position P200 of SEQ ID NO:6 is ARG, ASP, GLU, LEU, or MET; (82) the amino acid residue corresponding to position N201 of SEQ ID NO:6 is ARG, or GLU; (83) the amino acid residue corresponding to position W203 of SEQ ID NO:6 is ALA, ARG, HIS, LEU, PHE, or TYR; (84) the amino acid residue corresponding to position D204 of SEQ ID NO:6 is ARG, ASN, or SER; (85) the amino acid residue corresponding to position R205 of SEQ ID NO:6 is GLN, or LEU; (86) the amino acid residue corresponding to position G216 of SEQ ID NO:6 is ARG, ASN, or THR; (87) the amino acid residue corresponding to position S218 of SEQ ID NO:6 is THR; (88) the amino acid residue corresponding to position Y219 of SEQ ID NO:6 is ARG, or GLY; (89) the amino acid residue corresponding to position D220 of SEQ ID NO:6 is ARG, GLN, GLU, or THR; (90) the amino acid residue corresponding to position K221 of SEQ ID NO:6 is ARG, GLN, GLU, ILE, THR, or VAL; (91) the amino acid residue corresponding to position V222 of SEQ ID NO:6 is ILE; (92) the amino acid residue corresponding to position E224 of SEQ ID NO:6 is GLN, MET, or TYR; (93) the amino acid residue corresponding to position D228 of SEQ ID NO:6 is GLU, or SER; (94) the amino acid residue corresponding to position K229 of SEQ ID NO:6 is ALA, ARG, ASN, GLN, or GLU; (95) the amino acid residue corresponding to position R231 of SEQ ID NO:6 is ALA, GLU, LEU, or PHE; (96) the amino acid residue corresponding to position G232 of SEQ ID NO:6 is ARG, GLU, or PRO; (97) the amino acid residue corresponding to position E235 of SEQ ID NO:6 is ARG, or TRP; (98) the amino acid residue corresponding to position K238 of SEQ ID NO:6 is ARG, GLN, GLU, SER, or TRP; (99) the amino acid residue corresponding to position R239 of SEQ ID NO:6 is SER; (100) the amino acid residue corresponding to position E240 of SEQ ID NO:6 is ASN, ASP, HIS, MET, THR, TYR, or VAL; (101) the amino acid residue corresponding to position D241 of SEQ ID NO:6 is ARG, ASN, GLN, or PRO; (102) the amino acid residue corresponding to position R258 of SEQ ID NO:6 is GLU, or LEU; (103) the amino acid residue corresponding to position E262 of SEQ ID NO:6 is ARG, GLN, or LEU; (104) the amino acid residue corresponding to position N287 of SEQ ID NO:6 is ARG, GLN, GLU, HIS, LEU, or PHE; (105) the amino acid residue corresponding to position D290 of SEQ ID NO:6 is ARG, GLN, GLU, or PHE; (106) the amino acid residue corresponding to position E291 of SEQ ID NO:6 is ARG; (107) the amino acid residue corresponding to position 1292 of SEQ ID NO:6 is GLN, or GLU; (108) the amino acid residue corresponding to position E297 of SEQ ID NO:6 is ARG, HIS, or LEU; (109) the amino acid residue corresponding to position S299 of SEQ ID NO:6 is ALA, or GLN; (110) the amino acid residue corresponding to position N300 of SEQ ID NO:6 is ARG, ASP, GLN, or GLU; (111) the amino acid residue corresponding to position K302 of SEQ ID NO:6 is ARG, GLN, GLU, ILE, LEU, MET, or PRO; (112) the amino acid residue corresponding to position R303 of SEQ ID NO:6 is ASP, GLN, or GLU; (113) the amino acid residue corresponding to position E307 of SEQ ID NO:6 is ARG, or GLN; (114) the amino acid residue corresponding to position D313 of SEQ ID NO:6 is PRO; (115) the amino acid residue corresponding to position Y315 of SEQ ID NO:6 is TRP; (116) the amino acid residue corresponding to position K318 of SEQ ID NO:6 is ASN, or ASP; (117) the amino acid residue corresponding to position K321 of SEQ ID NO:6 is ARG, ASP, GLU, or SER; (118) the amino acid residue corresponding to position D322 of SEQ ID NO:6 is THR; (119) the amino acid residue corresponding to position S323 of SEQ ID NO:6 is ASP, or GLY; (120) the amino acid residue corresponding to position K324 of SEQ ID NO:6 is ASP, GLU, HIS, PRO, or TRP; (121) the amino acid residue corresponding to position R325 of SEQ ID NO:6 is ALA, ASP, GLN, GLU, GLY, SER, or TRP; (122) the amino acid residue corresponding to position L326 of SEQ ID NO:6 is HIS; (123) the amino acid residue corresponding to position E327 of SEQ ID NO:6 is ARG, ILE, or TYR; (124) the amino acid residue corresponding to position L328 of SEQ ID NO:6 is ARG, ASP, GLU, TRP, or TYR; (125) the amino acid residue corresponding to position W331 of SEQ ID NO:6 is GLU, LEU, or PHE; (126) the amino acid residue corresponding to position E343 of SEQ ID NO:6 is ASN, ASP, GLN, LEU, MET, or TYR; (127) the amino acid residue corresponding to position E345 of SEQ ID NO:6 is ASP, or PRO; (128) the amino acid residue corresponding to position K348 of SEQ ID NO:6 is ALA, ARG, GLN, GLU, LEU, TRP, or TYR; (129) the amino acid residue corresponding to position M349 of SEQ ID NO:6 is ARG, ASN, GLN, GLU, ILE, THR, TRP, or TYR; (130) the amino acid residue corresponding to position N352 of SEQ ID NO:6 is ARG, GLN, GLU, LEU, or MET; (131) the amino acid residue corresponding to position K353 of SEQ ID NO:6 is ALA, ARG, GLN, GLU, HIS, or LEU; (132) the amino acid residue corresponding to position E356 of SEQ ID NO:6 is ARG, or TRP; (133) the amino acid residue corresponding to position N357 of SEQ ID NO:6 is HIS; (134) the amino acid residue corresponding to position G361 of SEQ ID NO:6 is ASP, or PRO; (135) the amino acid residue corresponding to position D363 of SEQ ID NO:6 is HIS, or PRO; (136) the amino acid residue corresponding to position 1364 of SEQ ID NO:6 is GLU, LEU, MET, or PRO; (137) the amino acid residue corresponding to position K365 of SEQ ID NO:6 is ARG, ASN, ASP, GLU, or SER; (138) the amino acid residue corresponding to position F366 of SEQ ID NO:6 is ARG, HIS, LEU, or TYR; (139) the amino acid residue corresponding to position Y368 of SEQ ID NO:6 is ARG, or LEU; (140) the amino acid residue corresponding to position Q369 of SEQ ID NO:6 is ARG, ASP, GLU, or LEU; (141) the amino acid residue corresponding to position Y370 of SEQ ID NO:6 is HIS; (142) the amino acid residue corresponding to position D373 of SEQ ID NO:6 is ARG, ASN, GLU, or LEU; (143) the amino acid residue corresponding to position Y375 of SEQ ID NO:6 is ALA, or TRP; (144) the amino acid residue corresponding to position F376 of SEQ ID NO:6 is ARG, GLN, or GLU; (145) the amino acid residue corresponding to position D377 of SEQ ID NO:6 is ALA, ARG, ASN, HIS, or SER; (146) the amino acid residue corresponding to position E380 of SEQ ID NO:6 is ARG, ASN, ASP, or LEU; (147) the amino acid residue corresponding to position K382 of SEQ ID NO:6 is ARG, ASN, ASP, GLN, GLU, or LEU; (148) the amino acid residue corresponding to position K384 of SEQ ID NO:6 is ARG, ASP, GLN, GLU, LEU, SER, or THR; (149) the amino acid residue corresponding to position N385 of SEQ ID NO:6 is PRO, or THR; (150) the amino acid residue corresponding to position D386 of SEQ ID NO:6 is HIS; (151) the amino acid residue corresponding to position R388 of SEQ ID NO:6 is GLU; (152) the amino acid residue corresponding to position E389 of SEQ ID NO:6 is ARG, or ASP; (153) the amino acid residue corresponding to position K392 of SEQ ID NO:6 is ARG, GLU, HIS, LEU, PHE, or TYR; (154) the amino acid residue corresponding to position K393 of SEQ ID NO:6 is ALA, ARG, GLN, GLU, HIS, THR, TRP, or TYR; (155) the amino acid residue corresponding to position K396 of SEQ ID NO:6 is ALA, ARG, GLN, GLU, ILE, or MET; (156) the amino acid residue corresponding to position R397 of SEQ ID NO:6 is GLN, GLU, HIS, ILE, LEU, or SER; (157) the amino acid residue corresponding to position E400 of SEQ ID NO:6 is ARG, GLN, LEU, or TYR; (158) the amino acid residue corresponding to position S403 of SEQ ID NO:6 is ALA, ARG, GLU, LEU, PHE, THR, TRP, or TYR; (159) the amino acid residue corresponding to position N407 of SEQ ID NO:6 is ARG, ASP, GLN, GLU, HIS, ILE, LEU, PHE, TRP, or TYR; or (160) the amino acid residue corresponding to position L408 of SEQ ID NO:6 is ARG, ASN, ASP, GLY, THR, or TRP; or combinations thereof.

In some embodiments, the polypeptide comprises one or more of modifications: L3E, L3T, S4L, S4D, S4R, S4N, S4P, S4E, S4Q, S4M, K5L, K5V, K5A, K5H, K5R, K5F, K5Q, D6L, D6A, D6H, D6R, D6N, D6E, D6Q, Y7W, Y7N, Y7H, L8N, L8G, R9L, R9I, R9H, R9E, R9Q, R9T, K10D, K10A, K10R, K10N, K10P, K10E, K11I, K11V, K11H, K11Y, K11R, K11F, K11W, K11E, K11Q, S21R, S21E, S21Q, S21P, Y22W, E25R, E25L, E29L, E29R, E29Q, E29L, F30A, F30H, F30T, K32L, K32L, K32A, K32R, K32Q, K32M, E33D, E33H, E33R, E33N, E33Q, E33T, K34L, K34D, K34L, K34S, K34V, K34H, K34Y, K34R, K34F, K34Q, K34T, K34M, G35D, G35N, G35H, G35S, D36L, D36S, D36H, D36Y, D36R, D36E, D36N, D36F, D36W, D36Q, D36T, Y37E, Y37R, Y37D, Y37P, Q49W, Q49L, Q49H, Q49F, F50R, F50Q, F50H, F50S, M56W, E59R, E59S, E59T, K62R, K62A, N63R, N63E, N63D, N63Q, F64L, F64E, M66E, M66F, M66Y, K67D, K67S, K67R, K67E, K67Q, K67T, K70L, K70R, K70D, K70Q, E71R, E71Q, E71S, K72L, K72L, K72H, K72E, K72Q, K72T, E75R, E75D, E75S, E76L, E76R, E76P, D77R, D77N, D77S, K78L, K78R, K78D, K78Q, K78M, I80L, I80R, I80Q, E94L, E94R, E94Q, E94Y, S96R, S96E, S96A, T98L, T98V, T98R, T98W, T98E, T98Q, N101D, N101S, N101A, N101H, N101R, N101E, N101Q, N101T, K102Y, K102R, K102W, K102E, K102Q, K104R, K104E, K104Q, D105E, D105Q, D105I, R108I, K116L, K1161, K116H, K116Y, K116R, K116E, K116W, K116D, K116Q, K116T, P125A, D129L, D129R, D129W, D129E, D129Q, P130S, K131D, K131E, K131S, K131Y, V132S, V132Y, V132R, V132E, V132T, P134A, P134D, P134H, Y135L, Y135D, Y135R, Y135W, Y135Q, E136S, E136R, E136P, E136W, E136D, E136Q, E136T, K137L, K137L, K137V, K137R, K137W, K137E, K137Q, E140L, E140R, E140D, E140I, R141L, R141D, R141H, R141Y, R141W, R141Q, E144R, E144Q, E144D, E144I, E147R, E147Q, E147A, I148D, I148E, I148V, E150R, E150A, E151R, T152V, T152A, T152H, T152Y, T152R, T152Q, A153R, A153Q, A153G, A153S, R154S, R154P, R154E, R154Q, R154T, K155G, K155E, K155P, K155W, K155D, K155Q, K155T, Y156V, Y156R, Y156E, Y156F, Y156D, Y156Q, Y156T, Y156M, N157E, N157D, N157R, N157P, F158L, F158V, F158R, F158N, F158E, F158T, Q159L, Q159G, Q159R, Q159W, Q159E, Q159T, P160L, P160I, P160S, P160A, P160R, P160F, P160E, P160T, P160M, V161W, V161E, V161I, V161Y, V179R, V179L, S187R, S187Q, S187A, S190D, S190E, S190Y, S191L, S191A, S191H, S191Y, S191R, S191W, S191E, S191Q, S191T, K193L, K193L, K193Y, K193R, K193F, K193E, K193Q, K194L, K194D, K194A, K194R, K194E, K194Q, Y195A, Y195Q, Y195H, N197L, N197D, N197S, N197R, N197P, N197E, N197Q, P200L, P200D, P200R, P200E, P200M, N201R, N201E, W203L, W203A, W203H, W203Y, W203R, W203F, D204R, D204N, D204S, R205L, R205Q, G216R, G216N, G216T, S218T, Y219R, Y219G, D220E, D220R, D220Q, D220T, K221I, K221V, K221R, K221E, K221Q, K221T, V222L, E224Q, E224Y, E224M, D228E, D228S, K229A, K229R, K229N, K229E, K229Q, R231L, R231A, R231E, R231F, G232R, G232E, G232P, E235R, E235W, K238S, K238R, K238W, K238E, K238Q, R239S, E240V, E240H, E240Y, E240N, E240D, E240T, E240M, D241R, D241N, D241Q, D241P, R258L, R258E, E262L, E262R, E262Q, N287L, N287H, N287R, N287F, N287E, N287Q, D290R, D290E, D290Q, D290F, E291R, I292E, I292Q, E297L, E297R, E297H, S299A, S299Q, N300E, N300D, N300R, N300Q, K302L, K302L, K302R, K302P, K302E, K302Q, K302M, R303D, R303E, R303Q, E307R, E307Q, D313P, Y315W, K318D, K318N, K321E, K321D, K321R, K321S, D322T, S323D, S323G, K324D, K324H, K324P, K324W, K324E, R325D, R325S, R325A, R325G, R325W, R325E, R325Q, L326H, E327R, E327L, E327Y, L328D, L328Y, L328R, L328W, L328E, W331L, W331E, W331F, E343L, E343Y, E343N, E343D, E343Q, E343M, E345D, E345P, K348L, K348A, K348Y, K348R, K348W, K348E, K348Q, M349L, M349Y, M349R, M349N, M349W, M349E, M349Q, M349T, N352L, N352R, N352E, N352Q, N352M, K353L, K353A, K353H, K353R, K353E, K353Q, E356R, E356W, N357H, G361D, G361P, D363H, D363P, I364L, I364E, I364P, I364M, K365D, K365S, K365R, K365N, K365E, F366L, F366R, F366H, F366Y, Y368L, Y368R, Q369L, Q369R, Q369E, Q369D, Y370H, D373L, D373R, D373E, D373N, Y375W, Y375A, F376R, F376E, F376Q, D377S, D377A, D377H, D377R, D377N, E380L, E380R, E380D, E380N, K382L, K382D, K382R, K382N, K382E, K382Q, K384L, K384S, K384R, K384E, K384D, K384Q, K384T, N385P, N385T, D386H, R388E, E389R, E389D, K392L, K392H, K392Y, K392R, K392F, K392E, K393A, K393H, K393Y, K393R, K393W, K393E, K393Q, K393T, K396L, K396A, K396R, K396E, K396Q, K396M, R397L, R397L, R397S, R397H, R397E, R397Q, E400L, E400R, E400Q, E400Y, S403L, S403A, S403Y, S403R, S403F, S403W, S403E, S403T, N407L, N407D, N407L, N407H, N407Y, N407R, N407F, N407W, N407E, N407Q, L408G, L408R, L408N, L408W, L408D, or L408T; or combinations thereof.

Figure 22:
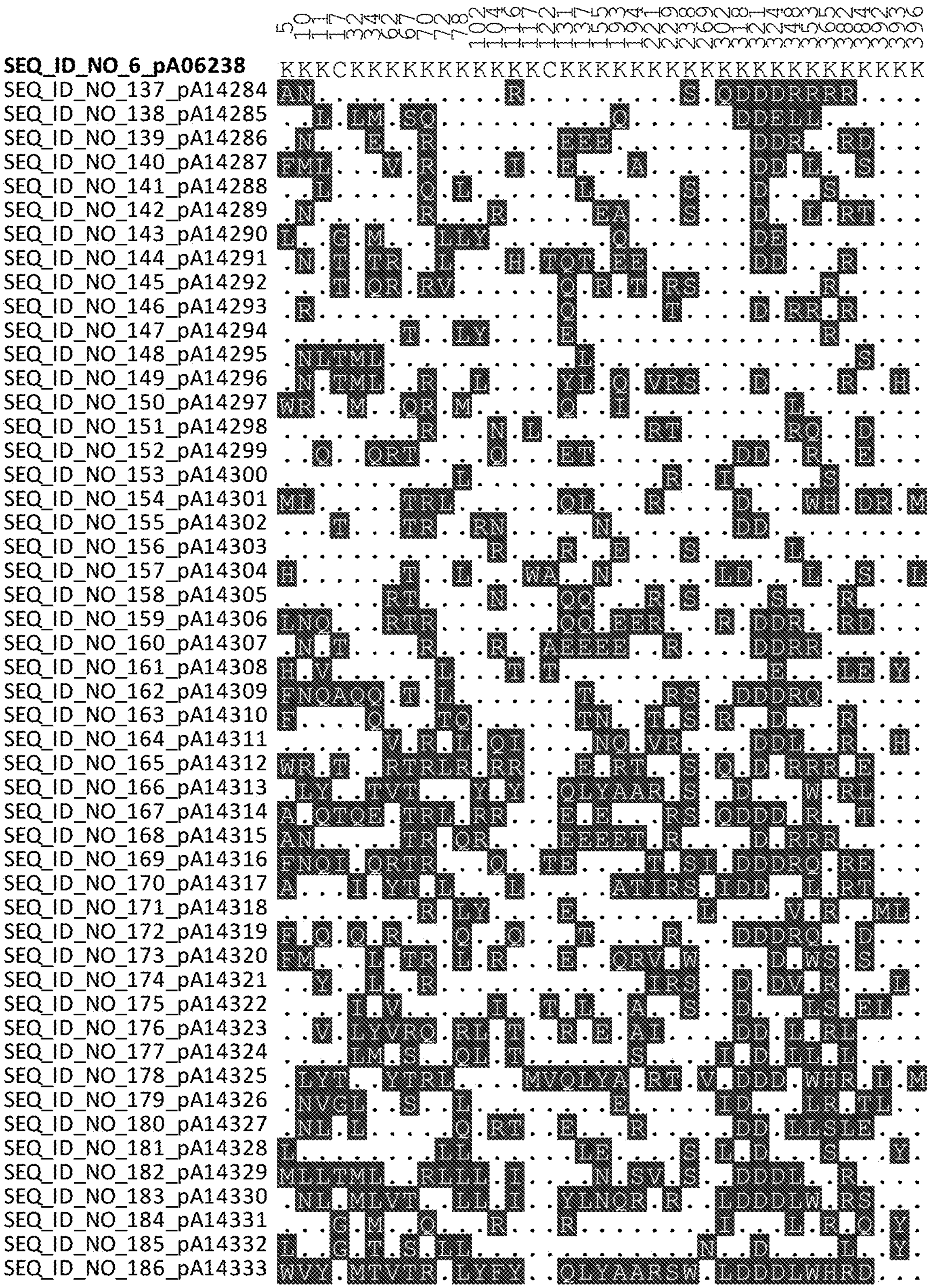
FIG. 22 depicts the sequence alignment of all lysine/cysteine only mutants from Example 14 (SEQ ID NOs 137-230). Only residue positions that were mutated in at least one mutant FC4E are shown. Amino acids that were not mutated are shown as a ".".

The amino acid modifications identified herein can be made in any one of the SEQ ID NOs: 1-444, or active variant or fragment thereof. The location of the amino acid modifications can be identified by referencing to SEQ ID NO: 6. Amino acid sequence alignment can be made using known methods. FIG. 17 depicts amino acid sequence alignments of the native thermophilic FC4Es (SEQ ID NOs: 1-23 and SEQ ID NOs: 321-373). FIG. 20 depicts the sequence alignment of all computationally designed stability/expression mutants from Example 13 (SEQ ID NOs 46-136). FIG. 22 depicts the sequence alignment of all lysine/cysteine only mutants from Example 14 (SEQ ID NOs 137-230). FIG. 23 depicts the sequence alignment of all lysine/cysteine mutants from Example 14 that allowed surrounding residues to mutate (SEQ ID Nos: 232-320). In some embodiments, the polypeptides carrying one or more of the amino acid modifications identified herein are capable of converting fructose to tagatose through epimerization at the carbon-4 position of fructose.

In some embodiments, the amino acid modifications are made relative to the native/wild-type sequences identified herein. In some embodiments, the polypeptide comprises an amino acid sequence having at least 60%, 65%, 70%, 75%, 80%, 85%, 90%, 95%, or 98% sequence identity to SEQ ID NO:1, and the one or more modifications are relative to SEQ ID NO:1. In some embodiments, the polypeptide has an improved D-fructose C4-epimerase activity and/or improved stability compared to the polypeptide of SEQ ID NO:1. In some embodiments, the polypeptide is derived from *Caldithrix abyssi*. In some embodiments, the polypeptide comprises an amino acid sequence having at least 60%, 65%, 70%, 75%, 80%, 85%, 90%, 95%, or 98% sequence identity to SEQ ID NO:2, and the one or more modifications are relative to SEQ ID NO:2. In some embodiments, the polypeptide has an improved D-fructose C4-epimerase activity and/or improved stability compared to the polypeptide of SEQ ID NO:2. In some embodiments, the polypeptide is derived from *Anaerolinea thermophila*. In some embodiments, the polypeptide comprises an amino acid sequence having at least 60%, 65%, 70%, 75%, 80%, 85%, 90%, 95%, or 98% sequence identity to SEQ ID NO:3, and the one or more modifications are relative to SEQ ID NO:3. In some embodiments, the polypeptide has an improved D-fructose C4-epimerase activity and/or improved stability compared to the polypeptide of SEQ ID NO:3. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:4, and the one or more modifications are relative to SEQ ID NO:4. In some embodiments, the polypeptide has an improved D-fructose C4-epimerase activity and/or improved stability compared to the polypeptide of SEQ ID NO:4. In some embodiments, the polypeptide is derived from *Thermoanaerobacter thermohydrosulfuricus*. In some embodiments, the polypeptide comprises an amino acid sequence having at least 60%, 65%, 70%, 75%, 80%, 85%, 90%, 95%, or 98% sequence identity to SEQ ID NO:5, and the one or more modifications are relative to SEQ ID NO:5. In some embodiments, the polypeptide has an improved D-fructose C4-epimerase activity and/or improved stability compared to the polypeptide of SEQ ID NO:5. In some embodiments, the polypeptide is derived from *Caldicellulosiruptor kronotskyensis*. In some embodiments, the polypeptide comprises an amino acid sequence having at least 60%, 65%, 70%, 75%, 80%, 85%, 90%, 95%, or 98% sequence identity to SEQ ID NO:6, and the one or more modifications are relative to SEQ ID NO:6. In some embodiments, the polypeptide has an improved D-fructose C4-epimerase activity and/or improved stability compared to the polypeptide of SEQ ID NO:6. In some embodiments, the polypeptide is derived from *Dictyoglomus turgidum*. In some embodiments, the polypeptide comprises an amino acid sequence having at least 60%, 65%, 70%, 75%, 80%, 85%, 90%, 95%, or 98% sequence identity to SEQ ID NO:7, and the one or more modifications are relative to SEQ ID NO:7. In some embodiments, the polypeptide has an improved D-fructose C4-epimerase activity and/or improved stability compared to the polypeptide of SEQ ID NO:7. In some embodiments, the polypeptide is derived from *Caldilinea aerophila*. In some embodiments, the polypeptide comprises an amino acid sequence having at least 60%, 65%, 70%, 75%, 80%, 85%, 90%, 95%, or 98% sequence identity to SEQ ID NO:8, and the one or more modifications are relative to SEQ ID NO:8. In some embodiments, the polypeptide has an improved D-fructose C4-epimerase activity and/or improved stability compared to the polypeptide of SEQ ID NO:8. In some embodiments, the polypeptide is derived from *Rhodothermus marinus*. In some embodiments, the polypeptide comprises an amino acid sequence having at least 60%, 65%, 70%, 75%, 80%, 85%, 90%, 95%, or 98% sequence identity to SEQ ID NO:9, and the one or more modifications are relative to SEQ ID NO:9. In some embodiments, the polypeptide has an improved D-fructose C4-epimerase activity and/or improved stability compared to the polypeptide of SEQ ID NO:9. In some embodiments, the polypeptide is derived from *Methanohalobium evestigatum*. In some embodiments, the polypeptide comprises an amino acid sequence having at least 60%, 65%, 70%, 75%, 80%, 85%, 90%, 95%, or 98% sequence identity to SEQ ID NO:10, and the one or more modifications are relative to SEQ ID NO:10. In some embodiments, the polypeptide has an improved D-fructose C4-epimerase activity and/or improved stability compared to the polypeptide of SEQ ID NO:10. In some embodiments, the polypeptide is derived from *Thermoanaerobacter thermohydrosulfuricus*.

In some embodiments, the polypeptide comprises an amino acid sequence having at least 60%, 65%, 70%, 75%, 80%, 85%, 90%, 95%, or 98% sequence identity to SEQ ID NO:11, and the one or more modifications are relative to SEQ ID NO:11. In some embodiments, the polypeptide has an improved D-fructose C4-epimerase activity and/or improved stability compared to the polypeptide of SEQ ID NO:11. In some embodiments, the polypeptide is derived from *Clostridium cavendishii*. In some embodiments, the polypeptide comprises an amino acid sequence having at least 60%, 65%, 70%, 75%, 80%, 85%, 90%, 95%, or 98% sequence identity to SEQ ID NO:12, and the one or more modifications are relative to SEQ ID NO:12. In some embodiments, the polypeptide has an improved D-fructose C4-epimerase activity and/or improved stability compared to the polypeptide of SEQ ID NO:12. In some embodiments, the polypeptide is derived from *Kosmotoga olearia*. In some embodiments, the polypeptide comprises an amino acid sequence having at least 60%, 65%, 70%, 75%, 80%, 85%, 90%, 95%, or 98% sequence identity to SEQ ID NO:13, and the one or more modifications are relative to SEQ ID NO:13. In some embodiments, the polypeptide has an improved D-fructose C4-epimerase activity and/or improved stability compared to the polypeptide of SEQ ID NO:13. In some embodiments, the polypeptide is derived from *Butyricicoccus pullicaecorum*. In some embodiments, the polypeptide comprises an amino acid sequence having at least 60%, 65%, 70%, 75%, 80%, 85%, 90%, 95%, or 98% sequence identity to SEQ ID NO:14, and the one or more modifications are relative to SEQ ID NO:14. In some embodiments, the polypeptide has an improved D-fructose C4-epimerase activity and/or improved stability compared to the polypeptide of SEQ ID NO:14. In some embodiments, the polypeptide is derived from *Clostridium thermobutyricum*. In some embodiments, the polypeptide comprises an amino acid sequence having at least 60%, 65%, 70%, 75%, 80%, 85%, 90%, 95%, or 98% sequence identity to SEQ ID NO:15, and the one or more modifications are relative to SEQ ID NO:15. In some embodiments, the polypeptide has an improved D-fructose C4-epimerase activity and/or improved stability compared to the polypeptide of SEQ ID NO:15. In some embodiments, the polypeptide is derived from *Litorilinea aerophila*. In some embodiments, the polypeptide comprises an amino acid sequence having at least 60%, 65%, 70%, 75%, 80%, 85%, 90%, 95%, or 98% sequence identity to SEQ ID NO:16, and the one or more modifications are relative to SEQ ID NO:16. In some embodiments, the polypeptide has an improved D-fructose C4-epimerase activity and/or improved stability compared to the polypeptide of SEQ ID NO:16. In some embodiments, the polypeptide is derived from *Enterobacter mori*. In some embodiments, the polypeptide comprises an amino acid sequence having at least 60%, 65%, 70%, 75%, 80%, 85%, 90%, 95%, or 98% sequence identity to SEQ ID NO:17, and the one or more modifications are relative to SEQ ID NO:17. In some embodiments, the polypeptide has an improved D-fructose C4-epimerase activity and/or improved stability compared to the polypeptide of SEQ ID NO:17. In some embodiments, the polypeptide is derived from *Caldisericum exile*. In some embodiments, the polypeptide comprises an amino acid sequence having at least 60%, 65%, 70%, 75%, 80%, 85%, 90%, 95%, or 98% sequence identity to SEQ ID NO:18, and the one or more modifications are relative to SEQ ID NO:18. In some embodiments, the polypeptide has an improved D-fructose C4-epimerase activity and/or improved stability compared to the polypeptide of SEQ ID NO:18. In some embodiments, the polypeptide is derived from *Dictyoglomus thermophilum*. In some embodiments, the polypeptide comprises an amino acid sequence having at least 60%, 65%, 70%, 75%, 80%, 85%, 90%, 95%, or 98% sequence identity to SEQ ID NO:19, and the one or more modifications are relative to SEQ ID NO:19. In some embodiments, the polypeptide has an improved D-fructose C4-epimerase activity and/or improved stability compared to the polypeptide of SEQ ID NO:19. In some embodiments, the polypeptide is derived from *Rhodothermus marinus*. In some embodiments, the polypeptide comprises an amino acid sequence having at least 60%, 65%, 70%, 75%, 80%, 85%, 90%, 95%, or 98% sequence identity to SEQ ID NO:20, and the one or more modifications are relative to SEQ ID NO:20. In some embodiments, the polypeptide has an improved D-fructose C4-epimerase activity and/or improved stability compared to the polypeptide of SEQ ID NO:20.

In some embodiments, the polypeptide is derived from *Rhodothermus profundi*. In some embodiments, the polypeptide comprises an amino acid sequence having at least 60%, 65%, 70%, 75%, 80%, 85%, 90%, 95%, or 98% sequence identity to SEQ ID NO:21, and the one or more modifications are relative to SEQ ID NO:21. In some embodiments, the polypeptide has an improved D-fructose C4-epimerase activity and/or improved stability compared to the polypeptide of SEQ ID NO:21. In some embodiments, the polypeptide is derived from *Caldibacillus debilis*. In some embodiments, the polypeptide comprises an amino acid sequence having at least 60%, 65%, 70%, 75%, 80%, 85%, 90%, 95%, or 98% sequence identity to SEQ ID NO:22, and the one or more modifications are relative to SEQ ID NO:22. In some embodiments, the polypeptide has an improved D-fructose C4-epimerase activity and/or improved stability compared to the polypeptide of SEQ ID NO:22. In some embodiments, the polypeptide is derived from *Caloramator quimbayensis*. In some embodiments, the polypeptide comprises an amino acid sequence having at least 60%, 65%, 70%, 75%, 80%, 85%, 90%, 95%, or 98% sequence identity to SEQ ID NO:23, and the one or more modifications are relative to SEQ ID NO:23. In some embodiments, the polypeptide has an improved D-fructose C4-epimerase activity and/or improved stability compared to the polypeptide of SEQ ID NO:23.

In some embodiments, the polypeptide is derived from *Methanosalsum zhilinae*. In some embodiments, the polypeptide comprises an amino acid sequence having at least 60%, 65%, 70%, 75%, 80%, 85%, 90%, 95%, or 98% sequence identity to SEQ ID NO:321, and the one or more modifications are relative to SEQ ID NO:321. In some embodiments, the polypeptide has an improved D-fructose C4-epimerase activity and/or improved stability compared to the polypeptide of SEQ ID NO:321. In some embodiments, the polypeptide is derived from *Pseudothermotoga thermarum*. In some embodiments, the polypeptide comprises an amino acid sequence having at least 60%, 65%, 70%, 75%, 80%, 85%, 90%, 95%, or 98% sequence identity to SEQ ID NO:322, and the one or more modifications are relative to SEQ ID NO:322. In some embodiments, the polypeptide has an improved D-fructose C4-epimerase activity and/or improved stability compared to the polypeptide of SEQ ID NO:322. In some embodiments, the polypeptide is derived from *Pseudothermotoga hypogea*. In some embodiments, the polypeptide comprises an amino acid sequence having at least 60%, 65%, 70%, 75%, 80%, 85%, 90%, 95%, or 98% sequence identity to SEQ ID NO:323, and the one or more modifications are relative to SEQ ID NO:323. In some embodiments, the polypeptide has an improved D-fructose C4-epimerase activity and/or improved stability compared to the polypeptide of SEQ ID NO:323. In some embodiments, the polypeptide is derived from *Pseudothermotoga lettingae*. In some embodiments, the polypeptide comprises an amino acid sequence having at least 60%, 65%, 70%, 75%, 80%, 85%, 90%, 95%, or 98% sequence identity to SEQ ID NO:324, and the one or more modifications are relative to SEQ ID NO:324. In some embodiments, the polypeptide has an improved D-fructose C4-epimerase activity and/or improved stability compared to the polypeptide of SEQ ID NO:324. In some embodiments, the polypeptide is derived from *Rhodothermus marinus*. In some embodiments, the polypeptide comprises an amino acid sequence having at least 60%, 65%, 70%, 75%, 80%, 85%, 90%, 95%, or 98% sequence identity to SEQ ID NO:325, and the one or more modifications are relative to SEQ ID NO:325. In some embodiments, the polypeptide has an improved D-fructose C4-epimerase activity and/or improved stability compared to the polypeptide of SEQ ID NO:325. In some embodiments, the polypeptide is derived from *Geosporobacter subterraneus*. In some embodiments, the polypeptide comprises an amino acid sequence having at least 60%, 65%, 70%, 75%, 80%, 85%, 90%, 95%, or 98% sequence identity to SEQ ID NO:326, and the one or more modifications are relative to SEQ ID NO:326. In some embodiments, the polypeptide has an improved D-fructose C4-epimerase activity and/or improved stability compared to the polypeptide of SEQ ID NO:326. In some embodiments, the polypeptide is derived from *Melioribacter roseus. In some embodiments, the polypeptide comprises an amino acid sequence having at least* 60%, 65%, 70%, 75%, 80%, 85%, 90%, 95%, or 98% sequence identity to SEQ ID NO:327, and the one or more modifications are relative to SEQ ID NO:327. In some embodiments, the polypeptide has an improved D-fructose C4-epimerase activity and/or improved stability compared to the polypeptide of SEQ ID NO:327. In some embodiments, the polypeptide is derived from *Lysinibacillus sphaericus*. In some embodiments, the polypeptide comprises an amino acid sequence having at least 60%, 65%, 70%, 75%, 80%, 85%, 90%, 95%, or 98% sequence identity to SEQ ID NO:328, and the one or more modifications are relative to SEQ ID NO:328. In some embodiments, the polypeptide has an improved D-fructose C4-epimerase activity and/or improved stability compared to the polypeptide of SEQ ID NO:328. In some embodiments, the polypeptide is derived from *Clostridium stercorarium*. In some embodiments, the polypeptide comprises an amino acid sequence having at least 60%, 65%, 70%, 75%, 80%, 85%, 90%, 95%, or 98% sequence identity to SEQ ID NO:329, and the one or more modifications are relative to SEQ ID NO:329. In some embodiments, the polypeptide has an improved D-fructose C4-epimerase activity and/or improved stability compared to the polypeptide of SEQ ID NO:329. In some embodiments, the polypeptide is derived from *Truepera radiovictrix*. In some embodiments, the polypeptide comprises an amino acid sequence having at least 60%, 65%, 70%, 75%, 80%, 85%, 90%, 95%, or 98% sequence identity to SEQ ID NO:330, and the one or more modifications are relative to SEQ ID NO:330. In some embodiments, the polypeptide has an improved D-fructose C4-epimerase activity and/or improved stability compared to the polypeptide of SEQ ID NO:330. In some embodiments, the polypeptide is derived from *Dictyoglomus turgidum*. In some embodiments, the polypeptide comprises an amino acid sequence having at least 60%, 65%, 70%, 75%, 80%, 85%, 90%, 95%, or 98% sequence identity to SEQ ID NO:331, and the one or more modifications are relative to SEQ ID NO:331. In some embodiments, the polypeptide has an improved D-fructose C4-epimerase activity and/or improved stability compared to the polypeptide of SEQ ID NO:331. In some embodiments, the polypeptide is derived from *Caldilinea aerophila*. In some embodiments, the polypeptide comprises an amino acid sequence having at least 60%, 65%, 70%, 75%, 80%, 85%, 90%, 95%, or 98% sequence identity to SEQ ID NO:332, and the one or more modifications are relative to SEQ ID NO:332. In some embodiments, the polypeptide has an improved D-fructose C4-epimerase activity and/or improved stability compared to the polypeptide of SEQ ID NO:332. In some embodiments, the polypeptide is derived from *Thermoflexus hugenholtzii*. In some embodiments, the polypeptide comprises an amino acid sequence having at least 60%, 65%, 70%, 75%, 80%, 85%, 90%, 95%, or 98% sequence identity to SEQ ID NO:333, and the one or more modifications are relative to SEQ ID NO:333. In some embodiments, the polypeptide has an improved D-fructose C4-epimerase activity and/or improved stability compared to the polypeptide of SEQ ID NO:333. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:334, and the one or more modifications are relative to SEQ ID NO:334. In some embodiments, the polypeptide has an improved D-fructose C4-epimerase activity and/or improved stability compared to the polypeptide of SEQ ID NO:334. In some embodiments, the polypeptide is derived from *Petrotoga mobilis*. In some embodiments, the polypeptide comprises an amino acid sequence having at least 60%, 65%, 70%, 75%, 80%, 85%, 90%, 95%, or 98% sequence identity to SEQ ID NO:335, and the one or more modifications are relative to SEQ ID NO:335. In some embodiments, the polypeptide has an improved D-fructose C4-epimerase activity and/or improved stability compared to the polypeptide of SEQ ID NO:335. In some embodiments, the polypeptide is derived from *Spirochaeta thermophila*. In some embodiments, the polypeptide comprises an amino acid sequence having at least 60%, 65%, 70%, 75%, 80%, 85%, 90%, 95%, or 98% sequence identity to SEQ ID NO:336, and the one or more modifications are relative to SEQ ID NO:336. In some embodiments, the polypeptide has an improved D-fructose C4-epimerase activity and/or improved stability compared to the polypeptide of SEQ ID NO:336. In some embodiments, the polypeptide is derived from *Thermofilum pendens*.

In some embodiments, the polypeptide comprises an amino acid sequence having at least 60%, 65%, 70%, 75%, 80%, 85%, 90%, 95%, or 98% sequence identity to SEQ ID NO:337, and the one or more modifications are relative to SEQ ID NO:337. In some embodiments, the polypeptide has an improved D-fructose C4-epimerase activity and/or improved stability compared to the polypeptide of SEQ ID NO:337. In some embodiments, the polypeptide is derived from *Rhodothermus marinus*. In some embodiments, the polypeptide comprises an amino acid sequence having at least 60%, 65%, 70%, 75%, 80%, 85%, 90%, 95%, or 98% sequence identity to SEQ ID NO:338, and the one or more modifications are relative to SEQ ID NO:338. In some embodiments, the polypeptide has an improved D-fructose C4-epimerase activity and/or improved stability compared to the polypeptide of SEQ ID NO:338. In some embodiments, the polypeptide is derived from *Dictyoglomus thermophilum*. In some embodiments, the polypeptide comprises an amino acid sequence having at least 60%, 65%, 70%, 75%, 80%, 85%, 90%, 95%, or 98% sequence identity to SEQ ID NO:339, and the one or more modifications are relative to SEQ ID NO:339. In some embodiments, the polypeptide has an improved D-fructose C4-epimerase activity and/or improved stability compared to the polypeptide of SEQ ID NO:339. In some embodiments, the polypeptide is derived from *Thermoanaerobacter siderophilus*. In some embodiments, the polypeptide comprises an amino acid sequence having at least 60%, 65%, 70%, 75%, 80%, 85%, 90%, 95%, or 98% sequence identity to SEQ ID NO:340, and the one or more modifications are relative to SEQ ID NO:340. In some embodiments, the polypeptide has an improved D-fructose C4-epimerase activity and/or improved stability compared to the polypeptide of SEQ ID NO:340.

In some embodiments, the polypeptide is derived from *Thermoanaerobacter mathranii*. In some embodiments, the polypeptide comprises an amino acid sequence having at least 60%, 65%, 70%, 75%, 80%, 85%, 90%, 95%, or 98% sequence identity to SEQ ID NO:341, and the one or more modifications are relative to SEQ ID NO:341. In some embodiments, the polypeptide has an improved D-fructose C4-epimerase activity and/or improved stability compared to the polypeptide of SEQ ID NO:341. In some embodiments, the polypeptide is derived from *Thermoanaerobacter italicus*. In some embodiments, the polypeptide comprises an amino acid sequence having at least 60%, 65%, 70%, 75%, 80%, 85%, 90%, 95%, or 98% sequence identity to SEQ ID NO:342, and the one or more modifications are relative to SEQ ID NO:342. In some embodiments, the polypeptide has an improved D-fructose C4-epimerase activity and/or improved stability compared to the polypeptide of SEQ ID NO:342. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:343, and the one or more modifications are relative to SEQ ID NO:343. In some embodiments, the polypeptide has an improved D-fructose C4-epimerase activity and/or improved stability compared to the polypeptide of SEQ ID NO:343. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:344, and the one or more modifications are relative to SEQ ID NO:344. In some embodiments, the polypeptide has an improved D-fructose C4-epimerase activity and/or improved stability compared to the polypeptide of SEQ ID NO:344. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:345, and the one or more modifications are relative to SEQ ID NO:345. In some embodiments, the polypeptide has an improved D-fructose C4-epimerase activity and/or improved stability compared to the polypeptide of SEQ ID NO:345. In some embodiments, the polypeptide is derived from *Thermoanaerobacterium thermosaccharolyticum*. In some embodiments, the polypeptide comprises an amino acid sequence having at least 60%, 65%, 70%, 75%, 80%, 85%, 90%, 95%, or 98% sequence identity to SEQ ID NO:346, and the one or more modifications are relative to SEQ ID NO:346. In some embodiments, the polypeptide has an improved D-fructose C4-epimerase activity and/or improved stability compared to the polypeptide of SEQ ID NO:346. In some embodiments, the polypeptide is derived from *Thermoanaerobacterium xylanolyticum*. In some embodiments, the polypeptide comprises an amino acid sequence having at least 60%, 65%, 70%, 75%, 80%, 85%, 90%, 95%, or 98% sequence identity to SEQ ID NO:347, and the one or more modifications are relative to SEQ ID NO:347. In some embodiments, the polypeptide has an improved D-fructose C4-epimerase activity and/or improved stability compared to the polypeptide of SEQ ID NO:347. In some embodiments, the polypeptide is derived from *Petrotoga mobilis*. In some embodiments, the polypeptide comprises an amino acid sequence having at least 60%, 65%, 70%, 75%, 80%, 85%, 90%, 95%, or 98% sequence identity to SEQ ID NO:348, and the one or more modifications are relative to SEQ ID NO:348. In some embodiments, the polypeptide has an improved D-fructose C4-epimerase activity and/or improved stability compared to the polypeptide of SEQ ID NO:348. In some embodiments, the polypeptide is derived from *Thermoanaerobacterium saccharolyticum*. In some embodiments, the polypeptide comprises an amino acid sequence having at least 60%, 65%, 70%, 75%, 80%, 85%, 90%, 95%, or 98% sequence identity to SEQ ID NO:349, and the one or more modifications are relative to SEQ ID NO:349. In some embodiments, the polypeptide has an improved D-fructose C4-epimerase activity and/or improved stability compared to the polypeptide of SEQ ID NO:349. In some embodiments, the polypeptide is derived from *Petrotoga mobilis*. In some embodiments, the polypeptide comprises an amino acid sequence having at least 60%, 65%, 70%, 75%, 80%, 85%, 90%, 95%, or 98% sequence identity to SEQ ID NO:350, and the one or more modifications are relative to SEQ ID NO:350. In some embodiments, the polypeptide has an improved D-fructose C4-epimerase activity and/or improved stability compared to the polypeptide of SEQ ID NO:350. In some embodiments, the polypeptide is derived from *Spirochaeta thermophila*.

In some embodiments, the polypeptide comprises an amino acid sequence having at least 60%, 65%, 70%, 75%, 80%, 85%, 90%, 95%, or 98% sequence identity to SEQ ID NO:351, and the one or more modifications are relative to SEQ ID NO:351. In some embodiments, the polypeptide has an improved D-fructose C4-epimerase activity and/or improved stability compared to the polypeptide of SEQ ID NO:351. In some embodiments, the polypeptide is derived from *Ignisphaera aggregans*. In some embodiments, the polypeptide comprises an amino acid sequence having at least 60%, 65%, 70%, 75%, 80%, 85%, 90%, 95%, or 98% sequence identity to SEQ ID NO:352, and the one or more modifications are relative to SEQ ID NO:352. In some embodiments, the polypeptide has an improved D-fructose C4-epimerase activity and/or improved stability compared to the polypeptide of SEQ ID NO:352. In some embodiments, the polypeptide is derived from *Thermotoga maritima*. In some embodiments, the polypeptide comprises an amino acid sequence having at least 60%, 65%, 70%, 75%, 80%, 85%, 90%, 95%, or 98% sequence identity to SEQ ID NO:353, and the one or more modifications are relative to SEQ ID NO:353. In some embodiments, the polypeptide has an improved D-fructose C4-epimerase activity and/or improved stability compared to the polypeptide of SEQ ID NO:353. In some embodiments, the polypeptide is derived from *Caldanaerobacter subterraneus*. In some embodiments, the polypeptide comprises an amino acid sequence having at least 60%, 65%, 70%, 75%, 80%, 85%, 90%, 95%, or 98% sequence identity to SEQ ID NO:354, and the one or more modifications are relative to SEQ ID NO:354. In some embodiments, the polypeptide has an improved D-fructose C4-epimerase activity and/or improved stability compared to the polypeptide of SEQ ID NO:354. In some embodiments, the polypeptide is derived from *Mesotoga infera*. In some embodiments, the polypeptide comprises an amino acid sequence having at least 60%, 65%, 70%, 75%, 80%, 85%, 90%, 95%, or 98% sequence identity to SEQ ID NO:355, and the one or more modifications are relative to SEQ ID NO:355. In some embodiments, the polypeptide has an improved D-fructose C4-epimerase activity and/or improved stability compared to the polypeptide of SEQ ID NO:355. In some embodiments, the polypeptide is derived from *Thermosinus carboxydivorans*. In some embodiments, the polypeptide comprises an amino acid sequence having at least 60%, 65%, 70%, 75%, 80%, 85%, 90%, 95%, or 98% sequence identity to SEQ ID NO:356, and the one or more modifications are relative to SEQ ID NO:356. In some embodiments, the polypeptide has an improved D-fructose C4-epimerase activity and/or improved stability compared to the polypeptide of SEQ ID NO:356. In some embodiments, the polypeptide is derived from *Halanaerobium congolense*. In some embodiments, the polypeptide comprises an amino acid sequence having at least 60%, 65%, 70%, 75%, 80%, 85%, 90%, 95%, or 98% sequence identity to SEQ ID NO:357, and the one or more modifications are relative to SEQ ID NO:357. In some embodiments, the polypeptide has an improved D-fructose C4-epimerase activity and/or improved stability compared to the polypeptide of SEQ ID NO:357. In some embodiments, the polypeptide is derived from *Halanaerobium congolense*. In some embodiments, the polypeptide comprises an amino acid sequence having at least 60%, 65%, 70%, 75%, 80%, 85%, 90%, 95%, or 98% sequence identity to SEQ ID NO:358, and the one or more modifications are relative to SEQ ID NO:358. In some embodiments, the polypeptide has an improved D-fructose C4-epimerase activity and/or improved stability compared to the polypeptide of SEQ ID NO:358. In some embodiments, the polypeptide is derived from *Halanaerobium saccharolyticum*. In some embodiments, the polypeptide comprises an amino acid sequence having at least 60%, 65%, 70%, 75%, 80%, 85%, 90%, 95%, or 98% sequence identity to SEQ ID NO:359, and the one or more modifications are relative to SEQ ID NO:359. In some embodiments, the polypeptide has an improved D-fructose C4-epimerase activity and/or improved stability compared to the polypeptide of SEQ ID NO:359. In some embodiments, the polypeptide is derived from *Gracilibacillus halophilus*. In some embodiments, the polypeptide comprises an amino acid sequence having at least 60%, 65%, 70%, 75%, 80%, 85%, 90%, 95%, or 98% sequence identity to SEQ ID NO:360, and the one or more modifications are relative to SEQ ID NO:360. In some embodiments, the polypeptide has an improved D-fructose C4-epimerase activity and/or improved stability compared to the polypeptide of SEQ ID NO:360.

In some embodiments, the polypeptide is derived from *Caldanaerobacter subterraneus*. In some embodiments, the polypeptide comprises an amino acid sequence having at least 60%, 65%, 70%, 75%, 80%, 85%, 90%, 95%, or 98% sequence identity to SEQ ID NO:361, and the one or more modifications are relative to SEQ ID NO:361. In some embodiments, the polypeptide has an improved D-fructose C4-epimerase activity and/or improved stability compared to the polypeptide of SEQ ID NO:361. In some embodiments, the polypeptide is derived from *Litorilinea aerophila*. In some embodiments, the polypeptide comprises an amino acid sequence having at least 60%, 65%, 70%, 75%, 80%, 85%, 90%, 95%, or 98% sequence identity to SEQ ID NO:362, and the one or more modifications are relative to SEQ ID NO:362. In some embodiments, the polypeptide has an improved D-fructose C4-epimerase activity and/or improved stability compared to the polypeptide of SEQ ID NO:362. In some embodiments, the polypeptide is derived from *Caldanaerobacter subterraneus*. In some embodiments, the polypeptide comprises an amino acid sequence having at least 60%, 65%, 70%, 75%, 80%, 85%, 90%, 95%, or 98% sequence identity to SEQ ID NO:363, and the one or more modifications are relative to SEQ ID NO:363. In some embodiments, the polypeptide has an improved D-fructose C4-epimerase activity and/or improved stability compared to the polypeptide of SEQ ID NO:363. In some embodiments, the polypeptide is derived from *Caldanaerobacter subterraneus*. In some embodiments, the polypeptide comprises an amino acid sequence having at least 60%, 65%, 70%, 75%, 80%, 85%, 90%, 95%, or 98% sequence identity to SEQ ID NO:364, and the one or more modifications are relative to SEQ ID NO:364. In some embodiments, the polypeptide has an improved D-fructose C4-epimerase activity and/or improved stability compared to the polypeptide of SEQ ID NO:364. In some embodiments, the polypeptide is derived from *Caldicoprobacter faecalis*. In some embodiments, the polypeptide comprises an amino acid sequence having at least 60%, 65%, 70%, 75%, 80%, 85%, 90%, 95%, or 98% sequence identity to SEQ ID NO:365, and the one or more modifications are relative to SEQ ID NO:365. In some embodiments, the polypeptide has an improved D-fructose C4-epimerase activity and/or improved stability compared to the polypeptide of SEQ ID NO:365. In some embodiments, the polypeptide is derived from *Thermoanaerobacter uzonensis*. In some embodiments, the polypeptide comprises an amino acid sequence having at least 60%, 65%, 70%, 75%, 80%, 85%, 90%, 95%, or 98% sequence identity to SEQ ID NO:366, and the one or more modifications are relative to SEQ ID NO:366. In some embodiments, the polypeptide has an improved D-fructose C4-epimerase activity and/or improved stability compared to the polypeptide of SEQ ID NO:366. In some embodiments, the polypeptide is derived from *Lactobacillus ingluviei*. In some embodiments, the polypeptide comprises an amino acid sequence having at least 60%, 65%, 70%, 75%, 80%, 85%, 90%, 95%, or 98% sequence identity to SEQ ID NO:367, and the one or more modifications are relative to SEQ ID NO:367. In some embodiments, the polypeptide has an improved D-fructose C4-epimerase activity and/or improved stability compared to the polypeptide of SEQ ID NO:367. In some embodiments, the polypeptide is derived from *Petrotoga mexicana*. In some embodiments, the polypeptide comprises an amino acid sequence having at least 60%, 65%, 70%, 75%, 80%, 85%, 90%, 95%, or 98% sequence identity to SEQ ID NO:368, and the one or more modifications are relative to SEQ ID NO:368. In some embodiments, the polypeptide has an improved D-fructose C4-epimerase activity and/or improved stability compared to the polypeptide of SEQ ID NO:368. In some embodiments, the polypeptide is derived from *Defluviitoga tunisiensis*. In some embodiments, the polypeptide comprises an amino acid sequence having at least 60%, 65%, 70%, 75%, 80%, 85%, 90%, 95%, or 98% sequence identity to SEQ ID NO:369, and the one or more modifications are relative to SEQ ID NO:369. In some embodiments, the polypeptide has an improved D-fructose C4-epimerase activity and/or improved stability compared to the polypeptide of SEQ ID NO:369. In some embodiments, the polypeptide is derived from *Petrotoga miotherma*. In some embodiments, the polypeptide comprises an amino acid sequence having at least 60%, 65%, 70%, 75%, 80%, 85%, 90%, 95%, or 98% sequence identity to SEQ ID NO:370, and the one or more modifications are relative to SEQ ID NO:370. In some embodiments, the polypeptide has an improved D-fructose C4-epimerase activity and/or improved stability compared to the polypeptide of SEQ ID NO:370. In some embodiments, the polypeptide is derived from *Petrotoga olearia*. In some embodiments, the polypeptide comprises an amino acid sequence having at least 60%, 65%, 70%, 75%, 80%, 85%, 90%, 95%, or 98% sequence identity to SEQ ID NO:371, and the one or more modifications are relative to SEQ ID NO:371. In some embodiments, the polypeptide has an improved D-fructose C4-epimerase activity and/or improved stability compared to the polypeptide of SEQ ID NO:371. In some embodiments, the polypeptide is derived from *Thermophagus xiamenensis*. In some embodiments, the polypeptide comprises an amino acid sequence having at least 60%, 65%, 70%, 75%, 80, 85%, 90, 95%, or 98% sequence identity to SEQ ID NO:372, and the one or more modifications are relative to SEQ ID NO:372. In some embodiments, the polypeptide has an improved D-fructose C4-epimerase activity and/or improved stability compared to the polypeptide of SEQ ID NO:372. In some embodiments, the polypeptide is derived from *Treponema caldarium*. In some embodiments, the polypeptide comprises an amino acid sequence having at least 60%, 65%, 70%, 75%, 80%, 85%, 90%, 95%, or 98% sequence identity to SEQ ID NO:373, and the one or more modifications are relative to SEQ ID NO:373. In some embodiments, the polypeptide has an improved D-fructose C4-epimerase activity and/or improved stability compared to the polypeptide of SEQ ID NO:373. In some embodiments, the polypeptide is derived from *Thermofilum uzonense*.

TABLE 1

Modified Polypeptides

| SEQ NO. | Plasmid ID | Parent Wild Type SEQ ID NO. | Mutation Position (correspond to SEQ ID NO.: 2) | Mutation Position (correspond to SEQ ID NO.: 6) |
|---|---|---|---|---|
| 24 | pA07199 | 2 | C28A | C17A |
| 25 | pA07200 | 2 | E52A | E41A |
| 26 | pA07201 | 2 | E52Q | E41Q |
| 27 | pA07202 | 2 | Y64A | Y53A |
| 28 | pA07203 | 2 | Y64F | Y53F |
| 29 | pA07204 | 2 | D95A | D84A |
| 30 | pA07205 | 2 | D95N | D84N |
| 31 | pA07206 | 2 | H96A | H85A |
| 32 | pA07207 | 2 | H130A | H119A |
| 33 | pA07208 | 2 | D132A | D121A |
| 34 | pA07209 | 2 | D132N | D121N |
| 35 | pA07210 | 2 | E178A | D167A |
| 36 | pA07211 | 2 | E178Q | D167Q |
| 37 | pA07212 | 2 | E263A | E245A |
| 38 | pA07213 | 2 | E263Q | E245Q |
| 39 | pA07214 | 2 | H265A | H247A |
| 40 | pA07215 | 2 | D268A | D250A |
| 41 | pA07216 | 2 | D268N | D250N |
| 42 | pA07217 | 2 | G289A | G271A |
| 43 | pA07218 | 2 | G289D | G271D |
| 44 | pA07219 | 2 | Y361A | Y340A |
| 45 | pA07220 | 2 | Y361F | Y340F |

TABLE 2

Modified Polypeptides

| SEQ NO. | Plasmid ID | Parent Wild Type SEQ ID NO. | Mutation Position(s) (correspond to SEQ ID NO.: 6) |
|---|---|---|---|
| 46 | pA12584 | 6 | E75P, S96A, P97E, S113A, P160A, A188T, I189L, S191V, Y195A, N197K, V199L, G232E, L234M, G246A, A253D, N259A, N333S, S374Q |
| 47 | pA12585 | 6 | P97E, S113A, Y135L, R143V, E147K, V182P, S191Y, V199I, G232E, G246A, G281A, L328F, S403A |
| 48 | pA12586 | 6 | K72L, S96A, P97E, S113A, R143A, T152A, P160A, A188M, S191T, G232K, M349K |
| 49 | pA12587 | 6 | S96A, P97E, S113A, R143V, S191T, G232D, A253S, S374Q, M383L |
| 50 | pA12588 | 6 | S21P, E75P, S96E, P97E, S113A, I189L, S191I, G232E, I233L, G281A, M349K |
| 51 | pA12589 | 6 | S21P, S96A, G232E, M349K, V350A |
| 52 | pA12590 | 6 | S96A, P97E, V182P, S191T, G232E, S286A, R325E |
| 53 | pA12591 | 6 | S96A, P97E, S113A, P160E, V182P, S191I, D198K, G246A |
| 54 | pA12592 | 6 | E75P, P97E, V182P, N197K, G246A, A253S, G281A, S286V, M349K, Y372P, S403Y |
| 55 | pA12593 | 6 | E75P, S113A, F146C, S190D, Y344H, Y372P |
| 56 | pA12594 | 6 | E147R, V182P, S191L, G281A, S374Q |
| 57 | pA12595 | 6 | S21P, P97E, Y135L, E345P |
| 58 | pA12596 | 6 | I202A, Y372P |
| 59 | pA12597 | 6 | E75P, P97E, Y135P, S191L, N197E |
| 60 | pA12598 | 6 | S113A, N333S |
| 61 | pA12599 | 6 | R143A, V182P, Y344H, E345P |
| 62 | pA12600 | 6 | S54T, S96A, R143A, A188M, S191V, G208A, G232E, E240T, A253S, R266V, S286A, R325E, I330L, E345P, F376R |
| 63 | pA12601 | 6 | S54T, S96A, P97E, N101E, S113A, R143A, G232E, G246A, G281A, E295P, R296E, F358L, E360D, M383L |
| 64 | pA12602 | 6 | K34R, S54T, S96A, S113A, A188T, N197K, G246A, N287D, V350A |
| 65 | pA12603 | 6 | S21P, S54T, S96A, S113A, R143A, S191I, M349R |
| 66 | pA12604 | 6 | K34R, P97E, S113A, G232E |
| 67 | pA12605 | 6 | S54T, E75P, S96A, P97E, S113A, L126C, S127A, R143V, V182P, A188T, S191T, N197K, V199H, G208A, G232E, G246C, A253S, R266V, G281A, N287D, E345P, V350A, E360D, V362I, F376R |
| 68 | pA12606 | 6 | S54T, E75P, S96A, S113A, E140I, E147R, A188M, S191T, N259W, E360D, S374A, N385P |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| 69 | pA12607 | 6 | S21P, S54T, S96A, P97E, V182P, G208A, E240T, S374C |
| 70 | pA12608 | 6 | S21P, S27A, S54T, K78R, P97D, T98E, N101E, S113A, L126C, S127A, E147R, V182P, A188T, S191T, N197E, V199H, I202M, I215V, Y219H, G232D, E240T, A273W, G281A, Y344H, E345P, V350A, D363P, S374C |
| 71 | pA12609 | 6 | S27A, K34D, Y37P, S54T, E75P, S113A, L126C, S127A, F146C, Y219H, N259W, R266V, N333S, E345P, V350A, D363P |
| 72 | pA12610 | 6 | S21P, S113A, S127A, E151R, A188T, G232D, E240T, Y344H, V350A, F358L, F366L |
| 73 | pA12611 | 6 | S21P, Y37P, T98E, F146C, A188T, Y219H, N259W, D363P |
| 74 | pA12612 | 6 | Y22W, S54T, L126C, E151R, V182P, A188T, Y219H, G232E, E345P, V350A, F358L |
| 75 | pA12613 | 6 | P97E, N101E, S113A, S127A, V199H, Y219H, E240T, N259W, Y344H |
| 76 | pA12614 | 6 | S27A, S54T, E75P, T98E, N101E, S113A, A188T, E240T, E297G, V350A |
| 77 | pA12615 | 6 | Y14F, P97E, F110Y, Y115F, Y135M, R143A, E147K, S191Y, G246A, G281A, L328F, M349K, S403A |
| 78 | pA12616 | 6 | P97E, S113A, V182P, A188F, G232E, V237L, A253S, M349T, M383L |
| 79 | pA12617 | 6 | S96A, P97E, S113A, E147K, P160A, V182A, S191I, G232D, G246A, S286A, R325E, M349K |
| 80 | pA12618 | 6 | S21P, E75P, R143A, I148V, S191I, V244L, E345P |
| 81 | pA12619 | 6 | S54T, K72L, P97E, A188M, S191T, D198K, G232E, R325E, S403A |
| 82 | pA12620 | 6 | S19N, K72V, S96A, P97E, S190D, S191T, N197K, G232E, G246A, G281A, Y372P, S403Y |
| 83 | pA12621 | 6 | S21K, E75P, P97E, S113A, R143V, S191T, V199I, G208A, G232E, V244L, G246A, N259A, G281A, S286A, E345P, Y372P, S374Q |
| 84 | pA12622 | 6 | S27A, E75P, Y135L, E147R, V182P, S190E, S191T, E240T, Y344H, M349K, S374Q |
| 85 | pA12623 | 6 | S21P, S27A, P97E, S113A, Y135T, L192F, Y219D, G281A, S286A, Y344H, E345P, F376E |
| 86 | pA12624 | 6 | S27A, E75P, S96A, G232D, S286A, E345P, Y372P |
| 87 | pA12625 | 6 | S27A, N101E, S113A, Y135P, S187E, S190E, Y344H |
| 88 | pA12626 | 6 | S96A, Y135L, E151R, V182P, S190D, G232D, K365R |
| 89 | pA12627 | 6 | S27A, E75P, S187R, G281A |
| 90 | pA12628 | 6 | S27A, S54T, S96A, F146C, V182P, Y344H, V350A, S403A |
| 91 | pA12629 | 6 | S21P, Y22W, S54T, E75P, S113A, V182P, N197E, E240T, G246V, S286A, R325E, I330L, Y344H, E345P, F376R |
| 92 | pA12630 | 6 | S21P, E75P, S96A, N101E, S127A, A188T, S191T, N197E, V199H, N201R, G208A, G232E, E240T, G246C, S286A, N287D, R296E, N333A, M349R, S374C |
| 93 | pA12631 | 6 | S27A, S113A, E140I, R143A, V182P, A188M, S191T, G232E, L242W, G246A, A253P, N259W, G281A, R325E, N333A, V350A, E360D, R379C, N385P |
| 94 | pA12632 | 6 | E75P, S96A, P97E, S127A, R143V, V182P, S191T, V199C, V237L, Y344H, M349A, F358L |
| 95 | pA12633 | 6 | S21P, S27A, P97E, S113A, S127A, T152A, A188M, S191V, G232E, R266V, A273W, S286A, N287D, N333A, E345P, M349K, V362I |
| 96 | pA12634 | 6 | S54T, E75P, S96A, P97E, A188T, L213M, G232E, Y344H, S374C |
| 97 | pA12635 | 6 | S54T, P97E, S127A, R143A, E345P, M349K, V350A |
| 98 | pA12636 | 6 | Y22W, K34D, Y37P, S54T, E75P, S113A, F146C, A188T, G232D, R266A, S286A, R296E, Y344H, E345P, K393H |
| 99 | pA12637 | 6 | S21P, Y22W, S27A, D36T, S54T, E75P, P97E, T98E, S127A, E147R, S191L, N197E, V199H, G232E, D241P, Y255E, N287D, Y344H, V350A, K365T, S374C |
| 100 | pA12638 | 6 | S21P, S27A, E75P, P97E, N101E, S113A, E147K, V182P, A188T, S190E, Y219H, Y255D, G281A, E343N, Y344H, V350A, E360D, K393H |
| 101 | pA12639 | 6 | Y22W, D36S, E75P, P97D, N101E, S113A, L126C, S127A, V182P, N197E, Y219H, D241P, A253S, Y255D, S286A, R296E, E343N, E345P, K365T, F376R |
| 102 | pA12640 | 6 | S54T, K62R, P97E, S113A, G232E, E240T, N259W, S286A, E297G, F376H |
| 103 | pA12641 | 6 | V13I, S21P, S27A, S54T, E75P, P97E, T98E, L126C, F146C, E147R, A188T, S190E, I202A, D241P, N259W, G281A, R296E, R303E, W331H, E345P, M349A, V350A, E360D, S374A, F376H |
| 104 | pA12642 | 6 | S27A, S96A, T98E, N101E, L126C, Y219H, E240T, A253T, R296Y, Y344H, E345P, M349A, F366L |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| 105 | pA12643 | 6 | S27A, G35D, K72L, E75P, P97E, F110Y, S113A, Y135M, E147K, S191L, N197K, G232E, G281A, L284K, I292L, L328F, M349K, Y372P, F376K |
| 106 | pA12644 | 6 | P97E, Y135K, R143V, G232D, V237L, S286A, D290K, Y344H, M349T, M383L |
| 107 | pA12645 | 6 | S27A, K72L, E75P, S191V, L192F, N197K, V199L, I211V, G232E, S286A, S374Q |
| 108 | pA12646 | 6 | S21P, S27A, S54T, K72V, K78R, P97E, S190D, S191I, D198K, S286A, R325E, M349K |
| 109 | pA12647 | 6 | S27A, S113A, Y135L, A188M, S190D, S191T, N197E, R325E, F376Q |
| 110 | pA12648 | 6 | S27A, N101E, S113A, Y135L, E147K, I148V, L192F, N197K, E240T, A253D, Y255K, N259D, G281A, S286A, D290K, E345P, M349C, K365R, S374Q |
| 111 | pA12649 | 6 | S21P, S27A, S54T, E75P, P97E, N101E, Y135L, S187E, S190E, S191Y, N197E, V199L, G232D, A253D, R296D, Y344H, E345P, K365R |
| 112 | pA12650 | 6 | S21E, S54T, S96A, D105E, S113A, Y135L, V182P, S190E, S191A, E240T, A253T, S286A, K365R |
| 113 | pA12651 | 6 | S21E, S54T, E75P, N101E, S113A, Y135M, E147K, S190E, G232P, Y344H, M349K, K365R, S403A |
| 114 | pA12652 | 6 | S54T, E75P, P97E, N101E, S113A, Y135T, I148V, S187E, S190E, L192F, Y219D, G232D, L234A, S286A, E297K, E327R, V350A, K353R |
| 115 | pA12653 | 6 | S27A, S54T, E75P, P97E, T98E, N101A, S113A, S127A, S191V, N197K, V199L, L213M, G232E, G246A, N259W, S286A, N287D, K321H, N333S, Y344H, E345P, M349A, V350A |
| 116 | pA12654 | 6 | S21P, S27C, S54T, E75P, T98E, S113A, S127A, V182P, A188F, S191V, G232E, A253S, Y255E, S286D, D290K, E291D, N333S, Y344H, V350A, F358L, V362I, F366L, S374T |
| 117 | pA12655 | 6 | S21P, G35D, S54T, P97E, Y135Q, R143A, A188T, N197K, G232E, G246A, G281A, N287D, E295P, L328F, N333A, M349A, Y372P |
| 118 | pA12656 | 6 | S21P, E75P, P97E, T98E, N101A, R143V, V182P, G208A, E240T, G246V, A253S, R266V, S286A, K321H, R325D, Y344H, F366L |
| 119 | pA12657 | 6 | Y22W, S27A, S54T, E75P, S96A, P97E, N101A, S113A, S127A, R143A, G232E, E240T, V244L, S286D, M349R, V350A |
| 120 | pA12658 | 6 | S21P, D36S, S54T, N63R, E75P, D93H, P97D, N101E, Y115F, L126C, S127A, Y135N, E147R, V182P, S187R, A188T, V199H, Y219H, G246A, Y255E, N259W, R266A, G281A, N287D, K324D, W331H, N333S, Y344H, M349A, E360D, M383L, K393H, S403A |
| 121 | pA12659 | 6 | Y22W, S27A, K62R, N63R, S96A, P97E, T98E, D105E, S113A, L126C, S127A, E151R, V182P, S187K, S190E, S191A, N197A, G232E, E240T, Y255D, S286A, R296Y, E297R, R303E, K324D, E343N, E345P, M349A, V350A, F358L, F366L |
| 122 | pA12660 | 6 | V131, S21P, K34D, Y37P, N63R, M66Y, E75P, P97D, T98E, L126C, V179I, S190E, S191L, L192H, N197K, Y219H, G232D, N259W, R266A, E291D, R303E, K324D, N333S, Y344H, V350A, D363P, M383L, K393H |
| 123 | pA12661 | 6 | S21P, Y22W, S27A, S54T, E75P, P97E, R143A, E144R, A188T, S191A, V199H, Y219H, V230A, N259W, S286A, N287D, K324E, E327R, W331H, Y344H, E345P, M349E, K353R, E360D, I364W, F376H |
| 124 | pA12662 | 6 | S21P, Y22W, Y37P, S54T, M66Y, D77N, P97E, S127A, A188T, S190E, S191A, Y219H, G232E, E240T, E262Q, R266A, S286A, R296Y, N333S, Y344H, E345P, M349A, V350A, D363P, K365T, S403A |
| 125 | pA12663 | 6 | S21P, S54T, S96A, P97E, N101K, S113A, Y135K, R143V, R154Q, V182K, A188F, S191T, N197D, G232E, V237L, A253D, Y255Q, N259R, V282I, S286A, D290Q, I292L, K302L, Y344H, M349K, S374Q, M383L |
| 126 | pA12664 | 6 | Y14F, S21K, S27A, K34M, G35H, K72L, E75P, S96A, F146C, P160A, S187T, Y195A, N197K, V199L, N201K, Y255K, A256L, G281A, K302L, Y344H, S374Q |
| 127 | pA12665 | 6 | S27A, G35D, S54T, E75P, S96A, Y115F, E147K, I148V, T152A, P160A, A188M, S190E, S191V, V199I, M349K |
| 128 | pA12666 | 6 | K34M, Y37P, S54T, M66F, E75P, E76P, S96A, I148V, T152A, V182P, S190D, S191Y, L192F, N197K, I202A, D241G, A253D, N259E, S286A, R296D, E297K, K324E, E327R, N333S, Y344H, E345P, V350A, Y372P |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| 129 | pA12667 | 6 | S27A, S54T, M66F, E75P, E76P, P97E, D105E, S113A, Y135D, T142E, E147K, V1791, S187R, A188F, S190E, G232P, E240T, A253D, Y255Q, G281A, S286A, D290N, K324E, E327R, L334Y, E345P, M349K |
| 130 | pA12668 | 6 | M66F, S96A, T98Q, N101E, D105E, Y135P, R154Q, V182P, D184E, S187N, A188M, S190E, L192F, N197D, S218G, G232D, E240T, A253S, Y255K, D290N, E297K, E327R, E345P, M349A, K365R |
| 131 | pA12669 | 6 | S15A, S21P, G35D, S54T, E75P, S96A, T98E, N101A, S113A, K131A, V182P, S191T, G232E, E240T, G246A, N259W, R266V, G281A, N287D, D290A, K321T, K324D, M349K, E360D, V362I, S374A, F376H, R379C, N385P, S403A |
| 132 | pA12670 | 6 | S21P, K34Y, S54T, N63R, K78R, S96A, P97E, N101A, S113A, E147K, V182P, S190E, S191V, N197E, V199H, I202A, G208A, G232E, G246C, Y255E, G281A, N287D, D290K, E297H, K324D, M349A, S374C, R397K |
| 133 | pA12671 | 6 | S21P, S27A, K62R, E75P, P97E, S113A, S127A, D129E, R143A, V179I, S191T, V199H, N201R, Y219H, E240T, G246V, A253P, Y255E, R266V, N287D, R296E, M349A, N352E, Y372P, D373A, S374C |
| 134 | pA12672 | 6 | Y22W, K62R, N63R, M66Y, K67Q, E75P, D93H, S96A, N101A, F110Y, Y115F, L126C, D128G, R143A, E144R, I148V, E151R, S187K, S190E, V199H, I202A, I215V, G232E, D241P, R266A, G281A, S286A, N287D, D290K, E297H, R303E, K321R, K324E, R325N, E327R, N333S, Y344H, E345P, S374C, F376H, D377A |
| 135 | pA12673 | 6 | V13I, S21P, Y22W, S27A, F30H, K34D, S54T, N63R, E75P, D93H, S96A, P97E, T98E, N101E, D105E, F110Y, Y115F, K131A, E136D, R143A, F146C, E147R, I148V, S187K, L192F, N197Q, N201Q, D204N, G232D, D241P, A253N, Y255D, R280E. S286A, N287D, R296E, E297Q, R325Q, E327R, L328W, N333S, E343N, V350A, N352E, D363P, S374A, M383L |
| 136 | pA12674 | 6 | V13I, I16V, S21P, Y22W, S27A, D36S, M66Y, D77N, D93H, T98E, N101A, L126C, S127A, D128G, K131A, Y135Q, F146C, V182P, S187K, L192F, V199H, P200G, V230A, G232E, E240T, Y255D, G281A, E297Q, R303E, R325N, W331H, N333S, E343N, Y344H, N352E, V362I, I364W, F376R, S403H |
| 137 | pA14284 | 6 | K5A, K10N, K116R, K238S, K302Q, K318D, K321D, K324D, K348R, K353R, K365R, K382R |
| 138 | pA14285 | 6 | K11L, K32L, K34M, K67S, K70Q, K193Q, K318D, K321D, K324E, K348L, K353L |
| 139 | pA14286 | 6 | K10N, K34E, K70R, K131E, K137E, K155E, K321D, K324D, K348R, K382R, K384D |
| 140 | pA14287 | 6 | K5F, K10M, K11L, K62V, K70R, K116I, K131E, K194A, K321D, K324D, K353L, K384S |
| 141 | pA14288 | 6 | K11L, K70Q, K78L, K137L, K238S, K321D, K365S |
| 142 | pA14289 | 6 | K10N, K70R, K104R, K155E, K193A, K238S, K321D, K353L, K382R, K384T |
| 143 | pA14290 | 6 | K5L, C17G, K34M, K72L, K78L, K102Y, K193Q, K321D, K324E |
| 144 | pA14291 | 6 | K10N, C17T, K34T, K62R, K72L, K116H, C122T, K131Q, K137T, K193E, K194E, K321D, K324D, K382R |
| 145 | pA14292 | 6 | C17T, K34Q, K62R, K70R, K72V, K131Q, K155R, K194T, K229R, K238S, K365R |
| 146 | pA14293 | 6 | K10R, K131Q, K229T, K321D, K348R, K353R, K382R |
| 147 | pA14294 | 6 | K67T, K78L, K102Y, K131E, K365R |
| 148 | pA14295 | 6 | K10N, K11L, C17T, K32M, K34L, K137L, K384S |
| 149 | pA14296 | 6 | K10N, C17T, K32M, K34L, K70R, K102L, K131Y, K137L, K193Q, K221V, K229R, K238S, K321D, K382R, K393H |
| 150 | pA14297 | 6 | K5W, K10R, K32M, K67Q, K70R, K78M, K131Q, K193I, K348L |
| 151 | pA14298 | 6 | K70R, K104N, K117L, K221R, K229T, K348R, K353Q, K384D |
| 152 | pA14299 | 6 | K11Q, K34Q, K62R, K67T, K104Q, K131E, K137T, K318D, K321D, K353R, K384E |
| 153 | pA14300 | 6 | K78L, K229R, K302I, K365S |
| 154 | pA14301 | 6 | K5M, K10L, K67T, K70R, K72L, K131Q, K137L, K221R, K318D, K353W, K365H, K384D, K392R, K396M |
| 155 | pA14302 | 6 | C17T, K67T, K70R, K102R, K104N, K155N, K318D, K321D |
| 156 | pA14303 | 6 | K104R, K131R, K193E, K238S, K348L |
| 157 | pA14304 | 6 | K5H, K67T, K78L, K117W, C122A, K155N, K302L, K318D, K353L, K384S, K396L |
| 158 | pA14305 | 6 | K62R, K67T, K104N, K131Q, K137Q, K221R, K238S, K324S, K382R |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| 159 | pA14306 | 6 | K5L, K10N, K11Q, K62R, K67T, K70R, K131Q, K137Q, K193E, K194E, K221R, K302R, K321D, K324D, K348R, K382R, K384D |
| 160 | pA14307 | 6 | K10N, C17T, K70R, K104R, C122A, K131E, K137E, K155E, K193E, K229R, K321D, K324D, K348R, K353R |
| 161 | pA14308 | 6 | K5H, K11V, K72L, K116T, C122T, K324E, K382L, K384E, K393Y |
| 162 | pA14309 | 6 | K5F, K10N, K11Q, C17A, K32Q, K34Q, K67T, K72L, K137T, K229R, K238S, K318D, K321D, K324D, K348R, K353Q |
| 163 | pA14310 | 6 | K5F, K34Q, K72T, K78Q, K137T, K155N, K221T, K238S, K302R, K324D, K382R |
| 164 | pA14311 | 6 | K62V, K70R, K78L, K104Q, K116I, K155N, K193Q, K221V, K229R, K321D, K324D, K348L, K382R, K393H |
| 165 | pA14312 | 6 | K5W, K10R, C17T, K62R, K67T, K70R, K72L, K78R, K104R, K116R, K137E, K193R, K194T, K238S, K302Q, K321D, K348R, K353R, K365R, K384E |
| 166 | pA14313 | 6 | K10L, K11Y, K34T, K62V, K67T, K102Y, K116Y, K131Q, K137L, K155Y, K193A, K194A, K221R, K238S, K318D, K353W, K382R, K384L |
| 167 | pA14314 | 6 | K5A, K11Q, C17T, K32Q, K34E, K67T, K70R, K72L, K102R, K104R, K131E, K155E, K229R, K238S, K302Q, K318D, K321D, K324D, K353R, K384T |
| 168 | pA14315 | 6 | K5A, K10N, K67T, K70R, K78Q, K102R, K131E, K137E, K155E, K193E, K194T, K229R, K321D, K348R, K353R, K365R |
| 169 | pA14316 | 6 | K5F, K10N, K11Q, C17I, K34Q, K62R, K67T, K70R, K104Q, C122T, K131E, K221T, K238S, K269I, K318D, K321D, K324D, K348R, K353Q, K382R, K384E |
| 170 | pA14317 | 6 | K5A, K32I, K62Y, K67T, K72L, K116L, K193A, K194T, K221I, K229R, K238S, K302I, K318D, K321D, K353L, K382R, K384T |
| 171 | pA14318 | 6 | K70R, K78L, K102Y, K131E, K269L, K348V, K365R, K392M, K393L |
| 172 | pA14319 | 6 | K5F, K11Q, K32Q, K62R, K78Q, K116Q, K137T, K229R, K318D, K321D, K324D, K348R, K353Q, K384D |
| 173 | pA14320 | 6 | K5F, K10M, K34L, K67T, K70R, K78L, K104R, K131E, K193Q, K194R, K221V, K238W, K324D, K353W, K365S, K384S |
| 174 | pA14321 | 6 | K11Y, K34L, K70R, K221I, K229R, K238S, K318D, K324D, K348V, K365R, K393L |
| 175 | pA14322 | 6 | K32I, K62V, K104I, C122T, K137L, K194A, K238S, K318D, K353L, K365S, K384E, K392L |
| 176 | pA14323 | 6 | K11V, K32L, K34Y, K62V, K67R, K70Q, K78R, K102L, K116T, K131R, K155E, K194A, K221I, K318D, K321D, K348L, K365R, K382L |
| 177 | pA14324 | 6 | K32L, K34M, K67S, K78Q, K102L, K116T, K194S, K302I, K321D, K348L, K353L, K382L |
| 178 | pA14325 | 6 | K10L, K11Y, C17T, K62Y, K67T, K70R, K72L, K117M, C122V, K131Q, K137L, K155Y, K193A, K221R, K229T, K269V, K318D, K321D, K324D, K353W, K365H, K382R, K392L, K396M |
| 179 | pA14326 | 6 | K10N, K11V, C17G, K32L, K67S, K78L, K193E, K302I, K318D, K353L, K365R, K384T, K392L |
| 180 | pA14327 | 6 | K10N, K11L, K32L, K78Q, K104R, K116T, K131E, K194R, K318D, K321D, K348L, K353L, K365S, K382L, K384E |
| 181 | pA14328 | 6 | K5L, K72L, K78L, K137L, K155E, K238S, K302L, K321D, K365S, K393Y |
| 182 | pA14329 | 6 | K5M, K10L, K11L, C17T, K32M, K34L, K70R, K72L, K78L, K102L, K116I, K155N, K194S, K221V, K238S, K318D, K321D, K324D, K348L, K382R |
| 183 | pA14330 | 6 | K10N, K11L, K32M, K34L, K62V, K67T, K78L, K102L, K116I, K131Y, K137L, K155N, K193Q, K194R, K229R, K302L, K318D, K321D, K324D, K348L, K353W, K382R, K384S |
| 184 | pA14331 | 6 | C17G, K34M, K70Q, K104R, K131R, K302I, K348L, K365R, K384Q, K393Y |
| 185 | pA14332 | 6 | K5L, C17G, K34T, K67S, K72L, K78L, K269N, K321D, K382L, K393Y |
| 186 | pA14333 | 6 | K5W, K10V, K11Y, K32M, K34T, K62V, K67T, K70R, K78L, K102Y, K104F, K116Y, K131Q, K137L, K155Y, K193A, K194A, K221R, K229S, K238W, K302L, K318D, K321D, K324D, K348L, K353W, K365H, K382R, K384D |
| 187 | pA14334 | 6 | K5W, K11Y, K32M, K34T, K70R, K72L, K78M, K102Y, K104F, K116Y, C122V, K131Q, K193A, K194A, K238W, K269L, K302L, K318D, K321D, K324D, K348L, K382R, K384D, K392L, K393Y |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| 188 | pA14335 | 6 | K5A, K10N, K11Q, C17L, K32Q, K34E, K67T, K70R, K72L, K78Q, K102R, K104R, K116R, K117W, C122T, K131E, K155E, K194R, K229R, K238S, K269L, K302R, K321D, K365R, K382R, K384D |
| 189 | pA14336 | 6 | K5L, K10A, C17G, K32L, K34Y, K70Q, K72L, K116T, K131R, K155E, K194A, K221I, K238S, K302I, K318D, K321D, K324E, K348L, K353L, K384Q, K396M |
| 190 | pA14337 | 6 | K10N, K11L, C17I, K32M, K34L, K62Y, K67T, K72T, K78L, K116L, K117W, C122A, K131E, K155N, K221V, K229R, K269I, K302M, K321D, K324D, K348L, K353W, K382R, K384R, K392L, K396R |
| 191 | pA14338 | 6 | K11Q, K34E, K62R, K72L, K104R, C122A, K137E, K193E, K221Q, K229R, K318D, K321D, K324D, K348R, K353R, K365R, K384D |
| 192 | pA14339 | 6 | K5A, K10L, K11Q, K32I, K62V, K70R, K72L, K78L, K102Y, K104R, K116L, K131E, K137L, K155E, K229R, K318D, K321D, K348V, K353L, K382R, K384T, K392R |
| 193 | pA14340 | 6 | K5M, K11Q, C17S, K34L, K62V, K67T, K70R, K72L, K102Y, K104Q, K131Y, K137L, K193Q, K221V, K229R, K238W, K302L, K318D, K321D, K353L, K365S, K384R, K392L, K393H, K396I |
| 194 | pA14341 | 6 | K5H, K10N, K32L, K34T, K67S, K70Q, K78L, K102L, K104R, K116T, K131E, K137L, K194R, K229R, K238S, K318D, K321D, K365R, K382L |
| 195 | pA14342 | 6 | K5F, K10L, K11L, K32M, K34L, K62V, K67T, K70R, K78L, K102Y, K104Q, K116I, K131E, K137L, K155N, K193Q, K194A, K221I, K229R, K238W, K302L, K318D, K321D, K324D, K348L, K353W, K365S, K382R, K384D |
| 196 | pA14343 | 6 | K5L, K11V, K32L, K34M, K62V, K67S, K70Q, K78L, K155R, K194A, K229R, K302L, K321D, K324E, K348L, K365R, K384Q, K393Y |
| 197 | pA14344 | 6 | K5W, K10N, K11Q, C17T, K34T, K62R, K67T, K72L, K102R, K131Q, K137Q, K155H, K194E, K221R, K229T, K302Q, K318D, K321D, K353R, K382R |
| 198 | pA14345 | 6 | K5L, K11L, K32I, K34T, K62V, K67S, K70Q, K72L, K116T, K131E, K137L, K155E, K193E, K229A, K324E, K348L, K353L, K382L, K384R, K392L, K393Y |
| 199 | pA14346 | 6 | K11L, K67S, K72L, K104I, C122T, K131R, K193E, K194A, K221I, K229A, K302L, K318D, K321D, K324E, K348L, K353L, K365S, K382L, K392L, K396M |
| 200 | pA14347 | 6 | K5H, K11V, C17G, K32I, K34T, K70Q, K72L, K78L, K104R, K117L, K131E, K155E, K194T, K221I, K229R, K269N, K321D, K348L, K353L, K365R, K382L, K393Y, K396I |
| 201 | pA14348 | 6 | K5F, K10M, K11L, C17I, K32M, K34L, K62V, K67T, K70R, K72L, K78L, K102L, K104Q, K116I, K117V, C122T, K131E, K137E, K155N, K193Q, K194A, K221V, K229R, K238S, K269I, K302L, K318D, K321D, K324D, K348L, K353L, K365S, K382R, K384R, K392L, K393H, K396M |
| 202 | pA14349 | 6 | K5W, K10N, K11Q, C17I, K32Q, K34T, K62R, K67T, K70R, K72L, K78R, K102R, K104R, K116H, K117V, C122V, K131Q, K137T, K155H, K193E, K194E, K221R, K229T, K238R, K269V, K302Q, K318D, K321D, K324D, K348R, K353R, K365H, K382R, K384D |
| 203 | pA14350 | 6 | K5A, K10N, K11Q, C17T, K32Q, K34E, K62R, K67T, K70R, K72L, K78Q, K102R, K104R, K116R, K131E, K137E, K155E, K193E, K194T, K221Q, K229R, K238S, K302Q, K318D, K321D, K324D, K348R, K353R, K365R, K382R, K384D |
| 204 | pA14351 | 6 | K5L, C17G, K32I, K34M, K62V, K72L, K78L, K102L, K116T, C122T, K131E, K137L, K155E, K193Q, K194R, K229R, K269N, K302I, K318D, K321D, K324E, K348L, K353L, K365S, K384R, K392L, K393Y |
| 205 | pA14352 | 6 | K5F, K10N, K11Q, K32Q, K34Q, K62R, K67T, K70R, K78Q, K102R, K104Q, K116Q, K131E, K137T, K155N, K193Q, K194S, K221T, K229R, K238S, K302Q, K318D, K321D, K324D, K348R, K353R, K365S, K382R, K384E |
| 206 | pA14353 | 6 | K5L, K10N, K11E, C17V, K32Q, K34H, K62R, K67Q, K70R, K72L, K78R, K102R, K104R, K116R, K131R, K137E, K155E, K193E, K194T, K221R, K229N, K238S, K302R, K318D, K321D, K324S, K348R, K353Q, K365R, K382N, K384Q |
| 207 | pA14354 | 6 | K5L, K10N, K11V, C17I, K32S, K34F, K62V, K67Q, K70R, K72I, K78M, K102L, K104F, K116W, K117V, C122A, K131R, K137E, K155E, K193A, K194A, K221I, K229Q, K238S, K269V, K302L, K318D, K321D, K324S, K348L, K353L, K365R, K382N, K384R, K392L, K393F, K396F |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| 208 | pA14355 | 6 | K5L, K10N, K11L, K32L, K34M, K62V, K67S, K70Q, K78L, K102Y, K104R, K116T, K131E, K137L, K155E, K193Q, K194R, K221I, K229R, K238S, K302I, K318D, K321D, K324E, K348L, K353L, K365S, K382L, K384E |
| 209 | pA14356 | 6 | K5L, K10A, K11L, K32I, K34T, K62V, K67S, K70Q, K78L, K102Y, K104I, K116T, K131E, K137L, K155E, K193E, K194A, K221I, K229A, K238S, K302L, K318D, K321D, K324E, K348L, K353L, K365S, K382L, K384E |
| 210 | pA14357 | 6 | K5W, K10R, K11R, K32Q, K34Q, K62R, K67T, K70R, K78Q, K102R, K104R, K116R, K131Q, K137E, K155D, K193R, K194T, K221R, K229T, K238S, K302Q, K318E, K321D, K324D, K348R, K353R, K365R, K382R, K384E |
| 211 | pA14358 | 6 | K5M, K10M, K11Q, C17S, K32M, K34L, K62V, K67T, K70R, K72L, K78M, K102L, K104R, K116I, K131Y, K137L, K155N, K193A, K194S, K221I, K229R, K238S, K302L, K318D, K321D, K324D, K348L, K353W, K365S, K382R, K384R, K392L, K393Y, K396M |
| 212 | pA14359 | 6 | K5F, K10L, K11L, C17T, K32M, K34L, K62Y, K67Q, K70R, K72L, K78R, K102Y, K104V, K116R, K131L, K137E, K155E, K193E, K194A, K221V, K229A, K238S, K302M, K318D, K321D, K324S, K348R, K353L, K365S, K382R, K384R, K392L, K393Y, K396I |
| 213 | pA14360 | 6 | K5L, K10N, K11Q, C17S, K32Q, K34R, K62R, K67T, K70R, K72L, K78R, K102R, K104R, K116Q, K117V, C122T, K131E, K137E, K155E, K193E, K194S, K221R, K229S, K238S, K269V, K302Q, K318D, K321D, K324S, K348R, K353R, K365S, K382R, K384Q |
| 214 | pA14361 | 6 | K5L, K10A, K11V, C17G, K32L, K34Y, K62V, K67R, K70Q, K72L, K78R, K102L, K104R, K116T, K131R, K137I, K155E, K193E, K194A, K221I, K229N, K238S, K302L, K318D, K321D, K324E, K348L, K353L, K365R, K382L, K384R, K392L, K393Y, K396I |
| 215 | pA14362 | 6 | K5A, K10N, K11V, C17G, K32I, K34T, K62V, K67S, K70Q, K72L, K78L, K102Y, K104R, K116T, K131E, K137L, K155E, K193E, K194R, K221I, K229R, K238S, K302I, K318D, K321D, K324E, K348L, K353L, K365R, K382L, K384T, K392L, K393Y, K396I |
| 216 | pA14363 | 6 | K5A, K10N, K11V, C17G, K32I, K34M, K62V, K67S, K70Q, K72L, K78R, K102Y, K104I, K116S, K117L, C122T, K131E, K137L, K155E, K193E, K194A, K221I, K229A, K238S, K269N, K302L, K318D, K321D, K324E, K348R, K353L, K365S, K382L, K384R, K392L, K393Y, K396I |
| 217 | pA14364 | 6 | K5L, K10R, K11V, C17G, K32I, K34M, K62V, K67S, K70Q, K72L, K78L, K102Y, K104R, K116T, K117L, C122T, K131R, K137L, K155R, K193I, K194A, K221I, K229R, K238S, K269N, K302L, K318D, K321D, K324E, K348L, K353L, K365R, K382L, K384R, K392L, K393Y, K396I |
| 218 | pA14365 | 6 | K5R, K10R, K11R, K32R, K34R, K62R, K67R, K70R, K78R, K102R, K104R, K116R, K131R, K137R, K155R, K193R, K194R, K221R, K229R, K238R, K302R, K318R, K321R, K324R, K348R, K353R, K365R, K382R, K384R |
| 219 | pA14366 | 6 | K5R, K10R, K11R, C17R, K32R, K34R, K62R, K67R, K70R, K72R, K78R, K102R, K104R, K116R, K131R, K137R, K155R, K193R, K194R, K221R, K229R, K238R, K302R, K318R, K321R, K324R, K348R, K353R, K365R, K382R, K384R, K392R, K393R, K396R |
| 220 | pA14367 | 6 | K5R, K10R, K11R, C17R, K32R, K34R, K62R, K67R, K70R, K72R, K78R, K102R, K104R, K116R, K117R, C122R, K131R, K137R, K155R, K193R, K194R, K221R, K229R, K238R, K269R, K302R, K318R, K321R, K324R, K348R, K353R, K365R, K382R, K384R, K392R, K393R, K396R |
| 221 | pA14368 | 6 | K102Y, K131Q, K221R, K318D, K321D |
| 222 | pA14369 | 6 | K102L, K131E, K221I, K318D, K321D |
| 223 | pA14370 | 6 | K102R, K131E, K221T, K318D, K321D |
| 224 | pA14371 | 6 | C17T, K102R, K131Q, K221R, K269V, K318D, K321D |
| 225 | pA14372 | 6 | C17L, K102L, K131E, K221R, K269L, K318D, K321D |
| 226 | pA14373 | 6 | C17G, K102Y, K131E, K221I, K318D, K321D |
| 227 | pA14374 | 6 | C17S, K102L, K131E, K221V, K318D, K321D |
| 228 | pA14375 | 6 | C17T, K102R, K131E, K221Q, K318D, K321D |
| 229 | pA14376 | 6 | C17G, K102L, K131E, K221Q, K269N, K318D, K321D |
| 230 | pA14377 | 6 | C17G, K269N |
| 231 | pA14378 | 6 | Y53F, D167A, Y340A |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| 232 | pA15875 | 6 | L3E, S4R, K5R, D6E, Y7N, L8G, R9Q, K10R, K11E, S21E, E25R, E29R, K32R, K34R, G35H, Y37R, Q49H, F50R, K62R, N63R, F64E, M66E, K67R, K70R, K72E, E75D, D77R, K78R, E94R, S96R, T98E, K102E, K104R, D105Q, K116D, D129E, K131E, P134D, E136R, K137E, R141Q, E144Q, I148E, E151R, T152R, A153R, R154T, K155E, Y156R, N157D, F158R, S187R, S190E, S191Y, K193E, K194R, N197P, S218T, Y219R, K221R, E224Q, D228E, K229E, G232R, K238R, E240T, N287E, D290R, E297R, S299Q, N300D, K302R, K318D, K321D, D322T, K324D, R325E, L326H, E327R, L328R, W331E, E343D, E345P, K348R, M349E, N352R, K353R, I364P, K365E, Y368R, Q369E, D373R, F376E, D377R, E380D, K382E, K384R, K392E, K393E, K396R, R397Q, S403R, N407D, L408R |
| 233 | pA15876 | 6 | L3E, S4R, K5R, D6R, Y7H, L8G, R9E, K10E, K11R, S21E, E25R, K32R, E33Q, K34R, D36R, Y37D, F50H, N63R, K67E, K70R, K72E, E75D, D77R, K78R, I80R, E94R, S96E, T98E, N101Q, K102E, K104R, D105E, K116R, Y135Q, K137E, E140R, I148V, E151R, T152R, A153R, R154Q, K155E, N157E, F158E, Q159E, S187R, S190E, S191H, K193E, K194E, N197P, W203R, S218T, Y219R, K221R, E224Q, E240T, E262R, N287E, D290R, E297R, S299Q, N300D, K302R, K318D, K321E, D322T, K324D, R325Q, E327R, W331E, E343D, E345P, K348R, M349E, N352R, K353R, I364E, K365R, F366R, Q369E, D373E, F376Q, E380D, K382R, K384R, K392R, K393E, K396R, S403E, N407D, L408G |
| 234 | pA15877 | 6 | S4R, D6Q, Y7N, L8N, R9E, K10P, K11V, S21P, K32M, K34L, G35S, Q49F, F50Q, K62R, N63R, K67E, K70R, E71S, E75D, D77R, K78M, E94L, S96E, T98Q, N101E, K102Y, K104R, D105Q, K116Q, K131E, V132T, P134D, Y135W, E136R, K137R, E151R, A153S, R154P, K155P, Y156V, N157P, F158N, Q159T, P160I, S190E, S191T, K193E, K194R, N197E, W203R, G216N, D220R, K221T, K229Q, R231E, G232E, E235R, K238E, E240T, R258E, E262R, N287Q, D290R, E297H, N300D, K302R, D313P, K318D, K321D, K324P, R325Q, L328E, E345P, K348E, M349E, N352R, K353Q, I364E, K365R, E380N, K382N, K384D, N385T, S403A, N407Q |
| 235 | pA15878 | 6 | S4R, K5Q, D6R, Y7N, L8G, R9E, K10P, K11V, S21E, K32Q, K34S, G35N, D36T, Q49H, F50R, E59R, K62R, N63R, M66E, K67E, K70R, E71S, E75D, D77R, K78R, E94R, S96E, T98E, N101Q, K102E, K104R, D105E, K116R, D129Q, P130S, K131E, V132T, P134D, E136R, K137E, E140R, R141Q, E147R, I148E, R154T, K155T, Y156D, N157P, F158N, Q159E, P160T, V179R, S190E, S191E, K193E, K194R, N197R, P200D, W203R, G216T, Y219R, K221R, K229Q, G232E, K238R, E240T, N287R, D290R, E297H, K302E, R303E, E307R, K318N, K321E, K324D, R325Q, E327R, L328E, E343D, E345P, K348R, M349E, N352R, K353Q, I364E, K365R, Q369R, E380D, K382R, K384Q, S403R, N407E |
| 236 | pA15879 | 6 | S4R, K5H, D6Q, Y7N, L8N, R9E, K10P, K11V, S21P, K32Q, K34S, G35N, D36S, F50H, N63E, K67R, K70R, E71S, E75D, D77R, K78R, E94Q, S96E, T98E, N101Q, K102E, K104R, D105E, K116L, D129Q, K131E, V132T, P134D, E136R, K137E, E140R, R141H, E147Q, A153S, R154P, K155P, Y156R, N157P, F158N, P160T, S190E, S191A, K193E, K194R, N197E, W203R, G216N, D220R, K221E, K229Q, R231E, G232E, E235R, K238E, E240T, N287Q, D290R, E297H, K302Q, R303E, E307Q, D313P, K318D, K321D, K324P, R325Q, L328E, E343D, E345P, K348E, M349E, N352R, K353Q, I364E, K365R, Q369R, S403R, N407E |
| 237 | pA15880 | 6 | S4R, K5Q, D6R, Y7N, L8G, R9Q, K10R, K11W, S21E, E25R, E29R, E33Q, K34R, G35D, D36Q, Q49H, F50R, E59R, K62R, N63R, M66E, K67Q, K70R, K72E, E76P, D77R, K78R, E94R, S96E, T98E, N101E, K102E, K104R, D105E, K116E, P130S, K131E, V132T, P134D, E136R, K137E, E140R, E147R, I148E, R154T, K155T, Y156D, N157P, F158N, Q159R, P160T, V179R, S190E, S191Y, K193R, K194Q, N197Q, G216T, Y219R, D220R, K221R, K229Q, G232E, K238R, E240T, N287E, D290R, E297R, K302R, R303E, E307R, K321E, K324D, R325E, L328E, W331E, E343D, E345P, K348R, M349R, N352E, K353E, E356R, I364E, K365R, Q369R, D377H, E380D, K382R, K384R, K392E, K393Q, K396R, R397E, S403R, N407E |
| 238 | pA15881 | 6 | S4E, K5R, D6H, L8N, R9L, K10E, K11R, S21P, K32R, E33N, K34R, G35H, D36L, Y37P, Q49I, E59T, K62R, N63D, K67D, K70R, E71R, E75D, D77R, K78D, E94L, S96A, T98E, N101D, |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| | | | K102R, K104R, D105Q, K116R, D129Q, K131E, P134H, Y135W, E136D, K137E, R141L, E147R, I148V, T152V, R154Q, K155D, N157P, F158N, Q159L, P160L, V179I, S190E, S191A, K193R, K194R, P200L, G216R, K221R, E224M, K229R, G232E, K238R, E240V, D241P, E262Q, N287L, E297R, N300E, K302R, D313P, K318D, K321D, K324D, E327Y, L328W, W331L, E343D, E345P, K348R, M349T, N352E, K353R, E356R, G361P, D363P, I364L, K365E, F366H, Y368R, Q369D, F376E, E380D, K382R, K384E, S403A, N407D, L408T |
| 239 | pA15882 | 6 | L3E, S4R, K5R, D6E, L8G, R9Q, K10R, K11E, S21R, K32R, E33T, K34R, G35H, Y37R, Q49H, F50R, N63R, F64E, K67R, K70R, E75D, D77R, K78R, E94R, S96R, T98E, K102E, K104R, D105Q, K116R, D129E, Y135W, K137E, R141Q, E144Q, I148E, E151R, T152R, A153R, R154T, K155E, V161E, S187R, S190E, S191E, K194R, N197P, W203R, Y219R, I292Q, S299Q, K318D, K321D, D322T, K324D, L326H, E327R, L328E, M349R, N352E, K353E, E356R, I364P, K365E, Y368R, Q369R, F376E, E380N, K382R, K384R, S403R, N407E, L408R |
| 240 | pA15883 | 6 | S4R, K5H, D6Q, L8G, R9Q, K10E, K11E, S21E, E25R, E29R, K32Q, E33R, G35H, D36E, Y37R, Q49H, F50R, E59R, K62R, N63E, F64E, K67R, K70R, K72E, E75D, D77R, K78Q, E94R, S96R, T98E, K102E, K104R, D105Q, K116R, D129E, K137E, E140R, R141Q, I148E, E151R, T152R, V161E, S187R, S190E, S191E, K194R, N197P, W203R, Y219R, K229Q, G232E, K238R, E262Q, N287E, D290R, I292Q, K302R, R303E, E307R, K321D, D322T, K324D, L326H, E327R, L328E, W331E, E343D, E345P, K348R, M349E, N352R, K365R, Q369R, D373R, F376E, K382R, K384Q, K392H, K393R, K396E, R397E, E400Q, S403R, N407E, L408R |
| 241 | pA15884 | 6 | L3E, S4E, K5H, D6R, Y7H, L8G, R9Q, K10E, K11F, S21E, K34Q, D36T, Q49H, F50R, K62R, N63R, M66E, K67E, K70R, E71R, E75D, D77R, K78M, E94Q, S96R, K102E, K104R, D105E, K116T, K131E, Y135D, K137E, E140R, I148E, E151R, T152H, A153R, R154Q, K155Q, N157P, F158T, Q159E, S187R, S190E, S191A, K193Q, K194R, N197P, P200E, W203R, S218T, Y219R, K221R, E224Q, K229R, G232E, K238R, E240T, E262R, N287E, D290R, E297R, S299Q, N300D, K302R, K318D, K321E, D322T, R325Q, L328E, W331E, E343D, E345P, K348R, M349R, K353E, E356R, I364E, K365R, F376Q, E380D, K382R, K384T, N407H, L408R |
| 242 | pA15885 | 6 | S4R, D6Q, Y7N, L8N, R9E, K11R, S21P, K32R, K34R, G35N, N63R, K67E, K70R, E71S, E75D, D77R, K78R, E94L, T98E, N101R, K102R, K104E, D105E, K116R, K131E, V132T, Y135W, E144R, E151R, R154P, K155E, Y156V, N157P, F158N, Q159E, P160M, S191T, K193E, K194R, N197E, W203R, E240T, N287Q, D290R, E297H, N300D, K302R, K321D, K324D, R325Q, M349R, N352E, K353E, E356R, I364E, K365R, E380N, K382R, S403A, N407Q |
| 243 | pA15886 | 6 | S4E, D6Q, Y7N, L8N, R9Q, K10D, K11R, S21P, K32R, K34R, G35D, D36Q, N63R, K67E, K70R, E71Q, K78M, 596E, N101E, K104R, D105Q, K116R, D129Q, K131E, V132T, P134D, Y135W, E136R, K137E, E140R, R141L, E151R, R154P, K155E, Y156V, N157P, F158N, Q159E, P160M, S190E, S191T, K194R, N197S, W203A, G216N, D220R, K221E, K229R, G232E, R258E, E262R, N287Q, D290R, E297H, K302E, K321D, K324D, R325Q, L328E, E343D, K348R, M349R, N352E, K353E, E356R, I364E, K365R, E380N, K382R, K384E, S403A, N407E |
| 244 | pA15887 | 6 | S4R, K5H, D6E, L8G, R9Q, K10R, K11E, S21R, K32Q, E33T, K34R, G35H, D36E, Y37R, Q49H, F50R, N63R, F64E, K67R, K70R, E75D, E94R, T98E, N101E, K102E, D105E, K116R, D129E, K131E, A153R, R154T, K155Q, V161E, S190E, S191Q, K193Q, K194R, Y195H, N197P, P200E, W203R, Y219R, K229Q, G232E, K238R, E240T, N287E, D290R, E297R, S299Q, N300D, K302R, K318N, K321D, D322T, K324D, R325E, L326H, E327R, L328R, W331E, E343N, E345P, K348E, M349E, N352R, K353R, I364P, K365E, Y368R, Q369R, F376E, K382R, K384Q, S403R, N407E, L408R |
| 245 | pA15888 | 6 | S4E, K5H, D6H, L8G, K10P, K11Q, S21E, E25R, E29R, K32Q, E33R, K34Q, G35H, D36H, Y37P, Q49H, F50R, K62R, N63R, M66E, K67Q, K70R, K72E, D77R, K78M, E94R, S96E, T98E, K102E, K104R, D105E, K116W, P130S, K131E, V132T, P134D, E136R, K137R, E147R, I148E, K155G, N157P, V179R, S190E, S191Y, K193R, K194Q, P200R, G216R, Y219R, K221R, |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| | | | K229Q, G232E, K238R, E240H, N287E, D290R, E297R, N300D, K302R, K318D, K321E, D322T, K324E, R325Q, L328R, E343D, E345P, K348R, M349E, N352R, K353R, G361P, K365R, Q369R, F376E, E380D, K382R, K384Q, N385P, K392L, K393H, K396E, R397E, E400R, L408D |
| 246 | pA15889 | 6 | S4R, K5H, D6H, L8N, R9E, K10P, K11Q, S21P, K32Q, E33H, K34R, G35H, D36E, Y37P, F50H, K62R, N63R, K67E, K70R, E71R, E75D, D77R, K78L, E94Q, S96E, T98E, K102Q, K104Q, D105E, K116L, D129Q, K131E, K137E, R141H, E147R, I148V, R154Q, K155D, N157P, P160L, S190E, S191H, K193R, K194Q, N197R, G216R, K221R, K229Q, G232E, K238R, D241P, N287Q, K302R, R303Q, D313P, K318D, K321D, K324D, L328E, E343D, K348R, M349R, N352E, K353R, E356R, G361P, K365R, Q369R, F376E, E380D, K382R, K384E, N385P, S403R, N407D, L408T |
| 247 | pA15890 | 6 | L3E, S4E, D6R, Y7H, L8G, K10E, K11R, S21E, K32I, K34M, D36Y, Q49W, F50S, M56W, K62R, N63R, M66E, K67E, K70R, E71R, E75D, E76P, K78M, E94L, S96E, T98R, N101E, K102Y, K104R, D105E, K116L, D129R, K131D, V132E, Y135R, K137E, E140R, R141W, E144D, E151R, T152Y, A153R, R154Q, K155T, Y156F, N157R, F158T, Q159E, S190E, S191Y, K193Q, K194R, N197P, W203R, S218T, Y219R, D220R, K221R, E224Q, K229R, G232E, K238R, E240T, E262R, N287E, D290R, E297R, S299Q, K302R, R303E, E307R, K318D, K321E, D322T, K324D, L328E, W331E, E343D, E345P, K348R, M349E, N352R, K353R, I364P, K365R, Q369R, F376E, E380R, K382Q, K384T, S403A, N407W, L408D |
| 248 | pA15891 | 6 | S4R, K5H, D6Q, Y7N, L8N, R9E, K10P, K11V, S21P, E29R, F30A, K32Q, E33Q, K34T, G35N, D36T, F50H, K62R, N63E, K67R, K70R, E71S, K72T, E75D, D77R, K78R, E94Q, S96E, T98E, N101E, K102Q, K104R, D105Q, K116L, K131E, V132T, P134D, E136R, K137R, E151R, A153S, R154P, K155P, Y156R, N157P, F158N, P160T, S190E, S191H, K193R, K194Q, N197S, W203H, G216N, D220R, K221T, K229Q, R231E, G232E, E235R, K238R, E240T, R258E, E262R, N287Q, D290R, E297H, N300D, K302R, D313P, K318D, K321D, K324P, R325Q, L328E, E343D, K348R, M349R, N352E, K353Q, E356R, I364E, K365R, E380N, K382R, K384S, K392L, K393A, K396E, R397H, E400R, S403W, N407E |
| 249 | pA15892 | 6 | S4R, D6Q, Y7N, L8N, R9E, K10P, K11V, S21P, K32M, K34L, G35D, D36L, K62R, N63E, K67R, K70R, E71S, E75D, D77R, K78M, K104R, D105E, K116Q, K131E, V132T, Y135W, E151R, R154P, K155P, Y156V, N157P, F158N, Q159T, P160M, S191T, K193R, K194R, N197S, W203A, D204R, G216N, D220R, K221T, K238R, E240T, E297H, K318D, K321D, K324P, R325Q, L328E, E345P, K348R, M349E, N352R, K353L, I364E, K365R, K384Q, N407R |
| 250 | pA15893 | 6 | L3E, S4R, D6Q, Y7N, L8G, R9E, K10R, K11H, S21E, K32I, E33T, K34R, G35H, D36E, Y37R, K62R, N63R, F64E, M66E, K67R, K70R, E75D, D77R, K78L, K104E, D105E, K116Y, D129L, K131E, P134D, Y135W, E136R, K137E, E144R, T152R, A153R, R154T, K155Q, Y156Q, F158T, Q159E, P160F, V179I, S190E, S191W, K193R, K194R, N197P, W203R, Y219R, K229A, K238R, N287E, D290R, I292E, E297R, S299Q, N300D, K302R, Y315W, K318N, K321D, D322T, K324D, L326H, E327R, L328E, W331E, E343D, E345P, K348R, M349E, N352E, K353R, E356R, K365R, F366R, Q369E, F376E, K382R, K384R, S403R, N407E, L408N |
| 251 | pA15894 | 6 | S4R, D6Q, Y7N, L8N, R9E, K10P, K11V, S21P, K34L, G35N, K62R, N63R, K67E, K70R, E71S, E75D, D77R, K78M, E94L, S96E, T98Q, N101H, K102Y, K104E, D105Q, K116R, K131E, V132T, P134D, Y135W, E136R, K137R, E144R, E151R, R154P, K155P, Y156V, N157P, F158N, Q159E, P160M, S191T, K193R, K194R, N197S, W203A, D204R, G216N, K221R, E224Q, K229Q, G232E, K238R, E240T, R258E, E262R, E297H, K318D, M349R, N352E, K353L, E356R, I364E, K365R, E380N, K382N, K384S, E389D, K392R, K396A, R397L, S403A, N407Q |
| 252 | pA15895 | 6 | S4R, D6Q, L8N, R9E, K10P, K11V, S21P, K32M, K34L, G35N, D36T, N63E, K67R, K70R, E71S, E75D, D77R, K78R, E94L, T98Q, N101E, K102Y, D105E, K116Q, K131E, V132T, R154P, K155P, Y156V, N157P, F158N, Q159T, P160M, S190E, K193R, N197S, K229Q, G232E, E240T, R258E, E262R, N287Q, |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| | | | D290R, E297H, N300D, K302R, D313P, K318D, K321D, K324P, R325Q, E343D, E345P, K348R, M349R, N352E, K353A, E356R, K384D, N385T, R397L |
| 253 | pA15896 | 6 | L3E, S4R, K5R, D6Q, Y7N, L8G, R9Q, K11E, S21E, E25R, K34R, G35H, D36S, Y37R, Q49H, F50R, N63R, F64E, K67R, K70R, E75D, D77R, K78R, E94R, T98E, K102E, K104R, D105Q, K116R, E147R, I148E, T152R, V161E, S190E, S191Y, K194R, N197P, W203R, K238R, I292Q, K318D, E343N, E345P, K348R, M349E, N352R, I364P, K365E, Y368R, Q369R, F376E, E380D, K382R, K384D, E389R, K392E, N407H, L408R |
| 254 | pA15897 | 6 | S4E, K5R, D6E, L8G, S21E, E33T, K34R, Y37R, Q49H, F50R, E59R, K62R, N63E, F64E, K67R, K70R, K78R, E94R, S96R, T98E, N101E, K102E, D105E, D129E, K137E, R141Q, S190E, K193E, K194R, N197P, P200E, W203R, S218T, Y219R, K221R, E224Q, E240T, N287E, D290R, I292Q, N300D, K302R, K318D, K321D, D322T, R325E, L326H, L328R, W331E, E343D, E345P, K348R, M349E, N352R, K365R, F376E, K382R, S403R, N407E |
| 255 | pA15898 | 6 | L3E, D6R, Y7H, L8G, K10E, K11H, S21E, Y22W, K32I, E33R, D36Y, M56W, K62R, N63R, M66E, K67E, E71R, E76P, D77R, K78M, S96E, N101Q, K104R, D105E, K131D, Y135D, K137E, E140R, E151R, T152Y, A153R, R154Q, K155Q, Y156F, S187R, S190E, S191A, K194R, N197P, W203L, Y219R, K229R, G232E, E262R, N287E, D290R, E297R, S299Q, N300D, K302R, K318D, K321E, D322T, K324D, R325Q, E327R, L328E, W331E, E343D, E345P, K348R, M349E, N352E, K353R, E356R, I364E, K365R, F366Y, F376Q, E380D, K382R, K384T, E389R, K392L, K396Q, R397L, S403A, N407Y, L408D |
| 256 | pA15899 | 6 | S4R, D6R, Y7N, L8G, R9E, K10P, K11V, S21R, K32Q, E33Q, K34Y, G35N, D36R, Y37E, E59R, K62R, N63R, M66E, K67E, E71S, E76P, D77R, K78R, I80L, S96E, N101Q, K104R, D105E, K116R, K131E, V132T, P134D, Y135W, E136R, K137E, E140R, E151R, K155T, N157P, F158N, Q159E, P160F, V179R, S190E, S191W, K193R, K194R, N197Q, G216T, D220Q, K221R, K229N, G232E, K238R, E240T, N287E, D290R, E297H, K302R, R303E, E307R, D313P, K318D, K321R, K324E, R325E, E327R, L328R, W331E, E343N, E345P, K348E, M349R, N352Q, K353Q, E356R, I364E, K365R, Q369R, K384Q, K392R, K396R, R397I, S403A, N407E |
| 257 | pA15900 | 6 | L3E, S4E, K5H, Y7H, L8N, R9Q, K10P, K11I, S21P, E25R, E33H, K34R, G35H, D36E, F50H, K62R, N63R, K67E, K70R, E71Q, K72Q, E75D, D77R, K78Q, E94R, S96E, T98E, N101E, K102E, K104R, D105Q, K116H, K137E, E140R, E150R, K155E, Y156E, N157E, Q159G, P160S, S190E, S191H, K193R, K194Q, N197Q, N201E, D204R, R205L, S218T, Y219R, K221Q, E224Q, K229R, G232E, E240N, N287R, K302R, R303E, E307R, K318D, K321D, K324D, E343D, K348E, M349R, N352R, G361D, I364E, K365R, Q369R, D373E, F376E, E380R, K382R, K384D, N385T, K393H, E400R, S403R, N407Q, L408R |
| 258 | pA15901 | 6 | L3E, D6R, Y7H, L8N, R9E, K10P, K11R, S21P, Y22W, K32M, E33R, K34Q, K62R, N63Q, K67E, K70R, E71R, E75D, D77R, K78M, E94L, S96E, T98R, N101E, K102Y, K104R, D105Q, K116I, D129Q, K131D, V132R, Y135L, K137E, E140R, R141L, E151R, T152Y, R154Q, K155E, Y156F, N157D, F158R, Q159E, P160M, S190E, S191A, K193E, K194R, N197D, W203R, S218T, K221Q, K229R, R231E, G232E, E235R, K238Q, E240T, N287L, D290E, 5299Q, N300D, K302R, D313P, K318D, K321D, K324D, E343D, K348R, M349R, N352E, K353L, E356R, I364E, K365R, F366Y, F376E, E380R, K382R, K384E, N385P, E389R, K392H, K396I, R397L, S403A, N407L, L408T |
| 259 | pA15902 | 6 | S4Q, K5Q, D6R, Y7N, L8G, R9Q, K11W, S21E, E25R, K32Q, K34S, G35N, D36T, N63R, K67Q, K70R, K72H, E75D, D77R, K78R, E94R, S96E, T98E, K102R, K104R, D105E, K116R, P134D, E136R, K137E, E140R, E147R, I148E, T152Q, A153S, R154S, K155T, Y156D, N157P, F158N, Q159E, P160T, V179R, S190E, S191E, K193R, K194R, Y195Q, N197Q, W203H, G216T, Y219R, D220R, K221R, K229Q, G232E, N287E, D290R, K302R, R303E, E307R, K321E, K324E, R325Q, E327R, L328E, W331E, I364E, K365R, Q369R, K384Q, K392R, K393R, R397E, S403R, N407E |
| 260 | pA15903 | 6 | L3E, S4E, K5H, Y7H, R9T, K11I, S21P, K32Q, K34Q, F50H, N63R, K67E, K70R, E71R, E75D, D77R, K78M, S96E, T98E, N101E, K102Q, D105Q, K116Y, D129Q, K137E, E140R, R141Q, A153Q, R154Q, K155E, Y156T, N157D, F158R, Q159E, S190E, |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| | | | S191H, K193E, K194R, N197D, W203R, S218T, D220R, K221T, K229R, G232E, E240T, N287H, D290Q, S299Q, N300D, K302Q, D313P, K318D, K321D, K324D, R325Q, L328E, E343D, K348R, M349R, N352E, K353H, E356R, I364E, K365R, Q369R, F376E, E380R, K382R, K384E, N385P, L408R |
| 261 | pA15904 | 6 | S4E, K5R, D6H, L8N, R9L, K10P, E33N, K34R, G35H, D36E, Y37P, E59T, K62R, N63D, M66Y, E75D, E76L, D77R, K78D, E94L, S96A, T98E, N101S, K102R, K104E, D105E, K116R, D129Q, K131E, P134H, Y135W, E136W, K137E, E140L, R141L, E144D, E147A, I148V, T152V, Y156F, P160L, V179I, S190Y, S191Y, K194E, Y195A, N197R, G216R, K221R, D228S, K229R, R231E, G232E, E262L, E297R, N300E, K321D, L328W, M349R, N352E, K353R, E356R, G361P, F376E, E380D, K382R, K384E, N385P, S403A, N407D |
| 262 | pA15905 | 6 | L3E, S4E, D6E, L8G, R9Q, K10E, K11Q, S21E, K32I, K34Q, D36Y, Q49H, F50R, M56W, K62R, N63R, M66E, K67E, K70R, E71R, E75D, D77R, K78M, E94R, S96E, T98E, N101R, K102E, K104E, D105E, K116L, D129W, K131D, V132E, Y135R, K137W, E140R, R141W, E144R, E151R, T152Y, A153R, R154Q, K155T, Y156F, F158T, Q159E, P160M, S190E, S191Y, K193R, K194R, N197P, W203R, S218T, Y219R, D220R, K221R, E224Q, K229R, G232E, E240T, E262R, E297R, S299Q, K321E, D322T, L328E, E343Q, K348R, M349R, N352E, K353E, E356R, I364E, K365R, F366Y, F376Q, E380D, K382R, S403A, N407W, L408R |
| 263 | pA15906 | 6 | S4P, K5H, D6H, L8G, K10P, K11F, S21E, Y22W, E29R, K32M, E33R, K34L, G35H, D36Y, Y37P, Q49H, F50R, M56W, E59T, K62A, M66Y, K67E, K70R, E71R, K72L, E75S, D77S, K78M, E94L, S96E, T98V, K102E, K104R, D105E, K116W, D129W, P130S, K131E, V132T, P134H, Y135W, E136Q, K137V, E140D, R141W, E147R, I148E, T152Q, K155G, Y156F, Q159W, V161I, V179R, S190E, S191Y, K193R, K194R, P200R, G216R, Y219R, K221R, D228S, K229Q, R231E, G232P, E235R, K238S, E240Y, E262L, N287E, E291R, E297R, N300E, K302M, K318D, K321E, D322T, S323G, K324P, R325Q, L328W, W331F, E343D, E345P, K348R, M349E, N352R, K353R, G361P, D363P, I364P, K365D, Y368R, Q369D, Y370H, D373E, Y375W, F376R, E380D, K382R, K384R, N385P, K392Y, K393H, K396E, R397L, E400R, S403A, N407L, L408D |
| 264 | pA15907 | 6 | S4R, D6Q, Y7N, L8N, R9E, K11V, S21P, K32M, E33R, K34L, G35N, Q49F, F50Q, K62R, N63E, K67R, K70R, E71S, E75D, D77R, K78M, E94L, S96R, T98Q, N101E, K102Y, K104R, D105Q, K116R, P134D, Y135W, E136R, K137I, R141W, E151R, A153S, R154P, K155P, Y156V, N157P, F158N, Q159E, P160M, S190E, S191T, K193R, K194E, N197S, W203Y, G216N, D220T, K221E, N287Q, D290R, E297H, K302Q, K321R, S323D, K324H, R325Q, E343D, K348R, M349R, N352E, K353L, E356R, E380N, K382N, K384Q, K396M, R397L, S403A, N407Q |
| 265 | pA15908 | 6 | S4R, K5H, D6Q, Y7N, L8N, R9E, K10P, K11V, S21P, E29R, F30H, K32Q, E33R, K34H, G35N, F50H, N63E, K67R, K70R, E71S, K72T, E75D, D77R, K78R, E94Q, S96E, T98E, K102Q, K104E, D105E, K116Q, K131E, V132T, P134D, E136R, K137R, E144R, I148V, E151R, A153S, R154P, K155P, Y156Q, N157P, F158N, P160T, S190E, K193E, K194R, N197E, W203R, G216N, K221R, E224Q, K229Q, G232E, K238R, E240T, R258E, E262R, E297H, K318D, E343D, K348E, M349R, N352R, K353Q, D377R, E380N, K382E, K384D, N385T, K392L, K393A, K396E, N407Q |
| 266 | pA15909 | 6 | L3E, S4E, K5H, R9Q, K11F, S21E, K34Q, D36T, Y37E, Q49H, F50R, K62R, N63R, M66E, K67E, K70R, E71R, E75D, I80R, E94Q, S96E, N101E, K102E, K104R, D105E, K116T, K131D, V132E, Y135R, K137E, E140R, I148D, E151R, T152H, R154Q, N157P, F158E, Q159E, S190E, S191R, K194E, N197P, W203R, Y219R, K229R, G232E, E297R, S299Q, K318D, K321E, D322T, K324D, R325Q, E327R, L328E, E343Q, E345D, K348R, M349E, N352R, K353R, N407H, L408R |
| 267 | pA15910 | 6 | S4R, K5H, D6E, L8G, R9Q, K10P, K11E, S21E, E25R, E33R, G35H, D36E, Y37R, N63R, F64E, K67R, K70R, K72E, E75D, D77R, K78Q, S96R, K116R, D129E, P134D, E136R, K137E, R141Q, A153R, R154T, K155E, V161E, S190E, S191H, K193E, K194R, Y195H, N197P, P200E, W203R, S218T, Y219R, K221R, E224Q, K229Q, G232E, E240T, I292Q, K318N, K321D, D322T, L326H, L328E, K365R, Q369R, F376E, K382R, K384Q, E389R, K392H, K393H, K396E, E400R, S403R, N407E, L408R |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| 268 | pA15911 | 6 | S4M, K5V, D6Q, Y7N, L8N, R9I, K10P, K11I, S21P, K32M, G35N, D36S, N63R, K67E, K70R, E71S, K78M, S96A, N101S, K104Q, D105E, K116L, D129Q, K131E, V132T, P134D, Y135W, E136R, K137E, E140I, R141L, E144I, I148V, E151R, T152V, R154P, K155P, Y156V, N157P, F158N, Q159L, P160M, S190E, S191W, K193Y, K194R, N197S, W203A, K238S, E262L, N287L, D290R, E297H, N300D, K302L, D313P, K318D, K321R, K324P, R325A, L328D, W331L, M349R, N352E, K353L, E356R, N407L |
| 269 | pA15912 | 6 | D6Q, L8N, S21P, K34L, G35D, D36Q, E75D, D77R, K78R, S96E, N101E, K104R, D105Q, K116R, D129Q, P134D, Y135W, E136R, K137E, E140R, R141L, E151R, R154P, K155E, Y156V, N157P, F158N, Q159E, P160M, S190E, S191T, K194R, N197S, W203A, K229R, R231E, G232E, E235R, K238E, D313P, K318D, K321D, K324P, R325Q, E343D, E345P, K348E, M349R, N352R, I364E, K365R, K384E, K392R |
| 270 | pA15913 | 6 | L8N, R9E, K10P, S21P, E33H, K34I, G35H, D36E, Y37P, K62R, N63R, K70R, E75D, D77R, K78L, K104Q, D105E, K116R, E147R, R154Q, K155D, Y156F, N157P, Q159L, S190E, K193R, N197R, G216R, D220R, K221E, E240M, N287L, D290E, K302R, R303E, E307R, K324D, R325E, L328E, E343D, K348E, M349R, N352R, G361P, K365R, Q369R, F376E, E380D, K382R, K384E, N385P, S403A, N407F, L408T |
| 271 | pA15914 | 6 | S4R, Y7N, L8N, R9E, K10P, K11V, S21P, K34L, G35S, Q49F, F50Q, N63E, K67R, K70R, E71S, K78M, E94L, S96E, T98Q, N101E, K102Y, D105Q, D129Q, K131E, V132T, P134D, E136R, K137E, E140R, R141L, A153S, R154P, K155P, Y156Q, N157P, F158N, S190E, K193R, N197S, K229Q, G232E, E240T, N287Q, D290R, K302Q, K321D, K324P, R325Q, E343D, E345P, K348E, M349R, N352R, I364P, K365R, F366Y, Q369R, Y375A, E380N, K382N, S403A, N407Q |
| 272 | pA15915 | 6 | S4R, D6Q, Y7N, L8N, R9E, K10P, K11V, S21P, K32M, E33R, K34T, G35N, N63E, K67R, K70R, E71S, E75D, D77R, K78M, S96E, K116Q, D129Q, P134D, E136R, K137E, E140R, R141L, R154P, K155P, Y156V, N157P, F158N, Q159T, P160I, S190E, K193R, K194E, N197E, K229Q, G232E, E240T, N287Q, D290R, N300D, K302R, D313P, K318D, K321D, K324P, R325Q, K396M, R397L, S403L, N407Q |
| 273 | pA15916 | 6 | S4E, D6H, L8G, K10E, K11Q, S21E, Y22W, K32M, E33Q, K34L, G35H, D36N, Y37P, Q49W, F50S, M56W, K62R, N63R, M66E, K67E, K70R, E71R, E75D, D77R, K78L, E94L, S96E, T98Q, N101Q, K102Y, K104Q, D105E, K116E, K131E, V132T, P134D, Y135W, E136R, K137R, E147R, R154S, K155G, Y156F, N157P, Q159R, V161I, V179R, S190E, S191Y, K193R, K194Q, P200R, G216R, Y219R, K221R, K229Q, G232E, K238R, E240Y, E262Q, N287L, D290E, E297R, N300D, K302R, K318D, K321E, D322T, K324D, R325Q, E327R, E343D, E345P, K348R, M349E, N352R, K353R, G361P, I364P, K365R, Q369R, D373R, F376E, E380D, K382R, K384Q, N385P, K392R, K396R, R397L, L408D |
| 274 | pA15917 | 6 | S4R, K5H, D6Q, L8N, R9E, K11V, S21P, F30H, K32Q, K34H, G35N, F50H, N63R, K67E, K70R, E71S, E75D, D77R, K78R, E94Q, S96E, T98E, N101E, K102Q, D105E, K116R, P134D, E136R, K137R, A153S, R154P, K155P, Y156Q, N157P, F158N, Q159E, P160T, S190E, K193R, N197S, W203H, K229Q, G232E, E240T, N287Q, D290Q, K302R, R303E, E307R, K321D, K324P, R325Q, E343D, K348E, M349R, N352R, K384Q, N407Q |
| 275 | pA15918 | 6 | S4R, D6Q, Y7N, L8N, R9E, K11V, S21P, D36Y, N63E, K67R, K70R, E71S, E94L, T98Q, N101E, K102Y, D105E, K116R, K131E, V132T, A153S, R154P, K155P, Y156V, N157P, F158N, Q159E, P160M, S190E, S191T, K193R, K194Q, N197E, W203Y, K229Q, G232E, E240T, N287Q, D290R, K302Q, K318D, K321D, K324P, R325Q, I364E, K365R, K384Q, N407E |
| 276 | pA15919 | 6 | S4D, K5H, D6H, L8G, K10P, K11F, F30A, K32M, E33N, K34Q, G35H, D36Y, Y37P, Q49H, F50R, M56W, K62R, N63R, M66E, E75S, E76L, D77S, K78M, E94Y, T98W, K102E, K104R, D105E, P130S, K131E, V132T, Y135W, E136R, R141W, E147R, I148E, T152Q, K155G, Y156F, N157P, V179R, S190E, S191E, K193R, K194E, N197R, P200L, G216R, Y219R, K221R, D228S, K229Q, R231E, G232P, E235R, K238W, E240Y, E262L, N287L, E297R, N300E, K302P, D313P, K318D, K321E, D322T, K324D, R325Q, E327R, L328W, W331L, M349R, N352E, K353Q, E356R, G361P, D363P, I364P, K365E, Y368R, Q369R, |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| | | | Y375W, F376E, E380D, K382R, K384R, N385P, S403W, N407L, L408D |
| 277 | pA15920 | 6 | L3E, S4R, K5H, D6E, L8G, R9Q, K10A, K11F, S21E, K32I, E33T, K34R, G35H, D36E, Y37R, Q49H, F50R, E59S, K62R, N63D, F64E, M66F, K67R, K70R, E75D, D77R, K78L, E94Y, S96R, T98W, K102E, K104R, D105Q, K116Y, D129E, K131E, Y135W, E136P, K137E, E144D, I148E, E151R, T152R, A153R, R154T, K155Q, Y156F, F158T, Q159E, V161W, V179I, S187R, S190E, S191W, K193R, K194R, N197P, P200M, W203Y, S218T, Y219R, K221R, E224Y, K229A, G232P, E235W, K238S, E240T, N287L, E297R, S299Q, N300E, K302L, D313P, Y315W, K318D, K321D, D322T, K324W, R325W, L326H, L328W, W331F, E343D, E345P, K348R, M349E, N352E, K353R, E356R, D363H, I364P, K365E, Y368R, Q369R, F376E, E380N, K382R, K384R, S403Y, N407F, L408W |
| 278 | pA15921 | 6 | S4R, K5F, D6H, L8N, R9E, K10P, K11I, S21E, K32M, E33H, K34I, G35H, D36Y, Y37P, E59T, K62R, N63D, K70R, E75D, D77R, K78L, E94L, S96A, T98Q, N101T, K102Y, D105E, K116L, K131E, P134H, Y135W, K137E, P160L, V179I, S190Y, S191Y, K194E, N197R, G216R, K221V, D228S, K229Q, R231E, G232E, E262L, E297R, N300Q, D313P, K318D, K321D, K324D, E327I, L328W, E343D, E345P, K348Y, M349Y, N352L, K353L, E356W, G361P, D363P, I364L, K365E, F366H, Y368R, Q369D, F376E, E380D, K382R, K384S, S403A, N407W, L408T |
| 279 | pA15922 | 6 | L3E, S4L, K5H, Y7N, L8G, R9Q, K10R, K11F, S21E, E33N, K34R, G35H, D36W, Y37R, N63R, F64E, K67R, K70R, D77N, K78M, K116Y, D129E, K131E, Y135W, E136P, A153R, R154T, K155Q, Y156Q, F158T, Q159E, P160F, V161W, V179I, S190E, S191W, K194R, N197P, W203L, S218T, Y219R, K221T, E224Y, K229A, G232P, N287L, E297R, S299Q, N300E, K302L, K321S, D322T, R325S, L326H, L328W, W331F, E343D, E345P, K348R, M349E, N352R, K353R, D363H, I364P, K365S, Y368R, Q369D, F376E, K382R, S403W, N407Y, L408W |
| 280 | pA15923 | 6 | L3E, S4E, L8G, R9Q, K10R, K11R, S21E, K34R, D36E, F50H, M56W, K62R, N63Q, M66E, K67E, K70R, E71R, E75D, E76P, E94L, S96E, T98E, N101R, K102E, D105E, K131S, E136Q, K137E, E140R, E150A, K155D, Y156Q, N157E, Q159G, P160R, S190E, S191Y, K193R, K194R, N197S, N201R, R205Q, Y219R, K229Q, G232E, N287R, N300D, K302R, K321E, L326H, E343Y, E345P, K348R, M349E, N352R, I364E, K365R, Y368R, Q369R, F376E, E380N, K382R, S403W, L408R |
| 281 | pA15924 | 6 | S4E, K5H, D6H, L8G, R9Q, K11Q, S21Q, K34Q, G35H, D36H, Y37P, Q49H, F50R, K62R, N63R, M66E, K67E, K70R, E71R, E75D, D77R, K78L, E94R, T98E, N101E, K102E, K104R, P130S, K131E, V132T, E136R, E147R, I148E, V179R, S190E, S191Y, K194E, N197R, W203R, Y219R, K229Q, G232E, K238R, K321E, D322T, K324D, R325Q, E327R, L328E, E343Q, E345P, K348Q, M349E, N352R, G361P, I364E, K365E, Y368R, Q369R, K384R, N385P |
| 282 | pA15925 | 6 | S4L, K5H, D6Q, L8G, R9Q, K10R, K11F, S21E, Y22W, E25R, E29Q, K32I, E33T, K34R, G35H, D36H, Y37R, Q49H, F50R, N63R, F64E, K67R, K70R, K72E, D77N, K78M, E94Y, S96R, T98W, N101E, K102E, D105E, K116Y, D129L, K131E, P134H, Y135W, E136S, K137E, R141Q, A153R, R154T, K155Q, Y156Q, F158T, Q159E, P160F, V161Y, V179I, S190E, S191Q, K193R, K194R, Y195H, N197P, P200M, W203Y, Y219R, K229A, G232P, E240T, I292Q, K321D, D322T, R325D, L326H, L328W, E343D, E345P, K348R, M349E, N352R, D363H, I364P, K365S, Y368R, Q369D, D373R, F376E, K382R, K384R, K392F, K393R, K396R, R397E, E400Q, S403Y, N407F, L408W |
| 283 | pA15926 | 6 | S4R, D6H, L8N, R9E, K10P, K11Q, S21P, E33H, K34R, D36E, K155D, N157P, G216R, K221R, K229Q, G232E, K238R, D241P, N287Q, K302R, K321D, K324D, E343D, K348E, M349R, N352R, G361P, K365R, Q369R, K384E, N385P, S403R, N407D, L408T |
| 284 | pA15927 | 6 | S4D, K5A, D6H, L8G, K10P, K11F, S21E, Y22W, E25R, E29R, E33R, K34L, G35H, D36Y, Y37P, Q49H, F50R, N63R, K67R, K70R, K72L, D77N, K78M, E94Y, T98W, N101Q, K102E, D105E, K116W, P130S, K131E, V132T, K155G, Y156F, Q159W, V161I, G216R, Y219R, K221R, K238S, E262L, N287E, D290R, E297R, N300R, K302R, R303D, K318D, K321E, D322T, K324D, R325Q, E327R, L328Y, W331E, E343N, E345P, K348E, M349E, N352R, K353R, G361P, D363P, I364P, K365E, |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| | | | Y368R, Q369R, F376E, E380D, K382R, K384Q, N385P, K392F, K393H, K396E, R397L, E400R, S403A, N407L, L408D |
| 285 | pA15928 | 6 | S4R, K5H, D6Q, Y7N, L8N, R9E, K10P, K11V, S21P, E25R, K34T, G35N, N63R, K67E, K70R, E71Q, K72T, K78R, N101E, K104R, D105Q, D129Q, K131E, V132T, R141Q, E151R, A153S, R154P, K155P, Y156Q, N157P, F158N, K229Q, G232E, R258E, E262R, N287Q, D290R, E297H, K302Q, R303E, E307Q, D313P, K318D, K321D, K324P, R325Q, E343D, K348R, M349R, N352E, K353Q, E356R, I364E, K365R, E380N, K382N, S403R, N407Q |
| 286 | pA15929 | 6 | L3E, S4Q, K5H, D6R, L8N, K11Y, K32Q, D36T, E75D, D77R, K78M, K116Y, K131D, V132R, A153Q, R154Q, K155E, Y156T, N157D, F158R, K193E, N197D, W203R, K229R, G232E, E240T, S299Q, D313P, K318D, M349R, N352E, K353R, E356R, I364E, K365R, Q369R, F376E, E380R, K382R, K384E, N385P |
| 287 | pA15930 | 6 | S4L, K5V, D6Q, Y7W, L8N, R9I, K11I, S21P, Y22W, E25I, E29L, F30T, K32M, K34F, G35N, D36Y, E59S, K62R, N63D, M66Y, K67E, K70L, E71Q, K72L, E76L, K78M, E94L, S96A, T98R, N101T, K102Y, K104R, D105Q, K116L, D129Q, K131E, V132T, P134D, Y135W, E136R, K137Q, E140I, R141Y, I148V, E151R, T152V, R154P, K155P, Y156V, N157P, F158N, Q159L, P160M, S190E, S191T, K193L, K194R, N197S, W203A, D204S, D228S, K229Q, R231L, G232P, E240T, E297H, D313P, K318D, K321R, K324P, R325A, L328D, M349R, N352E, K353L, E356R, D377A, K384S, E389D, K392L, K393W, R397L, E400L, S403W, N407I |
| 288 | pA15931 | 6 | S4R, D6H, L8G, R9E, K10P, K11Q, S21E, Y37P, K116E, K155G, Y156F, N157P, Q159R, V161I, V179R, G216R, Y219R, K221R, V222I, K229Q, G232E, N287E, D290R, N300D, K302R, K321E, R325Q, W331E, E343D, E345P, K348R, M349E, N352R, G361P, F376E, E380D, K382R, K384R, N385P, L408N |
| 289 | pA15932 | 6 | S4M, K5V, D6Q, Y7N, L8N, R9L, K10P, K11Y, S21P, F30A, K34Y, G35N, D36F, N63E, K67R, K70R, E71S, K78M, S96A, D129Q, K131E, V132T, P134D, E136R, K137I, E140I, R141Y, R154P, K155P, Y156V, N157P, F158N, P160M, K238S, E262L, N287L, D290R, E297H, N300D, K302L, K321R, K324P, R325A, W331F, E343M, E345P, K348W, M349T, N352M, K353L, I364E, K365R, Q369L, S403W, N407I |
| 290 | pA15933 | 6 | S4L, K5V, D6Q, Y7W, L8N, R9I, K10P, K11I, F30A, K32M, K34T, G35D, D36Q, K70R, E71S, K78M, S96A, D129Q, K131E, V132T, P134D, E136R, K137Q, E140I, R141Y, R154P, K155P, Y156V, N157P, F158N, P160M, K193L, N197S, W203A, D204N, D228S, K229Q, R231E, G232E, E235R, K238S, E240T, E262L, N287L, D290R, N300D, K302L, D313P, K318D, K321R, K324P, R325A, W331L, K384L, S403W, N407L |
| 291 | pA15934 | 6 | S4R, D6Q, L8G, R9H, K11E, S21R, K34L, G35H, D36S, Y37R, N63R, F64L, K67E, K70R, E71R, E75D, D77R, K78L, N101Q, K104R, D105E, K116Y, D129E, K131E, E144Q, E151R, T152Y, A153R, F158T, S190E, K193R, K194R, N197P, W203R, Y219R, E240T, N287E, D290R, N300D, K302R, K321D, D322T, R325E, L326H, L328R, W331E, E343Y, E345P, K348E, M349R, N352R, D373N, F376E, K382R, K384Q, R397S, N407H, L408R |
| 292 | pA15935 | 6 | S4E, K5L, D6L, Y7W, L8N, R9Q, K10P, K11V, F30T, D36W, Q49F, F50Q, E59S, K62R, N63D, M66Y, K67Q, E76L, E94L, S96A, T98Q, N101E, K102Y, D105I, K116L, P125A, D129Q, K131Y, V132Y, P134D, E136R, K137Q, E140I, R141Y, R154P, K155P, Y156V, N157P, F158N, Q159L, P160M, S190E, S191T, K194R, N197S, W203F, E262L, N287L, D290R, N300D, K302L, D313P, K318D, W331L, I364E, K365R, F366Y, Q369L, D377A, E380R, K382E, K393W, K396I, R397L, E400Y, S403W, N407I |
| 293 | pA15936 | 6 | S4M, K5V, D6Q, L8N, R9L, K10P, K11Y, S21P, F30A, K34Y, G35N, D36F, K70D, E71S, E76R, K78M, Y135W, R154P, K155P, Y156V, N157P, F158N, P160M, S190E, S191T, K193Y, K194R, N197S, W203A, E262L, N287L, D290R, N300D, K302L, W331L, E343D, K348A, M349R, E380L, K382R, S403W, N407I |
| 294 | pA15937 | 6 | S4M, K5L, D6Q, R9I, K10N, K11I, S21P, F30A, K32Q, K34Y, G35D, D36L, E59S, K62R, N63D, K67E, K70D, E71R, E76R, D77N, K78R, S96A, N101A, K104E, D105E, K116T, K131E, V132T, Y135L, K137V, E144R, I148V, E151R, K155E, F158N, P160E, S190D, S191T, K193R, K194R, N197E, W203Y, D204N, E240T, E262L, N287F, D290Q, K302L, D313P, K318D, |

TABLE 2-continued

| Modified Polypeptides | | | |
|---|---|---|---|
| SEQ NO. | Plasmid ID | Parent Wild Type SEQ ID NO. | Mutation Position(s) (correspond to SEQ ID NO.: 6) |
| | | | K321D, K324E, W331L, E343N, E345P, K348E, M349T, N352R, I364P, K365R, E380R, K382L, S403F, N407I |
| 295 | pA15938 | 6 | S4E, D6H, L8G, K11H, S21E, K32M, E33Q, G35D, D36E, Y37P, Q49F, F50S, M56W, K62R, N63R, M66E, K67E, K70R, E71R, E75D, E76P, I80Q, E94Y, S96E, T98Q, N101Q, K102W, K104R, D105E, K116E, D129W, K137V, R141W, E147R, Y156F, Q159R, V161I, V179R, S191L, G216R, Y219R, K221R, K229Q, G232E, K238R, K321E, D322T, K324D, R325Q, E327R, E343D, E345P, K348R, M349E, N352R, G361P, K365R, Q369R, F376E, E380R, K382Q, K384R, N385P, N407H, L408D |
| 296 | pA15939 | 6 | S4M, K5L, D6Q, R9I, K10N, K11I, S21P, F30H, K32Q, K34T, G35N, E59S, K62R, N63D, K67S, D77N, K78R, S96A, N101E, K104R, D105Q, K116T, K131E, V132T, Y135L, K137V, I148V, E151R, K155E, F158N, P160E, S191T, K193R, K194D, N197S, W203Y, D204N, G216R, K221Q, D228S, K229Q, R231E, G232E, E235R, K238S, E240T, E262L, D290R, E297L, K302L, D313P, K318D, K321D, K324E, W331L, E345P, K348E, M349E, N352R, K353Q, I364P, K365R, F366Y, K384Q, S403T, N407Q |
| 297 | pA15940 | 6 | S4M, K5V, D6Q, L8N, R9L, K10P, K11Y, S21P, Y22W, F30T, E33Q, K34Y, G35N, D36F, E59S, K62R, N63D, K67E, K70R, E71Q, E75D, D77R, K78M, E94L, T98Q, N101E, K102Y, D105E, K116L, Y135W, Q159E, P160M, S191T, K193L, K194A, N197S, W203A, D204R, E240T, E262L, N287L, D290R, N300D, K302L, D313P, K318D, K321R, K324P, R325A, W331L, I364E, K365R, F366Y, Q369L, D377A, K384S, E389D, K392L, K393W, K396I, R397L, E400Y, S403W, N407I |
| 298 | pA15941 | 6 | S4M, K5H, D6E, L8G, K11F, E33N, K34R, G35H, D36H, Y37R, E75D, D77R, K78L, S96R, K104R, D105E, K116Y, D129E, P134H, Y135W, E136S, K137R, R141D, E144D, I148E, E151R, T152R, Y156E, F158T, P160F, V161E, V179I, S187Q, S190E, S191Q, K193I, K194R, Y195H, N197P, P200L, W203L, S218T, Y219R, K221T, E224Y, K229A, G232P, E240T, I292Q, K321S, D322T, R325S, L326H, L328W, E343Y, E345P, K348E, M349W, N352R, D363H, I364P, K365S, Y368R, Q369D, F376E, K382R, S403Y, N407F |
| 299 | pA15942 | 6 | L3E, S4R, K5H, Y7N, R9Q, K11F, S21E, Y22W, E25R, E29R, E33T, K34R, D36E, Y37R, Q49H, F50R, E59S, K62R, N63D, F64E, M66Y, K67R, K70R, K72E, K78R, E94Y, T98W, N101E, K102E, D105E, K116Y, D129E, K131E, Y135W, E136P, A153R, R154T, K155Q, Y156F, F158T, Q159E, P160F, V161W, V179I, S190E, S191W, K194R, N197P, W203L, S218T, Y219R, K221T, E224Y, K229A, G232P, N287L, D290F, I292Q, K302L, R303E, E307R, K321S, D322T, R325S, L326H, L328W, W331F, D363H, I364P, K365S, Y368L, K384R, K392H, K396M, S403Y, N407F, L408W |
| 300 | pA15943 | 6 | S4D, K5Q, D6R, Y7N, L8G, R9Q, K10P, K11W, S21E, E25R, K32Q, G35D, D36Q, K62A, N63R, M66Y, K67E, K70R, K72H, E75R, K78R, N101Q, K104R, D105E, K116Y, Y135W, E136P, I148V, E151R, T152V, R154Q, K155W, N157P, F158N, Q159L, P160F, V179R, S190E, S191W, K193R, K194R, N197E, P200L, D228S, K229Q, R231F, G232P, E240T, D241R, E262L, E343D, E345P, K348R, M349R, D363H, I364E, K365S, Q369R, E380N, K382N, N407E |
| 301 | pA15944 | 6 | S4E, K5H, D6H, L8G, K10P, K11F, S21E, K34L, G35H, D36Y, Y37P, M56W, E59S, K62R, N63D, M66F, K67E, E71R, E75D, E76L, D77R, K78L, V179R, G216R, Y219R, K221R, D228S, K229Q, G232P, E262L, N287L, N300D, K302P, K321E, D322T, K324D, R325Q, E327R, L328W, W331L, E343D, E345P, K348R, M349E, N352R, G361P, D363P, K365D, Y368R, Q369R, K384R, N385P, L408D |
| 302 | pA15945 | 6 | S4R, K5F, D6H, L8N, R9E, K10P, K11I, S21P, F30A, K32M, E33H, K34V, G35H, D36E, Y37P, Q49W, F50Q, E59T, K62R, N63D, K67T, K70R, E75D, D77R, K78L, E94L, S96A, T98Q, N101T, K102Y, K104Q, D105I, K116L, D129W, P130S, K131E, Y135W, K137L, R141L, E147R, I148V, T152V, A153G, R154Q, K155D, Y156M, N157P, Q159L, P160M, V179I, S190Y, S191Y, K193F, K194L, P200L, W203R, G216R, K221V, E224M, D228S, K229Q, R231E, G232E, E235R, K238S, E240Y, D241P, E262L, N287L, E297R, N300Q, K302I, D313P, K318D, K321D, K324D, E327Y, L328W, W331L, E343L, E345P, K348W, M349Y, N352L, K353L, E356W, G361P, I364L, K365R, Y368L, Q369R, F376E, E380D, K382R, K384S, S403W |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| 303 | pA15946 | 6 | S4P, K5A, D6H, K10E, K11H, S21R, K32Q, E33N, K34M, G35H, D36E, Y37P, M56W, E59S, K62R, N63D, M66Y, E75R, E76L, K78L, E94L, S96E, T98I, N101Q, K102Y, K104R, D105E, K131E, V132T, P134D, Y135L, E136T, K137R, E147R, I148E, V179I, S190D, S191R, K193R, K194E, G216R, K221Q, K229Q, G232P, E262Q, N287R, K302R, R303E, E307R, K321R, D322T, K324E, R325D, E327R, L328Y, E345P, K348Q, M349E, N352R, K353R, G361P, D363P, I364P, K365N, F376E, E380R, K382L, K384R, N385P, S403A, N407H, L408D |
| 304 | pA15947 | 6 | S4D, K5H, D6H, R9L, K10N, K11I, S21P, K32A, E33N, K34M, G35H, D36L, Y37P, E59S, K62R, N63D, K67D, K70D, E71R, E75D, E76R, D77N, K78L, E94L, S96A, T98Q, N101D, K102Y, K104R, D105Q, K116T, K131E, K137V, E147R, I148V, K155E, P160A, V179I, S190E, S191L, K193R, K194R, G216R, K221I, D228S, K229Q, R231E, G232E, E235R, K238S, D241N, E262L, N287H, D290E, K302I, R303E, E307R, D313P, K318D, K321D, K324E, L328Y, W331L, E345P, K348R, M349T, N352E, K353L, E356R, G361P, D363P, I364L, K365S, F376E, E380R, K382L, K384E, S403A |
| 305 | pA15948 | 6 | S4D, K5A, D6H, K10D, K11I, S21P, E25R, E29I, K32I, E33R, K34T, E59S, K62R, N63D, K67S, K70D, K72L, E75D, E76R, D77N, K78L, E94L, S96A, T98R, N101E, K102Y, K104R, D105Q, R108I, K116T, K131E, V132R, Y135L, K137V, E140R, E151R, T152Y, R154Q, K155E, F158V, S187A, S190E, S191A, K193R, K194R, N197D, W203F, D220E, K221T, D228S, K229R, R231E, G232E, E235R, K238S, E240D, D241Q, R258L, E262R, N287H, D290E, S299A, K302I, R303E, E307R, D313P, K318D, K321D, K324E, L328Y, W331L, E345P, K348L, M349T, N352E, K353R, E356R, I364M, K365R, F366Y, F376E, D377R, E380R, K382E, K384T, N385P, K392L, K393T, K396M, R397L, S403A, L408D |
| 306 | pA15949 | 6 | L3T, S4D, K5H, D6N, K10E, K11I, S21E, K32I, K34M, D36S, M56W, E59S, K62R, N63D, M66F, K67E, K70D, E71R, E76R, D77N, K78L, E94L, S96E, T98R, N101R, K102Y, K104E, D105E, K116T, K131E, Y135L, K137R, E144R, I148V, E151R, T152Y, A153R, R154Q, K155Q, F158V, S187A, S190E, S191A, K193R, K194R, N197S, P200M, W203Y, D220Q, K221T, E224Y, D228S, K229R, R231E, G232P, E235R, K238S, E240T, E262Q, N287E, D290R, K302I, R303E, E307R, D313P, K318D, K321R, D322T, K324E, R325D, L328Y, W331L, E343N, E345P, K348R, M349E, N352R, K353R, I364P, K365R, F366L, F376E, E380R, K382L, K384T, S403A, N407H, L408D |
| 307 | pA15950 | 6 | S4M, K5L, D6Q, R9I, K10N, K11I, E25R, E29I, F30A, K32L, E33R, K34Y, G35D, D36L, E59S, K62A, N63E, M66Y, K67R, K70Q, K72I, D77N, K78R, S96A, K116T, K131E, V132T, Y135L, K137V, K155E, F158N, P160E, S191T, K193R, K194D, N197S, W203Y, D204N, G216R, K221Q, D228S, K229Q, R231E, G232E, E235R, K238S, E240T, E262L, N287F, D290Q, K302L, D313P, K318D, K321R, K324E, R325D, W331L, E345P, K348E, M349T, N352R, D377S, E380R, K382L, K384S, E389D, K392L, K393Y, K396M, R397L, S403F, N407I |
| 308 | pA15951 | 6 | S4N, K5Q, D6Q, K10R, K11E, S21P, K32Q, K34Y, G35N, D36R, E59S, K62R, N63D, M66F, K67E, K70D, E71R, E76R, D77N, K78R, S96E, K104R, D105E, P130S, K131E, V132T, E136P, K137R, E144I, I148E, E151R, K155E, F158N, S190E, S191Y, K193R, K194R, N197L, G216R, K221Q, K229N, G232P, D241R, K321R, K324E, R325D, E327R, E343N, E345P, K348E, M349N, N352R, I364P, K365R, S403A, N407E |
| 309 | pA15952 | 6 | S4L, K5L, D6Q, K10N, K11I, S21P, N63R, K67E, K70D, E71R, E76R, E94L, S96A, T98Q, N101E, K102Y, D105E, K116T, Y135L, K137V, K155E, F158N, P160E, S190D, S191T, K193R, K194R, N197S, W203Y, K238S, E262L, N287F, D290Q, K302L, D313P, K318D, W331L, I364P, K365R |
| 310 | pA15953 | 6 | S4M, K5L, D6Q, R9I, K10N, K11I, S21P, E25R, K32L, K34T, G35N, E59S, K62R, N63E, K67R, K70Q, K72I, K78R, N101A, K104E, D105E, K131E, V132T, Y135L, E144R, I148V, E151R, K155E, F158N, P160E, S190D, S191T, K193R, K194R, N197S, W203Y, D204N, D228S, K229Q, R231E, G232E, E235R, K238S, E240T, E262L, E297L, D313P, K318D, K321D, K324E, M349I, N352E, K353L, E356R, I364P, K365R, D377R, E380N, K382D, K393Y, S403L, N407Q |
| 311 | pA15954 | 6 | K5A, D6Q, S21P, K32Q, K34Y, G35N, D36T, N63R, K67E, K70D, E71R, E76R, D77N, K78R, N101A, K104E, D105E, Y135L, E144R, I148V, E151R, K155E, F158N, P160E, S190E, |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| | | | S191T, K193E, K194R, N197S, W203F, G216R, K221Q, K238S, E297L, K321D, K324E, M349I, N352E, K353L, E356R, I364P, K365R, K384Q |
| 312 | pA15955 | 6 | L3T, S4D, K5H, K10R, K11V, S21E, E25R, E29R, K32R, E33D, K34D, G35D, D36T, F50H, E59S, K62R, N63D, M66Y, K67R, K70D, K72E, E75R, E76R, K78L, E94R, S96E, T98E, K102E, K104R, D105E, D129R, K131S, V132S, E136P, K137R, I148E, E151R, T152Y, R154E, K155Q, F158L, S190E, S191Y, K193R, K194E, N197R, P200E, D228S, K229Q, R231E, G232P, E235R, K238S, E240T, N287R, D290E, K302I, R303E, E307R, K318N, K321R, K324E, R325G, L328Y, W331L, D363P, K365N, D373E, F376E, D377N, E380R, K382L, K384Q, E389R, K392L, K393E, K396M, E400R, S403A, N407R |
| 313 | pA15956 | 6 | S4M, K5L, D6Q, R9I, K10N, K11I, S21P, E29R, K32Q, E33R, K34T, G35N, D36L, N63R, K67E, K70D, E71R, K72T, E76R, D77N, K78R, E94L, S96A, T98Q, N101E, K102Y, D105E, K131E, V132T, K137V, K155E, F158N, P160E, K193R, K194D, N197S, W203Y, D228S, K229Q, R231A, G232P, E240T, E262L, N287F, D290Q, K302L, R303E, E307R, W331L, E345P, K348E, M349T, N352R, D377S, K382L, K384S, E389D, K392L, K393Y, K396M, R397L, S403L, N407Q |
| 314 | pA15957 | 6 | S4M, K5L, D6Q, R9I, K10N, K11I, E29R, F30A, K32Q, K34Y, G35N, D36L, E59S, K62R, N63D, K67E, K70D, E71R, K72T, E76R, D77N, K78R, S96A, N101E, K104R, D105Q, K116T, Y135L, K137V, I148V, E151R, P160E, S190E, S191T, K193R, K194A, N197S, W203Y, G216R, K221Q, E262L, D290E, K302L, R303E, E307R, D313P, K318D, W331L, E345P, K348E, M349T, N352R, E380R, K382L, K384S, E389D, K392L, K393A, K396I, R397L, E400R, S403F, N407H |
| 315 | pA15958 | 6 | S4P, K5A, D6H, K10E, K11H, S21E, E33N, K34M, D36E, M56W, E59S, K62R, N63D, M66Y, K67E, K70D, E71R, E76R, K78R, K131E, V132T, E136D, K155Q, Y156M, S190E, S191R, K193R, K194E, N197R, Y219G, K238S, E262Q, N287R, K302I, R303E, E307R, K321R, D322T, R325G, L328Y, W331L, E343N, E345P, K348R, M349E, N352R, G361P, K384R, N385P, S403A, N407H, L408D |
| 316 | pA15959 | 6 | L3T, S4D, K5H, D6A, K10E, K11I, S21E, E25R, E29R, K32I, D36T, N63R, K67E, K70D, K72E, E75R, E76R, K78L, S96E, N101Q, K104R, D105E, K116T, K131E, P134D, Y135D, K137R, E140R, I148V, E151R, T152Y, A153R, R154Q, K155Q, N157R, F158V, S187R, S190D, S191A, K193R, K194R, N197S, W203F, Y219G, K221Q, D228S, K229R, R231E, G232P, E235R, K238S, E262R, S299A, K318D, E343N, E345P, K348R, M349E, N352R, K353R, I364P, K365R, F366Y, D373E, F376E, E380R, K382L, K384R, E389D, K392L, K393A, K396M, R397L, E400R, L408D |
| 317 | pA15960 | 6 | S4P, K5A, D6H, K10R, K11R, S21E, E33N, K34M, N63R, K67E, K70D, E71R, E75R, E76R, K78L, S96E, K104R, D105E, K116D, K131E, V132T, P134A, Y135L, E136P, K137R, E147R, I148E, K155Q, Y156M, Q159R, V179I, S190E, S191Y, K193R, K194R, Y219G, D228S, K229Q, G232P, N287R, K302I, R303E, E307R, K321S, D322T, S323G, R325D, L328Y, W331L, E343N, E345P, K348R, M349E, N352R, K353R, I364L, K365S, F366L, F376E, E380R, K382L, N407H, L408D |
| 318 | pA15961 | 6 | S4M, K5Q, D6A, R9I, K10A, K11I, S21E, E25R, E29R, F30A, K32Q, E33N, K34Y, G35N, D36T, E59S, K62R, N63D, M66Y, K67R, K70D, K72E, E76R, D77N, K78R, E94L, S96E, T98Q, N101Q, K102Y, K104R, D105E, K116T, P130S, K131E, V132T, E136P, K137R, I148V, E151R, K155E, N157D, F158N, S190E, S191Y, K193R, K194R, N197E, P200M, G216R, D220Q, K221T, D228S, K229Q, R231E, G232P, E235R, K238S, R239S, E240T, E262L, N287R, D290Q, E297L, K302L, R303E, E307R, K318N, K321R, K324E, R325D, E327R, L328Y, W331L, E343N, E345P, K348E, M349Q, N352R, K353E, E356R, N357H, I364P, K365R, D377R, E380N, K382E, K384R, E389D, K392E, K393A, K396Q, R397E, S403F, N407I |
| 319 | pA15962 | 6 | K5H, K10E, K11H, S21E, E29R, K32I, E33N, K34M, G35H, Y37P, M56W, E59S, K62R, N63D, M66Y, K67E, K70D, E71R, K72T, E76R, D77N, K78L, S96E, N101Q, K104R, D105E, K116D, K131E, V132T, P134A, Y135L, E136P, K137R, E147R, I148E, T152A, Y156M, Q159R, V179I, S190E, S191Y, K193R, K194R, G216R, K221Q, D228S, K229Q, G232P, E262Q, K318D, K321R, D322T, K324E, R325G, E327R, L328Y, E343N, E345P, |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| | | | K348R, M349E, N352R, D373R, K382L, K384R, K392L, K393A, K396M, R397E, E400R, S403A, N407H, L408D |
| 320 | pA15963 | 6 | S4P, K5A, D6H, K10E, K11H, S21E, K32I, K34M, G35H, Y37P, N63R, K67E, K70D, E71R, K72L, E76R, D77N, K78L, E94L, T98Q, N101Q, K102Y, K104R, D105E, K116T, Y135L, E136P, E147R, I148E, K155Q, Y156M, V179I, S190D, S191E, K193R, K194R, K229Q, G232P, E262Q, K318D, K321S, D322T, R325D, L328Y, E343N, E345P, K348R, M349E, N352R, G361P, D363P, I364L, K365S, D373L, K382L, K384E, N385P, D386H, R388E, E389R, K392R, K393A, K396M, R397E, E400R, N407H, L408D |
| 374 | pA16624 | 6 | C17T |
| 375 | pA16625 | 6 | S18N |
| 376 | pA16626 | 6 | S18A |
| 377 | pA16631 | 6 | Q46W |
| 378 | pA16632 | 6 | Q46R |
| 379 | pA16633 | 6 | D84P |
| 380 | pA16634 | 6 | D84A |
| 381 | pA16635 | 6 | L89G |
| 382 | pA16637 | 6 | H45Q |
| 383 | pA16638 | 6 | H45A |
| 384 | pA16639 | 6 | H45K |
| 385 | pA16640 | 6 | Q46A |
| 386 | pA16643 | 6 | D84G |
| 387 | pA16645 | 6 | L89S |
| 388 | pA16647 | 6 | H45F |
| 389 | pA16649 | 6 | Q46S |
| 390 | pA16651 | 6 | Q46T |
| 391 | pA16653 | 6 | Q92A |
| 392 | pA16654 | 6 | Q92M |
| 393 | pA16655 | 6 | Q92P |
| 394 | pA16656 | 6 | Q92D |
| 395 | pA16657 | 6 | S123A |
| 396 | pA16659 | 6 | Q92G |
| 397 | pA16660 | 6 | H119N |
| 398 | pA16663 | 6 | H119G |
| 399 | pA16664 | 6 | H119P |
| 400 | pA16665 | 6 | C122G |
| 401 | pA16668 | 6 | C122E |
| 402 | pA16669 | 6 | C122K |
| 403 | pA16670 | 6 | H119S |
| 404 | pA16671 | 6 | S123M |
| 405 | pA16672 | 6 | S123R |
| 406 | pA16673 | 6 | S123T |
| 407 | pA16674 | 6 | M124R |
| 408 | pA16675 | 6 | M124K |
| 409 | pA16678 | 6 | T166M |
| 410 | pA16680 | 6 | T166I |
| 411 | pA16682 | 6 | T166L |
| 412 | pA16684 | 6 | D167A |
| 413 | pA16685 | 6 | D167V |
| 414 | pA16686 | 6 | D167T |
| 415 | pA16687 | 6 | D167N |
| 416 | pA16688 | 6 | V168M |
| 417 | pA16689 | 6 | V168R |
| 418 | pA16691 | 6 | I170K |
| 419 | pA16693 | 6 | A171P |
| 420 | pA16694 | 6 | I170T |
| 421 | pA16695 | 6 | I170M |
| 422 | pA16705 | 6 | E175K |
| 423 | pA16706 | 6 | E176Y |
| 424 | pA16707 | 6 | E175V |
| 425 | pA16708 | 6 | E176F |
| 426 | pA16710 | 6 | G173S |
| 427 | pA16712 | 6 | E175R |
| 428 | pA16719 | 6 | G178P |
| 429 | pA16720 | 6 | V210P |
| 430 | pA16722 | 6 | V210T |
| 431 | pA16726 | 6 | M212K |
| 432 | pA16729 | 6 | M212L |
| 433 | pA16730 | 6 | M212R |
| 434 | pA16733 | 6 | T249S |
| 435 | pA16736 | 6 | R339G |
| 436 | pA16737 | 6 | R339A |

TABLE 2-continued

Modified Polypeptides

| SEQ NO. | Plasmid ID | Parent Wild Type SEQ ID NO. | Mutation Position(s) (correspond to SEQ ID NO.: 6) |
|---|---|---|---|
| 437 | pA16738 | 6 | R339T |
| 438 | pA16740 | 6 | R339E |
| 439 | pA16741 | 6 | Y340P |
| 440 | pA16742 | 6 | Y340R |
| 441 | pA16743 | 6 | Y340H |
| 442 | pA16744 | 6 | Y53V |
| 443 | pA16745 | 6 | Y53S |
| 444 | pA16746 | 6 | Y53A |

In some embodiments, the polypeptide comprises the amino acid sequence set forth in SEQ ID NO: 1 is derived from *Caldithrix abyssi*. In some embodiments, the polypeptide may have a molecular weight of 50.0 kDa to 52.0 kDa. In some embodiments, the polypeptide comprises the amino acid sequence set forth in SEQ ID NO: 2 is derived from *Anaerolinea thermophila*. In some embodiments, the polypeptide may have a molecular weight of 46.3 kDa to 48.3 kDa. In some embodiments, the polypeptide comprises the amino acid sequence set forth in SEQ ID NO: 3 is derived from *Thermoanaerobacterium thermosaccharolyticum*. In some embodiments, the polypeptide may have a molecular weight of 48.4 kDa to 50.4 kDa. In some embodiments, the polypeptide comprises the amino acid sequence set forth in SEQ ID NO: 4 is derived from *Thermoanaerobacter thermohydrosulfuricus*. In some embodiments, the polypeptide may have a molecular weight of 50.0 kDa to 52.0 kDa. In some embodiments, the polypeptide comprises the amino acid sequence set forth in SEQ ID NO: 5 is derived from *Caldicellulosiruptor kronotskyensis*. In some embodiments, the polypeptide may have a molecular weight of 48.3 kDa to 50.3 kDa. In some embodiments, the polypeptide comprises the amino acid sequence set forth in SEQ ID NO: 6 is derived from *Dictyoglomus turgidum*. In some embodiments, the polypeptide may have a molecular weight of 46.9 kDa to 48.9 kDa. In some embodiments, the polypeptide comprises the amino acid sequence set forth in SEQ ID NO: 7 is derived from *Caldilinea aerophila*. In some embodiments, the polypeptide may have a molecular weight of 44.7 kDa to 46.7 kDa. In some embodiments, the polypeptide comprises the amino acid sequence set forth in SEQ ID NO: 8 is derived from *Rhodothermus marinus*. In some embodiments, the polypeptide may have a molecular weight of 45.9 kDa to 47.9 kDa. In some embodiments, the polypeptide comprises the amino acid sequence set forth in SEQ ID NO: 9 is derived from *Methanohalobium evestigatum*. In some embodiments, the polypeptide may have a molecular weight of 44.7 kDa to 46.7 kDa. In some embodiments, the polypeptide comprises the amino acid sequence set forth in SEQ ID NO: 10 is derived from *Thermoanaerobacter thermohydrosulfuricus*. In some embodiments, the polypeptide may have a molecular weight of 37.6 kDa to 39.6 kDa. In some embodiments, the polypeptide comprises the amino acid sequence set forth in SEQ ID NO: 11 is derived from *Clostridium cavendishii*. In some embodiments, the polypeptide may have a molecular weight of 48.7 kDa to 50.7 kDa. In some embodiments, the polypeptide comprises the amino acid sequence set forth in SEQ ID NO: 12 is derived from *Kosmotoga olearia*. In some embodiments, the polypeptide may have a molecular weight of 48.3 kDa to 50.3 kDa. In some embodiments, the polypeptide comprises the amino acid sequence set forth in SEQ ID NO: 13 is derived from *Butyricicoccus pullicaecorum*. In some embodiments, the polypeptide may have a molecular weight of 48.0 kDa to 50.0 kDa. In some embodiments, the polypeptide comprises the amino acid sequence set forth in SEQ ID NO: 14 is derived from *Clostridium thermobutyricum*. In some embodiments, the polypeptide may have a molecular weight of 50.6 kDa to 52.6 kDa. In some embodiments, the polypeptide comprises the amino acid sequence set forth in SEQ ID NO: 15 is derived from *Litorilinea aerophila*. In some embodiments, the polypeptide may have a molecular weight of 46.5 kDa to 48.5 kDa. In some embodiments, the polypeptide comprises the amino acid sequence set forth in SEQ ID NO: 16 is derived from *Enterobacter mori*. In some embodiments, the polypeptide may have a molecular weight of 47.5 kDa to 49.5 kDa. In some embodiments, the polypeptide comprises the amino acid sequence set forth in SEQ ID NO: 17 is derived from *Caldisericum exile*. In some embodiments, the polypeptide may have a molecular weight of 47.1 kDa to 49.1 kDa. In some embodiments, the polypeptide comprises the amino acid sequence set forth in SEQ ID NO: 18 is derived from *Dictyoglomus thermophilum*. In some embodiments, the polypeptide may have a molecular weight of 46.9 kDa to 48.9 kDa. In some embodiments, the polypeptide comprises the amino acid sequence set forth in SEQ ID NO: 19 is derived from *Rhodothermus marinus*. In some embodiments, the polypeptide may have a molecular weight of 45.9 kDa to 47.9 kDa. In some embodiments, the polypeptide comprises the amino acid sequence set forth in SEQ ID NO: 20 is derived from *Rhodothermus profundi*. In some embodiments, the polypeptide may have a molecular weight of 46.3 kDa to 48.3 kDa. In some embodiments, the polypeptide comprises the amino acid sequence set forth in SEQ ID NO: 21 is derived from *Caldibacillus debilis*. In some embodiments, the polypeptide may have a molecular weight of 47.5 kDa to 49.5 kDa. In some embodiments, the polypeptide comprises the amino acid sequence set forth in SEQ ID NO: 22 is derived from *Caloramator quimbayensis*. In some embodiments, the polypeptide may have a molecular weight of 46.8 kDa to 48.8 kDa. In some embodiments, the polypeptide comprises the amino acid sequence set forth in SEQ ID NO: 23 is derived from *Methanosalsum zhilinae*. In some embodiments, the polypeptide may have a molecular weight of 41.6 kDa to 43.6 kDa. In some embodiments, the polypeptide comprises the amino acid sequence set forth in SEQ ID NO: 321 is derived from *Pseudothermotoga thermarum*. In some embodiments, the polypeptide may have a molecular weight of 56.2 kDa to 58.2 kDa. In some embodiments, the polypeptide comprises the amino acid sequence set forth in SEQ ID NO: 322 is derived from *Pseudothermotoga hypogea*. In some embodiments, the polypeptide may have a molecular weight of 54.8 kDa to 56.8 kDa. In some embodiments, the polypeptide comprises the amino acid sequence set forth in SEQ ID NO: 323 is derived from *Pseudothermotoga lettingae*. In some embodiments, the polypeptide may have a molecular weight of 55.9 kDa to 57.9 kDa. In some embodiments, the polypeptide comprises the amino acid sequence set forth in SEQ ID NO: 324 is derived from *Rhodothermus marinus*. In some embodiments, the polypeptide may have a molecular weight of 57.5 kDa to 59.5 kDa. In some embodiments, the polypeptide comprises the amino acid sequence set forth in SEQ ID NO: 325 is derived from *Geosporobacter subterraneus*. In some embodiments, the polypeptide may have a molecular weight of 56.2 kDa to 58.2 kDa. In some embodiments, the polypeptide comprises the amino acid sequence set forth in SEQ ID NO: 326 is derived from *Melioribacter roseus*. In some embodiments, the polypeptide may have a molecular weight of 58.0 kDa to 60.0 kDa. In some embodiments, the polypeptide comprises the amino acid sequence set forth in SEQ ID NO: 327 is derived from *Lysinibacillus sphaericus*. In some embodiments, the polypeptide may have a molecular weight of 55.2 kDa to 57.2 kDa. In some embodiments, the polypeptide comprises the amino acid sequence set forth in SEQ ID NO: 328 is derived from *Clostridium stercorarium*. In some embodiments, the polypeptide may have a molecular weight of 56.9 kDa to 58.9 kDa. In some embodiments, the polypeptide comprises the amino acid sequence set forth in SEQ ID NO: 329 is derived from *Truepera radiovictrix*. In some embodiments, the polypeptide may have a molecular weight of 51.8 kDa to 53.8 kDa. In some embodiments, the polypeptide comprises the amino acid sequence set forth in SEQ ID NO: 330 is derived from *Dictyoglomus turgidum*. In some embodiments, the polypeptide may have a molecular weight of 55.7 kDa to 57.7 kDa. In some embodiments, the polypeptide comprises the amino acid sequence set forth in SEQ ID NO: 331 is derived from *Caldilinea aerophila*. In some embodiments, the polypeptide may have a molecular weight of 51.0 kDa to 53.0 kDa. In some embodiments, the polypeptide comprises the amino acid sequence set forth in SEQ ID NO: 332 is derived from *Thermoflexus hugenholtzii*. In some embodiments, the polypeptide may have a molecular weight of 51.5 kDa to 53.5 kDa. In some embodiments, the polypeptide comprises the amino acid sequence set forth in SEQ ID NO: 333 is derived from *Thermoanaerobacterium thermosaccharolyticum*. In some embodiments, the polypeptide may have a molecular weight of 54.7 kDa to 56.7 kDa. In some embodiments, the polypeptide comprises the amino acid sequence set forth in SEQ ID NO: 334 is derived from *Petrotoga mobilis*. In some embodiments, the polypeptide may have a molecular weight of 43.8 kDa to 45.8 kDa. In some embodiments, the polypeptide comprises the amino acid sequence set forth in SEQ ID NO: 335 is derived from *Spirochaeta thermophila*. In some embodiments, the polypeptide may have a molecular weight of 46.2 kDa to 48.2 kDa. In some embodiments, the polypeptide comprises the amino acid sequence set forth in SEQ ID NO: 336 is derived from *Thermofilum pendens*. In some embodiments, the polypeptide may have a molecular weight of 53.4 kDa to 55.4 kDa. In some embodiments, the polypeptide comprises the amino acid sequence set forth in SEQ ID NO: 337 is derived from *Rhodothermus marinus*. In some embodiments, the polypeptide may have a molecular weight of 57.3 kDa to 59.3 kDa. In some embodiments, the polypeptide comprises the amino acid sequence set forth in SEQ ID NO: 338 is derived from *Dictyoglomus thermophilum*. In some embodiments, the polypeptide may have a molecular weight of 55.9 kDa to 57.9 kDa. In some embodiments, the polypeptide comprises the amino acid sequence set forth in SEQ ID NO: 339 is derived from *Thermoanaerobacter siderophilus*. In some embodiments, the polypeptide may have a molecular weight of 55.0 kDa to 57.0 kDa. In some embodiments, the polypeptide comprises the amino acid sequence set forth in SEQ ID NO: 340 is derived from *Thermoanaerobacter mathranii*. In some embodiments, the polypeptide may have a molecular weight of 54.8 kDa to 56.8 kDa. In some embodiments, the polypeptide comprises the amino acid sequence set forth in SEQ ID NO: 341 is derived from *Thermoanaerobacter italicus*. In some embodiments, the polypeptide may have a molecular weight of 54.9 kDa to 56.9 kDa. In some embodiments, the polypeptide comprises the amino acid sequence set forth in SEQ ID NO: 342 is derived from *Thermoanaerobacterium thermosaccharolyticum*. In some embodiments, the polypeptide may have a molecular weight of 54.7 kDa to 56.7 kDa. In some embodiments, the polypeptide comprises the amino acid sequence set forth in SEQ ID NO: 343 is derived from *Thermoanaerobacterium thermosaccharolyticum*. In some embodiments, the polypeptide may have a molecular weight of 54.7 kDa to 56.7 kDa. In some embodiments, the polypeptide comprises the amino acid sequence set forth in SEQ ID NO: 344 is derived from *Thermoanaerobacterium thermosaccharolyticum*. In some embodiments, the polypeptide may have a molecular weight of 54.6 kDa to 56.6 kDa. In some embodiments, the polypeptide comprises the amino acid sequence set forth in SEQ ID NO: 345 is derived from *Thermoanaerobacterium thermosaccharolyticum*. In some embodiments, the polypeptide may have a molecular weight of 54.5 kDa to 56.5 kDa. In some embodiments, the polypeptide comprises the amino acid sequence set forth in SEQ ID NO: 346 is derived from *Thermoanaerobacterium xylanolyticum*. In some embodiments, the polypeptide may have a molecular weight of 54.2 kDa to 56.2 kDa. In some embodiments, the polypeptide comprises the amino acid sequence set forth in SEQ ID NO: 347 is derived from *Petrotoga mobilis*. In some embodiments, the polypeptide may have a molecular weight of 43.9 kDa to 45.9 kDa. In some embodiments, the polypeptide comprises the amino acid sequence set forth in SEQ ID NO: 348 is derived from *Thermoanaerobacterium saccharolyticum*. In some embodiments, the polypeptide may have a molecular weight of 54.0 kDa to 56.0 kDa. In some embodiments, the polypeptide comprises the amino acid sequence set forth in SEQ ID NO: 349 is derived from *Petrotoga mobilis*. In some embodiments, the polypeptide may have a molecular weight of 44.4 kDa to 46.4 kDa. In some embodiments, the polypeptide comprises the amino acid sequence set forth in SEQ ID NO: 350 is derived from *Spirochaeta thermophila*. In some embodiments, the polypeptide may have a molecular weight of 46.5 kDa to 48.5 kDa. In some embodiments, the polypeptide comprises the amino acid sequence set forth in SEQ ID NO: 351 is derived from *Ignisphaera aggregans*. In some embodiments, the polypeptide may have a molecular weight of 29.1 kDa to 31.1 kDa. In some embodiments, the polypeptide comprises the amino acid sequence set forth in SEQ ID NO: 352 is derived from *Thermotoga maritima*. In some embodiments, the polypeptide may have a molecular weight of 54.6 kDa to 56.6 kDa. In some embodiments, the polypeptide comprises the amino acid sequence set forth in SEQ ID NO: 353 is derived from *Caldanaerobacter subterraneus. In some embodiments, the polypeptide may have a molecular weight of* 55.2 kDa to 57.2 kDa. In some embodiments, the polypeptide comprises the amino acid sequence set forth in SEQ ID NO: 354 is derived from *Mesotoga infera*. In some embodiments, the polypeptide may have a molecular weight of 57.1 kDa to 59.1 kDa. In some embodiments, the polypeptide comprises the amino acid sequence set forth in SEQ ID NO: 355 is derived from *Thermosinus carboxydivorans*. In some embodiments, the polypeptide may have a molecular weight of 54.5 kDa to 56.5 kDa. In some embodiments, the polypeptide comprises the amino acid sequence set forth in SEQ ID NO: 356 is derived from *Halanaerobium congolense*. In some embodiments, the polypeptide may have a molecular weight of 57.5 kDa to 59.5 kDa. In some embodiments, the polypeptide comprises the amino acid sequence set forth in SEQ ID NO: 357 is derived from *Halanaerobium congolense*. In some embodiments, the polypeptide may have a molecular weight of 57.5 kDa to 59.5 kDa. In some embodiments, the polypeptide comprises the amino acid sequence set forth in SEQ ID NO: 358 is derived from *Halanaerobium saccharolyticum*. In some embodiments, the polypeptide may have a molecular weight of 57.2 kDa to 59.2 kDa. In some embodiments, the polypeptide comprises the amino acid sequence set forth in SEQ ID NO: 359 is derived from *Gracilibacillus halophilus*. In some embodiments, the polypeptide may have a molecular weight of 56.1 kDa to 58.1 kDa. In some embodiments, the polypeptide comprises the amino acid sequence set forth in SEQ ID NO: 360 is derived from *Caldanaerobacter subterraneus*. In some embodiments, the polypeptide may have a molecular weight of 55.6 kDa to 57.6 kDa. In some embodiments, the polypeptide comprises the amino acid sequence set forth in SEQ ID NO: 361 is derived from *Litorilinea aerophila*. In some embodiments, the polypeptide may have a molecular weight of 45.2 kDa to 47.2 kDa. In some embodiments, the polypeptide comprises the amino acid sequence set forth in SEQ ID NO: 362 is derived from *Caldanaerobacter subterraneus*. In some embodiments, the polypeptide may have a molecular weight of 55.4 kDa to 57.4 kDa. In some embodiments, the polypeptide comprises the amino acid sequence set forth in SEQ ID NO: 363 is derived from *Caldanaerobacter subterraneus*. In some embodiments, the polypeptide may have a molecular weight of 56.3 kDa to 58.3 kDa. In some embodiments, the polypeptide comprises the amino acid sequence set forth in SEQ ID NO: 364 is derived from *Caldicoprobacter faecalis*. In some embodiments, the polypeptide may have a molecular weight of 54.4 kDa to 56.4 kDa. In some embodiments, the polypeptide comprises the amino acid sequence set forth in SEQ ID NO: 365 is derived from *Thermoanaerobacter uzonensis*. In some embodiments, the polypeptide may have a molecular weight of 55.2 kDa to 57.2 kDa. In some embodiments, the polypeptide comprises the amino acid sequence set forth in SEQ ID NO: 366 is derived from *Lactobacillus ingluviei*. In some embodiments, the polypeptide may have a molecular weight of 60.1 kDa to 62.1 kDa. In some embodiments, the polypeptide comprises the amino acid sequence set forth in SEQ ID NO: 367 is derived from *Petrotoga mexicana*. In some embodiments, the polypeptide may have a molecular weight of 44.4 kDa to 46.4 kDa. In some embodiments, the polypeptide comprises the amino acid sequence set forth in SEQ ID NO: 368 is derived from *Defluviitoga tunisiensis*. In some embodiments, the polypeptide may have a molecular weight of 44.0 kDa to 46.0 kDa. In some embodiments, the polypeptide comprises the amino acid sequence set forth in SEQ ID NO: 369 is derived from *Petrotoga miotherma*. In some embodiments, the polypeptide may have a molecular weight of 43.8 kDa to 45.8 kDa. In some embodiments, the polypeptide comprises the amino acid sequence set forth in SEQ ID NO: 370 is derived from *Petrotoga olearia*. In some embodiments, the polypeptide may have a molecular weight of 43.7 kDa to 45.7 kDa. In some embodiments, the polypeptide comprises the amino acid sequence set forth in SEQ ID NO: 371 is derived from *Thermophagus xiamenensis*. In some embodiments, the polypeptide may have a molecular weight of 46.4 kDa to 48.4 kDa. In some embodiments, the polypeptide comprises the amino acid sequence set forth in SEQ ID NO: 372 is derived from *Treponema caldarium*. In some embodiments, the polypeptide may have a molecular weight of 45.9 kDa to 47.9 kDa. In some embodiments, the polypeptide comprises the amino acid sequence set forth in SEQ ID NO: 373 is derived from *Thermofilum uzonense*. In some embodiments, the polypeptide may have a molecular weight of 52.9 kDa to 54.9 kDa.

Polypeptides having D-fructose C4-epimerase activity according to the disclosure can be provided by means of recombinant DNA technology methods allowing it to be produced by cultivating in a culturing medium an appropriate host organism cell comprising a gene coding for the D-fructose C4-epimerase, and recovering the enzyme from the cells and/or the culturing medium. Examples of host cells for transformation include *Escherichia. coli*, (hereinafter referred to as *E. coli*), *Corynebacterum glutamicum, Aspergillus oryzae, Pichia pastoris*, or *Bacillus subtilis*, and the like. Examples of transformed *E. coli* microorganisms may include *E. coli* NEBT7EL-pA06233, NEBT7EL-pA06234, NEBT7EL-pA06235, NEBT7EL-pA06236, NEBT7EL-pA06237, NEBT7EL-pA06238, NEBT7EL-pA06239, NEBT7EL-pA06240, NEBT7EL-pA06241, NEBT7EL-pA07068, NEBT7EL-pA07069, NEBT7EL-pA07070, NEBT7EL-pA07071, NEBT7EL-pA07072, NEBT7EL-pA07073, NEBT7EL-pA07074, NEBT7EL-pA07075, NEBT7EL-pA07076, NEBT7EL-pA07077, NEBT7EL-pA07078, NEBT7EL-pA07079, NEBT7EL-pA07080, NEBT7EL-pA07081, NEBT7EL-pA06242, NEBT7EL-pA06243, NEBT7EL-pA06246, NEBT7EL-pA06247, NEBT7EL-pA06248, NEBT7EL-pA06249, NEBT7EL-pA06250, NEBT7EL-pA06252, NEBT7EL-pA06253, NEBT7EL-pA06254, NEBT7EL-pA06255, NEBT7EL-pA06256, NEBT7EL-pA06257, NEBT7EL-pA06261, NEBT7EL-pA06265, NEBT7EL-pA06266, NEBT7EL-pA06267, NEBT7EL-pA06268, NEBT7EL-pA06270, NEBT7EL-pA06271, NEBT7EL-pA06272, NEBT7EL-pA06273, NEBT7EL-pA06274, NEBT7EL-pA07082, NEBT7EL-pA07083, NEBT7EL-pA07084, NEBT7EL-pA07085, NEBT7EL-pA07086, NEBT7EL-pA07087, NEBT7EL-pA07088, NEBT7EL-pA07089, NEBT7EL-pA07090, NEBT7EL-pA07091, NEBT7EL-pA07092, NEBT7EL-pA07094, NEBT7EL-pA07095, NEBT7EL-pA07096, NEBT7EL-pA07097, NEBT7EL-pA07098, NEBT7EL-pA07099, NEBT7EL-pA07100, and NEBT7EL-pA07101.

In some embodiments, the polypeptide comprises the amino acid sequence set forth in SEQ ID NO: 1. In some embodiments, the polypeptide comprises the amino acid sequence set forth in SEQ ID NO: 2. In some embodiments, the polypeptide comprises the amino acid sequence set forth in SEQ ID NO: 3. In some embodiments, the polypeptide comprises the amino acid sequence set forth in SEQ ID NO: 4. In some embodiments, the polypeptide comprises the amino acid sequence set forth in SEQ ID NO: 5. In some embodiments, the polypeptide comprises the amino acid sequence set forth in SEQ ID NO: 6. In some embodiments, the polypeptide comprises the amino acid sequence set forth in SEQ ID NO: 7. In some embodiments, the polypeptide comprises the amino acid sequence set forth in SEQ ID NO: 8. In some embodiments, the polypeptide comprises the amino acid sequence set forth in SEQ ID NO: 9. In some embodiments, the polypeptide comprises the amino acid sequence set forth in SEQ ID NO: 10. In some embodiments, the polypeptide comprises the amino acid sequence set forth in SEQ ID NO: 11. In some embodiments, the polypeptide comprises the amino acid sequence set forth in SEQ ID NO: 12. In some embodiments, the polypeptide comprises the amino acid sequence set forth in SEQ ID NO: 13. In some embodiments, the polypeptide comprises the amino acid sequence set forth in SEQ ID NO: 14. In some embodiments, the polypeptide comprises the amino acid sequence set forth in SEQ ID NO: 15. In some embodiments, the polypeptide comprises the amino acid sequence set forth in SEQ ID NO: 16. In some embodiments, the polypeptide comprises the amino acid sequence set forth in SEQ ID NO: 17. In some embodiments, the polypeptide comprises the amino acid sequence set forth in SEQ ID NO: 18. In some embodiments, the polypeptide comprises the amino acid sequence set forth in SEQ ID NO: 19. In some embodiments, the polypeptide comprises the amino acid sequence set forth in SEQ ID NO: 20. In some embodiments, the polypeptide comprises the amino acid sequence set forth in SEQ ID NO: 21. In some embodiments, the polypeptide comprises the amino acid sequence set forth in SEQ ID NO: 22. In some embodiments, the polypeptide comprises the amino acid sequence set forth in SEQ ID NO: 23. In some embodiments, the polypeptide comprises the amino acid sequence set forth in SEQ ID NO: 321. In some embodiments, the polypeptide comprises the amino acid sequence set forth in SEQ ID NO: 322. In some embodiments, the polypeptide comprises the amino acid sequence set forth in SEQ ID NO: 323. In some embodiments, the polypeptide comprises the amino acid sequence set forth in SEQ ID NO: 324. In some embodiments, the polypeptide comprises the amino acid sequence set forth in SEQ ID NO: 325. In some embodiments, the polypeptide comprises the amino acid sequence set forth in SEQ ID NO: 326. In some embodiments, the polypeptide comprises the amino acid sequence set forth in SEQ ID NO: 327. In some embodiments, the polypeptide comprises the amino acid sequence set forth in SEQ ID NO: 328. In some embodiments, the polypeptide comprises the amino acid sequence set forth in SEQ ID NO: 329. In some embodiments, the polypeptide comprises the amino acid sequence set forth in SEQ ID NO: 330. In some embodiments, the polypeptide comprises the amino acid sequence set forth in SEQ ID NO: 331. In some embodiments, the polypeptide comprises the amino acid sequence set forth in SEQ ID NO: 332. In some embodiments, the polypeptide comprises the amino acid sequence set forth in SEQ ID NO: 333. In some embodiments, the polypeptide comprises the amino acid sequence set forth in SEQ ID NO: 334. In some embodiments, the polypeptide comprises the amino acid sequence set forth in SEQ ID NO: 335. In some embodiments, the polypeptide comprises the amino acid sequence set forth in SEQ ID NO: 336. In some embodiments, the polypeptide comprises the amino acid sequence set forth in SEQ ID NO: 337. In some embodiments, the polypeptide comprises the amino acid sequence set forth in SEQ ID NO: 338. In some embodiments, the polypeptide comprises the amino acid sequence set forth in SEQ ID NO: 339. In some embodiments, the polypeptide comprises the amino acid sequence set forth in SEQ ID NO: 340. In some embodiments, the polypeptide comprises the amino acid sequence set forth in SEQ ID NO: 341. In some embodiments, the polypeptide comprises the amino acid sequence set forth in SEQ ID NO: 342. In some embodiments, the polypeptide comprises the amino acid sequence set forth in SEQ ID NO: 343. In some embodiments, the polypeptide comprises the amino acid sequence set forth in SEQ ID NO: 344. In some embodiments, the polypeptide comprises the amino acid sequence set forth in SEQ ID NO: 345. In some embodiments, the polypeptide comprises the amino acid sequence set forth in SEQ ID NO: 346. In some embodiments, the polypeptide comprises the amino acid sequence set forth in SEQ ID NO: 347. In some embodiments, the polypeptide comprises the amino acid sequence set forth in SEQ ID NO: 348. In some embodiments, the polypeptide comprises the amino acid sequence set forth in SEQ ID NO: 349. In some embodiments, the polypeptide comprises the amino acid sequence set forth in SEQ ID NO: 350. In some embodiments, the polypeptide comprises the amino acid sequence set forth in SEQ ID NO: 351. In some embodiments, the polypeptide comprises the amino acid sequence set forth in SEQ ID NO: 352. In some embodiments, the polypeptide comprises the amino acid sequence set forth in SEQ ID NO: 353. In some embodiments, the polypeptide comprises the amino acid sequence set forth in SEQ ID NO: 354. In some embodiments, the polypeptide comprises the amino acid sequence set forth in SEQ ID NO: 355. In some embodiments, the polypeptide comprises the amino acid sequence set forth in SEQ ID NO: 356. In some embodiments, the polypeptide comprises the amino acid sequence set forth in SEQ ID NO: 357. In some embodiments, the polypeptide comprises the amino acid sequence set forth in SEQ ID NO: 358. In some embodiments, the polypeptide comprises the amino acid sequence set forth in SEQ ID NO: 359. In some embodiments, the polypeptide comprises the amino acid sequence set forth in SEQ ID NO: 360. In some embodiments, the polypeptide comprises the amino acid sequence set forth in SEQ ID NO: 361. In some embodiments, the polypeptide comprises the amino acid sequence set forth in SEQ ID NO: 362. In some embodiments, the polypeptide comprises the amino acid sequence set forth in SEQ ID NO: 363. In some embodiments, the polypeptide comprises the amino acid sequence set forth in SEQ ID NO: 364. In some embodiments, the polypeptide comprises the amino acid sequence set forth in SEQ ID NO: 365. In some embodiments, the polypeptide comprises the amino acid sequence set forth in SEQ ID NO: 366. In some embodiments, the polypeptide comprises the amino acid sequence set forth in SEQ ID NO: 367. In some embodiments, the polypeptide comprises the amino acid sequence set forth in SEQ ID NO: 368. In some embodiments, the polypeptide comprises the amino acid sequence set forth in SEQ ID NO: 369. In some embodiments, the polypeptide comprises the amino acid sequence set forth in SEQ ID NO: 370. In some embodiments, the polypeptide comprises the amino acid sequence set forth in SEQ ID NO: 371. In some embodiments, the polypeptide comprises the amino acid sequence set forth in SEQ ID NO: 372. In some embodiments, the polypeptide comprises the amino acid sequence set forth in SEQ ID NO: 373.

TABLE 3

| Native Sequences | | | |
|---|---|---|---|
| SEQ NO. | Plasmid ID | Sequence | Organism |
| 1 | pA06233 | MSLHPLNKLIERHKKGTPVGIYSVCSANPFVL KAAMLQAQKDQSLLLIEATSNQVDQFGGYTG MRPEDFKTMTLELAAENNYDPQGLILGGDHL GPNRWTKLSASRAMDYAREQIAAYVKAGFSK IHLDATMPLQNDATDSAGRLPVETIAQRTAEL CAVAEQTYRQSDQLFPPPVYIVGSDVPIPGGA QEALNQIHITEVKEVQQTIDHVRRAFEKNGLE AAYERVCAVVVQPGVEFADQIVFEYAPDRAA ALKDFIESHSQLVYEAHSTDYQTAPLLRQMVK DHFAILKVGPALTFALREAIFALAFMEKELLPL HRALKPSAILETLDQTMDKNPAYWQKHYGGT KEEVRFAQRFSLSDRIRYYWPFPKVQKALRQL LKNLQQISIPLTLVSQFMPEEYQRIRQGTLTND PQALILNKIQSVLKQYAEATQIQNSLTFTQNQN SLAMERL | *Caldithrix abyssi* |
| 2 | pA06234 | MMFGSPAPLLDMVTAQKQGMARGIPSICSAH PVVLSAACHLARRSGAPLLIETTCNQVNHQGG YSGMTPADFVRFLREILEREGIPPQQVILGGDH LGPYPWRKEPAETAIAQALEMVRAYVQAGYT KIHLDASMPCADDDPERPLPLERIARRAAQLC AAAEAAAGAVQPVYVIGSEVPPPGGAQGQEA RLHVTTPQEAQAALDAFREAFLQAGLTPVWE RVIALVVQPGVEFGVDSIHAYQREAARPLKTFI EGVPGMVYEAHSTDYQTRASLRALVEDHFSIL KVGPALTFAYREAVFALEHIEREILGRQDMPLS RLSEVLDEVMLNDPRHWQGYFAGAPAEQALA RRYSFSDRIRYYWHHPAAQEAVRRLLANLIET PPPLSLLSQYLPREYEMVRAGEISSHPQDLIRA HIQHTLEDYAAACG | *Anaerolinea thermophila* |
| 3 | pA06235 | MAKEHPLKELVNKQKSGISEGIVSICSSNEFVIE ASMERALTNGDYVLIESTANQVNQYGGYIGM TPIEFKKFVFSIAKKVDFPLDKLILGGDHLGPLI WKNESSNLALAKASELIKEYVLAGYTKIHIDTS MRLKDDTDFNTEIIAQRSAVLLKAAENAYMEL NKNNKNVLHPVYVIGSEVPIPGGSQGSDESLQI TDAKDFENTVEIFKDVFSKYGLINEWENIVAF VVQPGVEFGNDFVHEYKRDEAKELTDALKNY KTFVFEGHSTDYQTRESLKQMVEDGIAILKVG PALTFALREALIALNNIENELLNNVDSIKLSNFT NVLVSEMINNPEHWKNHYFGDDARKKFLCKY SYSDRCRYYLPTRNVKNSLNLLIRNLENVKIP MTLISQFMPLQYDNIRRGLIKNEPISLIKNAIMN RLNDYYYAIKP | *Thermoanaero- bacterium thermo- saccharolyticum* |
| 4 | pA06236 | MNTEHPLKNVVKLQKKGIPIGIYSVCSANEIVI QVAMEKALSMDSYVLIEATANQVNQYGGYT NMKPIDFRDFVYSIAKRINFPENRIILGGDHLGP LPWKNQQAKKAMEEAKELVKQFVMAGFTKI HVDTSMLLGDDNINIKLDTETIAERGAILVSVA ERAFEELKKFNPYALHPVYVIGSEVPVPGGSQ KENNNEIQVTKPTDFEETVEVYKSTFYKYGLG NAWEDVVAVVVQAGVEFGVEDIHEYDHQQA ENLVSALKKYPNLVFEAHSTDYQPAKLLKEM VRDGFAILKVGPELTFALREGLFALNIIEKELFK DNHDIEMSNFIDILDTAMLNNPKYWEQYYYG DDNKIRIARKYSYSDRCRYYLIENEVRASMSR LFKNLTNVEIPLTLISQYMPIQYEKIRMGLLKN DPENLVKDKIGNCIDKYLYATNPTSGEFKLI | *Thermoanaero- bacter thermo- hydrosulfuricus* |
| 5 | pA06237 | MSPQNPLIGLFKNREKEFKGIISVCSSNEIVLEA VLKRMKDTNLPIIIEATANQVNQFGGYSGLTPS QFKERVIKIAQKVDFPLERIILGGDHLGPFVWR DQEPEIAMEYAKQMIKEYIKAGFTKIHIDTSMP LKGENSIDDEIIAKRTAVLCRIAEECFEKISINNP YITRPVYVIGADVPPPGGESSICQTITTKDELER SLEYFKEAFKKEGIEHVFDYVVAVVANFGVEF GSDEIVDFDMEKVKPLKELLAKYNIVFEGHT DYQTKENLKRMVECGIAILKVGPALTFTLREA LVALSHIEEEIYSNEKEKLSRFREVLLNTMLTC KDHWSKYFDENDKLIKSKLLYSYLDRWRYYF ENESVKSAVYSLIGNLENVKIPPWLVSQYFPSQ YQKMRKKDLKNGAADLILDKIGEVIDHYVYA VKE | *Caldicellulosiruptor kronotskyensis* |

TABLE 3-continued

| Native Sequences | | | |
|---|---|---|---|
| SEQ NO. | Plasmid ID | Sequence | Organism |
| 6 | pA06238 | MWLSKDYLRKKGVYSICSSNSYVIEASIEFAKE<br>KGDYILIEATPHQVNQFGGYSGMTPEDFKNFV<br>MKIAKEKGLEEDKIILGGDHLGPLPWQDEPSPT<br>AMNKAKDLIRAFVESGYKKIHIDCSMPLSDDP<br>KVLPYEKIAERTRELFEIAEETARKYNFQPVYV<br>VGTDVPIAGGGEEEGVTSVEDFRSAISSLKKYF<br>NDVPNIWDRVVGFVIMLGIGFSYDKVFEYDRD<br>KVRGILEEVKREDLFVEGHSTDYQARYALRN<br>MVEDGVRILKVGPALTAAFRRGVFLLSNIEDEI<br>IPERERSNIKRVILETMLRDDRYWRKYYKDSK<br>RLELDIWYNLLDRIRYYWEYEDVKMVLNKLF<br>ENFSEGVDIKFIYQYFYDSYFDVREGKMKNDP<br>RELIKKEIKRVLEDYSYAINL | *Dictyoglomus turgidum* |
| 7 | pA06239 | MSTLRHIILRLIELREREQIHLTLLAVCPNSAAV<br>LEAAVKVAARCHTPMLFAATLNQVDRDGGY<br>TGWTPAQFVAEMRRYAVRYGCTTPLYPCLDH<br>GGPWLKDRHAQEKLPLDQAMHEVKLSLTACL<br>EAGYALLHIDPTVDRTLPPGEAPLVPIVVERTV<br>ELIEHAEQERQRLNLPAVAYEVGTEEVHGGLV<br>NFDNFVAFLDLLKARLEQRALMHAWPAFVVA<br>QVGTDLHTTYFDPSAAQRLTEIVRPTGALLKG<br>HYTDWVENPADYPRVGMGGANVGPEFTAAE<br>FEALEALERREQRLCANRKLQPACFLAALEEA<br>VVASDRWRKWLQPDEIGKPFAELTPARRRWL<br>VQTGARYVWTAPKVIAAREQLYAHLSLVQAD<br>PHAYVVESVARSIERYIDAFNLYDAATLLG | *Caldilinea aerophila* |
| 8 | pA06240 | MQAQALLTVPFDRVATHARGFVGWVAELLQ<br>GPLAYQHTLLAVCPNSEAVTRAALEAAAEAN<br>APLLFAATLNQVDLDGGYTGWTPATLARFVA<br>DELARLDLHIPVVLGLDHGGPWKKDLHARNR<br>LSFEETFQAVLRAIEACLDAGYGLLHLDPTVD<br>LELSPGTPVPIPRIVERSVALLRHAETYRLRRNL<br>PPVAYEVGTEEVGGGLQAEARMAEFLDRLWT<br>ALDREGLPHPVFVVGDIGTRLDTRTFDFERAR<br>RLDALVRRYGALIKGHYTDDVDRLDLYPKAG<br>IGGANVGPGLAAIEFEALEALVEEARRRGLSV<br>TFDQAIRRAVVESGRWTKWLQPEEKGQPFDA<br>LDPERQRWLVATGSRYVWTHPAVLQARRELY<br>EALAPWLDADAFVRTRIKARLMDYFRAFNLIH<br>FNERLQAFLPE | *Rhodothermus marimus* |
| 9 | pA06241 | MTDEDFEPICEISEQFRNYCNQMLESEYDPKPS<br>KYIFNILQNQKTIVMAANPRIGLVTRGILRAAK<br>DADAPIILELARSECNLENGYTGLYPSDFSEQC<br>YQAAKDVGYDIWALHADHIGIKKGDREDIEK<br>TKELVKAQIDAGYTSFAIDASHLFNFQGGDLR<br>EELKDNIDATTEIAKFIEEQMDDREYGLEVEV<br>GEIGREDEHGRVLTNPEEAVTFIKALNENGVY<br>PQVLAIANGSAHGNTYDSQGRLIEQVSIDIPQTI<br>KVAQALKENNLKVRIAQHGITGTPRELIHDHF<br>PHGEIIKGNVGTFYMNLVWDAFKLFEPELYND<br>IWNWTVENYKQKSPDKTDSEIFGKYSKFAIKQ<br>FFDRIYSVNEDTKRAIDAMAYAETLYFLKSFN<br>AERTASIVRDGIK | *Methanohalobium evestigatum* |
| 10 | pA07068 | MNTEHPLKNVVKLQKKGIPIGIYSVCSANEIVI<br>QVAMEKALSMDSYVLIEATANQVNQYGGYT<br>NMKPIDFRDFVYSIAKRINFPENRIILGGDHLGP<br>LPWKNQQAKKAMEEAKELVKQFVMAGFTKI<br>HVDTSMFLGDDNINIKLDTETIAERGAILVSVA<br>ERAFEELKKSNPYALHPVYVIGSEVPVPGGSQ<br>KENNNEIQVTKPADFEETVEVYKSTFYKYGLG<br>NAWEDVVAVVVQPGVEFGVENIHEYDHQQA<br>ENLVSALKKYPNLVFEAHSTDYQPAKLLKEM<br>VRDGFAILKVGPELTFALREGLFALNIIEKELFK<br>DNHDIEMSNFIDILDTAMLNNPKY | *Thermoanaero-bacter thermo-hydrosulfuricus* |
| 11 | pA07069 | MQRNYLLDIVEAQNNGIHKGIYSACSANEYVI<br>EAAMERAKNTNEYVLIEATANQVNQYGGYTG<br>MKPIDFKNFVYDIADKINFDKDKIILGGDHLGP<br>LTWSKETEKEAMAKSHELVKEYVMAGFTKIH<br>LDTSMYLADDDRSKKLATEVIARRGAELCKT | *Clostridium cavendishii* |

TABLE 3-continued

| Native Sequences | | | |
|---|---|---|---|
| SEQ NO. | Plasmid ID | Sequence | Organism |
| | | AEESFKALKERNSMAVAPVYIVGSEVPIPGGIQ DEEEGIQVTKPEDFLETVKVYKAEFKDKGIDE VWNRVIGVVVQPGVEFGDESVHEYNREKAEK LVNSLRGVKGIVFEGHSTDYQTKTKLKEMVE DGIAILKVGPALTYGLREALFALNHIENEIFKY RADIKLSNFINVLETSMVEEPTHWKQHYHGDA EDIKYAMRYSYSDRCRYYMPTEAVNKAMNIL IENLESVEIPLTIIDQYMPMQYKKIREGLIQNKP KELIKDRIGDYIDDYLYALR | |
| 12 | pA07070 | MKKHPLQDIVSLQKQGIPKGVFSVCSANRFVIE TTLEYAKMKGTTVLIEATCNQVNQFGGYTGM TPADFREMVFSIAEDIGLPKNKIILGGDHLGPN PWKGQPSDQAMRNAIEMIREYAKAGFTKLHL DASMRLADDPGNENEPLNPEVIAERTALLCLE AERAFKESAGSLRPVYVIGTDVPPPGGAQNEG KSIHVTSVQDFERTVELTKKAFFDHGLYEAWG RVIAVVVQPGVEFGNEHIFEYDRNRARELTEAI KKHPNIVFEGHSTDYQTAKALKEMVEDGVAIL KVGPALTFALREAFFALSSIEKELFYDTPGLCS NFVEVVERAMLDNPKHWEKYYQGEERENRL ARKYSFLDRLRYYWNLPEVRTAVNKLITNLET KEIPLTLISQFMPMQYQKIRNGLLRKDPISLIKD RITLVLDDYYFATHPEC | *Kosmotoga olearia* |
| 13 | pA07071 | MNHNPLKKIVELQKQGKNVGIYSVCSANGYVI EAALKRGKSDGSCVLIESTANQCDQNGGYTG MTPLDFKNFVLGIADKVGFDPKRLFLGGDHLG PLTFAGMDEAQAMENAEELIRHYVGAGFTKIH IDTSMKVASDDPNTRLSDETIAKRGARLARVA QDTYHKLLESDPDAIAPVYIVGSEVPIPGGAVG AVDQGVQVTKVEDFKNTVATFEKAFREQGLD EAWDNVIGVVVQPGVEEKDSGCTEYDREKAK DLMASIQEFPNLVFEGHSTDYQTKIKLRELVED GVGILKVGPALTFAMREGMFALENIEKELIYG TDITPSGFQDALEAEMLKEGKHWRKHYQGTE LELRMKRKYSFSDRCRYYMPTPAVEAAKERLI SNLRTLGIPLNLLSQFMPIQYTKVREGLLVNDP VELVEDRIINTIDEYLYATHQKELL | *Butyricicoccus pullicaecorum* |
| 14 | pA07072 | MLLKVKEHPIRELVNRYKNGENVGIFSVCTSN EYVIEAAMERVIDKDLDLLIESTANQVNQDGG YTGMQPKDFVNYVYKIADKVNFPKDRIILGGD HLGPLTWTKLVQEEAMEKAKVLIRDYVLAGF TKIHIDTSMPIYDDLEKGVFGDDLIAERAAILC NVAEIAYRELLKTNEDAIHPIYVVGSEVPVPGG VQAEEAEEEIENGIKVTRVEDFKNTVEVFKKK FKEHGVEEAFNYVVGVVVQPGVEFSSDTVWK YEREKAKDLSKALKEYDNLVFEAHSTDYQSP KSLREMVLDGFNILKVGPALTFGFREAAFALN KIEEEMFRFRPDIEESRFIQTLDYNMVKHPENW IKHYSGTSENIRFSRMYSLSDRCRYYMPNEEV EYSFNKMINNLDKEEIPIALISQYMHNQYKKV RDGELKPKGLNLLKDFIGEYVDDYIFAVEDK | *Clostridium thermobutyricum* |
| 15 | pA07073 | MYPVLENILRAQQQGEALGIPSICSAHPFVLEA TFRHALTTGRTVLIESTCNQVNQHGGYTGMTP GDFVAYVAALADRLHFPRERILLGGDHLGPNP WRDRPADQALNQARILVQEYVRAGYGKIHLD ASMACGGDPADAPLDKAVAAERAAALAEAA EAAFQRMGSGTPPCYVIGTEVPPPGGAQGDD MPLAITAPREVAETIELTQAAFRRRGLEAAWE RVIAVVVQPGVEFGDEQVHPYDRAAAAGLAR AIEPYGRLVYEAHSTDYQTRQALRDLVADHF AILKVGPALTFAFREAVFALAAVEEEWLAGQA GVVLSRLREELEAAMIQDPTHWRGYYRGDER HQRLARRYSYSDRARYYWPRPSVQAALERLL HNLEAAPPPLTLLSQYLPVQYWSVREGLLEPT PRSLIVDKIIQVLNDYTWACGG | *Litorilinea aerophila* |
| 16 | pA07074 | MERKVKHLTHMVEQHKRGNANGIYAVCSAH PLVLEAAIRYAQSHQTPLLIEATSNQVDQFGG YTGMTPEDFYGFVCCLAESLDFPTSQLILGGD HLGPNRWQNLPAQQAMANADDLIKSYVAAG FKKIHLDCSMSCEDDPVPLTDAIVAERAARLA | *Enterobacter mori.* |

TABLE 3-continued

| Native Sequences | | | |
|---|---|---|---|
| SEQ NO. | Plasmid ID | Sequence | Organism |
| | | KIAEATCREQFGVTDLVYVIGTEVPVPGGAHE TLTELEVTTPDAARATLEAHRHALEKEGLNDI WPRIIGLVVQPGVEFDHAHVCDYQPHKAVAL SKMVEAYDTLLFEAHSTDYQTPQALRQLVKD HFAILKVGPALTFALREALFSLAAIEEELLPAK ASSGLRHVLENVMLDRPEYWQSHYHGDGNA RRLARGYSYSDRVRYYWPDSQIDDAFERLVR NLADEPIPLPLISQYLPLQYGKVREGALKSTPR ELIIDHIQDILQQYHAACEGVTTQNA | |
| 17 | pA07075 | MWLDSNFLKNRGIFSICSSNENVLDASIEFAKE KEDFLLIEATCHQVNQFGGYTKMTPESFSKKIF KKAEEMNFNPERLLLGGDHLGPEPWKNENAD TAMDKAKQLVIEFVKNGFNKIHLDCSMPLKG DSDFSTTLVADREAELCAVAEETYEKYGGNRP VYVVGTEVPAPGGSTNEVPEVTSIEELDEMIEE LQNAFLRLGLKNAWDRVIAIVVRLGIGFGGDS VSEYESEKTKELCTYLSRYYPSLYFEAHSTDY QTAGSLKQMVKDGIRILKVGPALTDAYRRGM FALNFIEKESIDEEKQSRLVENVLKVMDEYPR YWEDYYNSVGKTLRLDQMYSYFDRIRYYWG FEEVEKSKNRLIENLKDMQMNLIRQYLPEQYE KIRENKLNKDPRALINYEIKKVLNDYQKSVILE | *Caldisericum exile* |
| 18 | pA07076 | MWLSKDYLRKKGVYSICSSNPYVIEASVEFAK EKNDYILIEATPHQINQFGGYSGMTPEDFKNFV MGIIKEKGIEEDRVILGGDHLGPLPWQDEPSSS AMKKAKDLIRAFVESGYKKIHLDCSMSLSDDP VVLSPEKIAERERELLEVAEETARKYNFQPVY VVGTDVPVAGGGEEEGITSVEDFRVAISSLKK YFEDVPRIWDRIIGFVIMLGIGFNYEKVFEYDRI KVRKILEEVKKENLFVEGHSTDYQTKRALRD MVEDGVRILKVGPALTASFRRGVFLLSSIEDEL ISEDKRSNIKKVVLETMLKDDKYWRKYYKDS ERLELDIWYNLLDRIRYYWEYKEIKIALNRLFE NFSEGVDIRYIYQYFYDSYFKVREGKIRNDPRE LIKNEIKKVLEDYHYAVNL | *Dictyoglomus thermophilum* |
| 19 | pA07077 | MQAQALLTVPFDRVATHARGFVGWVAELLL GPLAHQHTLLAVCPNSEAVTRAALEAAAEVN APLLFAATLNQVDLDGGYTGWTPATLARFVA DELARLDLHIPVVLGLDHGGPWKKDLHARNR LSFAETVQAVLRAIEACLDAGYGLLHLDPTVD LELPPGTPVPIPRIVERTVALLRHAETYRLRRN LPPVAYEVGTEEVGGGLQAEARMAEFLDRLW TALDREGLPHPIFVVGDIGTRLDTRTFDFERAC RLDALVRRYGALIKGHYTDDVDRLDLYPKAG IGGANVGPGLAAIEFEALEVLVDEARRRGLSV TFDQAIRRAVVESGRWTKWLQPEEKGRPFEAL DPERQRWLVATGSRYVWTHPAVLQARRELYE ALAPWLDADAFVRERIKARLMDYFRAFNLIHF NERLQAFLPE | *Rhodothermus marinus* |
| 20 | pA07078 | MQAHVLLAPSFEQLADHRHGFVGWLVDLLRG PLAYRHTLLAVCPNSEAVTRAALEAAREANAP LFFAATLNQVDLDGGYTGWTPATLARFVADE RIRLGLRAPVVLGLDHGGPWKKDWHVRNRLP YEATLQAVLRAIEACLDAGYGLLHLDPTVDLE LPPGTPVPIPRIVERTVALLQHAETYRQQRRLP PVAYEVGTEEVGGGLQAEARMAEFLDRLWTV LDREGLPRPVFVVGDIGTRLDTHTFDFERARR LDALVRRYGALIKGHYTDGVDRLDLYPQAGI GGANVGPGLAAIEFEALEALVAEAHRRKLPVT FDRTIRQAVIESGRWQKWLRPEEKGRPFEALP PERQRWLVATGSRYVWTHPAVRQARHQLYQ VLAPWLDADAFVRARIKARLMDYFRAFNLIGF NERLQAFLPN | *Rhodothermus profundi* |
| 21 | pA07079 | MAKIPIQSAVKALLELQDEGKGGTLLGIGPMS TNVLQASFELARDYDFPLMFIASRNQVDLDEL GGGYVNGWNQYTFVQAIREMAELTGFDGLY YVCRDHGGPWQRDKERNDHLPVEEAMALGK KSYLADIEAGFDLLMIDPTKDPFEIGKVIPLEK VIERTVELIEFCEKERQARDLPEIGYEVGTEET NGGLTSTETYETFILRLQEELGRRDLPMPTFIV | *Caldibacillus debilis.* |

TABLE 3-continued

| Native Sequences | | | |
|---|---|---|---|
| SEQ NO. | Plasmid ID | Sequence | Organism |
| | | GQTGTLVRKTEQAGRFSFENAADLAKMAKKY GVGLKEHNGDYLDDVILLAHIPSQITATNVAP QYGTEETRALLKLAKLEEKLKEQGLIGQPSKV KDVLLYHSIKSERWRKWMVGSQRELSVEEIV KDEELSTEILDIAGHYTFNIDEVKEEINKLYRN LSKAHIDGQRFVVDHIKRSIRNYVECFNLKGLT SRIKEKLNGSKNA | |
| 22 | pA07080 | MKKISIFEIVKASLNMKGKDKATLLGIGPMSK TLIKASMILAKEKDFPLMFIASRNQVDLKELGG GYVCNWDQKSFASDIKKIAEEVGFNGLYFLCR DHGGPWQRDNERNAHLPENEAMELGKKSYL EDLINGFDLLHIDPTKDPYIVGKTVPMEIVLKR TIELIEYVERERKERNLPPISYEVGTEETNGGLT SEEAYETFIKTLIEELDKRNLPKPSFIVGQTGTL TRLTENVGNFNTKNSKKLADIAKKYSVGLKE HNGDYLDEAILLEHPALGITAMNVAPEFGSVE TQAYLKLIEVENNLYEHGIISKKSNLEKVIKEE AVKSLRWKKWMVGDKVNLSIEEVLSDKDLT DLITEISGHYTFNNERVKCEIQLMFDNLNKAG VDGEKYVINKIKDSIDKYIKYFNLEGFTTKVLS NV | *Caloramator quimbayensis* |
| 23 | pA07081 | MTDTNYKAKPGSLLFESLMDKETIILAINPRISL LNKGILKAAKDMDAPIILELAKSECNLEGGYT GFTPSEFSKRAYESAEEIGIDIWSLHADHIGIKK GTDEEIESIKKLVKAQIDAGYTSFAIDASHLFNF RGGNLREELKDNIEATTKVARFIDEQMEDRDY GLEVEVGEIGREDEYGRVLTQPEEAVTFIKAL NENGVYPQVLAIANGSAHGNTYDEYGHLIEQ VSIDIPQTMAVARALRDNNLNVRIAQHGITGTP IEMIHNHFPHGDIIKGNVGTFYLNLVWDVLKV FEPQLYGDIWDWTIENFSEKYPDKSENEIFGKY SKYAIKEFFDRIYSVGDDTIRAVESRAYADTLV FLKAFKAAGMAEHVRKNL | *Methanosalsum zhilinae* |
| 321 | pA06242 | MKLLEEFLKAFPGRFKVYGSSLRIITDSYFFLG NDGKEKLLFVVGKKGICQLFDGQKIGQIGSND VLMCKKTHENLLALRKIINLNPTTINKKASFGF GDRIGLATPAHAKVAKDFEVFPIFAQQSVRELS RTGRTYKDVLDDAVWGVFESGYNFEFGADA DHVKEIEDLEKASNEGFTMYTVDPSDHIKDVS KLSQKEFQSLYQDNKIRRELEMRYVGKLYKF KDFEFRMTDEEFAEIFVTYIDAIEHVCKCYDVL KAKGKPFDFEVSIDETAVPTTPLAHIFIVKELRR RGIDFKTLALRFSGEWQKGIDYIGDMEMFRKE IITHSKISKELGGYKLSLHSGSDKFSVYPIFSEA TEGEFHVKTAGTNYLEAIRVVAVKDPELYREI HKFALTKFEQDRKSYHVTTDLSKIPDVDKMK NEELVKLLDMPDSRQLIHITYGSVLTAKDENG RWLFKERILKVLQENEDLHYDFVEKHMRKHL SLLGLERRIEK | *Pseudothermotoga thermarum* |
| 322 | pA06243 | MFAEFQHLTRGKFVPYATSLRKSTDATFFLVR DELDKYLIVIGKKGICELFEGQKIGEIDRQDVV LCAKNDRNCQSLMSLFPSLKPQICNAKLSFGF GDRLGVATAAHAQCVQKEKLFPIFAQQSVREI SRTERNWLDVLHSAVWGVFESGYDGPFGADA DHVKKIEDLESAARAGYTMFTIDPSDHVKDPA KFDKRELVRFYEEHPMRRTLEMKYIGKSFTVL GEKLTFDEENFAEVFVTYIDAIEHVEKCYRAL RAVCKTSFDLEVSIDETSVPTTSLAHIFFVQELV RRGVEFRTLALRFPGEWQKGIDYVGDIDLFSE NLDKHVAIVKMFTGYRLSLHSGSDKFSVYPIL AEKTDRTIHVKTAGTSYLEAIRVVAKFAPDLY RQIHKYALSRFDQDKASYHVTTELSKIPDVDK LEDSELPSLLDQPDSRQLIHITYGSVLTAKKEG RSLFKDRIMRVLFEHEAEHYDFLKKHLGKHIQ LLGV | *Pseudothermotoga hypogea* |
| 323 | pA06244 | MAENIVEKFEKLFKGKYKIYYSSIRKLEKSFFF MIRDQKQKYLISIAKKRICEKFEGKKIGRINDL DILMCPTNDYNCKVIRTLFNINPSVCKKNTSFG FGDRLGLATPAHTTLINKYDVFPVLAQQSVRE LSRTHRNFKDVLDSAIWGIFESGYEGEFGADA | *Pseudothermotoga lettingae* |

TABLE 3-continued

Native Sequences

| SEQ NO. | Plasmid ID | Sequence | Organism |
|---|---|---|---|
| | | DHVKDINDLMQAAYEGYSMYTVDPSDHVKNI<br>DKINQGELVEFYKSHPLRKEIEMIYSGKVFSFE<br>KSKFTMEDKELFRIFVTYVDAIEHVVKCYEAI<br>KNTKKNFDFEVSIDETSIPTSPLAHIFIVHELRR<br>RGVDFQTLALRFVGQWQKAIDYIGDLSVLESE<br>LSMHCEIVKSLSGYRLSLHSGSDKFSVYRIFTH<br>YCDGKLHVKTAGTSYLEAIRTVAEASPSLYRN<br>IHKYALTCFEKDNTSYHVTADINKIPDVDNVE<br>DSKVVNLLDIPEVRQLIHITYGSVLTEKINGKY<br>LFRDEIYRILHENEFLHYKRIRDHLGKHLELLK<br>N | |
| 324 | pA06245 | MVTVLQTLLQRPRPLAEIDRTSLARFLTDVIRQ<br>QVYPTSLEPTSEGVFFLARDGREKRLGILSEAG<br>LHDFEGVRHQLSLDGRTLIFQSCPLTAANARA<br>LRRHIPWTAPRPLGLRASVGCGDRLGLATPGH<br>VRAVRKHKLAPVFAQQSIREMTRTGRTPQQV<br>LDEAMWGVFQEGWRQGYGADADHLKTEED<br>ADRCIEAGFTFFTIDPSAYVDNEVDTADAATLE<br>AKVAALPWEALETTLADLRRAYLGQHFQVGP<br>YELSFEERTLMQALAKYGGAIAHTARMYRHI<br>AGRMGNRPFELEMSVDETEVPTSPAEHFFVAR<br>ELQRLGVRWISLAPRFVGRLEKGVDYIGDLEE<br>FEAHLKLHVAIARTLGPYKLSLHSGSDKFALY<br>PLFARHAGELFHLKTAGTSYLEALRAVAELDP<br>PLFREILDFARDRYETDRATYHVSALLERVPK<br>ASDVPDDALPALLEQFDTRQVLHVTFGSVLTA<br>TDADGRPRFRDRLLAVLQENEETYYRLLEAHF<br>DRHLAPFDAE | *Rhodothermus marinus* |
| 325 | pA06246 | MDIYEKIAAALKDNRHNIQLDGVKIYPQSYVE<br>VDMVKMIMVKAAEKKVILAQGSGPLFQELEG<br>EAYDDYKVCNCSHLNRVVLNKYLPYTKPSAF<br>GKEIATIGLGDRLGIASPGHIQAVKGREIRPILA<br>QQSIRELNLTNRTYRNVLDAACFAVFQEGYKD<br>GFGADGDHLKTEEDIQSALDLGFTMITLDCSE<br>MIDNTIDKLTDTEVEEKYYQLPQSVRERYETR<br>YLDKCFELRNSKICFSKENLMKNVLIYGAAAD<br>FIVAIYEKQIKHRDQKIDFEVSIDETVTPTTPEA<br>HYFVAREIYDRQVDINSMAPRFCGEFQKGIDYI<br>GDIHQFEKEFQVHAEIADHFGYKISIHSGSDKF<br>SVFQTIGRYTEGRFHVKTAGTNWLEAVRVVA<br>EKNPNLYRKMHQYALEHFDEARAYYHVTTDI<br>EGIVPLEKVNDHELSQYMNENNARQLLHITYG<br>ILLQAKDASGQYLFREDFFYTLEQHEAEYDEA<br>LRKHIGRHLEQLGK | *Geosporobacter subterraneus* |
| 326 | pA06247 | MEMQKLYEEVENKNIVKNDLVDLTIGESLKIK<br>AYPLSVLKKDDAFFFIGKENYDKFLFVISAGKE<br>NGLLNEFEGELIDAGKDVTVKKCNLSTKNRK<br>AVQKIFPHTAPIVLGLCNSFGCGDRLGVANAG<br>HIRAIKQSNFRPILAQQSIRELTRTNRTPDDVM<br>DAAVWAVLQEGYKDGFGSDADHLKTFEDIDL<br>MLNAGFTMFTFDPSEHVDNEADNYSEDQLKQ<br>KLGEIDWSGLQDTSADAAKRYVDMTFNISERL<br>SLTIQESDFLRAYAKYGNAIAHIKKMYDYLAS<br>KADKDTFEIEVSVDETESVTSPFEHFFFANELN<br>RLGVKYVSLAPRFIGDFEKGIDYKGDLNVFKT<br>EYEKHLDITKYFGSYKISLHSGSDKFSAYRVIG<br>SLKGAYTHVKTAGTSYLEALRVVAAKEPALF<br>RDILDFCRDLYETEKRSYHVSADINKVKPANQ<br>YSDTELIELFNQNDTRQVLHVTFGKVLTEKDS<br>SGHFLFKDKIMKCLVENEESHYEFLEKHFLKH<br>LECFK | *Melioribacter roseus* |
| 327 | pA06248 | MKQFLPAIELLAKGELPSNSNQIKVYEKSYTVE<br>GNVHLLMVKNSGEKFILATGEGAIFDELTGTD<br>VDGKGKACPLTYENRLVLNKYFDYTVPQAFG<br>TEIATIGLGDRLGLASPGHIETVREKNIKPVLA<br>QQSIRELTLTNRSMNDMLDAAAFAVFQEGYK<br>GGYGADGDHIKEESDIQYALSLGASMITLDCS<br>DHIDNTIEKASPEVLDEKFNALSEVVKQRYME<br>QYLGKTFEVNGLTLTLDETELKKNVLLYDKAI<br>DYTTHVYNEYISKENRAIDFEISIDETETVTSPIS<br>HFFVANELINRGVKVVSLAPRFCGEFQKGIDYI | *Lysinibacillus sphaericus* |

TABLE 3-continued

Native Sequences

| SEQ NO. | Plasmid ID | Sequence | Organism |
|---|---|---|---|
| | | GDVEQFEVELREHALIAEHFGYKLSIHSGSDKF MVFPIIAEYTKGVFHVKTAGTNWLEAIRVIAA TNPDLYRRMHVFALENFEEALKYYHVTPDLN SFEKLENVEDAKLPEYMNNDAARQLFHVTYG LLLTAKGENDTFLFRDEFFKTLDKYEEEYRDA LVSHIGKHIELLGL | |
| 328 | pA06249 | MGNWKDFVKDFCTKEKNIEVLRAEAEKAFGN YGVYPRSINEVGNAIVMMARGENEKCLVVVG EDSRLQELKGNQTEENGLKVKVCPLSNENCY VIRKIFPYTNPQPHKGKNITIGLGDRLGLASPG HIRLIRDLDVFPVLAQQSIRELNLTGRTYEDVIS AAAWAVFQEGYTKGYGADGDHLKTAEEVKM SLNVGMTMITLDCSEHIDNSAAHAGLSELREK YSRFTEEERERWERKYLNRDVKIGNYSFHISEE DLIRMACVYGGAIRHTLDIYHNIIAKCGRPIDF EMSIDETLTPTSPASHYFVAQELIDGGVEITSLA PRFCGEFQKGIDYIGDLKQFTDEFAVHAAIAD HFGYKISVHSGSDKFKVFPVVGEKTNGRYHLK TAGTNWLEAVRVIARHKPDLYRRMHAFALEH LEDAKKYYHIGAKVENIPALETLADSELPELM NRDDSRQVMHITYGHILQAKDENGNPLFKDEL YKVLYEYEEEYANALKKHIGRHLEGLGLL | *Clostridium stercorarium* |
| 329 | pA06250 | MPSQLPEPLPVPPEARAHPSFRLHEGAALWLA GARLAVLAPPEHPALTRFRGEVQHVGDHRLL RAERRAENAAALRALLPDLQPRPLGLVTSAGF GDRLGVATPGHVRAAQRYGAGVAPVFAQQSI REMTRTGRTPQEVLDDATWGAFAAGWRGAL GADADHQKTVADLERCAAAGFTLFTVDPSDH VDDSAHGAPASDLEAKVAALPWRELETTRAD FERYAGRRLELGDRELVLAREAVLRAGAKYA RAVLHVATLYRHLEGKGAPFELEVSVDETATP TSHAEHAVVALELRRLGVRWVGLAPRFVGRF EKGVDYRGDLGELKADLAGHAALARSLGPYK LSLHSGSDKFSVYPLIAEATGGMVHLKTAGTS YLEALRVAAQVAPGLFREILTLGRERFAVDKQ SYHISAALARVSEADTLTDDELPRLLDDDDAR QVLHVTFGSALDRYRAPLLRVLEAHDEAYQA GLAAHFAKHLTPFAEVAP | *Truepera radiovictrix* |
| 330 | pA06251 | MLKLLNESLKPLSIFIYSESLRKINDDLYIFVAK IKDLKKIGIVKQNQILYFSSPYFSEDKKIEGTNF LVNLYPLNFENYQKLKEIIPISPKVCDKKISFGT GDRLGLITSAQLSALKEYDLFPILAQQSPRELIK TKRDFKDVLLKSAMGVLETGYTGKYGADAD HIKDEKYLMEAIDAGYTMYTLDISDFIEKIKDL SEKALKEKYEKVSSFSKKIIDKYAGKRVKISDE EYFELSYNELCKSAIVYEKALSFVEMVYEILKS KLSEFDIEVSIDEGERDTTPEDHFFVAQFLHDK GIDFKSLAPKFPGEFQKGIDYIGDIKEFERALKK HYALTKALEGYRLSLHSGSDKFSIYKIFYKITE GNFHIKTSGTSWLEAVKVIAKFFPDLFVELYQI ALENLEESKKAYKVNITKEEFPKEIKEDYMEFL HKDNVRQLFHISYGVLLDEKRKEIYDLLNQKE KEHYQYVSENIKKHLKNLFEEE | *Dictyoglomus turgidum* |
| 331 | pA06252 | MNDAVYALGRSSRNGTLQLIVRGNSTGFHGE QQGDALICPLDAENARTLQERLPWLRPQPLGN RLSFGFGDRIGLATPGHVDALRSADPTGRIAPI FAQQSVRENQRLNRTPQEVMTAAVWSLFAEN WRLPWGADADHVKEPEHLAPYVAAGYTFYTI DPSDHVDNAAHTDDLAVLRSKCEALPWDILE TTYLSLCENYCGRTIVAEKTTLHFDKETLLRAL AKYGRALAHTVRIAAALRTALGGTSFDLEMS VDETDTPTSAHEHFFIANELLRRNIPLVSLAPRF VGKFQKGVDYMGNLAEFEAELIRHVAVMRHF HCYKLSVHTGSDKFSIYPILARCAGENVHIKTA GTSYLEALRVAALRAPDLFRQMLETGRTCYE KDKKTYFLDCRPERVPPAATLDDADLPNLLDQ FDARQLLHVTFGSILTTHGAALRNLLATYPND YRSALRDHFARHIQPFVQA | *Caldilinea aerophila* |

TABLE 3-continued

| SEQ NO. | Plasmid ID | Sequence | Organism |
|---|---|---|---|
| | | Native Sequences | |
| 332 | pA06253 | MMLSPEALAEGLRLYGLHLIVGSIRELPDGGAI FAARQGSERRIGWIGETSPFPAPDPRMSMRVQ EHLVWIHPWTWAHYRILRERLPALSPTRCDRP ASFGAGDRLGMATAAQIAALERYPVFPVLAQ QSPRELARTGRDFRSVLLDAAWGVFASGFAG PFGADADHLQDDEQLRAAAEAGYSLYTFDLR RALARGPRPWEALSPLARSVVAELADRRVEAP QGPRTLEESALRAAACRYEPALEEVVRGAEIL RDQGIDADLEVSVDETEEETTPEAHAFIAVYL QRRGVALWSLAPRFPGVFEKAVDYEGEVERF AQAAALHTAVARTFGGHRLSLHSGSEKFRILP VFREATGGRFHVKTSGTTWLQAVRVVARAVP ALFAELYAIARAHLEESRRDYPIALQPEALPPA LPDDPEAALADRAVRQLFHISYGVLLRERGPAI RALLEAHEAEHFTAVRENLERHLEALLK | *Thermoflexus hugenholtzii* |
| 333 | pA06254 | MIGNVLSTLEENGFKVYPDSLRKLGENIYIFVV KRQNEKMVGILSSSDVKLNGAYFSEDKNVSD KLRLNIYPFTFENYVTLNGKFHIGPTVCRGNSS FGTGDRLGLVTAAQLTALKKYDVFPILAQQSP RELIKTNRDFKDVLLKVVLGVLETGYIGHFGA DADHIKDEYYLLEGINAGYTMYTLDLSEQLIDI SSLNPSEMRNKAQELSQVSKDIIKDFSGKKLDII SDSGYVVSEEELYKSAVAYENAMKFVDKVNN ILKEKLSDFDMEISIDEGGKVTTLEDHLYVAEY LHRNGIDFFSIAPKFPGEFEKAVDYIGDLDEFLL ELKKHYQLSRMIGGYKISLHSGSDKFSIYRIFS DITEKNFHIKTSGTSWLQAINLIYNYDKEFYRE LYKIALENLEESKKSYKVLIKREDFCKEPELNN PKFILKPEIKQLFHISFGVLLNLKRKEIVDFLNK YEEEHYKMVSKNIDNHLKEIFYKN | *Thermoanaero-bacterium thermo-saccharolyticum* |
| 334 | pA06255 | MFTILPKKGISLGLGDRIGIATPGHIKVAKKYN FFPVFAQQSIRELNFTGRTFTDVRKDVLNALVE ENYVGNSGFDGDHLKSDEEIQYALDSGITMLT LDCSEHMNKDSSIKDQIFEQFYNKSFFVNDMPI EYSDKNELNKIVSIYASVIERVIDVWNKFPKVN KKEVTFEVSVDETDVPTDEKTHFLISKYIYDEG VKIDTLAPRFPGEFQKAIDYIGNIQEFKKSLIKQ DKIAKYFGYRLSIHSGSDKFSIYPIIGEVTQGNY HLKTSGTSYLEAIKVVAQKDPEFFKKIWQTCL DKREEMDKYYHLSCDPFSVPKDLSPTEYLQNP DARQTLHVSYMFVLNPQYDFREKFFEILTKYQ NEYHENVANHIEKHVKELKIEEKS | *Petrotoga mobilis* |
| 335 | pA06256 | MATPGSLSFPRYSIGTGDRFGHEAEAQLRAVIE AGRLGRALGIVWNKSYREHTIIGSRPEDVRRM ADRAVSSLGWEGPYFVDADHITTKTVDLFLDS ADFFTIDVAEAIGKGEVSPQEEEDLLASLGDLL NRELAIPGLSSPLAISEETARGTIRAYWPAVRE AARIYRRIEQGASRPFVVEVSMDETDEPQRPPE LLLILAMIRKAGIPARTIAPKFSGAFYKGVDYV GDPHTFAREFEDDLCVVRYAREQFALPEGLKL SVHSGSDKFSLYPLVREILSRHPQEGVHLKTAG TTWLEEVAGLAEAGGEALALAKEIALTCYSMI EELCAPYAAVIDIDPERLPSPGEIEEWSSGRFVE ALEHDPSNPSYNRDFRQLIHVGYKVAAQMGE RFHQALEAHREVIAARVTRNLLERHIIPLFPGDI P | *Spirochaeta thermophila* |
| 336 | pA06257 | MLHVYLGKIPRPGFGIRIPEVVAPPLLSAFKSL GMTGSLMLSFNRETAPAEYIESSDPRLFYFGHT GTSIGGFIRSVKEYSKALSVPVEVEADHVSILG SVERALKKIAGVPVEEPLSEEEVSWSIGYVERE LREAAEAGGVDFVTIDTCELIDYSYDKVGAEE VAAAYEEVFDGDERRALEERYEGVHYFLGGD RVVAVRLSREDVARLAVKYRRSLDYAERIYR AAREAMGVELGFEVAFDETPGVSEAREVFFYL SELLRRGLRVDFIAPNVGFRKREDYSGDLHAL YERLRNLHAVVSSMNAYLSIHSGSGSHPYSDK GFGVWGVVGRATGGAVKYKMSGVLVQLLLE VMASYPPGSETRRLYEEIYSEVVEHLRWVVKA KASLYSPELETLLKRYEAAQDRFDPRADVFRH YFYVFQALRDEGGARRLRERLVEHYRENPGL | *Thermofilum pendens* |

TABLE 3-continued

| SEQ NO. | Plasmid ID | Sequence | Organism |
|---|---|---|---|
| | | Native Sequences | |
| | | RERYEKELRGLVERLASQLGYAGNAYRYRVV YA | |
| 337 | pA06258 | MVTVLQTLLQRPRPLAEIDRAALARFLTDLIRQ QVYPASLEPTSEGVFFLARDGREKRLGILSEAG LHDFEGARHQLSLDGRTLIFQSCPLTAANARA LRQHLAWTAPRPLGLRASVGCGDRLGLATPG HVRAVRKHKLAPVFAQQSIREMTRTGRTPQQ VLDEAMWGVFQEGWRQGYGADADHLKTEE DADRCIEAGFTFFTIDPSAYVDNEVDTADAAT LEAKVAALPWDALETTLADLRRAYLGQHFQV GPYELSFEERTLLQALAKYGGAIAHTARVYRH IAGRIVIGNRPFELEMSVDETEVPTSPAEHFFVA RELQRLGVRWISLAPRFVGRLEKGVDYIGDLE EFEAHLKLHVAIARTLGPYKLSLHSGSDKFAL YPLFARHAGELFHLKTAGTSYLEALRAVAELD PPLFREILDFARDRYETDRATYHVSALLERVPK ASDVPDDALPALLEQFDTRQVLHVTFGSVLTA TDADGRPRFRDRLLAVLQENEETYYRLLEAHF DRHLAPFDAK | *Rhodothermus marinus* |
| 338 | pA06261 | MLNLLEELLKPFSIFVYPQSLRKINEELYIFVAK INNTKNIGIIKQNQSIYFSNPYFSEDKKIEKTGFS VNIYPLNFENYQKLKEIIPINPKTCNKKISFGTG DRLGLVTSAQLSVLKDYNLFPILAQQSPRELIK TKRDFKDVLLKSVIGVLEIGYTDSYGADADHI KDEKYLMEAIDAGYTMYTLDISDFIERIENLTS KEIREKYEKISSFSKKIIEKYAGKKIKISNEEYFE LSYDELCKSAIVYEKALSFVEMVYEILRSKLLE FDIEVSIDEGERDTTPEDHFFVVQFLHEKGIDF KSLAPKFPGEFQKGIDYIGDIKKFENELKKQYA LTKALEGYRLSLHSGSDKFSIYKSFYKITEGNF HIKTSGTSWLEAVKTIARYSPDLFLELYHIALE NLEESKKAYKVSITKEEFPKEIKEDYIEFLKKP NVRQLFHISYGVLLDEKREEIYEILNKNEKEHY QYVSENIRKHLKNLFEEE | *Dictyoglomus thermophilum* |
| 339 | pA06262 | MKEELSDYLLKNSFLLYPDSFRRLREDVYIFV AKKDSDKKIGLLTNGNFKLSSPHFAEDKYVEE LGFYINLYPLTYENYLILKDNFGISPVTCKEKA SFGTGDRLGLATPAHIKALKNYNVFPVLAQQS PRELVKTHRDFKDVFLKVILGVLEAGYAGGY GADADHIKDEKYLIEAIDAGYTMYTLDLSDLL VKISDMPKSQLKEKAQSLSSQSREIIDRFKGKK FSISTDEDFAVSEDELYKSALTYEKAMKFVEK VYGILKDRLQHFDLEISIDEGEKDTTVEDHIFV AEYLHRKGIDFWSLAPKFPGEFQKAIDYKGDI KKFTSGLKKHYFLSKKLGGYKLSLHSGSDKFS IYKIFNEITEGNFHIKTSGTSWLQAINIIFERDKD LFNDLYKIALDNLEESKKAYKVLIDRDDFPQTI QTEDSQILLKPEIKQLFHISYGVLLDERRKEIYE VLNKYEEEHYEFVSKNIENHLKEIFNI | *Thermoanaero-bacter siderophilus* |
| 340 | pA06263 | MVEKSILEKLTDFLLNHSFVLYPNSLRKLKEDT YIFVAKKDADKKIGILTKENFKLTSPYFVEDKN VKEIDFYLNLYPLSFENYLILKNFGISPTPCRQK SSFGTGDRLGLVTPAHIVALKEYPVFPVLAQQ SPRELEKTHRDFKDALLKVILGVLEAGYTGEF GADADHIKDEKYLLRAIEAGYTMYTLDVSELL TKILDISSNQVMQISPQSKEIIEAFKGKKISISEE EYTIREDELYKSALIYEKAMNFVEKVYSILKEK VKDFDLEISIDEGEKDTTVEDHIFVAEYLHKKG IDFWSLAPKFPGEFQKAIDYKGDINKFAVELK KHYAISQQLGGYKLSLHSGSDKFSIYEIFSEVT QHSFHIKTSGTSWLQAVNLIFEKNKKLFYELY KIALNNLEESKKAYKVLIDKDDFAEEPNLENV QILSQPEIKQLFHISYGVLLDEKKEEIYDVLDK YEEEHYQFVSANIKNHLGKIFNN | *Thermoanaero-bacter mathranii* |
| 341 | pA06264 | MVEKGILEKLTDFLLNHSFVLYPNSLRKLKED TYIFVAKKDADKKIGILTKENFKLSSPYFVEDK NVKEIDFYLNLYPLSFENYLILKNFGISPTPCRQ KSSFGTGDRLGLVTPAHIVALKEYPVFPVLVQ QSPRELEKTRRDFKDALLKVILGVLEAGYTGE FGADADHIKDEKYLLRAIEAGYTMYTLDVSEL | *Thermoanaero-bacter italicus* |

TABLE 3-continued

Native Sequences

| SEQ NO. | Plasmid ID | Sequence | Organism |
|---|---|---|---|
| | | LTKISDISSNQVMQISPQSKEIIEAFKGKKISISE<br>EEYTIREDELYKSALIYEKAMNFVEKVYSILKE<br>KVKDFDLEISIDEGEKDTTVEDHIFVAEYLHKK<br>GIDFWSLAPKFPGEFQKAIDYKGDINKFAVEL<br>KKHYAISQQFGGYKLSLHSGSDKFSIYEIFSEV<br>TQHSFHIKTSGTSWLQAVNLIFEKDKKLFYEL<br>YKIALNNLEESKKAYKVLIDKDDFAEEPNLEN<br>AQILSQPEIKQLFHISYGVLLDEKKEEIYDVLD<br>KYEEEHYQFVSANIKNHLEKIFNK | |
| 342 | pA06265 | MIGNVLSTLEENGFKVYPDSLRKLGENIYIFVV<br>KRQNEKMVGILSSSDVKLNGAYFSEDKNVSD<br>KLRLNIYPFTFENYVTLNGKFHIGPTVCRGNSS<br>FGTGDRLGLVTAAQLTALKKYDVFPILAQQSP<br>RELIKTNRDFKDVLLKVVLGVLETGYIGHFGA<br>DADHIKDEYYLLEGINAGYTMYTLDLSEQLIDI<br>SSLNPSEMRNKAQELSQVSKDIIKDFSGKKLDII<br>SDSGYVVSEEELYKSAVAYENSMKFVDKVNN<br>ILKEKLSDFDMEISIDEGGKVTTLEDHLYVAEY<br>LHRSGIDFFSIAPKFPGEFEKAVDYIGDLDEFSL<br>ELKKHYQLSRMIGGYKISLHSGSDKFSIYRIFS<br>DITEKNFHIKTSGTSWLQAINLIYNYDKEFYRE<br>LYKIALENLEESKKSYKVLIKREDFCKEPELNN<br>PNFILKPEIKQLFHISFGVLLDLKRKEMVDFLN<br>KYEEEHYKMVSKNIDNHLKEIFYKN | *Thermoanaero-<br>bacterium<br>thermo-<br>saccharolyticum* |
| 343 | pA06266 | MIGNVLSTLEENGFKVYPDSLRKLGENIYIFVV<br>KRQNEKMVGILSSSDVKLNGAYFSEDKNVSD<br>KLRLNIYPFTFENYVTLNGKFHIGPTVCRGNSS<br>FGTGDRLGLVTAAQLTALKKYDVFPILAQQSP<br>RELIKTNRDFKDVLLKVVLGVLETGYIGHFGA<br>DADHIKDEYYLLEGINAGYTMYTLDLSEQLIDI<br>SSLNASEMRNKAQELSQVSKDIIKDFSGKKLDI<br>ISDSGYVVSEEELYKSAVAYENAMKFVDKVN<br>NILKEKLSDFDMEISIDEGGKVTTLEDHLYVAE<br>YLHRNGIDFFSIAPKFPGEFEKAVDYIGDLDEF<br>LLELKKHYQLSRMIGGYKISLHSGSDKFSIYRIF<br>SDITEKNFHIKTSGTSWLQAINLIYNYDKEFYR<br>ELYKIALENLEESKKSYKVLIKREDFCKEPELN<br>NPKFILKPEIKQLFHISFGVLLNLKRKEIVDFLN<br>KYEEEHYKMVSKNIDNHLKEIFYKN | *Thermoanaero-<br>bacterium<br>thermo-<br>saccharolyticum* |
| 344 | pA06267 | MIGNVLSTLEENGFKVYPDSLMKLGENIYIFV<br>VKRQNEKMVGILSSSDVKLNGAYFSEDKNVS<br>DKLRLNIYPFTFENYVTLNGKFHIGPTVCRGNS<br>SFGTGDRLGLVTAAQLTALKKYDVFPILAQQS<br>PRELIKTNRDFKDVLLKVVLGVLETGYIGHFG<br>ADADHIKDEYYLLEGINAGYTMYTLDLSEQLI<br>DISSLNPSEMRNKAQELSQVSKDIIKDFSGKKL<br>DIISDSGYVVSEEELYKSAVAYENAMKFVDKV<br>NNILKEKLSDFDMEISIDEGGKVTTLEDHLYVA<br>EYLHRNGIDFFSIAPKFPGEFEKAVDYIGDLDE<br>FLLELKKHYQLSRMIGGYKISLHSGSDKFSIYRI<br>FSDITEKNFHIKTSGTSWLQAINLIYDYDKEFY<br>RELYKIALENLEESKKSYKVLIKKEDFGKEPEL<br>NNPKFILKPEIKQLFHISFGVLLDLKRKEIVDFL<br>NKYEEEHYKMVSKNIDNHLKEIFYKN | *Thermoanaero-<br>bacterium<br>thermo-<br>saccharolyticum* |
| 345 | pA06268 | MIGNVLSTLEENGFKVYPDSLRKLGENIYIFVV<br>KRQNEKMVGILSSSDVKLNGAYFSEDKNVSD<br>KLRLNIYPFTFENYVTLNGKFHIGPTVCRGNSS<br>FGTGDRLGLVTAAQLTALKKYDVFPILAQQSP<br>RELIKTNRDFKDVLLKVVLGVLETGYIGHFGA<br>DADHIKDEYNLLEGINAGYTMYTLDLSEQLIDI<br>SSLNASEMRNKAQELSQVSKDIIKDFSGKKLDI<br>ISDSGYVVSEEELYKSAVAYENAMKFVDKVN<br>NILKEKLSDFDMEISIDEGGKVTTLEDHLYVAE<br>YLHRNGIDFFSIAPKFPGEFEKAVDYIGDLDEF<br>LLELKKHYQLSRMIGGYKISLHSGSDKFSIYRIF<br>SDITEKNFHIKTSGTSWLQAVNLIYKFDKEFYR<br>KLYKIALSNLEESKKSYKVLIKKDDFKDEPELD<br>NPEFTLRPEIKQLFHISFGVLLDLKGKEIKDML<br>NDYEEEHYKMVSDNIENHLKEIYYEK | *Thermoanaero-<br>bacterium<br>thermo-<br>saccharolyticum* |

TABLE 3-continued

| Native Sequences | | | |
|---|---|---|---|
| SEQ NO. | Plasmid ID | Sequence | Organism |
| 346 | pA06269 | MVGNVSSVLKESGFQIYPDSLRKLGENTYIFV VKKQKEKMIGILSNDELKLKEPYFSENKKISDN LQFNVYSFTFDNYVTLNGRFHIGPTICRENASF GTGDRLGLATAAQLDALKKFNVFPILAQQSPR ELVKTNRDFKDVLLKVVLGVLETGYIGHYGA DADHIKDEKYLLEGIDAGYTMYTLDLSEQLFD VSGATSLEIKEKAKTLSDVSRKIVEDFSGKSLN VGFGGHLVSEDELLKSAVAYEAAMKFVEKVN DILKEKLNDFDLEISIDEGGKVTTLEDHLFVAE YLHRNGIDFFSIAPKFPGEFEKAIDYVGDVNEF ERELKKHYDLTKLIGGYKLSLHSGSDKFSIYKI FSQTTEKNFHIKTSGTSWLQAVNLIYKSDKEFY RELYKIALSNLEESKKSYKVLIKKDDFKDEPEL DNSEFIIRPEIKQLFHISFGVLLDLKGKEIKDML YDYEEEHYKMVSDNIENHLKEIFYEK | *Thermoanaero-bacterium xylanolyticum* |
| 347 | pA06270 | MLTILPNKGISLGLGDRIGIATHGHIKVAKKYN FFPVFAQQSIRELNFTGRTFSDVRKDVLNALIE ENYVGNSGFDGDHLKSDEEIQYALDSGITMLT LDCSEHMNNKDSSIKERIFDQFYNKSFFVNDM PIEYSNKNELNKIVSIYAGVIERVIDVWNKFPK VNKKEVTFEVSVDETDVPTDEKTHFLISKYIYD EGVKIDTLAPRFPGEFQKAIDYIGNLQEFKKSLI KQDKIAKYFGYRLSIHSGSDKFSIYPIIGEVTQG NYHLKTSGTSYLEAIKIVAQKDPEFFKKIWKTC LDKREEMDKYYHLSCDPFSVPKNLSPTEYLQN PDARQTLHVSYMFVLNPQYDFREKFFEILTKY QNEYHQNVANHIEKHVKELKVEEKS | *Petrotoga mobilis* |
| 348 | pA06271 | MVGNVSAVLKENGFKIYPDSLRKLGESTYIFV VKKQKEKMIGILSNDELNLKEPYFSENKKISDN LQFNVYPFTFDNYVTLNGRFHIGPTVCRENAS FGTGDRLGMATAAQLGALKKFDVFPVLAQQS PRELVKTNRDFKDVLLKVVLGVLETGYIGHY GADADHIKDEKYLLEGIDAGYTMYTLDLSEQL FDISGATPSAIKEKAEALSDVSKKIVEDFSGQSL NVGLEGHLVSEDELLKSAIAYEGAMKFVEKV NDILKEKLNDFDLEISIDEGGKVTTLEDHLFVA EYLHRNGIDFFSIAPKFPGEFEKAIDYVGDVDE FKKALKKHYDLTKLIGGYKLSLHSGSDKFSIY KIFSQTTERNFHIKTSGTSWLQAVNLIYKSDRE FYRELYKIALSNLEESKKSYKVLIKKDDFKDEP ELDNPEFIVRPEIKQLFHISFGVLLDLKGKEIKD MLYEHEEEHYKMVSNNIENHLKEIYYEK | *Thermoanaero-bacterium saccharolyticum* |
| 349 | pA06272 | MFTILPKRGISLGLGDRIGIATTGHIKVAKKYN FFPVFAQQSIRELNFTGRTFIDVRKDALNALVE ENYVGNSGFDGDHLKSDEEIQYALDSGITMLT LDCSEHMNKDSSIKDQIFEQFYNKSFFVNDMPI EYSDKNELNKIVSIYASVIERVIDVWNKFPKVN KKEVTFEVSVDETDVPTDEKTHFLISKYIYDEG VKIDTLAPRFPGEFQKGIDYIGNIQEFKKSLIKQ DKIAKYFGYRLSIHSGSDKFSIYPIIGEVTQGNY HLKTSGTSYLEAIKVVAQKDPEFFKKIWQTCL DKREEMDKYYHLSCDPFSVPKDLSPTEYLKNP DARQTLHVSYMFVLNPQYDFREKFIEILTKYQ NEYHQNAANHIEKHVKELKVEEKIHKQKN | *Petrotoga mobilis* |
| 350 | pA06273 | MTTPGSLSLPRYSIGTGDRFGHEAEAQLRAVIE AERLGMALGIVWNKSYREHTIIGSRPEDVRRM ADKAVSALEWEGPYFVDADHITTKTVELFLDS SDFFTIDVAEAIGQEEISPQEEEDLLSSLDDLLN RELAIPGLSNPLTISEETARETIRAYWPAVREA ARIHQRIEKGTSRPFVVEVSMDETADPQRPPEL LLILAMIRKAGIPARTIAPKFSGSFYKGVDYVG DPEVFAREFEDDLCVVRYAREAFRLPEGLKLS VHSGSDKFSLYPLIKDILSRHPQEGVHLKTAGT TWLEEVTGLAESGGEALALAKEIALTCYSMIE ELCAPYAAVIDINPDRLPSPGEIEDWSSGRFVE ALEHDPSNPSYNRDFRQLIHVGYKVAAQMGE RFHEALEAHREVIAARVTRNLLERHIIPLFPGG AA | *Spirochaeta thermoila* |

TABLE 3-continued

| Native Sequences | | | |
|---|---|---|---|
| SEQ NO. | Plasmid ID | Sequence | Organism |
| 351 | pA06274 | MRAKELFGEDVSIEIALDESPSETQLKELFFYIN ELLYKGLRFEFIAPNIGFRKREDYRGDLQELYN RVRKLHTIASNNGVYLSIHSGSGAHPYSDKGV GVWSTIGRATDGLVKYKMSGVLIQLLLEVMS RFPKGSTVRRVYEEIYDAVLDHLKKDISRGRG LASETLRKMIEDYEEHSNKYDVRADVFRHYFF VFQCIRDDSGVRYLRNRVIELFNEVKELRDRY REEVANLITREAEALGYINSVIRYRKYEYS | *Ignisphaera aggregans* |
| 352 | pA04536 | MVLKVFKDHFGRGYEVYEKSYREKDSLSFFLT KEEEGKILVVAGEKAPEGLSFFKKQRAEGVSF FFCERNHENLEVLRKYFPDLKPVRAGLRASFG TGDRLGITTPAHVRALKDSGLFPIFAQQSVREN ERTGRTWRDVLDDATWGVFQEGYSEGFGAD ADHVKRPEDLVSAAREGFTMFTIDPSDHVRNL SKLTEKERNEKFEEILRKERIDRIYLGKKYSVL GEKIEFDEKNLRDAALVYYDAIAHVDMMYQI LKDETPDFDFEVSVDETETPTSPLFHIFVVEELR RRGVEFTNLALRFIGEWEKGIDYKGDLAQFER EIKMHAEIARMFEGYKISLHSGSDKFSVYPAFA SATGGLFHVKTAGTSYLEAVKVISMVNPELFR EIYRCTLDHFEEDRKSYHISADLSKVPEVEKVK DEDLPGLFEDINVRQLIHVTYGSVLKDASLKE RLFKTLEQNEELFYETVAKHIKRHVDLLEG | *Thermotoga maritima* |
| 353 | pA04539 | MINKVAEYLSGEGFYFYEKSFRKLSEDIYIFVV KKANEKSIGLLTQGDFTLSSPHFTERKYLKETG YYLNLYPLTYENFVILKDKFNIAPAPCDKKASF GMGDRLGLVTAAHIRAVENYDVFPVLAQQSP RELMKTHRSFKEAILKAILGVLEEGYTGKFGA DADHIKDENYLMEAIDAGYTMYTLDLSDMLV KLSDYTESQLKEKAEKLNITSKRIIERFKGKKF VMPTKEAFTVSEEELYKSALTYEKAMDFVEK VYGILKDKVKNFDLEISIDEGDKDTTVEDHIFV AEYLHEKGIDFWSLAPKFPGEFQKAIDYIGDV DKFAVELKKHQFLSREFGGYKLSLHSGSDKFS IYKVFSEITEGEFHIKTSGTSWFQAVNLIFEKDK ELFKELYQIALYNLEESKKAYKVLIDKKDFPE NINLEDSQIVSKPEIKQLFHISYGVLLEERKKQI FEVLNKYEEEHYEFVRKNIENHFKEIFSK | *Caldanaerobacter subterraneus* |
| 354 | pA07082 | MKENKVMNSFSAIYGNRYKVYEKSLKRKEKE FFFVIKDFQRKYLVAAGPSYRIRKRDFQPDEEG VADNEGEFLFQICRLTHEINLTQLQSIFNYLQPS TTKMKPSFGTGDRLGIATPAHIQAFEDKNIFPIL AQQSVREMERTESNWQKVLDNAIWGCFEAG YEGKFGADADHVKDLKNLKEAIDCGFTFYTID PSDHIDANILKLDKDELRNKYQQLPEKDALEN SYLNKEYQIGSQKLTFTQDILIEIVLTYLEAIKH VEKCYKFLKDSHKGDFELEVSVDETPTPTSPL AHLWIASELQRRGVDFQNLAPHFIGDWEKGID YIGNIDTFKEEFKLHCQIASQMGGYKLSLHSGS DKFSVYPIFAEETNGYFHVKTAGTSWLEAVKA IVVCDPALYREMYEFALKCFEKDSFSYLLSTD LQKIPNIKELQDKELIQLFSNNNARQLIHITYGS ILREKDSQNRYKFRDRIYKVLFENEDIHYENVS KHIRHEILGLLSV | *Mesotoga infera* |
| 355 | pA07083 | MQSREELKRAILSEFGDYNIYSESIYRAGGCVL FLAKDMGQKLLVVVEEETGSAFDRFVGPQVY HPSGKRVKEAPLQPVNAGIVRELLPFTAPVAL GATGLSLGLGDRLGVASPGHLRLIKKTGVRPV LAQQSVRELTLTNRTYSDVLDAATWAVLQEG YEGGFGADGDHLKTAEEIKGALDLGFTMITLD ASAHIDNTVGQKAAKQVAELYHTLPADYTAD MEEHYLGKAFIVGGMAITFDTETLQRLVLTYG KALAFMGYIYHTLIVNAGREVDFEISIDETATP TTPAAHYFVASELGRMGVKFTSLAPRFCGEFQ KGIDYIGDLYQFEDEFKRHAAIADHFGYRLSIH SGSDKFSVFPIIGQYTRGRVHIKTAGTNWLEAL RVVARINPALFREIYAFAGEVFGEAKKYYHVT TDLTRLPDVAAMADDGLPTVLDHNDARQML HITYGLVLTAANADGSYRFKDALYELLFDHED EYYAALERHIGRHLEKLTENLKG | *Thermosimus carboxydivorans* |

TABLE 3-continued

| Native Sequences | | | |
|---|---|---|---|
| SEQ NO. | Plasmid ID | Sequence | Organism |
| 356 | pA07084 | MSWKDFAEELVGTSKEAVMKVAEYAEDYRIY PRSIIKKDKSFYFLAKIDQKKKLVILNKSKNFEL FQGRIEELAGFKAKIGPLSHYNAEILREVFPFTA PSALGNKKPSIGLGDRLGIATPGHIEAVKESAA MPVFAQQSVRELNLTGRTFKSVLDDVSWAVF QEGYQAGFAADADHLKEKPDIKEALDLGYTM LTLDCTDYINDDLDQMSESEIENAYAEVPDYL REGLENQYLNKTFVLNSGYQLEYNQDNFKEIV LIYYKMLDFAKEIQHLIKTSARNVDFEISIDETS TPTTPEAHFFVANELKRNNIEVNSLAPRFVGEF QKGIDYIGDLEQFEKEFKVHADIADRFGYKLSI HSGSDKFSVFPIIGRHTQGRVHVKTAGTNWLE AIRVVAENNPSLYRDIHAYALKKFEAAKEYYH VTTDLDKVPELARMSDQELGELLEINEVRQLL HITYGFILQDKKDGRYIFRDKLYKFWDEYDKE YRRALERHIGRHLNKLGFYKN | *Halanaerobium congolense* |
| 357 | pA07085 | MSWKDFAEELVGTSKEAVMKVAEYAEDYRIY PRSIIKKDKSFYFLAKIDQKKKLVILNKSKNFEL FQGRIEELAGFKAKIGPLSHYNAEILRKVFPFT APSALGNKKPSIGLGDRLGIATPGHIEAVKESA AMPVFAQQSVRELNLTGRTFKSVLDDVSWAV FQEGYQAGFAADADHLKEKPDIKEALDLGYT MLTLDCTDYINDDLDQMSESEVENAYAEVPD YLREGLENQYLNKTFVLNSGYQLEYNQDNFK EIVLIYYKMLDFAKEIQHLIKTSARNVDFEISID ETSTPTTPEAHFFVANELKRNNIEVNSLAPRFV GEFQKGIDYIGDLEQFEKEFKVHADIADRFGY KLSIHSGSDKFSVFPIIGRHTQGRVHVKTAGTN WLEAIRVVAENNPSLYRDIHAYALKKFEAAKE YYHVTTDLDKVPELARMSDQELGELLEINEVR QLLHITYGFILQDKKDGRYIFRDKLYKFWDEY DKEYRRALERHIGRHLNKLGFYKN | *Halanaerobium congolense* |
| 358 | pA07086 | MSWKDFAEELVGTSKDAVKKVAEYAEDYRIY PRSIIKKEKSFYFLAKIDQKKKLVILNKSKNFDI FQGKTEKLAGFKAKIAPLSHYNAEIIREVFPFT APSKIGNQTASIGLGDRLGIATPGHIEAVKKSN AMPVFAQQSVKELKLTGRSFKSVLDDVSWAV FQEGYQNGFGADADRLKEKPEIKEALDLGYT MLTLDCTDYINDNFDQTAESDIESAYAEVPDY LRDGLESKYLNKTFVLNSGYQLEYNKVNFKKI VLSYYQILDFVKEIQHLIKRSARDVDLEISIADS LNSTSPEAHFFVANEFKRNNIEVNSLALNFVGE FQKGIDYIGDLEKFEKDFEIHADIADRFGYKLSI HSGSDKFSIFPIIGRQTEGRAHIKTAGTNWLEAI RVVAENDPSLYREIHSYALKKFEEAKEFYQVN TDLSKVPELAVMSDQELGELLEIDAVRQLLHIT YGFILQDKKDGRYIFRDRLYKLLDEYDKDYRS GLERHIGRHLNKLGFYKN | *Halanaerobium saccharolyticum* |
| 359 | pA07087 | MVKHFESVLEELSQRKVPTSTEEVTVYTPSFEE HAGSQVVMVKSGTEKMIVAAGAGELFEALSG EDIGKGKVCPLTHENRLVLNQFFSYTAPQAFG TDIATMGLGDRLGIASPGHIDTVKERNVKPILA QQSIRELTLLNRTMTDILDAAAFAVFQEGYKD GYGADADHIKLESDIEHALQLGFSFLTLDCSEQ IRNDVESQTSDEIQNEFASLSDEKRAYFSNYYL DQTFNVHERQISFDQANLAKNVLVYGEAIDFM EHVYHTYLQSLDRDVDFEISIDETETVTSPEAH FFVAEELRRRGVKVESLAPRFCGEFQKGIDYIG DMDQFEKELKEHADIAKHFGYKLSIHSGSDKF SVFPIIGKYTDGLLHIKTAGTNWLEAVRVVAQ ENPDLYRRMHVYAEEHFEETLKYYHVTPDLD SVTPLKEQPDDQLPEYMNHDAARQLFHVTYGI LLTAKDDAGNDLFRDEFFDTLLNKEDAYRQA LAHHIGREILDLLGLSKKVGIE | *Gracihbacillus halophilus* |
| 360 | pA07088 | MINKVAEYLSREGFHFYEKSFRKFSEDIYIFVV KKANEKSIGLLTQRDFTLSSPYFTERKYLKEIG YYLNLYPLTYENFVILKDKFSIAPSPCNKKVSF GMGDRLGLVTAAHIRAVQNYDVFPVLAQQSP RELMKTHRSFREAILKAILGVLEEGYTGKFGA DADHIKDENYLMEAIDAGYTMYTLDLSDMLV | *Caldanaerobacter subterraneus* |

TABLE 3-continued

Native Sequences

| SEQ NO. | Plasmid ID | Sequence | Organism |
|---|---|---|---|
| | | KLSDYTESQLKEKAEKLNITSKRIIEKFKGKKF VMPTEEAFTVSEEELYKSALTYEKAMDFVEK VYGILKDKVKNFDLEISIDEGDKDTTVEDHIFV AEYLHEKGIDFWSLAPKFPGEFQKAIDYIGDV DKFAVELKKHQFLSREFGGYKLSLHSGSDKFS IYKVFSEITEREFHIKTSGTSWLQAVNLIFEKDK KLFKELYQIALYNLEESKKAYKVLIDKKDFPE NINLEDSQIVSKPEIKQLFHISYGVLLEERKKQI FEVLNKYEEEHYEFVRKNIENHFKEIFSK | |
| 361 | pA07089 | MLPYLVARPLGLRKSAGCGDRLGLATPGHIRA LRATFGRDEDAAMAPIFAQQSIRENARTGRTP QEVMDDAMWGVFQEGWRAGFGADADHLKT LADVDICAAAGYTFYTVDPGDHVDDEANTAA FPALEARVDALPWDVLDSSPADLAARLADRPI DLGTLKVTLDRETLWRAAAKYGRAVAHTVT MYRHLAGAMGERPFELEMSVDETATVTSLAE HVYIAAELQRLGVRCVSLAPRYVGTFEKGVD YIGDLDAFEQSIAQHMAVSRTFGPYKLSLHSG SDKFSIYPIASRVAGDLVHLKTAGTSYLEALRA IAAMAPDLFRQIVAFARERYPTDRASYHVSAE LEKMPDIAGWPDDRLPELLNDFHAREILHVTF GSVLNHPPFREPFFTALRTHEETYSEMLERHFC RHFAPFAG | *Litorilinea aerophila* |
| 362 | pA07090 | MINKVAEYLSREGFYFYEKSFRKFSEDIYIFVV KKANEKSIGLLTQGDFTLSSPYFTERKYLKEIG YYLNLYPLTYENFVILKDKFSIAPSPCNKKVSF GMGDRLGLVTAAHIRAVENYDVFPVLAQQSP RELMKTHRSFKEAILKAILGVLEEGYTGKFGA DADHIKDENYLMEAIDAGYTMYTLDLSDMLV KLSDYTESQLKEKAEKLNITSKRIIERFKGKKF VMPTKEAFTVSEEELYKSALTYEKAMDFVEK VYGILKDKVKNFDLEISIDEGDKDTTVEDHIFV AEYLHEKGIDFWSLAPKFPGEFQKAIDYIGDV DKFAVELKKHQFLSREFGGYKLSLHSGSDKFS IYKVFSEITEGEFHIKTSGTSWLQAVNLIFEKDK ELFKELYQIALYNLEESKKAYKVLIDKKDFPE NINLEDSQIVSKPEIKQLFHISYGVLLEERKKQI FEVLNKYEEEHYEFVRKNIENHFKEIFSK | *Caldanaerobacter subterraneus* |
| 363 | pA07091 | MFERKIEMINKVAEYLSREGFYFYEKSFRKFSE DIYIFVVKKANEKSIGLLTQGDFTLSSPYFTER KYLKEIGYYLNLYPLTYENFVILKDKFSIAPSP CNKKVSFGMGDRLGLVTAAHIRAVENYDVFP VLAQQSPRELMKTHRSFKEAILKAILGVLEEG YTGKFGADADHIKDENYLMEAIDAGYTMYTL DLSDMLVKLSDYTESQLKEKAEKLNITSKRIIE KFKGKKFVMPTEEAFTVSEEELYKSALTYEKA MDFVEKVYGILKDKVKNFDLEISIDEGDKDTT VEDHIFVAEYLHEKGIDFWSLAPKFPGEFQKAI DYIGDVDKFAVELKKHQFLSREFGGYKLSLHS GSDKFSIYKVFSEITEGEFHIKTSGTSWLQAVN LIFEKDKKLFKELYQIALYNLEESKKAYKVLID KKDFPENINLEDSQIVSKPEIKQLFHISYGVLLE ERKKQIFEVLNKYEEEHYEFVRKNVENHFKEI FSK | *Caldanaerobacter subterraneus* |
| 364 | pA07092 | MGMMDKDVLNQLSSLLSRHSFVLYPNSVRNL AEDIYVFVAKGNADKKVGILSKGKALGFKAPF FAEDIKVEATGFSFNLYPLSFENYLILRDEFGIA LVPCKNKASFGTGDRLGLATPAHLDAFKSYN MFPVLAQQSPRELEKTHRDFRDVLLKAVLGV LEAGYTGEFGADADHIKDERYLLEAADAGYT MYTLDVSEMLVKGDVSPDKADHLSQHSRDIIK DFSGKRISFEGGEYTVKEEELYRSAVIYEKAM NFVERVHGLLKERLKDFDLEVSIDEGDRDTTV EDHIFVAEYLHRRGIDFWSLAPKFPGEFEKAV DYRGDIDKFTVELNKHCAVARMLGGYRLSLH SGSDKFSVYRIFNDATQHNFHIKTSGTSWLQA LNVIHEKDRQLFKELYNIALDNLEESKKAYKIS IYRQDFEEGLDLDNLHVLQNPKVKQLLHISYG VLLDEKRQEIYEVLNQHEAEHYRYVSDNIKKH LELLK | *Caldicoprobacter faecalis* |

TABLE 3-continued

| Native Sequences | | | |
|---|---|---|---|
| SEQ NO. | Plasmid ID | Sequence | Organism |
| 365 | pA07093 | MKEELSNYLLKNSFLLYPDSFRRLKEDVYIFV AKKDSDKKIGFLTNGNFKLSSPHFLEDKYVEE LGFYLNLYPLTYENYLILKDNFGISPVTCKEKT SFGTGDRLGLVTPAHIKVLKNYDIFPVLAQQSP RELVKTNRDFKDVLLKAILGVLEAGYAGGG ADADHIKDEKYLMEAIDAGYTMYTLDLSDLL VKISDMPESQLKEKAQSLSSQSREIIDRYKGKK FSISTDEDFVVSEDELYKSALTYEKAMKFVEK VYGILKDRLQHFDLEISIDEGEKDTTVEDHIFV VEYLHRKGIDFWSLAPKFPGEFQKAIDYKGDI KKFTSELKKHYFLTKELGGYKLSLHSGSDKFSI YKIFNEITEGNFHIKTSGTSWLQAISLIFEKDKD LFNDLYKIALDNLEESKKAYKVLIDRDDFPQTI QTEDSQILSKPEIKQLFHISYGVLLDERRKEIYE VLNKYEEEHYEFVSKNIKNHLKEIFNI | *Thermoanaero-bacter uzonensis* |
| 366 | pA07094 | MDLNGLLKDVEEILAKVDAGEKVESLSDAGV YVPSVQVDRRNVYFIYHTKDEKDHTVKTLVV YEENPTIGDFDALETLKGENSTLITAALTDHNN QALAKRFPWIKPTSRRNYKYTFGLGDRLGNAS NAHLRLFKGTGIMPVLAQQSIRELTLMHRTNT DVLLSASWAVFEEGFTFGWGADGDHVKTEYE VDYAVKVGCSMITLDCTDVINNDAVTMSDEE LDKTFNALDDDQKKYFNDTYLDKTFDLGNGN SVHFTKHDVEESVLTFYGAILFAADIYKKFVVP YNLDFEISMDETPYQTTNPNHFFFGNELHKRGI VPTTMAPRFYGEFQKAIDYIGDKDRFEREFVL HEAIAEYFGYKLSIHSGSDKLSVYEIIGRVAKN GWHVKTAGTNWLEALRVIAHKDPEFMVELY KYAYEHLDDVKDFYVFNAQTDGKAPKPENVT VDNVVDVLSDDDGRQVLHTMYGSLMNLKHN YHYVFRDKFWDILLKNQDLYDKYLNIHIAEHI DLLQGKYKTKEEALAALEPKTDISKEY | *Lactobacillus ingluviei* |
| 367 | pA07095 | MFTILPKKGISLGLGDRIGIATTGHIKVAKKYN FFPVFAQQSIRELNFTGRTFTDVRKDVLNALIE ENYVGNSGFDGDHLKSDEEIQYALDSGITMLT LDCSEHMNKDSSIKDQIFEQFYNKSFFVNDMPI EYSDKNELNEIVSIYASVIERVIDVWNKFPKVN KKEVSFEVSVDETDVPTDEKTHFLISKYINDEG VKIDTLAPRFPGEFQKGIDYIGNVQEFKKSLIK QEKIAKYFGYRLSIHSGSDKFSIYPIIGEVTQGN YHLKTSGTSFLEAIKVVAQKDPEFFKKIWQTC LDKREEMDKYYHLSCNPFSVPKDLSPTEYLKN PDARQTLHVSYMFVLNPQYDFREKFFEILTKY QNEYHENVANHIEKHVKELKIEETIHKQKK | *Petrotoga mexicana* |
| 368 | pA07096 | MFSKLPKQGISLGLGDRVGLATPGHIKVAKRH EFFPVFAQQSIRELNFTGRTFHDVKKDVENAVI KENYEGKSGFDGDHLKTDEEIKMAIDSGITML TLDCSEYMGVVSKIKEKIYKGFYGKTFKVKDL DLEYSQEELEKILSIYSGVIERIIYIWNNFPKVK NKDVSFEVSIDETNIPTDEKTHFLLSKYLYDEG ITIDTLAPRFPGEFQKGIDYIGNIKEFKNSLMKH HKIASYFGYRLSIHSGSDKFSIYPYVSQITQGN YHLKTSGTSYLQALKIIAQKAPDFFKEIWKTCL DKRTEMDKYYHLSCDPFSVPKDLKPIEYLNNP DARQTLHVSYMFVLNPKYDFRNRFFEILTKYE NEYHIEVAEHIKRHVKELKIPEKIQN | *Defluviitoga tunisiensis* |
| 369 | pA07097 | MFTILPKKGISLGLGDRIGIATPGHIKVAKKYN FFPVFAQQSIRELNFTGRTFTDVRKDVLNALVE ENYVGNSGFDGDHLKSDEEIQYALDSGITMLT LDCSEHMNKDSSIKDQIFEQFYNKSFFVNDMPI EYSDKNELNKIVSIYASVIERVIDVWNKFPKVN KKEVTFEVSVDETDVPTDEKTHFLISKYIYDEG VKIDTLAPRFPGEFQKAIDYIGNIQEFKKSLIKQ NKIAKYFGYRLSIHSGSDKFSIYPIIGEVTQGNY HLKTSGTSYLEAIKVVAQKDPEFFKKIWQTCL DKREEMDKYYHLSCDPFSVPKDLSPTEYLKNI DARQTLHVSYMFVLNPQYDFREKFFEILTKYQ NEYYENVANHIEKHVKELKIEETK | *Petrotoga miotherma* |

TABLE 3-continued

| Native Sequences | | | |
|---|---|---|---|
| SEQ NO. | Plasmid ID | Sequence | Organism |
| 370 | pA07098 | MFTILPKKGISIGLGDRIGIATPGHIKVAKKYNF FPVFAQQSIRELNFTGRTFRDVRKDVLNALVE ENYVGNSGFDGDHLKSDEEIQYALDSGITMLT LDCSEHMNKDSSVKESIFDQFYNKSFFVNDMP IEYSDKNELNKIVSIYGGVIERVIDVWNKFPKV NKKEVSFEVSVDETDVPTDEKTHFLISKYIYDE GVKIDTLAPRFPGEFQKGIDYIGNIQEFKKSLIK QDKIAKYFGYRLSIHSGSDKFSIYPIIGEVTQGN YHLKTSGTSYLEAIKVIAQKDPEFFKKIWQTCL DKREEMDKYYHLSCDPFSVPKDLSPTEYLQNP DARQTLHVSYMFVLNPQYDFRKKFFEILTKYQ NEYHENVAHHIEKHVKELKVEETK | *Petrotoga olearia* |
| 371 | pA07099 | MKKLAKYSFGMGDRFAHQASWQLKAITEIEK QGIEVTPVWNKSNREHTTIGSKPEDNRDAAQK AIQKAGWSKPWYIDADHINLDTVDNFLESSDF FTIDVASYIGKKGDSKEEETFISKMKPLIGNLNI PGVNSPFKITEQQLRNIAGQYLHAAFMAGETY KYIESVKGKGNFITEVSMDEVPEPQTPVELFFIL AMLAHYGVPAQTIAPKFTGRFNKGVDYVGDI ETFRKEYEANLMVIDYAIQKFGFPPELKLSIHS GSDKFSIYPVIKELSQKHNKGFHLKTAGTTWL EEVIGLAMAGGEALLFVKNIYSRALDNIEKLC APYADVIDINTDNLPKLSEVNNWTGEEFANAL RHVPDHPMYNPDLRQLIHVAYKLAAENINQF NSFLEQHSEIVGKCVFENLYKRHAERLFVFSN | *Thermophagus xiamenensis* |
| 372 | pA07100 | MKQLERFSMGIGDRFGHQGKAQLEALAEAKH LGCTIIPVWNKSYREHSIIHTEPGQVRKEADWA VAALGWQDPYHVDADHISMKTVDLFLDSSDF FTLDVADYTGKAADEASIARFVAKHQHCIGKL QIPGIEQPITITETTLTSVARKYLLAIQEAGKLY RHIANKKGPENFITEVSIDETDQPQGPEDLLFIL AMIADEGIPAQTIAPKFTGRFNKGVDYVGNLT QFEREFNQDILVIAYASKEFGLPKNLKLSVHSG SDKFSIYPIIKKAIYTHHAGLHLKTAGTTWLEE LIGLASAGDEGLRIVQQIYRETYYRFDELCAPY ATVIDIHKDKLPEPNSVQAWNGETYAAALRHI ENHPQYNPHFRQLLHVGYKVAAELGETYLKA LEAHEHHIALQVKENLLDRHIRPIFIQ | *Treponema caldarium* |
| 373 | pA07101 | MLDTPRYLGKLPHLSVGVRLPEVFLEGIMSGF KTGNSAGGVMLSYHRETAPEYVINAPPGDFEL TRGHTGTSIRHYIEASVAKAKEKGVVVEVEAD HVSVSVSSEAVKRISGGGTHRVLSEEEVRSAL KYIEDEIREAVSTRNIYFYTIDTCDLIDYSSEKIA VDELRTVFKDLYPASLIERYKDINVVVNGTRIR FDEEKVMRLSLKLMRSIDVSERIYRIIKEMTPW PFGIEIAFDETPVTSDPHELFFVLNELRTRGIPV DFIAPNVGFQKREDFTGDLETLHSRVKTLHEV ASFFGSLLSFHSGSGSSPYSMKGKGVHDIIRRA AGGLFKYKISGVYFELLMQLMSRSDIPSVRRL YEEIYDAVIELLEDQVKRKGELYDEVLVKRLE EHRKKSLNGYVRDSESPVFRYYSFLALNIRRN GERYLRNAIVELYLEDKGFREQVDREISALTV AFLDSLGFRGNVRLLR | *Thermofilum uzonense* |

Furthermore, the present disclosure provides polynucleotides encoding any of the polypeptides disclosed herein. The present disclosure also provides constructs, vectors, plasmids that comprises the polynucleotides. An expression vector carrying the polynucleotides of the disclosure may be any vector which is capable of expressing polypeptides having D-fructose C4-epimerase activity in the selected host organism, and the choice of vector will depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, a minichromosome or an artificial chromosome. Alternatively, the vector may be one which, when introduced into a host cell, is integrated into the host cell genome and replicated together with the chromosome.

In the vector, the polynucleotides encoding for the D-fructose C4-epimerase active polypeptide should be operably combined with a suitable promoter sequence. The promoter may be any DNA sequence which confers transcriptional activity to the host organism of choice and may be derived from genes encoding proteins which are either homologous or heterologous to the host organism. Examples of suitable promoters for directing the transcription of the DNA fragment of the disclosure in a bacterial host are the promoter of the lac operon of *E. coli*, the promoter of the T7 RNA polymerase of T7 bacteriophage, the *Streptomyces coelicolor* agarase gene dagA promoters, the promoters of the *Bacillus lichenmformis* α-amylase gene (amyL), the promoters of the *Bacillus stearothermophilus* maltogenic amylase gene (amyM), the promoters of the *Bacillus amyloliquefaciens* α-amylase gene (aqyQ), the promoters of the *Bacillus subtilis* xylA and xylB genes.

The host organism of the disclosure either comprising a polynucleotide or an expression vector as described above is advantageously used as a host cell in the recombinant production of a polypeptide according to the disclosure. The cell may be transformed with a DNA construct comprising the gene coding for the polypeptide of the disclosure or, conveniently by integrating the DNA construct into the host chromosome. Such an integration is generally considered to be advantageous as the DNA fragment is more likely to be stably maintained in the cell. Integration of the DNA constructs into the host chromosome may be carried out according to conventional methods such as e.g. by homologous or heterologous recombination or by means of a transposable element. Alternatively, the host organism may be transformed with an expression vector as described above.

In accordance with the disclosure, the host organism may be a cell of a higher organism such as an animal cell, including a mammal, an avian or an insect cell, or a plant cell. However, in preferred embodiments, the host organism is a microbial cell, e.g. a bacterial or a fungal cell including a yeast cell.

In some embodiments, the foregoing polypeptide or microorganism expressing the polypeptide is immobilized. In some embodiments, the polypeptide or the microorganism expressing the polypeptide is immobilized to a carrier or support. In some embodiments, the polypeptide or the microorganism expressing the polypeptide is immobilized to the carrier or support through adsorption, covalent attachment, non-covalent attachment, ionic interaction, entrapment, cross-linking, or metal-linking. In some embodiments, the carrier or support is an organic composition. In some embodiments, the organic composition is a natural polymer. In some embodiments the natural polymer is alginate, chitosan, chitin, collagen, carrageenan, gelatin, cellulose, starch, pectin, or sepharose. In some embodiments, the organic composition is a synthetic polymer. In some embodiments, the synthetic polymer is polystyrene, styrene divinylbenzene, polyvinyl chloride, polyacrylate, polyamide, polypropylene, diethylaminoethyl cellulose (DEAE cellulose), UV-activated polyethylene glycerol, or methacrylate. In some embodiments, the organic composition is functionalized with a chemical group to facilitate enzyme immobilization. In some embodiments, the functional group is an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid. In some embodiments, the carrier or support is an inorganic composition. In some embodiments, the inorganic composition is alumina, Zeolite, ceramics, celite, glass, silica, activated carbon, or charcoal. In some embodiments, the polypeptide or the microorganism expressing the polypeptide is immobilized without a carrier or support. In some embodiments, the polypeptide or the microorganism expressing the polypeptide is cross-linked to itself and/or an inert feeder protein using glutaraldehyde.

III. Modified Microorganisms

In another aspect, the disclosure provides a microorganism expressing any of the polypeptides disclosed herein. In some embodiments, the disclosure provides a microorganism expressing a polypeptide comprising an amino acid sequence that is at least 60%, at least 65%, at least 70%, at least 75%, at least 80%, at least 85%, at least 90%, at least 95%, at least 98%, or at least 99% identical to an amino acid sequence selected from the group consisting of SEQ ID NOs: 1-444. In some embodiments, the microorganism is modified. In some embodiments, wherein the modified microorganism is genetically modified. In some embodiments, the modified microorganism is non-naturally occurring.

In some embodiments, the modified microorganism is derived from *Escherichia coli, Corynebacterum glutamicum, Aspergillus oryzae, Pichia pastoris, Bacillus subtilis, Caldithrix abyssi, Anaerolinea thermophila, Thermoanaerobacterium thermosaccharolyticum, Thermoanaerobacter thermohydrosulfuricus, Caldicellulosiruptor kronotskyensis, Dictyoglomus turgidum, Caldilinea aerophila, Rhodothermus marinus, Methanohalobium evestigatum, Clostridium cavendishii, Kosmotoga olearia, Butyricicoccus pullicaecorum, Clostridium thermobutyricum, Litorilinea aerophila, Enterobacter mori., Caldisericum exile, Dictyoglomus thermophilum, Rhodothermus profundi, Caldibacillus debilis., Caloramator quimbayensis, Methanosalsum zhilinae, Pseudothermotoga thermarum, Pseudothermotoga hypogea, Pseudothermotoga lettingae, Geosporobacter subterraneus, Melioribacter roseus, Lysinibacillus sphaericus, Clostridium stercorarium, Truepera radiovictrix, Thermoflexus hugenholtzii, Petrotoga mobilis, Spirochaeta thermophila, Thermofilum pendens, Thermoanaerobacter siderophilus, Thermoanaerobacter mathranii, Thermoanaerobacter italicus, Thermoanaerobacterium xylanolyticum, Thermoanaerobacterium saccharolyticum, Ignisphaera aggregans, Thermotoga maritima, Caldanaerobacter subterraneus, Mesotoga infera, Thermosinus carboxydivorans, Halanaerobium congolense, Halanaerobium saccharolyticum, Gracilibacillus halophilus, Caldicoprobacter faecalis, Thermoanaerobacter uzonensis, Lactobacillus ingluviei, Petrotoga mexicana, Defluviitoga tunisiensis, Petrotoga miotherma, Petrotoga olearia, Thermophagus xiamenensis, Treponema caldarium, Thermofilum uzonense.*

The modified microorganism according to the disclosure may, if it is intended for direct addition to a product where it is desired to have D-fructose C4-epimerase activity, e.g. during a manufacturing process, be provided in the form of a microbial culture, preferably in a concentrate form. Thus, such a culture may advantageously contain the microbial cell according to the disclosure in a concentration which is preferably in the range of 10' to $10^{12}$ per g of culture. The culture may be a fresh culture, i.e. a non-frozen suspension of the cells in a liquid medium or it may in the form of a frozen or dried culture, e.g. a freeze-dried culture. The microbial cell may also for specific purposes be immobilized on a solid substrate.

In some embodiments, the foregoing microorganism expressing the polypeptide is immobilized. In some embodiments, the microorganism expressing the polypeptide is immobilized to a carrier or support. In some embodiments, the microorganism expressing the polypeptide is immobilized to the carrier or support through adsorption, covalent attachment, non-covalent attachment, ionic interaction, entrapment, cross-linking, or metal-linking. In some embodiments, the carrier or support is an organic composition. In some embodiments, the organic composition is a natural polymer. In some embodiments the natural polymer is alginate, chitosan, chitin, collagen, carrageenan, gelatin, cellulose, starch, pectin, or sepharose. In some embodiments, the organic composition is a synthetic polymer. In some embodiments, the synthetic polymer is polystyrene, styrene divinylbenzene, polyvinyl chloride, polyacrylate, polyamide, polypropylene, diethylaminoethyl cellulose (DEAE cellulose), UV-activated polyethylene glycerol, or methacrylate. In some embodiments, the organic composition is functionalized with a chemical group to facilitate enzyme immobilization. In some embodiments, the functional group is an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid. In some embodiments, the carrier or support is an inorganic composition. In some embodiments, the inorganic composition is alumina, zeolite, ceramics, celite, glass, silica, activated carbon, or charcoal. In some embodiments, the microorganism expressing the polypeptide is immobilized without a carrier or support. In some embodiments, the microorganism expressing the polypeptide is cross-linked to itself and/or an inert feeder protein using glutaraldehyde.

IV. Immobilization

The immobilization of the foregoing polypeptides and microorganisms can be achieved using techniques known in the art. Immobilized enzymes have a number of distinct advantages over soluble enzymes such as, for example, their use in continuous conversion systems. Exemplary of publications which review the art directed to enzyme immobilization are the following: Goldstein, in Fermentation Advances, Academic Press, New York, N.Y. (1969), pp. 391-424; Goldstein et al., Z. Anal. Chem., 243, pp. 375-396 (1968); Kay, Process Biochem., 3 (8), pp. 36-39 (1968); Tosa et al., Kagaku To Seibutsu, 7 (3), pp. 147-155 (1967); Silman et al., Ann. Rev. Biochem., 35 (2), pp. 873-908 (1966); Gryszkiewicz, Folia Biologica, 19 (1), pp. 119-150 (1971); Zaborsky, "Immobilized Enzymes", CRC Press, Cleveland, Ohio (1973); Datta et al., 3 Biotech. "Enzyme immobilization: an overview on techniques and support materials," 3(1): 1-9 (2013); Gotovtsev et al., "Immobilization of microbial cells for biotechnological production: Modern solutions and promising technologies," Appl. Biochem. Microbiol., 51: 792 (2015).

From the above noted publications, it is apparent that a number of enzyme immobilization techniques have been described. These techniques include covalently bonding an enzyme to a suitable insoluble carrier or support, encapsulation of an enzyme within a material which is impermeable to the enzyme but permeable to the substrate and the products of the catalyzed reaction, adsorption of an enzyme on an insoluble carrier and entrapment of an enzyme within a porous polymeric material wherein the pores are of such a size that will provide free access of the substrate and the catalyzed reaction products but which are sufficiently small to prevent the escape of the enzyme.

In some embodiments, the polypeptides disclosed herein or microorganism expressing the polypeptide is immobilized. In some embodiments, the polypeptide or the microorganism expressing the polypeptide is immobilized to a carrier or support. In some embodiments, the polypeptide or the microorganism expressing the polypeptide is immobilized to the carrier or support through adsorption, covalent attachment, non-covalent attachment, ionic interaction, entrapment, cross-linking, or metal-linking.

In some embodiments, the carrier or support is an organic composition. In some embodiments, the organic composition is alginate, chitosan, chitin, collagen, carrageenan, gelatin, cellulose, starch, pectin, sepharose, polystyrene, styrene divinylbenzene, polyvinyl chloride, polyacrylate, polyamide, polypropylene, diethylaminoethyl cellulose (DEAE cellulose), UV-activated polyethylene glycerol, or methacrylate. In some embodiments, the organic composition is functionalized with a chemical group. In some embodiments, the chemical group is an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid. In some embodiments, the organic composition is a natural polymer. In some embodiments the natural polymer is alginate, chitosan, chitin, collagen, carrageenan, gelatin, cellulose, starch, pectin, or sepharose. In some embodiments, the organic composition is a synthetic polymer. In some embodiments, the synthetic polymer is polystyrene, styrene divinylbenzene, polyvinyl chloride, polyacrylate, polyamide, polypropylene, diethylaminoethyl cellulose (DEAE cellulose), UV-activated polyethylene glycerol, or methacrylate. In some embodiments, the organic composition is functionalized with a chemical group to facilitate enzyme immobilization. In some embodiments, the functional group is an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid.

In some embodiments, the carrier or support is an inorganic composition. In some embodiments, the inorganic composition is alumina, zeolite, ceramics, celite, glass, silica, activated carbon, or charcoal. In some embodiments, the polypeptide or the microorganism expressing the polypeptide is immobilized without a carrier or support. In some embodiments, the polypeptide or the microorganism expressing the polypeptide is cross-linked to itself and/or an inert feeder protein using a cross-linking agent. In some embodiments, the cross-linking agent is glutaraldehyde.

V. Methods for Producing Tagatose

The present invention provides methods and compositions for converting fructose to tagatose. An economic biocatalytic process for conversion of fructose to tagatose will likely require an enzyme that remains active for extended periods of time at elevated temperatures. Elevated temperatures prevent contamination, can increase substrate solubility and can increase reaction rate. Enzymes from thermophiles are necessarily thermostable and active at elevated temperatures due to their organism's native environment. Therefore, enzymes from thermophiles were screened for D-fructose C4-epimerase (FC4E) activity.

In another aspect, the disclosure provides a method of producing tagatose, the method comprising: (a) contacting fructose with any of the polypeptides disclosed herein or a microorganism expressing the polypeptide; and (b) converting fructose to tagatose. In some embodiments, the method comprises: (a) contacting fructose with a polypeptide or a microorganism expressing the polypeptide, wherein the polypeptide comprises an amino acid sequence that is at least 60%, 65%, 70%, 75%, 80%, 85%, 90%, 95%, or 98% identical to an amino acid sequence selected from the group consisting of SEQ ID NOs: 1-444; and (b) converting fructose to tagatose. In some embodiments, step (b) converts fructose to tagatose through C4-epimerization of fructose. In some embodiments, the polypeptide comprises an amino acid sequence selected from the group consisting of SEQ ID NOs: 1-444. In some embodiments, the polypeptide consists essentially of an amino acid sequence selected from the group consisting of SEQ ID NOs: 1-444. In some embodiments, the polypeptide consists of an amino acid sequence selected from the group consisting of SEQ ID NOs: 1-444. In some embodiments, the polypeptide is capable of converting fructose to tagatose through C4-epimerization of fructose. In some embodiments, the polypeptide has D-fructose C4-epimerase activity.

In one aspect, the disclosure provides a method for producing a tagatose composition, comprising the steps of: (a) providing a starting composition comprising greater than about 0.3%, about 0.5%, about 1%, about 2%, about 3%, about 4%, about 5%, about 10%, about 20%, about 30%, about 40%, about 50%, about 60%, about 70%, about 80%, about 90% of fructose by weight; (b) contacting the starting composition with any of the polypeptide disclosed herein or a microorganism expressing the polypeptide; and (c) producing a tagatose composition comprising tagatose. In some embodiments, the polypeptide is capable of converting fructose to tagatose through epimerization at the carbon-4 position of fructose.

In some embodiments, the tagatose composition comprises tagatose in an amount greater than about 0.1%, about 0.2%, about 0.3%, about 0.5%, about 1%, about 5%, about 10%, about 15%, about 20%, about 25%, about 30%, about 35%, or about 40% by weight. In some embodiments, the tagatose composition comprises tagatose in an amount between about 0.3-80 wt %. In some embodiments, the tagatose composition comprises tagatose in an amount between about 0.5-60 wt %. In some embodiments, the tagatose composition comprises tagatose in an amount between about 1-40 wt %.

In some embodiments, the starting composition comprises fructose in an amount between about 0.3% to about 70% by weight. In some embodiments, the starting composition comprises fructose in an amount between about 10% to about 60% by weight. In some embodiments, the starting composition comprises fructose in an amount between about 20% to about 60% by weight. In some embodiments, the starting composition comprises fructose in an amount between about 20% to about 40% by weight. In some embodiments, the starting composition comprises fructose in an amount between about 30% by weight.

In some embodiments, contacting fructose with the polypeptide or the microorganism expressing the polypeptide is performed at a temperature between about 40° C. and about 100° C. In some embodiments, contacting fructose with the polypeptide or the microorganism expressing the polypeptide is performed at a temperature between about 50° C. and about 90° C. In some embodiments, contacting fructose with the polypeptide or the microorganism expressing the polypeptide is performed at a temperature between about 60° C. and about 80° C. In some embodiments, the contacting of fructose with the polypeptide or the microorganism expressing the polypeptide is performed at a temperature of about 60° C.

In some embodiments, the contacting of fructose with the polypeptide or the microorganism expressing the polypeptide is performed at between about pH 4.5 and about pH 8. In some embodiments, the contacting of fructose with the polypeptide or the microorganism expressing the polypeptide is performed at about pH 7.5.

In some embodiments, the contacting of fructose with the polypeptide or the microorganism expressing the polypeptide is performed in the presence of a metal ion. In some embodiments, the metal ion is a divalent metal cation. In some embodiments, the metal ion is $Zn^{2+}$, $Co^{2+}$, or $Ni^{2+}$.

In some embodiments, the method disclosed herein is a batch process. In some embodiments, the method disclosed herein is a continuous process. In some embodiments, the continuous process uses a fixed bed or fluidized bed reactor.

In some embodiments, the tagatose product is separated from the feed stock (fructose, glucose, and/or sucrose, etc.) through chromatographic means. In some embodiments, the tagatose is isolated from the feed using a chromatographic method. In some embodiments, the chromatographic method is simulated moving bed chromatography.

In some embodiments, the isolated tagatose is further purified with crystallization. In some embodiments, evaporative crystallization is used to make crystalline tagatose. In some embodiments, the tagatose product is crystallized. In some embodiments, the evaporative crystallization process is isothermal, and in another embodiment evaporative cooling is used. In some embodiments, the crystallization is isothermal evaporative crystallization or evaporative cooling crystallization. In some embodiments, the fructose is produced from glucose or sucrose.

In some embodiments, the polypeptide or the microorganism expressing the polypeptide is immobilized to a carrier or support. In some embodiments, In some embodiments, the polypeptide or the microorganism expressing the polypeptide is immobilized to the carrier or support through adsorption, covalent attachment, non-covalent attachment, ionic interaction, entrapment, cross-linking, or metal-linking. In some embodiments, the carrier or support is an organic composition. In some embodiments, the organic composition is alginate, chitosan, chitin, collagen, carrageenan, gelatin, cellulose, starch, pectin, sepharose, polystyrene, styrene divinylbenzene, polyvinyl chloride, polyacrylate, polyamide, polypropylene, diethylaminoethyl cellulose (DEAE cellulose), UV-activated polyethylene glycerol, or methacrylate. In some embodiments, the organic composition is functionalized with a chemical group. In some embodiments, the chemical group is an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid.

In some embodiments, the carrier or support is an inorganic composition. In some embodiments, the inorganic composition is alumina, zeolite, ceramics, celite, glass, silica, activated carbon, or charcoal. In some embodiments, the polypeptide or the microorganism expressing the polypeptide is cross-linked by a cross-linking agent. In some embodiments, the cross-linking agent is glutaraldehyde.

In some embodiments, the fructose is produced from glucose or sucrose. As a result, the present disclosure can provide a method for producing tagatose in high yield using common and inexpensive raw materials such as glucose, fructose, sucrose, and the like, which enables mass production of tagatose.

Accordingly, the present disclosure may further include hydrolyzing sucrose or isomerizing glucose to produce fructose prior to reaction of fructose with the composition according to any one of embodiments of the present disclosure. Enzymes utilized in hydrolysis may be β-D-fructosidase including β-fructofuranosidase, invertase, saccharase, sucrase, α-glucosidase, or α-D-glucohydrolase, without being limited thereto. Examples of the enzyme isomerizing glucose may include glucose (xylose) isomerase and phosphoglucoisomerase, without being limited thereto.

EXAMPLES

The following working examples are illustrative and are not intended to be limiting, and it will be readily understood by one of skill in the art that other embodiments may be utilized.

Example 1 Preparation of Recombinant Microorganisms Producing D-Fructose 4-Epimerase (FC4E)

The genomes of thermophilic organisms were searched for enzymes with putative FC4E activity. Two protein scaffolds were identified, and polynucleotides encoding amino acid sequences SEQ ID NO:1 to SEQ ID NO:23 (Scaffold1) and SEQ ID NO:321 to SEQ ID NO:373 (Scaffold2) derived from 56 thermophilic microorganisms (Table 3) were synthesized (GenScript) and inserted into the pARZ4 expression vector, generating the corresponding recombinant vectors: pA06233, pA06234, pA06235, pA06236, pA06237, pA06238, pA06239, pA06240, pA06241, pA07068, pA07069, pA07070, pA07071, pA07072, pA07073, pA07074, pA07075, pA07076, pA07077, pA07078, pA07079, pA07080, pA07081, pA06242, pA06243, pA06246, pA06247, pA06248, pA06249, pA06250, pA06252, pA06253, pA06254, pA06255, pA06256, pA06257, pA06261, pA06265, pA06266, pA06267, pA06268, pA06270, pA06271, pA06272, pA06273, pA06274, pA07082, pA07083, pA07084, pA07085, pA07086, pA07087, pA07088, pA07089, pA07090, pA07091, pA07092, pA07094, pA07095, pA07096, pA07097, pA07098, pA07099, pA07100, pA07101. The recombinant vectors were used in a heat shock method to transform competent *E. coli* (NEBT7EL; New England Biolabs), thereby preparing recombinant microorganisms.

Each transformed recombinant microorganism was inoculated into 1 ml LB-kanamycin medium, cultured by shaking at 37° C. overnight. The culture was inoculated to 5 ml TB-kanamycin medium and grown for 2 hours at 37° C., followed by 25° C. for 1 hour. The culture was induced with 50 uL 50 mM IPTG and grown overnight. Finally, the culture was centrifuged at top-speed for 5-minutes and stored at −80° C.

The prepared *E. coli* recombinant microorganisms were named as NEBT7EL-pA06233, NEBT7EL-pA06234, NEBT7EL-pA06235, NEBT7EL-pA06236, NEBT7EL-pA06237, NEBT7EL-pA06238, NEBT7EL-pA06239, NEBT7EL-pA06240, NEBT7EL-pA06241, NEBT7EL-pA07068, NEBT7EL-pA07069, NEBT7EL-pA07070, NEBT7EL-pA07071, NEBT7EL-pA07072, NEBT7EL-pA07073, NEBT7EL-pA07074, NEBT7EL-pA07075, NEBT7EL-pA07076, NEBT7EL-pA07077, NEBT7EL-pA07078, NEBT7EL-pA07079, NEBT7EL-pA07080, NEBT7EL-pA07081, NEBT7EL-pA06242, NEBT7EL-pA06243, NEBT7EL-pA06246, NEBT7EL-pA06247, NEBT7EL-pA06248, NEBT7EL-pA06249, NEBT7EL-pA06250, NEBT7EL-pA06252, NEBT7EL-pA06253, NEBT7EL-pA06254, NEBT7EL-pA06255, NEBT7EL-pA06256, NEBT7EL-pA06257, NEBT7EL-pA06261, NEBT7EL-pA06265, NEBT7EL-pA06266, NEBT7EL-pA06267, NEBT7EL-pA06268, NEBT7EL-pA06270, NEBT7EL-pA06271, NEBT7EL-pA06272, NEBT7EL-pA06273, NEBT7EL-pA06274, NEBT7EL-pA07082, NEBT7EL-pA07083, NEBT7EL-pA07084, NEBT7EL-pA07085, NEBT7EL-pA07086, NEBT7EL-pA07087, NEBT7EL-pA07088, NEBT7EL-pA07089, NEBT7EL-pA07090, NEBT7EL-pA07091, NEBT7EL-pA07092, NEBT7EL-pA07094, NEBT7EL-pA07095, NEBT7EL-pA07096, NEBT7EL-pA07097, NEBT7EL-pA07098, NEBT7EL-pA07099, NEBT7EL-pA07100, and NEBT7EL-pA07101.

Example 2 Purification and Measurement of D-Fructose 4-Epimerase Activity 2-1. Purification of D-Fructose 4-Epimerase The 76 microorganisms expressing D-fructose C4-epimerases created in Example 1 were dissolved in lysis buffer (lysozyme, DNAseI, Bugbuster, 300 mL 20 mM $PO_4$ pH 7.5, 500 mM NaCl, and 20 mM Imidazole). Two to three glass beads were added to each well and were disrupted by shaking at 25° C. and 220 rpm for 30 minutes. The disrupted liquid was centrifuged at 2200×g for 6-10 minutes. The obtained supernatant was loaded onto a Ni-NTA plate and shaken for 10 minutes at room temperature. The plate was centrifuged for 4 minutes at 100× g followed by two washes of 500 uL binding buffer (300 mL 20 mM $PO_4$ pH 7.5, 500 mM NaCl, 20 mM Imidazole) and two minute centrifugation (500×g). The proteins were eluted with 150 uL elution buffer (15 mL 20 mM $PO_4$ pH 7.5.5, 500 mM NaCl, 500 mM Imidazole) and shaken for 1 minute at 0.25 maximum shaking speed followed by centrifugation for 2 minutes at 500× g. The recovered protein was desalted into a buffer solution for enzyme activity evaluation (Scaffold1: 20 mM $KPO_4$, 50 mM NaCl, 300 uM $CoCl_2$, pH 7.5; Scaffold2: 20 mM $KPO_4$, 50 mM NaCl, 300 uM $NiCl_2$, pH 7.5).

2-2. Measurement of D-Fructose 4-Epimerase Activity

In order to identify the activity of the 76 D-fructose C4-epimerases purified in Example 2-1, the enzymes were reacted with fructose substrate at 60° C. The reaction was started by reacting 20 mM fructose with purified enzyme in buffer (Scaffold1: 20 mM $KPO_4$, 50 mM NaCl, 300 uM $CoCl_2$, pH 7.5; Scaffold2: 20 mM $KPO_4$, 50 mM NaCl, 300 uM $NiCl_2$, pH 7.5) and allowed to react overnight, followed by quenching the reaction product by placing the reaction at −80° C.

All monosaccharides were analyzed using an Agilent 6545 q-tof run in negative/high sensitivity mode. Sugars were separated using a Varian Hi-plex Pb++ column (100 mm×7.7 mm). A 4:1 mixture of methanol and chloroform was added to the reference mix to induce the formation of Cl+ adducts. Quantification was performed on the (M+Cl)- adduct of 215.0320 m/z. Standards of fructose and tagatose were purchased from Sigma Aldrich and calibration was performed from 1 to 1000 ppM.

Figure 2:
FIG. 2 depicts the measured fructose to tagatose yield for fifty-three thermophilic D-fructose C4-epimerases (Scaffold2). The FC4Es were reacted with 20 mM fructose at 60° C. overnight.
Figure 3:
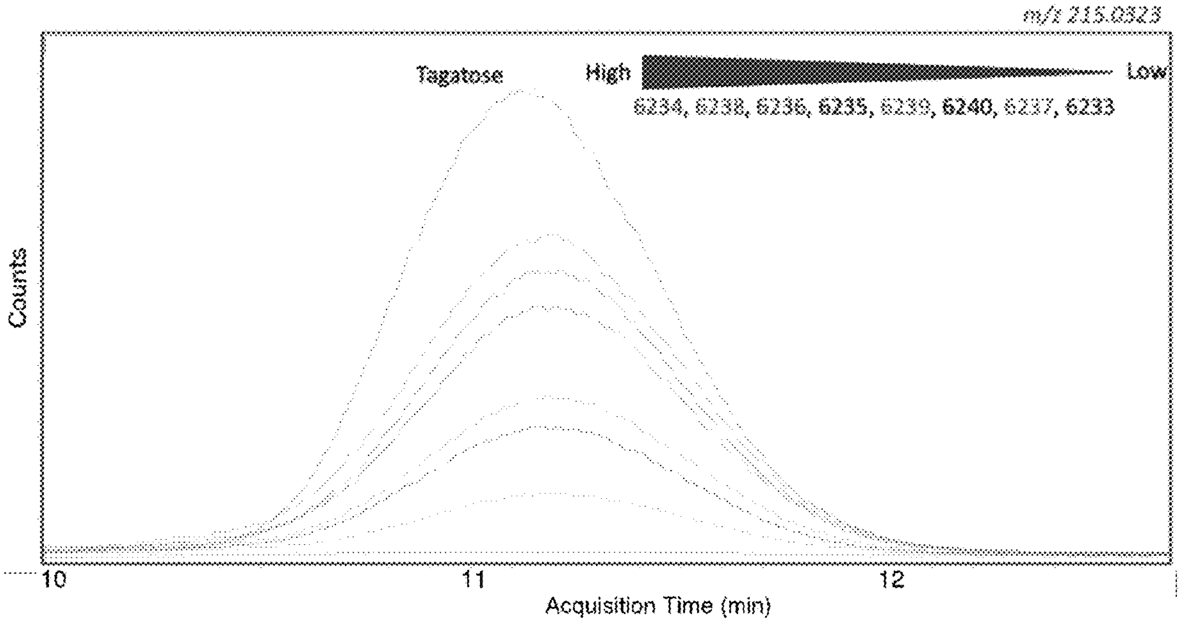
FIG. 3 depicts measured Q-tof traces of the conversion of fructose (20 mM) to tagatose for 8 of the thermophilic D-fructose C4-epimerases (Scaffold 1).
Figure 4:
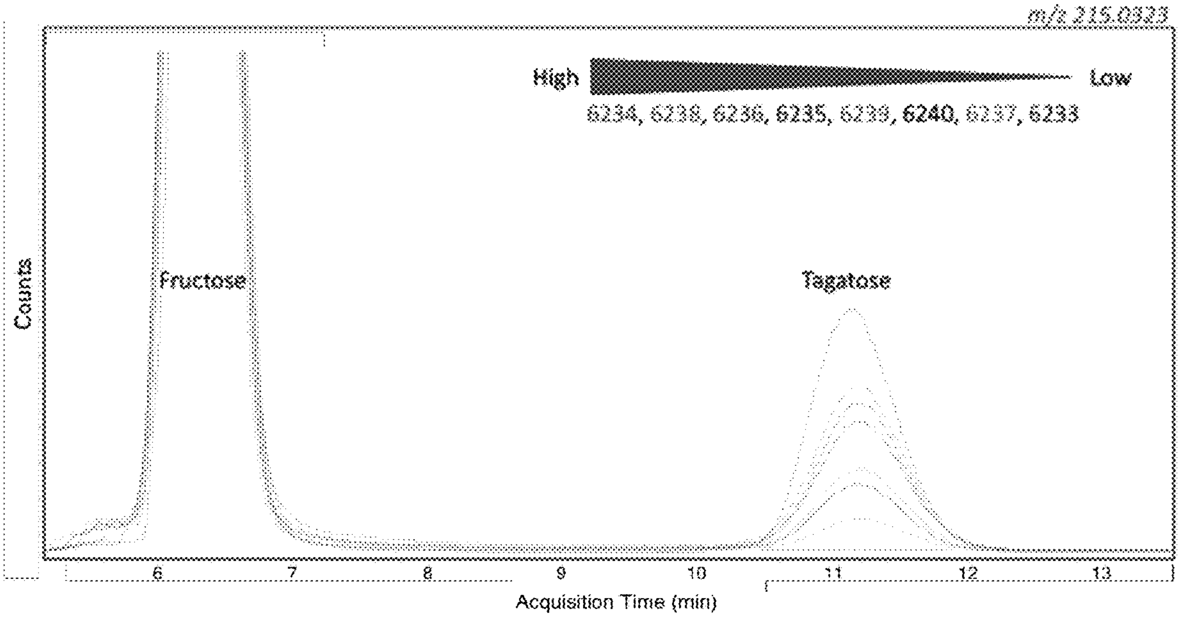
FIG. 4 depicts measured Q-tof traces of the conversion of fructose (20 mM) to tagatose for 8 of the thermophilic D-fructose C4-epimerases (Scaffold 1).

The D-fructose C4-epimerases successfully produced tagatose from fructose. The relative conversion rates are shown in FIG. 1 (Scaffold1) and FIG. 2 (Scaffold2). Specific Q-tof traces for a subset of the FC4Es are shown in FIG. 3 and FIG. 4.

2-3. Activity Analysis of Alternate Metal Ions

Figure 5:
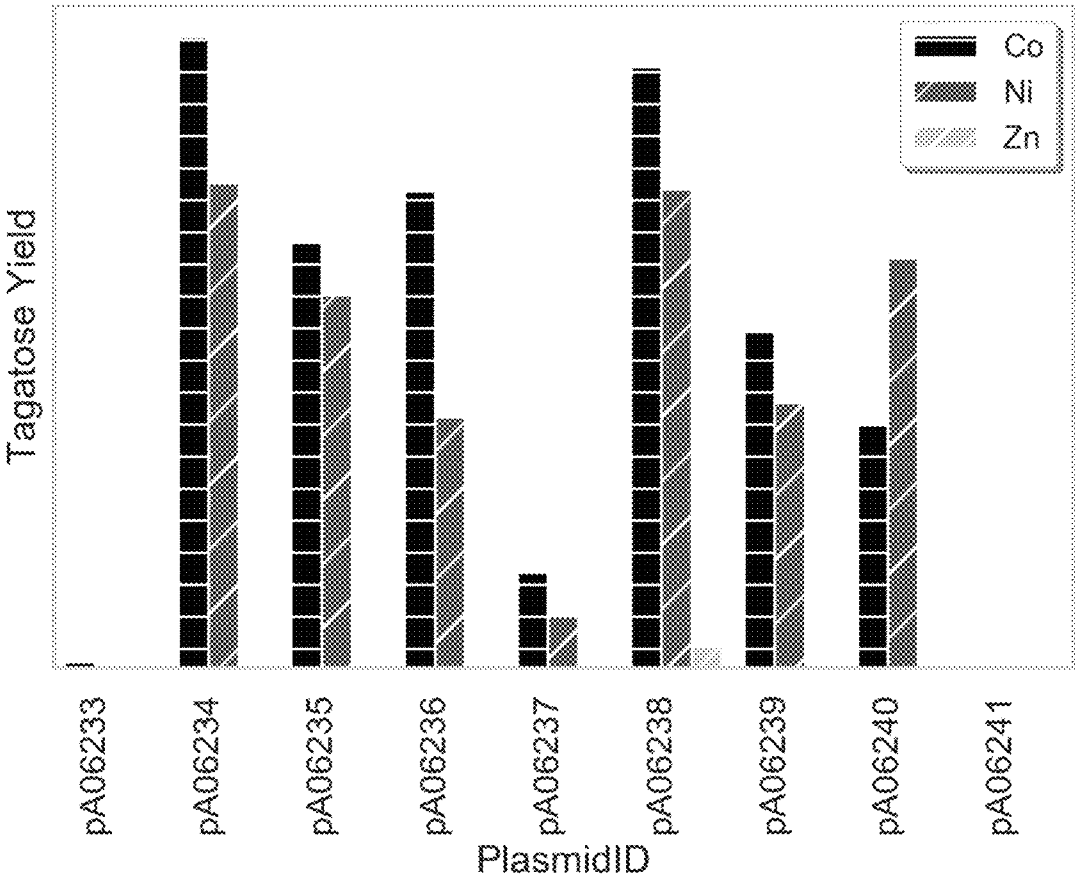
FIG. 5 depicts the impact of metal salt on measured tagatose yield from fructose for 9 FC4Es.

In order to determine the dependence of epimerase activity on metal salt type, a subset of the Scaffold1 purified enzymes from Example 2-1 were tested for activity with alternative metal salts: 0.3 mM $NiCl_2$ and 0.3 mM $ZnCl_2$ (FIG. 5). All conditions were the same as in Example 2-2 except $CoCl_2$ was substituted with an alternate metal salt.

Example 3 Activity of D-Fructose 4-Epimerases in High Sugar

Figure 6:
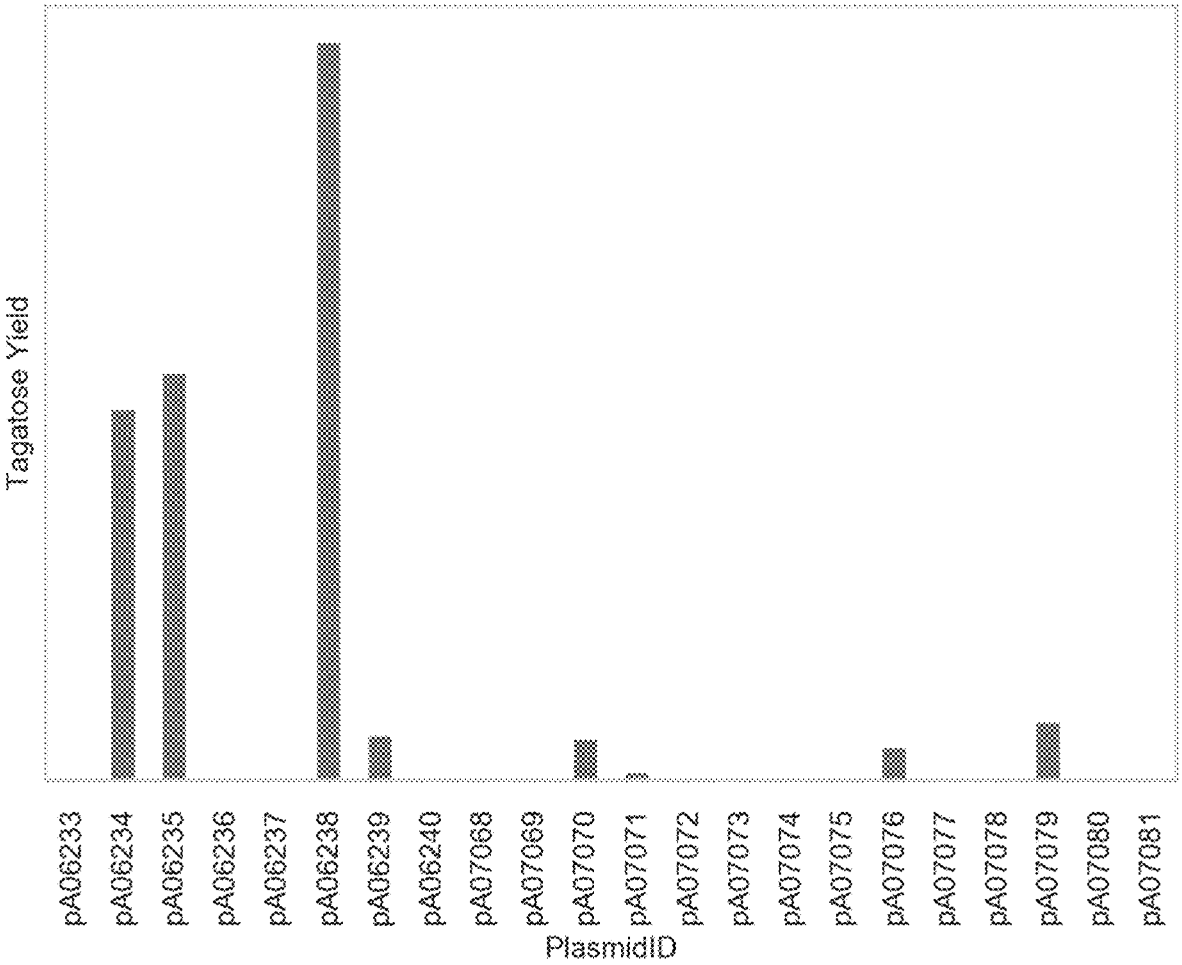
FIG. 6 depicts the relative fructose to tagatose yield when a high concentration of fructose substrate (1M) was used in the reaction.

In Example 2-2, the putative D-fructose C4-epimerases were screened at a low sugar concentration to determine if any activity was present. However, an industrially useful enzyme should be active at higher substrate concentrations. Therefore, the FC4Es were challenged with 1 M fructose. The experiments were conducted similarly to those in Example 2-2, except 1 M fructose was used as substrate and the reaction was limited to 20 minutes instead of overnight. Several FC4Es showed activity in these more challenging conditions (FIG. 6).

Example 4 Heat Stability of D-Fructose 4-Epimerases

Figure 7:
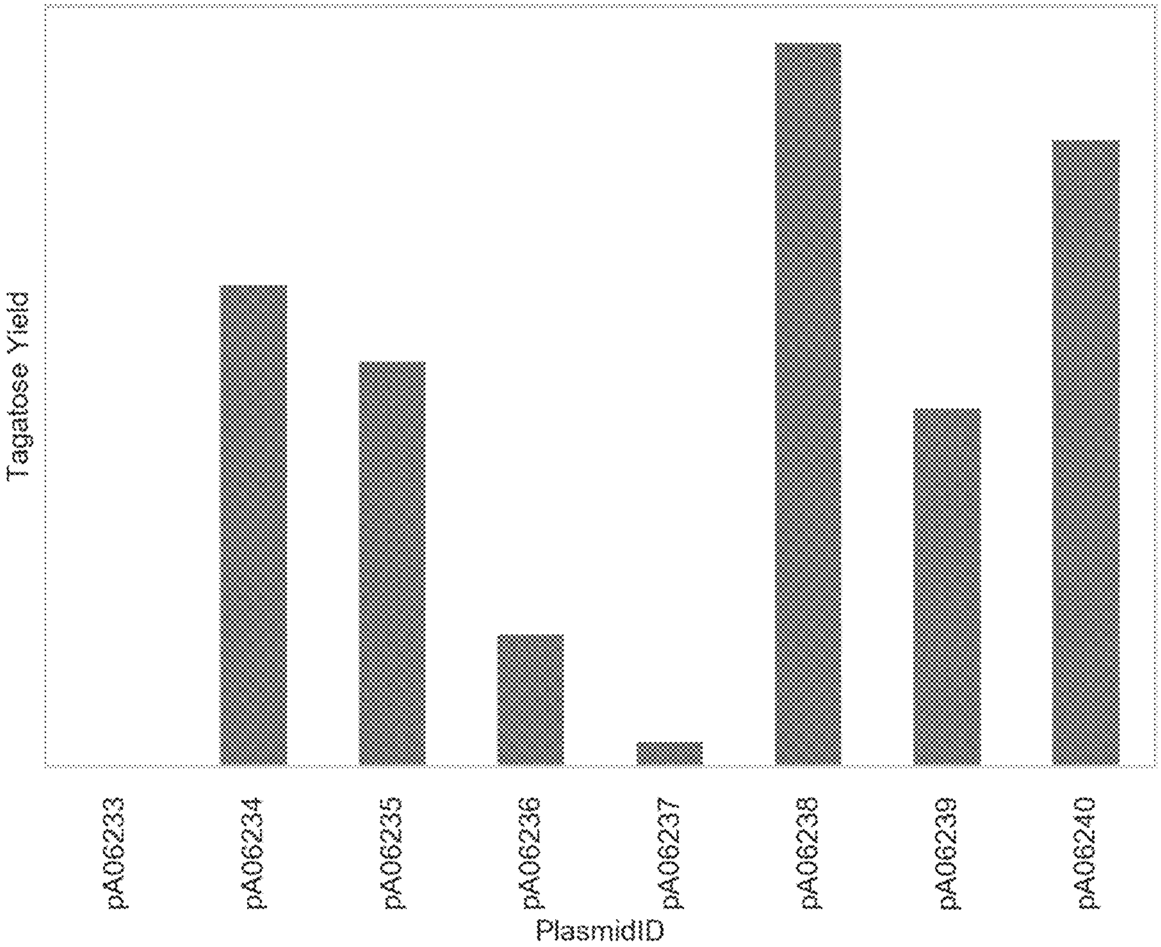
FIG. 7 depicts the relative fructose to tagatose yield for 8 FC4Es after the FC4Es were incubated at 60° C. for 24 hours prior to reacting with fructose.

Eight FC4Es pA06233-pA06240 were tested for heat stability. Enzymes were expressed and purified similar to Example 2-1. The FC4Es were incubated at 60° C. for 24 hours and then each enzyme was reacted with fructose (final concentration of 0.57M) for 20 minutes at 60° C. The conversion of fructose to tagatose was measured as described in Example 2-2. The relative tagatose yield for the enzymes can be seen in FIG. 7.

Example 5 Characterization of Top D-Fructose 4-Epimerases

Figure 8:
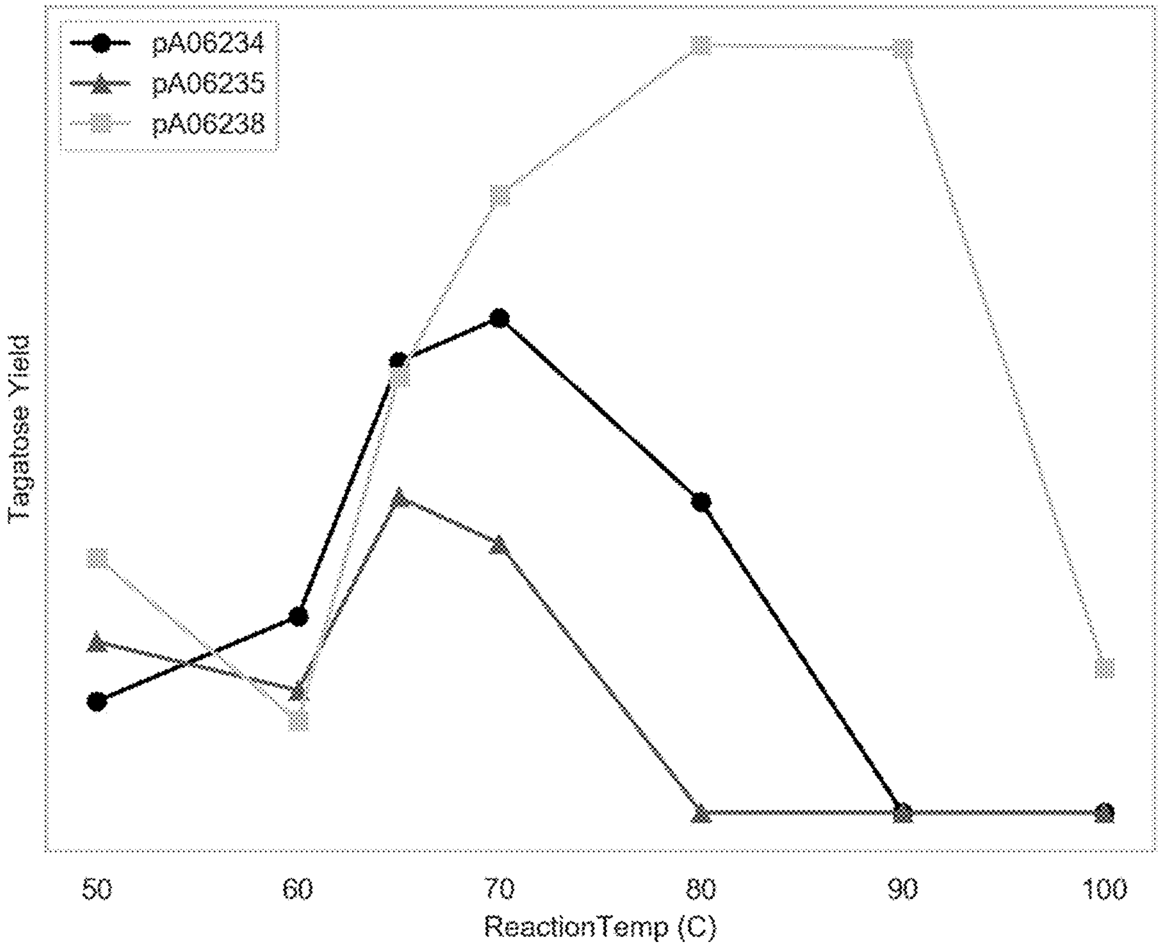
FIG. 8 depicts the impact of temperature on tagatose yield for 3 FC4Es.

Top FC4Es were further characterized to determine how their activity varied with temperature, sugar concentration, reaction time, and protein concentration. To determine the temperature optimum, enzymes pA06234, pA06235, pA06238 were purified as in Example 2-1 and reacted with 1.9 M sugar for 20 minutes in buffer (20 mM $KPO_4$, 50 mM NaCl, 300 uM $CoCl_2$, pH 7.5) at the following temperatures: 50° C., 60° C., 65° C., 70° C., 80° C., 90° C. and 100° C. The conversion of fructose to tagatose was measured the same as Example 2-2. The relative yield of tagatose over the measured temperature range is shown in FIG. 8.

Figure 9:
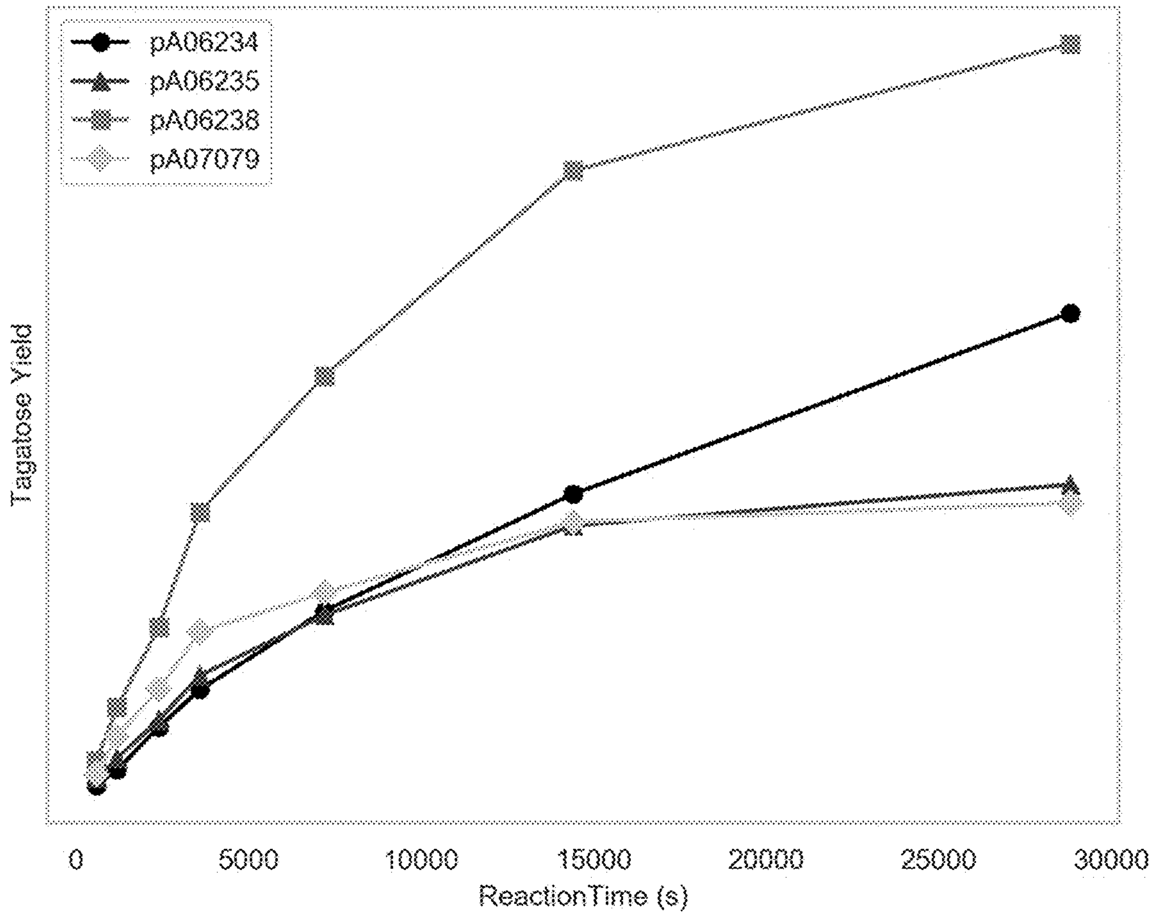
FIG. 9 depicts the fructose to tagatose yield over time for 4 FC4Es.

Next, the conversion of fructose over time was measured for FC4Es pA06234, pA06235, pA06238 and pA07079. Purified protein was obtained as in Example 2-1. FC4E was reacted with 1.9 M fructose in 20 mM $KPO_4$, 50 mM NaCl, 300 uM $CoCl_2$, pH 7.5 for 0-24 hours at 60° C. The conversion of fructose to tagatose was measured as in Example 2-2. The relative yield for the measured reaction times is shown in FIG. 9.

Figure 10:
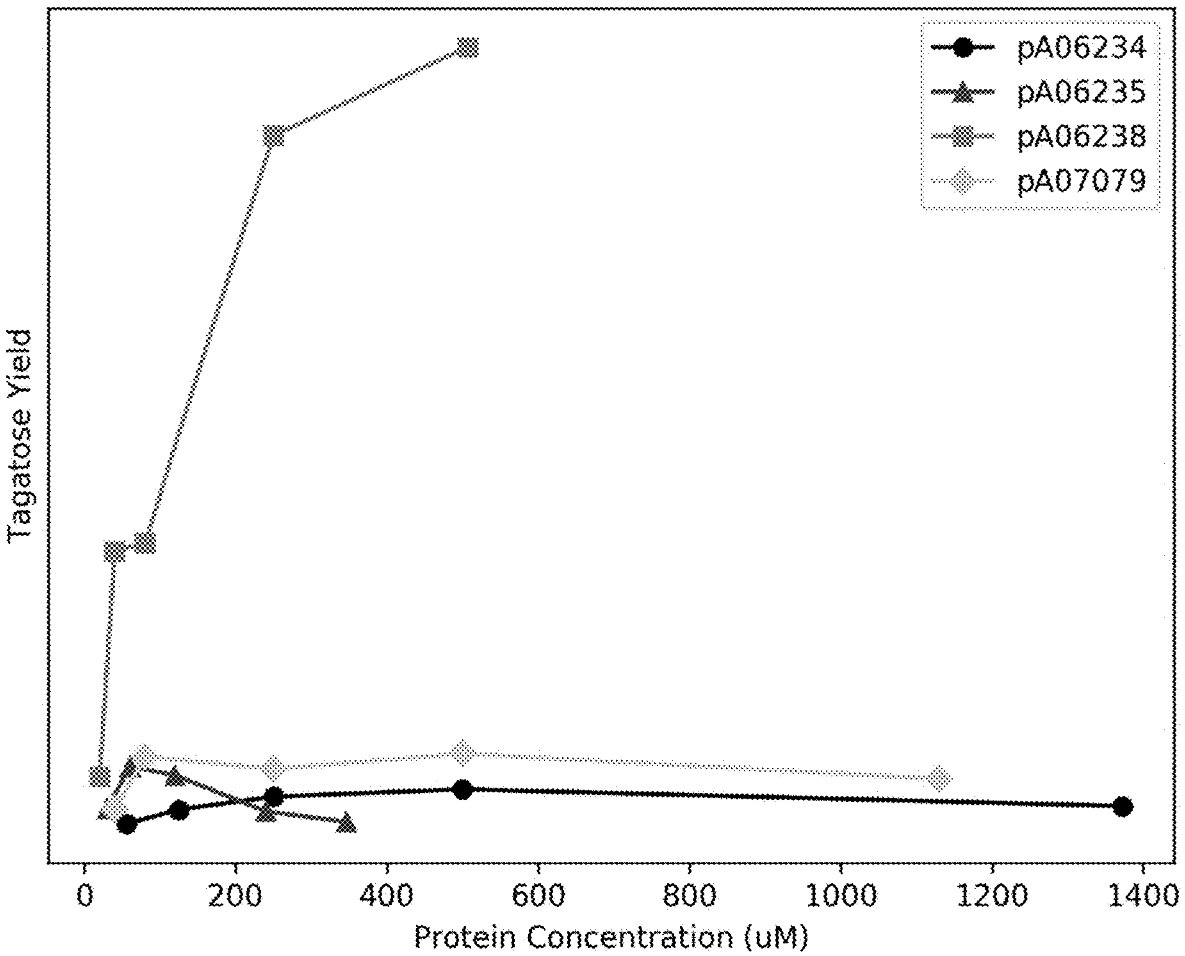
FIG. 10 depicts the effect of protein concentration on tagatose yield for 4 FC4Es.

The effect of protein concentration was determined for FC4Es pA06234, pA06235, pA06238 and pA07079. Purified protein was obtained as in Example 2-1. The protein was then concentrated using Vivaspin 6, 5 kDa molecular weight protein concentrators. Five different dilutions of each FC4E was reacted with 1.9 M fructose in 20 mM $KPO_4$, 50 mM NaCl, 300 uM $CoCl_2$, pH 7.5 at 60° C. for 20 minutes. The conversion of fructose to tagatose was measured as in Example 2-2. The relative yield for the different protein concentrations is shown in FIG. 10.

Figure 11:
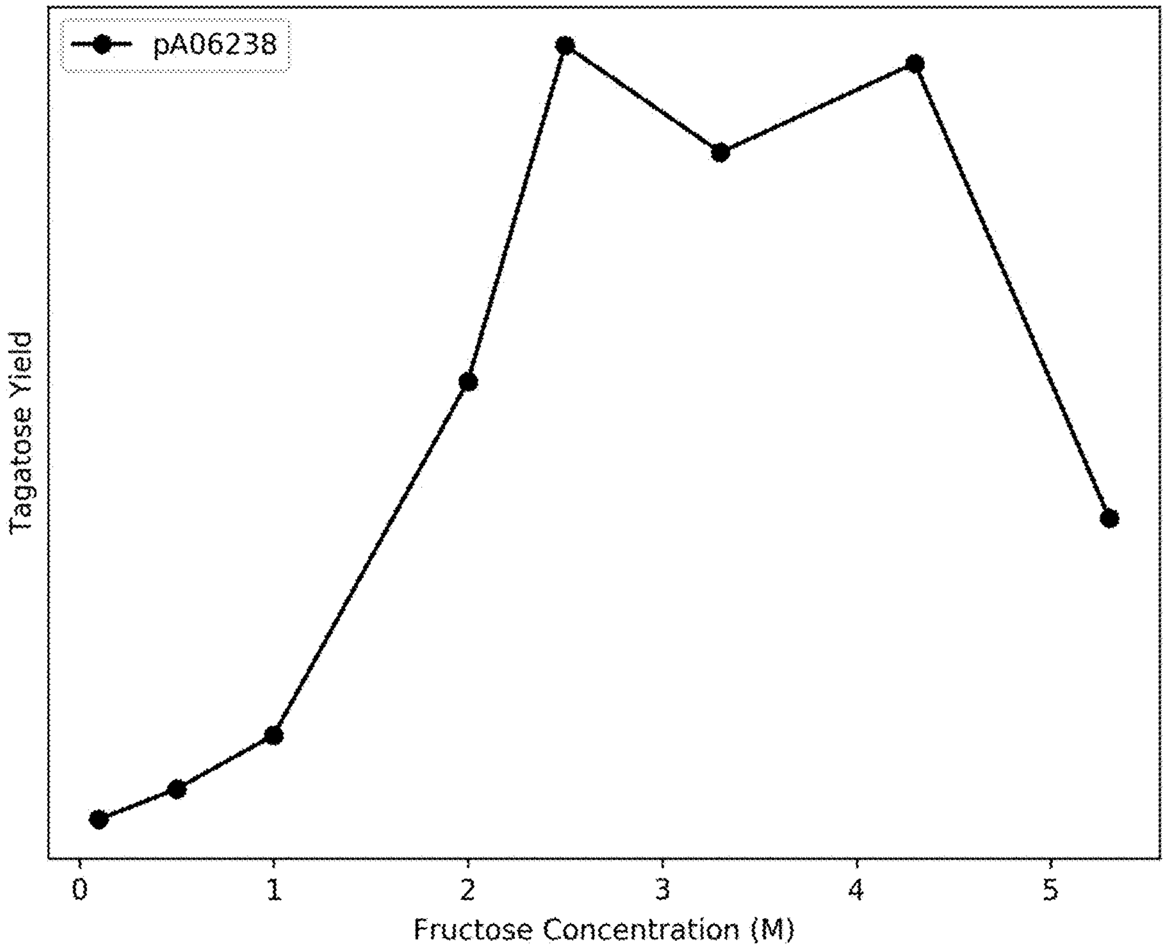
FIG. 11 depicts the impact of fructose concentration on tagatose yield for the FC4E, pA06238.

The effect of substrate concentration on fructose to tagatose conversion was measured for pA06238. Purified protein was obtained as in Example 2-1. pA06238 was reacted with 50 mM-2.8 M fructose in 20 mM $KPO_4$, 50 mM NaCl, 300 uM CoCl2, pH 7.5 for 20 minutes at 60° C. The conversion of fructose to tagatose was measured as in Example 2-2. The relative tagatose yield for the tested sugar concentrations is shown in FIG. 11.

Example 6 Thermostability of pA06238

Figure 12:
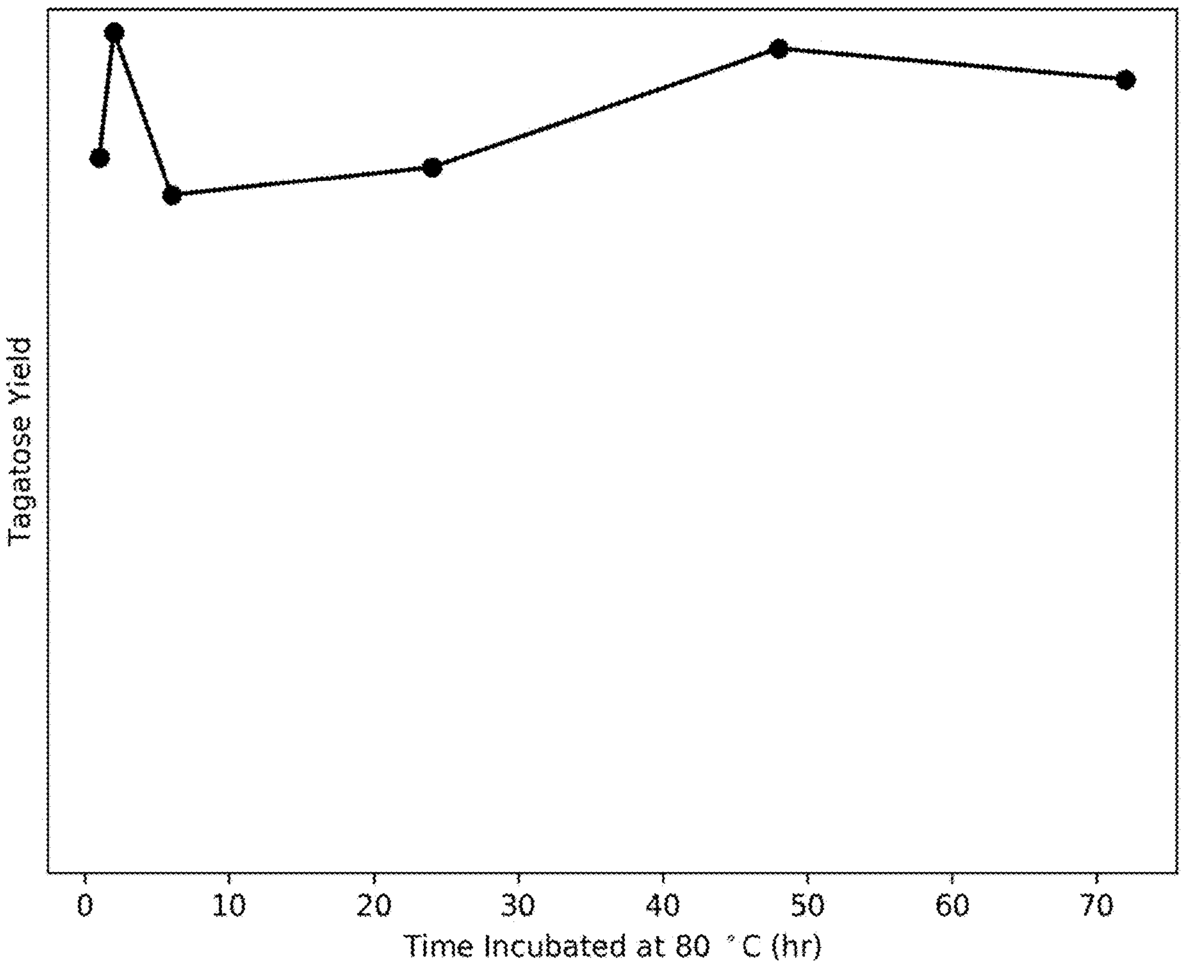
FIG. 12 depicts the effect of preincubating pA06238 at 80° C. for different amounts of time on tagatose yield.

An industrially useful enzyme will likely need to operate at sustained elevated temperatures. Example 4 demonstrates that pA06238 is stable when incubated at 60° C. for a day. To further investigate the thermostability of pA06238, the lifetime of pA06238 at 80° C. was investigated. Purified protein was obtained as in Example 2-1. pA06238 was incubated at 80° C. for 0-72 hours. Following incubation, the enzyme was reacted with 1.9 M fructose in 20 mM $KPO_4$, 50 mM NaCl, 300 uM $CoCl_2$, pH 7.5 for 20 minutes at 60° C. The conversion of fructose to tagatose was measured as in Example 2-2. The relative tagatose yield for the tested sugar concentrations is shown in FIG. 12. After 3 days incubation, there was not a statistically significant loss of activity compared to the early timepoints.

Example 7 Improved Expression of pA06238 Through Coding Sequence Optimization

Figure 13:
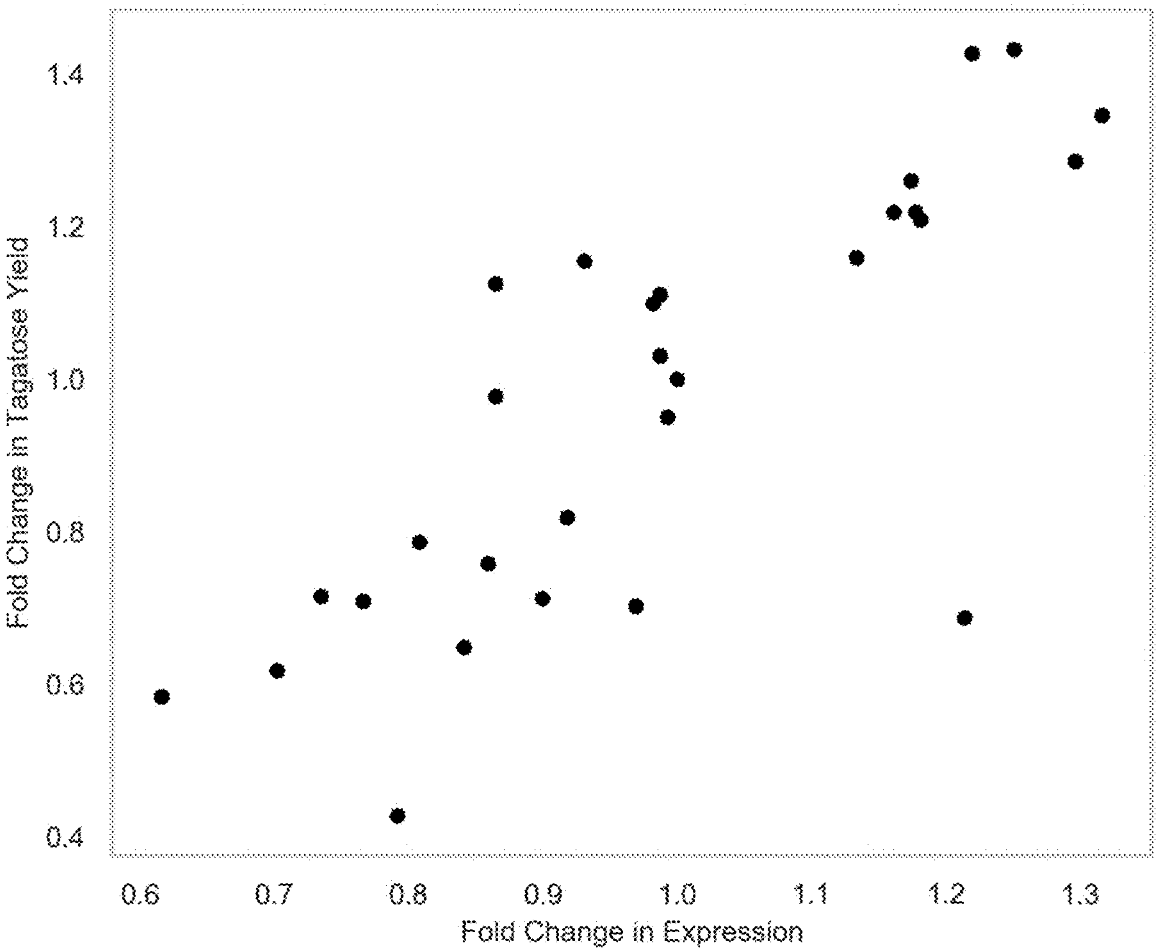
FIG. 13 depicts the fold change in expression and activity for 30 DNA optimized variants of pA06238.

We used our in-house DNA optimization software, Scribe™, to improve expression of pA06238. Thirty optimized polynucleotide sequences that code for the pA06238 amino acid sequence inserted in the pARZ4 expression vector were ordered from Twist Bioscience. The plasmids were transformed into NEBT7EL and the FC4Es were expressed and purified as in Example 2-1. Purified enzyme was reacted in buffer (20 mM $KPO_4$, 50 mM NaCl, 300 uM $CoCl_2$, pH 7.5) with 1.9 M fructose at 60° C. for 24 hours. To detect the formation of tagatose, reaction assays were diluted 20-fold with water. Plates were sealed and placed into a Waters AQUITY-H UPLC system consisting of an FTN samples manager, RI and UV detector. Separation of tagatose from fructose was conducted on an Agilent Hi-plex Pb 150×4.0 mm column (p/n PL1115-9999) with 100% water at 85° C. at a flow rate of 0.45 ml/min. Quantification was done using the RI detector channel. The purified protein yield and corresponding enzyme activity for the 30 optimized polynucleotide sequences compared to the parent pA06238 (square) is shown in FIG. 13. The most improved variant improved expression by 1.32-fold with a corresponding 1.35 fold improvement in tagatose yield.

Example 8 Immobilization of pA06238 on Commercially Available Supports 8-1. Enzyme Immobilization Resins The FC4E pA06238 enables a one-step enzymatic process to convert fructose to tagatose. An example biocatalytic process for making tagatose from fructose involves the use of immobilized FC4E in a fixed bed reactor or fluidized bed reactor. We successfully demonstrated the immobilization of pA06238 on several commercially available supports.

Enzyme immobilization resins were purchased from Chiralvision (IB-ADS-1, IB-ADS-2, IB-ADS-3, IB-ADS-4, IB-ANI-1, IB-ANI-2, IB-ANI-3, IB-ANI-4, IB-CAT-1, IB-COV-1, IB-COV-2, IB-COV-3) and Purolite (ECR1030M, ECR1090F, ECR1504, ECR1640, ECR8204F, ECR8209F, ECR8285, ECR8309F, ECR8409F, ECR8806F). These resins vary in composition (methacrylate, styrene or polyacrylic) as well as functional group (epoxy, amino, octadecyl, tertiary amine, quaternary amine, carboxylic ester, phenyl, sulphonic, or no functional group).

Figure 14:
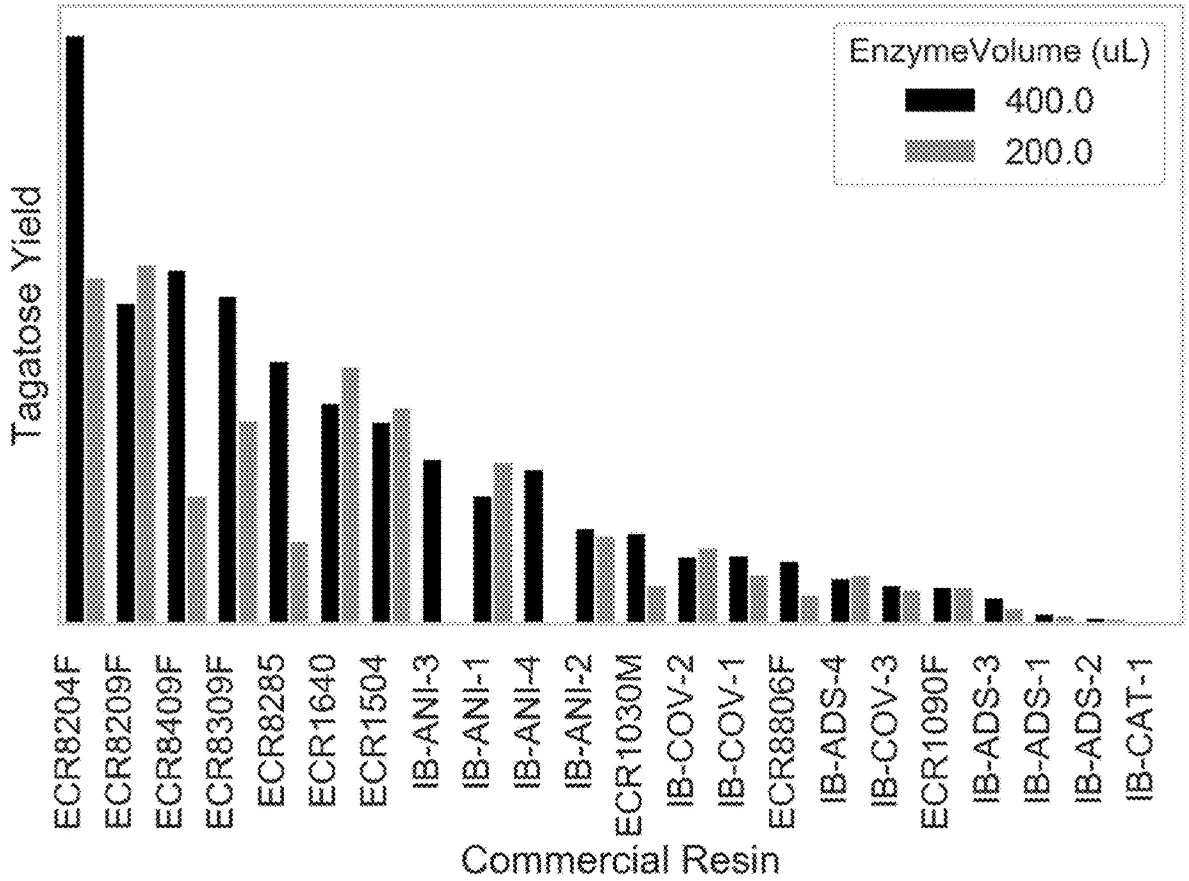
FIG. 14 depicts the fructose to tagatose yield of pA06238 immobilized on 22 commercially available resins.

The standard protocol for each resin from each company was used to immobilize pA06238 onto 100 mg resin. Two different volumes of enzyme (400 uL and 200 uL) were incubated with resin at room temperature to immobilize the enzyme onto the support. After incubation, the immobilized enzyme was washed five times with either water (Chiralvision) or buffer (Purolite). The immobilized enzyme was reacted with 1 M fructose in buffer at 60° C. for 20 minutes. The relative activity obtained for each support is shown in FIG. 14.

8-2. Metal Chelating Resins

Since pA06238 contains a hexahistidine tag, the enzyme should immobilize onto loaded metal chelating resins through a metal-hexahistidine tag interaction. The following commercial metal chelating resins were obtained to test enzyme immobilization: Ni-NTA agarose (Qiagen), Nuvia IMAC (Bio-Rad), S930 plus (Purolite), S940 (Purolite), S950 (Purolite), Lewatit MDS TP 208 (Lanxess), Lewatit MDS TP 260 (Lanxess), Lewatit MDS TP 260 (Lanxess), Relite MAC5 (Mitsubishi), Relite MACi (Mitsubishi), DIAION CR11 (Mitsubishi), DIAION CR20 (Mitsubishi), Amberlite IRC748 (Dow), and Amberlite IRC747 (Dow). The metal chelating resins utilize one of the following functional groups for metal binding: nitrilotriacetic acid (NTA), iminodiacetic acid (IDA), aminophosphonic acid (AMPA), polyamine, or carboxylic acid. The NTA resins were pre-loaded with nickel. For the remaining resins, copper was loaded onto the resin by incubating 100 mg of resin with 400 μL of 200 mM $CuSO_4$ followed by washing with 100 mM sodium acetate. To immobilize pA06238, all resins were washed with buffer (20 mM $KPO_4$, 50 mM NaCl, 300 uM $CoCl_2$, pH 7.5) and 8 mg of protein was incubated with 100 mg for 18 hours with mixing and let stand for 20 hours at room temperature. Immobilized enzyme was washed with buffer to remove unbound protein, and then assayed for fructose to tagatose conversion by reacting with 1 M fructose for 20 minutes at 60° C. Four metal chelating resins had detectable activity, but all were lower than the best enzyme immobilization resins from Example 8-1 (Table 4).

TABLE 4

Relative activity of pA06238 immobilized on metal chelating resins compared to ECR8204F

| Resin | Percent of ECR8204F Yield |
|---|---|
| Qiagen Ni-NTA | 18.1% |
| Nuvia IMAC | 16.0% |
| Amberlite IRC747 | 6.7% |
| DIAION CR20 | 5.6% |

Example 9 Conversion of Fructose to Tagatose in a Fixed Bed Reactor

NEBT7EL-pA06238 was grown on LB with 50 μg/ml kanamycin. A 600 ml culture of $TB_{kan50}$ was inoculated with NEBT7EL-pA06238 and incubated overnight at 37° C. at 200 rpm. The next morning, a 10 L fermentor was prepared with 9.5 L of TB and then inoculated with 500 ml of the overnight culture. The culture was grown at 37° C. The pH was maintained at 6.2 with NaOH and the $dO_2$ was maintained ≥20%. After 2 hours of growth, the temperature was dropped to 25° C. The culture was grown for an additional 1 hour with the $OD_{600}$ around 7. IPTG was added to a final concentration of 1 mM and $CoCl_2$ was added to 25 μM. Additional $CoCl_2$ was added 1 and 2 hours after induction to bring the final concentration to 300 μM. The cells were grown for 20 hours at which point the fermentor was chilled to 10° C. and the cells were harvested by centrifugation. The cell pellet was stored at −80° C. until use.

The cell pellet from the fermentation was lysed by stirring in buffer with lysozyme and DNAse. Cell debris was removed by centrifugation and the supernatant was filtered through a 0.45 micron filter. Filtered supernatant was incubated with Ni-NTA agarose resin and then enzyme was eluted with imidazole. Purified FC4E pA06238 was immobilized onto 5.25 grams of ECR8204F resin using the standard published protocol from Purolite.

Figure 15:
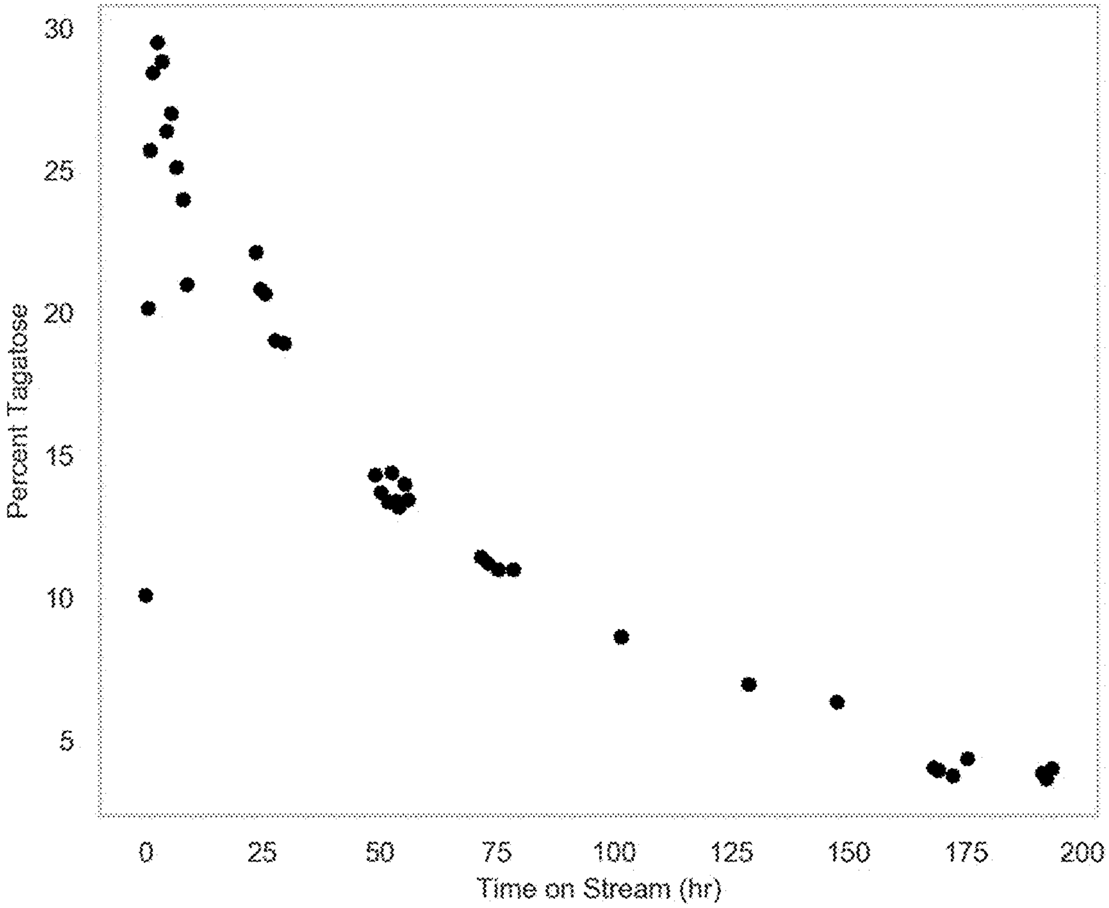
FIG. 15 depicts the percent tagatose converted from fructose over time from a fixed bed reactor packed with immobilized pA06238.

The immobilized enzyme was loaded into a 11×300 mm glass fixed bed reactor and run for approximately 200 h at constant temperature (60° C.) with a constant feed composition of 30 wt % fructose+70 wt % aqueous buffer solution (20 mM $KPO_4$, 50 mM NaCl, 300 uM $CoCl_2$). Feed rate was held constant at 140 uL/min throughout the run. The fixed bed reaction reached a maximal conversion of approximately 30% tagatose and had a half-life of −50 hours (FIG. 15).

Example 10 Simulated Moving Bed Separation of Tagatose From a Mixed Sugar Solution Eight 25 mm×300 mm glass, jacketed chromatography columns were loaded with Dowex™ monosphere 99 Ca/320 resin and connected to a temperature control system including a recirculating hot water system (Polyscience, AP20S150-A11B) and electrical heat-loss compensation capable of temperature control to within ±1° C. The columns were plumbed in a 3-zone simulated moving bed configuration using a Semba Biosciences Octave chromatography system (SMB unit). A degassed feed sugar solution of 10 wt % tagatose, 20 wt/o fructose and 70 wt % purified water was metered into the SMB unit via a dual-piston positive displacement pump (Octave 100) including pre- and post-filters and pulse-dampening to ensure smooth continuous flow at specified volumetric flow rates. The eluent feed to the system was a degassed purified water solution, similarly, fed to the SMB unit using a larger dual-piston positive displacement pump (Octave 300) including pre- and post-filters and pulse-dampening. At steady-state, a smaller extract stream was continuously withdrawn from the unit using a third dual-piston positive displacement pump (Octave 100), while the larger raffinate stream flowed from the unit via a back-pressure control valve. Product rates were monitored intermittently by manual volumetric measurement.

A range of experiments were performed to demonstrate purification of tagatose in the extract stream. In Condition 1 the SMB separation was performed on 1 L of the degassed sugar feed solution, collecting 3.6 L of extract and 12.2 L of raffinate over 24 h. Table 5 shows that a highly purified tagatose stream can be collected using SMB separation.

TABLE 5

Measured concentrations of tagatose and fructose during SMB Condition 1.

| | Tagatose concentration, g/L | Fructose Concentration, g/L |
|---|---|---|
| Extract Stream | 33.35 | 0.25 |
| Raffinate Stream | 1.87 | 31.30 |

Example 11 Isothermal Batch Crystallization of Tagatose From a Mixed Sugar Solution A mixed sugar solution comprising 200 g tagatose, and 50 g fructose was solvated in 120 g water by gently heating the solution with rotary agitation using a rotary evaporator (Eyela, N-1200BS) to a temperature of 60° C. Isothermal batch crystallization was performed by pulling vacuum of the evaporation flask to a constant pressure of 100 mmHg, then slowly evaporating water from the flask under constant vacuum over a 270 min period. Once 20 ml of condensate had been collected, the experiment was paused briefly, 0.25 g of pure tagatose seed crystals were added to the flask, and then vacuum conditions were restored, and the evaporation was continued. Slow crystallization was observed. The experiment was continued until 80 ml condensate had been collected, after which the flask was quickly disconnected from the rotary evaporator and the slurry of mother liquor and crystals was quickly filtered via a Buchner funnel fitted with a cellulose filter. The collected crystals were washed with 62.5 g of ice-cold water, then dried under vacuum at 60° C. for 2 h. The final tagatose crystals contained 98.51 wt % tagatose and 1.49 wt % fructose, a significant improvement versus the feed mixture.

Example 12 Active Site Mutants Improve FC4E Activity 12-1. Active Site Mutants of pA06234

Active site mutants of pA06234 were generated to determine the impact of these residues on catalysis. For each mutant, primer pairs were designed to 1) open the parent CDS at the desired insertion point (omitting the codon intended to be replaced) and 2) split the plasmid backbone within the antibiotic selection marker. Polymerase chain reaction (PCR) then successfully generated two linear fragments from each plasmid. The new, desired codon was embedded in the forward primer of the first PCR. Primers were designed to also include flanking homology. Subsequent two-way flanking homology-based DNA assembly produced plasmids used to transform our standard cloning strain. After confirming DNA sequence by Sanger sequencing, sequence-perfect plasmids were used to transform NEBT7EL.

Figure 16:
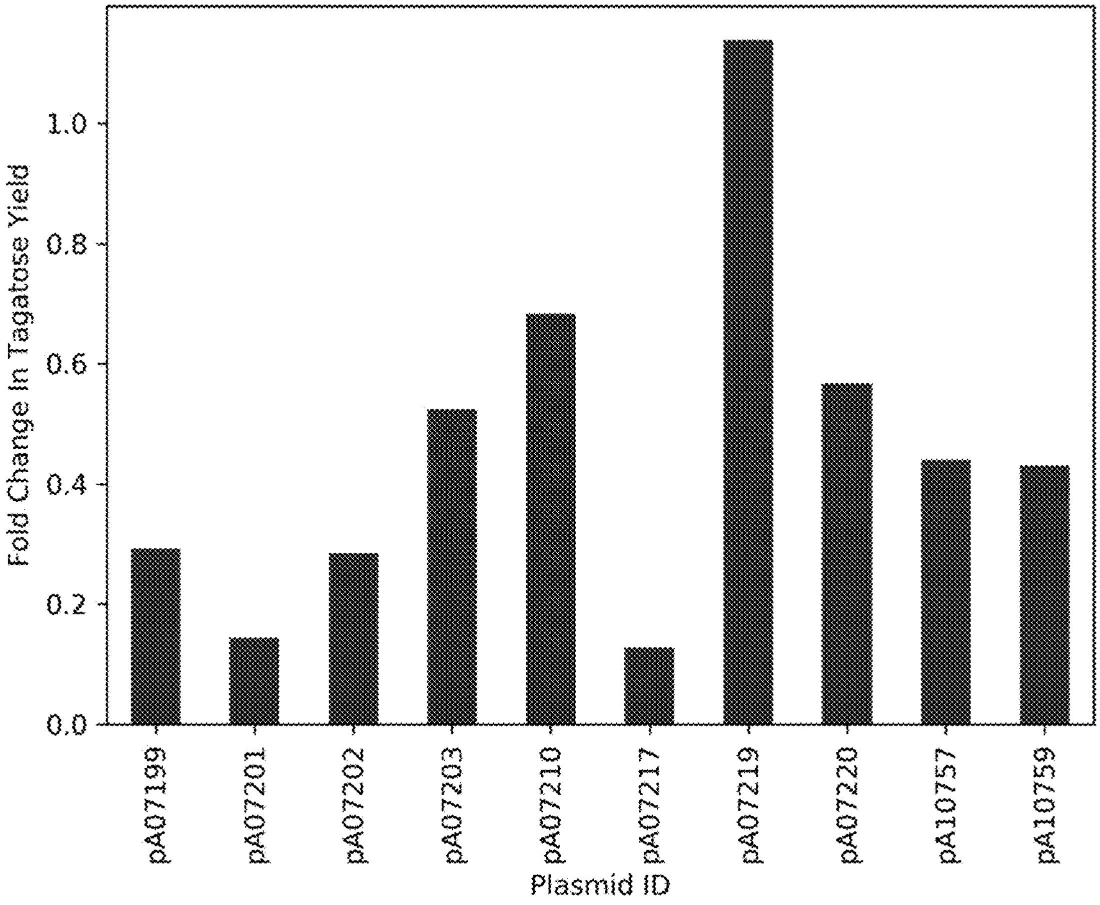
FIG. 16 depicts the fold change in fructose to tagatose conversion for active site mutants of pA06234.

FC4E active site mutants (SEQ ID NOs: 24-45) were expressed and purified as in Example 2-1. Purified enzyme was reacted with 1.9 M fructose in buffer (20 mM $KPO_4$, 50 mM NaCl, 300 uM $CoCl_2$) overnight at 60° C. Conversion of fructose to tagatose was measured as in Example 2-2 (FIG. 16). Promising active site mutants with tagatose conversion similar to or better than the parent were further investigated by reacting with fructose for 20 minutes. Four mutants with increased activity compared to the parent enzyme (pA06234) are shown in Table 6.

TABLE 6

| Plasmid ID | Mutation | Fold Increase in Tagatose Yield |
|---|---|---|
| pA07219 | Y361A | 2.14 |
| pA07210 | E178A | 2.14 |
| pA07203 | Y64F | 1.40 |
| pA07202 | Y64A | 1.18 |

12-2. Transferring pA06234 Active Site Mutations into pA06238

The native FC4Es (SEQ ID NOs: 1-23, 321-373) are sufficiently similar (FIG. 17) that beneficial mutations in one enzyme can be transferred to the corresponding position in another FC4E enzyme and have correspondingly beneficial impacts. We demonstrate this by transferring the top three mutations from Example 12-1 (Y64F, E178A, Y361A) into the pA06238 sequence (Y53F, D167A, Y340A; SEQ ID NO: 231). The polynucleotide sequence for SEQ ID NO: 231 was ordered from Twist Bioscience. The plasmid was transformed, and the protein was expressed and purified as in Example 2-1. The purified enzyme was reacted with 1.9 M fructose in buffer (20 mM $KPO_4$, 50 mM NaCl, 300 uM $CoCl_2$) for 24 hours at 60° C. The mutant enzyme, SEQ ID NO: 231, had a 1.4-fold improvement in tagatose conversion compared to the parent enzyme, pA06238.

12-3. Active Site Mutants of pA06238

Forty-two active site residue positions in pA06238 were chosen for site-saturation mutagenesis to create a library of pA06238 mutants. Mutant plasmids were generated similar to Example 12-1, except that primers were used that encoded all amino acids at the specified mutant residue position, and clones were selected for use without sequence verification.

Figure 18:
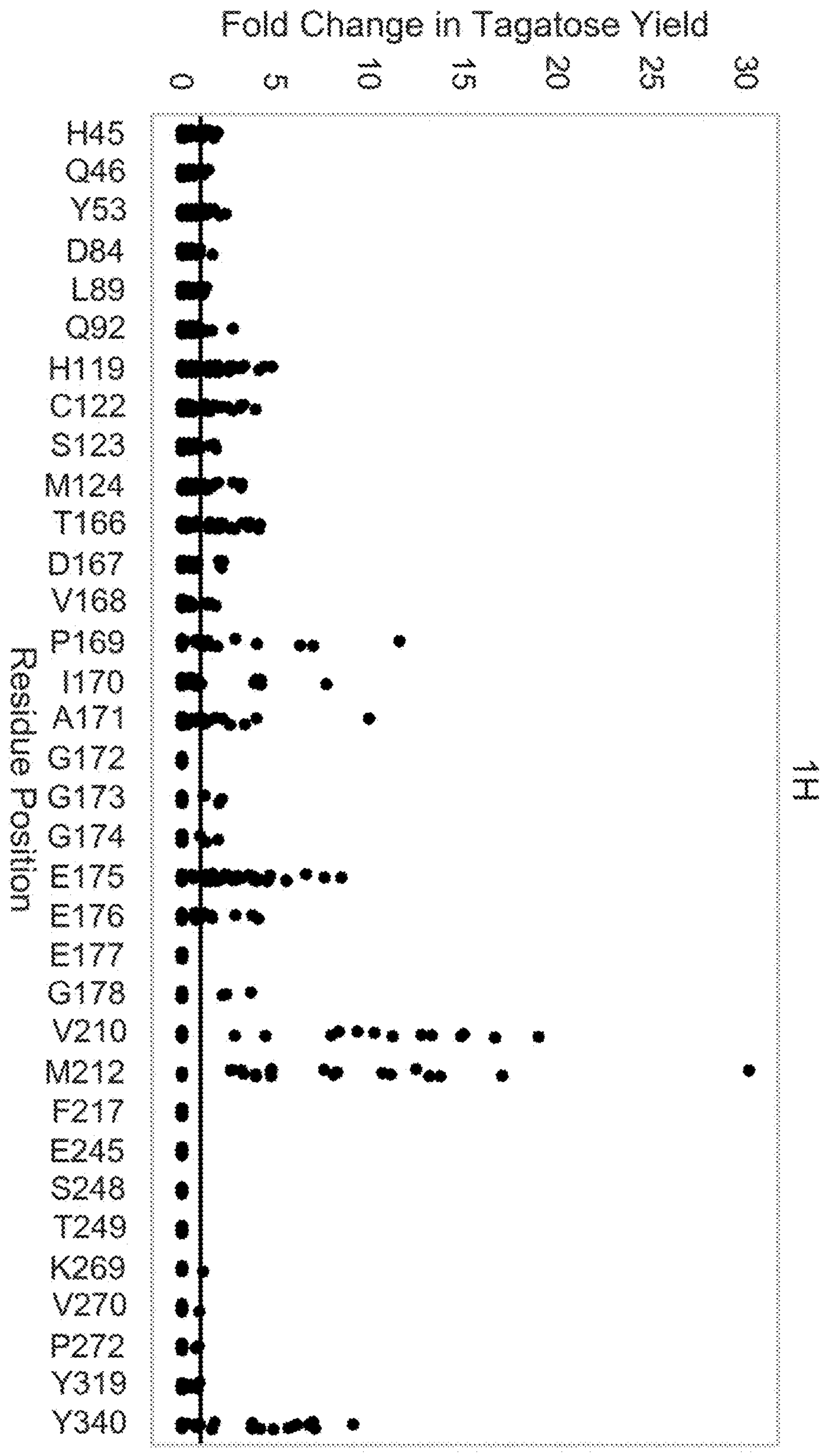
FIG. 18 depicts the fold change in fructose to tagatose conversion for members of the FC4E active site mutant library (reaction time 1 hour).
Figure 19:
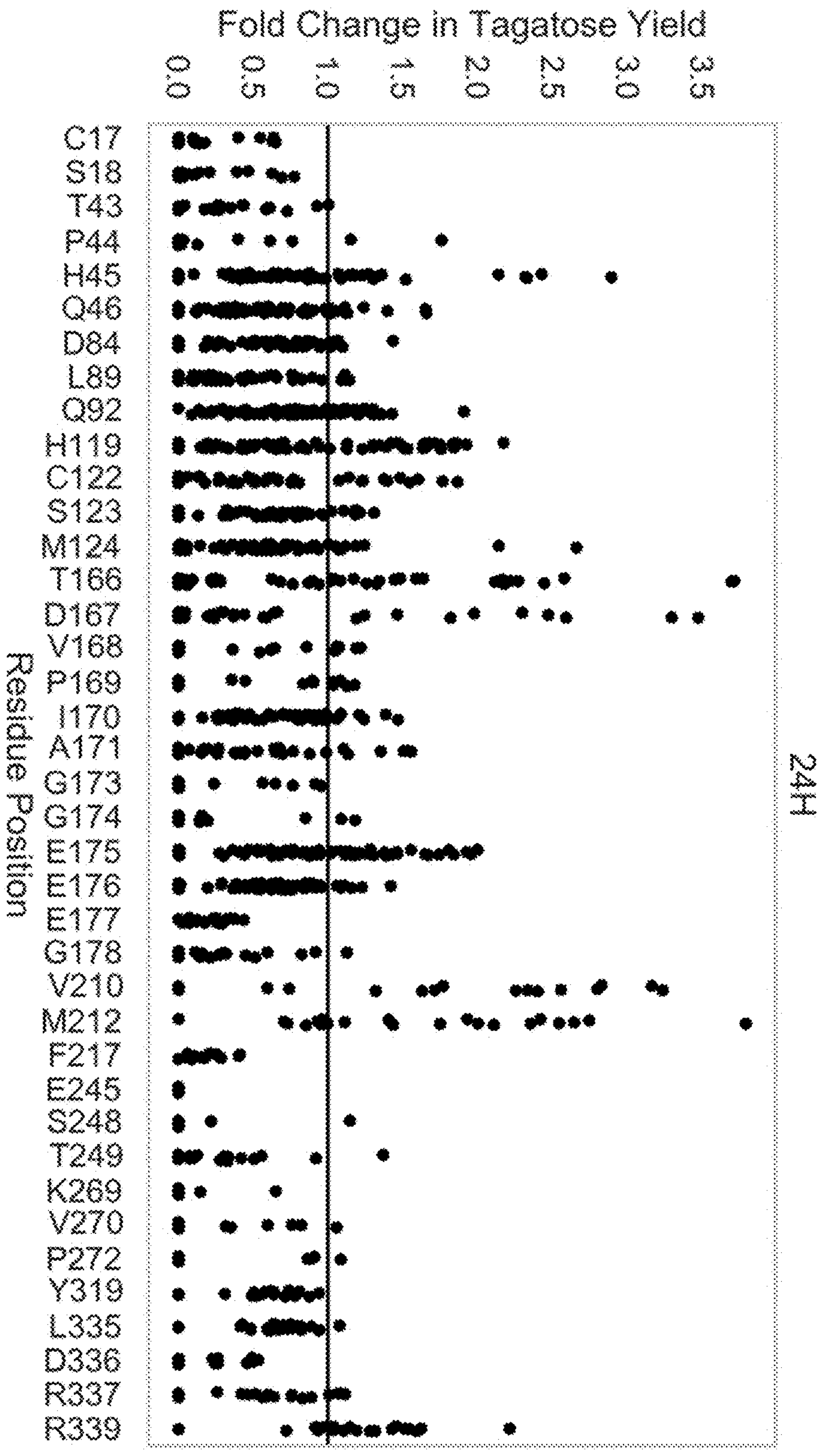
FIG. 19 depicts the fold change in fructose to tagatose conversion for members of the FC4E active site mutant library (reaction time 24 hours).

FC4Es from the mutant library were expressed and purified similar to Example 2-1. Purified enzyme was reacted with 1.9 M fructose in buffer (20 mM $KPO_4$, 50 mM NaCl, 300 uM $CoCl_2$, pH 7.5) at 60° C. for 1 and 24 hours. Conversion of fructose to tagatose was measured as in Example 7. Fold increase in percent tagatose conversion for each tested mutant is shown in FIG. 18 (1 hour data) and FIG. 19 (24 hour measurements). The following wild-type residue positions had mutant library members that showed increased conversion of tagatose compared to their parent FC4E: T43, P44, H45, Q46, Y53, D84, L89, Q92, H119, C122, S123, M124, T166, D167, V168, P169, I170, A171, G173, G174, E175, E176, G178, V210, M212, S248, T249, K269, V270, P272, L335, R337, R339, Y340. The top mutants from the library were sequenced and are included here as SEQ ID NOs: 371-444.

Example 13 Computational Design of pA06238 to Improve Expression and Stability Computational design of pA06238 guided by native sequence alignment was used to improve protein expression and stability. In order for a given amino acid at a specific residue position to be allowed in the final design, it had to pass two filters: one based on native sequence alignment and one based on computational modeling. A position-specific scoring matrix (PSSM) was created from a native sequence alignment. Two different alignments were used: 1) aligned sequences were only from thermophilic organisms and 2) aligned sequences were allowed from any organism. Any amino acid with a positive score in the PSSM passed the first filter. For each passing amino acid, the Archytas™ protein design software was used to predict if mutating to the given amino acid was predicted to have a ΔΔG below a given cutoff. Several cutoffs, −2.5, −2.0, −1.5, −1.0, −0.5, were used to select the final designs. All amino acids that passed both filters were combined in a final computational design. Homology models of pA06238 built with Archytas™ were used as input for both the ΔΔG calculations and final computational designs.

Figure 21:
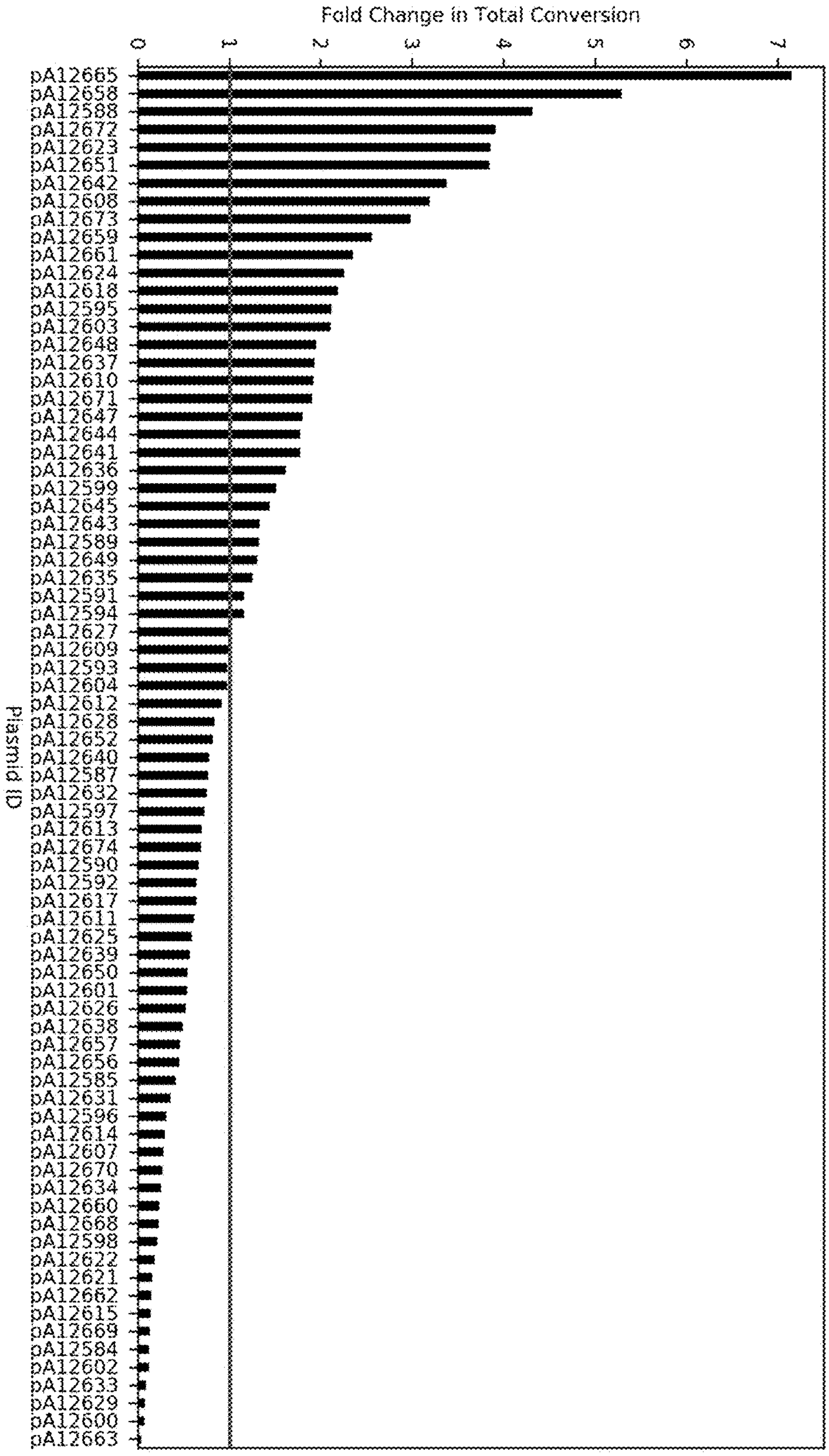
FIG. 21 depicts the fold change in total conversion (amount of expressed protein multiplied by the tagatose yield from a standard amount of enzyme) for the FC4E computational designs.

Ninety two designed enzymes were chosen for characterization (FIG. 20). The number of mutations per design ranged from 2-47 with an average of 15 mutations per design. Mutations occurred at 138 residue positions within pA06238. A sequence alignment of the designs with all mutations highlighted is shown in FIG. 20. Polynucleotide sequences for the 92 designed enzymes (SEQ ID NOs: 46-136) were ordered from Twist Bioscience. The plasmids were transformed, and the protein was expressed and purified as in Example 2-1. The purified FC4Es were reacted with 1.9 M fructose in buffer (20 mM $KPO_4$, 50 mM NaCl, 300 uM $CoCl_2$) for 24 hours at 60° C. The fold change in total conversion (total purified protein multiplied by percent conversion to tagatose for a standard amount of enzyme) is shown in FIG. 21.

Example 14 Computational Design of pA06238 for Increased Stability

Figure 24:
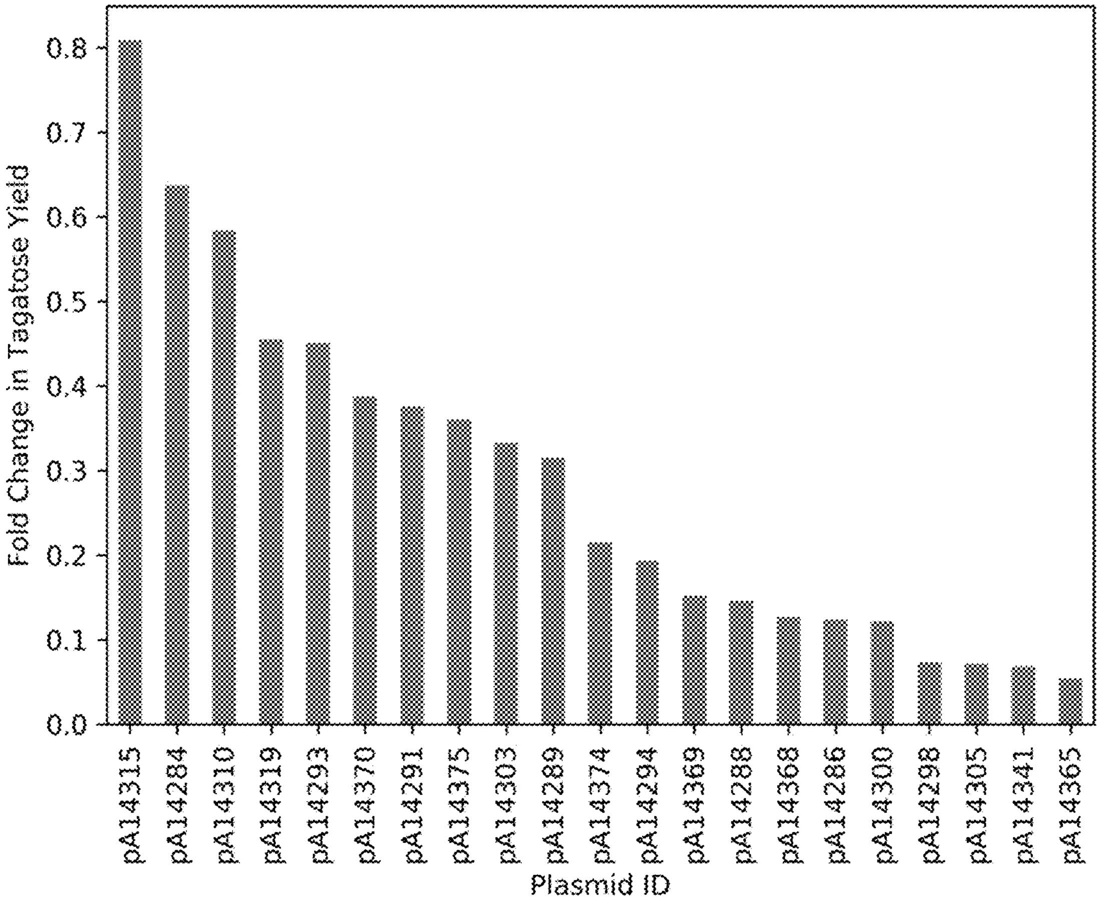
FIG. 24 depicts the fold change in tagatose yield for a subset of the FC4E computational designs from Example 14.

Enzyme inactivation has been observed when enzymes are exposed to aldehydes (Jennewein et al., 2006; Lorenzo et al., 2007). Lysines and to a lesser extent cysteines are particularly susceptible to modification by aldehydes, causing enzyme inactivation. The Archytas™ design software was used to design mutants of pA06238 with a reduced number of exposed lysine and cysteine residues. 184 designed lysine mutant enzymes were chosen to be experimentally characterized. Half of the designed mutants only mutated lysine and cysteine residues (SEQ ID NOs: 137-231; FIG. 22), and the other half allowed mutations surrounding the lysine and cysteine positions (SEQ ID NOs: 232-320; FIG. 23). The mutants were ordered from Twist Bioscience and tested for FC4E activity. The plasmids were transformed, and the enzymes were expressed and purified as in Example 2-1. The purified FC4Es were reacted with 1.9M fructose in buffer (20 mM $KPO_4$, 50 mM NaCl, 300 uM $CoCl_2$) for 24 hours at 60° C. The fold change in tagatose conversion for a subset of lysine mutants is shown in FIG. 24.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

The invention claimed is:

1. A modified polypeptide comprising an amino acid sequence having at least 90% sequence identity to SEQ ID NO:6, wherein the modified polypeptide directly converts fructose to tagatose through epimerization at the carbon-4 position of fructose, wherein the modified polypeptide comprises one or more amino acid substitutions as compared to an unmodified polypeptide, wherein the amino acid sequence of the unmodified polypeptide is SEQ ID NO: 6, wherein the one or more amino acid substitutions include at least one substituted amino acid at the amino acid residues corresponding to position K5, K10, V13, C17, Y22, S21, S27, F30, K34, G35, S54, K62, N63, M66, K67, K70, K72, E75, K78, D93, S96, P97, T98, N101, K102, D105, F110, S113, Y115, L126, S127, D128, K131, Y135, E136, K137, R143, E144, F146, E147, I148, E151, K155, S187, S190, S191, L192, K193, K194, N197, V199, N201, I202, D204, I215, K229, G232, D241, A253, Y255, R266, R280, G281, L284, S286, N287, D290, I292, R296, E297, R303, K321, K324, R325, E327, L328, N333, E343, Y344, E345, K348, M349, V350, N352, K353, D363, K365, Y372, S374, F376, D377 or M383 and wherein the modified polypeptide comprises H at position 85, D at position 121, H at position 247, D at position 250, and G at position 271.

2. The modified polypeptide of claim 1, wherein the modified polypeptide is at least 91% identical to SEQ ID NO:6.

3. The modified polypeptide of claim 2, wherein the one or more amino acid substitutions further include at least one substituted amino acid at the amino acid residues corresponding to position P44, H45, Q46, Y53, D84, Q92, H119, C122, S123, M124, T166, D167, P169, I170, A171, G173, E175, E176, G178, V210, M212, T249, R339, or Y340.

4. The modified polypeptide of claim 1, wherein the modified polypeptide is at least 95% identical to SEQ ID NO: 6.

5. The modified polypeptide of claim 1, wherein the modified polypeptide is immobilized to a carrier or support.

6. The modified polypeptide of claim 5, wherein the carrier or support is an organic composition comprising one or more of alginate, chitosan, chitin, collagen, carrageenan, gelatin, cellulose, starch, pectin, sepharose, polystyrene, styrene divinylbenzene, polyvinyl chloride, polyacrylate, polyamide, polypropylene, diethylaminoethyl cellulose (DEAE cellulose), UV-activated polyethylene glycerol, and methacrylate.

7. The modified polypeptide of claim 6, wherein the organic composition is functionalized with at least one chemical group, the at least one chemical group being one or more of an epoxy group, an amino group, a hydrocarbon, a tertiary amine, a quaternary amine, a carboxylic ester, nitrilotriacetic acid (NTA), iminodiacetic acid (IDA), aminophosphonic acid (AMPA), polyamine, or a carboxylic acid.

8. The modified polypeptide of claim 5, wherein the carrier or support is an inorganic composition comprising one or more of alumina, Zeolite, ceramics, celite, glass, silica, activated carbon, and charcoal.

9. A method of producing tagatose, the method comprising:

contacting fructose with the modified polypeptide of claim 1 to directly convert the fructose to tagatose.

10. The method of claim 9, wherein contacting the fructose with the modified polypeptide is performed at a temperature between about 40° C. and about 100° C.

11. The method of claim 9, wherein contacting the fructose with the modified polypeptide is performed at between about pH 4.5 and about pH 8.

12. The method of claim 9, wherein contacting the fructose with the modified polypeptide is performed in the presence of a metal ion.

13. The method of claim 9, further comprising isolating the tagatose using a chromatographic method.

14. The method of claim 9, wherein the modified polypeptide is at least 91% identical to SEQ ID NO: 6.

15. The method of claim 9, wherein the modified polypeptide is at least 95% identical to SEQ ID NO: 6.

16. A method for producing a tagatose composition, comprising the steps of:

(a) providing a starting composition comprising greater than about 0.3%, about 0.5%, about 1%, about 2%, about 3%, about 4%, about 5%, about 10%, about 20%, about 30%, about 40%, about 50%, about 60%, about 70%, about 80%, about 90% of fructose by weight;

(b) contacting the starting composition with the modified polypeptide of claim 1 to directly convert the fructose to tagatose; and (c) producing a tagatose composition comprising tagatose.

17. The method of claim 16, wherein the tagatose composition comprises tagatose in an amount greater than about 0.1%, about 0.2%, about 0.3%, about 0.5%, about 1%, about 5%, about 10%, about 15%, about 20%, about 25%, about 30%, about 35%, or about 40%.

* * * * *

SEQUENCE LISTING

```
Sequence total quantity: 444
SEQ ID NO: 1           moltype = AA  length = 453
FEATURE                Location/Qualifiers
source                 1..453
                       mol_type = protein
                       organism = Caldithrix abyssi
SEQUENCE: 1
MSLHPLNKLI ERHKKGTPVG IYSVCSANPF VLKAAMLQAQ KDQSLLLIEA TSNQVDQFGG  60
YTGMRPEDFK TMTLELAAEN NYDPQGLILG GDHLGPNRWT KLSASRAMDY AREQIAAYVK  120
AGFSKIHLDA TMPLQNDATD SAGRLPVETI AQRTAELCAV AEQTYRQSDQ LFPPPVYIVG  180
SDVPIPGGAQ EALNQIHITE VKEVQQTIDH VRRAFEKNGL EAAYERVCAV VVQPGVEFAD  240
QIVFEYAPDR AAALKDFIES HSQLVYEAHS TDYQTAPLLR QMVKDHFAIL KVGPALTFAL  300
REAIFALAFM EKELLPLHRA LKPSAILETL DQTMDKNPAY WQKHYGGTKE EVRFAQRFSL  360
SDRIRYYWPF PKVQKALRQL LKNLQQISIP LTLVSQFMPE EYQRIRQGTL TNDPQALILN  420
KIQSVLKQYA EATQIQNSLT FTQNQNSLAM ERL                              453

SEQ ID NO: 2           moltype = AA  length = 429
FEATURE                Location/Qualifiers
source                 1..429
                       mol_type = protein
                       organism = Anaerolinea thermophila
SEQUENCE: 2
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 3           moltype = AA  length = 434
FEATURE                Location/Qualifiers
source                 1..434
                       mol_type = protein
                       organism = Thermoanaerobacterium thermosaccharolyticum
SEQUENCE: 3
MAKEHPLKEL VNKQKSGISE GIVSICSSNE FVIEASMERA LTNGDYVLIE STANQVNQYG  60
GYIGMTPIEF KKFVFSIAKK VDFPLDKLIL GGDHLGPLIW KNESSNLALA KASELIKEYV  120
LAGYTKIHID TSMRLKDDTD FNTEIIAQRS AVLLKAAENA YMELNKNNKN VLHPVYVIGS  180
EVPIPGGSQG SDESLQITDA KDFENTVEIF KDVFSKYGLI NEWENIVAFV VQPGVEFGND  240
FVHEYKRDEA KELTDALKNY KTFVFEGHST DYQTRESLKQ MVEDGIAILK VGPALTFALR  300
EALIALNNIE NELLNNVDSI KLSNFTNVLV SEMINNPEHW KNHYFGDDAR KKFLCKYSYS  360
DRCRYYLPTR NVKNSLNLLI RNLENVKIPM TLISQFMPLQ YDNIRRGLIK NEPISLIKNA  420
IMNRLNDYYY AIKP                                                   434

SEQ ID NO: 4           moltype = AA  length = 446
FEATURE                Location/Qualifiers
source                 1..446
                       mol_type = protein
                       organism = Thermoanaerobacter thermohydrosulfuricus
```

```
SEQUENCE: 4
MNTEHPLKNV VKLQKKGIPI GIYSVCSANE IVIQVAMEKA LSMDSYVLIE ATANQVNQYG  60
GYTNMKPIDF RDFVYSIAKR INFPENRIIL GGDHLGPLPW KNQQAKKAME EAKELVKQFV  120
MAGFTKIHVD TSMLLGDDNI NIKLDTETIA ERGAILVSVA ERAFEELKKF NPYALHPVYV  180
IGSEVPVPGG SQKENNNEIQ VTKPTDFEET VEVYKSTFYK YGLGNAWEDV VAVVVQAGVE  240
FGVEDIHEYD HQQAENLVSA LKKYPNLVFE AHSTDYQPAK LLKEMVRDGF AILKVGPELT  300
FALREGLFAL NIIEKELFKD NHDIEMSNFI DILDTAMLNN PKYWEQYYYG DDNKIRIARK  360
YSYSDRCRYY LIENEVRASM SRLFKNLTNV EIPLTLISQY MPIQYEKIRM GLLKNDPENL  420
VKDKIGNCID KYLYATNPTS GEFKLI                                     446

SEQ ID NO: 5            moltype = AA  length = 429
FEATURE                 Location/Qualifiers
source                  1..429
                        mol_type = protein
                        organism = Caldicellulosiruptor kronotskyensis
SEQUENCE: 5
MSPQNPLIGL FKNREKEFKG IISVCSSNEI VLEAVLKRMK DTNLPIIIEA TANQVNQFGG  60
YSGLTPSQFK ERVIKIAQKV DFPLERIILG GDHLGPFVWR DQEPEIAMEY AKQMIKEYIK  120
AGFTKIHIDT SMPLKGENSI DDEIIAKRTA VLCRIAEECF EKISINNPYI TRPVYVIGAD  180
VPPPGGESSI CQTITTKDEL ERSLEYFKEA FKKEGIEHVF DYVVAVVANF GVEFGSDEIV  240
DFDMEKVKPL KELLAKYNIV FEGHSTDYQT KENLKRMVEC GIAILKVGPA LTFTLREALV  300
ALSHIEEEIY SNEKEKLSRF REVLLNTMLT CKDHWSKYFD ENDKLIKSKL LYSYLDRWRY  360
YFENESVKSA VYSLIGNLEN VKIPPWLVSQ YFPSQYQKMR KKDLKNGAAD LILDKIGEVI  420
DHYVYAVKE                                                        429

SEQ ID NO: 6            moltype = AA  length = 408
FEATURE                 Location/Qualifiers
source                  1..408
                        mol_type = protein
                        organism = Dictyoglomus turgidum
SEQUENCE: 6
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 7            moltype = AA  length = 408
FEATURE                 Location/Qualifiers
source                  1..408
                        mol_type = protein
                        organism = Caldilinea aerophila
SEQUENCE: 7
MSTLRHIILR LIELREREQI HLTLLAVCPN SAAVLEAAVK VAARCHTPML FAATLNQVDR  60
DGGYTGWTPA QFVAEMRRYA VRYGCTTPLY PCLDHGGPWL KDRHAQEKLP LDQAMHEVKL  120
SLTACLEAGY ALLHIDPTVD RTLPPGEAPL VPIVVERTVE LIEHAEQERQ RLNLPAVAYE  180
VGTEEVHGGL VNFDNFVAFL DLLKARLEQR ALMHAWPAFV VAQVGTDLHT TYFDPSAAQR  240
LTEIVRPTGA LLKGHYTDWV ENPADYPRVG MGGANVGPEF TAAEFEALEA LERREQRLCA  300
NRKLQPACFL AALEEAVVAS DRWRKWLQPD EIGKPFAELT PARRRWLVQT GARYVWTAPK  360
VIAAREQLYA HLSLVQADPH AYVVESVARS IERYIDAFNL YDAATLLG              408

SEQ ID NO: 8            moltype = AA  length = 420
FEATURE                 Location/Qualifiers
source                  1..420
                        mol_type = protein
                        organism = Rhodothermus marinus
SEQUENCE: 8
MQAQALLTVP FDRVATHARG FVGWVAELLQ GPLAYQHTLL AVCPNSEAVT RAALEAAAEA  60
NAPLLFAATL NQVDLDGGYT GWTPATLARF VADELARLDL HIPVVLGLDH GGPWKKDLHA  120
RNRLSFEETF QAVLRAIEAC LDAGYGLLHL DPTVDLELSP GTPVPIPRIV ERSVALLRHA  180
ETYRLRRNLP PVAYEVGTEE VGGGLQAEAR MAEFLDRLWT ALDREGLPHP VFVVGDIGTR  240
LDTRTFDFER ARRLDALVRR YGALIKGHYT DDVDRLDLYP KAGIGGANVG PGLAAIEFEA  300
LEALVEEARR RGLSVTFDQA IRRAVVESGR WTKWLQPEEK GQPFDALDPE RQRWLVATGS  360
RYVWTHPAVL QARRELYEAL APWLDADAFV RTRIKARLMD YFRAFNLIHF NERLQAFLPE  420

SEQ ID NO: 9            moltype = AA  length = 401
FEATURE                 Location/Qualifiers
source                  1..401
                        mol_type = protein
                        organism = Methanohalobium evestigatum
SEQUENCE: 9
MTDEDFEPIC EISEQFRNYC NQMLESEYDP KPSKYIFNIL QNQKTIVMAA NPRIGLVTRG  60
ILRAAKDADA PIILELARSE CNLENGYTGL YPSDFSEQCY QAAKDVGYDI WALHADHIGI  120
KKGDREDIEK TKELVKAQID AGYTSFAIDA SHLFNFQGGD LREELKDNID ATTEIAKFIE  180
EQMDDREYGL EVEVGEIGRE DEHGRVLTNP EEAVTFIKAL NENGVYPQVL AIANGSAHGN  240
TYDSQGRLIE QVSIDIPQTI KVAQALKENN LKVRIAQHGI TGTPRELIHD HFPHGEIIKG  300
NVGTFYMNLV WDAFKLFEPE LYNDIWNWTV ENYKQKSPDK TDSEIFGKYS KFAIKQFFDR  360
```

```
IYSVNEDTKR AIDAMAYAET LYFLKSFNAE RTASIVRDGI K                    401

SEQ ID NO: 10          moltype = AA  length = 343
FEATURE                Location/Qualifiers
source                 1..343
                       mol_type = protein
                       organism = Thermoanaerobacter thermohydrosulfuricus
SEQUENCE: 10
MNTEHPLKNV VKLQKKGIPI GIYSVCSANE IVIQVAMEKA LSMDSYVLIE ATANQVNQYG  60
GYTNMKPIDF RDFVYSIAKR INFPENRIIL GGDHLGPLPW KNQQAKKAME EAKELVKQFV  120
MAGFTKIHVD TSMFLGDDNI NIKLDTETIA ERGAILVSVA ERAFEELKKS NPYALHPVYV  180
IGSEVPVPGG SQKENNNEIQ VTKPADFEET VEVYKSTFYK YGLGNAWEDV VAVVVQPGVE  240
FGVENIHEYD HQQAENLVSA LKKYPNLVFE AHSTDYQPAK LLKEMVRDGF AILKVGPELT  300
FALREGLFAL NIIEKELFKD NHDIEMSNFI DILDTAMLNN PKY                  343

SEQ ID NO: 11          moltype = AA  length = 435
FEATURE                Location/Qualifiers
source                 1..435
                       mol_type = protein
                       organism = Clostridium cavendishii
SEQUENCE: 11
MQRNYLLDIV EAQNNGIHKG IYSACSANEY VIEAAMERAK NTNEYVLIEA TANQVNQYGG  60
YTGMKPIDFK NFVYDIADKI NFDKDKIILG GDHLGPLTWS KETEKEAMAK SHELVKEYVM  120
AGFTKIHLDT SMYLADDDRS KKLATEVIAR RGAELCKTAE ESFKALKERN SMAVAPVYIV  180
GSEVPIPGGI QDEEEGIQVT KPEDFLETVK VYKAEFKDKG IDEVWNRVIG VVVQPGVEFG  240
DESVHEYNRE KAEKLVNSLR GVKGIVFEGH STDYQTKTKL KEMVEDGIAI LKVGPALTYG  300
LREALFALNH IENEIFKYRA DIKLSNFINV LETSMVEEPT HWKQHYHGDA EDIKYAMRYS  360
YSDRCRYYMP TEAVNKAMNI LIENLESVEI PLTIIDQYMP MQYKKIREGL IQNKPKELIK  420
DRIGDYIDDY LYALR                                                 435

SEQ ID NO: 12          moltype = AA  length = 435
FEATURE                Location/Qualifiers
source                 1..435
                       mol_type = protein
                       organism = Kosmotoga olearia
SEQUENCE: 12
MKKHPLQDIV SLQKQGIPKG VFSVCSANRF VIETTLEYAK MKGTTVLIEA TCNQVNQFGG  60
YTGMTPADFR EMVFSIAEDI GLPKNKIILG GDHLGPNPWK GQPSDQAMRN AIEMIREYAK  120
AGFTKLHLDA SMRLADDPGN ENEPLNPEVI AERTALLCLE AERAFKESAG SLRPVYVIGT  180
DVPPPGGAQN EGKSIHVTSV QDFERTVELT KKAFFDHGLY EAWGRVIAVV VQPGVEFGNE  240
HIFEYDRNRA RELTEAIKKH PNIVFEGHST DYQTAKALKE MVEDGVAILK VGPALTFALR  300
EAFFALSSIE KELFYDTPGL CSNFVEVVER AMLDNPKHWE KYYQGEEREN RLARKYSFLD  360
RLRYYWNLPE VRTAVNKLIT NLETKEIPLT LISQFMPMQY QKIRNGLLRK DPISLIKDRI  420
TLVLDDYYFA THPEC                                                 435

SEQ ID NO: 13          moltype = AA  length = 440
FEATURE                Location/Qualifiers
source                 1..440
                       mol_type = protein
                       organism = Butyricicoccus pullicaecorum
SEQUENCE: 13
MNHNPLKKIV ELQKQGKNVG IYSVCSANGY VIEAALKRGK SDGSCVLIES TANQCDQNGG  60
YTGMTPLDFK NFVLGIADKV GFDPKRLFLG GDHLGPLTFA GMDEAQAMEN AEELIRHYVG  120
AGFTKIHIDT SMKVASDDPN TRLSDETIAK RGARLARVAQ DTYHKLLESD PDAIAPVYIV  180
GSEVPIPGGA VGAVDQGVQV TKVEDFKNTV ATFEKAFREQ GLDEAWDNVI GVVVQPGVEE  240
KDSGCTEYDR EKAKDLMASI QEFPNLVFEG HSTDYQTKIK LRELVEDGVG ILKVGPALTF  300
AMREGMFALE NIEKELIYGT DITPSGFQDA LEAEMLKEGK HWRKHYQGTE LELRMKRKYS  360
FSDRCRYYMP TPAVEAAKER LISNLRTLGI PLNLLSQFMP IQYTKVREGL LVNDPVELVE  420
DRIINTIDEY LYATHQKELL                                            440

SEQ ID NO: 14          moltype = AA  length = 447
FEATURE                Location/Qualifiers
source                 1..447
                       mol_type = protein
                       organism = Clostridium thermobutyricum
SEQUENCE: 14
MLLKVKEHPI RELVNRYKNG ENVGIFSVCT SNEYVIEAAM ERVIDKDLDL LIESTANQVN  60
QDGGYTGMQP KDFVNYVYKI ADKVNFPKDR IILGGDHLGP LTWTKLVQEE AMEKAKVLIR  120
DYVLAGFTKI HIDTSMPIYD DLEKGVFGDD LIAERAAILC NVAEIAYREL LKTNEDAIHP  180
IYVVGSEVPV PGGVQAEEAE EEIENGIKVT RVEDFKNTVE VFKKKFKEHG VEEAFNYVVG  240
VVVQPGVEFS SDTVWKYERE KAKDLSKALK EYDNLVFEAH STDYQSPKSL REMVLDGFNI  300
LKVGPALTFG FREAAFALNK IEEEMFRFRP DIEESRFIQT LDYNMVKHPE NWIKHYSGTS  360
ENIRFSRMYS LSDRCRYYMP NEEVEYSFNK MINNLDKEEI PIALISQYMH NQYKKVRDGE  420
LKPKGLNLLK DFIGEYVDDY IFAVEDK                                    447

SEQ ID NO: 15          moltype = AA  length = 431
FEATURE                Location/Qualifiers
source                 1..431
                       mol_type = protein
```

```
                        organism = Litorilinea aerophila
SEQUENCE: 15
MYPVLENILR AQQQGEALGI PSICSAHPFV LEATFRHALT TGRTVLIEST CNQVNQHGGY  60
TGMTPGDFVA YVAALADRLH FPRERILLGG DHLGPNPWRD RPADQALNQA RILVQEYVRA  120
GYGKIHLDAS MACGGDPADA PLDKAVAAER AAALAEAAEA AFQRMGSGTP PCYVIGTEVP  180
PPGGAQGDDM PLAITAPREV AETIELTQAA FRRRGLEAAW ERVIAVVVQP GVEFGDEQVH  240
PYDRAAAAGL ARAIEPYGRL VYEAHSTDYQ TRQALRDLVA DHFAILKVGP ALTFAFREAV  300
FALAAVEEEW LAGQAGVVLS RLREELEAAM IQDPTHWRGY YRGDERHQRL ARRYSYSDRA  360
RYYWPRPSVQ AALERLLHNL EAAPPPLTLL SQYLPVQYWS VREGLLEPTP RSLIVDKIIQ  420
VLNDYTWACG G                                                   431

SEQ ID NO: 16           moltype = AA  length = 435
FEATURE                 Location/Qualifiers
source                  1..435
                        mol_type = protein
                        organism = Enterobacter mori
SEQUENCE: 16
MERKVKHLTH MVEQHKRGNA NGIYAVCSAH PLVLEAAIRY AQSHQTPLLI EATSNQVDQF  60
GGYTGMTPED FYGFVCCLAE SLDFPTSQLI LGGDHLGPNR WQNLPAQQAM ANADDLIKSY  120
VAAGFKKIHL DCSMSCEDDP VPLTDAIVAE RAARLAKIAE ATCREQFGVT DLVYVIGTEV  180
PVPGGAHETL TELEVTTPDA ARATLEAHRH ALEKEGLNDI WPRIIGLVVQ PGVEFDHAHV  240
CDYQPHKAVA LSKMVEAYDT LLFEAHSTDY QTPQALRQLV KDHFAILKVG PALTFALREA  300
LFSLAAIEEE LLPAKASSGL RHVLENVMLD RPEYWQSHYH GDGNARRLAR GYSYSDRVRY  360
YWPDSQIDDA FERLVRNLAD EPIPLPLISQ YLPLQYGKVR EGALKSTPRE LIIDHIQDIL  420
QQYHAACEGV TTQNA                                               435

SEQ ID NO: 17           moltype = AA  length = 415
FEATURE                 Location/Qualifiers
source                  1..415
                        mol_type = protein
                        organism = Caldisericum exile
SEQUENCE: 17
MWLDSNFLKN RGIFSICSSN ENVLDASIEF AKEKEDFLLI EATCHQVNQF GGYTKMTPES  60
FSKKIFKKAE EMNFNPERLL LGGDHLGPEP WKNENADTAM DKAKQLVIEF VKNGFNKIHL  120
DCSMPLKGDS DFSTTLVADR EAELCAVAEE TYEKYGGNRP VYVVGTEVPA PGGSTNEVPE  180
VTSIEELDEM IEELQNAFLR LGLKNAWDRV IAIVVRLGIG FGGDSVSEYE SEKTKELCTY  240
LSRYYPSLYF EAHSTDYQTA GSLKQMVKDG IRILKVGPAL TDAYRRGMFA LNFIEKESID  300
EEKQSRLVEN VLKVMDEYPR YWEDYYNSVG KTLRLDQMYS YFDRIRYYWG FEEVEKSKNR  360
LIENLKDMQM NLIRQYLPEQ YEKIRENKLN KDPRALINYE IKKVLNDYQK SVILE       415

SEQ ID NO: 18           moltype = AA  length = 408
FEATURE                 Location/Qualifiers
source                  1..408
                        mol_type = protein
                        organism = Dictyoglomus thermophilum
SEQUENCE: 18
MWLSKDYLRK KGVYSICSSN PYVIEASVEF AKEKNDYILI EATPHQINQF GGYSGMTPED  60
FKNFVMGIIK EKGIEEDRVI LGGDHLGPLP WQDEPSSSAM KKAKDLIRAF VESGYKKIHL  120
DCSMSLSDDP VVLSPEKIAE RERELLEVAE ETARKYNFQP VYVVGTDVPV AGGGEEEGIT  180
SVEDFRVAIS SLKKYFEDVP RIWDRIIGFV IMLGIGFNYE KVFEYDRIKV RKILEEVKKE  240
NLFVEGHSTD YQTKRALRDM VEDGVRILKV GPALTASFRR GVFLLSSIED ELISEDKRSN  300
IKKVVLETML KDDKYWRKYY KDSERLELDI WYNLLDRIRY YWEYKEIKIA LNRLFENFSE  360
GVDIRYIYQY FYDSYFKVRE GKIRNDPREL IKNEIKKVLE DYHYAVNL           408

SEQ ID NO: 19           moltype = AA  length = 420
FEATURE                 Location/Qualifiers
source                  1..420
                        mol_type = protein
                        organism = Rhodothermus marinus
SEQUENCE: 19
MQAQALLTVP FDRVATHARG FVGWVAELLL GPLAHQHTLL AVCPNSEAVT RAALEAAAEV  60
NAPLLFAATL NQVDLDGGYT GWTPATLARF VADELARLDL HIPVVLGLDH GGPWKKDLHA  120
RNRLSFAETV QAVLRAIEAC LDAGYGLLHL DPTVDLELPP GTPVPIPRIV ERTVALLRHA  180
ETYRLRRNLP PVAYEVGTEE VGGGLQAEAR MAEFLDRLWT ALDREGLPHP IFVVGDIGTR  240
LDTRTFDFER ACRLDALVRR YGALIKGHYT DDVDRLDLYP KAGIGGANVG PGLAAIEFEA  300
LEVLVDEARR RGLSVTFDQA IRRAVVESGR WTKWLQPEEK GRPFEALDPE RQRWLVATGS  360
RYVWTHPAVL QARRELYEAL APWLDADAFV RERIKARLMD YFRAFNLIHF NERLQAFLPE  420

SEQ ID NO: 20           moltype = AA  length = 420
FEATURE                 Location/Qualifiers
source                  1..420
                        mol_type = protein
                        organism = Rhodothermus profundi
SEQUENCE: 20
MQAHVLLAPS FEQLADHRHG FVGWLVDLLR GPLAYRHTLL AVCPNSEAVT RAALEAAREA  60
NAPLFFAATL NQVDLDGGYT GWTPATLARF VADERIRLGL RAPVVLGLDH GGPWKKDWHV  120
RNRLPYEATL QAVLRAIEAC LDAGYGLLHL DPTVDLELPP GTPVPIPRIV ERTVALLQHA  180
ETYRQQRRLP PVAYEVGTEE VGGGLQAEAR MAEFLDRLWT VLDREGLPRP VFVVGDIGTR  240
LDTHTFDFER ARRLDALVRR YGALIKGHYT DGVDRLDLYP QAGIGGANVG PGLAAIEFEA  300
```

```
LEALVAEAHR RKLPVTFDRT IRQAVIESGR WQKWLRPEEK GRPFEALPPE RQRWLVATGS  360
RYVWTHPAVR QARHQLYQVL APWLDADAFV RARIKARLMD YFRAFNLIGF NERLQAFLPN  420

SEQ ID NO: 21          moltype = AA  length = 428
FEATURE                Location/Qualifiers
source                 1..428
                       mol_type = protein
                       organism = Caldibacillus debilis
SEQUENCE: 21
MAKIPIQSAV KALLELQDEG KGGTLLGIGP MSTNVLQASF ELARDYDFPL MFIASRNQVD  60
LDELGGGYVN GWNQYTFVQA IREMAELTGF DGLYYVCRDH GGPWQRDKER NDHLPVEEAM  120
ALGKKSYLAD IEAGFDLLMI DPTKDPFEIG KVIPLEKVIE RTVELIEFCE KERQARDLPE  180
IGYEVGTEET NGGLTSTETY ETFILRLQEE LGRRDLPMPT FIVGQTGTLV RKTEQAGRFS  240
FENAADLAKM AKKYGVGLKE HNGDYLDDVI LLAHIPSQIT ATNVAPQYGT EETRALLKLA  300
KLEEKLKEQG LIGQPSKVKD VLLYHSIKSE RWRKWMVGSQ RELSVEEIVK DEELSTEILD  360
IAGHYTFNID EVKEEINKLY RNLSKAHIDG QRFVVDHIKR SIRNYVECFN LKGLTSRIKE  420
KLNGSKNA                                                          428

SEQ ID NO: 22          moltype = AA  length = 421
FEATURE                Location/Qualifiers
source                 1..421
                       mol_type = protein
                       organism = Caloramator quimbayensis
SEQUENCE: 22
MKKISIFEIV KASLNMKGKD KATLLGIGPM SKTLIKASMI LAKEKDFPLM FIASRNQVDL  60
KELGGGYVCN WDQKSFASDI KKIAEEVGFN GLYFLCRDHG GPWQRDNERN AHLPENEAME  120
LGKKSYLEDL INGFDLLHID PTKDPYIVGK TVPMEIVLKR TIELIEYVER ERKERNLPPI  180
SYEVGTEETN GGLTSEEAYE TFIKTLIEEL DKRNLPKPSF IVGQTGTLTR LTENVGNFNT  240
KNSKKLADIA KKYSVGLKEH NGDYLDEAIL LEHPALGITA MNVAPEFGSV ETQAYLKLIE  300
VENNLYEHGI ISKKSNLEKV IKEEAVKSLR WKKWMVGDKV NLSIEEVLSD KDLTDLITEI  360
SGHYTFNNER VKCEIQLMFD NLNKAGVDGE KYVINKIKDS IDKYIKYFNL EGFTTKVLSN  420
V                                                                 421

SEQ ID NO: 23          moltype = AA  length = 378
FEATURE                Location/Qualifiers
source                 1..378
                       mol_type = protein
                       organism = Methanosalsum zhilinae
SEQUENCE: 23
MTDTNYKAKP GSLLFESLMD KETIILAINP RISLLNKGIL KAAKDMDAPI ILELAKSECN  60
LEGGYTGFTP SEFSKRAYES AEEIGIDIWS LHADHIGIKK GTDEEIESIK KLVKAQIDAG  120
YTSFAIDASH LFNFRGGNLR EELKDNIEAT TKVARFIDEQ MEDRDYGLEV EVGEIGREDE  180
YGRVLTQPEE AVTFIKALNE NGVYPQVLAI ANGSAHGNTY DEYGHLIEQV SIDIPQTMAV  240
ARALRDNNLN VRIAQHGITG TPIEMIHNHF PHGDIIKGNV GTFYLNLVWD VLKVFEPQLY  300
GDIWDWTIEN FSEKYPDKSE NEIFGKYSKY AIKEFFDRIY SVGDDTIRAV ESRAYADTLV  360
FLKAFKAAGM AEHVRKNL                                               378

SEQ ID NO: 24          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 24
MMFGSPAPLL DMVTAQKQGM ARGIPSIASA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 25          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 25
MMFGSPAPLL DMVTAQKQGM ARGIPSICSA HPVVLSAACH LARRSGAPLL IATTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
```

```
LEDYAAACG                                                         429

SEQ ID NO: 26           moltype = AA  length = 429
FEATURE                 Location/Qualifiers
REGION                  1..429
                        note = mutant D-fructose C4-epimerase
source                  1..429
                        mol_type = protein
                        organism = synthetic construct
SEQUENCE: 26
MMFGSPAPLL DMVTAQKQGM ARGIPSICSA HPVVLSAACH LARRSGAPLL IQTTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 27           moltype = AA  length = 429
FEATURE                 Location/Qualifiers
REGION                  1..429
                        note = mutant D-fructose C4-epimerase
source                  1..429
                        mol_type = protein
                        organism = synthetic construct
SEQUENCE: 27
MMFGSPAPLL DMVTAQKQGM ARGIPSICSA HPVVLSAACH LARRSGAPLL IETTCNQVNH  60
QGGASGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 28           moltype = AA  length = 429
FEATURE                 Location/Qualifiers
REGION                  1..429
                        note = mutant D-fructose C4-epimerase
source                  1..429
                        mol_type = protein
                        organism = synthetic construct
SEQUENCE: 28
MMFGSPAPLL DMVTAQKQGM ARGIPSICSA HPVVLSAACH LARRSGAPLL IETTCNQVNH  60
QGGFSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 29           moltype = AA  length = 429
FEATURE                 Location/Qualifiers
REGION                  1..429
                        note = mutant D-fructose C4-epimerase
source                  1..429
                        mol_type = protein
                        organism = synthetic construct
SEQUENCE: 29
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGAHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                         429

SEQ ID NO: 30           moltype = AA  length = 429
FEATURE                 Location/Qualifiers
REGION                  1..429
                        note = mutant D-fructose C4-epimerase
source                  1..429
                        mol_type = protein
                        organism = synthetic construct
SEQUENCE: 30
MMFGSPAPLL DMVTAQKQGM ARGIPSICSA HPVVLSAACH LARRSGAPLL IETTCNQVNH  60
```

```
QGGYSGMTPA DFVRFLREIL EREGIPPQQV ILGGNHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 31          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 31
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDALGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 32          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 32
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIA LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 33          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 33
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LAASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 34          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 34
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LNASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 35          moltype = AA  length = 429
FEATURE                Location/Qualifiers
REGION                 1..429
```

```
                         note = mutant D-fructose C4-epimerase
source                   1..429
                         mol_type = protein
                         organism = synthetic construct
SEQUENCE: 35
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSAVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                        429

SEQ ID NO: 36            moltype = AA  length = 429
FEATURE                  Location/Qualifiers
REGION                   1..429
                         note = mutant D-fructose C4-epimerase
source                   1..429
                         mol_type = protein
                         organism = synthetic construct
SEQUENCE: 36
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSQVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                        429

SEQ ID NO: 37            moltype = AA  length = 429
FEATURE                  Location/Qualifiers
REGION                   1..429
                         note = mutant D-fructose C4-epimerase
source                   1..429
                         mol_type = protein
                         organism = synthetic construct
SEQUENCE: 37
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYAAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                        429

SEQ ID NO: 38            moltype = AA  length = 429
FEATURE                  Location/Qualifiers
REGION                   1..429
                         note = mutant D-fructose C4-epimerase
source                   1..429
                         mol_type = protein
                         organism = synthetic construct
SEQUENCE: 38
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYQAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                        429

SEQ ID NO: 39            moltype = AA  length = 429
FEATURE                  Location/Qualifiers
REGION                   1..429
                         note = mutant D-fructose C4-epimerase
source                   1..429
                         mol_type = protein
                         organism = synthetic construct
SEQUENCE: 39
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAASTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
```

```
YYWHHPAAQE AVRRLLANLI ETPPPLSLLS QYLPREYEMV RAGEISSHPQ DLIRAHIQHT  420
LEDYAAACG                                                          429

SEQ ID NO: 40          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 40
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTAYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 41          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 41
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTNYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 42          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 42
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVAP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 43          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 43
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVDP ALTFAYREAV  300
FALEHIEREI LGRQDMPLSR LSEVLDEVML NDPRHWQGYF AGAPAEQALA RRYSFSDRIR  360
YYWHHPAAQE AVRRLLANLI ETPPPLSLLS QYLPREYEMV RAGEISSHPQ DLIRAHIQHT  420
LEDYAAACG                                                          429

SEQ ID NO: 44          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 44
```

```
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
AYWHHPAAQE AVRRLLANLI ETPPPLSLLS QYLPREYEMV RAGEISSHPQ DLIRAHIQHT  420
LEDYAAACG                                                          429

SEQ ID NO: 45          moltype = AA  length = 429
FEATURE                Location/Qualifiers
REGION                 1..429
                       note = mutant D-fructose C4-epimerase
source                 1..429
                       mol_type = protein
                       organism = synthetic construct
SEQUENCE: 45
MMFGSPAPLL DMVTAQKQGM ARGIPSICSA HPVVLSAACH LARRSGAPLL IETTCNQVNH  60
QGGYSGMTPA DFVRFLREIL EREGIPPQQV ILGGDHLGPY PWRKEPAETA IAQALEMVRA  120
YVQAGYTKIH LDASMPCADD DPERPLPLER IARRAAQLCA AAEAAAGAVQ PVYVIGSEVP  180
PPGGAQGQEA RLHVTTPQEA QAALDAFREA FLQAGLTPVW ERVIALVVQP GVEFGVDSIH  240
AYQREAARPL KTFIEGVPGM VYEAHSTDYQ TRASLRALVE DHFSILKVGP ALTFAYREAV  300
FALEHIEREI LGRQDMPLSR LSEVLDEVML NDPRHWQGYF AGAPAEQALA RRYSFSDRIR  360
FYWHHPAAQE AVRRLLANLI ETPPPLSLLS QYLPREYEMV RAGEISSHPQ DLIRAHIQHT  420
LEDYAAACG                                                          429

SEQ ID NO: 46          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 46
MWLSKDYLRK KGVYSICSSN SYVIEASIEF AKEKGDYILI EATPHQVNQF GGYSGMTPED  60
FKNFVMKIAK EKGLPEDKII LGGDHLGPLP WQDEPAETAM NKAKDLIRAF VEAGYKKIHI  120
DCSMPLSDDP KVLPYEKIAE RTRELFEIAE ETARKYNFQA VYVVGTDVPI AGGGEEEGVT  180
SVEDFRSTLS VLKKAFKDLP NIWDRVVGFV IMLGIGFSYD KVFEYDRDKV REIMEEVKRE  240
DLFVEAHSTD YQDRYALRAM VEDGVRILKV GPALTAAFRR GVFLLSNIED EIIPERERSN  300
IKRVILETML RDDRYWRKYY KDSKRLELDI WYSLLDRIRY YWEYEDVKMV LNKLFENFSE  360
GVDIKFIYQY FYDQYFDVRE GKMKNDPREL IKKEIKRVLE DYSYAINL                408

SEQ ID NO: 47          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 47
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSETAM NKAKDLIRAF VEAGYKKIHI  120
DCSMPLSDDP KVLPLEKIAE RTVELFKIAE ETARKYNFQP VYVVGTDVPI AGGGEEEGVT  180
SPEDFRSAIS YLKKYFNDIP NIWDRVVGFV IMLGIGFSYD KVFEYDRDKV REILEEVKRE  240
DLFVEAHSTD YQARYALRNM VEDGVRILKV GPALTAAFRR AVFLLSNIED EIIPERERSN  300
IKRVILETML RDDRYWRKYY KDSKRLEFDI WYNLLDRIRY YWEYEDVKMV LNKLFENFSE  360
GVDIKFIYQY FYDSYFDVRE GKMKNDPREL IKKEIKRVLE DYAYAINL                408

SEQ ID NO: 48          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 48
MWLSKDYLRK KGVYSICSSN SYVIEASIEF AKEKGDYILI EATPHQVNQF GGYSGMTPED  60
FKNFVMKIAK ELGLEEDKII LGGDHLGPLP WQDEPAETAM NKAKDLIRAF VEAGYKKIHI  120
DCSMPLSDDP KVLPYEKIAE RTAELFEIAE EAARKYNFQA VYVVGTDVPI AGGGEEEGVT  180
SVEDFRSMIS TLKKYFNDVP NIWDRVVGFV IMLGIGFSYD KVFEYDRDKV RKILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKKV LNKLFENFSE  360
GVDIKFIYQY FYDSYFDVRE GKMKNDPREL IKKEIKRVLE DYSYAINL                408

SEQ ID NO: 49          moltype = AA  length = 408
FEATURE                Location/Qualifiers
REGION                 1..408
                       note = mutant D-fructose C4-epimerase
source                 1..408
```

```
                         mol_type = protein
                         organism = synthetic construct
SEQUENCE: 49
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPAETAM NKAKDLIRAF VEAGYKKIHI  120
DCSMPLSDDP KVLPYEKIAE RTVELFEIAE ETARKYNFQP VYVVGTDVPI AGGGEEEGVT  180
SVEDFRSAIS TLKKYFNDVP NIWDRVVGFV IMLGIGFSYD KVFEYDRDKV RDILEEVKRE  240
DLFVEGHSTD YQSRYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDQYFDVRE GKLKNDPREL IKKEIKRVLE DYSYAINL              408

SEQ ID NO: 50            moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 50
MWLSKDYLRK KGVYSICSSN PYVIEASIEF AKEKGDYILI EATPHQVNQF GGYSGMTPED  60
FKNFVMKIAK EKGLPEDKII LGGDHLGPLP WQDEPEETAM NKAKDLIRAF VEAGYKKIHI  120
DCSMPLSDDP KVLPYEKIAE RTRELFEIAE ETARKYNFQP VYVVGTDVPI AGGGEEEGVT  180
SVEDFRSALS ILKKYFNDVP NIWDRVVGFV IMLGIGFSYD KVFEYDRDKV RELLEEVKRE  240
DLFVEGHSTD YQARYALRNM VEDGVRILKV GPALTAAFRR AVFLLSNIED EIIPERERSN  300
IKRVILETML RDDRYWRKYY KDSKRLELDI WYNLLDRIRY YWEYEDVKKV LNKLFENFSE  360
GVDIKFIYQY FYDSYFDVRE GKMKNDPREL IKKEIKRVLE DYSYAINL              408

SEQ ID NO: 51            moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 51
MWLSKDYLRK KGVYSICSSN PYVIEASIEF AKEKGDYILI EATPHQVNQF GGYSGMTPED  60
FKNFVMKIAK EKGLEEDKII LGGDHLGPLP WQDEPAPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV REILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKKA LNKLFENFSE  360
GVDIKFIYQY FYDSYFDVRE GKMKNDPREL IKKEIKRVLE DYSYAINL              408

SEQ ID NO: 52            moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 52
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPAETAM NKAKDLIRAF VESGYKKIHI  120
DCSMPLSDDP KVLPYEKIAE RTRELFEIAE ETARKYNFQP VYVVGTDVPI AGGGEEEGVT  180
SPEDFRSAIS TLKKYFNDVP NIWDRVVGFV IMLGIGFSYD KVFEYDRDKV REILEEVKRE  240
DLFVEGHSTD YQARYALRNM VEDGVRILKV GPALTAAFRR GVFLLANIED EIIPERERSN  300
IKRVILETML RDDRYWRKYY KDSKELELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 53            moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 53
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPAETAM NKAKDLIRAF VEAGYKKIHI  120
DCSMPLSDDP KVLPYEKIAE RTRELFEIAE ETARKYNFQE VYVVGTDVPI AGGGEEEGVT  180
SPEDFRSAIS ILKKYFNKVP NIWDRVVGFV IMLGIGFSYD KVFEYDRDKV RGILEEVKRE  240
DLFVEAHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 54            moltype = AA  length = 408
FEATURE                  Location/Qualifiers
REGION                   1..408
                         note = mutant D-fructose C4-epimerase
```

```
source                 1..408
                       mol_type = protein
                       organism = synthetic construct
SEQUENCE: 54
MWLSKDYLRK KGVYSICSSN SYVIEASIEF AKEKGDYILI EATPHQVNQF GGYSGMTPED  60
FKNFVMKIAK EKGLPEDKII LGGDHLGPLP WQDEPSETAM NKAKDLIRAF VESGYKKIHI  120
DCSMPLSDDP KVLPYEKIAE RTRELFEIAE ETARKYNFQP VYVVGTDVPI AGGGEEEGVT  180
SPEDFRSAIS SLKKYFKDVP NIWDRVVGFV IMLGIGFSYD KVFEYDRDKV RGILEEVKRE  240
DLFVEAHSTD YQSRYALRNM VEDGVRILKV GPALTAAFRR AVFLLVNIED EIIPERERSN  300
IKRVILETML RDDRYWRKYY KDSKRLELDI WYNLLDRIRY YWEYEDVKKV LNKLFENFSE  360
GVDIKFIYQY FPDSYFDVRE GKMKNDPREL IKKEIKRVLE DYYYAINL              408

SEQ ID NO: 55          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 55
MWLSKDYLRK KGVYSICSSN SYVIEASIEF AKEKGDYILI EATPHQVNQF GGYSGMTPED  60
FKNFVMKIAK EKGLPEDKII LGGDHLGPLP WQDEPSPTAM NKAKDLIRAF VEAGYKKIHI  120
DCSMPLSDDP KVLPYEKIAE RTRELCEIAE ETARKYNFQP VYVVGTDVPI AGGGEEEGVT  180
SVEDFRSAID SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKMV LNKLFENFSE  360
GVDIKFIYQY FPDSYFDVRE GKMKNDPREL IKKEIKRVLE DYSYAINL              408

SEQ ID NO: 56          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 56
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFRIAE ETARKYNFQP VYVVGTDVPI AGGGEEEGVT  180
SPEDFRSAIS LLKKYFNDVP NIWDRVVGFV IMLGIGFSYD KVFEYDRDKV RGILEEVKRE  240
DLFVEGHSTD YQARYALRNM VEDGVRILKV GPALTAAFRR AVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDQYFDVRE GKMKNDPREL IKKEIKRVLE DYSYAINL              408

SEQ ID NO: 57          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 57
MWLSKDYLRK KGVYSICSSN PYVIEASIEF AKEKGDYILI EATPHQVNQF GGYSGMTPED  60
FKNFVMKIAK EKGLEEDKII LGGDHLGPLP WQDEPSETAM NKAKDLIRAF VESGYKKIHI  120
DCSMPLSDDP KVLPLEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYPDVKMV LNKLFENFSE  360
GVDIKFIYQY FYDSYFDVRE GKMKNDPREL IKKEIKRVLE DYSYAINL              408

SEQ ID NO: 58          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 58
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NAWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FPDSYFDVRE GKMKNDPREL IKKEIKRVLE DYSYAINL              408

SEQ ID NO: 59          moltype = AA  length = 408
FEATURE                Location/Qualifiers
REGION                 1..408
```

note = mutant D-fructose C4-epimerase
source 1..408
mol_type = protein
organism = synthetic construct
SEQUENCE: 59
MWLSKDYLRK KGVYSICSSN SYVIEASIEF AKEKGDYILI EATPHQVNQF GGYSGMTPED 60
FKNFVMKIAK EKGLPEDKII LGGDHLGPLP WQDEPSETAM NKAKDLIRAF VESGYKKIHI 120
DCSMPLSDDP KVLPPEKIAE RTRELFEIAE ETARKYNFQP VYVVGTDVPI AGGGEEEGVT 180
SVEDFRSAIS LLKKYFEDVP NIWDRVVGFV IMLGIGFSYD KVFEYDRDKV RGILEEVKRE 240
DLFVEGHSTD YQARYALRNM VEDGVRILKV GPALTAAFRR GVFLLSNIED EIIPERERSN 300
IKRVILETML RDDRYWRKYY KDSKRLELDI WYNLLDRIRY YWEYEDVKMV LNKLFENFSE 360
GVDIKFIYQY FYDSYFDVRE GKMKNDPREL IKKEIKRVLE DYSYAINL 408

SEQ ID NO: 60 moltype = AA length = 408
FEATURE Location/Qualifiers
REGION 1..408
note = mutant D-fructose C4-epimerase
source 1..408
mol_type = protein
organism = synthetic construct
SEQUENCE: 60
MWLSKDYLRK KGVYSICSSN SYVIEASIEF AKEKGDYILI EATPHQVNQF GGYSGMTPED 60
FKNFVMKIAK EKGLEEDKII LGGDHLGPLP WQDEPSPTAM NKAKDLIRAF VEAGYKKIHI 120
DCSMPLSDDP KVLPYEKIAE RTRELFEIAE ETARKYNFQP VYVVGTDVPI AGGGEEEGVT 180
SVEDFRSAIS SLKKYFNDVP NIWDRVVGFV IMLGIGFSYD KVFEYDRDKV RGILEEVKRE 240
DLFVEGHSTD YQARYALRNM VEDGVRILKV GPALTAAFRR GVFLLSNIED EIIPERERSN 300
IKRVILETML RDDRYWRKYY KDSKRLELDI WYSLLDRIRY YWEYEDVKMV LNKLFENFSE 360
GVDIKFIYQY FYDSYFDVRE GKMKNDPREL IKKEIKRVLE DYSYAINL 408

SEQ ID NO: 61 moltype = AA length = 408
FEATURE Location/Qualifiers
REGION 1..408
note = mutant D-fructose C4-epimerase
source 1..408
mol_type = protein
organism = synthetic construct
SEQUENCE: 61
MWLSKDYLRK KGVYSICSSN SYVIEASIEF AKEKGDYILI EATPHQVNQF GGYSGMTPED 60
FKNFVMKIAK EKGLEEDKII LGGDHLGPLP WQDEPSPTAM NKAKDLIRAF VESGYKKIHI 120
DCSMPLSDDP KVLPYEKIAE RTAELFEIAE ETARKYNFQP VYVVGTDVPI AGGGEEEGVT 180
SPEDFRSAIS SLKKYFNDVP NIWDRVVGFV IMLGIGFSYD KVFEYDRDKV RGILEEVKRE 240
DLFVEGHSTD YQARYALRNM VEDGVRILKV GPALTAAFRR GVFLLSNIED EIIPERERSN 300
IKRVILETML RDDRYWRKYY KDSKRLELDI WYNLLDRIRY YWEHPDVKMV LNKLFENFSE 360
GVDIKFIYQY FYDSYFDVRE GKMKNDPREL IKKEIKRVLE DYSYAINL 408

SEQ ID NO: 62 moltype = AA length = 408
FEATURE Location/Qualifiers
REGION 1..408
note = mutant D-fructose C4-epimerase
source 1..408
mol_type = protein
organism = synthetic construct
SEQUENCE: 62
MWLSKDYLRK KGVYSICSSN SYVIEASIEF AKEKGDYILI EATPHQVNQF GGYTGMTPED 60
FKNFVMKIAK EKGLEEDKII LGGDHLGPLP WQDEPAPTAM NKAKDLIRAF VESGYKKIHI 120
DCSMPLSDDP KVLPYEKIAE RTAELFEIAE ETARKYNFQP VYVVGTDVPI AGGGEEEGVT 180
SVEDFRSMIS VLKKYFNDVP NIWDRVVAFV IMLGIGFSYD KVFEYDRDKV REILEEVKRT 240
DLFVEGHSTD YQSRYALRNM VEDGVVILKV GPALTAAFRR GVFLLANIED EIIPERERSN 300
IKRVILETML RDDRYWRKYY KDSKELELDL WYNLLDRIRY YWEYPDVKMV LNKLFENFSE 360
GVDIKFIYQY FYDSYRDVRE GKMKNDPREL IKKEIKRVLE DYSYAINL 408

SEQ ID NO: 63 moltype = AA length = 408
FEATURE Location/Qualifiers
REGION 1..408
note = mutant D-fructose C4-epimerase
source 1..408
mol_type = protein
organism = synthetic construct
SEQUENCE: 63
MWLSKDYLRK KGVYSICSSN SYVIEASIEF AKEKGDYILI EATPHQVNQF GGYTGMTPED 60
FKNFVMKIAK EKGLEEDKII LGGDHLGPLP WQDEPAETAM EKAKDLIRAF VEAGYKKIHI 120
DCSMPLSDDP KVLPYEKIAE RTAELFEIAE ETARKYNFQP VYVVGTDVPI AGGGEEEGVT 180
SVEDFRSAIS SLKKYFNDVP NIWDRVVGFV IMLGIGFSYD KVFEYDRDKV REILEEVKRE 240
DLFVEAHSTD YQARYALRNM VEDGVRILKV GPALTAAFRR AVFLLSNIED EIIPPEERSN 300
IKRVILETML RDDRYWRKYY KDSKRLELDI WYNLLDRIRY YWEYEDVKMV LNKLFENLSD 360
GVDIKFIYQY FYDSYFDVRE GKLKNDPREL IKKEIKRVLE DYSYAINL 408

SEQ ID NO: 64 moltype = AA length = 408
FEATURE Location/Qualifiers

-continued

```
REGION                  1..408
                        note = mutant D-fructose C4-epimerase
source                  1..408
                        mol_type = protein
                        organism = synthetic construct
SEQUENCE: 64
MWLSKDYLRK KGVYSICSSN SYVIEASIEF AKERGDYILI EATPHQVNQF GGYTGMTPED  60
FKNFVMKIAK EKGLEEDKII LGGDHLGPLP WQDEPAPTAM NKAKDLIRAF VEAGYKKIHI  120
DCSMPLSDDP KVLPYEKIAE RTRELFEIAE ETARKYNFQP VYVVGTDVPI AGGGEEEGVT  180
SVEDFRSTIS SLKKYFKDVP NIWDRVVGFV IMLGIGFSYD KVFEYDRDKV RGILEEVKRE  240
DLFVEAHSTD YQARYALRNM VEDGVRILKV GPALTAAFRR GVFLLSDIED EIIPERERSN  300
IKRVILETML RDDRYWRKYY KDSKRLELDI WYNLLDRIRY YWEYEDVKMA LNKLFENFSE  360
GVDIKFIYQY FYDSYFDVRE GKMKNDPREL IKKEIKRVLE DYSYAINL                408

SEQ ID NO: 65           moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 65
MWLSKDYLRK KGVYSICSSN PYVIEASIEF AKEKGDYILI EATPHQVNQF GGYTGMTPED  60
FKNFVMKIAK EKGLEEDKII LGGDHLGPLP WQDEPAPTAM NKAKDLIRAF VEAGYKKIHI  120
DCSMPLSDDP KVLPYEKIAE RTAELFEIAE ETARKYNFQP VYVVGTDVPI AGGGEEEGVT  180
SVEDFRSAIS ILKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKRV LNKLFENFSE  360
GVDIKFIYQY FYDSYFDVRE GKMKNDPREL IKKEIKRVLE DYSYAINL                408

SEQ ID NO: 66           moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 66
MWLSKDYLRK KGVYSICSSN SYVIEASIEF AKERGDYILI EATPHQVNQF GGYSGMTPED  60
FKNFVMKIAK EKGLEEDKII LGGDHLGPLP WQDEPSETAM NKAKDLIRAF VEAGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV REILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL                408

SEQ ID NO: 67           moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 67
MWLSKDYLRK KGVYSICSSN SYVIEASIEF AKEKGDYILI EATPHQVNQF GGYTGMTPED  60
FKNFVMKIAK EKGLPEDKII LGGDHLGPLP WQDEPAETAM NKAKDLIRAF VEAGYKKIHI  120
DCSMPCADDP KVLPYEKIAE RTVELFEIAE ETARKYNFQP VYVVGTDVPI AGGGEEEGVT  180
SPEDFRSTIS TLKKYFKDHP NIWDRVVAFV IMLGIGFSYD KVFEYDRDKV REILEEVKRE  240
DLFVECHSTD YQSRYALRNM VEDGVVILKV GPALTAAFRR AVFLLSDIED EIIPERERSN  300
IKRVILETML RDDRYWRKYY KDSKRLELDI WYNLLDRIRY YWEYPDVKMA LNKLFENFSD  360
GIDIKFIYQY FYDSYRDVRE GKMKNDPREL IKKEIKRVLE DYSYAINL                408

SEQ ID NO: 68           moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 68
MWLSKDYLRK KGVYSICSSN SYVIEASIEF AKEKGDYILI EATPHQVNQF GGYTGMTPED  60
FKNFVMKIAK EKGLPEDKII LGGDHLGPLP WQDEPAPTAM NKAKDLIRAF VEAGYKKIHI  120
DCSMPLSDDP KVLPYEKIAI RTRELFRIAE ETARKYNFQP VYVVGTDVPI AGGGEEEGVT  180
SVEDFRSMIS TLKKYFNDVP NIWDRVVGFV IMLGIGFSYD KVFEYDRDKV RGILEEVKRE  240
DLFVEGHSTD YQARYALRWM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSD  360
GVDIKFIYQY FYDAYFDVRE GKMKPDPREL IKKEIKRVLE DYSYAINL                408

SEQ ID NO: 69           moltype = AA  length = 408
```

-continued

```
FEATURE                Location/Qualifiers
REGION                 1..408
                       note = mutant D-fructose C4-epimerase
source                 1..408
                       mol_type = protein
                       organism = synthetic construct
SEQUENCE: 69
MWLSKDYLRK KGVYSICSSN PYVIEASIEF AKEKGDYILI EATPHQVNQF GGYTGMTPED  60
FKNFVMKIAK EKGLEEDKII LGGDHLGPLP WQDEPAETAM NKAKDLIRAF VESGYKKIHI  120
DCSMPLSDDP KVLPYEKIAE RTRELFEIAE ETARKYNFQP VYVVGTDVPI AGGGEEEGVT  180
SPEDFRSAIS SLKKYFNDVP NIWDRVVAFV IMLGIGFSYD KVFEYDRDKV RGILEEVKRT  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDCYFDVRE GKMKNDPREL IKKEIKRVLE DYSYAINL              408

SEQ ID NO: 70          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 70
MWLSKDYLRK KGVYSICSSN PYVIEAAIEF AKEKGDYILI EATPHQVNQF GGYTGMTPED  60
FKNFVMKIAK EKGLEEDRII LGGDHLGPLP WQDEPSDEAM EKAKDLIRAF VEAGYKKIHI  120
DCSMPCADDP KVLPYEKIAE RTRELFRIAE ETARKYNFQP VYVVGTDVPI AGGGEEEGVT  180
SPEDFRSTIS TLKKYFEDHP NMWDRVVGFV IMLGVGFSHD KVFEYDRDKV RDILEEVKRT  240
DLFVEGHSTD YQARYALRNM VEDGVRILKV GPWLTAAFRR AVFLLSNIED EIIPERERSN  300
IKRVILETML RDDRYWRKYY KDSKRLELDI WYNLLDRIRY YWEHPDVKMA LNKLFENFSE  360
GVPIKFIYQY FYDCYFDVRE GKMKNDPREL IKKEIKRVLE DYSYAINL              408

SEQ ID NO: 71          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 71
MWLSKDYLRK KGVYSICSSN SYVIEAAIEF AKEDGDPILI EATPHQVNQF GGYTGMTPED  60
FKNFVMKIAK EKGLPEDKII LGGDHLGPLP WQDEPSPTAM NKAKDLIRAF VEAGYKKIHI  120
DCSMPCADDP KVLPYEKIAE RTRELCEIAE ETARKYNFQP VYVVGTDVPI AGGGEEEGVT  180
SVEDFRSAIS SLKKYFNDVP NIWDRVVGFV IMLGIGFSHD KVFEYDRDKV RGILEEVKRE  240
DLFVEGHSTD YQARYALRWM VEDGVVILKV GPALTAAFRR GVFLLSNIED EIIPERERSN  300
IKRVILETML RDDRYWRKYY KDSKRLELDI WYSLLDRIRY YWEYPDVKMA LNKLFENFSE  360
GVPIKFIYQY FYDSYFDVRE GKMKNDPREL IKKEIKRVLE DYSYAINL              408

SEQ ID NO: 72          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 72
MWLSKDYLRK KGVYSICSSN PYVIEASIEF AKEKGDYILI EATPHQVNQF GGYSGMTPED  60
FKNFVMKIAK EKGLEEDKII LGGDHLGPLP WQDEPSPTAM NKAKDLIRAF VEAGYKKIHI  120
DCSMPLADDP KVLPYEKIAE RTRELFEIAE RTARKYNFQP VYVVGTDVPI AGGGEEEGVT  180
SVEDFRSTIS SLKKYFNDVP NIWDRVVGFV IMLGIGFSYD KVFEYDRDKV RDILEEVKRT  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKMA LNKLFENLSE  360
GVDIKLIYQY FYDSYFDVRE GKMKNDPREL IKKEIKRVLE DYSYAINL              408

SEQ ID NO: 73          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 73
MWLSKDYLRK KGVYSICSSN PYVIEASIEF AKEKGDPILI EATPHQVNQF GGYSGMTPED  60
FKNFVMKIAK EKGLEEDKII LGGDHLGPLP WQDEPSPEAM NKAKDLIRAF VESGYKKIHI  120
DCSMPLSDDP KVLPYEKIAE RTRELCEIAE ETARKYNFQP VYVVGTDVPI AGGGEEEGVT  180
SVEDFRSTIS SLKKYFNDVP NIWDRVVGFV IMLGIGFSHD KVFEYDRDKV RGILEEVKRE  240
DLFVEGHSTD YQARYALRWM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVPIKFIYQY FYDSYFDVRE GKMKNDPREL IKKEIKRVLE DYSYAINL              408
```

-continued

SEQ ID NO: 74 moltype = AA length = 408
FEATURE Location/Qualifiers
REGION 1..408
note = mutant D-fructose C4-epimerase
source 1..408
mol_type = protein
organism = synthetic construct
SEQUENCE: 74
MWLSKDYLRK KGVYSICSSN SWVIEASIEF AKEKGDYILI EATPHQVNQF GGYTGMTPED 60
FKNFVMKIAK EKGLEEDKII LGGDHLGPLP WQDEPSPTAM NKAKDLIRAF VESGYKKIHI 120
DCSMPCSDDP KVLPYEKIAE RTRELFEIAE RTARKYNFQP VYVVGTDVPI AGGGEEEGVT 180
SPEDFRSTIS SLKKYFNDVP NIWDRVVGFV IMLGIGFSHD KVFEYDRDKV REILEEVKRE 240
DLFVEGHSTD YQARYALRNM VEDGVRILKV GPALTAAFRR GVFLLSNIED EIIPERERSN 300
IKRVILETML RDDRYWRKYY KDSKRLELDI WYNLLDRIRY YWEYPDVKMA LNKLFENLSE 360
GVDIKFIYQY FYDSYFDVRE GKMKNDPREL IKKEIKRVLE DYSYAINL 408

SEQ ID NO: 75 moltype = AA length = 408
FEATURE Location/Qualifiers
REGION 1..408
note = mutant D-fructose C4-epimerase
source 1..408
mol_type = protein
organism = synthetic construct
SEQUENCE: 75
MWLSKDYLRK KGVYSICSSN SYVIEASIEF AKEKGDYILI EATPHQVNQF GGYSGMTPED 60
FKNFVMKIAK EKGLEEDKII LGGDHLGPLP WQDEPSETAM EKAKDLIRAF VEAGYKKIHI 120
DCSMPLADDP KVLPYEKIAE RTRELFEIAE ETARKYNFQP VYVVGTDVPI AGGGEEEGVT 180
SVEDFRSAIS SLKKYFNDHP NIWDRVVGFV IMLGIGFSHD KVFEYDRDKV RGILEEVKRT 240
DLFVEGHSTD YQARYALRWM VEDGVRILKV GPALTAAFRR GVFLLSNIED EIIPERERSN 300
IKRVILETML RDDRYWRKYY KDSKRLELDI WYNLLDRIRY YWEHEDVKMV LNKLFENFSE 360
GVDIKFIYQY FYDSYFDVRE GKMKNDPREL IKKEIKRVLE DYSYAINL 408

SEQ ID NO: 76 moltype = AA length = 408
FEATURE Location/Qualifiers
REGION 1..408
note = mutant D-fructose C4-epimerase
source 1..408
mol_type = protein
organism = synthetic construct
SEQUENCE: 76
MWLSKDYLRK KGVYSICSSN SYVIEAAIEF AKEKGDYILI EATPHQVNQF GGYTGMTPED 60
FKNFVMKIAK EKGLPEDKII LGGDHLGPLP WQDEPSPEAM EKAKDLIRAF VEAGYKKIHI 120
DCSMPLSDDP KVLPYEKIAE RTRELFEIAE ETARKYNFQP VYVVGTDVPI AGGGEEEGVT 180
SVEDFRSTIS SLKKYFNDVP NIWDRVVGFV IMLGIGFSYD KVFEYDRDKV RGILEEVKRT 240
DLFVEGHSTD YQARYALRNM VEDGVRILKV GPALTAAFRR GVFLLSNIED EIIPERGRSN 300
IKRVILETML RDDRYWRKYY KDSKRLELDI WYNLLDRIRY YWEYEDVKMA LNKLFENFSE 360
GVDIKFIYQY FYDSYFDVRE GKMKNDPREL IKKEIKRVLE DYSYAINL 408

SEQ ID NO: 77 moltype = AA length = 408
FEATURE Location/Qualifiers
REGION 1..408
note = mutant D-fructose C4-epimerase
source 1..408
mol_type = protein
organism = synthetic construct
SEQUENCE: 77
MWLSKDYLRK KGVFSICSSN SYVIEASIEF AKEKGDYILI EATPHQVNQF GGYSGMTPED 60
FKNFVMKIAK EKGLEEDKII LGGDHLGPLP WQDEPSETAM NKAKDLIRAY VESGFKKIHI 120
DCSMPLSDDP KVLPMEKIAE RTAELFKIAE ETARKYNFQP VYVVGTDVPI AGGGEEEGVT 180
SVEDFRSAIS YLKKYFNDVP NIWDRVVGFV IMLGIGFSYD KVFEYDRDKV RGILEEVKRE 240
DLFVEAHSTD YQARYALRNM VEDGVRILKV GPALTAAFRR AVFLLSNIED EIIPERERSN 300
IKRVILETML RDDRYWRKYY KDSKRLEFDI WYNLLDRIRY YWEYEDVKKV LNKLFENFSE 360
GVDIKFIYQY FYDSYFDVRE GKMKNDPREL IKKEIKRVLE DYAYAINL 408

SEQ ID NO: 78 moltype = AA length = 408
FEATURE Location/Qualifiers
REGION 1..408
note = mutant D-fructose C4-epimerase
source 1..408
mol_type = protein
organism = synthetic construct
SEQUENCE: 78
MWLSKDYLRK KGVYSICSSN SYVIEASIEF AKEKGDYILI EATPHQVNQF GGYSGMTPED 60
FKNFVMKIAK EKGLEEDKII LGGDHLGPLP WQDEPSETAM NKAKDLIRAF VEAGYKKIHI 120
DCSMPLSDDP KVLPYEKIAE RTRELFEIAE ETARKYNFQP VYVVGTDVPI AGGGEEEGVT 180
SPEDFRSFIS SLKKYFNDVP NIWDRVVGFV IMLGIGFSYD KVFEYDRDKV REILEELKRE 240
DLFVEGHSTD YQSRYALRNM VEDGVRILKV GPALTAAFRR GVFLLSNIED EIIPERERSN 300
IKRVILETML RDDRYWRKYY KDSKRLELDI WYNLLDRIRY YWEYEDVKTV LNKLFENFSE 360
GVDIKFIYQY FYDSYFDVRE GKLKNDPREL IKKEIKRVLE DYSYAINL 408

```
SEQ ID NO: 79          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 79
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPAETAM NKAKDLIRAF VEAGYKKIHI  120
DCSMPLSDDP KVLPYEKIAE RTRELFKIAE ETARKYNFQA VYVVGTDVPI AGGGEEEGVT  180
SAEDFRSAIS ILKKYFNDVP NIWDRVVGFV IMLGIGFSYD KVFEYDRDKV RDILEEVKRE  240
DLFVEAHSTD YQARYALRNM VEDGVRILKV GPALTAAFRR GVFLLANIED EIIPERERSN  300
IKRVILETML RDDRYWRKYY KDSKELELDI WYNLLDRIRY YWEYEDVKKV LNKLFENFSE  360
GVDIKFIYQY FYDSYFDVRE GKMKNDPREL IKKEIKRVLE DYSYAINL              408

SEQ ID NO: 80          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 80
MWLSKDYLRK KGVYSICSSN PYVIEASIEF AKEKGDYILI EATPHQVNQF GGYSGMTPED  60
FKNFVMKIAK EKGLPEDKII LGGDHLGPLP WQDEPSPTAM NKAKDLIRAF VESGYKKIHI  120
DCSMPLSDDP KVLPYEKIAE RTAELFEVAE ETARKYNFQP VYVVGTDVPI AGGGEEEGVT  180
SVEDFRSAIS ILKKYFNDVP NIWDRVVGFV IMLGIGFSYD KVFEYDRDKV RGILEEVKRE  240
DLFLEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYPDVKMV LNKLFENFSE  360
GVDIKFIYQY FYDSYFDVRE GKMKNDPREL IKKEIKRVLE DYSYAINL              408

SEQ ID NO: 81          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 81
MWLSKDYLRK KGVYSICSSN SYVIEASIEF AKEKGDYILI EATPHQVNQF GGYTGMTPED  60
FKNFVMKIAK ELGLEEDKII LGGDHLGPLP WQDEPSETAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSMIS TLKKYFNKVP NIWDRVVGFV IMLGIGFSYD KVFEYDRDKV REILEEVKRE  240
DLFVEGHSTD YQARYALRNM VEDGVRILKV GPALTAAFRR GVFLLSNIED EIIPERERSN  300
IKRVILETML RDDRYWRKYY KDSKELELDI WYNLLDRIRY YWEYEDVKMV LNKLFENFSE  360
GVDIKFIYQY FYDSYFDVRE GKMKNDPREL IKKEIKRVLE DYAYAINL              408

SEQ ID NO: 82          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 82
MWLSKDYLRK KGVYSICSNN SYVIEASIEF AKEKGDYILI EATPHQVNQF GGYSGMTPED  60
FKNFVMKIAK EVGLEEDKII LGGDHLGPLP WQDEPAETAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAID TLKKYFKDVP NIWDRVVGFV IMLGIGFSYD KVFEYDRDKV REILEEVKRE  240
DLFVEAHSTD YQARYALRNM VEDGVRILKV GPALTAAFRR AVFLLSNIED EIIPERERSN  300
IKRVILETML RDDRYWRKYY KDSKRLELDI WYNLLDRIRY YWEYEDVKMV LNKLFENFSE  360
GVDIKFIYQY FPDSYFDVRE GKMKNDPREL IKKEIKRVLE DYYYAINL              408

SEQ ID NO: 83          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 83
MWLSKDYLRK KGVYSICSSN KYVIEASIEF AKEKGDYILI EATPHQVNQF GGYSGMTPED  60
FKNFVMKIAK EKGLPEDKII LGGDHLGPLP WQDEPSETAM NKAKDLIRAF VEAGYKKIHI  120
DCSMPLSDDP KVLPYEKIAE RTVELFEIAE ETARKYNFQP VYVVGTDVPI AGGGEEEGVT  180
SVEDFRSAIS TLKKYFNDIP NIWDRVVAFV IMLGIGFSYD KVFEYDRDKV REILEEVKRE  240
DLFLEAHSTD YQARYALRAM VEDGVRILKV GPALTAAFRR AVFLLANIED EIIPERERSN  300
IKRVILETML RDDRYWRKYY KDSKRLELDI WYNLLDRIRY YWEYPDVKMV LNKLFENFSE  360
```

```
GVDIKFIYQY FPDQYFDVRE GKMKNDPREL IKKEIKRVLE DYSYAINL              408

SEQ ID NO: 84          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 84
MWLSKDYLRK KGVYSICSSN SYVIEAAIEF AKEKGDYILI EATPHQVNQF GGYSGMTPED  60
FKNFVMKIAK EKGLPEDKII LGGDHLGPLP WQDEPSPTAM NKAKDLIRAF VESGYKKIHI  120
DCSMPLSDDP KVLPLEKIAE RTRELFRIAE ETARKYNFQP VYVVGTDVPI AGGGEEEGVT  180
SPEDFRSAIE TLKKYFNDVP NIWDRVVGFV IMLGIGFSYD KVFEYDRDKV RGILEEVKRT  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKKV LNKLFENFSE  360
GVDIKFIYQY FYDQYFDVRE GKMKNDPREL IKKEIKRVLE DYSYAINL              408

SEQ ID NO: 85          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 85
MWLSKDYLRK KGVYSICSSN PYVIEAAIEF AKEKGDYILI EATPHQVNQF GGYSGMTPED  60
FKNFVMKIAK EKGLEEDKII LGGDHLGPLP WQDEPSETAM NKAKDLIRAF VEAGYKKIHI  120
DCSMPLSDDP KVLPTEKIAE RTRELFEIAE ETARKYNFQP VYVVGTDVPI AGGGEEEGVT  180
SVEDFRSAIS SFKKYFNDVP NIWDRVVGFV IMLGIGFSDD KVFEYDRDKV RGILEEVKRE  240
DLFVEGHSTD YQARYALRNM VEDGVRILKV GPALTAAFRR AVFLLANIED EIIPERERSN  300
IKRVILETML RDDRYWRKYY KDSKRLELDI WYNLLDRIRY YWEHPDVKMV LNKLFENFSE  360
GVDIKFIYQY FYDSYEDVRE GKMKNDPREL IKKEIKRVLE DYSYAINL              408

SEQ ID NO: 86          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 86
MWLSKDYLRK KGVYSICSSN SYVIEAAIEF AKEKGDYILI EATPHQVNQF GGYSGMTPED  60
FKNFVMKIAK EKGLPEDKII LGGDHLGPLP WQDEPAPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RDILEEVKRE  240
DLFVEGHSTD YQARYALRNM VEDGVRILKV GPALTAAFRR GVFLLANIED EIIPERERSN  300
IKRVILETML RDDRYWRKYY KDSKRLELDI WYNLLDRIRY YWEYPDVKMV LNKLFENFSE  360
GVDIKFIYQY FPDSYFDVRE GKMKNDPREL IKKEIKRVLE DYSYAINL              408

SEQ ID NO: 87          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 87
MWLSKDYLRK KGVYSICSSN SYVIEAAIEF AKEKGDYILI EATPHQVNQF GGYSGMTPED  60
FKNFVMKIAK EKGLEEDKII LGGDHLGPLP WQDEPSPTAM EKAKDLIRAF VEAGYKKIHI  120
DCSMPLSDDP KVLPPEKIAE RTRELFEIAE ETARKYNFQP VYVVGTDVPI AGGGEEEGVT  180
SVEDFREAIE SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKMV LNKLFENFSE  360
GVDIKFIYQY FYDSYFDVRE GKMKNDPREL IKKEIKRVLE DYSYAINL              408

SEQ ID NO: 88          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 88
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPAPTAM NKAKDLIRAF VESGYKKIHI  120
DCSMPLSDDP KVLPLEKIAE RTRELFEIAE RTARKYNFQP VYVVGTDVPI AGGGEEEGVT  180
SPEDFRSAID SLKKYFNDVP NIWDRVVGFV IMLGIGFSYD KVFEYDRDKV RDILEEVKRE  240
DLFVEGHSTD YQARYALRNM VEDGVRILKV GPALTAAFRR GVFLLSNIED EIIPERERSN  300
```

```
IKRVILETML RDDRYWRKYY KDSKRLELDI WYNLLDRIRY YWEYEDVKMV LNKLFENFSE  360
GVDIRFIYQY FYDSYFDVRE GKMKNDPREL IKKEIKRVLE DYSYAINL               408

SEQ ID NO: 89          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 89
MWLSKDYLRK KGVYSICSSN SYVIEAAIEF AKEKGDYILI EATPHQVNQF GGYSGMTPED  60
FKNFVMKIAK EKGLPEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRRAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR AVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 90          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 90
MWLSKDYLRK KGVYSICSSN SYVIEAAIEF AKEKGDYILI EATPHQVNQF GGYTGMTPED  60
FKNFVMKIAK EKGLEEDKII LGGDHLGPLP WQDEPAPTAM NKAKDLIRAF VESGYKKIHI  120
DCSMPLSDDP KVLPYEKIAE RTRELCEIAE ETARKYNFQP VYVVGTDVPI AGGGEEEGVT  180
SPEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKMA LNKLFENFSE  360
GVDIKFIYQY FYDSYFDVRE GKMKNDPREL IKKEIKRVLE DYAYAINL               408

SEQ ID NO: 91          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 91
MWLSKDYLRK KGVYSICSSN PWVIEASIEF AKEKGDYILI EATPHQVNQF GGYTGMTPED  60
FKNFVMKIAK EKGLPEDKII LGGDHLGPLP WQDEPSPTAM NKAKDLIRAF VEAGYKKIHI  120
DCSMPLSDDP KVLPYEKIAE RTRELFEIAE ETARKYNFQP VYVVGTDVPI AGGGEEEGVT  180
SPEDFRSAIS SLKKYFEDVP NIWDRVVGFV IMLGIGFSYD KVFEYDRDKV RGILEEVKRT  240
DLFVEVHSTD YQARYALRNM VEDGVRILKV GPALTAAFRR GVFLLANIED EIIPERERSN  300
IKRVILETML RDDRYWRKYY KDSKELELDL WYNLLDRIRY YWEHPDVKMV LNKLFENFSE  360
GVDIKFIYQY FYDSYRDVRE GKMKNDPREL IKKEIKRVLE DYSYAINL               408

SEQ ID NO: 92          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 92
MWLSKDYLRK KGVYSICSSN PYVIEASIEF AKEKGDYILI EATPHQVNQF GGYSGMTPED  60
FKNFVMKIAK EKGLPEDKII LGGDHLGPLP WQDEPAPTAM EKAKDLIRAF VESGYKKIHI  120
DCSMPLADDP KVLPYEKIAE RTRELFEIAE ETARKYNFQP VYVVGTDVPI AGGGEEEGVT  180
SVEDFRSTIS TLKKYFEDHP RIWDRVVAFV IMLGIGFSYD KVFEYDRDKV REILEEVKRT  240
DLFVECHSTD YQARYALRNM VEDGVRILKV GPALTAAFRR GVFLLADIED EIIPEEERSN  300
IKRVILETML RDDRYWRKYY KDSKRLELDI WYALLDRIRY YWEYEDVKRV LNKLFENFSE  360
GVDIKFIYQY FYDCYFDVRE GKMKNDPREL IKKEIKRVLE DYSYAINL               408

SEQ ID NO: 93          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 93
MWLSKDYLRK KGVYSICSSN SYVIEAAIEF AKEKGDYILI EATPHQVNQF GGYSGMTPED  60
FKNFVMKIAK EKGLEEDKII LGGDHLGPLP WQDEPSPTAM NKAKDLIRAF VEAGYKKIHI  120
DCSMPLSDDP KVLPYEKIAI RTAELFEIAE ETARKYNFQP VYVVGTDVPI AGGGEEEGVT  180
SPEDFRSMIS TLKKYFNDVP NIWDRVVGFV IMLGIGFSYD KVFEYDRDKV REILEEVKRE  240
```

```
DWFVEAHSTD YQPRYALRWM VEDGVRILKV GPALTAAFRR AVFLLSNIED EIIPERERSN  300
IKRVILETML RDDRYWRKYY KDSKELELDI WYALLDRIRY YWEYEDVKMA LNKLFENFSD  360
GVDIKFIYQY FYDSYFDVCE GKMKPDPREL IKKEIKRVLE DYSYAINL              408

SEQ ID NO: 94          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 94
MWLSKDYLRK KGVYSICSSN SYVIEASIEF AKEKGDYILI EATPHQVNQF GGYSGMTPED  60
FKNFVMKIAK EKGLPEDKII LGGDHLGPLP WQDEPAETAM NKAKDLIRAF VESGYKKIHI  120
DCSMPLADDP KVLPYEKIAE RTVELFEIAE ETARKYNFQP VYVVGTDVPI AGGGEEEGVT  180
SPEDFRSAIS TLKKYFNDCP NIWDRVVGFV IMLGIGFSYD KVFEYDRDKV RGILEELKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKAV LNKLFENLSE  360
GVDIKFIYQY FYDSYFDVRE GKMKNDPREL IKKEIKRVLE DYSYAINL              408

SEQ ID NO: 95          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 95
MWLSKDYLRK KGVYSICSSN PYVIEAAIEF AKEKGDYILI EATPHQVNQF GGYSGMTPED  60
FKNFVMKIAK EKGLEEDKII LGGDHLGPLP WQDEPSETAM NKAKDLIRAF VEAGYKKIHI  120
DCSMPLADDP KVLPYEKIAE RTRELFEIAE EAARKYNFQP VYVVGTDVPI AGGGEEEGVT  180
SVEDFRSMIS VLKKYFNDVP NIWDRVVGFV IMLGIGFSYD KVFEYDRDKV REILEEVKRE  240
DLFVEGHSTD YQARYALRNM VEDGVVILKV GPWLTAAFRR GVFLLADIED EIIPERERSN  300
IKRVILETML RDDRYWRKYY KDSKRLELDI WYALLDRIRY YWEYPDVKKV LNKLFENFSE  360
GIDIKFIYQY FYDSYFDVRE GKMKNDPREL IKKEIKRVLE DYSYAINL              408

SEQ ID NO: 96          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 96
MWLSKDYLRK KGVYSICSSN SYVIEASIEF AKEKGDYILI EATPHQVNQF GGYTGMTPED  60
FKNFVMKIAK EKGLPEDKII LGGDHLGPLP WQDEPAETAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSTIS SLKKYFNDVP NIWDRVVGFV IMMGIGFSYD KVFEYDRDKV REILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKMV LNKLFENFSE  360
GVDIKFIYQY FYDCYFDVRE GKMKNDPREL IKKEIKRVLE DYSYAINL              408

SEQ ID NO: 97          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 97
MWLSKDYLRK KGVYSICSSN SYVIEASIEF AKEKGDYILI EATPHQVNQF GGYTGMTPED  60
FKNFVMKIAK EKGLEEDKII LGGDHLGPLP WQDEPSETAM NKAKDLIRAF VESGYKKIHI  120
DCSMPLADDP KVLPYEKIAE RTAELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYPDVKKA LNKLFENFSE  360
GVDIKFIYQY FYDSYFDVRE GKMKNDPREL IKKEIKRVLE DYSYAINL              408

SEQ ID NO: 98          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 98
MWLSKDYLRK KGVYSICSSN SWVIEASIEF AKEDGDPILI EATPHQVNQF GGYTGMTPED  60
FKNFVMKIAK EKGLPEDKII LGGDHLGPLP WQDEPSPTAM NKAKDLIRAF VEAGYKKIHI  120
DCSMPLSDDP KVLPYEKIAE RTRELCEIAE ETARKYNFQP VYVVGTDVPI AGGGEEEGVT  180
```

```
SVEDFRSTIS SLKKYFNDVP NIWDRVVGFV IMLGIGFSYD KVFEYDRDKV RDILEEVKRE  240
DLFVEGHSTD YQARYALRNM VEDGVAILKV GPALTAAFRR GVFLLANIED EIIPEEERSN  300
IKRVILETML RDDRYWRKYY KDSKRLELDI WYNLLDRIRY YWEHPDVKMV LNKLFENFSE  360
GVDIKFIYQY FYDSYFDVRE GKMKNDPREL IKHEIKRVLE DYSYAINL               408

SEQ ID NO: 99          moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 99
MWLSKDYLRK KGVYSICSSN PWVIEAAIEF AKEKGTYILI EATPHQVNQF GGYTGMTPED  60
FKNFVMKIAK EKGLPEDKII LGGDHLGPLP WQDEPSEEAM NKAKDLIRAF VESGYKKIHI  120
DCSMPLADDP KVLPYEKIAE RTRELFRIAE ETARKYNFQP VYVVGTDVPI AGGGEEEGVT  180
SVEDFRSAIS LLKKYFEDHP NIWDRVVGFV IMLGIGFSYD KVFEYDRDKV REILEEVKRE  240
PLFVEGHSTD YQAREALRNM VEDGVRILKV GPALTAAFRR GVFLLSDIED EIIPERERSN  300
IKRVILETML RDDRYWRKYY KDSKRLELDI WYNLLDRIRY YWEHEDVKMA LNKLFENFSE  360
GVDITFIYQY FYDCYFDVRE GKMKNDPREL IKKEIKRVLE DYSYAINL               408

SEQ ID NO: 100         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 100
MWLSKDYLRK KGVYSICSSN PYVIEAAIEF AKEKGDYILI EATPHQVNQF GGYSGMTPED  60
FKNFVMKIAK EKGLPEDKII LGGDHLGPLP WQDEPSETAM EKAKDLIRAF VEAGYKKIHI  120
DCSMPLSDDP KVLPYEKIAE RTRELFKIAE ETARKYNFQP VYVVGTDVPI AGGGEEEGVT  180
SPEDFRSTIE SLKKYFNDVP NIWDRVVGFV IMLGIGFSHD KVFEYDRDKV RGILEEVKRE  240
DLFVEGHSTD YQARDALRNM VEDGVRILKV GPALTAAFRR AVFLLSNIED EIIPERERSN  300
IKRVILETML RDDRYWRKYY KDSKRLELDI WYNLLDRIRY YWNHEDVKMA LNKLFENFSD  360
GVDIKFIYQY FYDSYFDVRE GKMKNDPREL IKHEIKRVLE DYSYAINL               408

SEQ ID NO: 101         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 101
MWLSKDYLRK KGVYSICSSN SWVIEASIEF AKEKGSYILI EATPHQVNQF GGYSGMTPED  60
FKNFVMKIAK EKGLPEDKII LGGDHLGPLP WQDEPSDTAM EKAKDLIRAF VEAGYKKIHI  120
DCSMPCADDP KVLPYEKIAE RTRELFEIAE ETARKYNFQP VYVVGTDVPI AGGGEEEGVT  180
SPEDFRSAIS SLKKYFNDVP NIWDRVVGFV IMLGIGFSHD KVFEYDRDKV RGILEEVKRE  240
PLFVEGHSTD YQSRDALRNM VEDGVRILKV GPALTAAFRR GVFLLANIED EIIPEEERSN  300
IKRVILETML RDDRYWRKYY KDSKRLELDI WYNLLDRIRY YWNYPDVKMV LNKLFENFSE  360
GVDITFIYQY FYDSYRDVRE GKMKNDPREL IKKEIKRVLE DYSYAINL               408

SEQ ID NO: 102         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 102
MWLSKDYLRK KGVYSICSSN SYVIEASIEF AKEKGDYILI EATPHQVNQF GGYTGMTPED  60
FRNFVMKIAK EKGLEEDKII LGGDHLGPLP WQDEPSETAM NKAKDLIRAF VEAGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV REILEEVKRT  240
DLFVEGHSTD YQARYALRWM VEDGVRILKV GPALTAAFRR GVFLLANIED EIIPERGRSN  300
IKRVILETML RDDRYWRKYY KDSKRLELDI WYNLLDRIRY YWEYEDVKMV LNKLFENFSE  360
GVDIKFIYQY FYDSYHDVRE GKMKNDPREL IKKEIKRVLE DYSYAINL               408

SEQ ID NO: 103         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 103
MWLSKDYLRK KGIYSICSSN PYVIEAAIEF AKEKGDYILI EATPHQVNQF GGYTGMTPED  60
FKNFVMKIAK EKGLPEDKII LGGDHLGPLP WQDEPSEEAM NKAKDLIRAF VESGYKKIHI  120
```

```
DCSMPCSDDP KVLPYEKIAE RTRELCRIAE ETARKYNFQP VYVVGTDVPI AGGGEEEGVT  180
SVEDFRSTIE SLKKYFNDVP NAWDRVVGFV IMLGIGFSYD KVFEYDRDKV RGILEEVKRE  240
PLFVEGHSTD YQARYALRWM VEDGVRILKV GPALTAAFRR AVFLLSNIED EIIPEEERSN  300
IKEVILETML RDDRYWRKYY KDSKRLELDI HYNLLDRIRY YWEYPDVKAA LNKLFENFSD  360
GVDIKFIYQY FYDAYHDVRE GKMKNDPREL IKKEIKRVLE DYSYAINL              408

SEQ ID NO: 104         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 104
MWLSKDYLRK KGVYSICSSN SYVIEAAIEF AKEKGDYILI EATPHQVNQF GGYSGMTPED  60
FKNFVMKIAK EKGLEEDKII LGGDHLGPLP WQDEPAPEAM EKAKDLIRAF VESGYKKIHI  120
DCSMPCSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSHD KVFEYDRDKV RGILEEVKRT  240
DLFVEGHSTD YQTRYALRNM VEDGVRILKV GPALTAAFRR GVFLLSNIED EIIPEYERSN  300
IKRVILETML RDDRYWRKYY KDSKRLELDI WYNLLDRIRY YWEHPDVKAV LNKLFENFSE  360
GVDIKLIYQY FYDSYFDVRE GKMKNDPREL IKKEIKRVLE DYSYAINL              408

SEQ ID NO: 105         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 105
MWLSKDYLRK KGVYSICSSN SYVIEAAIEF AKEKDDYILI EATPHQVNQF GGYSGMTPED  60
FKNFVMKIAK ELGLPEDKII LGGDHLGPLP WQDEPSETAM NKAKDLIRAY VEAGYKKIHI  120
DCSMPLSDDP KVLPMEKIAE RTRELFKIAE ETARKYNFQP VYVVGTDVPI AGGGEEEGVT  180
SVEDFRSAIS LLKKYFKDVP NIWDRVVGFV IMLGIGFSYD KVFEYDRDKV REILEEVKRE  240
DLFVEGHSTD YQARYALRNM VEDGVRILKV GPALTAAFRR AVFKLSNIED ELIPERERSN  300
IKRVILETML RDDRYWRKYY KDSKRLEFDI WYNLLDRIRY YWEYEDVKKV LNKLFENFSE  360
GVDIKFIYQY FPDSYKDVRE GKMKNDPREL IKKEIKRVLE DYSYAINL              408

SEQ ID NO: 106         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 106
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSETAM NKAKDLIRAF VESGYKKIHI  120
DCSMPLSDDP KVLPKEKIAE RTVELFEIAE ETARKYNFQP VYVVGTDVPI AGGGEEEGVT  180
SVEDFRSAIS SLKKYFNDVP NIWDRVVGFV IMLGIGFSYD KVFEYDRDKV RDILEELKRE  240
DLFVEGHSTD YQARYALRNM VEDGVRILKV GPALTAAFRR GVFLLANIEK EIIPERERSN  300
IKRVILETML RDDRYWRKYY KDSKRLELDI WYNLLDRIRY YWEHEDVKTV LNKLFENFSE  360
GVDIKFIYQY FYDSYFDVRE GKLKNDPREL IKKEIKRVLE DYSYAINL              408

SEQ ID NO: 107         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 107
MWLSKDYLRK KGVYSICSSN SYVIEAAIEF AKEKGDYILI EATPHQVNQF GGYSGMTPED  60
FKNFVMKIAK ELGLPEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS VFKKYFKDLP NIWDRVVGFV VMLGIGFSYD KVFEYDRDKV REILEEVKRE  240
DLFVEGHSTD YQARYALRNM VEDGVRILKV GPALTAAFRR GVFLLANIED EIIPERERSN  300
IKRVILETML RDDRYWRKYY KDSKRLELDI WYNLLDRIRY YWEYEDVKMV LNKLFENFSE  360
GVDIKFIYQY FYDQYFDVRE GKMKNDPREL IKKEIKRVLE DYSYAINL              408

SEQ ID NO: 108         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 108
MWLSKDYLRK KGVYSICSSN PYVIEAAIEF AKEKGDYILI EATPHQVNQF GGYTGMTPED  60
```

```
FKNFVMKIAK EVGLEEDRII LGGDHLGPLP WQDEPSETAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAID ILKKYFNKVP NIWDRVVGFV IMLGIGFSYD KVFEYDRDKV RGILEEVKRE  240
DLFVEGHSTD YQARYALRNM VEDGVRILKV GPALTAAFRR GVFLLANIED EIIPERERSN  300
IKRVILETML RDDRYWRKYY KDSKELELDI WYNLLDRIRY YWEYEDVKKV LNKLFENFSE  360
GVDIKFIYQY FYDSYFDVRE GKMKNDPREL IKKEIKRVLE DYSYAINL               408

SEQ ID NO: 109          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 109
MWLSKDYLRK KGVYSICSSN SYVIEAAIEF AKEKGDYILI EATPHQVNQF GGYSGMTPED  60
FKNFVMKIAK EKGLEEDKII LGGDHLGPLP WQDEPSPTAM NKAKDLIRAF VEAGYKKIHI  120
DCSMPLSDDP KVLPLEKIAE RTRELFEIAE ETARKYNFQP VYVVGTDVPI AGGGEEEGVT  180
SVEDFRSMID TLKKYFEDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKELELDI WYNLLDRIRY YWEYEDVKMV LNKLFENFSE  360
GVDIKFIYQY FYDSYQDVRE GKMKNDPREL IKKEIKRVLE DYSYAINL               408

SEQ ID NO: 110          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 110
MWLSKDYLRK KGVYSICSSN SYVIEAAIEF AKEKGDYILI EATPHQVNQF GGYSGMTPED  60
FKNFVMKIAK EKGLEEDKII LGGDHLGPLP WQDEPSPTAM EKAKDLIRAF VEAGYKKIHI  120
DCSMPLSDDP KVLPLEKIAE RTRELFKVAE ETARKYNFQP VYVVGTDVPI AGGGEEEGVT  180
SVEDFRSAIS SFKKYFKDVP NIWDRVVGFV IMLGIGFSYD KVFEYDRDKV RGILEEVKRT  240
DLFVEGHSTD YQDRKALRDM VEDGVRILKV GPALTAAFRR AVFLLANIEK EIIPERERSN  300
IKRVILETML RDDRYWRKYY KDSKRLELDI WYNLLDRIRY YWEYPDVKCV LNKLFENFSE  360
GVDIRFIYQY FYDQYFDVRE GKMKNDPREL IKKEIKRVLE DYSYAINL               408

SEQ ID NO: 111          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 111
MWLSKDYLRK KGVYSICSSN PYVIEAAIEF AKEKGDYILI EATPHQVNQF GGYTGMTPED  60
FKNFVMKIAK EKGLPEDKII LGGDHLGPLP WQDEPSETAM EKAKDLIRAF VESGYKKIHI  120
DCSMPLSDDP KVLPLEKIAE RTRELFEIAE ETARKYNFQP VYVVGTDVPI AGGGEEEGVT  180
SVEDFREAIE YLKKYFEDLP NIWDRVVGFV IMLGIGFSYD KVFEYDRDKV RDILEEVKRE  240
DLFVEGHSTD YQDRYALRNM VEDGVRILKV GPALTAAFRR GVFLLSNIED EIIPEDERSN  300
IKRVILETML RDDRYWRKYY KDSKRLELDI WYNLLDRIRY YWEHPDVKMV LNKLFENFSE  360
GVDIRFIYQY FYDSYFDVRE GKMKNDPREL IKKEIKRVLE DYSYAINL               408

SEQ ID NO: 112          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 112
MWLSKDYLRK KGVYSICSSN EYVIEASIEF AKEKGDYILI EATPHQVNQF GGYTGMTPED  60
FKNFVMKIAK EKGLEEDKII LGGDHLGPLP WQDEPAPTAM NKAKELIRAF VEAGYKKIHI  120
DCSMPLSDDP KVLPLEKIAE RTRELFEIAE ETARKYNFQP VYVVGTDVPI AGGGEEEGVT  180
SPEDFRSAIE ALKKYFNDVP NIWDRVVGFV IMLGIGFSYD KVFEYDRDKV RGILEEVKRT  240
DLFVEGHSTD YQTRYALRNM VEDGVRILKV GPALTAAFRR GVFLLANIED EIIPERERSN  300
IKRVILETML RDDRYWRKYY KDSKRLELDI WYNLLDRIRY YWEYEDVKMV LNKLFENFSE  360
GVDIRFIYQY FYDSYFDVRE GKMKNDPREL IKKEIKRVLE DYSYAINL               408

SEQ ID NO: 113          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 113
```

```
MWLSKDYLRK KGVYSICSSN EYVIEASIEF AKEKGDYILI EATPHQVNQF GGYTGMTPED  60
FKNFVMKIAK EKGLPEDKII LGGDHLGPLP WQDEPSPTAM EKAKDLIRAF VEAGYKKIHI  120
DCSMPLSDDP KVLPMEKIAE RTRELFKIAE ETARKYNFQP VYVVGTDVPI AGGGEEEGVT  180
SVEDFRSAIE SLKKYFNDVP NIWDRVVGFV IMLGIGFSYD KVFEYDRDKV RPILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEHEDVKKV LNKLFENFSE  360
GVDIRFIYQY FYDSYFDVRE GKMKNDPREL IKKEIKRVLE DYAYAINL               408

SEQ ID NO: 114         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 114
MWLSKDYLRK KGVYSICSSN SYVIEASIEF AKEKGDYILI EATPHQVNQF GGYTGMTPED  60
FKNFVMKIAK EKGLPEDKII LGGDHLGPLP WQDEPSETAM EKAKDLIRAF VEAGYKKIHI  120
DCSMPLSDDP KVLPTEKIAE RTRELFEVAE ETARKYNFQP VYVVGTDVPI AGGGEEEGVT  180
SVEDFREAIE SFKKYFNDVP NIWDRVVGFV IMLGIGFSDD KVFEYDRDKV RDIAEEVKRE  240
DLFVEGHSTD YQARYALRNM VEDGVRILKV GPALTAAFRR GVFLLANIED EIIPERKRSN  300
IKRVILETML RDDRYWRKYY KDSKRLRLDI WYNLLDRIRY YWEYEDVKMA LNRLFENFSE  360
GVDIKFIYQY FYDSYFDVRE GKMKNDPREL IKKEIKRVLE DYSYAINL               408

SEQ ID NO: 115         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 115
MWLSKDYLRK KGVYSICSSN SYVIEAAIEF AKEKGDYILI EATPHQVNQF GGYTGMTPED  60
FKNFVMKIAK EKGLPEDKII LGGDHLGPLP WQDEPSEEAM AKAKDLIRAF VEAGYKKIHI  120
DCSMPLADDP KVLPYEKIAE RTRELFEIAE ETARKYNFQP VYVVGTDVPI AGGGEEEGVT  180
SVEDFRSAIS VLKKYFKDLP NIWDRVVGFV IMMGIGFSYD KVFEYDRDKV REILEEVKRE  240
DLFVEAHSTD YQARYALRWM VEDGVRILKV GPALTAAFRR GVFLLADIED EIIPERERSN  300
IKRVILETML RDDRYWRKYY HDSKRLELDI WYSLLDRIRY YWEHPDVKAA LNKLFENFSE  360
GVDIKFIYQY FYDSYFDVRE GKMKNDPREL IKKEIKRVLE DYSYAINL               408

SEQ ID NO: 116         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 116
MWLSKDYLRK KGVYSICSSN PYVIEACIEF AKEKGDYILI EATPHQVNQF GGYTGMTPED  60
FKNFVMKIAK EKGLPEDKII LGGDHLGPLP WQDEPSPEAM NKAKDLIRAF VEAGYKKIHI  120
DCSMPLADDP KVLPYEKIAE RTRELFEIAE ETARKYNFQP VYVVGTDVPI AGGGEEEGVT  180
SPEDFRSFIS VLKKYFNDVP NIWDRVVGFV IMLGIGFSYD KVFEYDRDKV REILEEVKRE  240
DLFVEGHSTD YQSREALRNM VEDGVRILKV GPALTAAFRR GVFLLDNIEK DIIPERERSN  300
IKRVILETML RDDRYWRKYY KDSKRLELDI WYSLLDRIRY YWEHEDVKMA LNKLFENLSE  360
GIDIKLIYQY FYDTYFDVRE GKMKNDPREL IKKEIKRVLE DYSYAINL               408

SEQ ID NO: 117         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 117
MWLSKDYLRK KGVYSICSSN PYVIEASIEF AKEKDDYILI EATPHQVNQF GGYTGMTPED  60
FKNFVMKIAK EKGLEEDKII LGGDHLGPLP WQDEPSETAM NKAKDLIRAF VESGYKKIHI  120
DCSMPLSDDP KVLPQEKIAE RTAELFEIAE ETARKYNFQP VYVVGTDVPI AGGGEEEGVT  180
SVEDFRSTIS SLKKYFKDVP NIWDRVVGFV IMLGIGFSYD KVFEYDRDKV REILEEVKRE  240
DLFVEAHSTD YQARYALRNM VEDGVRILKV GPALTAAFRR AVFLLSDIED EIIPPRERSN  300
IKRVILETML RDDRYWRKYY KDSKRLEFDI WYALLDRIRY YWEYEDVKAV LNKLFENFSE  360
GVDIKFIYQY FPDSYFDVRE GKMKNDPREL IKKEIKRVLE DYSYAINL               408

SEQ ID NO: 118         moltype = AA  length = 408
FEATURE                Location/Qualifiers
REGION                 1..408
                       note = mutant D-fructose C4-epimerase
source                 1..408
                       mol_type = protein
                       organism = synthetic construct
```

```
SEQUENCE: 118
MWLSKDYLRK KGVYSICSSN PYVIEASIEF AKEKGDYILI EATPHQVNQF GGYSGMTPED  60
FKNFVMKIAK EKGLPEDKII LGGDHLGPLP WQDEPSEEAM AKAKDLIRAF VESGYKKIHI  120
DCSMPLSDDP KVLPYEKIAE RTVELFEIAE ETARKYNFQP VYVVGTDVPI AGGGEEEGVT  180
SPEDFRSAIS SLKKYFNDVP NIWDRVVAFV IMLGIGFSYD KVFEYDRDKV RGILEEVKRT  240
DLFVEVHSTD YQSRYALRNM VEDGVVILKV GPALTAAFRR GVFLLANIED EIIPERERSN  300
IKRVILETML RDDRYWRKYY HDSKDLELDI WYNLLDRIRY YWEHEDVKMV LNKLFENFSE  360
GVDIKLIYQY FYDSYFDVRE GKMKNDPREL IKKEIKRVLE DYSYAINL            408

SEQ ID NO: 119         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 119
MWLSKDYLRK KGVYSICSSN SWVIEAAIEF AKEKGDYILI EATPHQVNQF GGYTGMTPED  60
FKNFVMKIAK EKGLPEDKII LGGDHLGPLP WQDEPAETAM AKAKDLIRAF VEAGYKKIHI  120
DCSMPLADDP KVLPYEKIAE RTAELFEIAE ETARKYNFQP VYVVGTDVPI AGGGEEEGVT  180
SVEDFRSAIS SLKKYFNDVP NIWDRVVGFV IMLGIGFSYD KVFEYDRDKV REILEEVKRT  240
DLFLEGHSTD YQARYALRNM VEDGVRILKV GPALTAAFRR GVFLLDNIED EIIPERERSN  300
IKRVILETML RDDRYWRKYY KDSKRLELDI WYNLLDRIRY YWEYEDVKRA LNKLFENFSE  360
GVDIKFIYQY FYDSYFDVRE GKMKNDPREL IKKEIKRVLE DYSYAINL            408

SEQ ID NO: 120         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 120
MWLSKDYLRK KGVYSICSSN PYVIEASIEF AKEKGSYILI EATPHQVNQF GGYTGMTPED  60
FKRFVMKIAK EKGLPEDKII LGGDHLGPLP WQHEPSDTAM EKAKDLIRAF VESGFKKIHI  120
DCSMPCADDP KVLPNEKIAE RTRELFRIAE ETARKYNFQP VYVVGTDVPI AGGGEEEGVT  180
SPEDFRRTIS SLKKYFNDHP NIWDRVVGFV IMLGIGFSHD KVFEYDRDKV RGILEEVKRE  240
DLFVEAHSTD YQAREALRWM VEDGVAILKV GPALTAAFRR AVFLLSDIED EIIPERERSN  300
IKRVILETML RDDRYWRKYY KDSDRLELDI HYSLLDRIRY YWEHEDVKAV LNKLFENFSD  360
GVDIKFIYQY FYDSYFDVRE GKLKNDPREL IKHEIKRVLE DYAYAINL            408

SEQ ID NO: 121         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 121
MWLSKDYLRK KGVYSICSSN SWVIEAAIEF AKEKGDYILI EATPHQVNQF GGYSGMTPED  60
FRRFVMKIAK EKGLEEDKII LGGDHLGPLP WQDEPAEEAM NKAKELIRAF VEAGYKKIHI  120
DCSMPCADDP KVLPYEKIAE RTRELFEIAE RTARKYNFQP VYVVGTDVPI AGGGEEEGVT  180
SPEDFRKAIE ALKKYFADVP NIWDRVVGFV IMLGIGFSYD KVFEYDRDKV REILEEVKRT  240
DLFVEGHSTD YQARDALRNM VEDGVRILKV GPALTAAFRR GVFLLANIED EIIPEYRRSN  300
IKEVILETML RDDRYWRKYY KDSDRLELDI WYNLLDRIRY YWNYPDVKAA LNKLFENLSE  360
GVDIKLIYQY FYDSYFDVRE GKMKNDPREL IKKEIKRVLE DYSYAINL            408

SEQ ID NO: 122         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 122
MWLSKDYLRK KGIYSICSSN PYVIEASIEF AKEDGDPILI EATPHQVNQF GGYSGMTPED  60
FKRFVYKIAK EKGLPEDKII LGGDHLGPLP WQDEPSDEAM NKAKDLIRAF VESGYKKIHI  120
DCSMPCSDDP KVLPYEKIAE RTRELFEIAE ETARKYNFQP VYVVGTDVPI AGGGEEEGIT  180
SVEDFRSAIE LHKKYFKDVP NIWDRVVGFV IMLGIGFSHD KVFEYDRDKV RDILEEVKRE  240
DLFVEGHSTD YQARYALRWM VEDGVAILKV GPALTAAFRR GVFLLSNIED DIIPERERSN  300
IKEVILETML RDDRYWRKYY KDSDRLELDI WYSLLDRIRY YWEHEDVKMA LNKLFENFSE  360
GVPIKFIYQY FYDSYFDVRE GKLKNDPREL IKHEIKRVLE DYSYAINL            408

SEQ ID NO: 123         moltype = AA  length = 408
FEATURE                Location/Qualifiers
REGION                 1..408
                       note = mutant D-fructose C4-epimerase
source                 1..408
                       mol_type = protein
```

```
                         organism = synthetic construct
SEQUENCE: 123
MWLSKDYLRK KGVYSICSSN PWVIEAAIEF AKEKGDYILI EATPHQVNQF GGYTGMTPED  60
FKNFVMKIAK EKGLPEDKII LGGDHLGPLP WQDEPSETAM NKAKDLIRAF VESGYKKIHI  120
DCSMPLSDDP KVLPYEKIAE RTARLFEIAE ETARKYNFQP VYVVGTDVPI AGGGEEEGVT  180
SVEDFRSTIS ALKKYFNDHP NIWDRVVGFV IMLGIGFSHD KVFEYDRDKA RGILEEVKRE  240
DLFVEGHSTD YQARYALRWM VEDGVRILKV GPALTAAFRR GVFLLADIED EIIPERERSN  300
IKRVILETML RDDRYWRKYY KDSERLRLDI HYNLLDRIRY YWEHPDVKEV LNRLFENFSD  360
GVDWKFIYQY FYDSYHDVRE GKMKNDPREL IKKEIKRVLE DYSYAINL              408

SEQ ID NO: 124           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 124
MWLSKDYLRK KGVYSICSSN PWVIEASIEF AKEKGDPILI EATPHQVNQF GGYTGMTPED  60
FKNFVYKIAK EKGLEENKII LGGDHLGPLP WQDEPSETAM NKAKDLIRAF VESGYKKIHI  120
DCSMPLADDP KVLPYEKIAE RTRELFEIAE ETARKYNFQP VYVVGTDVPI AGGGEEEGVT  180
SVEDFRSTIE ALKKYFNDVP NIWDRVVGFV IMLGIGFSHD KVFEYDRDKV REILEEVKRT  240
DLFVEGHSTD YQARYALRNM VQDGVAILKV GPALTAAFRR GVFLLANIED EIIPEYERSN  300
IKRVILETML RDDRYWRKYY KDSKRLELDI WYSLLDRIRY YWEHPDVKAA LNKLFENFSE  360
GVPITFIYQY FYDSYFDVRE GKMKNDPREL IKKEIKRVLE DYAYAINL              408

SEQ ID NO: 125           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 125
MWLSKDYLRK KGVYSICSSN PYVIEASIEF AKEKGDYILI EATPHQVNQF GGYTGMTPED  60
FKNFVMKIAK EKGLEEDKII LGGDHLGPLP WQDEPAETAM KKAKDLIRAF VEAGYKKIHI  120
DCSMPLSDDP KVLPKEKIAE RTVELFEIAE ETAQKYNFQP VYVVGTDVPI AGGGEEEGVT  180
SKEDFRSFIS TLKKYFDDVP NIWDRVVGFV IMLGIGFSYD KVFEYDRDKV REILEELKRE  240
DLFVEGHSTD YQDRQALRRM VEDGVRILKV GPALTAAFRR GIFLLANIEQ ELIPERERSN  300
ILRVILETML RDDRYWRKYY KDSKRLELDI WYNLLDRIRY YWEHEDVKKV LNKLFENFSE  360
GVDIKFIYQY FYDQYFDVRE GKLKNDPREL IKKEIKRVLE DYSYAINL              408

SEQ ID NO: 126           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 126
MWLSKDYLRK KGVFSICSSN KYVIEAAIEF AKEMHDYILI EATPHQVNQF GGYSGMTPED  60
FKNFVMKIAK ELGLPEDKII LGGDHLGPLP WQDEPAPTAM NKAKDLIRAF VESGYKKIHI  120
DCSMPLSDDP KVLPYEKIAE RTRELCEIAE ETARKYNFQA VYVVGTDVPI AGGGEEEGVT  180
SVEDFRTAIS SLKKAFKDLP KIWDRVVGFV IMLGIGFSYD KVFEYDRDKV RGILEEVKRE  240
DLFVEGHSTD YQARKLLRNM VEDGVRILKV GPALTAAFRR AVFLLSNIED EIIPERERSN  300
ILRVILETML RDDRYWRKYY KDSKRLELDI WYNLLDRIRY YWEHEDVKMV LNKLFENFSE  360
GVDIKFIYQY FYDQYFDVRE GKMKNDPREL IKKEIKRVLE DYSYAINL              408

SEQ ID NO: 127           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 127
MWLSKDYLRK KGVYSICSSN SYVIEAAIEF AKEKDDYILI EATPHQVNQF GGYTGMTPED  60
FKNFVMKIAK EKGLPEDKII LGGDHLGPLP WQDEPAPTAM NKAKDLIRAF VESGFKKIHI  120
DCSMPLSDDP KVLPYEKIAE RTRELFKVAE EAARKYNFQA VYVVGTDVPI AGGGEEEGVT  180
SVEDFRSMIE VLKKYFNDIP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKKV LNKLFENFSE  360
GVDIKFIYQY FYDSYFDVRE GKMKNDPREL IKKEIKRVLE DYSYAINL              408

SEQ ID NO: 128           moltype = AA  length = 408
FEATURE                  Location/Qualifiers
REGION                   1..408
                         note = mutant D-fructose C4-epimerase
source                   1..408
```

```
                         mol_type = protein
                         organism = synthetic construct
SEQUENCE: 128
MWLSKDYLRK KGVYSICSSN SYVIEASIEF AKEMGDPILI EATPHQVNQF GGYTGMTPED  60
FKNFVFKIAK EKGLPPDKII LGGDHLGPLP WQDEPAPTAM NKAKDLIRAF VESGYKKIHI  120
DCSMPLSDDP KVLPYEKIAE RTRELFEVAE EAARKYNFQP VYVVGTDVPI AGGGEEEGVT  180
SPEDFRSAID YFKKYFKDVP NAWDRVVGFV IMLGIGFSYD KVFEYDRDKV RGILEEVKRE  240
GLFVEGHSTD YQDRYALREM VEDGVRILKV GPALTAAFRR GVFLLANIED EIIPEDKRSN  300
IKRVILETML RDDRYWRKYY KDSERLRLDI WYSLLDRIRY YWEHPDVKMA LNKLFENFSE  360
GVDIKFIYQY FPDSYFDVRE GKMKNDPREL IKKEIKRVLE DYSYAINL            408

SEQ ID NO: 129           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 129
MWLSKDYLRK KGVYSICSSN SYVIEAAIEF AKEKGDYILI EATPHQVNQF GGYTGMTPED  60
FKNFVFKIAK EKGLPPDKII LGGDHLGPLP WQDEPSETAM NKAKELIRAF VEAGYKKIHI  120
DCSMPLSDDP KVLPDEKIAE RERELFKIAE ETARKYNFQP VYVVGTDVPI AGGGEEEGIT  180
SVEDFRRFIE SLKKYFNDVP NIWDRVVGFV IMLGIGFSYD KVFEYDRDKV RPILEEVKRT  240
DLFVEGHSTD YQDRQALRNM VEDGVRILKV GPALTAAFRR AVFLLANIEN EIIPERERSN  300
IKRVILETML RDDRYWRKYY KDSERLRLDI WYNYLDRIRY YWEYPDVKKV LNKLFENFSE  360
GVDIKFIYQY FYDSYFDVRE GKMKNDPREL IKKEIKRVLE DYSYAINL            408

SEQ ID NO: 130           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 130
MWLSKDYLRK KGVYSICSSN SYVIEASIEF AKEKGDYILI EATPHQVNQF GGYSGMTPED  60
FKNFVFKIAK EKGLEEDKII LGGDHLGPLP WQDEPAPQAM EKAKELIRAF VESGYKKIHI  120
DCSMPLSDDP KVLPPEKIAE RTRELFEIAE ETAQKYNFQP VYVVGTDVPI AGGGEEEGVT  180
SPEEFRNMIE SFKKYFDDVP NIWDRVVGFV IMLGIGFGYD KVFEYDRDKV RDILEEVKRT  240
DLFVEGHSTD YQSRKALRNM VEDGVRILKV GPALTAAFRR GVFLLSNIEN EIIPERKRSN  300
IKRVILETML RDDRYWRKYY KDSKRLRLDI WYNLLDRIRY YWEYPDVKAV LNKLFENFSE  360
GVDIRFIYQY FYDSYFDVRE GKMKNDPREL IKKEIKRVLE DYSYAINL            408

SEQ ID NO: 131           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 131
MWLSKDYLRK KGVYAICSSN PYVIEASIEF AKEKDDYILI EATPHQVNQF GGYTGMTPED  60
FKNFVMKIAK EKGLPEDKII LGGDHLGPLP WQDEPAPEAM AKAKDLIRAF VEAGYKKIHI  120
DCSMPLSDDP AVLPYEKIAE RTRELFEIAE ETARKYNFQP VYVVGTDVPI AGGGEEEGVT  180
SPEDFRSAIS TLKKYFNDVP NIWDRVVGFV IMLGIGFSYD KVFEYDRDKV REILEEVKRT  240
DLFVEAHSTD YQARYALRWM VEDGVVILKV GPALTAAFRR AVFLLSDIEA EIIPERERSN  300
IKRVILETML RDDRYWRKYY TDSDRLELDI WYNLLDRIRY YWEYEDVKKV LNKLFENFSD  360
GIDIKFIYQY FYDAYHDVCE GKMKPDPREL IKKEIKRVLE DYAYAINL            408

SEQ ID NO: 132           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 132
MWLSKDYLRK KGVYSICSSN PYVIEASIEF AKEYGDYILI EATPHQVNQF GGYTGMTPED  60
FKRFVMKIAK EKGLEEDRII LGGDHLGPLP WQDEPAETAM AKAKDLIRAF VEAGYKKIHI  120
DCSMPLSDDP KVLPYEKIAE RTRELFKIAE ETARKYNFQP VYVVGTDVPI AGGGEEEGVT  180
SPEDFRSAIE VLKKYFEDHP NAWDRVVAFV IMLGIGFSYD KVFEYDRDKV REILEEVKRE  240
DLFVECHSTD YQAREALRNM VEDGVRILKV GPALTAAFRR AVFLLSDIEK EIIPERHRSN  300
IKRVILETML RDDRYWRKYY KDSDRLELDI WYNLLDRIRY YWEYEDVKAV LNKLFENFSE  360
GVDIKFIYQY FYDCYFDVRE GKMKNDPREL IKKEIKKVLE DYSYAINL            408

SEQ ID NO: 133           moltype = AA  length = 408
FEATURE                  Location/Qualifiers
REGION                   1..408
                         note = mutant D-fructose C4-epimerase
```

```
source                  1..408
                        mol_type = protein
                        organism = synthetic construct
SEQUENCE: 133
MWLSKDYLRK KGVYSICSSN PYVIEAAIEF AKEKGDYILI EATPHQVNQF GGYSGMTPED  60
FRNFVMKIAK EKGLPEDKII LGGDHLGPLP WQDEPSETAM NKAKDLIRAF VEAGYKKIHI  120
DCSMPLADEP KVLPYEKIAE RTAELFEIAE ETARKYNFQP VYVVGTDVPI AGGGEEEGIT  180
SVEDFRSAIS TLKKYFNDHP RIWDRVVGFV IMLGIGFSHD KVFEYDRDKV RGILEEVKRT  240
DLFVEVHSTD YQPREALRNM VEDGVVILKV GPALTAAFRR GVFLLSDIED EIIPEEERSN  300
IKRVILETML RDDRYWRKYY KDSKRLELDI WYNLLDRIRY YWEYEDVKAV LEKLFENFSE  360
GVDIKFIYQY FPACYFDVRE GKMKNDPREL IKKEIKRVLE DYSYAINL              408

SEQ ID NO: 134          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 134
MWLSKDYLRK KGVYSICSSN SWVIEASIEF AKEKGDYILI EATPHQVNQF GGYSGMTPED  60
FRRFVYQIAK EKGLPEDKII LGGDHLGPLP WQHEPAPTAM AKAKDLIRAY VESGFKKIHI  120
DCSMPCSGDP KVLPYEKIAE RTARLFEVAE RTARKYNFQP VYVVGTDVPI AGGGEEEGVT  180
SVEDFRKAIE SLKKYFNDHP NAWDRVVGFV IMLGVGFSYD KVFEYDRDKV REILEEVKRE  240
PLFVEGHSTD YQARYALRNM VEDGVAILKV GPALTAAFRR AVFLLADIEK EIIPERHRSN  300
IKEVILETML RDDRYWRKYY RDSENLRLDI WYSLLDRIRY YWEHPDVKMV LNKLFENFSE  360
GVDIKFIYQY FYDCYHAVRE GKMKNDPREL IKKEIKRVLE DYSYAINL              408

SEQ ID NO: 135          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 135
MWLSKDYLRK KGIYSICSSN PWVIEAAIEH AKEDGDYILI EATPHQVNQF GGYTGMTPED  60
FKRFVMKIAK EKGLPEDKII LGGDHLGPLP WQHEPAEEAM EKAKELIRAY VESGFKKIHI  120
DCSMPLSDDP AVLPYDKIAE RTAELCRVAE ETARKYNFQP VYVVGTDVPI AGGGEEEGVT  180
SVEDFRKAIS SFKKYFQDVP QIWNRVVGFV IMLGIGFSYD KVFEYDRDKV RDILEEVKRE  240
PLFVEGHSTD YQNRDALRNM VEDGVRILKV GPALTAAFRE GVFLLADIED EIIPEEQRSN  300
IKRVILETML RDDRYWRKYY KDSKQLRWDI WYSLLDRIRY YWNYEDVKMA LEKLFENFSE  360
GVPIKFIYQY FYDAYFDVRE GKLKNDPREL IKKEIKRVLE DYSYAINL              408

SEQ ID NO: 136          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 136
MWLSKDYLRK KGIYSVCSSN PWVIEAAIEF AKEKGSYILI EATPHQVNQF GGYSGMTPED  60
FKNFVYKIAK EKGLEENKII LGGDHLGPLP WQHEPSPEAM AKAKDLIRAF VESGYKKIHI  120
DCSMPCAGDP AVLPQEKIAE RTRELCEIAE ETARKYNFQP VYVVGTDVPI AGGGEEEGVT  180
SPEDFRKAIS SFKKYFNDHG NIWDRVVGFV IMLGIGFSYD KVFEYDRDKA REILEEVKRT  240
DLFVEGHSTD YQARDALRNM VEDGVRILKV GPALTAAFRR AVFLLSNIED EIIPERQRSN  300
IKEVILETML RDDRYWRKYY KDSKNLELDI HYSLLDRIRY YWNHEDVKMV LEKLFENFSE  360
GIDWKFIYQY FYDSYRDVRE GKMKNDPREL IKKEIKRVLE DYHYAINL              408

SEQ ID NO: 137          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 137
MWLSADYLRN KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYRKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IQRVILETML RDDRYWRDYY DDSDRLELDI WYNLLDRIRY YWEYEDVRMV LNRLFENFSE  360
GVDIRFIYQY FYDSYFDVRE GRMKNDPREL IKKEIKRVLE DYSYAINL              408

SEQ ID NO: 138          moltype = AA  length = 408
FEATURE                 Location/Qualifiers
REGION                  1..408
```

```
                         note = mutant D-fructose C4-epimerase
source                   1..408
                         mol_type = protein
                         organism = synthetic construct
SEQUENCE: 138
MWLSKDYLRK LGVYSICSSN SYVIEASIEF ALEMGDYILI EATPHQVNQF GGYSGMTPED  60
FKNFVMSIAQ EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLQKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSERLELDI WYNLLDRIRY YWEYEDVLMV LNLLFENFSE  360
GVDIKFIYQY FYDSYFDVRE GKMKNDPREL IKKEIKRVLE DYSYAINL                408

SEQ ID NO: 139           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 139
MWLSKDYLRN KGVYSICSSN SYVIEASIEF AKEEGDYILI EATPHQVNQF GGYSGMTPED  60
FKNFVMKIAR EKGLEEDKII LGGDHLGPLP WQDEPSPTAM NKAKDLIRAF VESGYKKIHI  120
DCSMPLSDDP EVLPYEEIAE RTRELFEIAE ETAREYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY DDSDRLELDI WYNLLDRIRY YWEYEDVRMV LNKLFENFSE  360
GVDIKFIYQY FYDSYFDVRE GRMDNDPREL IKKEIKRVLE DYSYAINL                408

SEQ ID NO: 140           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 140
MWLSFDYLRM LGVYSICSSN SYVIEASIEF AKEKGDYILI EATPHQVNQF GGYSGMTPED  60
FVNFVMKIAR EKGLEEDKII LGGDHLGPLP WQDEPSPTAM NKAKDLIRAF VESGYIKIHI  120
DCSMPLSDDP EVLPYEKIAE RTRELFEIAE ETARKYNFQP VYVVGTDVPI AGGGEEEGVT  180
SVEDFRSAIS SLKAYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY DDSDRLELDI WYNLLDRIRY YWEYEDVKMV LNLLFENFSE  360
GVDIKFIYQY FYDSYFDVRE GKMSNDPREL IKKEIKRVLE DYSYAINL                408

SEQ ID NO: 141           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 141
MWLSKDYLRK LGVYSICSSN SYVIEASIEF AKEKGDYILI EATPHQVNQF GGYSGMTPED  60
FKNFVMKIAQ EKGLEEDLII LGGDHLGPLP WQDEPSPTAM NKAKDLIRAF VESGYKKIHI  120
DCSMPLSDDP KVLPYELIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRKYY DDSKRLELDI WYNLLDRIRY YWEYEDVKMV LNKLFENFSE  360
GVDISFIYQY FYDSYFDVRE GKMKNDPREL IKKEIKRVLE DYSYAINL                408

SEQ ID NO: 142           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 142
MWLSKDYLRN KGVYSICSSN SYVIEASIEF AKEKGDYILI EATPHQVNQF GGYSGMTPED  60
FKNFVMKIAR EKGLEEDKII LGGDHLGPLP WQDEPSPTAM NKARDLIRAF VESGYKKIHI  120
DCSMPLSDDP KVLPYEKIAE RTRELFEIAE ETAREYNFQP VYVVGTDVPI AGGGEEEGVT  180
SVEDFRSAIS SLAKYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRKYY DDSKRLELDI WYNLLDRIRY YWEYEDVKMV LNLLFENFSE  360
GVDIKFIYQY FYDSYFDVRE GRMTNDPREL IKKEIKRVLE DYSYAINL                408

SEQ ID NO: 143           moltype = AA  length = 408
FEATURE                  Location/Qualifiers
```

```
REGION                  1..408
                        note = mutant D-fructose C4-epimerase
source                  1..408
                        mol_type = protein
                        organism = synthetic construct
SEQUENCE: 143
MWLSLDYLRK KGVYSIGSSN SYVIEASIEF AKEMGDYILI EATPHQVNQF GGYSGMTPED  60
FKNFVMKIAK ELGLEEDLII LGGDHLGPLP WQDEPSPTAM NYAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLQKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY DDSERLELDI WYNLLDRIRY YWEYEDVKMV LNKLFENFSE  360
GVDIKFIYQY FYDSYFDVRE GKMKNDPREL IKKEIKRVLE DYSYAINL                408

SEQ ID NO: 144          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 144
MWLSKDYLRN KGVYSITSSN SYVIEASIEF AKETGDYILI EATPHQVNQF GGYSGMTPED  60
FRNFVMKIAK ELGLEEDKII LGGDHLGPLP WQDEPSPTAM NKAKDLIRAF VESGYHKIHI  120
DTSMPLSDDP QVLPYETIAE RTRELFEIAE ETARKYNFQP VYVVGTDVPI AGGGEEEGVT  180
SVEDFRSAIS SLEEYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY DDSDRLELDI WYNLLDRIRY YWEYEDVKMV LNKLFENFSE  360
GVDIKFIYQY FYDSYFDVRE GRMKNDPREL IKKEIKRVLE DYSYAINL                408

SEQ ID NO: 145          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 145
MWLSKDYLRK KGVYSITSSN SYVIEASIEF AKEQGDYILI EATPHQVNQF GGYSGMTPED  60
FRNFVMKIAR EVGLEEDKII LGGDHLGPLP WQDEPSPTAM NKAKDLIRAF VESGYKKIHI  120
DCSMPLSDDP QVLPYEKIAE RTRELFEIAE ETARRYNFQP VYVVGTDVPI AGGGEEEGVT  180
SVEDFRSAIS SLKTYFNDVP NIWDRVVGFV IMLGIGFSYD KVFEYDRDRV RGILEEVSRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIRFIYQY FYDSYFDVRE GKMKNDPREL IKKEIKRVLE DYSYAINL                408

SEQ ID NO: 146          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 146
MWLSKDYLRR KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP QVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDTV RGILEEVKRE  240
DLFVEGHSTD YQARYALRNM VEDGVRILKV GPALTAAFRR GVFLLSNIED EIIPERERSN  300
IKRVILETML RDDRYWRKYY DDSKRLELDI WYNLLDRIRY YWEYEDVRMV LNRLFENFSE  360
GVDIKFIYQY FYDSYFDVRE GRMKNDPREL IKKEIKRVLE DYSYAINL                408

SEQ ID NO: 147          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 147
MWLSKDYLRK KGVYSICSSN SYVIEASIEF AKEKGDYILI EATPHQVNQF GGYSGMTPED  60
FKNFVMTIAK EKGLEEDLII LGGDHLGPLP WQDEPSPTAM NYAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIRFIYQY FYDSYFDVRE GKMKNDPREL IKKEIKRVLE DYSYAINL                408

SEQ ID NO: 148          moltype = AA  length = 408
```

```
FEATURE                 Location/Qualifiers
REGION                  1..408
                        note = mutant D-fructose C4-epimerase
source                  1..408
                        mol_type = protein
                        organism = synthetic construct
SEQUENCE: 148
MWLSKDYLRN LGVYSITSSN SYVIEASIEF AMELGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYELIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMSNDPREL IKKEIKRVLE DYSYAINL            408

SEQ ID NO: 149          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 149
MWLSKDYLRN KGVYSITSSN SYVIEASIEF AMELGDYILI EATPHQVNQF GGYSGMTPED  60
FKNFVMKIAR EKGLEEDKII LGGDHLGPLP WQDEPSPTAM NLAKDLIRAF VESGYKKIHI  120
DCSMPLSDDP YVLPYELIAE RTRELFEIAE ETARKYNFQP VYVVGTDVPI AGGGEEEGVT  180
SVEDFRSAIS SLQKYFNDVP NIWDRVVGFV IMLGIGFSYD VVFEYDRDRV RGILEEVSRE  240
DLFVEGHSTD YQARYALRNM VEDGVRILKV GPALTAAFRR GVFLLSNIED EIIPERERSN  300
IKRVILETML RDDRYWRKYY DDSKRLELDI WYNLLDRIRY YWEYEDVKMV LNKLFENFSE  360
GVDIKFIYQY FYDSYFDVRE GRMKNDPREL IKHEIKRVLE DYSYAINL            408

SEQ ID NO: 150          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 150
MWLSWDYLRR KGVYSICSSN SYVIEASIEF AMEKGDYILI EATPHQVNQF GGYSGMTPED  60
FKNFVMQIAR EKGLEEDMII LGGDHLGPLP WQDEPSPTAM NKAKDLIRAF VESGYKKIHI  120
DCSMPLSDDP QVLPYEKIAE RTRELFEIAE ETARKYNFQP VYVVGTDVPI AGGGEEEGVT  180
SVEDFRSAIS SLIKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVLMV LNKLFENFSE  360
GVDIKFIYQY FYDSYFDVRE GKMKNDPREL IKKEIKRVLE DYSYAINL            408

SEQ ID NO: 151          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 151
MWLSKDYLRK KGVYSICSSN SYVIEASIEF AKEKGDYILI EATPHQVNQF GGYSGMTPED  60
FKNFVMKIAR EKGLEEDKII LGGDHLGPLP WQDEPSPTAM NKANDLIRAF VESGYKLIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDTV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVRMV LNQLFENFSE  360
GVDIKFIYQY FYDSYFDVRE GKMDNDPREL IKKEIKRVLE DYSYAINL            408

SEQ ID NO: 152          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 152
MWLSKDYLRK QGVYSICSSN SYVIEASIEF AKEQGDYILI EATPHQVNQF GGYSGMTPED  60
FRNFVMTIAK EKGLEEDKII LGGDHLGPLP WQDEPSPTAM NKAQDLIRAF VESGYKKIHI  120
DCSMPLSDDP EVLPYETIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNRLFENFSE  360
GVDIKFIYQY FYDSYFDVRE GKMENDPREL IKKEIKRVLE DYSYAINL            408
```

```
SEQ ID NO: 153          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 153
MWLSKDYLRK KGVYSICSSN SYVIEASIEF AKEKGDYILI EATPHQVNQF GGYSGMTPED  60
FKNFVMKIAK EKGLEEDLII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
IIRVILETML RDDRYWRKYY KDSKRLELDI WYNLLDRIRY YWEYEDVKMV LNKLFENFSE  360
GVDISFIYQY FYDSYFDVRE GKMKNDPREL IKKEIKRVLE DYSYAINL            408

SEQ ID NO: 154          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 154
MWLSMDYLRL KGVYSICSSN SYVIEASIEF AKEKGDYILI EATPHQVNQF GGYSGMTPED  60
FKNFVMTIAR ELGLEEDKII LGGDHLGPLP WQDEPSPTAM NKAKDLIRAF VESGYKKIHI  120
DCSMPLSDDP QVLPYELIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY KDSKRLELDI WYNLLDRIRY YWEYEDVKMV LNWLFENFSE  360
GVDIHFIYQY FYDSYFDVRE GKMDNDPREL IRKEIMRVLE DYSYAINL            408

SEQ ID NO: 155          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 155
MWLSKDYLRK KGVYSITSSN SYVIEASIEF AKEKGDYILI EATPHQVNQF GGYSGMTPED  60
FKNFVMTIAR EKGLEEDKII LGGDHLGPLP WQDEPSPTAM NRANDLIRAF VESGYKKIHI  120
DCSMPLSDDP KVLPYEKIAE RTRELFEIAE ETARNYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL            408

SEQ ID NO: 156          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 156
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKARDLIRAF VESGYKKIHI  120
DCSMPLSDDP RVLPYEKIAE RTRELFEIAE ETARKYNFQP VYVVGTDVPI AGGGEEEGVT  180
SVEDFRSAIS SLEKYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVLMV LNKLFENFSE  360
GVDIKFIYQY FYDSYFDVRE GKMKNDPREL IKKEIKRVLE DYSYAINL            408

SEQ ID NO: 157          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 157
MWLSHDYLRK KGVYSICSSN SYVIEASIEF AKEKGDYILI EATPHQVNQF GGYSGMTPED  60
FKNFVMTIAK EKGLEEDLII LGGDHLGPLP WQDEPSPTAM NKAKDLIRAF VESGYKWIHI  120
DASMPLSDDP KVLPYEKIAE RTRELFEIAE ETARNYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
ILRVILETML RDDRYWRDYY KDSKRLELDI WYNLLDRIRY YWEYEDVKMV LNLLFENFSE  360
GVDIKFIYQY FYDSYFDVRE GKMSNDPREL IKKEILRVLE DYSYAINL            408
```

```
SEQ ID NO: 158          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 158
MWLSKDYLRK KGVYSICSSN SYVIEASIEF AKEKGDYILI EATPHQVNQF GGYSGMTPED  60
FRNFVMTIAK EKGLEEDKII LGGDHLGPLP WQDEPSPTAM NKANDLIRAF VESGYKKIHI  120
DCSMPLSDDP QVLPYEQIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRKYY KDSSRLELDI WYNLLDRIRY YWEYEDVKMV LNKLFENFSE  360
GVDIKFIYQY FYDSYFDVRE GRMKNDPREL IKKEIKRVLE DYSYAINL             408

SEQ ID NO: 159          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 159
MWLSLDYLRN QGVYSICSSN SYVIEASIEF AKEKGDYILI EATPHQVNQF GGYSGMTPED  60
FRNFVMTIAR EKGLEEDKII LGGDHLGPLP WQDEPSPTAM NKAKDLIRAF VESGYKKIHI  120
DCSMPLSDDP QVLPYEQIAE RTRELFEIAE ETARKYNFQP VYVVGTDVPI AGGGEEEGVT  180
SVEDFRSAIS SLEEYFNDVP NIWDRVVGFV IMLGIGFSYD RVFEYDRDKV RGILEEVKRE  240
DLFVEGHSTD YQARYALRNM VEDGVRILKV GPALTAAFRR GVFLLSNIED EIIPERERSN  300
IRRVILETML RDDRYWRKYY DDSDRLELDI WYNLLDRIRY YWEYEDVRMV LNKLFENFSE  360
GVDIKFIYQY FYDSYFDVRE GRMDNDPREL IKKEIKRVLE DYSYAINL             408

SEQ ID NO: 160          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 160
MWLSKDYLRN KGVYSITSSN SYVIEASIEF AKEKGDYILI EATPHQVNQF GGYSGMTPED  60
FKNFVMKIAR EKGLEEDKII LGGDHLGPLP WQDEPSPTAM NKARDLIRAF VESGYKKIHI  120
DASMPLSDDP EVLPYEEIAE RTRELFEIAE ETAREYNFQP VYVVGTDVPI AGGGEEEGVT  180
SVEDFRSAIS SLEKYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
IKRVILETML RDDRYWRKYY DDSDRLELDI WYNLLDRIRY YWEYEDVRMV LNRLFENFSE  360
GVDIKFIYQY FYDSYFDVRE GKMKNDPREL IKKEIKRVLE DYSYAINL             408

SEQ ID NO: 161          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 161
MWLSHDYLRK VGVYSICSSN SYVIEASIEF AKEKGDYILI EATPHQVNQF GGYSGMTPED  60
FKNFVMKIAK ELGLEEDKII LGGDHLGPLP WQDEPSPTAM NKAKDLIRAF VESGYTKIHI  120
DTSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSERLELDI WYNLLDRIRY YWEYEDVKMV LNKLFENFSE  360
GVDIKFIYQY FYDSYFDVRE GLMENDPREL IKYEIKRVLE DYSYAINL             408

SEQ ID NO: 162          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 162
MWLSFDYLRN QGVYSIASSN SYVIEASIEF AQEQGDYILI EATPHQVNQF GGYSGMTPED  60
FKNFVMTIAK ELGLEEDKII LGGDHLGPLP WQDEPSPTAM NKAKDLIRAF VESGYKKIHI  120
DCSMPLSDDP KVLPYETIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDRV RGILEEVSRE  240
DLFVEGHSTD YQARYALRNM VEDGVRILKV GPALTAAFRR GVFLLSNIED EIIPERERSN  300
IKRVILETML RDDRYWRDYY DDSDRLELDI WYNLLDRIRY YWEYEDVRMV LNQLFENFSE  360
```

```
GVDIKFIYQY FYDSYFDVRE GKMKNDPREL IKKEIKRVLE DYSYAINL              408

SEQ ID NO: 163          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 163
MWLSFDYLRK KGVYSICSSN SYVIEASIEF AKEQGDYILI EATPHQVNQF GGYSGMTPED  60
FKNFVMKIAK ETGLEEDQII LGGDHLGPLP WQDEPSPTAM NKAKDLIRAF VESGYKKIHI  120
DCSMPLSDDP KVLPYETIAE RTRELFEIAE ETARNYNFQP VYVVGTDVPI AGGGEEEGVT  180
SVEDFRSAIS SLKKYFNDVP NIWDRVVGFV IMLGIGFSYD TVFEYDRDKV RGILEEVSRE  240
DLFVEGHSTD YQARYALRNM VEDGVRILKV GPALTAAFRR GVFLLSNIED EIIPERERSN  300
IRRVILETML RDDRYWRKYY KDSDRLELDI WYNLLDRIRY YWEYEDVKMV LNKLFENFSE  360
GVDIKFIYQY FYDSYFDVRE GRMKNDPREL IKKEIKRVLE DYSYAINL              408

SEQ ID NO: 164          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 164
MWLSKDYLRK KGVYSICSSN SYVIEASIEF AKEKGDYILI EATPHQVNQF GGYSGMTPED  60
FVNFVMKIAR EKGLEEDLII LGGDHLGPLP WQDEPSPTAM NKAQDLIRAF VESGYIKIHI  120
DCSMPLSDDP KVLPYEKIAE RTRELFEIAE ETARNYNFQP VYVVGTDVPI AGGGEEEGVT  180
SVEDFRSAIS SLQKYFNDVP NIWDRVVGFV IMLGIGFSYD VVFEYDRDRV RGILEEVKRE  240
DLFVEGHSTD YQARYALRNM VEDGVRILKV GPALTAAFRR GVFLLSNIED EIIPERERSN  300
IKRVILETML RDDRYWRKYY DDSDRLELDI WYNLLDRIRY YWEYEDVLMV LNKLFENFSE  360
GVDIKFIYQY FYDSYFDVRE GRMKNDPREL IKHEIKRVLE DYSYAINL              408

SEQ ID NO: 165          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 165
MWLSWDYLRR KGVYSITSSN SYVIEASIEF AKEKGDYILI EATPHQVNQF GGYSGMTPED  60
FRNFVMTIAR ELGLEEDRII LGGDHLGPLP WQDEPSPTAM NKARDLIRAF VESGYRKIHI  120
DCSMPLSDDP KVLPYEEIAE RTRELFEIAE ETARKYNFQP VYVVGTDVPI AGGGEEEGVT  180
SVEDFRSAIS SLRTYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IQRVILETML RDDRYWRKYY DDSKRLELDI WYNLLDRIRY YWEYEDVRMV LNRLFENFSE  360
GVDIRFIYQY FYDSYFDVRE GKMENDPREL IKKEIKRVLE DYSYAINL              408

SEQ ID NO: 166          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 166
MWLSKDYLRL YGVYSICSSN SYVIEASIEF AKETGDYILI EATPHQVNQF GGYSGMTPED  60
FVNFVMTIAK EKGLEEDKII LGGDHLGPLP WQDEPSPTAM NYAKDLIRAF VESGYYKIHI  120
DCSMPLSDDP QVLPYELIAE RTRELFEIAE ETARYYNFQP VYVVGTDVPI AGGGEEEGVT  180
SVEDFRSAIS SLAAYFNDVP NIWDRVVGFV IMLGIGFSYD RVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRDYY KDSKRLELDI WYNLLDRIRY YWEYEDVKMV LNWLFENFSE  360
GVDIKFIYQY FYDSYFDVRE GRMLNDPREL IKKEIKRVLE DYSYAINL              408

SEQ ID NO: 167          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 167
MWLSADYLRK QGVYSITSSN SYVIEASIEF AQEEGDYILI EATPHQVNQF GGYSGMTPED  60
FKNFVMTIAR ELGLEEDKII LGGDHLGPLP WQDEPSPTAM NRARDLIRAF VESGYKKIHI  120
DCSMPLSDDP EVLPYEKIAE RTRELFEIAE ETAREYNFQP VYVVGTDVPI AGGGEEEGVT  180
SVEDFRSAIS SLKKYFNDVP NIWDRVVGFV IMLGIGFSYD KVFEYDRDRV RGILEEVSRE  240
DLFVEGHSTD YQARYALRNM VEDGVRILKV GPALTAAFRR GVFLLSNIED EIIPERERSN  300
```

```
IQRVILETML RDDRYWRDYY DDSDRLELDI WYNLLDRIRY YWEYEDVKMV LNRLFENFSE  360
GVDIKFIYQY FYDSYFDVRE GKMTNDPREL IKKEIKRVLE DYSYAINL              408

SEQ ID NO: 168         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 168
MWLSADYLRN KGVYSICSSN SYVIEASIEF AKEKGDYILI EATPHQVNQF GGYSGMTPED  60
FKNFVMTIAR EKGLEEDQII LGGDHLGPLP WQDEPSPTAM NRAKDLIRAF VESGYKKIHI  120
DCSMPLSDDP EVLPYEEIAE RTRELFEIAE ETAREYNFQP VYVVGTDVPI AGGGEEEGVT  180
SVEDFRSAIS SLETYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
IKRVILETML RDDRYWRKYY DDSKRLELDI WYNLLDRIRY YWEYEDVRMV LNRLFENFSE  360
GVDIRFIYQY FYDSYFDVRE GKMKNDPREL IKKEIKRVLE DYSYAINL              408

SEQ ID NO: 169         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 169
MWLSFDYLRN QGVYSIISSN SYVIEASIEF AKEQGDYILI EATPHQVNQF GGYSGMTPED  60
FRNFVMTIAR EKGLEEDKII LGGDHLGPLP WQDEPSPTAM NKAQDLIRAF VESGYKKIHI  120
DTSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD TVFEYDRDKV RGILEEVSRE  240
DLFVEGHSTD YQARYALRNM VEDGVRILIV GPALTAAFRR GVFLLSNIED EIIPERERSN  300
IKRVILETML RDDRYWRDYY DDSDRLELDI WYNLLDRIRY YWEYEDVRMV LNQLFENFSE  360
GVDIKFIYQY FYDSYFDVRE GRMENDPREL IKKEIKRVLE DYSYAINL              408

SEQ ID NO: 170         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 170
MWLSADYLRK KGVYSICSSN SYVIEASIEF AIEKGDYILI EATPHQVNQF GGYSGMTPED  60
FYNFVMTIAK ELGLEEDKII LGGDHLGPLP WQDEPSPTAM NKAKDLIRAF VESGYLKIHI  120
DCSMPLSDDP KVLPYEKIAE RTRELFEIAE ETARKYNFQP VYVVGTDVPI AGGGEEEGVT  180
SVEDFRSAIS SLATYFNDVP NIWDRVVGFV IMLGIGFSYD IVFEYDRDRV RGILEEVSRE  240
DLFVEGHSTD YQARYALRNM VEDGVRILKV GPALTAAFRR GVFLLSNIED EIIPERERSN  300
IIRVILETML RDDRYWRDYY DDSKRLELDI WYNLLDRIRY YWEYEDVKMV LNLLFENFSE  360
GVDIKFIYQY FYDSYFDVRE GRMTNDPREL IKKEIKRVLE DYSYAINL              408

SEQ ID NO: 171         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 171
MWLSKDYLRK KGVYSICSSN SYVIEASIEF AKEKGDYILI EATPHQVNQF GGYSGMTPED  60
FKNFVMKIAR EKGLEEDLII LGGDHLGPLP WQDEPSPTAM NYAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILLV GPALTAAFRR GVFLLSNIED EIIPERERSN  300
IKRVILETML RDDRYWRKYY KDSKRLELDI WYNLLDRIRY YWEYEDVVMV LNKLFENFSE  360
GVDIRFIYQY FYDSYFDVRE GKMKNDPREL IMLEIKRVLE DYSYAINL              408

SEQ ID NO: 172         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 172
MWLSFDYLRK QGVYSICSSN SYVIEASIEF AQEKGDYILI EATPHQVNQF GGYSGMTPED  60
FRNFVMKIAK EKGLEEDQII LGGDHLGPLP WQDEPSPTAM NKAKDLIRAF VESGYQKIHI  120
DCSMPLSDDP KVLPYETIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDRV RGILEEVKRE  240
```

```
DLFVEGHSTD YQARYALRNM VEDGVRILKV GPALTAAFRR GVFLLSNIED EIIPERERSN  300
IKRVILETML RDDRYWRDYY DDSDRLELDI WYNLLDRIRY YWEYEDVRMV LNQLFENFSE  360
GVDIKFIYQY FYDSYFDVRE GKMDNDPREL IKKEIKRVLE DYSYAINL              408

SEQ ID NO: 173         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 173
MWLSFDYLRM KGVYSICSSN SYVIEASIEF AKELGDYILI EATPHQVNQF GGYSGMTPED  60
FKNFVMTIAR EKGLEEDLII LGGDHLGPLP WQDEPSPTAM NKARDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLQRYFNDVP NIWDRVVGFV IMLGIGFSYD VVFEYDRDKV RGILEEVWRE  240
DLFVEGHSTD YQARYALRNM VEDGVRILKV GPALTAAFRR GVFLLSNIED EIIPERERSN  300
IKRVILETML RDDRYWRKYY KDSDRLELDI WYNLLDRIRY YWEYEDVKMV LNWLFENFSE  360
GVDISFIYQY FYDSYFDVRE GKMSNDPREL IKKEIKRVLE DYSYAINL              408

SEQ ID NO: 174         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 174
MWLSKDYLRK YGVYSICSSN SYVIEASIEF AKELGDYILI EATPHQVNQF GGYSGMTPED  60
FKNFVMKIAR EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD IVFEYDRDRV RGILEEVSRE  240
DLFVEGHSTD YQARYALRNM VEDGVRILKV GPALTAAFRR GVFLLSNIED EIIPERERSN  300
IKRVILETML RDDRYWRDYY KDSDRLELDI WYNLLDRIRY YWEYEDVVMV LNKLFENFSE  360
GVDIRFIYQY FYDSYFDVRE GKMKNDPREL IKLEIKRVLE DYSYAINL              408

SEQ ID NO: 175         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 175
MWLSKDYLRK KGVYSICSSN SYVIEASIEF AIEKGDYILI EATPHQVNQF GGYSGMTPED  60
FVNFVMKIAK EKGLEEDKII LGGDHLGPLP WQDEPSPTAM NKAIDLIRAF VESGYKKIHI  120
DTSMPLSDDP KVLPYELIAE RTRELFEIAE ETARKYNFQP VYVVGTDVPI AGGGEEEGVT  180
SVEDFRSAIS SLKAYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRDYY KDSKRLELDI WYNLLDRIRY YWEYEDVKMV LNLLFENFSE  360
GVDISFIYQY FYDSYFDVRE GKMENDPREL ILKEIKRVLE DYSYAINL              408

SEQ ID NO: 176         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 176
MWLSKDYLRK VGVYSICSSN SYVIEASIEF ALEYGDYILI EATPHQVNQF GGYSGMTPED  60
FVNFVMRIAQ EKGLEEDRII LGGDHLGPLP WQDEPSPTAM NLAKDLIRAF VESGYTKIHI  120
DCSMPLSDDP RVLPYEKIAE RTRELFEIAE ETAREYNFQP VYVVGTDVPI AGGGEEEGVT  180
SVEDFRSAIS SLKAYFNDVP NIWDRVVGFV IMLGIGFSYD IVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVLMV LNKLFENFSE  360
GVDIRFIYQY FYDSYFDVRE GLMKNDPREL IKKEIKRVLE DYSYAINL              408

SEQ ID NO: 177         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 177
MWLSKDYLRK KGVYSICSSN SYVIEASIEF ALEMGDYILI EATPHQVNQF GGYSGMTPED  60
FKNFVMSIAK EKGLEEDQII LGGDHLGPLP WQDEPSPTAM NLAKDLIRAF VESGYTKIHI  120
DCSMPLSDDP KVLPYEKIAE RTRELFEIAE ETARKYNFQP VYVVGTDVPI AGGGEEEGVT  180
```

```
SVEDFRSAIS SLKSYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IIRVILETML RDDRYWRKYY DDSKRLELDI WYNLLDRIRY YWEYEDVLMV LNLLFENFSE  360
GVDIKFIYQY FYDSYFDVRE GLMKNDPREL IKKEIKRVLE DYSYAINL              408

SEQ ID NO: 178         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 178
MWLSKDYLRL YGVYSITSSN SYVIEASIEF AKEKGDYILI EATPHQVNQF GGYSGMTPED  60
FYNFVMTIAR ELGLEEDKII LGGDHLGPLP WQDEPSPTAM NKAKDLIRAF VESGYKMIHI  120
DVSMPLSDDP QVLPYELIAE RTRELFEIAE ETARYYNFQP VYVVGTDVPI AGGGEEEGVT  180
SVEDFRSAIS SLAKYFNDVP NIWDRVVGFV IMLGIGFSYD RVFEYDRDTV RGILEEVKRE  240
DLFVEGHSTD YQARYALRNM VEDGVRILVV GPALTAAFRR GVFLLSNIED EIIPERERSN  300
IKRVILETML RDDRYWRDYY DDSDRLELDI WYNLLDRIRY YWEYEDVKMV LNWLFENFSE  360
GVDIHFIYQY FYDSYFDVRE GRMKNDPREL ILKEIMRVLE DYSYAINL              408

SEQ ID NO: 179         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 179
MWLSKDYLRN VGVYSIGSSN SYVIEASIEF ALEKGDYILI EATPHQVNQF GGYSGMTPED  60
FKNFVMSIAK EKGLEEDLII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLEKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IIRVILETML RDDRYWRDYY KDSKRLELDI WYNLLDRIRY YWEYEDVKMV LNLLFENFSE  360
GVDIRFIYQY FYDSYFDVRE GKMTNDPREL ILKEIKRVLE DYSYAINL              408

SEQ ID NO: 180         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 180
MWLSKDYLRN LGVYSICSSN SYVIEASIEF ALEKGDYILI EATPHQVNQF GGYSGMTPED  60
FKNFVMKIAK EKGLEEDQII LGGDHLGPLP WQDEPSPTAM NKARDLIRAF VESGYTKIHI  120
DCSMPLSDDP EVLPYEKIAE RTRELFEIAE ETARKYNFQP VYVVGTDVPI AGGGEEEGVT  180
SVEDFRSAIS SLKRYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVLMV LNLLFENFSE  360
GVDISFIYQY FYDSYFDVRE GLMENDPREL IKKEIKRVLE DYSYAINL              408

SEQ ID NO: 181         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 181
MWLSLDYLRK KGVYSICSSN SYVIEASIEF AKEKGDYILI EATPHQVNQF GGYSGMTPED  60
FKNFVMKIAK ELGLEEDLII LGGDHLGPLP WQDEPSPTAM NKAKDLIRAF VESGYKKIHI  120
DCSMPLSDDP KVLPYELIAE RTRELFEIAE ETAREYNFQP VYVVGTDVPI AGGGEEEGVT  180
SVEDFRSAIS SLKKYFNDVP NIWDRVVGFV IMLGIGFSYD KVFEYDRDKV RGILEEVSRE  240
DLFVEGHSTD YQARYALRNM VEDGVRILKV GPALTAAFRR GVFLLSNIED EIIPERERSN  300
ILRVILETML RDDRYWRKYY DDSKRLELDI WYNLLDRIRY YWEYEDVKMV LNKLFENFSE  360
GVDISFIYQY FYDSYFDVRE GKMKNDPREL IKYEIKRVLE DYSYAINL              408

SEQ ID NO: 182         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 182
MWLSMDYLRL LGVYSITSSN SYVIEASIEF AMELGDYILI EATPHQVNQF GGYSGMTPED  60
FKNFVMKIAR ELGLEEDLII LGGDHLGPLP WQDEPSPTAM NLAKDLIRAF VESGYIKIHI  120
```

```
DCSMPLSDDP KVLPYEKIAE RTRELFEIAE ETARNYNFQP VYVVGTDVPI AGGGEEEGVT  180
SVEDFRSAIS SLKSYFNDVP NIWDRVVGFV IMLGIGFSYD VVFEYDRDKV RGILEEVSRE  240
DLFVEGHSTD YQARYALRNM VEDGVRILKV GPALTAAFRR GVFLLSNIED EIIPERERSN  300
IKRVILETML RDDRYWRDYY DDSDRLELDI WYNLLDRIRY YWEYEDVLMV LNKLFENFSE  360
GVDIKFIYQY FYDSYFDVRE GRMKNDPREL IKKEIKRVLE DYSYAINL              408

SEQ ID NO: 183         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 183
MWLSKDYLRN LGVYSICSSN SYVIEASIEF AMELGDYILI EATPHQVNQF GGYSGMTPED  60
FVNFVMTIAK EKGLEEDLII LGGDHLGPLP WQDEPSPTAM NLAKDLIRAF VESGYIKIHI  120
DCSMPLSDDP YVLPYEKIAE RTRELFEIAE ETARNYNFQP VYVVGTDVPI AGGGEEEGVT  180
SVEDFRSAIS SLQRYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
ILRVILETML RDDRYWRDYY DDSDRLELDI WYNLLDRIRY YWEYEDVLMV LNWLFENFSE  360
GVDIKFIYQY FYDSYFDVRE GRMSNDPREL IKKEIKRVLE DYSYAINL              408

SEQ ID NO: 184         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 184
MWLSKDYLRK KGVYSIGSSN SYVIEASIEF AKEMGDYILI EATPHQVNQF GGYSGMTPED  60
FKNFVMKIAQ EKGLEEDKII LGGDHLGPLP WQDEPSPTAM NKARDLIRAF VESGYKKIHI  120
DCSMPLSDDP RVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IIRVILETML RDDRYWRKYY KDSKRLELDI WYNLLDRIRY YWEYEDVLMV LNKLFENFSE  360
GVDIRFIYQY FYDSYFDVRE GKMQNDPREL IKYEIKRVLE DYSYAINL              408

SEQ ID NO: 185         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 185
MWLSLDYLRK KGVYSIGSSN SYVIEASIEF AKETGDYILI EATPHQVNQF GGYSGMTPED  60
FKNFVMSIAK ELGLEEDLII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILNV GPALTAAFRR GVFLLSNIED EIIPERERSN  300
IKRVILETML RDDRYWRKYY DDSKRLELDI WYNLLDRIRY YWEYEDVKMV LNKLFENFSE  360
GVDIKFIYQY FYDSYFDVRE GLMKNDPREL IKYEIKRVLE DYSYAINL              408

SEQ ID NO: 186         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 186
MWLSWDYLRV YGVYSICSSN SYVIEASIEF AMETGDYILI EATPHQVNQF GGYSGMTPED  60
FVNFVMTIAR EKGLEEDLII LGGDHLGPLP WQDEPSPTAM NYAFDLIRAF VESGYYKIHI  120
DCSMPLSDDP QVLPYELIAE RTRELFEIAE ETARYYNFQP VYVVGTDVPI AGGGEEEGVT  180
SVEDFRSAIS SLAAYFNDVP NIWDRVVGFV IMLGIGFSYD RVFEYDRDSV RGILEEVWRE  240
DLFVEGHSTD YQARYALRNM VEDGVRILKV GPALTAAFRR GVFLLSNIED EIIPERERSN  300
ILRVILETML RDDRYWRDYY DDSDRLELDI WYNLLDRIRY YWEYEDVLMV LNWLFENFSE  360
GVDIHFIYQY FYDSYFDVRE GRMDNDPREL IKKEIKRVLE DYSYAINL              408

SEQ ID NO: 187         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 187
MWLSWDYLRK YGVYSICSSN SYVIEASIEF AMETGDYILI EATPHQVNQF GGYSGMTPED  60
```

```
FKNFVMKIAR ELGLEEDMII LGGDHLGPLP WQDEPSPTAM NYAFDLIRAF VESGYYKIHI  120
DVSMPLSDDP QVLPYEKIAE RTRELFEIAE ETARKYNFQP VYVVGTDVPI AGGGEEEGVT  180
SVEDFRSAIS SLAAYFNDVP NIWDRVVGFV IMLGIGFSYD KVFEYDRDKV RGILEEVWRE  240
DLFVEGHSTD YQARYALRNM VEDGVRILLV GPALTAAFRR GVFLLSNIED EIIPERERSN  300
ILRVILETML RDDRYWRDYY DDSDRLELDI WYNLLDRIRY YWEYEDVLMV LNKLFENFSE  360
GVDIKFIYQY FYDSYFDVRE GRMDNDPREL ILYEIKRVLE DYSYAINL              408

SEQ ID NO: 188         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 188
MWLSADYLRN QGVYSILSSN SYVIEASIEF AQEEGDYILI EATPHQVNQF GGYSGMTPED  60
FKNFVMTIAR ELGLEEDQII LGGDHLGPLP WQDEPSPTAM NRARDLIRAF VESGYRWIHI  120
DTSMPLSDDP EVLPYEKIAE RTRELFEIAE ETAREYNFQP VYVVGTDVPI AGGGEEEGVT  180
SVEDFRSAIS SLKRYFNDVP NIWDRVVGFV IMLGIGFSYD KVFEYDRDRV RGILEEVSRE  240
DLFVEGHSTD YQARYALRNM VEDGVRILLV GPALTAAFRR GVFLLSNIED EIIPERERSN  300
IRRVILETML RDDRYWRKYY DDSKRLELDI WYNLLDRIRY YWEYEDVKMV LNKLFENFSE  360
GVDIRFIYQY FYDSYFDVRE GRMDNDPREL IKKEIKRVLE DYSYAINL              408

SEQ ID NO: 189         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 189
MWLSLDYLRA KGVYSIGSSN SYVIEASIEF ALEYGDYILI EATPHQVNQF GGYSGMTPED  60
FKNFVMKIAQ ELGLEEDKII LGGDHLGPLP WQDEPSPTAM NKAKDLIRAF VESGYTKIHI  120
DCSMPLSDDP RVLPYEKIAE RTRELFEIAE ETAREYNFQP VYVVGTDVPI AGGGEEEGVT  180
SVEDFRSAIS SLKAYFNDVP NIWDRVVGFV IMLGIGFSYD IVFEYDRDKV RGILEEVSRE  240
DLFVEGHSTD YQARYALRNM VEDGVRILKV GPALTAAFRR GVFLLSNIED EIIPERERSN  300
IIRVILETML RDDRYWRDYY DDSERLELDI WYNLLDRIRY YWEYEDVLMV LNLLFENFSE  360
GVDIKFIYQY FYDSYFDVRE GKMQNDPREL IKKEIMRVLE DYSYAINL              408

SEQ ID NO: 190         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 190
MWLSKDYLRN LGVYSIISSN SYVIEASIEF AMELGDYILI EATPHQVNQF GGYSGMTPED  60
FYNFVMTIAK ETGLEEDLII LGGDHLGPLP WQDEPSPTAM NKAKDLIRAF VESGYLWIHI  120
DASMPLSDDP EVLPYEKIAE RTRELFEIAE ETARNYNFQP VYVVGTDVPI AGGGEEEGVT  180
SVEDFRSAIS SLKKYFNDVP NIWDRVVGFV IMLGIGFSYD VVFEYDRDRV RGILEEVKRE  240
DLFVEGHSTD YQARYALRNM VEDGVRILIV GPALTAAFRR GVFLLSNIED EIIPERERSN  300
IMRVILETML RDDRYWRKYY DDSDRLELDI WYNLLDRIRY YWEYEDVLMV LNWLFENFSE  360
GVDIKFIYQY FYDSYFDVRE GRMRNDPREL ILKEIRRVLE DYSYAINL              408

SEQ ID NO: 191         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 191
MWLSKDYLRK QGVYSICSSN SYVIEASIEF AKEEGDYILI EATPHQVNQF GGYSGMTPED  60
FRNFVMKIAK ELGLEEDKII LGGDHLGPLP WQDEPSPTAM NKARDLIRAF VESGYKKIHI  120
DASMPLSDDP KVLPYEEIAE RTRELFEIAE ETARKYNFQP VYVVGTDVPI AGGGEEEGVT  180
SVEDFRSAIS SLEKYFNDVP NIWDRVVGFV IMLGIGFSYD QVFEYDRDRV RGILEEVKRE  240
DLFVEGHSTD YQARYALRNM VEDGVRILKV GPALTAAFRR GVFLLSNIED EIIPERERSN  300
IKRVILETML RDDRYWRDYY DDSDRLELDI WYNLLDRIRY YWEYEDVRMV LNRLFENFSE  360
GVDIRFIYQY FYDSYFDVRE GKMDNDPREL IKKEIKRVLE DYSYAINL              408

SEQ ID NO: 192         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 192
```

-continued

```
MWLSADYLRL QGVYSICSSN SYVIEASIEF AIEKGDYILI EATPHQVNQF GGYSGMTPED  60
FVNFVMKIAR ELGLEEDLII LGGDHLGPLP WQDEPSPTAM NYARDLIRAF VESGYLKIHI  120
DCSMPLSDDP EVLPYELIAE RTRELFEIAE ETAREYNFQP VYVVGTDVPI AGGGEEEGVT  180
SVEDFRSAIS SLKKYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVVMV LNLLFENFSE  360
GVDIKFIYQY FYDSYFDVRE GRMTNDPREL IRKEIKRVLE DYSYAINL                408

SEQ ID NO: 193          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 193
MWLSMDYLRK QGVYSISSSN SYVIEASIEF AKELGDYILI EATPHQVNQF GGYSGMTPED  60
FVNFVMTIAR ELGLEEDKII LGGDHLGPLP WQDEPSPTAM NYAQDLIRAF VESGYKKIHI  120
DCSMPLSDDP YVLPYELIAE RTRELFEIAE ETARKYNFQP VYVVGTDVPI AGGGEEEGVT  180
SVEDFRSAIS SLQKYFNDVP NIWDRVVGFV IMLGIGFSYD VVFEYDRDRV RGILEEVWRE  240
DLFVEGHSTD YQARYALRNM VEDGVRILKV GPALTAAFRR GVFLLSNIED EIIPERERSN  300
ILRVILETML RDDRYWRDYY DDSKRLELDI WYNLLDRIRY YWEYEDVKMV LNLLFENFSE  360
GVDISFIYQY FYDSYFDVRE GKMRNDPREL ILHEIIRVLE DYSYAINL                408

SEQ ID NO: 194          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 194
MWLSHDYLRN KGVYSICSSN SYVIEASIEF ALETGDYILI EATPHQVNQF GGYSGMTPED  60
FKNFVMSIAQ EKGLEEDLII LGGDHLGPLP WQDEPSPTAM NLARDLIRAF VESGYTKIHI  120
DCSMPLSDDP EVLPYELIAE RTRELFEIAE ETARKYNFQP VYVVGTDVPI AGGGEEEGVT  180
SVEDFRSAIS SLKRYFNDVP NIWDRVVGFV IMLGIGFSYD KVFEYDRDRV RGILEEVSRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIRFIYQY FYDSYFDVRE GLMKNDPREL IKKEIKRVLE DYSYAINL                408

SEQ ID NO: 195          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 195
MWLSFDYLRL LGVYSICSSN SYVIEASIEF AMELGDYILI EATPHQVNQF GGYSGMTPED  60
FVNFVMTIAR EKGLEEDLII LGGDHLGPLP WQDEPSPTAM NYAQDLIRAF VESGYIKIHI  120
DCSMPLSDDP EVLPYELIAE RTRELFEIAE ETARNYNFQP VYVVGTDVPI AGGGEEEGVT  180
SVEDFRSAIS SLQAYFNDVP NIWDRVVGFV IMLGIGFSYD IVFEYDRDRV RGILEEVWRE  240
DLFVEGHSTD YQARYALRNM VEDGVRILKV GPALTAAFRR GVFLLSNIED EIIPERERSN  300
ILRVILETML RDDRYWRDYY DDSDRLELDI WYNLLDRIRY YWEYEDVLMV LNWLFENFSE  360
GVDISFIYQY FYDSYFDVRE GRMDNDPREL IKKEIKRVLE DYSYAINL                408

SEQ ID NO: 196          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 196
MWLSLDYLRK VGVYSICSSN SYVIEASIEF ALEMGDYILI EATPHQVNQF GGYSGMTPED  60
FVNFVMSIAQ EKGLEEDLII LGGDHLGPLP WQDEPSPTAM NKAKDLIRAF VESGYKKIHI  120
DCSMPLSDDP KVLPYEKIAE RTRELFEIAE ETARRYNFQP VYVVGTDVPI AGGGEEEGVT  180
SVEDFRSAIS SLKAYFNDVP NIWDRVVGFV IMLGIGFSYD KVFEYDRDRV RGILEEVKRE  240
DLFVEGHSTD YQARYALRNM VEDGVRILKV GPALTAAFRR GVFLLSNIED EIIPERERSN  300
ILRVILETML RDDRYWRKYY DDSERLELDI WYNLLDRIRY YWEYEDVLMV LNKLFENFSE  360
GVDIRFIYQY FYDSYFDVRE GKMQNDPREL IKYEIKRVLE DYSYAINL                408

SEQ ID NO: 197          moltype = AA  length = 408
FEATURE                 Location/Qualifiers
REGION                  1..408
                        note = mutant D-fructose C4-epimerase
source                  1..408
                        mol_type = protein
                        organism = synthetic construct
```

```
SEQUENCE: 197
MWLSWDYLRN QGVYSITSSN SYVIEASIEF AKETGDYILI EATPHQVNQF GGYSGMTPED  60
FRNFVMTIAK ELGLEEDKII LGGDHLGPLP WQDEPSPTAM NRAKDLIRAF VESGYKKIHI  120
DCSMPLSDDP QVLPYEQIAE RTRELFEIAE ETARHYNFQP VYVVGTDVPI AGGGEEEGVT  180
SVEDFRSAIS SLKEYFNDVP NIWDRVVGFV IMLGIGFSYD RVFEYDRDTV RGILEEVKRE  240
DLFVEGHSTD YQARYALRNM VEDGVRILKV GPALTAAFRR GVFLLSNIED EIIPERERSN  300
IQRVILETML RDDRYWRDYY DDSKRLELDI WYNLLDRIRY YWEYEDVKMV LNRLFENFSE  360
GVDIKFIYQY FYDSYFDVRE GRMKNDPREL IKKEIKRVLE DYSYAINL           408

SEQ ID NO: 198         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 198
MWLSLDYLRK LGVYSICSSN SYVIEASIEF AIETGDYILI EATPHQVNQF GGYSGMTPED  60
FVNFVMSIAQ ELGLEEDKII LGGDHLGPLP WQDEPSPTAM NKAKDLIRAF VESGYTKIHI  120
DCSMPLSDDP EVLPYELIAE RTRELFEIAE ETAREYNFQP VYVVGTDVPI AGGGEEEGVT  180
SVEDFRSAIS SLEKYFNDVP NIWDRVVGFV IMLGIGFSYD KVFEYDRDAV RGILEEVKRE  240
DLFVEGHSTD YQARYALRNM VEDGVRILKV GPALTAAFRR GVFLLSNIED EIIPERERSN  300
IKRVILETML RDDRYWRKYY KDSERLELDI WYNLLDRIRY YWEYEDVLMV LNLLFENFSE  360
GVDIKFIYQY FYDSYFDVRE GLMRNDPREL ILYEIKRVLE DYSYAINL           408

SEQ ID NO: 199         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 199
MWLSKDYLRK LGVYSICSSN SYVIEASIEF AKEKGDYILI EATPHQVNQF GGYSGMTPED  60
FKNFVMSIAK ELGLEEDKII LGGDHLGPLP WQDEPSPTAM NKAIDLIRAF VESGYKKIHI  120
DTSMPLSDDP RVLPYEKIAE RTRELFEIAE ETARKYNFQP VYVVGTDVPI AGGGEEEGVT  180
SVEDFRSAIS SLEAYFNDVP NIWDRVVGFV IMLGIGFSYD IVFEYDRDAV RGILEEVKRE  240
DLFVEGHSTD YQARYALRNM VEDGVRILKV GPALTAAFRR GVFLLSNIED EIIPERERSN  300
ILRVILETML RDDRYWRDYY DDSERLELDI WYNLLDRIRY YWEYEDVLMV LNLLFENFSE  360
GVDISFIYQY FYDSYFDVRE GLMKNDPREL ILKEIMRVLE DYSYAINL           408

SEQ ID NO: 200         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 200
MWLSHDYLRK VGVYSIGSSN SYVIEASIEF AIETGDYILI EATPHQVNQF GGYSGMTPED  60
FKNFVMKIAQ ELGLEEDLII LGGDHLGPLP WQDEPSPTAM NKARDLIRAF VESGYKLIHI  120
DCSMPLSDDP EVLPYEKIAE RTRELFEIAE ETAREYNFQP VYVVGTDVPI AGGGEEEGVT  180
SVEDFRSAIS SLKTYFNDVP NIWDRVVGFV IMLGIGFSYD IVFEYDRDRV RGILEEVKRE  240
DLFVEGHSTD YQARYALRNM VEDGVRILNV GPALTAAFRR GVFLLSNIED EIIPERERSN  300
IKRVILETML RDDRYWRKYY DDSKRLELDI WYNLLDRIRY YWEYEDVLMV LNLLFENFSE  360
GVDIRFIYQY FYDSYFDVRE GLMKNDPREL IKYEIIRVLE DYSYAINL           408

SEQ ID NO: 201         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 201
MWLSFDYLRM LGVYSIISSN SYVIEASIEF AMELGDYILI EATPHQVNQF GGYSGMTPED  60
FVNFVMTIAR ELGLEEDLII LGGDHLGPLP WQDEPSPTAM NLAQDLIRAF VESGYIVIHI  120
DTSMPLSDDP EVLPYEEIAE RTRELFEIAE ETARNYNFQP VYVVGTDVPI AGGGEEEGVT  180
SVEDFRSAIS SLQAYFNDVP NIWDRVVGFV IMLGIGFSYD VVFEYDRDRV RGILEEVSRE  240
DLFVEGHSTD YQARYALRNM VEDGVRILIV GPALTAAFRR GVFLLSNIED EIIPERERSN  300
ILRVILETML RDDRYWRDYY DDSDRLELDI WYNLLDRIRY YWEYEDVLMV LNLLFENFSE  360
GVDISFIYQY FYDSYFDVRE GRMRNDPREL ILHEIMRVLE DYSYAINL           408

SEQ ID NO: 202         moltype = AA  length = 408
FEATURE                Location/Qualifiers
REGION                 1..408
                       note = mutant D-fructose C4-epimerase
source                 1..408
                       mol_type = protein
```

```
                         organism = synthetic construct
SEQUENCE: 202
MWLSWDYLRN QGVYSIISSN SYVIEASIEF AQETGDYILI EATPHQVNQF GGYSGMTPED  60
FRNFVMTIAR ELGLEEDRII LGGDHLGPLP WQDEPSPTAM NRARDLIRAF VESGYHVIHI  120
DVSMPLSDDP QVLPYETIAE RTRELFEIAE ETARHYNFQP VYVVGTDVPI AGGGEEEGVT  180
SVEDFRSAIS SLEEYFNDVP NIWDRVVGFV IMLGIGFSYD RVFEYDRDTV RGILEEVRRE  240
DLFVEGHSTD YQARYALRNM VEDGVRILVV GPALTAAFRR GVFLLSNIED EIIPERERSN  300
IQRVILETML RDDRYWRDYY DDSDRLELDI WYNLLDRIRY YWEYEDVRMV LNRLFENFSE  360
GVDIHFIYQY FYDSYFDVRE GRMDNDPREL IKKEIKRVLE DYSYAINL                408

SEQ ID NO: 203           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 203
MWLSADYLRN QGVYSITSSN SYVIEASIEF AQEEGDYILI EATPHQVNQF GGYSGMTPED  60
FRNFVMTIAR ELGLEEDQII LGGDHLGPLP WQDEPSPTAM NRARDLIRAF VESGYRKIHI  120
DCSMPLSDDP EVLPYEEIAE RTRELFEIAE ETAREYNFQP VYVVGTDVPI AGGGEEEGVT  180
SVEDFRSAIS SLETYFNDVP NIWDRVVGFV IMLGIGFSYD QVFEYDRDRV RGILEEVSRE  240
DLFVEGHSTD YQARYALRNM VEDGVRILKV GPALTAAFRR GVFLLSNIED EIIPERERSN  300
IQRVILETML RDDRYWRDYY DDSDRLELDI WYNLLDRIRY YWEYEDVRMV LNRLFENFSE  360
GVDIRFIYQY FYDSYFDVRE GRMDNDPREL IKKEIKRVLE DYSYAINL                408

SEQ ID NO: 204           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 204
MWLSLDYLRK KGVYSIGSSN SYVIEASIEF AIEMGDYILI EATPHQVNQF GGYSGMTPED  60
FVNFVMKIAK ELGLEEDLII LGGDHLGPLP WQDEPSPTAM NLAKDLIRAF VESGYTKIHI  120
DTSMPLSDDP EVLPYELIAE RTRELFEIAE ETAREYNFQP VYVVGTDVPI AGGGEEEGVT  180
SVEDFRSAIS SLQRYFNDVP NIWDRVVGFV IMLGIGFSYD KVFEYDRDRV RGILEEVKRE  240
DLFVEGHSTD YQARYALRNM VEDGVRILNV GPALTAAFRR GVFLLSNIED EIIPERERSN  300
IIRVILETML RDDRYWRDYY DDSERLELDI WYNLLDRIRY YWEYEDVLMV LNLLFENFSE  360
GVDISFIYQY FYDSYFDVRE GKMRNDPREL ILYEIKRVLE DYSYAINL                408

SEQ ID NO: 205           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 205
MWLSFDYLRN QGVYSICSSN SYVIEASIEF AQEQGDYILI EATPHQVNQF GGYSGMTPED  60
FRNFVMTIAR EKGLEEDQII LGGDHLGPLP WQDEPSPTAM NRAQDLIRAF VESGYQKIHI  120
DCSMPLSDDP EVLPYETIAE RTRELFEIAE ETARNYNFQP VYVVGTDVPI AGGGEEEGVT  180
SVEDFRSAIS SLQSYFNDVP NIWDRVVGFV IMLGIGFSYD TVFEYDRDRV RGILEEVSRE  240
DLFVEGHSTD YQARYALRNM VEDGVRILKV GPALTAAFRR GVFLLSNIED EIIPERERSN  300
IQRVILETML RDDRYWRDYY DDSDRLELDI WYNLLDRIRY YWEYEDVRMV LNRLFENFSE  360
GVDISFIYQY FYDSYFDVRE GRMENDPREL IKKEIKRVLE DYSYAINL                408

SEQ ID NO: 206           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 206
MWLSLDYLRN EGVYSIVSSN SYVIEASIEF AQEHGDYILI EATPHQVNQF GGYSGMTPED  60
FRNFVMQIAR ELGLEEDRII LGGDHLGPLP WQDEPSPTAM NRARDLIRAF VESGYRKIHI  120
DCSMPLSDDP RVLPYEEIAE RTRELFEIAE ETAREYNFQP VYVVGTDVPI AGGGEEEGVT  180
SVEDFRSAIS SLETYFNDVP NIWDRVVGFV IMLGIGFSYD RVFEYDRDNV RGILEEVSRE  240
DLFVEGHSTD YQARYALRNM VEDGVRILKV GPALTAAFRR GVFLLSNIED EIIPERERSN  300
IRRVILETML RDDRYWRDYY DDSSRLELDI WYNLLDRIRY YWEYEDVRMV LNQLFENFSE  360
GVDIRFIYQY FYDSYFDVRE GNMQNDPREL IKKEIKRVLE DYSYAINL                408

SEQ ID NO: 207           moltype = AA  length = 408
FEATURE                  Location/Qualifiers
REGION                   1..408
                         note = mutant D-fructose C4-epimerase
source                   1..408
```

```
                         mol_type = protein
                         organism = synthetic construct
SEQUENCE: 207
MWLSLDYLRN VGVYSIISSN SYVIEASIEF ASEFGDYILI EATPHQVNQF GGYSGMTPED  60
FVNFVMQIAR EIGLEEDMII LGGDHLGPLP WQDEPSPTAM NLAFDLIRAF VESGYWVIHI  120
DASMPLSDDP RVLPYEEIAE RTRELFEIAE ETAREYNFQP VYVVGTDVPI AGGGEEEGVT  180
SVEDFRSAIS SLAAYFNDVP NIWDRVVGFV IMLGIGFSYD IVFEYDRDQV RGILEEVSRE  240
DLFVEGHSTD YQARYALRNM VEDGVRILVV GPALTAAFRR GVFLLSNIED EIIPERERSN  300
ILRVILETML RDDRYWRDYY DDSSRLELDI WYNLLDRIRY YWEYEDVLMV LNLLFENFSE  360
GVDIRFIYQY FYDSYFDVRE GNMRNDPREL ILFEIFRVLE DYSYAINL              408

SEQ ID NO: 208         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 208
MWLSLDYLRN LGVYSICSSN SYVIEASIEF ALEMGDYILI EATPHQVNQF GGYSGMTPED  60
FVNFVMSIAQ EKGLEEDLII LGGDHLGPLP WQDEPSPTAM NYARDLIRAF VESGYTKIHI  120
DCSMPLSDDP EVLPYELIAE RTRELFEIAE ETAREYNFQP VYVVGTDVPI AGGGEEEGVT  180
SVEDFRSAIS SLQRYFNDVP NIWDRVVGFV IMLGIGFSYD IVFEYDRDRV RGILEEVSRE  240
DLFVEGHSTD YQARYALRNM VEDGVRILKV GPALTAAFRR GVFLLSNIED EIIPERERSN  300
IIRVILETML RDDRYWRDYY DDSERLELDI WYNLLDRIRY YWEYEDVLMV LNLLFENFSE  360
GVDISFIYQY FYDSYFDVRE GLMENDPREL IKKEIKRVLE DYSYAINL              408

SEQ ID NO: 209         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 209
MWLSLDYLRA LGVYSICSSN SYVIEASIEF AIETGDYILI EATPHQVNQF GGYSGMTPED  60
FVNFVMSIAQ EKGLEEDLII LGGDHLGPLP WQDEPSPTAM NYAIDLIRAF VESGYTKIHI  120
DCSMPLSDDP EVLPYELIAE RTRELFEIAE ETAREYNFQP VYVVGTDVPI AGGGEEEGVT  180
SVEDFRSAIS SLEAYFNDVP NIWDRVVGFV IMLGIGFSYD IVFEYDRDAV RGILEEVSRE  240
DLFVEGHSTD YQARYALRNM VEDGVRILKV GPALTAAFRR GVFLLSNIED EIIPERERSN  300
ILRVILETML RDDRYWRDYY DDSERLELDI WYNLLDRIRY YWEYEDVLMV LNLLFENFSE  360
GVDISFIYQY FYDSYFDVRE GLMENDPREL IKKEIKRVLE DYSYAINL              408

SEQ ID NO: 210         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 210
MWLSWDYLRR RGVYSICSSN SYVIEASIEF AQEQGDYILI EATPHQVNQF GGYSGMTPED  60
FRNFVMTIAR EKGLEEDQII LGGDHLGPLP WQDEPSPTAM NRARDLIRAF VESGYRKIHI  120
DCSMPLSDDP QVLPYEEIAE RTRELFEIAE ETARDYNFQP VYVVGTDVPI AGGGEEEGVT  180
SVEDFRSAIS SLRTYFNDVP NIWDRVVGFV IMLGIGFSYD RVFEYDRDTV RGILEEVSRE  240
DLFVEGHSTD YQARYALRNM VEDGVRILKV GPALTAAFRR GVFLLSNIED EIIPERERSN  300
IQRVILETML RDDRYWREYY DDSDRLELDI WYNLLDRIRY YWEYEDVRMV LNRLFENFSE  360
GVDIRFIYQY FYDSYFDVRE GRMENDPREL IKKEIKRVLE DYSYAINL              408

SEQ ID NO: 211         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 211
MWLSMDYLRM QGVYSISSSN SYVIEASIEF AMELGDYILI EATPHQVNQF GGYSGMTPED  60
FVNFVMTIAR ELGLEEDMII LGGDHLGPLP WQDEPSPTAM NLARDLIRAF VESGYIKIHI  120
DCSMPLSDDP YVLPYELIAE RTRELFEIAE ETARNYNFQP VYVVGTDVPI AGGGEEEGVT  180
SVEDFRSAIS SLASYFNDVP NIWDRVVGFV IMLGIGFSYD IVFEYDRDRV RGILEEVSRE  240
DLFVEGHSTD YQARYALRNM VEDGVRILKV GPALTAAFRR GVFLLSNIED EIIPERERSN  300
ILRVILETML RDDRYWRDYY DDSDRLELDI WYNLLDRIRY YWEYEDVLMV LNWLFENFSE  360
GVDISFIYQY FYDSYFDVRE GRMRNDPREL ILYEIMRVLE DYSYAINL              408

SEQ ID NO: 212         moltype = AA  length = 408
FEATURE                Location/Qualifiers
REGION                 1..408
                       note = mutant D-fructose C4-epimerase
```

```
source                  1..408
                        mol_type = protein
                        organism = synthetic construct
SEQUENCE: 212
MWLSFDYLRL LGVYSITSSN SYVIEASIEF AMELGDYILI EATPHQVNQF GGYSGMTPED  60
FYNFVMQIAR ELGLEEDRII LGGDHLGPLP WQDEPSPTAM NYAVDLIRAF VESGYRKIHI  120
DCSMPLSDDP LVLPYEEIAE RTRELFEIAE ETAREYNFQP VYVVGTDVPI AGGGEEEGVT  180
SVEDFRSAIS SLEAYFNDVP NIWDRVVGFV IMLGIGFSYD VVFEYDRDAV RGILEEVSRE  240
DLFVEGHSTD YQARYALRNM VEDGVRILKV GPALTAAFRR GVFLLSNIED EIIPERERSN  300
IMRVILETML RDDRYWRDYY DDSSRLELDI WYNLLDRIRY YWEYEDVRMV LNLLFENFSE  360
GVDISFIYQY FYDSYFDVRE GRMRNDPREL ILYEIIRVLE DYSYAINL            408

SEQ ID NO: 213          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 213
MWLSLDYLRN QGVYSISSSN SYVIEASIEF AQERGDYILI EATPHQVNQF GGYSGMTPED  60
FRNFVMTIAR ELGLEEDRII LGGDHLGPLP WQDEPSPTAM NRARDLIRAF VESGYQVIHI  120
DTSMPLSDDP EVLPYEEIAE RTRELFEIAE ETAREYNFQP VYVVGTDVPI AGGGEEEGVT  180
SVEDFRSAIS SLESYFNDVP NIWDRVVGFV IMLGIGFSYD RVFEYDRDSV RGILEEVSRE  240
DLFVEGHSTD YQARYALRNM VEDGVRILVV GPALTAAFRR GVFLLSNIED EIIPERERSN  300
IQRVILETML RDDRYWRDYY DDSSRLELDI WYNLLDRIRY YWEYEDVRMV LNRLFENFSE  360
GVDISFIYQY FYDSYFDVRE GRMQNDPREL IKKEIKRVLE DYSYAINL            408

SEQ ID NO: 214          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 214
MWLSLDYLRA VGVYSIGSSN SYVIEASIEF ALEYGDYILI EATPHQVNQF GGYSGMTPED  60
FVNFVMRIAQ ELGLEEDRII LGGDHLGPLP WQDEPSPTAM NLARDLIRAF VESGYTKIHI  120
DCSMPLSDDP RVLPYEIIAE RTRELFEIAE ETAREYNFQP VYVVGTDVPI AGGGEEEGVT  180
SVEDFRSAIS SLEAYFNDVP NIWDRVVGFV IMLGIGFSYD IVFEYDRDNV RGILEEVSRE  240
DLFVEGHSTD YQARYALRNM VEDGVRILKV GPALTAAFRR GVFLLSNIED EIIPERERSN  300
ILRVILETML RDDRYWRDYY DDSERLELDI WYNLLDRIRY YWEYEDVLMV LNLLFENFSE  360
GVDIRFIYQY FYDSYFDVRE GLMRNDPREL ILYEIIRVLE DYSYAINL            408

SEQ ID NO: 215          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 215
MWLSADYLRN VGVYSIGSSN SYVIEASIEF AIETGDYILI EATPHQVNQF GGYSGMTPED  60
FVNFVMSIAQ ELGLEEDLII LGGDHLGPLP WQDEPSPTAM NYARDLIRAF VESGYTKIHI  120
DCSMPLSDDP EVLPYELIAE RTRELFEIAE ETAREYNFQP VYVVGTDVPI AGGGEEEGVT  180
SVEDFRSAIS SLERYFNDVP NIWDRVVGFV IMLGIGFSYD IVFEYDRDRV RGILEEVSRE  240
DLFVEGHSTD YQARYALRNM VEDGVRILKV GPALTAAFRR GVFLLSNIED EIIPERERSN  300
IIRVILETML RDDRYWRDYY DDSERLELDI WYNLLDRIRY YWEYEDVLMV LNLLFENFSE  360
GVDIRFIYQY FYDSYFDVRE GLMTNDPREL ILYEIIRVLE DYSYAINL            408

SEQ ID NO: 216          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 216
MWLSADYLRN VGVYSIGSSN SYVIEASIEF AIEMGDYILI EATPHQVNQF GGYSGMTPED  60
FVNFVMSIAQ ELGLEEDRII LGGDHLGPLP WQDEPSPTAM NYAIDLIRAF VESGYSLIHI  120
DTSMPLSDDP EVLPYELIAE RTRELFEIAE ETAREYNFQP VYVVGTDVPI AGGGEEEGVT  180
SVEDFRSAIS SLEAYFNDVP NIWDRVVGFV IMLGIGFSYD IVFEYDRDAV RGILEEVSRE  240
DLFVEGHSTD YQARYALRNM VEDGVRILNV GPALTAAFRR GVFLLSNIED EIIPERERSN  300
ILRVILETML RDDRYWRDYY DDSERLELDI WYNLLDRIRY YWEYEDVRMV LNLLFENFSE  360
GVDISFIYQY FYDSYFDVRE GLMRNDPREL ILYEIIRVLE DYSYAINL            408

SEQ ID NO: 217          moltype = AA  length = 408
FEATURE                 Location/Qualifiers
REGION                  1..408
```

```
                        note = mutant D-fructose C4-epimerase
source                  1..408
                        mol_type = protein
                        organism = synthetic construct
SEQUENCE: 217
MWLSLDYLRR VGVYSIGSSN SYVIEASIEF AIEMGDYILI EATPHQVNQF GGYSGMTPED  60
FVNFVMSIAQ ELGLEEDLII LGGDHLGPLP WQDEPSPTAM NYARDLIRAF VESGYTLIHI  120
DTSMPLSDDP RVLPYELIAE RTRELFEIAE ETARRYNFQP VYVVGTDVPI AGGGEEEGVT  180
SVEDFRSAIS SLIAYFNDVP NIWDRVVGFV IMLGIGFSYD IVFEYDRDRV RGILEEVSRE  240
DLFVEGHSTD YQARYALRNM VEDGVRILNV GPALTAAFRR GVFLLSNIED EIIPERERSN  300
ILRVILETML RDDRYWRDYY DDSERLELDI WYNLLDRIRY YWEYEDVLMV LNLLFENFSE  360
GVDIRFIYQY FYDSYFDVRE GLMRNDPREL ILYEIIRVLE DYSYAINL              408

SEQ ID NO: 218          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 218
MWLSRDYLRR RGVYSICSSN SYVIEASIEF ARERGDYILI EATPHQVNQF GGYSGMTPED  60
FRNFVMRIAR EKGLEEDRII LGGDHLGPLP WQDEPSPTAM NRARDLIRAF VESGYRKIHI  120
DCSMPLSDDP RVLPYERIAE RTRELFEIAE ETARRYNFQP VYVVGTDVPI AGGGEEEGVT  180
SVEDFRSAIS SLRRYFNDVP NIWDRVVGFV IMLGIGFSYD RVFEYDRDRV RGILEEVRRE  240
DLFVEGHSTD YQARYALRNM VEDGVRILKV GPALTAAFRR GVFLLSNIED EIIPERERSN  300
IRRVILETML RDDRYWRRYY RDSRRLELDI WYNLLDRIRY YWEYEDVRMV LNRLFENFSE  360
GVDIRFIYQY FYDSYFDVRE GRMRNDPREL IKKEIKRVLE DYSYAINL              408

SEQ ID NO: 219          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 219
MWLSRDYLRR RGVYSIRSSN SYVIEASIEF ARERGDYILI EATPHQVNQF GGYSGMTPED  60
FRNFVMRIAR ERGLEEDRII LGGDHLGPLP WQDEPSPTAM NRARDLIRAF VESGYRKIHI  120
DCSMPLSDDP RVLPYERIAE RTRELFEIAE ETARRYNFQP VYVVGTDVPI AGGGEEEGVT  180
SVEDFRSAIS SLRRYFNDVP NIWDRVVGFV IMLGIGFSYD RVFEYDRDRV RGILEEVRRE  240
DLFVEGHSTD YQARYALRNM VEDGVRILKV GPALTAAFRR GVFLLSNIED EIIPERERSN  300
IRRVILETML RDDRYWRRYY RDSRRLELDI WYNLLDRIRY YWEYEDVRMV LNRLFENFSE  360
GVDIRFIYQY FYDSYFDVRE GRMRNDPREL IRREIRRVLE DYSYAINL              408

SEQ ID NO: 220          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 220
MWLSRDYLRR RGVYSIRSSN SYVIEASIEF ARERGDYILI EATPHQVNQF GGYSGMTPED  60
FRNFVMRIAR ERGLEEDRII LGGDHLGPLP WQDEPSPTAM NRARDLIRAF VESGYRRIHI  120
DRSMPLSDDP RVLPYERIAE RTRELFEIAE ETARRYNFQP VYVVGTDVPI AGGGEEEGVT  180
SVEDFRSAIS SLRRYFNDVP NIWDRVVGFV IMLGIGFSYD RVFEYDRDRV RGILEEVRRE  240
DLFVEGHSTD YQARYALRNM VEDGVRILRV GPALTAAFRR GVFLLSNIED EIIPERERSN  300
IRRVILETML RDDRYWRRYY RDSRRLELDI WYNLLDRIRY YWEYEDVRMV LNRLFENFSE  360
GVDIRFIYQY FYDSYFDVRE GRMRNDPREL IRREIRRVLE DYSYAINL              408

SEQ ID NO: 221          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 221
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NYAKDLIRAF VESGYKKIHI  120
DCSMPLSDDP QVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 222          moltype = AA  length = 408
FEATURE                 Location/Qualifiers
```

```
REGION                  1..408
                        note = mutant D-fructose C4-epimerase
source                  1..408
                        mol_type = protein
                        organism = synthetic construct
SEQUENCE: 222
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NLAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD IVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 223          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 223
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NRAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD TVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 224          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 224
MWLSKDYLRK KGVYSITSSN SYVIEASIEF AKEKGDYILI EATPHQVNQF GGYSGMTPED  60
FKNFVMKIAK EKGLEEDKII LGGDHLGPLP WQDEPSPTAM NRAKDLIRAF VESGYKKIHI  120
DCSMPLSDDP QVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDKV RGILEEVKRE  240
DLFVEGHSTD YQARYALRNM VEDGVRILVV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 225          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 225
MWLSKDYLRK KGVYSILSSN SYVIEASIEF AKEKGDYILI EATPHQVNQF GGYSGMTPED  60
FKNFVMKIAK EKGLEEDKII LGGDHLGPLP WQDEPSPTAM NLAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD RVFEYDRDKV RGILEEVKRE  240
DLFVEGHSTD YQARYALRNM VEDGVRILLV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 226          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 226
MWLSKDYLRK KGVYSIGSSN SYVIEASIEF AKEKGDYILI EATPHQVNQF GGYSGMTPED  60
FKNFVMKIAK EKGLEEDKII LGGDHLGPLP WQDEPSPTAM NYAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD IVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 227          moltype = AA  length = 408
```

```
FEATURE                Location/Qualifiers
REGION                 1..408
                       note = mutant D-fructose C4-epimerase
source                 1..408
                       mol_type = protein
                       organism = synthetic construct
SEQUENCE: 227
MWLSKDYLRK KGVYSISSSN SYVIEASIEF AKEKGDYILI EATPHQVNQF GGYSGMTPED  60
FKNFVMKIAK EKGLEEDKII LGGDHLGPLP WQDEPSPTAM NLAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD VVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 228         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 228
MWLSKDYLRK KGVYSITSSN SYVIEASIEF AKEKGDYILI EATPHQVNQF GGYSGMTPED  60
FKNFVMKIAK EKGLEEDKII LGGDHLGPLP WQDEPSPTAM NRAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD QVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 229         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 229
MWLSKDYLRK KGVYSIGSSN SYVIEASIEF AKEKGDYILI EATPHQVNQF GGYSGMTPED  60
FKNFVMKIAK EKGLEEDKII LGGDHLGPLP WQDEPSPTAM NLAKDLIRAF VESGYKKIHI  120
DCSMPLSDDP EVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD QVFEYDRDKV RGILEEVKRE  240
DLFVEGHSTD YQARYALRNM VEDGVRILNV GPALTAAFRR GVFLLSNIED EIIPERERSN  300
IKRVILETML RDDRYWRDYY DDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 230         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 230
MWLSKDYLRK KGVYSIGSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILNV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 231         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 231
MWLSKDYLRK KGVYSICSSN SYVIEASIEF AKEKGDYILI EATPHQVNQF GGFSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTAVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRA YWEYEDVKMV LNKLFENFSE  360
GVDIKFIYQY FYDSYFDVRE GKMKNDPREL IKKEIKRVLE DYSYAINL              408
```

```
SEQ ID NO: 232         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 232
MWERRENGQR EGVYSICSSN EYVIRASIRF ARERHDRILI EATPHQVNHR GGYSGMTPED  60
FRREVERIAR EEGLDERRII LGGDHLGPLP WQDRPRPEAM NEARQLIRAF VESGYDKIHI  120
DCSMPLSDEP EVLDYREIAE QTRQLFEEAE RRRTERDRQP VYVVGTDVPI AGGGEEEGVT  180
SVEDFRRAIE YLERYFPDVP NIWDRVVGFV IMLGIGFTRD RVFQYDREEV RRILEEVRRT  240
DLFVEGHSTD YQARYALRNM VEDGVRILKV GPALTAAFRR GVFLLSEIER EIIPERRRQD  300
IRRVILETML RDDRYWRDYY DTSDEHRRDI EYNLLDRIRY YWDYPDVREV LRRLFENFSE  360
GVDPEFIREY FYRSYERVRD GEMRNDPREL IEEEIRQVLE DYRYAIDR            408

SEQ ID NO: 233         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 233
MWERRRHGEE RGVYSICSSN EYVIRASIEF ARQRGRDILI EATPHQVNQH GGYSGMTPED  60
FKRFVMEIAR EEGLDERRIR LGGDHLGPLP WQDRPEPEAM QEARELIRAF VESGYRKIHI  120
DCSMPLSDDP KVLPQEEIAR RTRELFEVAE RRRQEYEEEP VYVVGTDVPI AGGGEEEGVT  180
SVEDFRRAIE HLEEYFPDVP NIRDRVVGFV IMLGIGFTRD RVFQYDRDKV RGILEEVKRT  240
DLFVEGHSTD YQARYALRNM VRDGVRILKV GPALTAAFRR GVFLLSEIER EIIPERRRQD  300
IRRVILETML RDDRYWRDYY ETSDQLRLDI EYNLLDRIRY YWDYPDVREV LRRLFENFSE  360
GVDERRIYEY FYESYQDVRD GRMRNDPREL IREEIRRVLE DYEYAIDG            408

SEQ ID NO: 234         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 234
MWLRKQNNEP VGVYSICSSN PYVIEASIEF AMELSDYILI EATPHQVNFQ GGYSGMTPED  60
FRRFVMEIAR SKGLDERMII LGGDHLGPLP WQDLPEPQAM EYARQLIRAF VESGYQKIHI  120
DCSMPLSDDP ETLDWRRIAE RTRELFEIAE RTSPPVPNTI VYVVGTDVPI AGGGEEEGVT  180
SVEDFRSAIE TLERYFEDVP NIRDRVVGFV IMLGINFSYR TVFEYDRDQV EEILREVERT  240
DLFVEGHSTD YQARYALENM VRDGVRILKV GPALTAAFRR GVFLLSQIER EIIPERHRSD  300
IRRVILETML RDPRYWRDYY DDSPQLEEDI WYNLLDRIRY YWEYPDVEEV LRQLFENFSE  360
GVDERFIYQY FYDSYFDVRN GNMDTDPREL IKKEIKRVLE DYAYAIQL            408

SEQ ID NO: 235         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 235
MWLRQRNGEP VGVYSICSSN EYVIEASIEF AQESNTYILI EATPHQVNHR GGYSGMTPRD  60
FRRFVEEIAR SKGLDERRII LGGDHLGPLP WQDRPEPEAM QEARELIRAF VESGYRKIHI  120
DCSMPLSDQS ETLDYREIAR QTRELFREAE ETATTDPNET VYVVGTDVPI AGGGEEEGRT  180
SVEDFRSAIE ELERYFRDVD NIRDRVVGFV IMLGITFSRD RVFEYDRDQV REILEEVRRT  240
DLFVEGHSTD YQARYALRNM VEDGVRILKV GPALTAAFRR GVFLLSRIER EIIPERHRSN  300
IEEVILRTML RDDRYWRNYY EDSDQLREDI WYNLLDRIRY YWDYPDVREV LRQLFENFSE  360
GVDERFIYRY FYDSYFDVRD GRMQNDPREL IKKEIKRVLE DYRYAIEL            408

SEQ ID NO: 236         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 236
MWLRHQNNEP VGVYSICSSN PYVIEASIEF AQESNSYILI EATPHQVNQH GGYSGMTPED  60
FKEFVMRIAR SKGLDERRII LGGDHLGPLP WQDQPEPEAM QEARELIRAF VESGYLKIHI  120
DCSMPLSDQP ETLDYREIAR HTRELFQIAE ETSPPRPNQT VYVVGTDVPI AGGGEEEGVT  180
SVEDFRSAIE ALERYFEDVP NIRDRVVGFV IMLGINFSYR EVFEYDRDQV EEILREVERT  240
DLFVEGHSTD YQARYALRNM VEDGVRILKV GPALTAAFRR GVFLLSQIER EIIPERHRSN  300
IQEVILQTML RDPRYWRDYY DDSPQLEEDI WYNLLDRIRY YWDYPDVEEV LRQLFENFSE  360
GVDERFIYRY FYDSYFDVRE GKMKNDPREL IKKEIKRVLE DYRYAIEL            408
```

```
SEQ ID NO: 237          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 237
MWLRQRNGQR WGVYSICSSN EYVIRASIRF AKQRDQYILI EATPHQVNHR GGYSGMTPRD  60
FRRFVEQIAR EEGLEPRRII LGGDHLGPLP WQDRPEPEAM EEARELIRAF VESGYEKIHI  120
DCSMPLSDDS ETLDYREIAR RTRELFREAE ETATTDPNRT VYVVGTDVPI AGGGEEEGRT  180
SVEDFRSAIE YLRQYFQDVP NIWDRVVGFV IMLGITFSRR RVFEYDRDQV REILEEVRRT  240
DLFVEGHSTD YQARYALRNM VEDGVRILKV GPALTAAFRR GVFLLSEIER EIIPERRRSN  300
IREVILRTML RDDRYWRKYY EDSDELEEDI EYNLLDRIRY YWDYPDVRRV LEELFRNFSE  360
GVDERFIYRY FYDSYFHVRD GRMRNDPREL IEQEIREVLE DYRYAIEL                408

SEQ ID NO: 238          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 238
MWLERHYNLE RGVYSICSSN PYVIEASIEF ARNRHLPILI EATPHQVNIF GGYSGMTPTD  60
FRDFVMDIAR RKGLDERDII LGGDHLGPLP WQDLPAPEAM DRARQLIRAF VESGYRKIHI  120
DCSMPLSDQP EVLHWDEIAE LTRELFRVAE EVAQDYPNLL VYVVGTDVPI AGGGEEEGIT  180
SVEDFRSAIE ALRRYFNDVL NIWDRVVGFV IMLGIRFSYD RVFMYDRDRV REILEEVRRV  240
PLFVEGHSTD YQARYALRNM VQDGVRILKV GPALTAAFRR GVFLLSLIED EIIPERRRSE  300
IRRVILETML RDPRYWRDYY DDSDRLYWDI LYNLLDRIRY YWDYPDVRTV LERLFRNFSE  360
PVPLEHIRDY FYDSYEDVRD GRMENDPREL IKKEIKRVLE DYAYAIDT                408

SEQ ID NO: 239          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 239
MWERREYGQR EGVYSICSSN RYVIEASIEF ARTRHDRILI EATPHQVNHR GGYSGMTPED  60
FKREVMRIAR EKGLDERRII LGGDHLGPLP WQDRPRPEAM NEARQLIRAF VESGYRKIHI  120
DCSMPLSDEP KVLPWEEIAE QTRQLFEEAE RRRTEYNFQP EYVVGTDVPI AGGGEEEGVT  180
SVEDFRRAIE ELKRYFPDVP NIRDRVVGFV IMLGIGFSRD KVFEYDRDKV RGILEEVKRE  240
DLFVEGHSTD YQARYALRNM VEDGVRILKV GPALTAAFRR GVFLLSNIED EQIPERERQN  300
IKRVILETML RDDRYWRDYY DTSDRHREDI WYNLLDRIRY YWEYEDVKRV LEELFRNFSE  360
GVDPEFIRRY FYDSYEDVRN GRMRNDPREL IKKEIKRVLE DYRYAIER                408

SEQ ID NO: 240          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 240
MWLRHQYGQE EGVYSICSSN EYVIRASIRF AQRKHERILI EATPHQVNHR GGYSGMTPRD  60
FREEVMRIAR EEGLDERQII LGGDHLGPLP WQDRPRPEAM NEARQLIRAF VESGYRKIHI  120
DCSMPLSDEP KVLPYEEIAR QTRELFEEAE RRARKYNFQP EYVVGTDVPI AGGGEEEGVT  180
SVEDFRRAIE ELKRYFPDVP NIRDRVVGFV IMLGIGFSRD KVFEYDRDQV REILEEVRRE  240
DLFVEGHSTD YQARYALRNM VQDGVRILKV GPALTAAFRR GVFLLSEIER EQIPERERSN  300
IREVILRTML RDDRYWRKYY DTSDRHREDI EYNLLDRIRY YWDYPDVREV LRKLFENFSE  360
GVDIRFIYRY FYRSYEDVRE GRMQNDPREL IHREIEEVLQ DYRYAIER                408

SEQ ID NO: 241          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 241
MWEEHRHGQE FGVYSICSSN EYVIEASIEF AKEQGTYILI EATPHQVNHR GGYSGMTPED  60
FRRFVEEIAR RKGLDERMII LGGDHLGPLP WQDQPRPTAM NEARELIRAF VESGYTKIHI  120
DCSMPLSDDP EVLPDEEIAR RTRELFEEAE RHRQQYPTEP VYVVGTDVPI AGGGEEEGVT  180
SVEDFRRAIE ALQRYFPDVE NIRDRVVGFV IMLGIGFTRD RVFQYDRDRV REILEEVRRT  240
DLFVEGHSTD YQARYALRNM VRDGVRILKV GPALTAAFRR GVFLLSEIER EIIPERRRQD  300
IRRVILETML RDDRYWRDYY ETSKQLEEDI EYNLLDRIRY YWDYPDVRRV LNELFRNFSE  360
```

```
GVDERFIYQY FYDSYQDVRD GRMTNDPREL IKKEIKRVLE DYSYAIHR              408

SEQ ID NO: 242          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 242
MWLRKQNNEK RGVYSICSSN PYVIEASIEF ARERNDYILI EATPHQVNQF GGYSGMTPED  60
FKRFVMEIAR SKGLDERRII LGGDHLGPLP WQDLPSPEAM RRAEELIRAF VESGYRKIHI  120
DCSMPLSDDP ETLPWEKIAE RTRRLFEIAE RTAPEVPNEM VYVVGTDVPI AGGGEEEGVT  180
SVEDFRSAIS TLERYFEDVP NIRDRVVGFV IMLGIGFSYD KVFEYDRDKV RGILEEVKRT  240
DLFVEGHSTD YQARYALRNM VEDGVRILKV GPALTAAFRR GVFLLSQIER EIIPERHRSD  300
IRRVILETML RDDRYWRKYY DDSDQLELDI WYNLLDRIRY YWEYEDVKRV LEELFRNFSE  360
GVDERFIYQY FYDSYFDVRN GRMKNDPREL IKKEIKRVLE DYAYAIQL              408

SEQ ID NO: 243          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 243
MWLEKQNNQD RGVYSICSSN PYVIEASIEF ARERDQYILI EATPHQVNQF GGYSGMTPED  60
FKRFVMEIAR QKGLEEDMII LGGDHLGPLP WQDEPEPTAM EKARQLIRAF VESGYRKIHI  120
DCSMPLSDQP ETLDWREIAR LTRELFEIAE RTAPEVPNEM VYVVGTDVPI AGGGEEEGVT  180
SVEDFRSAIE TLKRYFSDVP NIADRVVGFV IMLGINFSYR EVFEYDRDRV REILEEVKRE  240
DLFVEGHSTD YQARYALENM VRDGVRILKV GPALTAAFRR GVFLLSQIER EIIPERHRSN  300
IERVILETML RDDRYWRKYY DDSDQLEEDI WYNLLDRIRY YWDYEDVRRV LEELFRNFSE  360
GVDERFIYQY FYDSYFDVRN GRMENDPREL IKKEIKRVLE DYAYAIEL              408

SEQ ID NO: 244          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 244
MWLRHEYGQR EGVYSICSSN RYVIEASIEF AQTRHERILI EATPHQVNHR GGYSGMTPED  60
FKREVMRIAR EKGLDEDKII LGGDHLGPLP WQDRPSPEAM EEAKELIRAF VESGYRKIHI  120
DCSMPLSDEP EVLPYEKIAE RTRELFEIAE ETRTQYNFQP EYVVGTDVPI AGGGEEEGVT  180
SVEDFRSAIE QLQRHFPDVE NIRDRVVGFV IMLGIGFSRD KVFEYDRDQV REILEEVRRT  240
DLFVEGHSTD YQARYALRNM VEDGVRILKV GPALTAAFRR GVFLLSEIER EIIPERRRQD  300
IRRVILETML RDDRYWRNYY DTSDEHRRDI EYNLLDRIRY YWNYPDVEEV LRRLFENFSE  360
GVDPEFIRRY FYDSYEDVRE GRMQNDPREL IKKEIKRVLE DYRYAIER              408

SEQ ID NO: 245          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 245
MWLEHHYGRP QGVYSICSSN EYVIRASIRF AQRQHHPILI EATPHQVNHR GGYSGMTPED  60
FRRFVEQIAR EEGLEERMII LGGDHLGPLP WQDRPEPEAM NEARELIRAF VESGYWKIHI  120
DCSMPLSDDS ETLDYRRIAE RTRELFREAE ETARGYPFQP VYVVGTDVPI AGGGEEEGRT  180
SVEDFRSAIE YLRQYFNDVR NIWDRVVGFV IMLGIRFSRD RVFEYDRDQV REILEEVRRH  240
DLFVEGHSTD YQARYALRNM VEDGVRILKV GPALTAAFRR GVFLLSEIER EIIPERRRSD  300
IRRVILETML RDDRYWRDYY ETSEQLERDI WYNLLDRIRY YWDYPDVREV LRRLFENFSE  360
PVDIRFIYRY FYDSYEDVRD GRMQPDPREL ILHEIEEVLR DYSYAIND              408

SEQ ID NO: 246          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 246
MWLRHHYNEP QGVYSICSSN PYVIEASIEF AQHRHEPILI EATPHQVNQH GGYSGMTPED  60
FRRFVMEIAR RKGLDERLII LGGDHLGPLP WQDQPEPEAM NQAQELIRAF VESGYLKIHI  120
DCSMPLSDQP EVLPYEEIAE HTRELFRVAE ETAQDYPFQL VYVVGTDVPI AGGGEEEGVT  180
SVEDFRSAIE HLRQYFRDVP NIWDRVVGFV IMLGIRFSYD RVFEYDRDQV REILEEVRRE  240
PLFVEGHSTD YQARYALRNM VEDGVRILKV GPALTAAFRR GVFLLSQIED EIIPERERSN  300
```

```
IRQVILETML RDPRYWRDYY DDSDRLEEDI WYNLLDRIRY YWDYEDVRRV LERLFRNFSE  360
PVDIRFIYRY FYDSYEDVRD GRMEPDPREL IKKEIKRVLE DYRYAIDT               408

SEQ ID NO: 247          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 247
MWEEKRHGRE RGVYSICSSN EYVIEASIEF AIEMGYYILI EATPHQVNWS GGYSGWTPED  60
FRRFVEEIAR RKGLDPDMII LGGDHLGPLP WQDLPEPRAM EYARELIRAF VESGYLKIHI  120
DCSMPLSDRP DELPREEIAR WTRDLFEIAE RYRQTFRTEP VYVVGTDVPI AGGGEEEGVT  180
SVEDFRSAIE YLQRYFPDVP NIRDRVVGFV IMLGIGFTRR RVFQYDRDRV REILEEVRRT  240
DLFVEGHSTD YQARYALRNM VRDGVRILKV GPALTAAFRR GVFLLSEIER EIIPERRRQN  300
IREVILRTML RDDRYWRDYY ETSDRLEEDI EYNLLDRIRY YWDYPDVREV LRRLFENFSE  360
GVDPRFIYRY FYDSYEDVRR GQMTNDPREL IKKEIKRVLE DYAYAIWD               408

SEQ ID NO: 248          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 248
MWLRHQNNEP VGVYSICSSN PYVIEASIRA AQQTNTYILI EATPHQVNQH GGYSGMTPED  60
FREFVMRIAR STGLDERRII LGGDHLGPLP WQDQPEPEAM EQARQLIRAF VESGYLKIHI  120
DCSMPLSDDP ETLDYRRIAE RTRELFEIAE RTSPPRPNQT VYVVGTDVPI AGGGEEEGVT  180
SVEDFRSAIE HLRQYFSDVP NIHDRVVGFV IMLGINFSYR TVFEYDRDQV EEILREVRRT  240
DLFVEGHSTD YQARYALENM VRDGVRILKV GPALTAAFRR GVFLLSQIER EIIPERHRSD  300
IRRVILETML RDPRYWRDYY DDSPQLEEDI WYNLLDRIRY YWDYEDVRRV LEQLFRNFSE  360
GVDERFIYQY FYDSYFDVRN GRMSNDPREL ILAEIEHVLR DYWYAIEL               408

SEQ ID NO: 249          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 249
MWLRKQNNEP VGVYSICSSN PYVIEASIEF AMELDLYILI EATPHQVNQF GGYSGMTPED  60
FREFVMRIAR SKGLDERMII LGGDHLGPLP WQDEPSPTAM NKARELIRAF VESGYQKIHI  120
DCSMPLSDDP ETLPWEKIAE RTRELFEIAE RTAPPVPNTM VYVVGTDVPI AGGGEEEGVT  180
SVEDFRSAIS TLRRYFSDVP NIARRVVGFV IMLGINFSYR TVFEYDRDKV RGILEEVRRT  240
DLFVEGHSTD YQARYALRNM VEDGVRILKV GPALTAAFRR GVFLLSNIED EIIPERHRSN  300
IKRVILETML RDDRYWRDYY DDSPQLEEDI WYNLLDRIRY YWEYPDVREV LRLLFENFSE  360
GVDERFIYQY FYDSYFDVRE GKMQNDPREL IKKEIKRVLE DYSYAIRL               408

SEQ ID NO: 250          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 250
MWERKQNGER HGVYSICSSN EYVIEASIEF AITRHERILI EATPHQVNQF GGYSGMTPED  60
FRREVERIAR EKGLDERLII LGGDHLGPLP WQDEPSPTAM NKAEELIRAF VESGYYKIHI  120
DCSMPLSDLP EVLDWREIAE RTRRLFEIAE ERRTQQNTEF VYVVGTDVPI AGGGEEEGIT  180
SVEDFRSAIE WLRRYFPDVP NIRDRVVGFV IMLGIGFSRD KVFEYDRDAV RGILEEVRRE  240
DLFVEGHSTD YQARYALRNM VEDGVRILKV GPALTAAFRR GVFLLSEIER EEIPERRRQD  300
IRRVILETML RDDRWWRNYY DTSDRHREDI EYNLLDRIRY YWDYPDVREV LERLFRNFSE  360
GVDIRRIYEY FYDSYEDVRE GRMRNDPREL IKKEIKRVLE DYRYAIEN               408

SEQ ID NO: 251          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 251
MWLRKQNNEP VGVYSICSSN PYVIEASIEF AKELNDYILI EATPHQVNQF GGYSGMTPED  60
FRRFVMEIAR SKGLDERMII LGGDHLGPLP WQDLPEPQAM HYAEQLIRAF VESGYRKIHI  120
DCSMPLSDDP ETLDWRRIAE RTRRLFEIAE RTAPPVPNEM VYVVGTDVPI AGGGEEEGVT  180
SVEDFRSAIS TLRRYFSDVP NIARRVVGFV IMLGINFSYD RVFQYDRDQV REILEEVRRT  240
```

```
DLFVEGHSTD YQARYALENM VRDGVRILKV GPALTAAFRR GVFLLSNIED EIIPERHRSN  300
IKRVILETML RDDRYWRDYY KDSKRLELDI WYNLLDRIRY YWEYEDVKRV LELLFRNFSE  360
GVDERFIYQY FYDSYFDVRN GNMSNDPRDL IRKEIALVLE DYAYAIQL              408

SEQ ID NO: 252         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 252
MWLRKQYNEP VGVYSICSSN PYVIEASIEF AMELNTYILI EATPHQVNQF GGYSGMTPED  60
FKEFVMRIAR SKGLDERRII LGGDHLGPLP WQDLPSPQAM EYAKELIRAF VESGYQKIHI  120
DCSMPLSDDP ETLPYEKIAE RTRELFEIAE ETAPPVPNTM VYVVGTDVPI AGGGEEEGVT  180
SVEDFRSAIE SLRKYFSDVP NIWDRVVGFV IMLGIGFSYD KVFEYDRDQV REILEEVKRT  240
DLFVEGHSTD YQARYALENM VRDGVRILKV GPALTAAFRR GVFLLSQIER EIIPERHRSD  300
IRRVILETML RDPRYWRDYY DDSPQLELDI WYNLLDRIRY YWDYPDVRRV LEALFRNFSE  360
GVDIKFIYQY FYDSYFDVRE GKMDTDPREL IKKEIKLVLE DYSYAINL              408

SEQ ID NO: 253         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 253
MWERRQNGQK EGVYSICSSN EYVIRASIEF AKERHSRILI EATPHQVNHR GGYSGMTPED  60
FKREVMRIAR EKGLDERRII LGGDHLGPLP WQDRPSPEAM NEARQLIRAF VESGYRKIHI  120
DCSMPLSDDP KVLPYEKIAE RTRELFREAE ERARKYNFQP EYVVGTDVPI AGGGEEEGVT  180
SVEDFRSAIE YLKRYFPDVP NIRDRVVGFV IMLGIGFSYD KVFEYDRDKV RGILEEVRRE  240
DLFVEGHSTD YQARYALRNM VEDGVRILKV GPALTAAFRR GVFLLSNIED EQIPERERSN  300
IKRVILETML RDDRYWRDYY KDSKRLELDI WYNLLDRIRY YWNYPDVREV LRKLFENFSE  360
GVDPEFIRRY FYDSYEDVRD GRMDNDPRRL IEKEIKRVLE DYSYAIHR              408

SEQ ID NO: 254         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 254
MWLEREYGRK KGVYSICSSN EYVIEASIEF AKTRGDRILI EATPHQVNHR GGYSGMTPRD  60
FREEVMRIAR EKGLEEDRII LGGDHLGPLP WQDRPRPEAM EEAKELIRAF VESGYKKIHI  120
DCSMPLSDEP KVLPYEEIAE QTRELFEIAE ETARKYNFQP VYVVGTDVPI AGGGEEEGVT  180
SVEDFRSAIE SLERYFPDVE NIRDRVVGFV IMLGIGFTRD RVFQYDRDKV RGILEEVKRT  240
DLFVEGHSTD YQARYALRNM VEDGVRILKV GPALTAAFRR GVFLLSEIER EQIPERERSD  300
IRRVILETML RDDRYWRDYY DTSKEHERDI EYNLLDRIRY YWDYPDVREV LRKLFENFSE  360
GVDIRFIYQY FYDSYEDVRE GRMKNDPREL IKKEIKRVLE DYRYAIEL              408

SEQ ID NO: 255         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 255
MWESKRHGRE HGVYSICSSN EWVIEASIEF AIRKGYYILI EATPHQVNQF GGYSGWTPED  60
FRRFVEEIAK RKGLEPRMII LGGDHLGPLP WQDEPEPTAM QKARELIRAF VESGYKKIHI  120
DCSMPLSDDP DVLPDEEIAR RTRELFEIAE RYRQQFNFQP VYVVGTDVPI AGGGEEEGVT  180
SVEDFRRAIE ALKRYFPDVP NILDRVVGFV IMLGIGFSRD KVFEYDRDRV REILEEVKRE  240
DLFVEGHSTD YQARYALRNM VRDGVRILKV GPALTAAFRR GVFLLSEIER EIIPERRRQD  300
IRRVILETML RDDRYWRDYY ETSDQLREDI EYNLLDRIRY YWDYPDVREV LERLFRNFSE  360
GVDERYIYQY FYDSYQDVRD GRMTNDPRRL ILKEIQLVLE DYAYAIYD              408

SEQ ID NO: 256         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 256
MWLRKRNGEP VGVYSICSSN RYVIEASIEF AQQYNREILI EATPHQVNQF GGYSGMTPRD  60
FRRFVEEIAK SKGLEPRRIL LGGDHLGPLP WQDEPEPTAM QKARELIRAF VESGYRKIHI  120
DCSMPLSDDP ETLDWREIAR RTRELFEIAE RTARTYPNEF VYVVGTDVPI AGGGEEEGRT  180
```

```
SVEDFRSAIE WLRRYFQDVP NIWDRVVGFV IMLGITFSYQ RVFEYDRDNV REILEEVRRT  240
DLFVEGHSTD YQARYALRNM VEDGVRILKV GPALTAAFRR GVFLLSEIER EIIPERHRSN  300
IREVILRTML RDPRYWRDYY RDSEELRRDI EYNLLDRIRY YWNYPDVERV LQQLFRNFSE  360
GVDERFIYRY FYDSYFDVRE GKMQNDPREL IRKEIRIVLE DYAYAIEL              408

SEQ ID NO: 257          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 257
MWEEHDHNQP IGVYSICSSN PYVIRASIEF AKHRHEYILI EATPHQVNQH GGYSGMTPED  60
FRRFVMEIAR QQGLDERQII LGGDHLGPLP WQDRPEPEAM EEARQLIRAF VESGYHKIHI  120
DCSMPLSDDP KVLPYEEIAR RTRELFEIAR ETAREEEFGS VYVVGTDVPI AGGGEEEGVT  180
SVEDFRSAIE HLRQYFQDVP EIWRLVVGFV IMLGIGFTRD QVFQYDRDRV REILEEVKRN  240
DLFVEGHSTD YQARYALRNM VEDGVRILKV GPALTAAFRR GVFLLSRIED EIIPERERSN  300
IREVILRTML RDDRYWRDYY DDSDRLELDI WYNLLDRIRY YWDYEDVERV LRKLFENFSE  360
DVDERFIYRY FYESYEDVRR GRMDTDPREL IKHEIKRVLR DYRYAIQR              408

SEQ ID NO: 258          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 258
MWESKRHNEP RGVYSICSSN PWVIEASIEF AMRQGDYILI EATPHQVNQF GGYSGMTPED  60
FRQFVMEIAR RKGLDERMII LGGDHLGPLP WQDLPEPRAM EYARQLIRAF VESGYIKIHI  120
DCSMPLSDQP DRLPLEEIAR LTRELFEIAE RYAQEFDREM VYVVGTDVPI AGGGEEEGVT  180
SVEDFRSAIE ALERYFDDVP NIRDRVVGFV IMLGIGFTYD QVFEYDRDRV EEILREVQRT  240
DLFVEGHSTD YQARYALRNM VEDGVRILKV GPALTAAFRR GVFLLSLIEE EIIPERERQD  300
IRRVILETML RDPRYWRDYY DDSDRLELDI WYNLLDRIRY YWDYEDVRRV LELLFRNFSE  360
GVDERYIYQY FYDSYEDVRR GRMEPDPRRL IHKEIILVLE DYAYAILT              408

SEQ ID NO: 259          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 259
MWLQQRNGQK WGVYSICSSN EYVIRASIEF AQESNTYILI EATPHQVNQF GGYSGMTPED  60
FKRFVMQIAR EHGLDERRII LGGDHLGPLP WQDRPEPEAM NRARELIRAF VESGYRKIHI  120
DCSMPLSDDP KVLDYREIAR RTRELFREAE EQSSTDPNET VYVVGTDVPI AGGGEEEGRT  180
SVEDFRSAIE ELRQFQDVP NIHDRVVGFV IMLGITFSRR RVFEYDRDQV REILEEVKRE  240
DLFVEGHSTD YQARYALRNM VEDGVRILKV GPALTAAFRR GVFLLSEIER EIIPERERSN  300
IREVILRTML RDDRYWRKYY EDSEQLREDI EYNLLDRIRY YWEYEDVKMV LNKLFENFSE  360
GVDERFIYRY FYDSYFDVRE GKMQNDPREL IRREIKEVLE DYRYAIEL              408

SEQ ID NO: 260          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 260
MWEEHDHLTK IGVYSICSSN PYVIEASIEF AQEQGDYILI EATPHQVNQH GGYSGMTPED  60
FKRFVMEIAR RKGLDERMII LGGDHLGPLP WQDEPEPEAM EQAKQLIRAF VESGYYKIHI  120
DCSMPLSDQP KVLPYEEIAR QTRELFEIAE ETQQETDREP VYVVGTDVPI AGGGEEEGVT  180
SVEDFRSAIE HLERYFDDVP NIRDRVVGFV IMLGIGFTYR TVFEYDRDRV REILEEVKRT  240
DLFVEGHSTD YQARYALRNM VEDGVRILKV GPALTAAFRR GVFLLSHIEQ EIIPERERQD  300
IQRVILETML RDPRYWRDYY DDSDQLEEDI WYNLLDRIRY YWDYEDVRRV LEHLFRNFSE  360
GVDERFIYRY FYDSYEDVRR GRMEPDPREL IKKEIKRVLE DYSYAINR              408

SEQ ID NO: 261          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 261
MWLERHYNLP KGVYSICSSN SYVIEASIEF AKNRHEPILI EATPHQVNQF GGYSGMTPTD  60
FRDFVYKIAK EKGLDLRDII LGGDHLGPLP WQDLPAPEAM SRAEELIRAF VESGYRKIHI  120
```

```
DCSMPLSDQP EVLHWWEIAL LTRDLFAVAE EVARKFNFQL VYVVGTDVPI AGGGEEEGIT  180
SVEDFRSAIY YLKEAFRDVP NIWDRVVGFV IMLGIRFSYD RVFEYDRSRV EEILEEVKRE  240
DLFVEGHSTD YQARYALRNM VLDGVRILKV GPALTAAFRR GVFLLSNIED EIIPERRRSE  300
IKRVILETML RDDRYWRKYY DDSKRLEWDI WYNLLDRIRY YWEYEDVKRV LERLFRNFSE  360
PVDIKFIYQY FYDSYEDVRD GRMEPDPREL IKKEIKRVLE DYAYAIDL              408

SEQ ID NO: 262          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 262
MWEEKEYGQE QGVYSICSSN EYVIEASIEF AIEQGYYILI EATPHQVNHR GGYSGWTPED  60
FRRFVEEIAR RKGLDERMII LGGDHLGPLP WQDRPEPEAM REAEELIRAF VESGYLKIHI  120
DCSMPLSDWP DELPREWIAR WTRRLFEIAE RYRQTFNTEM VYVVGTDVPI AGGGEEEGVT  180
SVEDFRSAIE YLRRYFPDVP NIRDRVVGFV IMLGIGFTRR RVFQYDRDRV REILEEVKRT  240
DLFVEGHSTD YQARYALRNM VRDGVRILKV GPALTAAFRR GVFLLSNIED EIIPERRRQN  300
IKRVILETML RDDRYWRKYY ETSKRLEEDI WYNLLDRIRY YWQYEDVRRV LEELFRNFSE  360
GVDERYIYQY FYDSYQDVRD GRMKNDPREL IKKEIKRVLE DYAYAIWR              408

SEQ ID NO: 263          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 263
MWLPHHYGRP FGVYSICSSN EWVIEASIRF AMRLHYPILI EATPHQVNHR GGYSGWTPTD  60
FANFVYEIAR RLGLSESMII LGGDHLGPLP WQDLPEPVAM NEARELIRAF VESGYWKIHI  120
DCSMPLSDWS ETLHWQVIAD WTRELFREAE EQARGFNFWP IYVVGTDVPI AGGGEEEGRT  180
SVEDFRSAIE YLRRYFNDVR NIWDRVVGFV IMLGIRFSRD RVFEYDRSQV EPILREVSRY  240
DLFVEGHSTD YQARYALRNM VLDGVRILKV GPALTAAFRR GVFLLSEIED RIIPERRRSE  300
IMRVILETML RDDRYWRDYY ETGPQLEWDI FYNLLDRIRY YWDYPDVREV LRRLFENFSE  360
PVPPDFIRDH FYESWRDVRD GRMRPDPREL IYHEIELVLR DYAYAILD              408

SEQ ID NO: 264          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 264
MWLRKQNNEK VGVYSICSSN PYVIEASIEF AMRLNDYILI EATPHQVNFQ GGYSGMTPED  60
FREFVMRIAR SKGLDERMII LGGDHLGPLP WQDLPRPQAM EYARQLIRAF VESGYRKIHI  120
DCSMPLSDDP KVLDWRIIAE WTRELFEIAE RTSPPVPNEM VYVVGTDVPI AGGGEEEGVT  180
SVEDFRSAIE TLREYFSDVP NIYDRVVGFV IMLGINFSYT EVFEYDRDKV RGILEEVKRE  240
DLFVEGHSTD YQARYALRNM VEDGVRILKV GPALTAAFRR GVFLLSQIER EIIPERHRSN  300
IQRVILETML RDDRYWRKYY RDDHQLELDI WYNLLDRIRY YWDYEDVRRV LELLFRNFSE  360
GVDIKFIYQY FYDSYFDVRN GNMQNDPREL IKKEIMLVLE DYAYAIQL              408

SEQ ID NO: 265          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 265
MWLRHQNNEP VGVYSICSSN PYVIEASIRH AQRHNDYILI EATPHQVNQH GGYSGMTPED  60
FKEFVMRIAR STGLDERRII LGGDHLGPLP WQDQPEPEAM NQAEELIRAF VESGYQKIHI  120
DCSMPLSDDP ETLDYRRIAE RTRRLFEVAE RTSPPQPNQT VYVVGTDVPI AGGGEEEGVT  180
SVEDFRSAIE SLERYFEDVP NIRDRVVGFV IMLGINFSYD RVFQYDRDQV REILEEVRRT  240
DLFVEGHSTD YQARYALENM VRDGVRILKV GPALTAAFRR GVFLLSNIED EIIPERHRSN  300
IKRVILETML RDDRYWRDYY KDSKRLELDI WYNLLDRIRY YWDYEDVERV LRQLFENFSE  360
GVDIKFIYQY FYDSYFRVRN GEMDTDPREL ILAEIERVLE DYSYAIQL              408

SEQ ID NO: 266          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 266
MWEEHDYLQK FGVYSICSSN EYVIEASIEF AKEQGTEILI EATPHQVNHR GGYSGMTPED  60
```

```
FRRFVEEIAR RKGLDEDKIR LGGDHLGPLP WQDQPEPTAM EEARELIRAF VESGYTKIHI  120
DCSMPLSDDP DELPREEIAR RTRELFEDAE RHAQKYPEEP VYVVGTDVPI AGGGEEEGVT  180
SVEDFRSAIE RLKEYFPDVP NIRDRVVGFV IMLGIGFSRD KVFEYDRDRV REILEEVKRE  240
DLFVEGHSTD YQARYALRNM VEDGVRILKV GPALTAAFRR GVFLLSNIED EIIPERRRQN  300
IKRVILETML RDDRYWRDYY ETSDQLREDI WYNLLDRIRY YWQYDDVREV LRRLFENFSE  360
GVDIKFIYQY FYDSYFDVRE GKMKNDPREL IKKEIKRVLE DYSYAIHR              408

SEQ ID NO: 267         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 267
MWLRHEYGQP EGVYSICSSN EYVIRASIEF AKRKHERILI EATPHQVNQF GGYSGMTPED  60
FKREVMRIAR EEGLDERQII LGGDHLGPLP WQDEPRPTAM NKAKDLIRAF VESGYRKIHI  120
DCSMPLSDEP KVLDYREIAE QTRELFEIAE ETRTEYNFQP EYVVGTDVPI AGGGEEEGVT  180
SVEDFRSAIE HLERHFPDVE NIRDRVVGFV IMLGIGFTRD RVFQYDRDQV REILEEVKRT  240
DLFVEGHSTD YQARYALRNM VEDGVRILKV GPALTAAFRR GVFLLSNIED EQIPERERSN  300
IKRVILETML RDDRYWRNYY DTSKRHEEDI WYNLLDRIRY YWEYEDVKMV LNKLFENFSE  360
GVDIRFIYRY FYDSYEDVRE GRMQNDPRRL IHHEIERVLR DYRYAIER              408

SEQ ID NO: 268         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 268
MWLMVQNNIP IGVYSICSSN PYVIEASIEF AMEKNSYILI EATPHQVNQF GGYSGMTPED  60
FKRFVMEIAR SKGLEEDMII LGGDHLGPLP WQDEPAPTAM SKAQELIRAF VESGYLKIHI  120
DCSMPLSDQP ETLDWREIAI LTRILFEVAE RVAPPVPNLM VYVVGTDVPI AGGGEEEGVT  180
SVEDFRSAIE WLYRYFSDVP NIADRVVGFV IMLGIGFSYD KVFEYDRDKV RGILEEVSRE  240
DLFVEGHSTD YQARYALRNM VLDGVRILKV GPALTAAFRR GVFLLSLIER EIIPERHRSD  300
ILRVILETML RDPRYWRDYY RDSPALEDDI LYNLLDRIRY YWEYEDVKRV LELLFRNFSE  360
GVDIKFIYQY FYDSYFDVRE GKMKNDPREL IKKEIKRVLE DYSYAILL              408

SEQ ID NO: 269         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 269
MWLSKQYNRK KGVYSICSSN PYVIEASIEF AKELDQYILI EATPHQVNQF GGYSGMTPED  60
FKNFVMKIAK EKGLDERRII LGGDHLGPLP WQDEPEPTAM EKARQLIRAF VESGYRKIHI  120
DCSMPLSDQP KVLDWREIAR LTRELFEIAE RTAPEVPNEM VYVVGTDVPI AGGGEEEGVT  180
SVEDFRSAIE TLKRYFSDVP NIADRVVGFV IMLGIGFSYD KVFEYDRDRV EEILREVERE  240
DLFVEGHSTD YQARYALRNM VEDGVRILKV GPALTAAFRR GVFLLSNIED EIIPERERSN  300
IKRVILETML RDPRYWRDYY DDSPQLELDI WYNLLDRIRY YWDYPDVERV LRKLFENFSE  360
GVDERFIYQY FYDSYFDVRE GKMENDPREL IRKEIKRVLE DYSYAINL              408

SEQ ID NO: 270         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 270
MWLSKDYNEP KGVYSICSSN PYVIEASIEF AKHIHEPILI EATPHQVNQF GGYSGMTPED  60
FRRFVMKIAR EKGLDERLII LGGDHLGPLP WQDEPSPTAM NKAQELIRAF VESGYRKIHI  120
DCSMPLSDDP KVLPYEKIAE RTRELFRIAE ETAQDFPFLP VYVVGTDVPI AGGGEEEGVT  180
SVEDFRSAIE SLRKYFRDVP NIWDRVVGFV IMLGIRFSYR EVFEYDRDKV RGILEEVKRM  240
DLFVEGHSTD YQARYALRNM VEDGVRILKV GPALTAAFRR GVFLLSLIEE EIIPERERSN  300
IREVILRTML RDDRYWRKYY KDSDELEEDI WYNLLDRIRY YWDYEDVERV LRKLFENFSE  360
PVDIRFIYRY FYDSYEDVRD GRMEPDPREL IKKEIKRVLE DYAYAIFT              408

SEQ ID NO: 271         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 271
```

```
MWLRKDNNEP VGVYSICSSN PYVIEASIEF AKELSDYILI EATPHQVNFQ GGYSGMTPED  60
FKEFVMRIAR SKGLEEDMII LGGDHLGPLP WQDLPEPQAM EYAKQLIRAF VESGYKKIHI  120
DCSMPLSDQP ETLDYREIAR LTRELFEIAE ETSPPQPNQP VYVVGTDVPI AGGGEEEGVT  180
SVEDFRSAIE SLRKYFSDVP NIWDRVVGFV IMLGIGFSYD KVFEYDRDQV REILEEVKRT  240
DLFVEGHSTD YQARYALRNM VEDGVRILKV GPALTAAFRR GVFLLSQIER EIIPERERSN  300
IQRVILETML RDDRYWRKYY DDSPQLELDI WYNLLDRIRY YWDYPDVERV LRKLFENFSE  360
GVDPRYIYRY FYDSAFDVRN GNMKNDPREL IKKEIKRVLE DYAYAIQL           408

SEQ ID NO: 272         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 272
MWLRKQNNEP VGVYSICSSN PYVIEASIEF AMRTNDYILI EATPHQVNQF GGYSGMTPED  60
FKEFVMRIAR SKGLDERMII LGGDHLGPLP WQDEPEPTAM NKAKDLIRAF VESGYQKIHI  120
DCSMPLSDQP KVLDYREIAR LTRELFEIAE ETAPPVPNTI VYVVGTDVPI AGGGEEEGVT  180
SVEDFRSAIE SLREYFEDVP NIWDRVVGFV IMLGIGFSYD KVFEYDRDQV REILEEVKRT  240
DLFVEGHSTD YQARYALRNM VEDGVRILKV GPALTAAFRR GVFLLSQIER EIIPERERSD  300
IRRVILETML RDPRYWRDYY DDSPQLELDI WYNLLDRIRY YWEYEDVKMV LNKLFENFSE  360
GVDIKFIYQY FYDSYFDVRE GKMKNDPREL IKKEIMLVLE DYLYAIQL           408

SEQ ID NO: 273         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 273
MWLEKHYGRE QGVYSICSSN EWVIEASIEF AMQLHNPILI EATPHQVNWS GGYSGWTPED  60
FRRFVEEIAR RKGLDERLII LGGDHLGPLP WQDLPEPQAM QYAQELIRAF VESGYEKIHI  120
DCSMPLSDDP ETLDWRRIAE RTRELFRIAE ETASGFPFRP IYVVGTDVPI AGGGEEEGRT  180
SVEDFRSAIE YLRQYFNDVR NIWDRVVGFV IMLGIRFSRD RVFEYDRDQV REILEEVRRY  240
DLFVEGHSTD YQARYALRNM VQDGVRILKV GPALTAAFRR GVFLLSLIEE EIIPERRRSD  300
IRRVILETML RDDRYWRDYY ETSDQLRLDI WYNLLDRIRY YWDYPDVREV LRRLFENFSE  360
PVDPRFIYRY FYRSYEDVRD GRMQPDPREL IRKEIRLVLE DYSYAIND           408

SEQ ID NO: 274         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 274
MWLRHQYNEK VGVYSICSSN PYVIEASIEH AQEHNDYILI EATPHQVNQH GGYSGMTPED  60
FKRFVMEIAR SKGLDERRII LGGDHLGPLP WQDQPEPEAM EQAKELIRAF VESGYRKIHI  120
DCSMPLSDDP KVLDYRRIAE RTRELFEIAE ETSPPQPNET VYVVGTDVPI AGGGEEEGVT  180
SVEDFRSAIE SLRKYFSDVP NIHDRVVGFV IMLGIGFSYD KVFEYDRDQV REILEEVKRT  240
DLFVEGHSTD YQARYALRNM VEDGVRILKV GPALTAAFRR GVFLLSQIEQ EIIPERERSN  300
IREVILRTML RDDRYWRKYY DDSPQLELDI WYNLLDRIRY YWDYEDVERV LRKLFENFSE  360
GVDIKFIYQY FYDSYFDVRE GKMQNDPREL IKKEIKRVLE DYSYAIQL           408

SEQ ID NO: 275         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 275
MWLRKQNNEK VGVYSICSSN PYVIEASIEF AKEKGYYILI EATPHQVNQF GGYSGMTPED  60
FKEFVMRIAR SKGLEEDKII LGGDHLGPLP WQDLPSPQAM EYAKELIRAF VESGYRKIHI  120
DCSMPLSDDP ETLPYEKIAE RTRELFEIAE ETSPPVPNEM VYVVGTDVPI AGGGEEEGVT  180
SVEDFRSAIE TLRQYFEDVP NIYDRVVGFV IMLGIGFSYD KVFEYDRDQV REILEEVKRT  240
DLFVEGHSTD YQARYALRNM VEDGVRILKV GPALTAAFRR GVFLLSQIER EIIPERERSN  300
IQRVILETML RDDRYWRDYY DDSPQLELDI WYNLLDRIRY YWEYEDVKMV LNKLFENFSE  360
GVDERFIYQY FYDSYFDVRE GKMQNDPREL IKKEIKRVLE DYSYAIEL           408

SEQ ID NO: 276         moltype = AA  length = 408
FEATURE                Location/Qualifiers
REGION                 1..408
                       note = mutant D-fructose C4-epimerase
source                 1..408
                       mol_type = protein
                       organism = synthetic construct
```

```
SEQUENCE: 276
MWLDHHYGRP FGVYSICSSN SYVIEASIEA AMNQHYPILI EATPHQVNHR GGYSGWTPED  60
FRRFVEKIAK EKGLSLSMII LGGDHLGPLP WQDYPSPWAM NEARELIRAF VESGYKKIHI  120
DCSMPLSDDS ETLPWRKIAE WTRELFREAE EQARGFPFQP VYVVGTDVPI AGGGEEEGRT  180
SVEDFRSAIE ELREYFRDVL NIWDRVVGFV IMLGIRFSRD RVFEYDRSQV EPILREVWRY  240
DLFVEGHSTD YQARYALRNM VLDGVRILKV GPALTAAFRR GVFLLSLIED EIIPERRRSE  300
IPRVILETML RDPRYWRDYY ETSDQLRWDI LYNLLDRIRY YWEYEDVKRV LEQLFRNFSE  360
PVPPEFIRRY FYDSWEDVRD GRMRPDPREL IKKEIKRVLE DYWYAILD              408

SEQ ID NO: 277         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 277
MWERHEYGQA FGVYSICSSN EYVIEASIEF AITRHERILI EATPHQVNHR GGYSGMTPSD  60
FRDEVFRIAR EKGLDERLII LGGDHLGPLP WQDYPRPWAM NEARQLIRAF VESGYYKIHI  120
DCSMPLSDEP EVLPWPEIAE RTRDLFEEAE RRRTQFNTEP WYVVGTDVPI AGGGEEEGIT  180
SVEDFRRAIE WLRRYFPDVM NIYDRVVGFV IMLGIGFTRD RVFYYDRDAV RPILWEVSRT  240
DLFVEGHSTD YQARYALRNM VEDGVRILKV GPALTAAFRR GVFLLSLIED EIIPERRRQE  300
ILRVILETML RDPRWWRDYY DTSWWHEWDI FYNLLDRIRY YWDYPDVREV LERLFRNFSE  360
GVHPEFIRRY FYDSYEDVRN GRMRNDPREL IKKEIKRVLE DYYYAIFW              408

SEQ ID NO: 278         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 278
MWLRFHYNEP IGVYSICSSN EYVIEASIEF AMHIHYPILI EATPHQVNQF GGYSGMTPTD  60
FRDFVMKIAR EKGLDERLII LGGDHLGPLP WQDLPAPQAM TYAKELIRAF VESGYLKIHI  120
DCSMPLSDDP EVLHWEEIAE RTRELFEIAE ETARKYNFQL VYVVGTDVPI AGGGEEEGIT  180
SVEDFRSAIY YLKEYFRDVP NIWDRVVGFV IMLGIRFSYD VVFEYDRSQV EEILEEVKRE  240
DLFVEGHSTD YQARYALRNM VLDGVRILKV GPALTAAFRR GVFLLSNIED EIIPERRRSQ  300
IKRVILETML RDPRYWRDYY DDSDRLIWDI WYNLLDRIRY YWDYPDVYYV LLLLFWNFSE  360
PVPLEHIRDY FYDSYEDVRD GRMSNDPREL IKKEIKRVLE DYAYAIWT              408

SEQ ID NO: 279         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 279
MWELHDNGQR FGVYSICSSN EYVIEASIEF AKNRHWRILI EATPHQVNQF GGYSGMTPED  60
FKREVMRIAR EKGLEENMII LGGDHLGPLP WQDEPSPTAM NKAKDLIRAF VESGYYKIHI  120
DCSMPLSDEP EVLPWPKIAE RTRELFEIAE ETRTQQNTEF WYVVGTDVPI AGGGEEEGIT  180
SVEDFRSAIE WLKRYFPDVP NILDRVVGFV IMLGIGFTRD TVFYYDRDAV RPILEEVKRE  240
DLFVEGHSTD YQARYALRNM VEDGVRILKV GPALTAAFRR GVFLLSLIED EIIPERRRQE  300
ILRVILETML RDDRYWRKYY STSKSHEWDI FYNLLDRIRY YWDYPDVREV LRRLFENFSE  360
GVHPSFIRDY FYDSYEDVRE GRMKNDPREL IKKEIKRVLE DYWYAIYW              408

SEQ ID NO: 280         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 280
MWEEKDYGQR RGVYSICSSN EYVIEASIEF AKERGEYILI EATPHQVNQH GGYSGWTPED  60
FRQFVEEIAR RKGLDPDKII LGGDHLGPLP WQDLPEPEAM REAKELIRAF VESGYKKIHI  120
DCSMPLSDDP SVLPYQEIAR RTRELFEIAA ETARDQEFGR VYVVGTDVPI AGGGEEEGVT  180
SVEDFRSAIE YLRRYFSDVP RIWDQVVGFV IMLGIGFSRD KVFEYDRDQV REILEEVKRE  240
DLFVEGHSTD YQARYALRNM VEDGVRILKV GPALTAAFRR GVFLLSRIED EIIPERERSD  300
IRRVILETML RDDRYWRKYY EDSKRHELDI WYNLLDRIRY YWYYPDVREV LRKLFENFSE  360
GVDERFIRRY FYDSYEDVRN GRMKNDPREL IKKEIKRVLE DYWYAINR              408

SEQ ID NO: 281         moltype = AA  length = 408
FEATURE                Location/Qualifiers
REGION                 1..408
                       note = mutant D-fructose C4-epimerase
source                 1..408
                       mol_type = protein
```

```
                        organism = synthetic construct
SEQUENCE: 281
MWLEHHYGQK QGVYSICSSN QYVIEASIEF AKEQHHPILI EATPHQVNHR GGYSGMTPED  60
FRRFVEEIAR RKGLDERLII LGGDHLGPLP WQDRPSPEAM EEARDLIRAF VESGYKKIHI  120
DCSMPLSDDS ETLPYRKIAE RTRELFREAE ETARKYNFQP VYVVGTDVPI AGGGEEEGRT  180
SVEDFRSAIE YLKEYFRDVP NIRDRVVGFV IMLGIGFSRD KVFEYDRDQV REILEEVRRE  240
DLFVEGHSTD YQARYALRNM VEDGVRILKV GPALTAAFRR GVFLLSNIED EIIPERERSN  300
IKRVILETML RDDRYWRKYY ETSDQLREDI WYNLLDRIRY YWQYPDVQEV LRKLFENFSE  360
PVDEEFIRRY FYDSYFDVRE GKMRPDPREL IKKEIKRVLE DYSYAINL              408

SEQ ID NO: 282          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 282
MWLLHQYGQR FGVYSICSSN EWVIRASIQF AITRHHRILI EATPHQVNHR GGYSGMTPED  60
FKREVMRIAR EEGLEENMII LGGDHLGPLP WQDYPRPWAM EEAKELIRAF VESGYYKIHI  120
DCSMPLSDLP EVLHWSEIAE QTRELFEIAE ETRTQQNTEF YYVVGTDVPI AGGGEEEGIT  180
SVEDFRSAIE QLRRHFPDVM NIYDRVVGFV IMLGIGFSRD KVFEYDRDAV RPILEEVKRT  240
DLFVEGHSTD YQARYALRNM VEDGVRILKV GPALTAAFRR GVFLLSNIED EQIPERERSN  300
IKRVILETML RDDRYWRKYY DTSKDHEWDI WYNLLDRIRY YWDYPDVREV LRKLFENFSE  360
GVHPSFIRDY FYRSYEDVRE GRMRNDPREL IFREIREVLQ DYYYAIFW              408

SEQ ID NO: 283          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 283
MWLRKHYNEP QGVYSICSSN PYVIEASIEF AKHRGEYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARDYPFQP VYVVGTDVPI AGGGEEEGVT  180
SVEDFRSAIS SLKKYFNDVP NIWDRVVGFV IMLGIRFSYD RVFEYDRDQV REILEEVRRE  240
PLFVEGHSTD YQARYALRNM VEDGVRILKV GPALTAAFRR GVFLLSQIED EIIPERERSN  300
IRRVILETML RDDRYWRKYY DDSDRLELDI WYNLLDRIRY YWDYEDVERV LRKLFENFSE  360
PVDIRFIYRY FYDSYFDVRE GKMEPDPREL IKKEIKRVLE DYRYAIDT              408

SEQ ID NO: 284          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 284
MWLDAHYGRP FGVYSICSSN EWVIRASIRF AKRLHYPILI EATPHQVNHR GGYSGMTPED  60
FKRFVMRIAR ELGLEENMII LGGDHLGPLP WQDYPSPWAM QEAKELIRAF VESGYWKIHI  120
DCSMPLSDDS ETLPYEKIAE RTRELFEIAE ETARGFNFWP IYVVGTDVPI AGGGEEEGVT  180
SVEDFRSAIS SLKKYFNDVP NIWDRVVGFV IMLGIRFSRD RVFEYDRDKV RGILEEVSRE  240
DLFVEGHSTD YQARYALRNM VLDGVRILKV GPALTAAFRR GVFLLSEIER EIIPERRRSR  300
IRDVILETML RDDRYWRDYY ETSDQLRYDI EYNLLDRIRY YWNYPDVEEV LRRLFENFSE  360
PVPPEFIRRY FYDSYEDVRD GRMQPDPREL IFHEIELVLR DYAYAILD              408

SEQ ID NO: 285          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 285
MWLRHQNNEP VGVYSICSSN PYVIRASIEF AKETNDYILI EATPHQVNQF GGYSGMTPED  60
FKRFVMEIAR QTGLEEDRII LGGDHLGPLP WQDEPSPTAM EKARQLIRAF VESGYKKIHI  120
DCSMPLSDQP ETLPYEKIAE QTRELFEIAE RTSPPQPNQP VYVVGTDVPI AGGGEEEGVT  180
SVEDFRSAIS SLKKYFNDVP NIWDRVVGFV IMLGIGFSYD KVFEYDRDQV REILEEVKRE  240
DLFVEGHSTD YQARYALENM VRDGVRILKV GPALTAAFRR GVFLLSQIER EIIPERHRSN  300
IQEVILQTML RDPRYWRDYY DDSPQLELDI WYNLLDRIRY YWDYEDVRRV LEQLFRNFSE  360
GVDERFIYQY FYDSYFDVRN GNMKNDPREL IKKEIKRVLE DYRYAIQL              408

SEQ ID NO: 286          moltype = AA  length = 408
FEATURE                 Location/Qualifiers
REGION                  1..408
                        note = mutant D-fructose C4-epimerase
source                  1..408
```

```
                        mol_type = protein
                        organism = synthetic construct
SEQUENCE: 286
MWEQHRYNRK YGVYSICSSN SYVIEASIEF AQEKGTYILI EATPHQVNQF GGYSGMTPED  60
FKNFVMKIAK EKGLDERMII LGGDHLGPLP WQDEPSPTAM NKAKDLIRAF VESGYYKIHI  120
DCSMPLSDDP DRLPYEKIAE RTRELFEIAE ETQQETDRQP VYVVGTDVPI AGGGEEEGVT  180
SVEDFRSAIS SLEKYFDDVP NIRDRVVGFV IMLGIGFSYD KVFEYDRDRV REILEEVKRT  240
DLFVEGHSTD YQARYALRNM VEDGVRILKV GPALTAAFRR GVFLLSNIED EIIPERERQN  300
IKRVILETML RDPRYWRDYY KDSKRLELDI WYNLLDRIRY YWEYEDVKRV LERLFRNFSE  360
GVDERFIYRY FYDSYEDVRR GRMEPDPREL IKKEIKRVLE DYSYAINL               408

SEQ ID NO: 287          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 287
MWLLVQWNIK IGVYSICSSN PWVIIASILT AMEFNYYILI EATPHQVNQF GGYSGMTPSD  60
FRDFVYEIAL QLGLELDMII LGGDHLGPLP WQDLPAPRAM TYARQLIRAF VESGYLKIHI  120
DCSMPLSDQP ETLDWRQIAI YTRELFEVAE RVAPPVPNLM VYVVGTDVPI AGGGEEEGVT  180
SVEDFRSAIE TLLRYFSDVP NIASRVVGFV IMLGIGFSYD KVFEYDRSQV LPILEEVKRT  240
DLFVEGHSTD YQARYALRNM VEDGVRILKV GPALTAAFRR GVFLLSNIED EIIPERHRSN  300
IKRVILETML RDPRYWRDYY RDSPALEDDI WYNLLDRIRY YWEYEDVKRV LELLFRNFSE  360
GVDIKFIYQY FYDSYFAVRE GKMSNDPRDL ILWEIKLVLL DYWYAIIL               408

SEQ ID NO: 288          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 288
MWLRKHYGEP QGVYSICSSN EYVIEASIEF AKEKGDPILI EATPHQVNQF GGYSGMTPED  60
FKNFVMKIAK EKGLEEDKII LGGDHLGPLP WQDEPSPTAM NKAKDLIRAF VESGYEKIHI  120
DCSMPLSDDP KVLPYEKIAE RTRELFEIAE ETARGFPFRP IYVVGTDVPI AGGGEEEGRT  180
SVEDFRSAIS SLKKYFNDVP NIWDRVVGFV IMLGIRFSRD RIFEYDRDQV REILEEVKRE  240
DLFVEGHSTD YQARYALRNM VEDGVRILKV GPALTAAFRR GVFLLSEIER EIIPERERSD  300
IRRVILETML RDDRYWRKYY EDSKQLELDI EYNLLDRIRY YWDYPDVREV LRKLFENFSE  360
PVDIKFIYQY FYDSYEDVRD GRMRPDPREL IKKEIKRVLE DYSYAINN               408

SEQ ID NO: 289          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 289
MWLMVQNNLP YGVYSICSSN PYVIEASIEA AKEYNFYILI EATPHQVNQF GGYSGMTPED  60
FKEFVMRIAR SKGLEEDMII LGGDHLGPLP WQDEPAPTAM NKAKDLIRAF VESGYKKIHI  120
DCSMPLSDQP ETLDYRIIAI YTRELFEIAE ETAPPVPNQM VYVVGTDVPI AGGGEEEGVT  180
SVEDFRSAIS SLKKYFNDVP NIWDRVVGFV IMLGIGFSYD KVFEYDRDKV RGILEEVSRE  240
DLFVEGHSTD YQARYALRNM VLDGVRILKV GPALTAAFRR GVFLLSLIER EIIPERHRSD  300
ILRVILETML RDDRYWRKYY RDSPALELDI FYNLLDRIRY YWMYPDVWTV LMLLFENFSE  360
GVDERFIYLY FYDSYFDVRE GKMKNDPREL IKKEIKRVLE DYWYAIIL               408

SEQ ID NO: 290          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 290
MWLLVQWNIP IGVYSICSSN SYVIEASIEA AMETDQYILI EATPHQVNQF GGYSGMTPED  60
FKNFVMKIAR SKGLEEDMII LGGDHLGPLP WQDEPAPTAM NKAKDLIRAF VESGYKKIHI  120
DCSMPLSDQP ETLDYRQIAI YTRELFEIAE ETAPPVPNQM VYVVGTDVPI AGGGEEEGVT  180
SVEDFRSAIS SLLKYFSDVP NIANRVVGFV IMLGIGFSYD KVFEYDRSQV EEILREVSRT  240
DLFVEGHSTD YQARYALRNM VLDGVRILKV GPALTAAFRR GVFLLSLIER EIIPERERSD  300
ILRVILETML RDPRYWRDYY RDSPALELDI LYNLLDRIRY YWEYEDVKMV LNKLFENFSE  360
GVDIKFIYQY FYDSYFDVRE GKMLNDPREL IKKEIKRVLE DYWYAILL               408

SEQ ID NO: 291          moltype = AA  length = 408
FEATURE                 Location/Qualifiers
REGION                  1..408
                        note = mutant D-fructose C4-epimerase
```

```
source                  1..408
                        mol_type = protein
                        organism = synthetic construct
SEQUENCE: 291
MWLRKQYGHK EGVYSICSSN RYVIEASIEF AKELHSRILI EATPHQVNQF GGYSGMTPED  60
FKRLVMEIAR RKGLDERLII LGGDHLGPLP WQDEPSPTAM QKARELIRAF VESGYYKIHI  120
DCSMPLSDEP EVLPYEKIAE RTRQLFEIAE RYRRKYNTQP VYVVGTDVPI AGGGEEEGVT  180
SVEDFRSAIE SLRRYFPDVP NIRDRVVGFV IMLGIGFSRD KVFEYDRDKV RGILEEVKRT  240
DLFVEGHSTD YQARYALRNM VEDGVRILKV GPALTAAFRR GVFLLSEIER EIIPERERSD  300
IRRVILETML RDDRYWRKYY DTSKEHERDI EYNLLDRIRY YWYYPDVERV LRKLFENFSE  360
GVDIKFIYQY FYNSYEDVRE GRMQNDPREL IKKEIKSVLE DYSYAIHR              408

SEQ ID NO: 292          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 292
MWLELLWNQP VGVYSICSSN SYVIEASIET AKEKGWYILI EATPHQVNFQ GGYSGMTPSD  60
FRDFVYQIAK EKGLELDKII LGGDHLGPLP WQDLPAPQAM EYAKILIRAF VESGYLKIHI  120
DCSMALSDQP YYLDYRQIAI YTRELFEIAE ETAPPVPNLM VYVVGTDVPI AGGGEEEGVT  180
SVEDFRSAIE TLKRYFSDVP NIFDRVVGFV IMLGIGFSYD KVFEYDRDKV RGILEEVKRE  240
DLFVEGHSTD YQARYALRNM VLDGVRILKV GPALTAAFRR GVFLLSLIER EIIPERERSD  300
ILRVILETML RDPRYWRDYY KDSKRLELDI LYNLLDRIRY YWEYEDVKMV LNKLFENFSE  360
GVDERYIYLY FYDSYFAVRR GEMKNDPREL IKWEIILVLY DYWYAIIL              408

SEQ ID NO: 293          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 293
MWLMVQYNLP YGVYSICSSN PYVIEASIEA AKEYNFYILI EATPHQVNQF GGYSGMTPED  60
FKNFVMKIAD SKGLERDMII LGGDHLGPLP WQDEPSPTAM NKAKDLIRAF VESGYKKIHI  120
DCSMPLSDDP KVLPWEKIAE RTRELFEIAE ETAPPVPNQM VYVVGTDVPI AGGGEEEGVT  180
SVEDFRSAIE TLYRYFSDVP NIADRVVGFV IMLGIGFSYD KVFEYDRDKV RGILEEVKRE  240
DLFVEGHSTD YQARYALRNM VLDGVRILKV GPALTAAFRR GVFLLSLIER EIIPERERSD  300
ILRVILETML RDDRYWRKYY KDSKRLELDI LYNLLDRIRY YWDYEDVARV LNKLFENFSE  360
GVDIKFIYQY FYDSYFDVRL GRMKNDPREL IKKEIKRVLE DYWYAIIL              408

SEQ ID NO: 294          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 294
MWLMLQYLIN IGVYSICSSN PYVIEASIEA AQEYDLYILI EATPHQVNQF GGYSGMTPSD  60
FRDFVMEIAD RKGLERNRII LGGDHLGPLP WQDEPAPTAM AKAEELIRAF VESGYTKIHI  120
DCSMPLSDDP ETLPLEVIAE RTRRLFEVAE RTAREYNNQE VYVVGTDVPI AGGGEEEGVT  180
SVEDFRSAID TLRRYFEDVP NIYNRVVGFV IMLGIGFSYD KVFEYDRDKV RGILEEVKRT  240
DLFVEGHSTD YQARYALRNM VLDGVRILKV GPALTAAFRR GVFLLSFIEQ EIIPERERSN  300
ILRVILETML RDPRYWRDYY DDSERLELDI LYNLLDRIRY YWNYPDVETV LRKLFENFSE  360
GVDPRFIYQY FYDSYFDVRR GLMKNDPREL IKKEIKRVLE DYFYAIIL              408

SEQ ID NO: 295          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 295
MWLEKHYGRK HGVYSICSSN EYVIEASIEF AMQKDEPILI EATPHQVNFS GGYSGWTPED  60
FRRFVEEIAR RKGLDPDKIQ LGGDHLGPLP WQDYPEPQAM QWARELIRAF VESGYEKIHI  120
DCSMPLSDWP KVLPYEVIAE WTRELFRIAE ETARKFNFRP IYVVGTDVPI AGGGEEEGRT  180
SVEDFRSAIS LLKKYFNDVP NIWDRVVGFV IMLGIRFSRD RVFEYDRDQV REILEEVRRE  240
DLFVEGHSTD YQARYALRNM VEDGVRILKV GPALTAAFRR GVFLLSNIED EIIPERERSN  300
IKRVILETML RDDRYWRKYY ETSDQLRLDI WYNLLDRIRY YWDYPDVREV LRKLFENFSE  360
PVDIRFIYRY FYDSYEDVRR GQMRPDPREL IKKEIKRVLE DYSYAIHD              408

SEQ ID NO: 296          moltype = AA  length = 408
FEATURE                 Location/Qualifiers
REGION                  1..408
```

```
                      note = mutant D-fructose C4-epimerase
source                1..408
                      mol_type = protein
                      organism = synthetic construct
SEQUENCE: 296
MWLMLQYLIN IGVYSICSSN PYVIEASIEH AQETNDYILI EATPHQVNQF GGYSGMTPSD  60
FRDFVMSIAK EKGLEENRII LGGDHLGPLP WQDEPAPTAM EKARQLIRAF VESGYTKIHI  120
DCSMPLSDDP ETLPLEVIAE RTRELFEVAE RTAREYNNQE VYVVGTDVPI AGGGEEEGVT  180
SVEDFRSAIS TLRDYFSDVP NIYNRVVGFV IMLGIRFSYD QVFEYDRSQV EEILREVSRT  240
DLFVEGHSTD YQARYALRNM VLDGVRILKV GPALTAAFRR GVFLLSNIER EIIPERLRSN  300
ILRVILETML RDPRYWRDYY DDSERLELDI LYNLLDRIRY YWEYPDVEEV LRQLFENFSE  360
GVDPRYIYQY FYDSYFDVRE GKMQNDPREL IKKEIKRVLE DYTYAIQL              408

SEQ ID NO: 297        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 297
MWLMVQYNLP YGVYSICSSN PWVIEASIET AKQYNFYILI EATPHQVNQF GGYSGMTPSD  60
FRDFVMEIAR QKGLDERMII LGGDHLGPLP WQDLPSPQAM EYAKELIRAF VESGYLKIHI  120
DCSMPLSDDP KVLPWEKIAE RTRELFEIAE ETARKYNFEM VYVVGTDVPI AGGGEEEGVT  180
SVEDFRSAIS TLLAYFSDVP NIARRVVGFV IMLGIGFSYD KVFEYDRDKV RGILEEVKRT  240
DLFVEGHSTD YQARYALRNM VLDGVRILKV GPALTAAFRR GVFLLSLIER EIIPERERSD  300
ILRVILETML RDPRYWRDYY RDSPALELDI LYNLLDRIRY YWEYEDVKMV LNKLFENFSE  360
GVDERYIYLY FYDSYFAVRE GKMSNDPRDL ILWEIILVLY DYWYAIIL              408

SEQ ID NO: 298        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 298
MWLMHEYGRK FGVYSICSSN SYVIEASIEF AKNRHHRILI EATPHQVNQF GGYSGMTPED  60
FKNFVMKIAK EKGLDERLII LGGDHLGPLP WQDEPRPTAM NKARELIRAF VESGYYKIHI  120
DCSMPLSDEP KVLHWSRIAE DTRDLFEEAE RRARKENTQF EYVVGTDVPI AGGGEEEGIT  180
SVEDFRQAIE QLIRHFPDVL NILDRVVGFV IMLGIGFTRD TVFYYDRDAV RPILEEVKRT  240
DLFVEGHSTD YQARYALRNM VEDGVRILKV GPALTAAFRR GVFLLSNIED EQIPERERSN  300
IKRVILETML RDDRYWRKYY STSKSHEWDI WYNLLDRIRY YWYYPDVEWV LRKLFENFSE  360
GVHPSFIRDY FYDSYEDVRE GRMKNDPREL IKKEIKRVLE DYYYAIFL              408

SEQ ID NO: 299        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 299
MWERHDNLQK FGVYSICSSN EWVIRASIRF AKTRGERILI EATPHQVNHR GGYSGMTPSD  60
FRDEVYRIAR EEGLEEDRII LGGDHLGPLP WQDYPSPWAM EEAKELIRAF VESGYYKIHI  120
DCSMPLSDEP EVLPWPKIAE RTRELFEIAE ETRTQFNTEF WYVVGTDVPI AGGGEEEGIT  180
SVEDFRSAIE WLKRYFPDVP NILDRVVGFV IMLGIGFTRD TVFYYDRDAV RPILEEVKRE  240
DLFVEGHSTD YQARYALRNM VEDGVRILKV GPALTAAFRR GVFLLSLIEF EQIPERERSN  300
ILEVILRTML RDDRYWRKYY STSKSHEWDI FYNLLDRIRY YWEYEDVKMV LNKLFENFSE  360
GVHPSFILQY FYDSYFDVRE GKMRNDPREL IHKEIMRVLE DYYYAIFW              408

SEQ ID NO: 300        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 300
MWLDQRNGQP WGVYSICSSN EYVIRASIEF AQEKDQYILI EATPHQVNQF GGYSGMTPED  60
FARFVYEIAR EHGLREDRII LGGDHLGPLP WQDEPSPTAM QKARELIRAF VESGYYKIHI  120
DCSMPLSDDP KVLPWPKIAE RTRELFEVAE RVAQWYPNLF VYVVGTDVPI AGGGEEEGRT  180
SVEDFRSAIE WLRRYFEDVL NIWDRVVGFV IMLGIGFSYD KVFEYDRSQV FPILEEVKRT  240
RLFVEGHSTD YQARYALRNM VLDGVRILKV GPALTAAFRR GVFLLSNIED EIIPERERSN  300
IKRVILETML RDDRYWRKYY KDSKRLELDI WYNLLDRIRY YWDYPDVRRV LNKLFENFSE  360
GVHESFIYRY FYDSYFDVRN GNMKNDPREL IKKEIKRVLE DYSYAIEL              408

SEQ ID NO: 301        moltype = AA  length = 408
FEATURE               Location/Qualifiers
```

```
REGION                  1..408
                        note = mutant D-fructose C4-epimerase
source                  1..408
                        mol_type = protein
                        organism = synthetic construct
SEQUENCE: 301
MWLEHHYGRP FGVYSICSSN EYVIEASIEF AKELHYPILI EATPHQVNQF GGYSGWTPSD  60
FRDFVFEIAK RKGLDLRLII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGRT  180
SVEDFRSAIS SLKKYFNDVP NIWDRVVGFV IMLGIRFSRD RVFEYDRSQV RPILEEVKRE  240
DLFVEGHSTD YQARYALRNM VLDGVRILKV GPALTAAFRR GVFLLSLIED EIIPERERSD  300
IPRVILETML RDDRYWRKYY ETSDQLRWDI LYNLLDRIRY YWDYPDVREV LRKLFENFSE  360
PVPIDFIRRY FYDSYFDVRE GKMRPDPREL IKKEIKRVLE DYSYAIND              408

SEQ ID NO: 302          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 302
MWLRFHYNEP IGVYSICSSN PYVIEASIEA AMHVHEPILI EATPHQVNWQ GGYSGMTPTD  60
FRDFVMTIAR EKGLDERLII LGGDHLGPLP WQDLPAPQAM TYAQILIRAF VESGYLKIHI  120
DCSMPLSDWS EVLPWELIAE LTRELFRVAE EVGQDMPFLM VYVVGTDVPI AGGGEEEGIT  180
SVEDFRSAIY YLFLYFNDVL NIRDRVVGFV IMLGIRFSYD VVFMYDRSQV EEILREVSRY  240
PLFVEGHSTD YQARYALRNM VLDGVRILKV GPALTAAFRR GVFLLSLIED EIIPERRRSQ  300
IIRVILETML RDPRYWRDYY DDSDRLYWDI LYNLLDRIRY YWLYPDVWYV LLLLFWNFSE  360
PVDLRFILRY FYDSYEDVRD GRMSNDPREL IKKEIKRVLE DYWYAINL              408

SEQ ID NO: 303          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 303
MWLPAHYLRE HGVYSICSSN RYVIEASIEF AQNMHEPILI EATPHQVNQF GGYSGWTPSD  60
FRDFVYKIAK EKGLRLDLII LGGDHLGPLP WQDLPEPIAM QYARELIRAF VESGYKKIHI  120
DCSMPLSDDP ETLDLTRIAE RTRELFREAE ETARKYNFQP VYVVGTDVPI AGGGEEEGIT  180
SVEDFRSAID RLREYFNDVP NIWDRVVGFV IMLGIRFSYD QVFEYDRDQV RPILEEVKRE  240
DLFVEGHSTD YQARYALRNM VQDGVRILKV GPALTAAFRR GVFLLSRIED EIIPERERSN  300
IREVILRTML RDDRYWRKYY RTSEDLRYDI WYNLLDRIRY YWEYPDVQEV LRRLFENFSE  360
PVPPNFIYQY FYDSYEDVRR GLMRPDPREL IKKEIKRVLE DYAYAIHD              408

SEQ ID NO: 304          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 304
MWLDHHYLLN IGVYSICSSN PYVIEASIEF AANMHLPILI EATPHQVNQF GGYSGMTPSD  60
FRDFVMDIAD RKGLDRNLII LGGDHLGPLP WQDLPAPQAM DYARQLIRAF VESGYTKIHI  120
DCSMPLSDDP EVLPYEVIAE RTRELFRVAE ETAREYNFQA VYVVGTDVPI AGGGEEEGIT  180
SVEDFRSAIE LLRRYFNDVP NIWDRVVGFV IMLGIRFSYD IVFEYDRSQV EEILREVSRE  240
NLFVEGHSTD YQARYALRNM VLDGVRILKV GPALTAAFRR GVFLLSHIEE EIIPERERSN  300
IIEVILRTML RDPRYWRDYY DDSERLEYDI LYNLLDRIRY YWEYPDVRTV LELLFRNFSE  360
PVPLSFIYQY FYDSYEDVRR GLMENDPREL IKKEIKRVLE DYAYAINL              408

SEQ ID NO: 305          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 305
MWLDAHYLRD IGVYSICSSN PYVIRASIIF AIRTGDYILI EATPHQVNQF GGYSGMTPSD  60
FRDFVMSIAD ELGLDRNLII LGGDHLGPLP WQDLPAPRAM EYARQLIIAF VESGYTKIHI  120
DCSMPLSDDP ERLPLEVIAR RTRELFEIAE RYAQEYNVQP VYVVGTDVPI AGGGEEEGVT  180
SVEDFRAAIE ALRRYFDDVP NIFDRVVGFV IMLGIGFSYE TVFEYDRSRV EEILREVSRD  240
QLFVEGHSTD YQARYALLNM VRDGVRILKV GPALTAAFRR GVFLLSHIEE EIIPERERAN  300
IIEVILRTML RDPRYWRDYY DDSERLEYDI LYNLLDRIRY YWEYPDVLTV LERLFRNFSE  360
GVDMRYIYQY FYDSYERVRR GEMTPDPREL ILTEIMLVLE DYAYAIND              408

SEQ ID NO: 306          moltype = AA  length = 408
```

```
FEATURE                Location/Qualifiers
REGION                 1..408
                       note = mutant D-fructose C4-epimerase
source                 1..408
                       mol_type = protein
                       organism = synthetic construct
SEQUENCE: 306
MWTDHNYLRE IGVYSICSSN EYVIEASIEF AIEMGSYILI EATPHQVNQF GGYSGWTPSD  60
FRDFVFEIAD RKGLERNLII LGGDHLGPLP WQDLPEPRAM RYAEELIRAF VESGYTKIHI  120
DCSMPLSDDP EVLPLERIAE RTRRLFEVAE RYRQQYNVQP VYVVGTDVPI AGGGEEEGVT  180
SVEDFRAAIE ALRRYFSDVM NIYDRVVGFV IMLGIGFSYQ TVFYYDRSRV EPILREVSRT  240
DLFVEGHSTD YQARYALRNM VQDGVRILKV GPALTAAFRR GVFLLSEIER EIIPERERSN  300
IIEVILRTML RDPRYWRDYY RTSEDLEYDI LYNLLDRIRY YWNYPDVREV LRRLFENFSE  360
GVDPRLIYQY FYDSYEDVRR GLMTNDPREL IKKEIKRVLE DYAYAIHD            408

SEQ ID NO: 307         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 307
MWLMLQYLIN IGVYSICSSN SYVIRASIIA ALRYDLYILI EATPHQVNQF GGYSGMTPSD  60
FAEFVYRIAQ EIGLEENRII LGGDHLGPLP WQDEPAPTAM NKAKDLIRAF VESGYTKIHI  120
DCSMPLSDDP ETLPLEVIAE RTRELFEIAE ETAREYNNQE VYVVGTDVPI AGGGEEEGVT  180
SVEDFRSAIS TLRDYFSDVP NIYNRVVGFV IMLGIRFSYD QVFEYDRSQV EEILREVSRT  240
DLFVEGHSTD YQARYALRNM VLDGVRILKV GPALTAAFRR GVFLLSFIEQ EIIPERERSN  300
ILRVILETML RDPRYWRDYY RDSEDLELDI LYNLLDRIRY YWEYPDVETV LRKLFENFSE  360
GVDIKFIYQY FYDSYFSVRR GLMSNDPRDL ILYEIMLVLE DYFYAIIL            408

SEQ ID NO: 308         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 308
MWLNQQYLRR EGVYSICSSN PYVIEASIEF AQEYNRYILI EATPHQVNQF GGYSGMTPSD  60
FRDFVFEIAD RKGLERNRII LGGDHLGPLP WQDEPEPTAM NKARELIRAF VESGYKKIHI  120
DCSMPLSDDS ETLPYPRIAE RTRILFEEAE RTAREYNNQP VYVVGTDVPI AGGGEEEGVT  180
SVEDFRSAIE YLRRYFLDVP NIWDRVVGFV IMLGIRFSYD QVFEYDRDNV RPILEEVKRE  240
RLFVEGHSTD YQARYALRNM VEDGVRILKV GPALTAAFRR GVFLLSNIED EIIPERERSN  300
IKRVILETML RDDRYWRKYY RDSEDLRLDI WYNLLDRIRY YWNYPDVENV LRKLFENFSE  360
GVDPRFIYQY FYDSYFDVRE GKMKNDPREL IKKEIKRVLE DYAYAIEL            408

SEQ ID NO: 309         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 309
MWLLLQYLRN IGVYSICSSN PYVIEASIEF AKEKGDYILI EATPHQVNQF GGYSGMTPED  60
FKRFVMEIAD RKGLERDKII LGGDHLGPLP WQDLPAPQAM EYAKELIRAF VESGYTKIHI  120
DCSMPLSDDP KVLPLEVIAE RTRELFEIAE ETAREYNNQE VYVVGTDVPI AGGGEEEGVT  180
SVEDFRSAID TLRRYFSDVP NIYDRVVGFV IMLGIGFSYD KVFEYDRDKV RGILEEVSRE  240
DLFVEGHSTD YQARYALRNM VLDGVRILKV GPALTAAFRR GVFLLSFIEQ EIIPERERSN  300
ILRVILETML RDPRYWRDYY KDSKRLELDI LYNLLDRIRY YWEYEDVKMV LNKLFENFSE  360
GVDPRFIYQY FYDSYFDVRE GKMKNDPREL IKKEIKRVLE DYSYAINL            408

SEQ ID NO: 310         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 310
MWLMLQYLIN IGVYSICSSN PYVIRASIEF ALETNDYILI EATPHQVNQF GGYSGMTPSD  60
FREFVMRIAQ EIGLEEDRII LGGDHLGPLP WQDEPSPTAM AKAEELIRAF VESGYKKIHI  120
DCSMPLSDDP ETLPLEKIAE RTRRLFEVAE RTAREYNNQE VYVVGTDVPI AGGGEEEGVT  180
SVEDFRSAID TLRRYFSDVP NIYNRVVGFV IMLGIGFSYD KVFEYDRSQV EEILREVSRT  240
DLFVEGHSTD YQARYALRNM VLDGVRILKV GPALTAAFRR GVFLLSNIED EIIPERLRSN  300
IKRVILETML RDPRYWRDYY DDSERLELDI WYNLLDRIRY YWEYEDVKIV LELLFRNFSE  360
GVDPRFIYQY FYDSYFRVRN GDMKNDPREL IKYEIKRVLE DYLYAIQL            408
```

```
SEQ ID NO: 311         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 311
MWLSAQYLRK KGVYSICSSN PYVIEASIEF AQEYNTYILI EATPHQVNQF GGYSGMTPED  60
FKRFVMEIAD RKGLERNRII LGGDHLGPLP WQDEPSPTAM AKAEELIRAF VESGYKKIHI  120
DCSMPLSDDP KVLPLEKIAE RTRRLFEVAE RTAREYNNQE VYVVGTDVPI AGGGEEEGVT  180
SVEDFRSAIE TLERYFSDVP NIFDRVVGFV IMLGIRFSYD QVFEYDRDKV RGILEEVSRE  240
DLFVEGHSTD YQARYALRNM VEDGVRILKV GPALTAAFRR GVFLLSNIED EIIPERLRSN  300
IKRVILETML RDDRYWRKYY DDSERLELDI WYNLLDRIRY YWEYEDVKIV LELLFRNFSE  360
GVDPRFIYQY FYDSYFDVRE GKMQNDPREL IKKEIKRVLE DYSYAINL          408

SEQ ID NO: 312         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 312
MWTDHDYLRR VGVYSICSSN EYVIRASIRF ARDDDTYILI EATPHQVNQH GGYSGMTPSD  60
FRDFVYRIAD EEGLRRDLII LGGDHLGPLP WQDRPEPEAM NEARELIRAF VESGYKKIHI  120
DCSMPLSDRP SSLPYPRIAE RTRELFEEAE RYAEQYNLQP VYVVGTDVPI AGGGEEEGVT  180
SVEDFRSAIE YLREYFRDVE NIWDRVVGFV IMLGIGFSYD KVFEYDRSQV EPILREVSRT  240
DLFVEGHSTD YQARYALRNM VEDGVRILKV GPALTAAFRR GVFLLSRIEE EIIPERERSN  300
IIEVILRTML RDDRYWRNYY RDSEGLEYDI LYNLLDRIRY YWEYEDVKMV LNKLFENFSE  360
GVPINFIYQY FYESYENVRR GLMQNDPRRL ILEEIMRVLR DYAYAIRL          408

SEQ ID NO: 313         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 313
MWLMLQYLIN IGVYSICSSN PYVIEASIRF AQRTNLYILI EATPHQVNQF GGYSGMTPED  60
FKRFVMEIAD RTGLERNRII LGGDHLGPLP WQDLPAPQAM EYAKELIRAF VESGYKKIHI  120
DCSMPLSDDP ETLPYEVIAE RTRELFEIAE ETAREYNNQE VYVVGTDVPI AGGGEEEGVT  180
SVEDFRSAIS SLRDYFSDVP NIYDRVVGFV IMLGIGFSYD KVFEYDRSQV APILEEVKRT  240
DLFVEGHSTD YQARYALRNM VLDGVRILKV GPALTAAFRR GVFLLSFIEQ EIIPERERSN  300
ILEVILRTML RDDRYWRKYY KDSKRLELDI LYNLLDRIRY YWEYPDVETV LRKLFENFSE  360
GVDIKFIYQY FYDSYFSVRE GLMSNDPRDL ILYEIMLVLE DYLYAIQL          408

SEQ ID NO: 314         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 314
MWLMLQYLIN IGVYSICSSN SYVIEASIRA AQEYNLYILI EATPHQVNQF GGYSGMTPSD  60
FRDFVMEIAD RTGLERNRII LGGDHLGPLP WQDEPAPTAM EKARQLIRAF VESGYTKIHI  120
DCSMPLSDDP KVLPLEVIAE RTRELFEVAE RTARKYNFQE VYVVGTDVPI AGGGEEEGVT  180
SVEDFRSAIE TLRAYFSDVP NIYDRVVGFV IMLGIRFSYD QVFEYDRDKV RGILEEVKRE  240
DLFVEGHSTD YQARYALRNM VLDGVRILKV GPALTAAFRR GVFLLSNIEE EIIPERERSN  300
ILEVILRTML RDPRYWRDYY KDSKRLELDI LYNLLDRIRY YWEYPDVETV LRKLFENFSE  360
GVDIKFIYQY FYDSYFDVRR GLMSNDPRDL ILAEIILVLR DYFYAIHL          408

SEQ ID NO: 315         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 315
MWLPAHYLRE HGVYSICSSN EYVIEASIEF AKNMGEYILI EATPHQVNQF GGYSGWTPSD  60
FRDFVYEIAD RKGLERDRII LGGDHLGPLP WQDEPSPTAM NKAKDLIRAF VESGYKKIHI  120
DCSMPLSDDP ETLPYDKIAE RTRELFEIAE ETARQMNFQP VYVVGTDVPI AGGGEEEGVT  180
SVEDFRSAIE RLREYFRDVP NIWDRVVGFV IMLGIGFSGD KVFEYDRDKV RGILEEVSRE  240
DLFVEGHSTD YQARYALRNM VQDGVRILKV GPALTAAFRR GVFLLSRIED EIIPERERSN  300
IIEVILRTML RDDRYWRKYY RTSKGLEYDI LYNLLDRIRY YWNYPDVREV LRKLFENFSE  360
PVDIKFIYQY FYDSYFDVRE GKMRPDPREL IKKEIKRVLE DYAYAIHD          408
```

```
SEQ ID NO: 316          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 316
MWTDHAYLRE IGVYSICSSN EYVIRASIRF AIEKGTYILI EATPHQVNQF GGYSGMTPED  60
FKRFVMEIAD EEGLRRDLII LGGDHLGPLP WQDEPEPTAM QKARELIRAF VESGYTKIHI  120
DCSMPLSDDP EVLDDERIAR RTRELFEVAE RYRQQYRVQP VYVVGTDVPI AGGGEEEGVT  180
SVEDFRRAID ALRRYFSDVP NIFDRVVGFV IMLGIGFSGD QVFEYDRSRV EPILREVSRE  240
DLFVEGHSTD YQARYALRNM VRDGVRILKV GPALTAAFRR GVFLLSNIED EIIPERERAN  300
IKRVILETML RDDRYWRDYY KDSKRLELDI WYNLLDRIRY YWNYPDVREV LRRLFENFSE  360
GVDPRYIYQY FYESYEDVRR GLMRNDPRDL ILAEIMLVLR DYSYAIND            408

SEQ ID NO: 317          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 317
MWLPAHYLRR RGVYSICSSN EYVIEASIEF AKNMGDYILI EATPHQVNQF GGYSGMTPED  60
FKRFVMEIAD RKGLRRDLII LGGDHLGPLP WQDEPEPTAM NKARELIRAF VESGYDKIHI  120
DCSMPLSDDP ETLALPRIAE RTRELFREAE ETARQMNFRP VYVVGTDVPI AGGGEEEGIT  180
SVEDFRSAIE YLRRYFNDVP NIWDRVVGFV IMLGIGFSGD KVFEYDRSQV RPILEEVKRE  240
DLFVEGHSTD YQARYALRNM VEDGVRILKV GPALTAAFRR GVFLLSRIED EIIPERERSN  300
IIEVILRTML RDDRYWRKYY STGKDLEYDI LYNLLDRIRY YWNYPDVREV LRRLFENFSE  360
GVDLSLIYQY FYDSYEDVRR GLMKNDPREL IKKEIKRVLE DYSYAIHD            408

SEQ ID NO: 318          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 318
MWLMQAYLIA IGVYSICSSN EYVIRASIRA AQNYNTYILI EATPHQVNQF GGYSGMTPSD  60
FRDFVYRIAD EEGLERNRII LGGDHLGPLP WQDLPEPQAM QYARELIRAF VESGYTKIHI  120
DCSMPLSDDS ETLPYPRIAE RTRELFEVAE RTAREYDNQP VYVVGTDVPI AGGGEEEGVT  180
SVEDFRSAIE YLRRYFEDVM NIWDRVVGFV IMLGIRFSYQ TVFEYDRSQV EPILREVSST  240
DLFVEGHSTD YQARYALRNM VLDGVRILKV GPALTAAFRR GVFLLSRIEQ EIIPERLRSN  300
ILEVILRTML RDDRYWRNYY RDSEDLRYDI LYNLLDRIRY YWNYPDVEQV LRELFRHFSE  360
GVDPRFIYQY FYDSYFRVRN GEMRNDPRDL IEAEIQEVLE DYFYAIIL            408

SEQ ID NO: 319          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 319
MWLSHDYLRE HGVYSICSSN EYVIEASIRF AINMHDPILI EATPHQVNQF GGYSGWTPSD  60
FRDFVYEIAD RTGLERNLII LGGDHLGPLP WQDEPEPTAM QKARELIRAF VESGYDKIHI  120
DCSMPLSDDP ETLALPRIAE RTRELFREAE EAARKMNFRP VYVVGTDVPI AGGGEEEGIT  180
SVEDFRSAIE YLRRYFNDVP NIWDRVVGFV IMLGIRFSYD QVFEYDRSQV RPILEEVKRE  240
DLFVEGHSTD YQARYALRNM VQDGVRILKV GPALTAAFRR GVFLLSNIED EIIPERERSN  300
IKRVILETML RDDRYWRDYY RTSEGLRYDI WYNLLDRIRY YWNYPDVREV LRKLFENFSE  360
GVDIKFIYQY FYRSYFDVRE GLMRNDPREL ILAEIMEVLR DYAYAIHD            408

SEQ ID NO: 320          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 320
MWLPAHYLRE HGVYSICSSN EYVIEASIEF AIEMHDPILI EATPHQVNQF GGYSGMTPED  60
FKRFVMEIAD RLGLERNLII LGGDHLGPLP WQDLPSPQAM QYARELIRAF VESGYTKIHI  120
DCSMPLSDDP KVLPLPKIAE RTRELFREAE ETARQMNFQP VYVVGTDVPI AGGGEEEGIT  180
SVEDFRSAID ELRRYFNDVP NIWDRVVGFV IMLGIGFSYD KVFEYDRDQV RPILEEVKRE  240
DLFVEGHSTD YQARYALRNM VQDGVRILKV GPALTAAFRR GVFLLSNIED EIIPERERSN  300
IKRVILETML RDDRYWRDYY STSKDLEYDI WYNLLDRIRY YWNYPDVREV LRKLFENFSE  360
```

```
PVPLSFIYQY FYLSYFDVRE GLMEPHPERL IRAEIMEVLR DYSYAIHD           408

SEQ ID NO: 321          moltype = AA  length = 494
FEATURE                 Location/Qualifiers
source                  1..494
                        mol_type = protein
                        organism = Pseudothermotoga thermarum
SEQUENCE: 321
MKLLEEFLKA FPGRFKVYGS SLRIITDSYF FLGNDGKEKL LFVVGKKGIC QLFDGQKIGQ  60
IGSNDVLMCK KTHENLLALR KIINLNPTTI NKKASFGFGD RIGLATPAHA KVAKDFEVFP  120
IFAQQSVREL SRTGRTYKDV LDDAVWGVFE SGYNFEFGAD ADHVKEIEDL EKASNEGFTM  180
YTVDPSDHIK DVSKLSQKEF QSLYQDNKIR RELEMRYVGK LYKFKDFEFR MTDEEFAEIF  240
VTYIDAIEHV CKCYDVLKAK GKPFDFEVSI DETAVPTTPL AHIFIVKELR RRGIDFKTLA  300
LRFSGEWQKG IDYIGDMEMF RKEIITHSKI SKELGGYKLS LHSGSDKFSV YPIFSEATEG  360
EFHVKTAGTN YLEAIRVVAV KDPELYREIH KFALTKFEQD RKSYHVTTDL SKIPDVDKMK  420
NEELVKLLDM PDSRQLIHIT YGSVLTAKDE NGRWLFKERI LKVLQENEDL HYDFVEKHMR  480
KHLSLLGLER RIEK                                                494

SEQ ID NO: 322          moltype = AA  length = 487
FEATURE                 Location/Qualifiers
source                  1..487
                        mol_type = protein
                        organism = Pseudothermotoga hypogea
SEQUENCE: 322
MFAEFQHLTR GKFVPYATSL RKSTDATFFL VRDELDKYLI VIGKKGICEL FEGQKIGEID  60
RQDVVLCAKN DRNCQSLMSL FPSLKPQICN AKLSFGFGDR LGVATAAHAQ CVQKEKLFPI  120
FAQQSVREIS RTERNWLDVL HSAVWGVFES GYDGPFGADA DHVKKIEDLE SAARAGYTMF  180
TIDPSDHVKD PAKFDKRELV RFYEEHPMRR TLEMKYIGKS FTVLGEKLTF DEENFAEVFV  240
TYIDAIEHVE KCYRALRAVC KTSFDLEVSI DETSVPTTSL AHIFFVQELV RRGVEFRTLA  300
LRFPGEWQKG IDYVGDIDLF SENLDKHVAI VKMFTGYRLS LHSGSDKFSV YPILAEKTDR  360
TIHVKTAGTS YLEAIRVVAK FAPDLYRQIH KYALSRFDQD KASYHVTTEL SKIPDVDKLE  420
DSELPSLLDQ PDSRQLIHIT YGSVLTAKKE GRSLFKDRIM RVLFEHEAEH YDFLKKHLGK  480
HIQLLGV                                                        487

SEQ ID NO: 323          moltype = AA  length = 489
FEATURE                 Location/Qualifiers
source                  1..489
                        mol_type = protein
                        organism = Pseudothermotoga lettingae
SEQUENCE: 323
MAENIVEKFE KLFKGKYKIY YSSIRKLEKS FFFMIRDQKQ KYLISIAKKR ICEKFEGKKI  60
GRINDLDILM CPTNDYNCKV IRTLFNINPS VCKKNTSFGF GDRLGLATPA HTTLINKYDV  120
FPVLAQQSVR ELSRTHRNFK DVLDSAIWGI FESGYEGEFG ADADHVKDIN DLMQAAYEGY  180
SMYTVDPSDH VKNIDKINQG ELVEFYKSHP LRKEIEMIYS GKVFSFEKSK FTMEDKELFR  240
IFVTYVDAIE HVVKCYEAIK NTKKNFDFEV SIDETSIPTS PLAHIFIVHE LRRRGVDFQT  300
LALRFVGQWQ KAIDYIGDLS VLESELSMHC EIVKSLSGYR LSLHSGSDKF SVYRIFTHYC  360
DGKLHVKTAG TSYLEAIRTV AEASPSLYRN IHKYALTCFE KDNTSYHVTA DINKIPDVDN  420
VEDSKVVNLL DIPEVRQLIH ITYGSVLTEK INGKYLFRDE IYRILHENEF LHYKRIRDHL  480
GKHLELLKN                                                      489

SEQ ID NO: 324          moltype = AA  length = 519
FEATURE                 Location/Qualifiers
source                  1..519
                        mol_type = protein
                        organism = Rhodothermus marinus
SEQUENCE: 324
MVTVLQTLLQ RPRPLAEIDR TSLARFLTDV IRQQVYPTSL EPTSEGVFFL ARDGREKRLG  60
ILSEAGLHDF EGVRHQLSLD GRTLIFQSCP LTAANARALR RHIPWTAPRP LGLRASVGCG  120
DRLGLATPGH VRAVRKHKLA PVFAQQSIRE MTRTGRTPQQ VLDEAMWGVF QEGWRQGYGA  180
DADHLKTEED ADRCIEAGFT FFTIDPSAYV DNEVDTADAA TLEAKVAALP WEALETTLAD  240
LRRAYLGQHF QVGPYELSFE ERTLMQALAK YGGAIAHTAR MYRHIAGRMG NRPFELEMSV  300
DETEVPTSPA EHFFVARELQ RLGVRWISLA PRFVGRLEKG VDYIGDLEEF EAHLKLHVAI  360
ARTLGPYKLS LHSGSDKFAL YPLFARHAGE LFHLKTAGTS YLEALRAVAE LDPPLFREIL  420
DFARDRYETD RATYHVSALL ERVPKASDVP DDALPALLEQ FDTRQVLHVT FGSVLTATDA  480
DGRPRFRDRL LAVLQENEET YYRLLEAHFD RHLAPFDAE                     519

SEQ ID NO: 325          moltype = AA  length = 496
FEATURE                 Location/Qualifiers
source                  1..496
                        mol_type = protein
                        organism = Geosporobacter subterraneus
SEQUENCE: 325
MDIYEKIAAA LKDNRHNIQL DGVKIYPQSY VEVDMVKMIM VKAAEKKVIL AQGSGPLFQE  60
LEGEAYDDYK VCNCSHLNRV VLNKYLPYTK PSAFGKEIAT IGLGDRLGIA SPGHIQAVKG  120
REIRPILAQQ SIRELNLTNR TYRNVLDAAC FAVFQEGYKD GFGADGDHLK TEEDIQSALD  180
LGFTMITLDC SEMIDNTIDK LTDTEVEEKY YQLPQSVRER YETRYLDKCF ELRNSKICFS  240
KENLMKNVLI YGAAADFIVA IYEKQIKHRD QKIDFEVSID ETVTPTTPEA HYFVAREIYD  300
RQVDINSMAP RFCGEFQKGI DYIGDIHQFE KEFQVHAEIA DHFGYKISIH SGSDKFSVFQ  360
TIGRYTEGRF HVKTAGTNWL EAVRVVAEKN PNLYRKMHQY ALEHFDEARA YYHVTTDIEG  420
```

```
IVPLEKVNDH ELSQYMNENN ARQLLHITYG ILLQAKDASG QYLFREDFFY TLEQHEAEYD  480
EALRKHIGRH LEQLGK                                                   496

SEQ ID NO: 326          moltype = AA  length = 517
FEATURE                 Location/Qualifiers
source                  1..517
                        mol_type = protein
                        organism = Melioribacter roseus
SEQUENCE: 326
MEMQKLYEEV ENKNIVKNDL VDLTIGESLK IKAYPLSVLK KDDAFFFIGK ENYDKFLFVI  60
SAGKENGLLN EFEGELIDAG KDVTVKKCNL STKNRKAVQK IFPHTAPIVL GLCNSFGCGD  120
RLGVANAGHI RAIKQSNFRP ILAQQSIREL TRTNRTPDDV MDAAVWAVLQ EGYKDGFGSD  180
ADHLKTFEDI DLMLNAGFTM FTFDPSEHVD NEADNYSEDQ LKQKLGEIDW SGLQDTSADA  240
AKRYVDMTFN ISERLSLTIQ ESDFLRAYAK YGNAIAHIKK MYDYLASKAD KDTFEIEVSV  300
DETESVTSPF EHFFFANELN RLGVKYVSLA PRFIGDFEKG IDYKGDLNVF KTEYEKHLDI  360
TKYFGSYKIS LHSGSDKFSA YRVIGSLKGA YTHVKTAGTS YLEALRVVAA KEPALFRDIL  420
DFCRDLYETE KRSYHVSADI NKVKPANQYS DTELIELFNQ NDTRQVLHVT FGKVLTEKDS  480
SGHFLFKDKI MKCLVENEES HYEFLEKHFL KHLECFK                            517

SEQ ID NO: 327          moltype = AA  length = 497
FEATURE                 Location/Qualifiers
source                  1..497
                        mol_type = protein
                        organism = Lysinibacillus sphaericus
SEQUENCE: 327
MKQFLPAIEL LAKGELPSNS NQIKVYEKSY TVEGNVHLLM VKNSGEKFIL ATGEGAIFDE  60
LTGTDVDGKG KACPLTYENR LVLNKYFDYT VPQAFGTEIA TIGLGDRLGL ASPGHIETVR  120
EKNIKPVLAQ QSIRELTLTN RSMNDMLDAA AFAVFQEGYK GGYGADGDHI KEESDIQYAL  180
SLGASMITLD CSDHIDNTIE KASPEVLDEK FNALSEVVKQ RYMEQYLGKT FEVNGLTLTL  240
DETELKKNVL LYDKAIDYTT HVYNEYISKE NRAIDFEISI DETETVTSPI SHFFVANELI  300
NRGVKVVSLA PRFCGEFQKG IDYIGDVEQF EVELREHALI AEHFGYKLSI HSGSDKFMVF  360
PIIAEYTKGV FHVKTAGTNW LEAIRVIAAT NPDLYRRMHV FALENFEEAL KYYHVTPDLN  420
SFEKLENVED AKLPEYMNND AARQLFHVTY GLLLTAKGEN DTFLFRDEFF KTLDKYEEEY  480
RDALVSHIGK HIELLGL                                                  497

SEQ ID NO: 328          moltype = AA  length = 510
FEATURE                 Location/Qualifiers
source                  1..510
                        mol_type = protein
                        organism = Clostridium stercorarium
SEQUENCE: 328
MGNWKDFVKD FCTKEKNIEV LRAEAEKAFG NYGVYPRSIN EVGNAIVMMA RGENEKCLVV  60
VGEDSRLQEL KGNQTEENGL KVKVCPLSNE NCYVIRKIFP YTNPQPHKGK NITIGLGDRL  120
GLASPGHIRL IRDLDVFPVL AQQSIRELNL TGRTYEDVIS AAAWAVFQEG YTKGYGADGD  180
HLKTAEEVKM SLNVGMTMIT LDCSEHIDNS AAHAGLSELR EKYSRFTEEE RERWERKYLN  240
RDVKIGNYSF HISEEDLIRM ACVYGGAIRH TLDIYHNIIA KCGRPIDFEM SIDETLTPTS  300
PASHYFVAQE LIDGGVEITS LAPRFCGEFQ KGIDYIGDLK QFTDEFAVHA AIADHFGYKI  360
SVHSGSDKFK VFPVVGEKTN GRYHLKTAGT NWLEAVRVIA RHKPDLYRRM HAFALEHLED  420
AKKYYHIGAK VENIPALETL ADSELPELMN RDDSRQVMHI TYGHILQAKD ENGNPLFKDE  480
LYKVLYEYEE EYANALKKHI GRHLEGLGLL                                    510

SEQ ID NO: 329          moltype = AA  length = 488
FEATURE                 Location/Qualifiers
source                  1..488
                        mol_type = protein
                        organism = Truepera radiovictrix
SEQUENCE: 329
MPSQLPEPLP VPPEARAHPS FRLHEGAALW LAGARLAVLA PPEHPALTRF RGEVQHVGDH  60
RLLRAERRAE NAAALRALLP DLQPRPLGLV TSAGFGDRLG VATPGHVRAA QRYGAGVAPV  120
FAQQSIREMT RTGRTPQEVL DDATWGAFAA GWRGALGADA DHQKTVADLE RCAAAGFTLF  180
TVDPSDHVDD SAHGAPASDL EAKVAALPWR ELETTRADFE RYAGRRLELG DRELVLAREA  240
VLRAGAKYAR AVLHVATLYR HLEGKGAPFE LEVSVDETAT PTSHAEHAVV ALELRRLGVR  300
WVGLAPRFVG RFEKGVDYRG DLGELKADLA GHAALARSLG PYKLSLHSGS DKFSVYPLIA  360
EATGGMVHLK TAGTSYLEAL RVAAQVAPGL FREILTLGRE RFAVDKQSYH ISAALARVSE  420
ADTLTDDELP RLLDDDDARQ VLHVTFGSAL DRYRAPLLRV LEAHDEAYQA GLAAHFAKHL  480
TPFAEVAP                                                            488

SEQ ID NO: 330          moltype = AA  length = 485
FEATURE                 Location/Qualifiers
source                  1..485
                        mol_type = protein
                        organism = Dictyoglomus turgidum
SEQUENCE: 330
MLKLLNESLK PLSIFIYSES LRKINDDLYI FVAKIKDLKK IGIVKQNQIL YFSSPYFSED  60
KKIEGTNFLV NLYPLNFENY QKLKEIIPIS PKVCDKKISF GTGDRLGLIT SAQLSALKEY  120
DLFPILAQQS PRELIKTKRD FKDVLLKSAM GVLETGYTGK YGADADHIKD EKYLMEAIDA  180
GYTMYTLDIS DFIEKIKDLS EKALKEKYEK VSSFSKKIID KYAGKRVKIS DEEYFELSYN  240
ELCKSAIVYE KALSFVEMVY EILKSKLSEF DIEVSIDEGE RDTTPEDHFF VAQFLHDKGI  300
DFKSLAPKFP GEFQKGIDYI GDIKEFERAL KKHYALTKAL EGYRLSLHSG SDKFSIYKIF  360
```

```
YKITEGNFHI KTSGTSWLEA VKVIAKFFPD LFVELYQIAL ENLEESKKAY KVNITKEEFP  420
KEIKEDYMEF LHKDNVRQLF HISYGVLLDE KRKEIYDLLN QKEKEHYQYV SENIKKHLKN  480
LFEEE                                                             485

SEQ ID NO: 331         moltype = AA  length = 465
FEATURE                Location/Qualifiers
source                 1..465
                       mol_type = protein
                       organism = Caldilinea aerophila
SEQUENCE: 331
MNDAVYALGR SSRNGTLQLI VRGNSTGFHG EQQGDALICP LDAENARTLQ ERLPWLRPQP  60
LGNRLSFGFG DRIGLATPGH VDALRSADPT GRIAPIFAQQ SVRENQRLNR TPQEVMTAAV  120
WSLFAENWRL PWGADADHVK EPEHLAPYVA AGYTFYTIDP SDHVDNAAHT DDLAVLRSKC  180
EALPWDILET TYLSLCENYC GRTIVAEKTT LHFDKETLLR ALAKYGRALA HTVRIAAALR  240
TALGGTSFDL EMSVDETDTP TSAHEHFFIA NELLRRNIPL VSLAPRFVGK FQKGVDYMGN  300
LAEFEAELIR HVAVMRHFHC YKLSVHTGSD KFSIYPILAR CAGENVHIKT AGTSYLEALR  360
VAALRAPDLF RQMLETGRTC YEKDKKTYFL DCRPERVPPA ATLDDADLPN LLDQFDARQL  420
LHVTFGSILT THGAALRNLL ATYPNDYRSA LRDHFARHIQ PFVQA                 465

SEQ ID NO: 332         moltype = AA  length = 474
FEATURE                Location/Qualifiers
source                 1..474
                       mol_type = protein
                       organism = Thermoflexus hugenholtzii
SEQUENCE: 332
MMLSPEALAE GLRLYGLHLI VGSIRELPDG GAIFAARQGS ERRIGWIGET SPFPAPDPRM  60
SMRVQEHLVW IHPWTWAHYR ILRERLPALS PTRCDRPASF GAGDRLGMAT AAQIAALERY  120
PVFPVLAQQS PRELARTGRD FRSVLLDAAW GVFASGFAGP FGADADHLQD DEQLRAAAEA  180
GYSLYTFDLR RALARGPRPW EALSPLARSV VAELADRRVE APQGPRTLEE SALRAAACRY  240
EPALEEVVRG AEILRDQGID ADLEVSVDET EEETTPEAHA FIAVYLQRRG VALWSLAPRF  300
PGVFEKAVDY EGEVERFAQA AALHTAVART FGGHRLSLHS GSEKFRILPV FREATGGRFH  360
VKTSGTTWLQ AVRVVARAVP ALFAELYAIA RAHLEESRRD YPIALQPEAL PPALPDDPEA  420
ALADRAVRQL FHISYGVLLR ERGPAIRALL EAHEAEHFTA VRENLERHLE ALLK        474

SEQ ID NO: 333         moltype = AA  length = 483
FEATURE                Location/Qualifiers
source                 1..483
                       mol_type = protein
                       organism = Thermoanaerobacterium thermosaccharolyticum
SEQUENCE: 333
MIGNVLSTLE ENGFKVYPDS LRKLGENIYI FVVKRQNEKM VGILSSSDVK LNGAYFSEDK  60
NVSDKLRLNI YPFTFENYVT LNGKFHIGPT VCRGNSSFGT GDRLGLVTAA QLTALKKYDV  120
FPILAQQSPR ELIKTNRDFK DVLLKVVLGV LETGYIGHFG ADADHIKDEY YLLEGINAGY  180
TMYTLDLSEQ LIDISSLNPS EMRNKAQELS QVSKDIIKDF SGKKLDIISD SGYVVSEEEL  240
YKSAVAYENA MKFVDKVNNI LKEKLSDFDM EISIDEGGKV TTLEDHLYVA EYLHRNGIDF  300
FSIAPKFPGE FEKAVDYIGD LDEFLLELKK HYQLSRMIGG YKISLHSGSD KFSIYRIFSD  360
ITEKNFHIKT SGTSWLQAIN LIYNYDKEFY RELYKIALEN LEESKKSYKV LIKREDFCKE  420
PELNNPKFIL KPEIKQLFHI SFGVLLNLKR KEIVDFLNKY EEEHYKMVSK NIDNHLKEIF  480
YKN                                                               483

SEQ ID NO: 334         moltype = AA  length = 385
FEATURE                Location/Qualifiers
source                 1..385
                       mol_type = protein
                       organism = Petrotoga mobilis
SEQUENCE: 334
MFTILPKKGI SLGLGDRIGI ATPGHIKVAK KYNFFPVFAQ QSIRELNFTG RTFTDVRKDV  60
LNALVEENYV GNSGFDGDHL KSDEEIQYAL DSGITMLTLD CSEHMNKDSS IKDQIFEQFY  120
NKSFFVNDMP IEYSDKNELN KIVSIYASVI ERVIDVWNKF PKVNKKEVTF EVSVDETDVP  180
TDEKTHFLIS KYIYDEGVKI DTLAPRFPGE FQKAIDYIGN IQEFKKSLIK QDKIAKYFGY  240
RLSIHSGSDK FSIYPIIGEV TQGNYHLKTS GTSYLEAIKV VAQKDPEFFK KIWQTCLDKR  300
EEMDKYYHLS CDPFSVPKDL SPTEYLQNPD ARQTLHVSYM FVLNPQYDFR EKFFEILTKY  360
QNEYHENVAN HIEKHVKELK IEEKS                                       385

SEQ ID NO: 335         moltype = AA  length = 426
FEATURE                Location/Qualifiers
source                 1..426
                       mol_type = protein
                       organism = Spirochaeta thermophila
SEQUENCE: 335
MATPGSLSFP RYSIGTGDRF GHEAEAQLRA VIEAGRLGRA LGIVWNKSYR EHTIIGSRPE  60
DVRRMADRAV SSLGWEGPYF VDADHITTKT VDLFLDSADF FTIDVAEAIG KGEVSPQEEE  120
DLLASLGDLL NRELAIPGLS SPLAISEETA RGTIRAYWPA VREAARIYRR IEQGASRPFV  180
VEVSMDETDE PQRPPELLLI LAMIRKAGIP ARTIAPKFSG AFYKGVDYVG DPHTFAREFE  240
DDLCVVRYAR EQFALPEGLK LSVHSGSDKF SLYPLVREIL SRHPQEGVHL KTAGTTWLEE  300
VAGLAEAGGE ALALAKEIAL TCYSMIEELC APYAAVIDID PERLPSPGEI EEWSSGRFVE  360
ALEHDPSNPS YNRDFRQLIH VGYKVAAQMG ERFHQALEAH REVIAARVTR NLLERHIIPL  420
FPGDIP                                                            426
```

```
SEQ ID NO: 336         moltype = AA  length = 480
FEATURE                Location/Qualifiers
source                 1..480
                       mol_type = protein
                       organism = Thermofilum pendens
SEQUENCE: 336
MLHVYLGKIP RPGFGIRIPE VVAPPLLSAF KSLGMTGSLM LSFNRETAPA EYIESSDPRL  60
FYFGHTGTSI GGFIRSVKEY SKALSVPVEV EADHVSILGS VERALKKIAG VPVEEPLSEE  120
EVSWSIGYVE RELREAAEAG GVDFVTIDTC ELIDYSYDKV GAEEVAAAYE EVFDGDERRA  180
LEERYEGVHY FLGGDRVVAV RLSREDVARL AVKYRRSLDY AERIYRAARE AMGVELGFEV  240
AFDETPGVSE AREVFFYLSE LLRRGLRVDF IAPNVGFRKR EDYSGDLHAL YERLRNLHAV  300
VSSMNAYLSI HSGSGSHPYS DKGFGVWGVV GRATGGAVKY KMSGVLVQLL LEVMASYPPG  360
SETRRLYEEI YSEVVEHLRW VVKAKASLYS PELETLLKRY EAAQDRFDPR ADVFRHYFYV  420
FQALRDEGGA RRLRERLVEH YRENPGLRER YEKELRGLVE RLASQLGYAG NAYRYRVVYA  480

SEQ ID NO: 337         moltype = AA  length = 519
FEATURE                Location/Qualifiers
source                 1..519
                       mol_type = protein
                       organism = Rhodothermus marinus
SEQUENCE: 337
MVTVLQTLLQ RPRPLAEIDR AALARFLTDL IRQQVYPASL EPTSEGVFFL ARDGREKRLG  60
ILSEAGLHDF EGARHQLSLD GRTLIFQSCP LTAANARALR QHLAWTAPRP LGLRASVGCG  120
DRLGLATPGH VRAVRKHKLA PVFAQQSIRE MTRTGRTPQQ VLDEAMWGVF QEGWRQGYGA  180
DADHLKTEED ADRCIEAGFT FFTIDPSAYV DNEVDTADAA TLEAKVAALP WDALETTLAD  240
LRRAYLGQHF QVGPYELSFE ERTLLQALAK YGGAIAHTAR VYRHIAGRMG NRPFELEMSV  300
DETEVPTSPA EHFFVARELQ RLGVRWISLA PRFVGRLEKG VDYIGDLEEF EAHLKLHVAI  360
ARTLGPYKLS LHSGSDKFAL YPLFARHAGE LFHLKTAGTS YLEALRAVAE LDPPLFREIL  420
DFARDRYETD RATYHVSALL ERVPKASDVP DDALPALLEQ FDTRQVLHVT FGSVLTATDA  480
DGRPRFRDRL LAVLQENEET YYRLLEAHFD RHLAPFDAK                        519

SEQ ID NO: 338         moltype = AA  length = 485
FEATURE                Location/Qualifiers
source                 1..485
                       mol_type = protein
                       organism = Dictyoglomus thermophilum
SEQUENCE: 338
MLNLLEELLK PFSIFVYPQS LRKINEELYI FVAKINNTKN IGIIKQNQSI YFSNPYFSED  60
KKIEKTGFSV NIYPLNFENY QKLKEIIPIN PKTCNKKISF GTGDRLGLVT SAQLSVLKDY  120
NLFPILAQQS PRELIKTKRD FKDVLLKSVI GVLEIGYTDS YGADADHIKD EKYLMEAIDA  180
GYTMYTLDIS DFIERIENLT SKEIREKYEK ISSFSKKIIE KYAGKKIKIS NEEYFELSYD  240
ELCKSAIVYE KALSFVEMVY EILRSKLLEF DIEVSIDEGE RDTTPEDHFF VVQFLHEKGI  300
DFKSLAPKFP GEFQKGIDYI GDIKKFENEL KKQYALTKAL EGYRLSLHSG SDKFSIYKSF  360
YKITEGNFHI KTSGTSWLEA VKTIARYSPD LFLELYHIAL ENLEESKKAY KVSITKEEFP  420
KEIKEDYIEF LKKPNVRQLF HISYGVLLDE KREEIYEILN KNEKEHYQYV SENIRKHLKN  480
LFEEE                                                             485

SEQ ID NO: 339         moltype = AA  length = 483
FEATURE                Location/Qualifiers
source                 1..483
                       mol_type = protein
                       organism = Thermoanaerobacter siderophilus
SEQUENCE: 339
MKEELSDYLL KNSFLLYPDS FRRLREDVYI FVAKKDSDKK IGLLTNGNFK LSSPHFAEDK  60
YVEELGFYIN LYPLTYENYL ILKDNFGISP VTCKEKASFG TGDRLGLATP AHIKALKNYN  120
VFPVLAQQSP RELVKTHRDF KDVFLKVILG VLEAGYAGGY GADADHIKDE KYLIEAIDAG  180
YTMYTLDLSD LLVKISDMPK SQLKEKAQSL SSQSREIIDR FKGKKFSIST DEDFAVSEDE  240
LYKSALTYEK AMKFVEKVYG ILKDRLQHFD LEISIDEGEK DTTVEDHIFV AEYLHRKGID  300
FWSLAPKFPG EFQKAIDYKG DIKKFTSGLK KHYFLSKKLG GYKLSLHSGS DKFSIYKIFN  360
EITEGNFHIK TSGTSWLQAI NIIFERDKDL FNDLYKIALD NLEESKKAYK VLIDRDDFPQ  420
TIQTEDSQIL LKPEIKQLFH ISYGVLLDER RKEIYEVLNK YEEEHYEFVS KNIENHLKEI  480
FNI                                                               483

SEQ ID NO: 340         moltype = AA  length = 482
FEATURE                Location/Qualifiers
source                 1..482
                       mol_type = protein
                       organism = Thermoanaerobacter mathranii
SEQUENCE: 340
MVEKSILEKL TDFLLNHSFV LYPNSLRKLK EDTYIFVAKK DADKKIGILT KENFKLTSPY  60
FVEDKNVKEI DFYLNLYPLS FENYLILKNF GISPTPCRQK SSFGTGDRLG LVTPAHIVAL  120
KEYPVFPVLA QQSPRELEKT HRDFKDALLK VILGVLEAGY TGEFGADADH IKDEKYLLRA  180
IEAGYTMYTL DVSELLTKIL DISSNQVMQI SPQSKEIIEA FKGKKISISE EEYTIREDEL  240
YKSALIYEKA MNFVEKVYSI LKEKVKDFDL EISIDEGEKD TTVEDHIFVA EYLHKKGIDF  300
WSLAPKFPGE FQKAIDYKGD INKFAVELKK HYAISQQLGG YKLSLHSGSD KFSIYEIFSE  360
VTQHSFHIKT SGTSWLQAVN LIFEKNKKLF YELYKIALNN LEESKKAYKV LIDKDDFAEE  420
PNLENVQILS QPEIKQLFHI SYGVLLDEKK EEIYDVLDKY EEEHYQFVSA NIKNHLGKIF  480
NN                                                                482
```

```
SEQ ID NO: 341          moltype = AA  length = 482
FEATURE                 Location/Qualifiers
source                  1..482
                        mol_type = protein
                        organism = Thermoanaerobacter italicus
SEQUENCE: 341
MVEKGILEKL TDFLLNHSFV LYPNSLRKLK EDTYIFVAKK DADKKIGILT KENFKLSSPY  60
FVEDKNVKEI DFYLNLYPLS FENYLILKNF GISPTPCRQK SSFGTGDRLG LVTPAHIVAL  120
KEYPVFPVLV QQSPRELEKT RRDFKDALLK VILGVLEAGY TGEFGADADH IKDEKYLLRA  180
IEAGYTMYTL DVSELLTKIS DISSNQVMQI SPQSKEIIEA FKGKKISISE EEYTIREDEL  240
YKSALIYEKA MNFVEKVYSI LKEKVKDFDL EISIDEGEKD TTVEDHIFVA EYLHKKGIDF  300
WSLAPKFPGE FQKAIDYKGD INKFAVELKK HYAISQQFGG YKLSLHSGSD KFSIYEIFSE  360
VTQHSFHIKT SGTSWLQAVN LIFEKDKKLF YELYKIALNN LEESKKAYKV LIDKDDFAEE  420
PNLENAQILS QPEIKQLFHI SYGVLLDEKK EEIYDVLDKY EEEHYQFVSA NIKNHLEKIF  480
NK                                                                482

SEQ ID NO: 342          moltype = AA  length = 483
FEATURE                 Location/Qualifiers
source                  1..483
                        mol_type = protein
                        organism = Thermoanaerobacterium thermosaccharolyticum
SEQUENCE: 342
MIGNVLSTLE ENGFKVYPDS LRKLGENIYI FVVKRQNEKM VGILSSSDVK LNGAYFSEDK  60
NVSDKLRLNI YPFTFENYVT LNGKFHIGPT VCRGNSSFGT GDRLGLVTAA QLTALKKYDV  120
FPILAQQSPR ELIKTNRDFK DVLLKVVLGV LETGYIGHFG ADADHIKDEY YLLEGINAGY  180
TMYTLDLSEQ LIDISSLNPS EMRNKAQELS QVSKDIIKDF SGKKLDIISD SGYVVSEEEL  240
YKSAVAYENS MKFVDKVNNI LKEKLSDFDM EISIDEGGKV TTLEDHLYVA EYLHRSGIDF  300
FSIAPKFPGE FEKAVDYIGD LDEFSLELKK HYQLSRMIGG YKISLHSGSD KFSIYRIFSD  360
ITEKNFHIKT SGTSWLQAIN LIYNYDKEFY RELYKIALEN LEESKKSYKV LIKREDFCKE  420
PELNNPNFIL KPEIKQLFHI SFGVLLDLKR KEMVDFLNKY EEEHYKMVSK NIDNHLKEIF  480
YKN                                                               483

SEQ ID NO: 343          moltype = AA  length = 483
FEATURE                 Location/Qualifiers
source                  1..483
                        mol_type = protein
                        organism = Thermoanaerobacterium thermosaccharolyticum
SEQUENCE: 343
MIGNVLSTLE ENGFKVYPDS LRKLGENIYI FVVKRQNEKM VGILSSSDVK LNGAYFSEDK  60
NVSDKLRLNI YPFTFENYVT LNGKFHIGPT VCRGNSSFGT GDRLGLVTAA QLTALKKYDV  120
FPILAQQSPR ELIKTNRDFK DVLLKVVLGV LETGYIGHFG ADADHIKDEY YLLEGINAGY  180
TMYTLDLSEQ LIDISSLNAS EMRNKAQELS QVSKDIIKDF SGKKLDIISD SGYVVSEEEL  240
YKSAVAYENA MKFVDKVNNI LKEKLSDFDM EISIDEGGKV TTLEDHLYVA EYLHRNGIDF  300
FSIAPKFPGE FEKAVDYIGD LDEFLLELKK HYQLSRMIGG YKISLHSGSD KFSIYRIFSD  360
ITEKNFHIKT SGTSWLQAIN LIYNYDKEFY RELYKIALEN LEESKKSYKV LIKREDFCKE  420
PELNNPKFIL KPEIKQLFHI SFGVLLNLKR KEIVDFLNKY EEEHYKMVSK NIDNHLKEIF  480
YKN                                                               483

SEQ ID NO: 344          moltype = AA  length = 483
FEATURE                 Location/Qualifiers
source                  1..483
                        mol_type = protein
                        organism = Thermoanaerobacterium thermosaccharolyticum
SEQUENCE: 344
MIGNVLSTLE ENGFKVYPDS LMKLGENIYI FVVKRQNEKM VGILSSSDVK LNGAYFSEDK  60
NVSDKLRLNI YPFTFENYVT LNGKFHIGPT VCRGNSSFGT GDRLGLVTAA QLTALKKYDV  120
FPILAQQSPR ELIKTNRDFK DVLLKVVLGV LETGYIGHFG ADADHIKDEY YLLEGINAGY  180
TMYTLDLSEQ LIDISSLNPS EMRNKAQELS QVSKDIIKDF SGKKLDIISD SGYVVSEEEL  240
YKSAVAYENA MKFVDKVNNI LKEKLSDFDM EISIDEGGKV TTLEDHLYVA EYLHRNGIDF  300
FSIAPKFPGE FEKAVDYIGD LDEFLLELKK HYQLSRMIGG YKISLHSGSD KFSIYRIFSD  360
ITEKNFHIKT SGTSWLQAIN LIYDYDKEFY RELYKIALEN LEESKKSYKV LIKKEDFGKE  420
PELNNPKFIL KPEIKQLFHI SFGVLLDLKR KEIVDFLNKY EEEHYKMVSK NIDNHLKEIF  480
YKN                                                               483

SEQ ID NO: 345          moltype = AA  length = 483
FEATURE                 Location/Qualifiers
source                  1..483
                        mol_type = protein
                        organism = Thermoanaerobacterium thermosaccharolyticum
SEQUENCE: 345
MIGNVLSTLE ENGFKVYPDS LRKLGENIYI FVVKRQNEKM VGILSSSDVK LNGAYFSEDK  60
NVSDKLRLNI YPFTFENYVT LNGKFHIGPT VCRGNSSFGT GDRLGLVTAA QLTALKKYDV  120
FPILAQQSPR ELIKTNRDFK DVLLKVVLGV LETGYIGHFG ADADHIKDEY NLLEGINAGY  180
TMYTLDLSEQ LIDISSLNAS EMRNKAQELS QVSKDIIKDF SGKKLDIISD SGYVVSEEEL  240
YKSAVAYENA MKFVDKVNNI LKEKLSDFDM EISIDEGGKV TTLEDHLYVA EYLHRNGIDF  300
FSIAPKFPGE FEKAVDYIGD LDEFLLELKK HYQLSRMIGG YKISLHSGSD KFSIYRIFSD  360
ITEKNFHIKT SGTSWLQAVN LIYKFDKEFY RKLYKIALSN LEESKKSYKV LIKKDDFKDE  420
PELDNPEFTL RPEIKQLFHI SFGVLLDLKG KEIKDMLNDY EEEHYKMVSD NIENHLKEIY  480
YEK                                                               483
```

```
SEQ ID NO: 346          moltype = AA  length = 482
FEATURE                 Location/Qualifiers
source                  1..482
                        mol_type = protein
                        organism = Thermoanaerobacterium xylanolyticum
SEQUENCE: 346
MVGNVSSVLK ESGFQIYPDS LRKLGENTYI FVVKKQKEKM IGILSNDELK LKEPYFSENK  60
KISDNLQFNV YSFTFDNYVT LNGRFHIGPT ICRENASFGT GDRLGLATAA QLDALKKFNV  120
FPILAQQSPR ELVKTNRDFK DVLLKVVLGV LETGYIGHYG ADADHIKDEK YLLEGIDAGY  180
TMYTLDLSEQ LFDVSGATSL EIKEKAKTLS DVSRKIVEDF SGKSLNVGFG GHLVSEDELL  240
KSAVAYEAAM KFVEKVNDIL KEKLNDFDLE ISIDEGGKVT TLEDHLFVAE YLHRNGIDFF  300
SIAPKFPGEF EKAIDYVGDV NEFERELKKH YDLTKLIGGY KLSLHSGSDK FSIYKIFSQT  360
TEKNFHIKTS GTSWLQAVNL IYKSDKEFYR ELYKIALSNL EESKKSYKVL IKKDDFKDEP  420
ELDNSEFIIR PEIKQLFHIS FGVLLDLKGK EIKDMLYDYE EEHYKMVSDN IENHLKEIFY  480
EK                                                                482

SEQ ID NO: 347          moltype = AA  length = 386
FEATURE                 Location/Qualifiers
source                  1..386
                        mol_type = protein
                        organism = Petrotoga mobilis
SEQUENCE: 347
MLTILPNKGI SLGLGDRIGI ATHGHIKVAK KYNFFPVFAQ QSIRELNFTG RTFSDVRKDV  60
LNALIEENYV GNSGFDGDHL KSDEEIQYAL DSGITMLTLD CSEHMNNKDS SIKERIFDQF  120
YNKSFFVNDM PIEYSNKNEL NKIVSIYAGV IERVIDVWNK FPKVNKKEVT FEVSVDETDV  180
PTDEKTHFLI SKYIYDEGVK IDTLAPRFPG EFQKAIDYIG NLQEFKKSLI KQDKIAKYFG  240
YRLSIHSGSD KFSIYPIIGE VTQGNYHLKT SGTSYLEAIK IVAQKDPEFF KKIWKTCLDK  300
REEMDKYYHL SCDPFSVPKN LSPTEYLQNP DARQTLHVSY MFVLNPQYDF REKFFEILTK  360
YQNEYHQNVA NHIEKHVKEL KVEEKS                                      386

SEQ ID NO: 348          moltype = AA  length = 482
FEATURE                 Location/Qualifiers
source                  1..482
                        mol_type = protein
                        organism = Thermoanaerobacterium saccharolyticum
SEQUENCE: 348
MVGNVSAVLK ENGFKIYPDS LRKLGESTYI FVVKKQKEKM IGILSNDELN LKEPYFSENK  60
KISDNLQFNV YPFTFDNYVT LNGRFHIGPT VCRENASFGT GDRLGMATAA QLGALKKFDV  120
FPVLAQQSPR ELVKTNRDFK DVLLKVVLGV LETGYIGHYG ADADHIKDEK YLLEGIDAGY  180
TMYTLDLSEQ LFDISGATPS AIKEKAEALS DVSKKIVEDF SGQSLNVGLE GHLVSEDELL  240
KSAIAYEGAM KFVEKVNDIL KEKLNDFDLE ISIDEGGKVT TLEDHLFVAE YLHRNGIDFF  300
SIAPKFPGEF EKAIDYVGDV DEFKKALKKH YDLTKLIGGY KLSLHSGSDK FSIYKIFSQT  360
TERNFHIKTS GTSWLQAVNL IYKSDREFYR ELYKIALSNL EESKKSYKVL IKKDDFKDEP  420
ELDNPEFIVR PEIKQLFHIS FGVLLDLKGK EIKDMLYEHE EEHYKMVSNN IENHLKEIYY  480
EK                                                                482

SEQ ID NO: 349          moltype = AA  length = 390
FEATURE                 Location/Qualifiers
source                  1..390
                        mol_type = protein
                        organism = Petrotoga mobilis
SEQUENCE: 349
MFTILPKRGI SLGLGDRIGI ATTGHIKVAK KYNFFPVFAQ QSIRELNFTG RTFIDVRKDA  60
LNALVEENYV GNSGFDGDHL KSDEEIQYAL DSGITMLTLD CSEHMNKDSS IKDQIFEQFY  120
NKSFFVNDMP IEYSDKNELN KIVSIYASVI ERVIDVWNKF PKVNKKEVTF EVSVDETDVP  180
TDEKTHFLIS KYIYDEGVKI DTLAPRFPGE FQKGIDYIGN IQEFKKSLIK QDKIAKYFGY  240
RLSIHSGSDK FSIYPIIGEV TQGNYHLKTS GTSYLEAIKV VAQKDPEFFK KIWQTCLDKR  300
EEMDKYYHLS CDPFSVPKDL SPTEYLKNPD ARQTLHVSYM FVLNPQYDFR EKFIEILTKY  360
QNEYHQNAAN HIEKHVKELK VEEKIHKQKN                                  390

SEQ ID NO: 350          moltype = AA  length = 426
FEATURE                 Location/Qualifiers
source                  1..426
                        mol_type = protein
                        organism = Spirochaeta thermophila
SEQUENCE: 350
MTTPGSLSLP RYSIGTGDRF GHEAEAQLRA VIEAERLGMA LGIVWNKSYR EHTIIGSRPE  60
DVRRMADKAV SALEWEGPYF VDADHITTKT VELFLDSSDF FTIDVAEAIG QEEISPQEEE  120
DLLSSLDDLL NRELAIPGLS NPLTISEETA RETIRAYWPA VREAARIHQR IEKGTSRPFV  180
VEVSMDETAD PQRPPELLLI LAMIRKAGIP ARTIAPKFSG SFYKGVDYVG DPEVFAREFE  240
DDLCVVRYAR EAFRLPEGLK LSVHSGSDKF SLYPLIKDIL SRHPQEGVHL KTAGTTWLEE  300
VTGLAESGGE ALALAKEIAL TCYSMIEELC APYAAVIDIN PDRLPSPGEI EDWSSGRFVE  360
ALEHDPSNPS YNRDFRQLIH VGYKVAAQMG ERFHEALEAH REVIAARVTR NLLERHIIPL  420
FPGGAA                                                            426

SEQ ID NO: 351          moltype = AA  length = 256
FEATURE                 Location/Qualifiers
source                  1..256
```

```
                         mol_type = protein
                         organism = Ignisphaera aggregans
SEQUENCE: 351
MRAKELFGED VSIEIALDES PSETQLKELF FYINELLYKG LRFEFIAPNI GFRKREDYRG  60
DLQELYNRVR KLHTIASNNG VYLSIHSGSG AHPYSDKGVG VWSTIGRATD GLVKYKMSGV  120
LIQLLLEVMS RFPKGSTVRR VYEEIYDAVL DHLKKDISRG RGLASETLRK MIEDYEEHSN  180
KYDVRADVFR HYFFVFQCIR DDSGVRYLRN RVIELFNEVK ELRDRYREEV ANLITREAEA  240
LGYINSVIRY RKYEYS                                                  256

SEQ ID NO: 352           moltype = AA  length = 481
FEATURE                  Location/Qualifiers
source                   1..481
                         mol_type = protein
                         organism = Thermotoga maritima
SEQUENCE: 352
MVLKVFKDHF GRGYEVYEKS YREKDSLSFF LTKEEEGKIL VVAGEKAPEG LSFFKKQRAE  60
GVSFFFCERN HENLEVLRKY FPDLKPVRAG LRASFGTGDR LGITTPAHVR ALKDSGLFPI  120
FAQQSVRENE RTGRTWRDVL DDATWGVFQE GYSEGFGADA DHVKRPEDLV SAAREGFTMF  180
TIDPSDHVRN LSKLTEKERN EKFEEILRKE RIDRIYLGKK YSVLGEKIEF DEKNLRDAAL  240
VYYDAIAHVD MMYQILKDET PDFDFEVSVD ETETPTSPLF HIFVVEELRR RGVEFTNLAL  300
RFIGEWEKGI DYKGDLAQFE REIKMHAEIA RMFEGYKISL HSGSDKFSVY PAFASATGGL  360
FHVKTAGTSY LEAVKVISMV NPELFREIYR CTLDHFEEDR KSYHISADLS KVPEVEKVKD  420
EDLPGLFEDI NVRQLIHVTY GSVLKDASLK ERLFKTLEQN EELFYETVAK HIKRHVDLLE  480
G                                                                  481

SEQ ID NO: 353           moltype = AA  length = 483
FEATURE                  Location/Qualifiers
source                   1..483
                         mol_type = protein
                         organism = Caldanaerobacter subterraneus
SEQUENCE: 353
MINKVAEYLS GEGFYFYEKS FRKLSEDIYI FVVKKANEKS IGLLTQGDFT LSSPHFTERK  60
YLKETGYYLN LYPLTYENFV ILKDKFNIAP APCDKKASFG MGDRLGLVTA AHIRAVENYD  120
VFPVLAQQSP RELMKTHRSF KEAILKAILG VLEEGYTGKF GADADHIKDE NYLMEAIDAG  180
YTMYTLDLSD MLVKLSDYTE SQLKEKAEKL NITSKRIIER FKGKKFVMPT KEAFTVSEEE  240
LYKSALTYEK AMDFVEKVYG ILKDKVKNFD LEISIDEGDK DTTVEDHIFV AEYLHEKGID  300
FWSLAPKFPG EFQKAIDYIG DVDKFAVELK KHQFLSREFG GYKLSLHSGS DKFSIYKVFS  360
EITEGEFHIK TSGTSWFQAV NLIFEKDKEL FKELYQIALY NLEESKKAYK VLIDKKDFPE  420
NINLEDSQIV SKPEIKQLFH ISYGVLLEER KKQIFEVLNK YEEEHYEFVR KNIENHFKEI  480
FSK                                                                483

SEQ ID NO: 354           moltype = AA  length = 499
FEATURE                  Location/Qualifiers
source                   1..499
                         mol_type = protein
                         organism = Mesotoga infera
SEQUENCE: 354
MKENKVMNSF SAIYGNRYKV YEKSLKRKEK EFFFVIKDFQ RKYLVAAGPS YRIRKRDFQP  60
DEEGVADNEG EFLFQICRLT HHNLTQLQSI FNYLQPSTTK MKPSFGTGDR LGIATPAHIQ  120
AFEDKNIFPI LAQQSVREME RTESNWQKVL DNAIWGCFEA GYEGKFGADA DHVKDLKNLK  180
EAIDCGFTFY TIDPSDHIDA NILKLDKDEL RNKYQQLPEK DALENSYLNK EYQIGSQKLT  240
FTQDILIEIV LTYLEAIKHV EKCYKFLKDS HKGDFELEVS VDETPTPTSP LAHLWIASEL  300
QRRGVDFQNL APHFIGDWEK GIDYIGNIDT FKEEFKLHCQ IASQMGGYKL SLHSGSDKFS  360
VYPIFAEETN GYFHVKTAGT SWLEAVKAIV VCDPALYREM YEFALKCFEK DSFSYLLSTD  420
LQKIPNIKEL QDKELIQLFS NNNARQLIHI TYGSILREKD SQNRYKFRDR IYKVLFENED  480
IHYENVSKHI RHHLGLLSV                                               499

SEQ ID NO: 355           moltype = AA  length = 502
FEATURE                  Location/Qualifiers
source                   1..502
                         mol_type = protein
                         organism = Thermosinus carboxydivorans
SEQUENCE: 355
MQSREELKRA ILSEFGDYNI YSESIYRAGG CVLFLAKDMG QKLLVVVEEE TGSAFDRFVG  60
PQVYHPSGKR VKEAPLQPVN AGIVRELLPF TAPVALGATG LSLGLGDRLG VASPGHLRLI  120
KKTGVRPVLA QQSVRELTLT NRTYSDVLDA ATWAVLQEGY EGGFGADGDH LKTAEEIKGA  180
LDLGFTMITL DASAHIDNTV GQKAAKQVAE LYHTLPADYT ADMEEHYLGK AFIVGGMAIT  240
FDTETLQRLV LTYGKALAFM GYIYHTLIVN AGREVDFEIS IDETATPTTP AAHYFVASEL  300
GRMGVKFTSL APRFCGEFQK GIDYIGDLYQ FEDEFKRHAA IADHFGYRLS IHSGSDKFSV  360
FPIIGQYTRG RVHIKTAGTN WLEALRVVAR INPALFREIY AFAGEVFGEA KKYYHVTTDL  420
TRLPDVAAMA DDGLPTVLDH NDARQMLHIT YGLVLTAANA DGSYRFKDAL YELLFDHEDE  480
YYAALERHIG RHLEKLTENL KG                                           502

SEQ ID NO: 356           moltype = AA  length = 507
FEATURE                  Location/Qualifiers
source                   1..507
                         mol_type = protein
                         organism = Halanaerobium congolense
SEQUENCE: 356
```

```
MSWKDFAEEL VGTSKEAVMK VAEYAEDYRI YPRSIIKKDK SFYFLAKIDQ KKKLVILNKS  60
KNFELFQGRI EELAGFKAKI GPLSHYNAEI LREVFPFTAP SALGNKKPSI GLGDRLGIAT  120
PGHIEAVKES AAMPVFAQQS VRELNLTGRT FKSVLDDVSW AVFQEGYQAG FAADADHLKE  180
KPDIKEALDL GYTMLTLDCT DYINDDLDQM SESEIENAYA EVPDYLREGL ENQYLNKTFV  240
LNSGYQLEYN QDNFKEIVLI YYKMLDFAKE IQHLIKTSAR NVDFEISIDE TSTPTTPEAH  300
FFVANELKRN NIEVNSLAPR FVGEFQKGID YIGDLEQFEK EFKVHADIAD RFGYKLSIHS  360
GSDKFSVFPI IGRHTQGRVH VKTAGTNWLE AIRVVAENNP SLYRDIHAYA LKKFEAAKEY  420
YHVTTDLDKV PELARMSDQE LGELLEINEV RQLLHITYGF ILQDKKDGRY IFRDKLYKFW  480
DEYDKEYRRA LERHIGRHLN KLGFYKN                                    507

SEQ ID NO: 357         moltype = AA  length = 507
FEATURE                Location/Qualifiers
source                 1..507
                       mol_type = protein
                       organism = Halanaerobium congolense
SEQUENCE: 357
MSWKDFAEEL VGTSKEAVMK VAEYAEDYRI YPRSIIKKDK SFYFLAKIDQ KKKLVILNKS  60
KNFELFQGRI EELAGFKAKI GPLSHYNAEI LRKVFPFTAP SALGNKKPSI GLGDRLGIAT  120
PGHIEAVKES AAMPVFAQQS VRELNLTGRT FKSVLDDVSW AVFQEGYQAG FAADADHLKE  180
KPDIKEALDL GYTMLTLDCT DYINDDLDQM SESEVENAYA EVPDYLREGL ENQYLNKTFV  240
LNSGYQLEYN QDNFKEIVLI YYKMLDFAKE IQHLIKTSAR NVDFEISIDE TSTPTTPEAH  300
FFVANELKRN NIEVNSLAPR FVGEFQKGID YIGDLEQFEK EFKVHADIAD RFGYKLSIHS  360
GSDKFSVFPI IGRHTQGRVH VKTAGTNWLE AIRVVAENNP SLYRDIHAYA LKKFEAAKEY  420
YHVTTDLDKV PELARMSDQE LGELLEINEV RQLLHITYGF ILQDKKDGRY IFRDKLYKFW  480
DEYDKEYRRA LERHIGRHLN KLGFYKN                                    507

SEQ ID NO: 358         moltype = AA  length = 507
FEATURE                Location/Qualifiers
source                 1..507
                       mol_type = protein
                       organism = Halanaerobium saccharolyticum
SEQUENCE: 358
MSWKDFAEEL VGTSKDAVKK VAEYAEDYRI YPRSIIKKEK SFYFLAKIDQ KKKLVILNKS  60
KNFDIFQGKT EKLAGFKAKI APLSHYNAEI IREVFPFTAP SKIGNQTASI GLGDRLGIAT  120
PGHIEAVKKS NAMPVFAQQS VKELKLTGRS FKSVLDDVSW AVFQEGYQNG FGADADRLKE  180
KPEIKEALDL GYTMLTLDCT DYINDNFDQT AESDIESAYA EVPDYLRDGL ESKYLNKTFV  240
LNSGYQLEYN KVNFKKIVLS YYQILDFVKE IQHLIKRSAR DVDLEISIAD SLNSTSPEAH  300
FFVANEFKRN NIEVNSLALN FVGEFQKGID YIGDLEKFEK DFEIHADIAD RFGYKLSIHS  360
GSDKFSIFPI IGRQTEGRAH IKTAGTNWLE AIRVVAENDP SLYREIHSYA LKKFEEAKEF  420
YQVNTDLSKV PELAVMSDQE LGELLEIDAV RQLLHITYGF ILQDKKDGRY IFRDRLYKLL  480
DEYDKDYRSG LERHIGRHLN KLGFYKN                                    507

SEQ ID NO: 359         moltype = AA  length = 504
FEATURE                Location/Qualifiers
source                 1..504
                       mol_type = protein
                       organism = Gracilibacillus halophilus
SEQUENCE: 359
MVKHFESVLE ELSQRKVPTS TEEVTVYTPS FEEHAGSQVV MVKSGTEKMI VAAGAGELFE  60
ALSGEDIGKG KVCPLTHENR LVLNQFFSYT APQAFGTDIA TMGLGDRLGI ASPGHIDTVK  120
ERNVKPILAQ QSIRELTLLN RTMTDILDAA AFAVFQEGYK DGYGADADHI KLESDIEHAL  180
QLGFSFLTLD CSEQIRNDVE SQTSDEIQNE FASLSDEKRA YFSNYYLDQT FNVHERQISF  240
DQANLAKNVL VYGEAIDFME HVYHTYLQSL DRDVDFEISI DETETVTSPE AHFFVAEELR  300
RRGVKVESLA PRFCGEFQKG IDYIGDMDQF EKELKEHADI AKHFGYKLSI HSGSDKFSVF  360
PIIGKYTDGL LHIKTAGTNW LEAVRVVAQE NPDLYRRMHV YAEEHFEETL KYYHVTPDLD  420
SVTPLKEQPD DQLPEYMNHD AARQLFHVTY GILLTAKDDA GNDLFRDEFF DTLLNKEDAY  480
RQALAHHIGR HLDLLGLSKK VGIE                                       504

SEQ ID NO: 360         moltype = AA  length = 483
FEATURE                Location/Qualifiers
source                 1..483
                       mol_type = protein
                       organism = Caldanaerobacter subterraneus
SEQUENCE: 360
MINKVAEYLS REGFHFYEKS FRKFSEDIYI FVVKKANEKS IGLLTQRDFT LSSPYFTERK  60
YLKEIGYYLN LYPLTYENFV ILKDKFSIAP SPCNKKVSFG MGDRLGLVTA AHIRAVQNYD  120
VFPVLAQQSP RELMKTHRSF REAILKAILG VLEEGYTGKF GADADHIKDE NYLMEAIDAG  180
YTMYTLDLSD MLVKLSDYTE SQLKEKAEKL NITSKRIIEK FKGKKFVMPT EEAFTVSEEE  240
LYKSALTYEK AMDFVEKVYG ILKDKVKNFD LEISIDEGDK DTTVEDHIFV AEYLHEKGID  300
FWSLAPKFPG EFQKAIDYIG DVDKFAVELK KHQFLSREFG GYKLSLHSGS DKFSIYKVFS  360
EITEREFHIK TSGTSWLQAV NLIFEKDKKL FKELYQIALY NLEESKKAYK VLIDKKDFPE  420
NINLEDSQIV SKPEIKQLFH ISYGVLLEER KKQIFEVLNK YEEEHYEFVR KNIENHFKEI  480
FSK                                                              483

SEQ ID NO: 361         moltype = AA  length = 418
FEATURE                Location/Qualifiers
source                 1..418
                       mol_type = protein
                       organism = Litorilinea aerophila
```

```
SEQUENCE: 361
MLPYLVARPL GLRKSAGCGD RLGLATPGHI RALRATFGRD EDAAMAPIFA QQSIRENART  60
GRTPQEVMDD AMWGVFQEGW RAGFGADADH LKTLADVDIC AAAGYTFYTV DPGDHVDDEA  120
NTAAFPALEA RVDALPWDVL DSSPADLAAR LADRPIDLGT LKVTLDRETL WRAAAKYGRA  180
VAHTVTMYRH LAGAMGERPF ELEMSVDETA TVTSLAEHVY IAAELQRLGV RCVSLAPRYV  240
GTFEKGVDYI GDLDAFEQSI AQHMAVSRTF GPYKLSLHSG SDKFSIYPIA SRVAGDLVHL  300
KTAGTSYLEA LRAIAAMAPD LFRQIVAFAR ERYPTDRASY HVSAELEKMP DIAGWPDDRL  360
PELLNDFHAR EILHVTFGSV LNHPPFREPF FTALRTHEET YSEMLERHFC RHFAPFAG    418

SEQ ID NO: 362          moltype = AA  length = 483
FEATURE                 Location/Qualifiers
source                  1..483
                        mol_type = protein
                        organism = Caldanaerobacter subterraneus
SEQUENCE: 362
MINKVAEYLS REGFYFYEKS FRKFSEDIYI FVVKKANEKS IGLLTQGDFT LSSPYFTERK  60
YLKEIGYYLN LYPLTYENFV ILKDKFSIAP SPCNKKVSFG MGDRLGLVTA AHIRAVENYD  120
VFPVLAQQSP RELMKTHRSF KEAILKAILG VLEEGYTGKF GADADHIKDE NYLMEAIDAG  180
YTMYTLDLSD MLVKLSDYTE SQLKEKAEKL NITSKRIIER FKGKKFVMPT KEAFTVSEEE  240
LYKSALTYEK AMDFVEKVYG ILKDKVKNFD LEISIDEGDK DTTVEDHIFV AEYLHEKGID  300
FWSLAPKFPG EFQKAIDYIG DVDKFAVELK KHQFLSREFG GYKLSLHSGS DKFSIYKVFS  360
EITEGEFHIK TSGTSWLQAV NLIFEKDKEL FKELYQIALY NLEESKKAYK VLIDKKDFPE  420
NINLEDSQIV SKPEIKQLFH ISYGVLLEER KKQIFEVLNK YEEEHYEFVR KNIENHFKEI  480
FSK                                                               483

SEQ ID NO: 363          moltype = AA  length = 490
FEATURE                 Location/Qualifiers
source                  1..490
                        mol_type = protein
                        organism = Caldanaerobacter subterraneus
SEQUENCE: 363
MFERKIEMIN KVAEYLSREG FYFYEKSFRK FSEDIYIFVV KKANEKSIGL LTQGDFTLSS  60
PYFTERKYLK EIGYYLNLYP LTYENFVILK DKFSIAPSPC NKKVSFGMGD RLGLVTAAHI  120
RAVENYDVFP VLAQQSPREL MKTHRSFKEA ILKAILGVLE EGYTGKFGAD ADHIKDENYL  180
MEAIDAGYTM YTLDLSDMLV KLSDYTESQL KEKAEKLNIT SKRIIEKFKG KKFVMPTEEA  240
FTVSEEELYK SALTYEKAMD FVEKVYGILK DKVKNFDLEI SIDEGDKDTT VEDHIFVAEY  300
LHEKGIDFWS LAPKFPGEFQ KAIDYIGDVD KFAVELKKHQ FLSREFGGYK LSLHSGSDKF  360
SIYKVFSEIT EGEFHIKTSG TSWLQAVNLI FEKDKKLFKE LYQIALYNLE ESKKAYKVLI  420
DKKDFPENIN LEDSQIVSKP EIKQLFHISY GVLLEERKKQ IFEVLNKYEE EHYEFVRKNV  480
ENHFKEIFSK                                                        490

SEQ ID NO: 364          moltype = AA  length = 483
FEATURE                 Location/Qualifiers
source                  1..483
                        mol_type = protein
                        organism = Caldicoprobacter faecalis
SEQUENCE: 364
MGMMDKDVLN QLSSLLSRHS FVLYPNSVRN LAEDIYVFVA KGNADKKVGI LSKGKALGFK  60
APFFAEDIKV EATGFSFNLY PLSFENYLIL RDEFGIALVP CKNKASFGTG DRLGLATPAH  120
LDAFKSYNMF PVLAQQSPRE LEKTHRDFRD VLLKAVLGVL EAGYTGEFGA DADHIKDERY  180
LLEAADAGYT MYTLDVSEML VKGDVSPDKA DHLSQHSRDI IKDFSGKRIS FEGGEYTVKE  240
EELYRSAVIY EKAMNFVERV HGLLKERLKD FDLEVSIDEG DRDTTVEDHI FVAEYLHRRG  300
IDFWSLAPKF PGEFEKAVDY RGDIDKFTVE LNKHCAVARM LGGYRLSLHS GSDKFSVYRI  360
FNDATQHNFH IKTSGTSWLQ ALNVIHEKDR QLFKELYNIA LDNLEESKKA YKISIYRQDF  420
EEGLDLDNLH VLQNPKVKQL LHISYGVLLD EKRQEIYEVL NQHEAEHYRY VSDNIKKHLE  480
LLK                                                               483

SEQ ID NO: 365          moltype = AA  length = 483
FEATURE                 Location/Qualifiers
source                  1..483
                        mol_type = protein
                        organism = Thermoanaerobacter uzonensis
SEQUENCE: 365
MKEELSNYLL KNSFLLYPDS FRRLKEDVYI FVAKKDSDKK IGFLTNGNFK LSSPHFLEDK  60
YVEELGFYLN LYPLTYENYL ILKDNFGISP VTCKEKTSFG TGDRLGLVTP AHIKVLKNYD  120
IFPVLAQQSP RELVKTNRDF KDVLLKAILG VLEAGYAGGF GADADHIKDE KYLMEAIDAG  180
YTMYTLDLSD LLVKISDMPE SQLKEKAQSL SSQSREIIDR YKGKKFSIST DEDFVVSEDE  240
LYKSALTYEK AMKFVEKVYG ILKDRLQHFD LEISIDEGEK DTTVEDHIFV VEYLHRKGID  300
FWSLAPKFPG EFQKAIDYKG DIKKFTSELK KHYFLTKELG GYKLSLHSGS DKFSIYKIFN  360
EITEGNFHIK TSGTSWLQAI SLIFEKDKDL FNDLYKIALD NLEESKKAYK VLIDRDDFPQ  420
TIQTEDSQIL SKPEIKQLFH ISYGVLLDER RKEIYEVLNK YEEEHYEFVS KNIKNHLKEI  480
FNI                                                               483

SEQ ID NO: 366          moltype = AA  length = 533
FEATURE                 Location/Qualifiers
source                  1..533
                        mol_type = protein
                        organism = Lactobacillus ingluviei
SEQUENCE: 366
```

```
MDLNGLLKDV EEILAKVDAG EKVESLSDAG VYVPSVQVDR RNVYFIYHTK DEKDHTVKTL  60
VVYEENPTIG DFDALETLKG ENSTLITAAL TDHNNQALAK RFPWIKPTSR RNYKYTFGLG 120
DRLGNASNAH LRLFKGTGIM PVLAQQSIRE LTLMHRTNTD VLLSASWAVF EEGFTFGWGA 180
DGDHVKTEYE VDYAVKVGCS MITLDCTDVI NNDAVTMSDE ELDKTFNALD DDQKKYFNDT 240
YLDKTFDLGN GNSVHFTKHD VEESVLTFYG AILFAADIYK KFVVPYNLDF EISMDETPYQ 300
TTNPNHFFFG NELHKRGIVP TTMAPRFYGE FQKAIDYIGD KDRFEREFVL HEAIAEYFGY 360
KLSIHSGSDK LSVYEIIGRV AKNGWHVKTA GTNWLEALRV IAHKDPEFMV ELYKYAYEHL 420
DDVKDFYVFN AQTDGKAPKP ENVTVDNVVD VLSDDDGRQV LHTMYGSLMN LKHNYHYVFR 480
DKFWDILLKN QDLYDKYLNI HIAEHIDLLQ GKYKTKEEAL AALEPKTDIS KEY        533

SEQ ID NO: 367          moltype = AA  length = 390
FEATURE                 Location/Qualifiers
source                  1..390
                        mol_type = protein
                        organism = Petrotoga mexicana
SEQUENCE: 367
MFTILPKKGI SLGLGDRIGI ATTGHIKVAK KYNFFPVFAQ QSIRELNFTG RTFTDVRKDV  60
LNALIEENYV GNSGFDGDHL KSDEEIQYAL DSGITMLTLD CSEHMNKDSS IKDQIFEQFY 120
NKSFFVNDMP IEYSDKNELN EIVSIYASVI ERVIDVWNKF PKVNKKEVSF EVSVDETDVP 180
TDEKTHFLIS KYINDEGVKI DTLAPRFPGE FQKGIDYIGN VQEFKKSLIK QEKIAKYFGY 240
RLSIHSGSDK FSIYPIIGEV TQGNYHLKTS GTSFLEAIKV VAQKDPEFFK KIWQTCLDKR 300
EEMDKYYHLS CNPFSVPKDL SPTEYLKNPD ARQTLHVSYM FVLNPQYDFR EKFFEILTKY 360
QNEYHENVAN HIEKHVKELK IEETIHKQKK                                  390

SEQ ID NO: 368          moltype = AA  length = 386
FEATURE                 Location/Qualifiers
source                  1..386
                        mol_type = protein
                        organism = Defluviitoga tunisiensis
SEQUENCE: 368
MFSKLPKQGI SLGLGDRVGL ATPGHIKVAK RHEFFPVFAQ QSIRELNFTG RTFHDVKKDV  60
ENAVIKENYE GKSGFDGDHL KTDEEIKMAI DSGITMLTLD CSEYMGVVSK IKEKIYKGFY 120
GKTFKVKDLD LEYSQEELEK ILSIYSGVIE RIIYIWNNFP KVKNKDVSFE VSIDETNIPT 180
DEKTHFLLSK YLYDEGITID TLAPRFPGEF QKGIDYIGNI KEFKNSLMKH HKIASYFGYR 240
LSIHSGSDKF SIYPYVSQIT QGNYHLKTSG TSYLQALKII AQKAPDFFKE IWKTCLDKRT 300
EMDKYYHLSC DPFSVPKDLK PIEYLNNPDA RQTLHVSYMF VLNPKYDFRN RFFEILTKYE 360
NEYHIEVAEH IKRHVKELKI PEKIQN                                      386

SEQ ID NO: 369          moltype = AA  length = 385
FEATURE                 Location/Qualifiers
source                  1..385
                        mol_type = protein
                        organism = Petrotoga miotherma
SEQUENCE: 369
MFTILPKKGI SLGLGDRIGI ATPGHIKVAK KYNFFPVFAQ QSIRELNFTG RTFTDVRKDV  60
LNALVEENYV GNSGFDGDHL KSDEEIQYAL DSGITMLTLD CSEHMNKDSS IKDQIFEQFY 120
NKSFFVNDMP IEYSDKNELN KIVSIYASVI ERVIDVWNKF PKVNKKEVTF EVSVDETDVP 180
TDEKTHFLIS KYIYDEGVKI DTLAPRFPGE FQKAIDYIGN IQEFKKSLIK QNKIAKYFGY 240
RLSIHSGSDK FSIYPIIGEV TQGNYHLKTS GTSYLEAIKV VAQKDPEFFK KIWQTCLDKR 300
EEMDKYYHLS CDPFSVPKDL SPTEYLKNID ARQTLHVSYM FVLNPQYDFR EKFFEILTKY 360
QNEYYENVAN HIEKHVKELK IEETK                                       385

SEQ ID NO: 370          moltype = AA  length = 385
FEATURE                 Location/Qualifiers
source                  1..385
                        mol_type = protein
                        organism = Petrotoga olearia
SEQUENCE: 370
MFTILPKKGI SIGLGDRIGI ATPGHIKVAK KYNFFPVFAQ QSIRELNFTG RTFRDVRKDV  60
LNALVEENYV GNSGFDGDHL KSDEEIQYAL DSGITMLTLD CSEHMNKDSS VKESIFDQFY 120
NKSFFVNDMP IEYSDKNELN KIVSIYGGVI ERVIDVWNKF PKVNKKEVSF EVSVDETDVP 180
TDEKTHFLIS KYIYDEGVKI DTLAPRFPGE FQKGIDYIGN IQEFKKSLIK QDKIAKYFGY 240
RLSIHSGSDK FSIYPIIGEV TQGNYHLKTS GTSYLEAIKV IAQKDPEFFK KIWQTCLDKR 300
EEMDKYYHLS CDPFSVPKDL SPTEYLQNPD ARQTLHVSYM FVLNPQYDFR KKFFEILTKY 360
QNEYHENVAH HIEKHVKELK VEETK                                       385

SEQ ID NO: 371          moltype = AA  length = 418
FEATURE                 Location/Qualifiers
source                  1..418
                        mol_type = protein
                        organism = Thermophagus xiamenensis
SEQUENCE: 371
MKKLAKYSFG MGDRFAHQAS WQLKAITEIE KQGIEVTPVW NKSNREHTTI GSKPEDNRDA  60
AQKAIQKAGW SKPWYIDADH INLDTVDNFL ESSDFFTIDV ASYIGKKGDS KEEETFISKM 120
KPLIGNLNIP GVNSPFKITE QQLRNIAGQY LHAAFMAGET YKYIESVKGK GNFITEVSMD 180
EVPEPQTPVE LFFILAMLAH YGVPAQTIAP KFTGRFNKGV DYVGDIETFR KEYEANLMVI 240
DYAIQKFGFP PELKLSIHSG SDKFSIYPVI KELSQKHNKG FHLKTAGTTW LEEVIGLAMA 300
GGEALLFVKN IYSRALDNIE KLCAPYADVI DINTDNLPKL SEVNNWTGEE FANALRHVPD 360
HPMYNPDLRQ LIHVAYKLAA ENINQFNSFL EQHSEIVGKC VFENLYKRHA ERLFVFSN   418
```

```
SEQ ID NO: 372         moltype = AA  length = 416
FEATURE                Location/Qualifiers
source                 1..416
                       mol_type = protein
                       organism = Treponema caldarium
SEQUENCE: 372
MKQLERFSMG IGDRFGHQGK AQLEALAEAK HLGCTIIPVW NKSYREHSII HTEPGQVRKE  60
ADWAVAALGW QDPYHVDADH ISMKTVDLFL DSSDFFTLDV ADYTGKAADE ASIARFVAKH  120
QHCIGKLQIP GIEQPITITE TTLTSVARKY LLAIQEAGKL YRHIANKKGP ENFITEVSID  180
ETDQPQGPED LLFILAMIAD EGIPAQTIAP KFTGRFNKGV DYVGNLTQFE REFNQDILVI  240
AYASKEFGLP KNLKLSVHSG SDKFSIYPII KKAIYTHHAG LHLKTAGTTW LEELIGLASA  300
GDEGLRIVQQ IYRETYYRFD ELCAPYATVI DIHKDKLPEP NSVQAWNGET YAAALRHIEN  360
HPQYNPHFRQ LLHVGYKVAA ELGETYLKAL EAHEHHIALQ VKENLLDRHI RPIFIQ      416

SEQ ID NO: 373         moltype = AA  length = 472
FEATURE                Location/Qualifiers
source                 1..472
                       mol_type = protein
                       note = previously known as Thermofilum uzonense
                       organism =  Infirmifilum uzonense
SEQUENCE: 373
MLDTPRYLGK LPHLSVGVRL PEVFLEGIMS GFKTGNSAGG VMLSYHRETA PEYVINAPPG  60
DFELTRGHTG TSIRHYIEAS VAKAKEKGVV VEVEADHVSV SVSSEAVKRI SGGGTHRVLS  120
EEEVRSALKY IEDEIREAVS TRNIYFYTID TCDLIDYSSE KIAVDELRTV FKDLYPASLI  180
ERYKDINVVV NGTRIRFDEE KVMRLSLKLM RSIDVSERIY RIIKEMTPWP FGIEIAFDET  240
PVTSDPHELF FVLNELRTRG IPVDFIAPNV GFQKREDFTG DLETLHSRVK TLHEVASFFG  300
SLLSFHSGSG SSPYSMKGKG VHDIIRRAAG GLFKYKISGV YFELLMQLMS RSDIPSVRRL  360
YEEIYDAVIE LLEDQVKRKG ELYDEVLVKR LEEHRKKSLN GYVRDSESPV FRYYSFLALN  420
IRRNGERYLR NAIVELYLED KGFREQVDRE ISALTVAFLD SLGFRGNVRL LR          472

SEQ ID NO: 374         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 374
MWLSKDYLRK KGVYSITSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL                408

SEQ ID NO: 375         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 375
MWLSKDYLRK KGVYSICNSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL                408

SEQ ID NO: 376         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 376
MWLSKDYLRK KGVYSICASN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL                408
```

```
SEQ ID NO: 377          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 377
MWLSKDYLRK KGVYSICSSN SYVIEASIEF AKEKGDYILI EATPHWVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 378          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 378
MWLSKDYLRK KGVYSICSSN SYVIEASIEF AKEKGDYILI EATPHRVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 379          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 379
MWLSKDYLRK KGVYSICSSN SYVIEASIEF AKEKGDYILI EATPHQVNQF GGYSGMTPED  60
FKNFVMKIAK EKGLEEDKII LGGPHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 380          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 380
MWLSKDYLRK KGVYSICSSN SYVIEASIEF AKEKGDYILI EATPHQVNQF GGYSGMTPED  60
FKNFVMKIAK EKGLEEDKII LGGAHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 381          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 381
MWLSKDYLRK KGVYSICSSN SYVIEASIEF AKEKGDYILI EATPHQVNQF GGYSGMTPED  60
FKNFVMKIAK EKGLEEDKII LGGDHLGPGP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408
```

```
SEQ ID NO: 382         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 382
MWLSKDYLRK KGVYSICSSN SYVIEASIEF AKEKGDYILI EATPQQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL            408

SEQ ID NO: 383         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 383
MWLSKDYLRK KGVYSICSSN SYVIEASIEF AKEKGDYILI EATPAQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL            408

SEQ ID NO: 384         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 384
MWLSKDYLRK KGVYSICSSN SYVIEASIEF AKEKGDYILI EATPKQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL            408

SEQ ID NO: 385         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 385
MWLSKDYLRK KGVYSICSSN SYVIEASIEF AKEKGDYILI EATPHAVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL            408

SEQ ID NO: 386         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 386
MWLSKDYLRK KGVYSICSSN SYVIEASIEF AKEKGDYILI EATPHQVNQF GGYSGMTPED  60
FKNFVMKIAK EKGLEEDKII LGGGHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
```

-continued

```
GVDIKFIYQY FYDSYFDVRE GKMKNDPREL IKKEIKRVLE DYSYAINL               408

SEQ ID NO: 387          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 387
MWLSKDYLRK KGVYSICSSN SYVIEASIEF AKEKGDYILI EATPHQVNQF GGYSGMTPED  60
FKNFVMKIAK EKGLEEDKII LGGDHLGPSP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 388          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 388
MWLSKDYLRK KGVYSICSSN SYVIEASIEF AKEKGDYILI EATPFQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 389          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 389
MWLSKDYLRK KGVYSICSSN SYVIEASIEF AKEKGDYILI EATPHSVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 390          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 390
MWLSKDYLRK KGVYSICSSN SYVIEASIEF AKEKGDYILI EATPHTVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 391          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 391
MWLSKDYLRK KGVYSICSSN SYVIEASIEF AKEKGDYILI EATPHQVNQF GGYSGMTPED  60
FKNFVMKIAK EKGLEEDKII LGGDHLGPLP WADEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
```

```
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 392         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 392
MWLSKDYLRK KGVYSICSSN SYVIEASIEF AKEKGDYILI EATPHQVNQF GGYSGMTPED  60
FKNFVMKIAK EKGLEEDKII LGGDHLGPLP WMDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 393         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 393
MWLSKDYLRK KGVYSICSSN SYVIEASIEF AKEKGDYILI EATPHQVNQF GGYSGMTPED  60
FKNFVMKIAK EKGLEEDKII LGGDHLGPLP WPDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 394         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 394
MWLSKDYLRK KGVYSICSSN SYVIEASIEF AKEKGDYILI EATPHQVNQF GGYSGMTPED  60
FKNFVMKIAK EKGLEEDKII LGGDHLGPLP WDDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 395         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 395
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCAMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 396         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 396
MWLSKDYLRK KGVYSICSSN SYVIEASIEF AKEKGDYILI EATPHQVNQF GGYSGMTPED  60
FKNFVMKIAK EKGLEEDKII LGGDHLGPLP WGDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
```

```
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 397         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 397
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKINI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 398         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 398
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIGI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 399         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 399
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIPI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 400         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 400
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DGSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 401         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 401
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DESMPLSDDP KVLPYEKIAE RTRELFEIAE ETARKYNFQP VYVVGTDVPI AGGGEEEGVT  180
```

-continued

```
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 402         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 402
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DKSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 403         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 403
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKISI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 404         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 404
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCMMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 405         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 405
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCRMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 406         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 406
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
```

```
DCTMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 407         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 407
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSRPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 408         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 408
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSKPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 409         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 409
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGMDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 410         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 410
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGIDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 411         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 411
MWLSKDYLRK KGVYSICSSN SYVIEASIEF AKEKGDYILI EATPHQVNQF GGYSGMTPED  60
```

```
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGLDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 412         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 412
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTAVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 413         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 413
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTVVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 414         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 414
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTTVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 415         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 415
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTNVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 416         moltype = AA  length = 408
FEATURE                Location/Qualifiers
REGION                 1..408
                       note = mutant D-fructose C4-epimerase
source                 1..408
                       mol_type = protein
                       organism = synthetic construct
SEQUENCE: 416
```

```
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDMPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 417          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 417
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDRPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 418          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 418
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPK AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 419          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 419
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI PGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 420          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 420
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPT AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 421          moltype = AA  length = 408
FEATURE                 Location/Qualifiers
REGION                  1..408
                        note = mutant D-fructose C4-epimerase
source                  1..408
                        mol_type = protein
                        organism = synthetic construct
```

```
SEQUENCE: 421
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPM AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 422          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 422
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGKEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 423          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 423
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEYEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 424          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 424
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGVEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 425          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 425
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEFEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 426          moltype = AA  length = 408
FEATURE                 Location/Qualifiers
REGION                  1..408
                        note = mutant D-fructose C4-epimerase
source                  1..408
                        mol_type = protein
```

```
                        organism = synthetic construct
SEQUENCE: 426
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGSGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 427          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 427
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGREEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 428          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 428
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEPVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 429          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 429
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFP IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 430          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 430
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFT IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL              408

SEQ ID NO: 431          moltype = AA  length = 408
FEATURE                 Location/Qualifiers
REGION                  1..408
                        note = mutant D-fructose C4-epimerase
source                  1..408
```

```
                         mol_type = protein
                         organism = synthetic construct
SEQUENCE: 431
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IKLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 432           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 432
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV ILLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 433           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 433
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IRLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 434           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 434
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSSD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL             408

SEQ ID NO: 435           moltype = AA  length = 408
FEATURE                  Location/Qualifiers
REGION                   1..408
                         note = mutant D-fructose C4-epimerase
source                   1..408
                         mol_type = protein
                         organism = synthetic construct
SEQUENCE: 435
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIGY YWEYEDVKMV LNKLFENFSE  360
GVDIKFIYQY FYDSYFDVRE GKMKNDPREL IKKEIKRVLE DYSYAINL             408

SEQ ID NO: 436           moltype = AA  length = 408
FEATURE                  Location/Qualifiers
REGION                   1..408
                         note = mutant D-fructose C4-epimerase
```

```
source                  1..408
                        mol_type = protein
                        organism = synthetic construct
SEQUENCE: 436
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIAY YWEYEDVKMV LNKLFENFSE  360
GVDIKFIYQY FYDSYFDVRE GKMKNDPREL IKKEIKRVLE DYSYAINL                408

SEQ ID NO: 437          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 437
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRITY YWEYEDVKMV LNKLFENFSE  360
GVDIKFIYQY FYDSYFDVRE GKMKNDPREL IKKEIKRVLE DYSYAINL                408

SEQ ID NO: 438          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 438
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIEY YWEYEDVKMV LNKLFENFSE  360
GVDIKFIYQY FYDSYFDVRE GKMKNDPREL IKKEIKRVLE DYSYAINL                408

SEQ ID NO: 439          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 439
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRP YWEYEDVKMV LNKLFENFSE  360
GVDIKFIYQY FYDSYFDVRE GKMKNDPREL IKKEIKRVLE DYSYAINL                408

SEQ ID NO: 440          moltype = AA  length = 408
FEATURE                 Location/Qualifiers
REGION                  1..408
                        note = mutant D-fructose C4-epimerase
source                  1..408
                        mol_type = protein
                        organism = synthetic construct
SEQUENCE: 440
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRR YWEYEDVKMV LNKLFENFSE  360
GVDIKFIYQY FYDSYFDVRE GKMKNDPREL IKKEIKRVLE DYSYAINL                408

SEQ ID NO: 441          moltype = AA  length = 408
FEATURE                 Location/Qualifiers
REGION                  1..408
```

```
                      note = mutant D-fructose C4-epimerase
source                1..408
                      mol_type = protein
                      organism = synthetic construct
SEQUENCE: 441
MWLSKDYLRK KGVYSICSSN SYVIEASIEF AKEKGDYILI EATPHQVNQF GGYSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRH YWEYEDVKMV LNKLFENFSE  360
GVDIKFIYQY FYDSYFDVRE GKMKNDPREL IKKEIKRVLE DYSYAINL               408

SEQ ID NO: 442        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 442
MWLSKDYLRK KGVYSICSSN SYVIEASIEF AKEKGDYILI EATPHQVNQF GGVSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 443        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 443
MWLSKDYLRK KGVYSICSSN SYVIEASIEF AKEKGDYILI EATPHQVNQF GGSSGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408

SEQ ID NO: 444        moltype = AA  length = 408
FEATURE               Location/Qualifiers
REGION                1..408
                      note = mutant D-fructose C4-epimerase
source                1..408
                      mol_type = protein
                      organism = synthetic construct
SEQUENCE: 444
MWLSKDYLRK KGVYSICSSN SYVIEASIEF AKEKGDYILI EATPHQVNQF GGASGMTPED  60
FKNFVMKIAK EKGLEEDKII LGGDHLGPLP WQDEPSPTAM NKAKDLIRAF VESGYKKIHI  120
DCSMPLSDDP KVLPYEKIAE RTRELFEIAE ETARKYNFQP VYVVGTDVPI AGGGEEEGVT  180
SVEDFRSAIS SLKKYFNDVP NIWDRVVGFV IMLGIGFSYD KVFEYDRDKV RGILEEVKRE  240
DLFVEGHSTD YQARYALRNM VEDGVRILKV GPALTAAFRR GVFLLSNIED EIIPERERSN  300
IKRVILETML RDDRYWRKYY KDSKRLELDI WYNLLDRIRY YWEYEDVKMV LNKLFENFSE  360
GVDIKFIYQY FYDSYFDVRE GKMKNDPREL IKKEIKRVLE DYSYAINL               408
```